US012459988B2

(12) United States Patent
Liu et al.

(10) Patent No.: US 12,459,988 B2
(45) Date of Patent: Nov. 4, 2025

(54) CHIMERIC PROTEIN COMPRISING AN ANTI-INFLUENZA VIRUS ANTIBODY MOIETY AND A MUCOADHESIVE PEPTIDE FRAGMENT FOR PREVENTING OR TREATING INFLUENZA INFECTIONS

(71) Applicant: InvisiShield Technologies Ltd., Emeryville, CA (US)

(72) Inventors: Cheng Liu, Orinda, CA (US); Ziyou Cui, Seattle, WA (US); Hongbing Zhang, Moraga, CA (US); Zhiyuan Yang, Richmond, CA (US); Guangyan Xiong, Emeryville, CA (US); Lu Jin, Emeryville, CA (US); Jinyun Chen, Emeryville, CA (US); Motao Liu, Emeryville, CA (US); Warner Greene, Hillsborough, CA (US)

(73) Assignee: INVISISHIELD TECHNOLOGIES LTD., Emeryville, CA (US)

( * ) Notice: Subject to any disclaimer, the term of this patent is extended or adjusted under 35 U.S.C. 154(b) by 0 days.

(21) Appl. No.: 18/914,010

(22) Filed: Oct. 11, 2024

(65) Prior Publication Data

US 2025/0034235 A1 Jan. 30, 2025

Related U.S. Application Data

(63) Continuation of application No. PCT/US2023/065734, filed on Apr. 13, 2023.

(60) Provisional application No. 63/331,100, filed on Apr. 14, 2022.

(51) Int. Cl.

| | |
|---|---|
| ***C07K 7/06*** | (2006.01) |
| ***A61K 38/08*** | (2019.01) |
| ***A61K 38/10*** | (2006.01) |
| ***A61K 39/42*** | (2006.01) |
| ***A61K 39/44*** | (2006.01) |
| ***A61K 47/64*** | (2017.01) |
| ***A61P 31/16*** | (2006.01) |
| ***C07K 7/08*** | (2006.01) |
| ***C07K 16/10*** | (2006.01) |
| *A61K 39/00* | (2006.01) |

(52) U.S. Cl.

CPC .......... *C07K 16/1018* (2013.01); *A61K 38/08* (2013.01); *A61K 38/10* (2013.01); *A61K 39/42* (2013.01); *A61K 39/44* (2013.01); *A61K 47/645* (2017.08); *A61P 31/16* (2018.01); *C07K 7/06* (2013.01); *C07K 7/08* (2013.01); *A61K 2039/505* (2013.01); *C07K 2317/565* (2013.01); *C07K 2319/00* (2013.01)

(58) Field of Classification Search

CPC ........ C07K 7/06; C07K 7/08; C07K 16/1018; A61K 38/08; A61K 38/10; A61K 39/42; A61K 47/645

See application file for complete search history.

(56) References Cited

U.S. PATENT DOCUMENTS

| | | | |
|---|---|---|---|
| 4,816,567 A | 3/1989 | Cabilly | |
| 5,591,828 A | 1/1997 | Bosslet | |
| 5,821,333 A | 10/1998 | Carter | |
| 7,642,228 B2 | 1/2010 | Carter | |
| 9,534,042 B2 | 1/2017 | Kurosawa | |
| 9,605,053 B2 | 3/2017 | Kurosawa | |
| 9,611,317 B2 | 4/2017 | Throsby | |
| 9,718,874 B2 | 8/2017 | Spits | |
| 10,079,518 B2 | 9/2018 | Hill | |
| 10,787,501 B1 | 9/2020 | Babb et al. | |
| 10,815,294 B2 | 10/2020 | Lanzavecchia | |
| 10,954,289 B1 | 3/2021 | Babb et al. | |
| 10,975,139 B1 | 4/2021 | Babb et al. | |
| 11,168,129 B2 | 11/2021 | Kobie | |
| 11,230,593 B2 | 1/2022 | Narayan | |
| 11,440,952 B2 | 9/2022 | Liu et al. | |
| 2011/0287009 A1 | 11/2011 | Scheer | |
| 2014/0120113 A1 * | 5/2014 | Kwaks | A61P 31/16 435/5 |
| 2018/0230447 A1 | 8/2018 | Batlle et al. | |
| 2018/0312575 A1 | 11/2018 | Marasco | |
| 2020/0095327 A1 | 3/2020 | Chang et al. | |
| 2021/0002354 A1 | 1/2021 | Wilson | |
| 2021/0025210 A1 | 1/2021 | Awad | |
| 2021/0047389 A1 | 2/2021 | Kobie | |
| 2021/0071505 A1 | 3/2021 | Boyd | |
| 2021/0171612 A1 | 6/2021 | Baum | |
| 2021/0261650 A1 | 8/2021 | Corti et al. | |
| 2021/0277092 A1 | 9/2021 | Crowe, Jr. et al. | |
| 2021/0292392 A1 | 9/2021 | Zhang et al. | |
| 2021/0292393 A1 | 9/2021 | Westendorf et al. | |
| 2021/0300999 A1 | 9/2021 | Crowe, Jr. et al. | |
| 2022/0033522 A1 | 2/2022 | Ganesan et al. | |
| 2022/0119501 A1 * | 4/2022 | Liu | C07K 16/1002 |
| 2023/0141962 A1 | 5/2023 | Liu | |

FOREIGN PATENT DOCUMENTS

| | | |
|---|---|---|
| CN | 111303280 A | 6/2020 |
| CN | 111704665 A | 9/2020 |

(Continued)

OTHER PUBLICATIONS

Abhinandan, K.R. et al. (Aug. 2008, e-pub. Jul. 9, 2008). "Analysis and Improvements To Kabat and Structurally Correct Numbering Of Antibody Variable Domains," Molecular Immunology 45(14):3832-3839.

(Continued)

*Primary Examiner* — Zachary C Howard
(74) *Attorney, Agent, or Firm* — MORRISON & FOERSTER LLP

(57) ABSTRACT

The present application provides chimeric proteins comprising an antibody moiety that specifically binds to a component of an influenza virus or a variant thereof, and a positively charged mucoadhesive peptide fragment. Compositions comprising the chimeric proteins described herein are useful for preventing or treating an infection caused by an influenza virus or a variant thereof in an individual.

26 Claims, 10 Drawing Sheets

Specification includes a Sequence Listing.

(56) References Cited

FOREIGN PATENT DOCUMENTS

| | | | |
|---|---|---|---|
| EP | 0404097 | B1 | 9/1996 |
| WO | 1993011161 | A1 | 6/1993 |
| WO | 199634103 | A1 | 10/1996 |
| WO | 2003048731 | A2 | 6/2003 |
| WO | 2003063772 | A2 | 8/2003 |
| WO | 2008016729 | A1 | 2/2008 |
| WO | 2010130636 | A1 | 11/2010 |
| WO | 2012029997 | A1 | 3/2012 |
| WO | 2013007770 | A1 | 1/2013 |
| WO | 2013011347 | A1 | 1/2013 |
| WO | 2013055958 | A1 | 4/2013 |
| WO | 2013081463 | A2 | 6/2013 |
| WO | 2017123685 | A1 | 7/2017 |
| WO | 2018187706 | A2 | 10/2018 |
| WO | 2019147867 | A1 | 8/2019 |
| WO | 2019169231 | A1 | 9/2019 |
| WO | 2019213384 | A1 | 11/2019 |
| WO | 2020041540 | A1 | 2/2020 |
| WO | 2020143799 | A1 | 7/2020 |
| WO | 2020167919 | A1 | 8/2020 |
| WO | 2020198329 | A1 | 10/2020 |
| WO | 2020221908 | A1 | 11/2020 |
| WO | 2020243572 | A2 | 12/2020 |
| WO | 2020251834 | A1 | 12/2020 |
| WO | 2021086899 | A1 | 5/2021 |
| WO | 2021158521 | A1 | 8/2021 |
| WO | 2021158960 | A1 | 8/2021 |
| WO | 2021167919 | A1 | 8/2021 |
| WO | 2021168305 | A1 | 8/2021 |
| WO | 2021189104 | A1 | 9/2021 |
| WO | 2021195326 | A1 | 9/2021 |
| WO | 2021195485 | A1 | 9/2021 |
| WO | 2021216547 | A1 | 10/2021 |
| WO | 2022075667 | A1 | 4/2022 |
| WO | 2022082217 | A1 | 4/2022 |

OTHER PUBLICATIONS

Adolf-Bryfogle, J. et al. (2015, e-pub. Nov. 11, 2014). "PyIgClassify: A Database of Antibody CDR Structural Classifications," Nucleic Acids Res. 43:D432-D438.

Al-Lazikani, B. et al. (1997). "Standard Conformations for the Canonical Structures of Immunoglobulins," J. Mol. Biol. 273:927-948.

Bottermann, M. et al. (Apr. 10, 2019). "Complement C4 Prevents Viral Infection Through Capsid Inactivation," Cell Host & Microbe 25:617-629.

Branttie, J.M. et al. (Feb. 25, 2020). "Parainfluenza Virus 5 Fusion Protein Maintains Pre-Fusion Stability but Not Fusogenic Activity Following Mutation of A Transmembrane Leucine/Isoleucine Domain," J. Gen. Virol. 101(5):467-472.

Burton, D.R. (1985). "Immunoglobulin G: Functional Sites," Molec. Immunol. 22(3):161-206.

Cardoso, F.M. et al. (Aug. 2014, e-pub. May 14, 2014). "Single-Domain Antibodies Targeting Neuraminidase Protect against an H5N1 Influenza Virus Challenge," Journal of Virology 88(15):8278-8296.

Chivers, C.E. et al. (2011). "How The Biotin-Streptavidin Interaction was Made Even Stronger: Investigation Via Crystallography and A Chimaeric Tetramer," Biochem J. 435(Pt 1):55-63.

Chothia, C. et al. (1987), "Canonical Structures for the Hypervariable Regions of Immunoglobulins," J. Mol. Biol, 196:901-917.

Chothia, C. et al. (Dec. 21/28, 1989). "Conformations of Immunoglobulin Hypervariable Regions," Nature 342(6252):877-883.

Chowdhury, P.S. (2008). "Engineering Hot Spots for Affinity Enhancement of Antibodies," Methods Mol. Biol. 207:179-196.

Corti, D. et al. (Mar. 2013, e-pub. Jan. 16, 2013). "Broadly Neutralizing Antiviral Antibodies," Annu. Rev. Immunol. 31:705-742.

Cui, Y. et al. (2017, e-pub. Jan. 4, 2017). "Monoclonal Antibodies: Formulations Of Marketed Products And Recent Advances In Novel Delivery System," Drug Development and Industrial Pharmacy 11:28, 40 pages.

Cunningham, B.C. et al. (Jun. 2, 1989). "High-Resolution Epitope Mapping of hGH-Receptor Interactions by Alanine-Scanning Mutagenesis," Science 244:1081-1085.

Dolton, G. et al. (2014). "Comparison Of Peptide-Major Histocompatibility Complex Tetramers and Dextramers for The Identification of Antigen-Specific T Cells," Clin. Exp. Immunol. 177(1):47-63.

Dreyfus, C. et al. (Sep. 14, 2012). "Highly Conserved Protective Epitopes on Influenza B Viruses," Science 337(6100):1343-1348, 14 pages.

Ehrenmann, F. et al. (Jan. 2010, e-pub. Nov. 9, 2009). "IMGT/3Dstructure-DB and IMGT/DomainGapAlign: A Database and a Tool For Immunoglobulins or Antibodies, T Cell Receptors, MHC, IgSF and MhcSF," Nucleic Acids Res. 38:D301-D307.

Ferkol, T. et al. (Feb. 1995). "Gene Transfer into the Airway Epithelium of Animals by Targeting the 1-3 Polymeric Immunoglobulin Receptor," The Journal of Clinical Investigation 95(2):493-502.

Gencel-Augusto, J. et al. (2020). "p53 Tetramerization: at the Center of the Dominant-Negative Effect of Mutant p53," Genes Dev. 34(17-18):1128-1146.

Guillaume, P. et al. (Feb. 14, 2003, e-pub. Oct. 28, 2002). "Soluble Major Histocompatibility Complex-Peptide Octamers withimpaired CD8 Binding Selectively Induce Fas-dependent Apoptosis," J. Biol. Chem. 278(7):4500-4509.

Hamers-Casterman, C. et al. (Jun. 3, 1993). "Naturally Occurring Antibodies Devoid of Light Chains," Nature 363:446-448.

Hassanzadeh-Ghassabeh, G. et al. (2013, e-pub. Jun. 4, 2013). "Nanobodies and their Potential Applications," Nanomedicine (Lond) 8(6):1013-1026.

Holler, N. et al. (2000). "Development if Improved Soluble Inhibitors of Fast and CD49K Based on Oligomerized Receptors," J. Immunol. Methods 237:159-173.

Holliger, P. et al. (Jul. 1993). ""Diabodies": Small Bivalent and Bispecific Antibody Fragments," Proceedings of the National Academy of Sciences USA 90:6444-6448.

Honegger, A. et al. (Jun. 8, 2001). "Yet Another Numbering Scheme For Immunoglobulin Variable Domains: An Automatic Modeling And Analysis Tool," J. Mol. Biol. 309:657-670.

Hoogenboom, H.R. (2001). "Overview of Antibody Phage-Display Technology and Its Applications," Methods in Molecular Biology 178:1-37.

Huber-Lang, M. et al. (Jun. 2006, e-pub. May 21, 2006). "Generation of C5a in the Absence of C3: A New Complement Activation Pathway," Nature Medicine 12(6):682-687.

International Preliminary Report on Patentability issued on Oct. 8, 2024, for PCT Application No. PCT/US2023/065734, filed on Apr. 13, 2023, 6 pages.

International Search Report and Written Opinion mailed on Aug. 21, 2023, for PCT Application No. PCT/US2023/065734, filed on Apr. 13, 2023, 18 pages.

Jagadesh, A. et al. (2016, e-pub. Jun. 2, 2016). "Influenza Virus Neuraminidase (NA): A Target for Antivirals and Vaccines," Arch. Virol. 161:2087-2094.

Jansen, F.K. et al. (1982). "Immunotoxins: Hybrid Molecules Combining High Specificity and Potent Cytotoxicity," Immunol. Rev. 62:185-216.

Jones, P.T. et al. (May 29, 1986). "Replacing The Complementarity-Determining Regions In A Human Antibody With Those From A Mouse," Nature 321:522-525.

Kabat, E.A. et al. (Oct. 10, 1977). "Unusual Distributions Of Amino Acids In Complementarity-Determining (Hypervariable) Segments Of Heavy And Light Chains Of Immunoglobulins And Their Possible Roles In Specificity Of Antibody-Combining Sites," J. Biol. Chem. 252(19):6609-6616.

Killen, J.A. et al. (Nov. 1, 1984). "Specific Killing Of Lymphocytes That Cause Experimental Autoimmune Myasthenia Gravis By Ricin Toxin-Acetylcholine Receptor Conjugates," J. Immunol. 133(5):2549-2553.

(56) References Cited

OTHER PUBLICATIONS

Kirkpartick, E. et al. (Jul. 18, 2018, e-pub. Jul. 11, 2018). "The Influenza Virus Hemagglutinin Head Evolves Faster Than the Stalk Domain," Scientific Rep. 8:10432, 14 pages.
Krammer, F. et al. (2018). "Influenza," Nat. Rev. Dis. Primers 4(3):1-21.
Kulkami, V. et al. (Jun. 2012). "Formulation and Characterization of Nasal Sprays," Inhalation 10-11, 5 pages.
Lefranc, M.P. et al. (Jan. 2005). "IMGT Unique Numbering for Immunoglobulin and T Cell Receptor Variable Domains and Ig Superfaamly V-Like Domains," Dev. Com. Immunol. 27(1):55-77.
Li, Y. et al. (Nov. 15, 2021). "Characterization of Canine Influenza Virus A (H3N2) Circulating in Dogs in China from 2016 to 2018," Viruses 13(11):2279, 14 pages.
Lobner, E. et al. (2016). "Engineered IgG1-Fc—One Fragment To Bind Them All," Immunol. Rev. 270(1)113-131.
Maccallum, R.M. et al. (Oct. 1996). "Antibody-Antigen Interactions: Contact Analysis and Binding Site Topography," J. Mol. Biol. 262(5):732-745.
Mckay, T. et al. (2005, e-pub. Jan. 5, 2006). "Influenza M2 Envelope Protein Augments Avian Influenza Hemagglutinin Pseudotyping of Lentiviral Vectors," Gene Therapy 13:715-724.
Mellors, J. et al. (Jul. 9, 2020). "Viral Evasion of the Complement System and Its Importance for Vaccines and Therapeutics," Frontiers in Immunology 11(1450):1-20.
Mordhorst, S. et al. (Nov. 23, 2020, E-Pub. Sep. 17, 2020). "Posttranslationally Acting Arginases Provide a Ribosomal Route To Non-Proteinogenic Ornithine Residues In Diverse Peptide Sequences," Angewandte Chemie 59(48):21442-21447.
Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.
Murphy, B.R. et al. (Jun. 22, 1972). "Association Of Serum Anti-Neuraminidase Antibody with Resistance to Influenza in Man," N. Engl. J. Med. 286(25):1329-1332.
Napolitano, G. et al. (2016). "TFEB at a Glance," J. Cell Sci. 129(13):2475-2481.
Parrish, C.R. et al. (Jul. 2019). "H3N8 and H3N2 Canine Influenza Viruses: Understanding These New Viruses in Dogs," Vet Clin North Am Small Anim. 49(4):643-649.
Plückthun, A. (1994). "Antibodies from *Escherichia coli*," in Chapter 11 The Pharmacology of Monoclonal Antibodies, vol. 113, Rosenburg and Moore eds., Springer-Verlag, New York, pp. 269-315, 48 pages.
Presta, L.G. (1992). "Antibody Engineering," Current Opinion in Structural Biology, 2:593-596.
Ramakrishnan, S. et al. (Jan. 1984). "Comparison of the Selective Cytotoxic Effects of Immunotoxins Containing Ricin A Chain or Pokeweed Antiviral Protein and Anti-Thy 1.1 Monoclonal Antibodies," Cancer Res. 44:201-208.
Reichmann, L. et al. (Mar. 1988). "Reshaping Human Antibodies for Therapy," Nature 332:323-327.
Scheraga. H.A. (1992). "Predicting Three Dimensional Structures of Oligopeptides," Chapter 2 in Review in Computational Chemistry III, pp. 73-142.
Thorat, S. (2016). "Formulation and Product Development of Nasal Spray: An Overview," Scholars Journal of Applied Medical Sciences (SJAMS) 4(8D):2976-2985.
Tyrrell, C.S.B. et al. (2021). "Influenza: Epidemiology and Hospital Management," Medicine (Abingdon) 49(12):797-804.
Vitetta, E.S. et al. (Nov. 20, 1987). "Redesigning Nature's Poisons to Create Anti-Tumor Reagents," Science 238:1098-1104.
Xie, X. et al. (2015). "Monoclonal antibody specific to HA2 glycopeptideprotects mice from H3N2 influenza virus infection," Veterinary Research 46:33, 14 pages.
Xiong, F-F. et al. (2020, e-pub. Jan. 2, 2020). "Protective Efficacy of Anti-Neuraminidase Monoclonal Antibodies Against H7N9 Influenza Virus Infection," Emerging Microbes & Infections 9(1):78-87.
Xu, X. et al. (2019). "Update: Influenza Activity In The United States During The 2018-2019 Season And Composition Of The 2019-2020 Influenza Vaccine," MMWR 68(24):544-551, 11 pages.
Yan, J et al. (Jan. 30, 2018). "Infectious Virus in Exhaled Breath of Symptomatic Seasonal Influenza Cases from A College Community," Proc. Nat. Sci. USA 115(5):1081-1086.
Yang, X. et al. (May 2002). "Highly Stable Trimers Formed By Human Immunodeficiency Virus Type 1 Envelope Glycoproteins Fused With The Trimeric Motif Of T4 Bacteriophage Fibritin," J. Virol. 76(9):4634-4642.
Zheng, M. et al. (2021, e-pub. Dec. 13, 2020). "Poly(alpha-L-Lysine }-Based Nanomaterials for Versatile Biomedical 1-3 C—Applications: Current Advances and Perspectives," Bioactive Materials 6(7):1878-1909.
Alves, N.J. (2019, Feb. 15, 2019). "Antibody Conjugation and Formulation," Antibody Therapeutics 2(1):33-39.
Azhar, E.M. et al. (Jun. 26, 2014). "Evidence for Camel-to Human Transmission of MERS-Coronavirus," New England Journal of Medicine 370(26):2499-2505.
Beyerstedt, S. et al. (2021, e-pub. Jan. 3, 2021). "COVID-19: Angiotensin-Converting Enzyme 2 (ACE2) Expression and Tissue Susceptibility To SARS-CoV-2 Infection," Eur. J. Clin. Microbiol. Infect. Dis. 40:905-919.
Bird, R.E. et al. (Oct. 21, 1988). "Single-Chain Antigen-Binding Proteins," Science 242(4877):423-426.
BPS Bioscience: ACE-2, His-tag. Available online at https://bpsbioscience.com/ace2-his-tag-11003 [Retrieved online Dec. 21, 2021] https://web.archive.org/web/2020*/https://bpsbioscience.com/ace2-his-tag-11003 published on Jun. 30, 2020 as per Wayback Machine, last visited on Jan. 28, 2022, 3 pages.
Celerion Applied Translational Medicine. (May 6, 2015). "Intranasal Drug Delivery: Drug Development Considerations," slide presentation by Morimoto, B. H. PhD, Executive Director, Applied Translational Medicine, 28 pages.
Cheadle, C. et al. (Jan. 1992). "Cloning And Expression Of The Variable Regions Of Mouse Myeloma Protein Mopc315 In *E. coli*: Recovery Of Active Fv Fragments," Molecular Immunology 29(1):21-30.
Clinical Trials. Eli Lilly and Company (Aug. 2, 2020). A Study of LY3819253 (LY-CoV555) and LY3832479 (Ly-CoV016) in Preventing S AR S-C oV-2 Infection and COVID-19 in Nursing Home Residents and Staff (BLAZE-2). Identifier NCT04497987 Located at https://clinicaltrials.gov/ct2/show/NCT04497987 last visited on Jan. 19, 2022, 27 pages.
Clinical Trials. Regeneron Pharmaceuticals (Jul. 26, 2020-Present). Study Assessing the Safety, Tolerability, Pharmacokinetics, and Immunogenicity of Repeated Subcutaneous Doses of Anti-Spike (S) SARS-CoV-2 Monoclonal Antibodies (REGN10933+REGN10987) in Adult Volunteers as Related to COVID-19. Identifier: NCT04519437, 19 pages.
Clinical Trials. Regeneron Pharmaceuticals (Jun. 11, 2020-Present). Safety, Tolerability, and Efficacy of Anti Spike (S) SARS-CoV-2 Monoclonal Antibodies for Hospitalized Adult Patients With COVID-19. Identifier NCT04426695, 35 pages.
Clinical Trials. Regeneron Pharmaceuticals (Jun. 16, 2020-Present). Safety, Tolerability, and Efficacy of Anti Spike (S) SARS-CoV-2 Monoclonal Antibodies for the Treatment of Ambulatory Adult and Pediatric Patients With COVID-19. Identifier NCT04425629, 32 pages.
Clinical Trials. Regeneron Pharmaceuticals (Jun. 30, 2020-Present). COVID-19 Study Assessing the Efficacy and Safety of Anti-Spike SARS CoV-2 Monoclonal Antibodies for Prevention of SARS CoV-2 Infection Asymptomatic in Healthy Adults and Adolescents Who Are Household Contacts to an Individual With a Positive SARS-CoV-2 RT-PCR Assay. Identifier NCT04452318, 42 pages.
Clinical Trials. Shanghai Junshi Bioscience Co., Ltd. (Jun. 5, 2020-Present). Tolerability, Safety, Pharmacokinetic Profile and Immunogenicity of a Recombinant Humanized Anti-SARS-CoV-2 Monoclonal Antibody (J5016) for Injection in Chinese Health Subjects. Identifier NCT04441918, 20 pages.
Clinical Trials. Vir Biotechnology, Inc. (Aug. 27, 2020-present). VIR-7831 for the Early Treatment of COVID-19 in Outpatients (COMET-ICE). Identifier NCT04545060, 17 pages.

(56) References Cited

OTHER PUBLICATIONS

Cohen, J. (Nov. 10, 2020). "Can A Nose-Full Of Chicken Antibodies Ward Off Coronavirus Infections?," Science Insider, located at https://www.science.org/content/article/can-nose-full-chicken-antibodies-ward-coronavirus-infections#.YfRjAoyfAO4.mailto , last visited on Jan. 30, 2022, 2 pages.
Crowe, J.E. Jr, et al. (Feb. 1994). "Recombinant Human Respiratory Syncytial Virus (RSV) Monoclonal Antibody Fab is Effective Therapeutically When Introduced Directly into the Lungs of RSV-Infected Mice," Proc Natl Acad Sci USA 91(4):1386-1390.
Dall'Acqua, W. et al. (1998). "Contribution of Domain Interface Residues to the Stability of Antibody CH3 Domain Homodimers," Biochemistry 37(26):9266-9273.
Dog ACE2 NCBI sequences NW_020267596.1, Jul. 5, 2018. Retrieved from https://www.ncbi.nlm.nih.gOv/nuccore/NW_020267596.1?report=genbank on May 13, 2025, 520 pages.
Ehrick, J.D. et al. (2013, e-pub. Jun. 22, 2013). "Considerations for the Development of Nasal Dosage Forms," Web PDF, Sterile Product Development, pp. 99-144, located at https://link.springer.com/content/pdf/10.1007/978-1-4614-7978-9_5.pdf, last visited on Jan. 31, 2022, 46 pages.
Eroshenko, N. et al. (Jul. 2020, e-pub. Jun. 17, 2020). "Implications of Antibody-Dependent Enhancement of Infection for SARS-CoV-2 Countermeasures," Nat. Biotechnol. 38:789-791.
Eureka Therapeutics. (Dec. 14, 2020). "Eureka Therapeutics Announces Successful Preclinical Results of InvisiMask™ Human Antibody Nasal Spray Against SARS-CoV-2 Infection," Press Release, located at https://www.eurekatherapeutics.com/media/press-releases/121420/, last visited on Jan. 28, 2022, 3 pages.
Eureka Therapeutics. (Dec. 14, 2020). "InvisiMask™ Nasal Spray," Web Brochure, located at https://www.eurekatherapeutics.com/COVID19/, last visited on Jan. 28, 2022, 5 pages.
Extended Search Report mailed Dec. 2, 2024, for European Patent Application No. 21881327.7, Filed May 16, 2023, 7 pages.
Fan, C-Y. et al. (Nov. 2008). "Production Of Multivalent Protein Binders Using A Self-Trimerizing Collagen-Like Peptide Scaffold," FASEB J. 22:3795-3804.
FDA. CDER. CMC. (Jul. 2002). "Guidance for Industry, Nasal Spray and Inhalation Solution, Suspension, and Spray Drug Products—Chemistry, Manufacturing, and Controls Documentation," Brochure, U.S. Department of Health and Human Services, Food and Drug Administration, Center for Drug Evaluation and Research (CDER), CMC, 49 pages.
Ge, J. et al. (Apr. 2013). "RNA Pesudouridylation: New Insights Into an Old Modification," Trends Biochem. Sci. 38(4):210-218, 20 pages.
GenBank Accession No. AAP41037, last updated May 27, 2020, located at http://www.ncbi.nlm.nih.gov/protein/AAP41037.1, last visited Dec. 11, 2024, three pages.
GenBank Accession No. NC045512.2, last updated Jul. 18, 2020, "Severe Acute Respiratory Syndrome Coronavirus 2 Isolate Wuhan-Hu-1, Complete Genome," located at "https://www.ncbi.nlm.nih.gov/nuccore/NC_045512.2/", last visited on Jan. 25, 2023, 16 pages.
Gizurarson, S. (2012). "Anatomical and Historical Factors Affecting Intranasal Drug and Vaccine Delivery," Current Drug Delivery 9(6):566-582.
GlobalData. (Sep. 17, 2020). "A Nasal Spray Vaccine for COVID-19," Analyst Briefing by Scotty Chung-Siu, MPH, Senior Analyst, 3 pages.
Goldsby, R.A. et al. (2003). "Antibodies: Structure and Function. Part II Generation of B-Cell and T-Cell Responses," Chapter 4 in Immunology, W.H. Freeman, pp. 82-85.
Gomez, C.E. et al. (Mar. 11, 2021). "Emerging SARS-CoV-2 Variants and Impact in Global Vaccination Programs against SARS-CoV-2/COVID-19," Vaccines 9(3):243, 13 pages.
Guan, Y. et al. (Aug. 10, 2003). "Isolation and Characterization of Viruses Related to the SARS Coronavirus from Animals in Southern China," Science 30:276-278.
Halwe, S. et al. (Jul. 29, 2021). "Intranasal Administration of a Monoclonal Neutralizing Antibody Protects Mice against SARS-CoV-2 Infection," Viruses 13(8):1498, 39 pages.
He, Y. et al. (2006). "Cross-Neutralization of Human and Palm Civet Severe Acute Respiratory Syndrome Coronaviruses by Antibodies Targeting the Receptor-Binding Domain of Spike Protein," The Journal of Immunology 176:6085-6092.
Heurich, A. et al. (Jan. 2014). "TMPRSS2 and ADAM17 Cleave ACE2 Differentially and Only Proteolysis by TMPRSS2 Augments Entry Driven by the Severe Acute Respiratory Syndrome Coronavirus Spike Protein," J. Virol. 88(2):1293-1307.
Higgins, T..S et al. (2020). "Intranasal Antiviral Drug Delivery and Coronavirus Disease (COVID-19): A State-of-the-Art Review," Preprint Manuscript, Intranasal Antiviral Agents and COVID-19, 37 pages.
Hoffman, M. et al. (Apr. 16, 2020). "SARS-CoV-2 Cell Entry Depends On ACE2 and TMPRSS2 And Is Blocked by A Clinically Proven Protease Inhibitor," Cell 181:271-280.
Hulswit, R.J. et al. (Feb. 12, 2019). "Human Coronaviruses OC43 and HKU1 Bind to 9-O-Acetylated Sialic Acids via a Conserved Receptor-Binding site in Spike Protein Domain A," PNAS 116(7):2681-2690.
Human ACE2 NCBI sequences NM_021804.2, Jun. 11, 2019. Retrieved from https://www.ncbi.nlm.nih.gOv/nuccore/NM_021804.2 on May 13, 2025, 11 pages.
Illum, L. (Dec. 2002). "Nasal Drug Delivery: New Developments and Strategies," Drug Discovery Today 7 (23):1184-1189.
Illum, L. et al. (1994). "Chitosan as a Novel Nasal Delivery System for Peptide Drugs," Pharmaceutical Research 11(8):1186-1189.
International Preliminary Report on Patentability issued on Oct. 8, 2024, for PCT Application No. PCT/US2023/065732, filed on Apr. 13, 2023, 5 pages.
International Preliminary Report on Patentability mailed Apr. 27, 2023, for International Patent Application No. PCT/US2021/071893, filed Oct. 14, 2021, 11 pages.
International Search Report and Written Opinion mailed on Aug. 21, 2023, for PCT Application No. PCT/US23/65732, filed on Apr. 13, 2023, 10 pages.
International Search Report and Written Opinion of the International Searching Authority mailed Jan. 4, 2022, for International Patent Application No. PCT/US2021/071893, filed Oct. 14, 2021, 19 pages.
Kaye, R.S. et al. (2008, e-pub. Nov. 24, 2008). "Development and Testing of Particulate Formulations For The Nasal Delivery Of Antibodies," Journal of Controlled Release 135(2009):127-135.
Koussoroplis, S.J. et al. (2014, e-pub. May 17, 2014). "PEGylation of Antibody Fragments Greatly Increases Their Local Residence Time Following Delivery to the Respiratory Tract," J Control Release 187:91-100.
Kulkarni, V. (Jun. 2012). "Formulation and Characterization of Nasal Sprays, An Examination of Nasal Spray Formulation Parameters and Excipients and Their Influence on Key in Vitro Tests," Web PDF, Inhalation, located at https://www.dptlabs.com/wp-content/uploads/2012/08/Formulation_and_Characterization_of_Nasal_Sprays.pdf , last visited on Jan. 31, 2022, 5 pages.
Kuznetsov, A. et al. (2022, e-pub. Dec. 1, 2021). "ACE2 Peptide Fragment Interaction with Different S1 Protein Sites," Int. J. Pept. Res Ther. 28(1):1-7.
Lefranc, M.-P. et al. (2015, e-pub. Nov. 5, 2014). "IMGT®, The International ImMunoGeneTics Information System® 25 Years On," Nucleic Acids Res. 43:D413-D422.
Li, F. (2016, e-pub. Aug. 25, 2016). "Structure, Function, and Evolution of Coronavirus Spike Proteins," Annu Rev Virol. 3(1):237-261.
Li, F. et al. (Sep. 16, 2005). "Structure of SARS Coronavirus Spike Receptor-Binding Domain Complexed with Receptor," Science 309:1864-1968.
Li, Q. et al. (Jun. 18, 2020). "Genetic Variability of Human Angiotensin-Converting Enzyme 2 (hACE2) Among Various Ethnic Populations," Mol. Genet. Genomic Med. 8(8):e1344, 6 pages.
Li, W. et al. (2005). "Receptor and viral determinants of SARS-coronavirus adaptation to human ACE2," The EMBO Journal 24(8):1634-1643.

(56) References Cited

OTHER PUBLICATIONS

Liu, L. et al. (Aug. 20, 2020, e-pub. Jul. 22, 2020). "Potent Neutralizing Antibodies Against Multiple Epitopes on SARS-CoV-2 Spike," Nature 584:450-456, 26 pages.
Lu, F. et al. (Aug. 2015). "Bat-to-Human: Spike Features Determining 'Host Jump' of Coronaviruses SRS-CoV, MERS-CoV, and Beyond," Tends in Microbiology 29(8):468-478.
Lu, G. et al. (Aug. 8, 2013). "Molecular Basis of Binding Between Novel Human Coronavirus MERS-CoV and its Receptor CD26," Nature 500:227-232.
Marple, B, et al. (2004). "Review Article, Safety Review of Benzalkonium Chloride Used As A Preservative In Intranasal Solutions: An Overview Of Conflicting Data And Opinions," Otolaryngol Head Neck Surg 130:131-41.
Millet, J. K. et al. (Apr. 16, 2015). "Host Cell Proteases: Critical Determinants of Coronavirus Tropism and Pathogenesis," Virus Res. 202:120-134.
Mohebbi, A. et al. (Aug. 17, 2020). "Susceptibility of the Iranian Population to Severe Acute Respiratory Syndrome Coronavirus 2 Infection Based on Variants of Angiotensin I Converting Enzyme 2," Future Virol. 10:2217-2235.
Morimoto, B. H. (PhD) (May 6, 2015). "Intranasal Drug Delivery: Drug Development Considerations," slide presentation for Celerion Applied Translational Medicine, 28 pages.
Partial European Search Report for European Patent Application No. 21881327.7, mailed on Sep. 10, 2024, Filed May 16, 2023, 10 pages.
Qiu, Y. et al. (2020). "Receptor Utilization of Angiotensin Converting Enzyme 2 (ACE2) Indicates a Narrower Host Range of SARS-CoV-2 Than That of SARS-CoV," BioRxiv, 21 pages.
Raag, R. et al. (Jan. 1995). "Single-chain Fvs," The FASEB Journal 9:73-80.
Riche, D. O. (Feb. 2021). "Two Different Antibody-Dependent Enhancement (ADE) Risks for SARS-CoV-2 Antibodies," Front. Immunol. 12:640093, 9 pages.
Riediker, M. et al. (Jul. 27, 2020). "Estimation of Viral Aerosol Emissions From Simulated Individuals With Asymptomatic to Moderate Coronavirus Disease 2019," JAMA Netw Open. 3(7):e2013807, 10 pages.
Rudikoff, S. et al. (Mar. 1982). "Single Amino Acid Substitution Altering Antigen-Binding Specificity," Proc. Natl. Acad. Sci. USA 79:1979-1983.
Suh, W. et al. (2001). "Anti-JL1 Antibody-Conjugated Poly (L-lysine) for Targeted Gene Delivery to Leukemia T Cells," Journal of Controlled Release 72(2001):171-178.
Sui, J. et al. (Feb. 24, 2004). "Potent Neutralization Of Severe Acute Respiratory Syndrome (SARS) Coronavirus By A Human mAb To S1 Protein That Blocks Receptor Association," 101(8):2536-2541.
Tanaka, S. et al. (2021, e-pub. Jun. 17, 2021). "An ACE2 Triple Decoy That Neutralizes SARS-CoV-2 Shows Enhanced Affinity For Virus Variants," Nature 11:12740-12753.
Tang, J.W. et al. (Apr. 2021). "Emergence of a New SARS-CoV-2 variant in the UK," Journal of Infection 82(4):e27-e28.
Taylor, P.C. et al. (Jun. 2021). "Neutralizing Monoclonal Antibodies For Treatment Of COVID-19," Nat Rev Immunol 21:382-393.
Tuekprakhon, A. et al. (2022). "Antibody Escape of SARS-CoV-2 Omicron BA.4 and BA.5 From Vaccine and BA.1 Serum," Cell 185(14):2422-2433.
UniProtKB ID: PODTC2, located at <http://www.uiprot.org/uniprotkb/PODtC2/entry>, last visited Dec. 10, 2024, sixteen pages.
UniProtKB ID P59594, located at http://www.uniprot.org/uniprotkb/P59594/entry, last visited on Dec. 10, 2024, nine pages.
Van Den Brink, E.N. et al. (Feb. 2005). "Molecular and Biological Characterization of Human Monoclonal Antibodies Binding to the Spike and Nucleocapsid Proteins of Severe Acute Respiratory Syndrome Coronavirus," Journal of Virology 79(3):1635-1644.
Viana, R. et al. (2022, e-pub. Jan. 7, 2022). "Rapid Epidemic Expansion of the SARS-CoV-Omicron Variant in Southern Africa," Nature 603:679-686.
Walls, A. C. et al. (Apr. 16, 2020). "Structure, Function, and Antigenicity of the SARS-CoV-2 Spike Glycoprotein," Cell 180(2):281-292, 38 pages.
Walsh, S. et al. (Oct. 2004). "Extended Nasal Residence Time of Lysostaphin and an Anti-Staphylococcal Monoclonal Antibody by Delivery in Semisolid or Polymeric Carriers," Pharm Res. 21(10):1770-1775.
Wang, Q. et al. (Jan. 19, 2023). "Alarming Antibody Evasion Properties of Rising SARS-CoV-2 BQ and XBB Subvariants," Cell 186:279-286.
Wang, Q. et al. (May 14, 2020). "Structural and Functional Basis of SARS-CoV-2 Entry by Using Human ACE2," Cell 181(4):894-904.
Wang, W. et al. (Jan. 2007). "Antibody Structure, Instability, and Formulation," J. Pharm. Sci. 96(1):1-26.
Ward, E.S. et al. (Oct. 12, 1989). "Binding Activities of a Repertoire of Single Immunoglobulin Variable Domains Secreted From *Escherichia coli*," Nature 341:544-546.
Weltzin, R. et al. (Jul. 1999). "Intranasal Antibody Prophylaxis for Protection Against Viral Disease," Clinical Microbiology Review 12(3):383-393.
Wevers, B.A. et al. (2009). "Recently Discovered Human Coronaviruses," Clin. Lab Med. 29(4):715-724.
Widjaja, I. et al. (2019, e-pub. Apr. 2, 2019). "Towards A Solution To MERS: Protective Human Monoclonal Antibodies Targeting Different Domains And Functions Of The MERS-Coronavirus Spike Glycoprotein," Emerging Microbes & Infections 8(1):516-530.
Ye, J. et al. (Jul. 2013). "IgBLAST: An Immunoglobulin Variable Domain Sequence Analysis Tool," Nucleic acids research 41(W1):W34-W40.
Zhang, H. et al. (Dec. 9, 2020). "Intranasal Administration of SARS-CoV-2 Neutralizing Human Antibody Prevents Infection in Mice." bioRxiv located at https://doi.org/10.1101/2020.12.08.416677, last visited on Jan. 30, 2022, 14 pages.
Zheng, J. et al. (Jan. 28, 2021, e-pub. Nov. 9, 2020). "COVID-19 Treatments and Pathogenesis Including Anosmia in K18-hACE2 Mice," Nature 589:603-607.
Zhou, P. et al. (Mar. 12, 2020, e-pub. Feb. 3, 2020). "A Pneumonia Outbreak Associated With a New Coronavirus of Probable Bat Origin," Nature 579:270-273, 20 pages.
Zhu, N. et al. (Feb. 20, 2020, e-pub. Jan. 24, 2020). "A Novel Coronavirus From Patients With Pneumonia In China 2019," N Engl. J. Med. 382(8):727-733.
Zhu, Z. et al. (Jul. 17, 2007). "Potent Cross-Reactive Neutralization Of SARS Coronavirus Isolates By Human Monoclonal Antibodies," PNAS 104(29):12123-12128.
Zola, H. (1987). Monoclonal Antibodies: A Manual of Techniques, CRC Press Inc. pp. 147-158.

* cited by examiner

CHIMERIC PROTEIN COMPRISING AN ANTI-INFLUENZA VIRUS ANTIBODY MOIETY AND A MUCOADHESIVE PEPTIDE FRAGMENT FOR PREVENTING OR TREATING INFLUENZA INFECTIONS

CROSS REFERENCE TO RELATED APPLICATIONS

This application is a continuation of International Application No. PCT/US2023/065734, filed on Apr. 13, 2023, which claims priority benefit of U.S. Provisional Application No. 63/331,100, filed Apr. 14, 2022, the contents of each of which are incorporated herein by reference in their entireties.

REFERENCE TO AN ELECTRONIC SEQUENCE LISTING

The content of the electronic sequence listing (256442000201SEQLIST.xml; Size: 503,697 bytes; and Date of Creation: Oct. 11, 2024) is herein incorporated by reference in its entirety.

FIELD OF THE INVENTION

The invention relates to compositions and methods for preventing or treating infections caused by an influenza virus or variants thereof.

BACKGROUND

Influenza, also commonly known as the flu, is a highly contagious respiratory illness caused by a number of RNA influenza viruses that infect humans. Influenza and its complications can cause significant morbidity and mortality. Worldwide, the WHO estimates about 1 billion infections, 3-5 million cases of severe illness and 300,000-500,000 deaths annually. In the United States, the Centers for Disease Control and Prevention (CDC) estimates that flu has resulted in 9 million-41 million illnesses, 140,000-710,000 hospitalizations and 12,000-52,000 deaths annually between 2010 and 2020. (Krammer et al., Nat Rev Dis Primers, 4(1):1-21 (2018); Tyrrell et al., Medicine (Abingdon), 49(12):797-804 (2021).

There are three types of influenza viruses that infect humans: types A, B, and C. Type A influenza virus is the most virulent and is most likely to give rise to epidemics and pandemics. Type A influenza virus, also called influenza A, can infect both humans and animals (e.g., bovine, equine, and avian). Influenza A is subclassified into two groups based on two virus surface proteins, hemagglutinin (HA) and neuraminidase (NA). There are 18 different HAs and 11 different NAs discovered among various influenza A viruses, resulting in many varying subtypes or strains (e.g., H1N1, H5N1). Type B influenza virus does not usually cause as severe disease as type A does, and is more commonly seen in children, long-term care facilities, college campuses, and military camps. Influenza C virus generally causes a mild respiratory illness.

People with viral influenza can spread it to others up to about 6 feet away, mainly through aerosolized droplets expelled when people with flu talk, cough or sneeze. These droplets enter through the mouths or noses of people nearby or can be inhaled into their lungs. A person can also contract the virus by touching a surface or object that has flu virus on it and then touching their own mouth, nose, or eyes. The period that an infected person may be contagious ranges from 1 day before they become symptomatic and 5 to 7 days afterwards. Infected asymptomatic people can still spread the virus.

Most influenza infections can be prevented with the annual influenza vaccine. Historically, influenza vaccines have been manufactured by inoculating eggs, generating virus-inactivated allantoic fluid from the eggs, and purifying relevant viral antigens. Currently, influenza vaccines are often produced in cell culture as either inactivated influenza vaccines (IIVs) or live attenuated influenza vaccines (LAIV). IIVs are produced to protect against three (trivalent) or four (quadrivalent) different strains of influenza viruses; LAIVs are produced exclusively as quadrivalent vaccines.

In addition, four antiviral medications have been approved by the Food and Drug Administration (FDA) for the treatment of influenza, they include three neuraminidase inhibitors, oseltamivir (Tamiflu), peramivir (Rapivab) and zanamivir (Relenza), along with an endonuclease inhibitor, baloxavir marboxil (Xofluza). Baloxavir inhibits the endonuclease activity of the polymerase acidic protein found in the influenza virus RNA polymerase complex, ultimately inhibiting viral replication.

Although influenza causes a mild, self-resolving upper respiratory illness in most people (e.g., cough, headache, chills, muscle aches and fever), complications can also occur, which include pneumonia, bronchitis and sinus infections. In rare cases, influenza infection can cause severe viral pneumonia and acute respiratory distress syndrome (ARDS) with multi-organ failure, caused by the exacerbation of underlying chronic conditions such as asthma, congestive heart failure and chronic obstructive pulmonary disease. People classified as high risk of developing complications from influenza include individuals who are 65 years or older or less than 5 years of age, immunocompromised, pregnant, within 2 weeks of giving birth, or living in group settings (e.g., dormitories, military barracks, nursing homes), and individuals who have preexisting chronic illnesses (e.g., asthma, congestive heart failure, and diabetes) or obesity.

Influenza viruses are constantly changing through a process called reassortment. The influenza A genome is composed of eight separate single-stranded RNA segments. When differing viruses co-infect a cell, they are able to exchange gene segments. The viral diversity generated through reassortment is immense and plays an important role in the global evolution of influenza viruses, making it challenging to predict which strains to include in the yearly upcoming influenza vaccine. To meet the global need for surveillance, the World Health Organization has established National Influenza Centers responsible for collecting and performing a preliminary analysis of influenza specimens in their regions, which are sent to WHO Collaborating Centers for advanced evaluation. These analyses are used to inform the composition of influenza vaccines each year. This is a daunting task every year, and the vaccine compositions each season are not always protective for the season. In the 2018-2019 season, the overall effectiveness of the 2018 vaccines was low (only 29%), and many of the 2020 predicted flu strains had to be changed in the influenza vaccine for the 2020-2021 flu season. (Xu et al., MMWR, 68(24):544-551 (2019)). These factors make prevention of influenza infection (currently mostly done with vaccination) costly (time-wise and resource-wise) and unpredictable (with regard to efficacy). In addition, some patients cannot or choose not to take the influenza vaccines due to various reasons, including patients having strong adverse reactions to vaccines. (Tyrrell et al., December; 49(12):797-804

(2021)). Currently circulating influenza strains (March 2023) are the Influenza A H1N1pdm09 strain (the 2009 pandemic strain) and H3N2 worldwide. The composition of the 2022-2023 vaccine was A/H1N1/pdm09 and A/Darwin/6/2021 (H3N2); for influenza B, the B/Yamagata and B/Austria/1359417/2021 strains, and closely mirror current infections.

As for medication, there are patients who cannot tolerate the adverse effects of the available flu medicines and patients for whom the medicines are not effective. Also, these medications are not readily accessible to many patients around the world.

Additional compositions and methods to prevent or treat influenza infection, especially using means that are inexpensive, safer, more efficacious, and more flexible, are still in great demand.

BRIEF SUMMARY

The present application provides compositions and methods for preventing or treating an infection caused by an influenza virus or a variant thereof. Thus, one aspect of the present application provides a chimeric protein comprising: (a) an antibody moiety that specifically binds to a component of an influenza virus or a variant thereof; and (b) a mucoadhesive peptide fragment comprising at least about 5 positively charged amino acid residues, wherein the mucoadhesive peptide fragment facilitates attachment of the chimeric protein to a mucosa.

In some embodiments, the chimeric protein comprises a single polypeptide chain.

In some embodiments, the chimeric protein comprises two or more polypeptide chains. In some embodiments, the chimeric protein comprises two or more mucoadhesive peptide fragments. In some embodiments, each of the two or more mucoadhesive peptide fragments comprises at least about 5 positively charged amino acid residues.

In some embodiments according to any of the preceding embodiments of the chimeric protein, the mucoadhesive peptide fragment comprises at least about 6 positively charged amino acid residues.

In some embodiments according to any of the preceding embodiments of the chimeric protein, the positively charged amino acid residues are selected from the group consisting of lysine, arginine, histidine, ornithine, and combinations thereof. In some embodiments, the positively charged amino acid residues comprise lysines. In some embodiments, the mucoadhesive peptide fragment comprises about 5, about 6, about 12, or about 30 lysines. In some embodiments, the positively charged amino acid residues comprise arginines. In some embodiments, the mucoadhesive peptide fragment comprises about 6, about 12, or about 30 arginines. In some embodiments, the positively charged amino acid residues comprise histidines. In some embodiments, the mucoadhesive peptide fragment comprises about 6, about 12, or about 30 histidines. In some embodiments, the positively charged amino acid residues comprise ornithines. In some embodiments, the mucoadhesive peptide fragment comprises about 6, about 12, or about 30 ornithines.

In some embodiments according to any of the preceding embodiments of the chimeric protein, the mucoadhesive peptide fragment comprises at least 5 contiguous positively charged amino acids.

In some embodiments according to any of the preceding embodiments of the chimeric protein, the positively charged amino acid residues are interspersed with one or more non-positively charged amino acid residues. In some embodiments, the non-positively charged amino acid residues are non-polar amino acids or polar uncharged amino acids. In some embodiments, the non-positively charged amino acid residues are selected from the group consisting of isoleucine, valine, alanine, tryptophan, leucine, glycine, methionine, proline, phenylalanine, threonine, cysteine, tyrosine, glutamine, serine, and asparagine, and combinations thereof. In some embodiments, at least 50% of the amino acid residues in the mucoadhesive peptide fragment are positively charged amino acid residues.

In some embodiments according to any of the preceding embodiments of the chimeric protein, the mucoadhesive peptide fragment is no more than about 15 kD. In some embodiments, the mucoadhesive peptide fragment has an isoelectric point (pI) higher than the pH of the mucosa. In some embodiments according to any of the preceding embodiments of the chimeric protein, the half-life of the chimeric protein on the mucosa is at least 12 hours. In some embodiments, the mucoadhesive peptide fragment does not facilitate penetration of the chimeric protein into a cell of the mucosa. In some embodiments, the mucoadhesive peptide fragment does not disrupt folding of the chimeric protein within a host cell expressing the chimeric protein. In some embodiments, the mucoadhesive peptide fragment does not block secretion of the chimeric protein from a host cell expressing the chimeric protein. In some embodiments, the mucoadhesive peptide fragment does not interfere with the binding between the antibody moiety and the component of the influenza virus or variant thereof.

In some embodiments according to any of the preceding embodiments of the chimeric protein, the mucoadhesive peptide fragment comprises an amino acid sequence of any one of SEQ ID NOs: 291-325 and 407-413, or variants thereof comprising up to about 3 amino acid substitutions.

In some embodiments according to any of the preceding embodiments of the chimeric protein, the mucoadhesive peptide fragment is fused to the antibody moiety.

In some embodiments according to any of the preceding embodiments of the chimeric protein, the mucoadhesive peptide fragment is fused to the antibody moiety via a bond.

In some embodiments according to any of the preceding embodiments of the chimeric protein, the mucoadhesive peptide fragment is fused to the antibody moiety via a peptide linker. In some embodiments, the peptide linker comprises one or more oligomerization and/or multimerization domains. In some embodiments, the peptide linker comprises the constant region of a heavy chain of a full-length antibody or a fragment thereof. In some embodiments, the peptide linker comprises the constant region of a light chain of a full-length antibody or a fragment thereof. In some embodiments, the linker comprises a $CH_1$, $CH_2$, $CH_3$, $CH_4$, and/or $C_L$ domain or fragments thereof. In some embodiments, the linker comprises an Fc region or a fragment thereof. In some embodiments, the linker comprises a detectable enzymatic tag. In some embodiments, the enzymatic tag is an alkaline phosphatase. In some embodiments, the enzymatic tag is a glutathione-s-transferase. In some embodiments, the peptide linker comprises a basic helix-loop-helix leucine zipper (bZIP) domain. In some embodiments, the peptide linker comprises a bZIP isoleucine zipper domain. In some embodiments, the peptide linker comprises a bZIP-leucine/isoleucine zipper domain. In some embodiments, the peptide linker comprises a collagen-like peptide. In some embodiments, the peptide linker comprises a p53 tetramerization domain. In some embodiments, the peptide linker comprises a streptavidin (SA) protein. In some embodiments, the peptide linker comprises a SA protein and a dextran scaffold. In some embodiments, the peptide linker comprises a SA protein and one or more maleimide polymers (DMGS). In some embodiments, the peptide linker comprises a bacteriophage T7 fibritin protein or a portion thereof. In some embodiments, the peptide linker comprises a cartilage oligomeric matrix protein (COMP) protein.

In some embodiments according to any of the preceding embodiments of the chimeric protein, the antibody moiety is a full-length antibody. In some embodiments, the antibody moiety is selected from the group consisting of an IgG, an IgA, an IgM, and an IgD.

In some embodiments according to any of the preceding embodiments of the chimeric protein, the antibody moiety is an antigen-binding fragment selected from the group consisting of a Fab, a Fab', a $(Fab')_2$, an Fv, a single chain Fv (scFv), an scFv-Fc, a disulfide stabilized Fv fragment (dsFv), a $(dsFv)_2$, an scFv dimer, a domain antibody, a camelized single domain antibody (sdAb), a bivalent domain antibody, a minibody, and a $V_HH$.

In some embodiments according to any of the preceding embodiments of the chimeric protein, the antibody moiety is animal, human, humanized, camelid, or chimeric.

In some embodiments according to any of the preceding embodiments of the chimeric protein, the mucoadhesive peptide fragment is fused to a C-terminus of the antibody moiety.

In some embodiments of the chimeric protein, the antibody moiety is a full-length antibody, and wherein the mucoadhesive peptide fragment is fused to the C-terminus of a heavy chain of the full-length antibody via a first optional peptide linker. In some embodiments, the antibody moiety is a full-length antibody, and wherein the mucoadhesive peptide fragment is fused to the C-terminus of a light chain of the full-length antibody via a second optional peptide linker. In some embodiments, the antibody moiety is a full-length antibody, and wherein: (1) the mucoadhesive peptide fragment is fused to the C-terminus of a heavy chain of the full-length antibody via a first optional peptide linker; and (2) the mucoadhesive peptide fragment is fused to the C-terminus of a light chain of the full-length antibody via a second optional peptide linker. In some embodiments, the chimeric protein comprises: i) a first and a second polypeptide chain each comprising from the N-terminus to the C-terminus: the heavy chain of the full-length antibody, the first optional peptide linker, and the mucoadhesive peptide fragment; and ii) a third and a fourth polypeptide chain each comprising the light chain of the full-length antibody.

In some embodiments according to any of the preceding embodiments of the chimeric protein, the influenza virus is a Type A influenza virus (IAV), a Type B influenza virus (IBV), a Type C influenza virus (ICV), a Type D influenza virus (IDV), or a variant, subtype, or reassortant thereof. In some embodiments, the influenza virus comprises a hemagglutinin (HA) antigen selected from the group consisting of H1, H2, H3, H5, H6, H7, H9, and H10, or a variant or reassortant thereof. In some embodiments, the influenza virus comprises a neuraminidase (NA) antigen selected from the group consisting of N1, N2, N3, N7, N8, and N9, or a variant or reassortant thereof. In some embodiments, the influenza virus is selected from the group consisting of H1N1, H1N2, H2N2, H3N2, H3N8, H5N1, H5N9, H6N1, H7N2, H7N3, H7N7, H7N9, H9N2, H10N7, or a variant or reassortant thereof.

In some embodiments according to any of the preceding embodiments of the chimeric protein, the component of the influenza virus or variant thereof is a viral surface protein or fragment thereof.

In some according to any of the preceding embodiments of the chimeric protein, the viral surface protein is HA. In some embodiments, the chimeric protein comprises a heavy chain complementarity determining region (HC-CDR) 1 comprising the amino acid sequence of SEQ ID NO: 1, an HC-CDR2 comprising the amino acid sequence of SEQ ID NO: 2, and an HC-CDR3 comprising the amino acid sequence of SEQ ID NO: 3, a light chain complementarity determining region (LC-CDR) 1 comprising the amino acid sequence of SEQ ID NO: 4, an LC-CDR2 comprising the amino acid sequence WAS, and an LC-CDR3 comprising the amino acid sequence of SEQ ID NO: 6. In some embodiments, the chimeric protein comprises an HC-CDR1 comprising the amino acid sequence of SEQ ID NO: 7, an HC-CDR2 comprising the amino acid sequence of SEQ ID NO: 8, and an HC-CDR3 comprising the amino acid sequence of SEQ ID NO: 9, an LC-CDR1 comprising the amino acid sequence of SEQ ID NO: 235, an LC-CDR2 comprising the amino acid sequence of SEQ ID NO: 238, and an LC-CDR3 comprising the amino acid sequence of SEQ ID NO: 415. In some embodiments, the chimeric protein comprises an HC-CDR1 comprising the amino acid sequence of SEQ ID NO: 439, an HC-CDR2 comprising the amino acid sequence of SEQ ID NO: 440, and an HC-CDR3 comprising the amino acid sequence of SEQ ID NO: 441, an LC-CDR1 comprising the amino acid sequence of SEQ ID NO: 443, an LC-CDR2 comprising the amino acid sequence of SND, and an LC-CDR3 comprising the amino acid sequence of SEQ ID NO: 445. In some embodiments, the chimeric protein comprises (i) a heavy chain variable domain ($V_H$) Comprising the amino acid sequence of SEQ ID NO: 76, or a variant thereof having at least about 90% sequence identity to the amino acid sequence of SEQ ID NO: 76, and a light chain variable domain ($V_L$) comprising the amino acid sequence of SEQ ID NO: 77, or a variant thereof having at least about 90% sequence identity to the amino acid sequence of SEQ ID NO: 77. In some embodiments, the chimeric protein comprises a $V_H$ comprising the amino acid sequence of SEQ ID NO: 78, or a variant thereof having at least about 90% sequence identity to the amino acid sequence of SEQ ID NO: 78, and a $V_L$ comprising the amino acid sequence of SEQ ID NO: 79, or a variant thereof having at least about 90% sequence identity to the amino acid sequence of SEQ ID NO: 79. In some embodiments, the chimeric protein comprises a $V_H$ comprising the amino acid sequence of SEQ ID NO: 438, or a variant thereof having at least about 90% sequence identity to the amino acid sequence of SEQ ID NO: 438, and a $V_L$ comprising the amino acid sequence of SEQ ID NO: 442, or a variant thereof having at least about 90% sequence identity to the amino acid sequence of SEQ ID NO: 442. In some embodiments, the chimeric protein comprises a heavy chain (HC) polypeptide comprising the amino acid sequence of SEQ ID NO: 414, or a variant thereof having at least about 90% sequence identity to the amino acid sequence of SEQ ID NO: 414, and a light chain (LC) polypeptide comprising the amino acid sequence of SEQ ID NO: 217, or a variant thereof having at least about 90% sequence identity to the amino acid sequence of SEQ ID NO: 217. In some embodiments, the chimeric protein comprises an HC polypeptide comprising the amino acid sequence of SEQ ID NO: 420, or a variant thereof having at least about 90% sequence identity to the amino acid sequence of SEQ ID NO: 420, and an LC polypeptide comprising the amino acid sequence of SEQ ID NO: 244, or a variant thereof having at least about 90% sequence identity to the amino acid sequence of SEQ ID NO: 244. In some embodiments, the chimeric protein comprises an HC polypeptide comprising the amino acid sequence of SEQ ID NO: 446, or a variant thereof having at least about 90% sequence identity to the amino acid sequence of SEQ ID NO: 446, and an LC polypeptide comprising the amino acid sequence of SEQ ID NO: 447, or a variant thereof having at least about 90% sequence identity to the amino acid sequence of SEQ ID NO: 447. In some embodiments, the chimeric protein comprises a first and a second polypeptide chain each independently having at least about 90% sequence identity to the amino acid sequence of any one of SEQ ID NOs: 216, 218-234, 236, 237, 239-242, and 416-419, and a third and a fourth polypeptide chain each having at least about 90% sequence identity to the amino acid sequence of SEQ ID NO: 217. In some embodiments, the chimeric protein comprises a first and a second polypeptide chain each independently having at least about 90% sequence identity to the amino acid sequence of any one of SEQ ID NOs: 243, 245-258, and 422-425, and a third and a fourth polypeptide chain each having at least about 90% sequence identity to the amino acid sequence of SEQ ID NO: 244. In some embodiments, the chimeric protein comprises a first and a second polypeptide chain each independently comprising the amino acid sequence of any one of SEQ ID NOs: 448-468, or a variant thereof comprising at least about 90% sequence identity to the amino acid sequence of any one of SEQ ID NOs: 448-468, and a third and a fourth polypeptide chain each independently comprising the amino acid sequence of SEQ ID NO: 447, or a variant thereof comprising at least about 90% sequence identity to the amino acid sequence of SEQ ID NO: 447.

In some embodiments according to any of the preceding embodiments of the chimeric protein, the viral surface protein is NA. In some embodiments, the chimeric protein comprises a HC-CDR1 comprising the amino acid sequence of SEQ ID NO: 104, an HC-CDR2 comprising the amino acid sequence of SEQ ID NO: 105, and an HC-CDR3 comprising the amino acid sequence of SEQ ID NO: 106, an LC-CDR1 comprising the amino acid sequence of SEQ ID NO: 107, an LC-CDR2 comprising the amino acid sequence of AAS, and an LC-CDR3 comprising the amino acid sequence of SEQ ID NO: 109. In some embodiments, the chimeric protein comprises an HC-CDR1 comprising the amino acid sequence of SEQ ID NO: 110, an HC-CDR2 comprising the amino acid sequence of SEQ ID NO: 111, and an HC-CDR3 comprising the amino acid sequence of SEQ ID NO: 112, an LC-CDR1 comprising the amino acid sequence of SEQ ID NO: 113, an LC-CDR2 comprising the amino acid sequence of GAS, and an LC-CDR3 comprising the amino acid sequence of SEQ ID NO: 115. In some embodiments, the chimeric protein comprises a $V_H$ comprising the amino acid sequence of SEQ ID NO: 188, or a variant thereof having at least about 90% sequence identity to the amino acid sequence of SEQ ID NO: 188, and a $V_L$ comprising the amino acid sequence of SEQ ID NO: 189, or a variant thereof having at least about 90% sequence identity to the amino acid sequence of SEQ ID NO: 189. In some embodiments, the chimeric protein comprises a $V_H$ comprising the amino acid sequence of SEQ ID NO: 190, or a variant thereof having at least about 90% sequence identity to the amino acid sequence of SEQ ID NO: 190, and a $V_L$ comprising the amino acid sequence of SEQ ID NO: 191, or a variant thereof having at least about 90% sequence identity to the amino acid sequence of SEQ ID NO: 191. In some embodiments, the chimeric protein comprises an HC polypeptide comprising the amino acid sequence of SEQ ID NO: 426, or a variant thereof having at least about 90% sequence identity to the amino acid sequence of SEQ ID NO: 426, and an LC polypeptide comprising the amino acid sequence of SEQ ID NO: 260, or a variant thereof having at least about 90% sequence identity to the amino acid sequence of SEQ ID NO: 260. In some embodiments, the chimeric protein comprises an HC polypeptide comprising the amino acid sequence of SEQ ID NO: 432, or a variant thereof having at least about 90% sequence identity to the amino acid sequence of SEQ ID NO: 432, and an LC polypeptide comprising the amino acid sequence of SEQ ID NO: 276, or a variant thereof having at least about 90% sequence identity to the amino acid sequence of SEQ ID NO: 276. In some embodiments, the chimeric protein comprises a first and a second polypeptide chains each independently having at least about 90% sequence identity to the amino acid sequence of any one of SEQ ID NOs: 259, 261-274, and 428-431, and a third and a fourth polypeptide chains each having at least about 90% sequence identity to the amino acid sequence of SEQ ID NO: 260. In some embodiments, the chimeric protein comprises a first and a second polypeptide chains each independently having at least about 90% sequence identity to the amino acid sequence of any one of SEQ ID NOs: 275, 277-290, and 434-437, and a third and a fourth polypeptide chains each having at least about 90% sequence identity to the amino acid sequence of SEQ ID NO: 276.

In some embodiments according to any of the preceding embodiments of the chimeric protein, the mucosa is selected from the group consisting of nasal mucosa, larynx mucosa, trachea mucosa, bronchi mucosa, lung mucosa, eye mucosa, and combinations thereof.

In some aspects, provided herein is a pharmaceutical composition comprising the chimeric protein of any one of the preceding embodiments, and a pharmaceutically acceptable carrier. In some embodiments, the pharmaceutical composition comprises a plurality of the chimeric proteins, and wherein at least two of the plurality of the chimeric proteins are different from each other. In some embodiments, the pharmaceutically acceptable carrier comprises about 0.05% to about 0.2% (w/w) methionine. In some embodiments, the pharmaceutically acceptable carrier has a pH of about 4.5 to about 7.5. In some embodiments, the pharmaceutically acceptable carrier comprises about 20 mM to about 50 mM citrate. In some embodiments, the pharmaceutically acceptable carrier comprises about 100 mM to about 150 mM NaCl. In some embodiments, the pharmaceutically acceptable carrier comprises about 0.01% to about 0.1% (w/w) polysorbate 80. In some embodiments, the pharmaceutically acceptable carrier comprises about 1% to about 10% (w/w) glycerin. In some embodiments, the pharmaceutically acceptable carrier comprises about 0.05% to about 0.2% (w/w) potassium sorbate. In some embodiments, the pharmaceutically acceptable carrier: (i) comprises about 0.05% to about 0.2% (w/w) methionine; (ii) has a pH of about 4.5 to about 7.5; (iii) comprises about 20 mM to about 50 mM citrate; (iv) comprises about 100 mM to about 150 mM NaCl; (v) comprises about 0.01% to about 0.1% (w/w) polysorbate 80; (vi) comprises about 1% to about 10% (w/w) glycerin; and (vii) comprises about 0.05% to about 0.2% (w/w) potassium sorbate. In some embodiments, the pharmaceutical composition is formulated for intranasal administration, intraocular administration, and/or intrabronchial administration.

In other aspects, provided herein is an isolated nucleic acid or a set of isolated nucleic acids encoding the chimeric protein of any one of the preceding embodiments.

In some aspects, provided herein is a vector or a set of vectors comprising the nucleic acid or the set of nucleic acids of the previous embodiment.

In additional aspects, provided herein is a host cell comprising the chimeric protein of any one of the preceding embodiments, the nucleic acid or set of nucleic acids of the preceding embodiment, the vector or set of vectors of the preceding embodiment.

In further aspects, provided herein is a method of preparing a chimeric protein, comprising: (a) culturing a host cell of the preceding embodiment under a condition effective to express the chimeric protein; and (b) obtaining the expressed chimeric protein from the host cell.

In further aspects, provided herein is a method of preventing or treating an infection caused by an influenza virus or a variant thereof in an individual, comprising administering to the individual an effective amount of any one of the chimeric proteins disclosed herein. In some embodiments, the chimeric protein or the pharmaceutical composition is administered to the individual before the individual is exposed to the influenza virus or variant thereof. In some embodiments, the chimeric protein or the pharmaceutical composition is administered to the individual within about 72 hours after the individual is exposed to the influenza virus or variant thereof. In some embodiments, the chimeric protein or the pharmaceutical composition is administered topically onto the mucosa. In some embodiments, the chimeric protein or the pharmaceutical composition is administered via a nasal spray, an inhaler, a nebulizer, or an eye drop. In some embodiments, the chimeric protein or the pharmaceutical composition is administered once daily.

In other aspects, provided herein is an in vitro method of killing or neutralizing a virus, comprising contacting a virus with the chimeric protein of any of the preceding embodiments, in the presence of at least one component of the complement system, optionally wherein the at least one component of the complement system is C1, C4, or membrane attack complex (MAC). In some aspects, provided herein is a method of killing or neutralizing a virus in an individual, comprising administering to the individual an effective amount of the chimeric protein of any one of the preceding embodiments, or the pharmaceutical composition of any one of any one of the preceding embodiments. In some aspects, provided herein is a method of activating the complement pathway in an individual, comprising administering to the individual an effective amount of the chimeric protein of any one of the preceding embodiments, or the pharmaceutical composition of any one of any one of the preceding embodiments. In some embodiments, at least one virus is killed or neutralized on the mucosa. In some aspects, provided herein is a method of preventing, treating, or reducing infection caused by a virus in an individual, comprising administering to the individual an effective amount of the chimeric protein of any one of the preceding embodiments, or the pharmaceutical composition of any one of the preceding embodiments, wherein at least one virus is killed or neutralized on the mucosa. In some embodiments, the chimeric protein activates the complement pathway in the individual. In some embodiments, the killing or neutralization is via activation of the complement pathway. In some embodiments, the virus is an influenza virus. In some embodiments, the influenza virus is selected from the group consisting of a Type A influenza virus (IAV), a Type B influenza virus (IBV), a Type C influenza virus (ICV), a Type D influenza virus (IDV), or a variant, subtype, or reassortant thereof. In some embodiments, the influenza virus comprises an HA antigen selected from the group consisting of H1, H2, H3, H5, H6, H7, H9, and H10, or a variant or reassortant thereof. In some embodiments, the influenza virus comprises an NA antigen selected from the group consisting of N1, N2, N3, N7, N8, and N9, or a variant or reassortant thereof. In some embodiments, the influenza virus is selected from the group consisting of H1N1, H1N2, H2N2, H3N2, H3N8, H5N1, H5N9, H6N1, H7N2, H7N3, H7N7, H7N9, H9N2, H10N7, or a variant or reassortant thereof.

BRIEF DESCRIPTION OF THE DRAWINGS

The drawings illustrate certain embodiments of the features and advantages of this disclosure. These embodiments are not intended to limit the scope of the appended claims in any manner.

DETAILED DESCRIPTION

Figure 1:
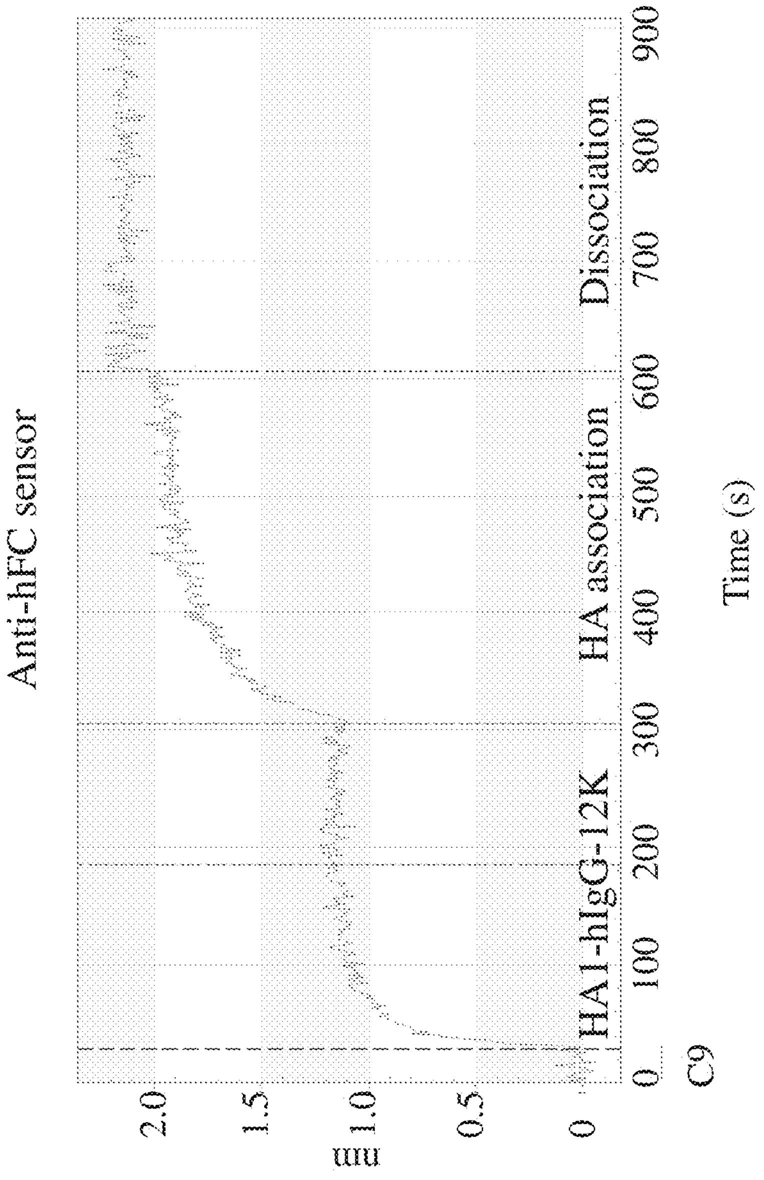
FIG. 1 shows that the exemplary mucoadhesive chimeric human antibody HA1-IgG-12K binds well to the hemagglutinin (His-tagged) from influenza A H1N1 (A/Wisconsin/588/2019)/(A/Victoria/2570/2019). Binding was unaffected by the presence of polycationic moieties. All steps were aligned by step sensor location).

The present application provides compositions and methods for preventing or treating an infection caused by an influenza virus or variant thereof that infects through a mucosa in an individual by targeting the influenza virus or variant thereof using a chimeric protein that has a positively charged mucoadhesive peptide fragment. For example, the compositions described herein may comprise a chimeric protein or cocktails of different chimeric proteins, comprising an antibody moiety that targets a viral surface protein (e.g., a hemagglutinin (HA) or a neuraminidase (NA) protein) and is modified with a positively charged peptide, that prevents the influenza virus or variant thereof from reaching its primary target cell population in the respiratory tract (e.g., nasal) mucosa for human infection. The compositions can be administered via the nasal passages using a respiratory spray.

Inventors of the present application developed chimeric proteins comprising antibodies (e.g., human and animal) that recognize the HA viral surface protein or the NA viral surface protein ("anti-HA antibodies" and "anti-NA antibodies") of an influenza virus or variant thereof and anti-HA and anti-NA antibodies fused to a positively charged mucoadhesive peptide fragments. The chimeric proteins have significantly enhanced affinity to mucin molecules compared to unmodified anti-HA or anti-NA antibodies, which leads to improved stability in respiratory mucosa. The chimeric proteins show improved potency as compared to unmodified anti-HA or anti-NA antibodies in blocking influenza infection in a cell-based assay. The protection against influenza virus is effective in both nasal and lung areas. Additionally, the chimeric proteins may activate innate immune functions, and may be able to kill influenza virus via activation of the complement pathway. The exemplary chimeric protein is highly stable and maintained its influenza virus neutralizing activity in a nasal spray formulation. Nasal spray of the chimeric proteins can be developed as an affordable and effective prophylactic product to protect people from infection by exposure to influenza virus in the air (e.g., via the nasal passages).

Compared to other methods that block microbial infection, which involve systemic administration of antibodies that do not have a positively charged mucoadhesive peptide fragment, the methods described herein require administration of much less protein, leading to a large cost reduction that is critical for any pandemic situation. The compositions may also be self-administered, which would greatly relieve the burden on an overwhelmed health care system. Importantly, the methods described herein can avoid the potential problem of antibody dependent enhancement (ADE) resulting from conventional antibody therapy or vaccination.

Accordingly, one aspect of the present application provides a chimeric protein comprising: (a) an antibody moiety that specifically binds to a component of an influenza virus or a variant thereof; and (b) a mucoadhesive peptide fragment comprising at least about 5 positively charged amino acid residues, wherein the mucoadhesive peptide fragment facilitates attachment of the chimeric protein to a mucosa. In some embodiments, the positively charged amino acid residues are interspersed with non-positively charged amino acid residues.

The chimeric proteins provided herein are useful for treating or preventing an infection by a virus (e.g., an influenza virus or a variant thereof) in an individual. The chimeric proteins provided herein may be useful for killing or neutralizing a virus (e.g., an influenza virus or a variant thereof) in an individual via activation of the complement pathway.

I. Definitions

As used herein, a "mucoadhesive peptide fragment" refers to a peptide that carries one or more positive charges and is capable of interacting with a mucosa, e.g., via electrostatic interactions.

As used herein, a "receptor" refers to a receptor on a host cell that facilitates or mediates microbial entry into the host cell. A receptor may be membrane-bound or a soluble receptor.

As used herein, "treatment" or "treating" is an approach for obtaining beneficial or desired results including clinical results. For purposes of this application, beneficial or desired clinical results include, but are not limited to, one or more of the following: decreasing one more symptoms resulting from the disease, diminishing the extent of the disease, stabilizing the disease (e.g., preventing or delaying the worsening of the disease), preventing or delaying the spread of the disease, preventing or delaying the occurrence or recurrence of the disease, delay or slowing the progression of the disease, ameliorating the disease state, providing a remission (whether partial or total) of the disease, decreasing the dose of one or more other medications required to treat the disease, delaying the progression of the disease, increasing the quality of life, and/or prolonging survival. Also encompassed by "treatment" is a reduction of pathological consequence of the disease. The methods of the present application contemplate any one or more of these aspects of treatment.

"Preventing," as used herein, includes providing prophylaxis with respect to the occurrence or recurrence of a disease in a subject that may be predisposed to the disease but has not yet been diagnosed with the disease.

An "effective amount" of an agent refers to an amount effective, at dosages and for periods of time necessary, to achieve the desired therapeutic or prophylactic result. An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. For purposes of this application, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved. The effective amount can be ascertained by measuring relevant physiological effects, and it can be adjusted in connection with the dosing regimen and diagnostic analysis of the subject's condition, and the like.

The terms "individual," "subject," and "patient" are used interchangeably herein to describe a mammal, including humans. In some embodiments, the individual is human. In some embodiments, an individual suffers from a respiratory infection. In some embodiments, the individual is in need of treatment.

The terms "polypeptide" and "protein" are used interchangeably to refer to a polymer of amino acid residues and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present application, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts, which produce the proteins or errors due to PCR amplification.

As used herein, the term "antibody" or "antibody moiety" includes full-length antibodies (including full-length 4-chain antibodies or full-length heavy chain antibodies, which have an immunoglobulin Fc region), and antigen-binding fragments thereof.

As used herein, a "neutralizing antibody" refers to an antibody that defends a host cell from an infectious agent by neutralizing any effect (e.g., cytotoxicity) it has biologically. A "non-neutralizing antibody" refers to an antibody that specifically binds to an infectious agent but is incapable of ameliorating the biological effects of the infectious agent on the host cell. A "sub-neutralizing antibody" refers to an antibody that is capable of partially neutralizing the biological effects of the infectious agent on the host cell. A sub-neutralizing antibody may ameliorate one or more biological effects of an infectious agent on the host cell by no more than about n % compared to a neutralizing antibody, where n % is selected from 90%, 80%, 70%, 60%, 50%, 40%, 30%, 20%, 10%, or less.

A full-length four-chain antibody comprises two heavy chains and two light chains. The variable regions of the light and heavy chains are responsible for antigen-binding. The variables region in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by the conventions of Kabat, Chothia, or Al-Lazikani (Al-Lazikani 1997; Chothia 1985; Chothia 1987; Chothia 1989; Kabat 1987; Kabat 1991). The three CDRs of the heavy or light chains are interposed between flanking stretches known as framework regions (FRs), which are more highly conserved than the CDRs and form a scaffold to support the hypervariable loops. The constant regions of the heavy and light chains are not involved in antigen-binding but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

The term "heavy chain-only antibody" or "HCAb" refers to a functional antibody, which comprises heavy chains, but lacks the light chains usually found in 4-chain antibodies. Camelid animals (such as camels, llamas, or alpacas) are known to produce HCAbs. The variable region of a heavy chain-only antibody is referred herein as "$V_HH$." A $V_HH$ is one type of single-domain antibody. A "single-domain antibody" or "sdAb" refers to a single antigen-binding polypeptide having three complementary determining regions (CDRs). The sdAb alone is capable of binding to the antigen without pairing with a corresponding CDR-containing polypeptide. Some $V_HH$s may also be known as Nanobodies. Camelid $V_HH$ is one of the smallest known antigen-binding antibody fragments (see, e.g., Hamers-Casterman et al., Nature 363:446-8 (1993); Greenberg et al., Nature 374:168-73 (1995); Hassanzadeh-Ghassabeh et al., Nanomedicine (Lond), 8:1013-26 (2013)). A basic $V_HH$ has the following structure from the N-terminus to the C-terminus: FR1-CDR1-FR2-CDR2-FR3-CDR3-FR4, in which FR1 to FR4 refer to framework regions 1 to 4, respectively, and in which CDR1 to CDR3 refer to the complementarity determining regions 1 to 3.

The term "antigen-binding fragment" as used herein refers to an antibody fragment including, for example, a diabody, a Fab, a Fab', a F(ab')2, an Fv fragment, a disulfide stabilized Fv fragment (dsFv), a $(dsFv)_2$, a bispecific dsFv (dsFv-dsFv'), a disulfide stabilized diabody (ds diabody), a single-chain antibody molecule (scFv), an scFv dimer (bivalent diabody), an scFv-Fc fusion protein, a minibody (i.e., scFv-CH3 fusion protein), a multispecific antibody formed from a portion of an antibody comprising one or more CDRs, a VHH, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment (e.g., a parent scFv) binds. In some embodiments, an antigen-binding fragment may comprise one or more CDRs from a particular human antibody grafted to a framework region from one or more different human antibodies.

The term "epitope" as used herein refers to the specific group of atoms or amino acids on an antigen to which an antibody or antibody moiety binds. Two antibodies or antibody moieties may bind the same epitope within an antigen if they exhibit competitive binding for the antigen.

As used herein, a first antibody moiety "competes" for binding to a target (e.g., influenza virus surface protein) with a second antibody moiety when the first antibody moiety inhibits target binding of the second antibody moiety by at least about 50% (such as at least about n %, where n % is selected from 55%, 60%, 65%, 70%, 75%, 80%, 85%, 90%, 95%, 98% and 99%) in the presence of an equimolar concentration of the first antibody moiety, or vice versa. A high throughput process for "binning" antibodies based upon their cross-competition is described in PCT Publication No. WO 03/48731.

As use herein, the term "specifically binds," "specifically recognizing," or "is specific for" refers to measurable and reproducible interactions, such as binding between a target and an antibody or antibody moiety that is determinative of the presence of the target in the presence of a heterogeneous population of molecules, including biological molecules. For example, an antibody or antibody moiety that specifically recognizes a target (which can be an epitope) is an antibody or antibody moiety that binds this target with greater affinity, avidity, more readily, and/or with greater duration than its bindings to other targets. In some embodiments, an antibody or antibody moiety that specifically recognizes an antigen reacts with one or more antigenic determinants of the antigen (such as an influenza virus surface protein) with a binding affinity that is at least about 10 times its binding affinity for other targets (such as a non-respiratory-pathogen protein).

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); Chothia et al., J. Mol. Biol. 196: 901-917 (1987); Al-Lazikani B. et al., J. Mol. Biol., 273: 927-948 (1997); MacCallum et al., *J. Mol. Biol.,* 262:732-745 (1996); Abhinandan and Martin, *Mol. Immunol.,* 45: 3832-3839 (2008); Lefranc M. P. et al., *Dev. Comp. Immunol.,* 27: 55-77 (2003); and Honegger and Plückthun, *J. Mol. Biol.,* 309:657-670 (2001), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table A as a comparison. CDR prediction algorithms and interfaces are known in the art, including, for example, Abhinandan and Martin, *Mol. Immunol.,* 45: 3832-3839 (2008); Ehrenmann F. et al., *Nucleic Acids Res.,* 38: D301-D307 (2010); and Adolf-Bryfogle J. et al., *Nucleic Acids Res.,* 43: D432-D438 (2015). The contents of the references cited in this paragraph are incorporated herein by reference in their entireties for use in the present invention and for possible inclusion in one or more claims herein.

TABLE A

| | CDR Definitions | | | | |
|---|---|---|---|---|---|
| | Kabat[1] | Chothia[2] | MacCallum[3] | IMGT[4] | AHo[5] |
| VH CDR1 | 31-35 | 26-32 | 30-35 | 27-38 | 25-40 |
| VH CDR2 | 50-65 | 53-55 | 47-58 | 56-65 | 58-77 |
| VH CDR3 | 95-102 | 96-101 | 93-101 | 105-117 | 109-137 |
| VL CDR1 | 24-34 | 26-32 | 30-36 | 27-38 | 25-40 |
| VL CDR2 | 50-56 | 50-52 | 46-55 | 56-65 | 58-77 |
| VL CDR3 | 89-97 | 91-96 | 89-96 | 105-117 | 109-137 |

[1]Residue numbering follows the nomenclature of Kabat et al., supra
[2]Residue numbering follows the nomenclature of Chothia et al., supra
[3]Residue numbering follows the nomenclature of MacCallum et al., supra
[4]Residue numbering follows the nomenclature of Lefranc et al., supra
[5]Residue numbering follows the nomenclature of Honegger and Plückthun, supra The term "chimeric antibodies" refer to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this invention (see U.S. Pat. No. 4,816,567; and Morrison et al., *Proc. Natl. Acad. Sci. USA,* 81:6851-6855 (1984)).

The term "semi-synthetic" in reference to an antibody or antibody moiety means that the antibody or antibody moiety has one or more naturally occurring sequences and one or more non-naturally occurring (i.e., synthetic) sequences.

"Fv" is the minimum antibody fragment, which contains a complete antigen-recognition and -binding site. This fragment consists of a dimer of one heavy- and one light-chain variable region domain in tight, non-covalent association. From the folding of these two domains emanate six hypervariable loops (3 loops each from the heavy and light chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv," also abbreviated as "sFv" or "scFv," are antibody fragments that comprise the VH and VL antibody domains connected into a single polypeptide chain. In some embodiments, the scFv polypeptide further comprises a polypeptide linker between the VH and VL domains, which enables the scFv to form the desired structure for antigen binding. For a review of scFv, see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments prepared by constructing scFv fragments (see preceding paragraph) typically with short linkers (such as about 5 to about 10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" scFv fragments in which the $V_H$ and $V_L$ domains of the two antibodies are present on different polypeptide chains. Diabodies are described more fully in, for example, EP 404,097; WO 93/011161; and Hollinger et al., *Proc. Natl. Acad. Sci. USA,* 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region (HVR) of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

The "$CH_1$ domain" of a human IgG Fc region (also referred to as "$C_1$" of "H1" domain) usually extends from about amino acid 118 to about amino acid 215 (EU numbering system).

"Hinge region" is generally defined as stretching from Glu216 to Pro230 of human $IgG_1$ (Burton, *Molec. Immunol.* 22:161-206 (1985)). Hinge regions of other IgG isotypes may be aligned with the $IgG_1$ sequence by placing the first and last cysteine residues forming inter-heavy chain S—S bonds in the same positions.

The "$CH_2$ domain" of a human IgG Fc region (also referred to as "$C_2$" of "H2" domain) usually extends from about amino acid 231 to about amino acid 340. The $CH_2$ domain is unique in that it is not closely paired with another domain. Rather, two N-linked branched carbohydrate chains are interposed between the two $CH_2$ domains of an intact native IgG molecule. It has been speculated that the carbohydrate may provide a substitute for the domain-domain pairing and help stabilize the $CH_2$ domain. Burton, *Molec Immunol.* 22:161-206 (1985).

The "$CH_3$ domain" (also referred to as "$C_2$" or "H3" domain) comprises the stretch of residues C-terminal to a $CH_2$ domain in an Fc region (i.e., from about amino acid residue 341 to the C-terminal end of an antibody sequence, typically at amino acid residue 446 or 447 of an IgG).

The "$CH_4$ domain" found in IgE and IgM molecules, is situated C-terminal to the $CH_3$ domain, comprising residues 466-572 of human IgM and residues 323-427 of hIgE. The term "substantially similar" or "substantially the same," as used herein, denotes a sufficiently high degree of similarity between two or more numeric values such that one of skill in the art would consider the difference between the two or more values to be of little or no biological and/or statistical significance within the context of the biological characteristic measured by said value. In some embodiments the two or more substantially similar values differ by no more than about n %, where n % is selected from 5%, 10%, 15%, 20%, 25%, and 50%.

A polypeptide "variant" means a biologically active polypeptide having at least about 80% amino acid sequence identity and no more than 100% identity with the native sequence polypeptide after aligning the sequences and introducing gaps, if necessary, to achieve the maximum percent sequence identity. Such variants include, for instance, polypeptides wherein one or more amino acid residues are added, or deleted, at the N- or C-terminus of the polypeptide. In some embodiments, a variant has at least about 80% amino acid sequence identity (such as at least about n % amino acid sequence identity, where n % is selected from 80%, 85%, 90%, 95%, and 99%). In some embodiments, a variant has at least about 90% amino acid sequence identity (such as at least about n % amino acid sequence identity, where n % is selected from 90%, 91%, 92%, 93%, 94%, 95%, 96%, 97%, 98%, and 99%). In some embodiments, a variant has at least about 95% amino acid sequence identity (such as at least about n % amino acid sequence identity, where n % is selected from 95%, 96%, 97%, 98%, and 99%) with the native sequence polypeptide.

As used herein, "Percent (%) amino acid sequence identity" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

The term "label" when used herein refers to a detectable compound or composition, which can be conjugated directly or indirectly to an antibody moiety (e.g., anti-HA or anti-NA antibody). The label may be detectable by itself (e.g., radioisotope labels or fluorescent labels) or, in the case of an enzymatic label, may catalyze chemical alteration of a substrate compound or composition, which is detectable.

The term "isolated nucleic acid" as used herein is intended to mean a nucleic acid of genomic, cDNA, or synthetic origin or some combination thereof, which by virtue of its origin the "isolated nucleic acid" (1) is not associated with all or a portion of a polynucleotide in which the "isolated nucleic acid" is found in nature, (2) is operably linked to a polynucleotide which it is not linked to in nature, or (3) does not occur in nature as part of a larger sequence.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "vector" is used to describe a polynucleotide that may be engineered to contain a cloned polynucleotide or polynucleotides that may be propagated in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that may be used in colorimetric assays, e.g., β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast cells; plant cells; and insect cells. Non-limiting exemplary mammalian cells include, but are not limited to, NSO cells, PER.C6® cells (Crucell), and 293 and CHO cells, and their derivatives, such as 293-6E and DG44 cells, respectively.

As used herein, a "variant" virus refers to an isolate of a virus whose genome sequence differs from that of a reference virus and the difference in the genome sequence confers new phenotypic properties such as increased fitness compared to the reference virus. When referring to a viral species in the present application, such as influenza virus, it is understood that the species encompass variants as well as the reference virus that was first isolated and identified.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

As used herein, "a pharmaceutically acceptable carrier" refers to a pharmaceutically acceptable substrate, composition or vehicle used in the process of drug delivery, which may have one or more ingredients including, but not limited to, excipient(s), binder(s), diluent(s), solvent(s), filler(s), and/or stabilizer(s).

It is understood that embodiments of the invention described herein include "consisting of" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter.

As used herein and in the appended claims, the singular forms "a," "an," and "the" include plural referents unless the context clearly dictates otherwise.

II. Chimeric Proteins

The present application provides chimeric proteins (such as fusion proteins) comprising: (a) an antibody moiety that specifically binds to a component of an influenza virus or a variant thereof; and (b) a mucoadhesive peptide fragment comprising at least about 5 positively charged amino acid residues (e.g., about 5 to about 30 positively charged amino acid residues), wherein the mucoadhesive peptide fragment facilitates attachment of the chimeric protein to a mucosa. In some embodiments, the positively charged amino acid residues are selected from the group consisting of lysine, arginine, histidine, ornithine, and combinations thereof. In some embodiments, the positively charged amino acid residues are lysines. In some embodiments, the mucoadhesive peptide fragment is a polylysine peptide having at least about 5 (e.g., about 5 to about 30, such as about 12) lysines (including for example at least about 5 (e.g., about 5 to about 30, such as about 12) contiguous lysines). In some embodiments, the positively charged amino acid residues are histidines. In some embodiments, the mucoadhesive peptide fragment is a polyhistidine peptide having at least about 5 (e.g., about 5 to about 30, such as about 12) histidines (including for example at least about 5 (e.g., about 5 to about 30, such as about 12) contiguous histidines). In some embodiments, the positively charged amino acid residues are arginines. In some embodiments, the mucoadhesive peptide fragment is a polyarginine peptide having at least about 5 (e.g., about 5 to about 30, such as about 12) arginines (including for example at least about 5 (e.g., about 5 to about 30, such as about 12) contiguous arginines). In some embodiments, the positively charged amino acid residues are ornithines. In some embodiments, the mucoadhesive peptide fragment is a polyornithine peptide having at least about 5 (e.g., about 5 to about 30, such as about 12) ornithines (including for example at least about 5 (e.g., about 5 to about 30, such as about 12) contiguous ornithines). In some embodiments, the positively charged amino acid residues are contiguous with each other. In some embodiments, the positively charged amino acid residues are interspersed with non-positively charged amino acid residues. In some embodiments, the mucoadhesive peptide fragment is covalently fused to the antibody moiety. In some embodiments, the mucoadhesive peptide fragment is non-covalently associated with the antibody moiety, e.g., via an oligomerization and/or multimerization domain. In some embodiments, the influenza virus is a Type A influenza virus (IAV), a Type B influenza virus (IBV), a Type C influenza virus (ICV), a Type D influenza virus (IDV), or a variant, subtype, or reassortant thereof. In some embodiments, the component of the influenza virus or variant thereof is a viral surface protein. In some embodiments, the viral surface protein is HA. In some embodiments, the viral surface protein is NA. In some embodiments, the influenza virus or variant thereof causes a respiratory infection. In some embodiments, the mucosa is selected from the group consisting of nasal mucosa, larynx mucosa, trachea mucosa, bronchi mucosa, lung mucosa, eye mucosa, and combinations thereof.

In some embodiments, there is provided a chimeric protein (e.g., fusion protein) comprising: (a) an antibody moiety that specifically binds to a HA protein of an influenza virus or a variant thereof; and (b) a mucoadhesive peptide fragment comprising at least about 5 positively charged amino acid residues (e.g., about 5 to about 30 positively charged amino acid residues), wherein the mucoadhesive peptide fragment facilitates attachment of the chimeric protein to a mucosa. In some embodiments, the positively charged amino acid residues are selected from the group consisting of lysine, arginine, histidine, ornithine, and combinations thereof. In some embodiments, the positively charged amino acid residues are lysines. In some embodiments, the mucoadhesive peptide fragment is a polylysine peptide having at least about 5 (e.g., about 5 to about 30, such as about 12) lysines (including for example at least about 5 (e.g., about 5 to about 30, such as about 12) contiguous lysines). In some embodiments, the positively charged amino acid residues are histidines. In some embodiments, the mucoadhesive peptide fragment is a polyhistidine peptide having at least about 5 (e.g., about 5 to about 30, such as about 12) histidines (including for example at least about 5 (e.g., about 5 to about 30, such as about 12) contiguous histidines). In some embodiments, the positively charged amino acid residues are arginines. In some embodiments, the mucoadhesive peptide fragment is a polyarginine peptide having at least about 5 (e.g., about 5 to about 30, such as about 12) arginines (including for example at least about 5 (e.g., about 5 to about 30, such as about 12) contiguous arginines). In some embodiments, the positively charged amino acid residues are ornithines. In some embodiments, the mucoadhesive peptide fragment is a polyornithine peptide having at least about 5 (e.g., about 5 to about 30, such as about 12) ornithines (including for example at least about 5 (e.g., about 5 to about 30, such as about 12) contiguous ornithines). In some embodiments, the positively charged amino acid residues are contiguous with each other. In some embodiments, the positively charged amino acid residues are interspersed with non-positively charged amino acid residues. In some embodiments, the mucoadhesive peptide fragment is covalently fused to the antibody moiety. In some embodiments, the mucoadhesive peptide fragment is non-covalently associated with the antibody moiety, e.g., via an oligomerization and/or multimerization domain. In some embodiments, the influenza virus is a Type A influenza virus (IAV), a Type B influenza virus (IBV), a Type C influenza virus (ICV), a Type D influenza virus (IDV), or a variant, subtype, or reassortant thereof. In some embodiments, the influenza virus comprises a hemagglutinin (HA) antigen, such as an HA antigen selected from the group consisting of H1, H2, H3, H5, H6, H7, H9, and H10, or a variant or reassortant thereof. In some embodiments, the influenza virus is selected from the group consisting of H1N1, H1N2, H2N2, H3N2, H3N8, H5N1, H5N9, H6N1, H7N2, H7N3, H7N7, H7N9, H9N2, H10N7, or a variant or reassortant thereof. In some embodiments, the mucosa is selected from the group consisting of nasal mucosa, larynx mucosa, trachea mucosa, bronchi mucosa, lung mucosa, eye mucosa, and combinations thereof. In some embodiments, the antibody moiety is a full-length antibody (e.g., IgG, IgA, IgM, IgE, or IgD). In some embodiments, the antibody moiety is an antigen-binding fragment selected from the group consisting of a Fab, a Fab', a $(Fab')_2$, an Fv, a single chain Fv (scFv), an scFv-Fc, a disulfide stabilized Fv fragment (dsFv), a $(dsFv)_2$, an scFv dimer, a domain antibody, a camelized single domain antibody, a bivalent domain antibody, a minibody, and a $V_HH$.

In some embodiments, there is provided a chimeric protein (e.g., fusion protein) comprising: (a) an antibody moiety that specifically binds to a HA protein of an influenza virus or a variant thereof; and (b) a mucoadhesive peptide fragment comprising at least about 5 positively charged amino acid residues (e.g., about 5 to about 30 positively charged amino acid residues), wherein the mucoadhesive peptide fragment facilitates attachment of the chimeric protein to a mucosa, and wherein the antibody moiety comprises any one of the antibodies or antigen binding fragments thereof as described in Table 4A or wherein the antibody moiety comprises any one of the antibodies or antigen binding fragments thereof as described in Table 6. In some embodiments, the antibody moiety binds with a HA antigen, such as an HA antigen selected from the group consisting of H1, H2, H3, H5, H6, H7, H9, and H10, or a variant or reassortant thereof. In some embodiments, the mucoadhesive peptide comprises any one of the mucoadhesive peptide fragments as described in Table 8.

In some embodiments, there is provided a chimeric protein (e.g., fusion protein) comprising: (a) an antibody moiety that specifically binds to a NA protein of an influenza virus or a variant thereof; and (b) a mucoadhesive peptide fragment comprising at least about 5 positively charged amino acid residues (e.g., about 5 to about 30 positively charged amino acid residues), wherein the mucoadhesive peptide fragment facilitates attachment of the chimeric protein to a mucosa. In some embodiments, the positively charged amino acid residues are selected from the group consisting of lysine, arginine, histidine, ornithine, and combinations thereof. In some embodiments, the positively charged amino acid residues are lysines. In some embodiments, the mucoadhesive peptide fragment is a polylysine peptide having at least about 5 (e.g., about 5 to about 30, such as about 12) lysines (including for example at least about 5 (e.g., about 5 to about 30, such as about 12) contiguous lysines). In some embodiments, the positively charged amino acid residues are histidines. In some embodiments, the mucoadhesive peptide fragment is a polyhistidine peptide having at least about 5 (e.g., about 5 to about 30, such as about 12) histidines (including for example at least about 5 (e.g., about 5 to about 30, such as about 12) contiguous histidines). In some embodiments, the positively charged amino acid residues are arginines. In some embodiments, the mucoadhesive peptide fragment is a polyarginine peptide having at least about 5 (e.g., about 5 to about 30, such as about 12) arginines (including for example at least about 5 (e.g., about 5 to about 30, such as about 12) contiguous arginines). In some embodiments, the positively charged amino acid residues are ornithines. In some embodiments, the mucoadhesive peptide fragment is a polyornithine peptide having at least about 5 (e.g., about 5 to about 30, such as about 12) ornithines (including for example at least about 5 (e.g., about 5 to about 30, such as about 12) contiguous ornithines). In some embodiments, the positively charged amino acid residues are contiguous with each other. In some embodiments, the positively charged amino acid residues are interspersed with non-positively charged amino acid residues. In some embodiments, the mucoadhesive peptide fragment is covalently fused to the antibody moiety. In some embodiments, the mucoadhesive peptide fragment is non-covalently associated with the antibody moiety, e.g., via an oligomerization and/or multimerization domain. In some embodiments, the influenza virus is a Type A influenza virus (IAV), a Type B influenza virus (IBV), a Type C influenza virus (ICV), a Type D influenza virus (IDV), or a variant, subtype, or reassortant thereof. In some embodiments, the influenza virus comprises a neuraminidase (NA) antigen, such as an NA antigen selected from the group consisting of N1, N2, N3, N7, N8, and N9, or a variant or reassortant thereof. In some embodiments, the influenza virus is selected from the group consisting of H1N1, H1N2, H2N2, H3N2, H3N8, H5N1, H5N9, H6N1, H7N2, H7N3, H7N7, H7N9, H9N2, H10N7, or a variant or reassortant thereof. In some embodiments, the mucosa is selected from the group consisting of nasal mucosa, larynx mucosa, trachea mucosa, bronchi mucosa, lung mucosa, eye mucosa, and combinations thereof. In some embodiments, the antibody moiety is a full-length antibody (e.g., IgG, IgA, IgM, IgE, or IgD). In some embodiments, the antibody moiety is an antigen-binding fragment selected from the group consisting of a Fab, a Fab', a $(Fab')_2$, an Fv, a single chain Fv (scFv), an scFv-Fc, a disulfide stabilized Fv fragment (dsFv), a $(dsFv)_2$, an scFv dimer, a domain antibody, a camelized single domain antibody, a bivalent domain antibody, a minibody, and a $V_HH$.

In some embodiments, there is provided a chimeric protein (e.g., fusion protein) comprising: (a) an antibody moiety that specifically binds to a NA protein of an influenza virus or a variant thereof; and (b) a mucoadhesive peptide fragment comprising at least about 5 positively charged amino acid residues (e.g., about 5 to about 30 positively charged amino acid residues), wherein the mucoadhesive peptide fragment facilitates attachment of the chimeric protein to a mucosa, and wherein the antibody moiety comprises any one of the antibodies or antigen binding fragments thereof as described in Table 4B or wherein the antibody moiety comprises any one of the antibodies or antigen binding fragments thereof as described in Table 6. In some embodiments, the antibody moiety binds with a NA antigen, such as an NA antigen selected from the group consisting of N1, N2, N3, N7, N8, and N9, or a variant or reassortant thereof. In some embodiments, the mucoadhesive peptide comprises any one of the mucoadhesive peptide fragments as described in Table 8.

In some embodiments, there is provided a chimeric protein (e.g., fusion protein) comprising a full-length antibody comprising: a first antibody heavy chain, a second antibody heavy chain, a first antibody light chain, and a second antibody light chain (e.g., a first, second, third, and fourth polypeptide chain, respectively), wherein the antibody specifically binds to a component of an influenza virus or variant thereof, wherein the chimeric protein comprises: (a) a first polypeptide chain comprising the first antibody heavy chain fused to a first mucoadhesive peptide fragment; (b) a second polypeptide chain comprising the second antibody heavy chain fused to a second mucoadhesive peptide fragment; (c) a third polypeptide chain comprising the first antibody light chain; and (d) the fourth polypeptide chain comprising a second antibody light chain, wherein the first and second mucoadhesive peptide fragments each comprise about at least about 5 positively charged amino acid residues (e.g., about 5 to about 30 positively charged amino acid residues), wherein the first and second mucoadhesive peptide fragments facilitate attachment of the chimeric protein to a mucosa. In some embodiments, the first polypeptide chain comprises from the N-terminus to the C-terminus: the first antibody heavy chain, an optional peptide linker, and the first mucoadhesive peptide fragment. In some embodiments, the second polypeptide chain comprises from the N-terminus to the C-terminus: the second antibody heavy chain, an optional peptide linker, and the second mucoadhesive peptide fragment. In some embodiments, the first mucoadhesive peptide fragment is identical to the second mucoadhesive peptide fragment. In some embodiments, the first mucoadhesive peptide fragment is different from the second mucoadhesive peptide fragment. In some embodiments, the optional linkers of the first and second polypeptide chains are identical. In some embodiments, the optional linkers of the first and second polypeptide chains are different. In some embodiments, the third polypeptide chain and the fourth polypeptide comprise the antibody light chain. In some embodiments, the full-length antibody is a monospecific antibody. In some embodiments, the full-length antibody is a multispecific antibody (e.g., a bispecific antibody). In some embodiments, the influenza virus or variant thereof causes a respiratory infection. In some embodiments, the influenza virus is a Type A influenza virus (IAV), a Type B influenza virus (IBV), a Type C influenza virus (ICV), a Type D influenza virus (IDV), or a variant, subtype, or reassortant thereof. In some embodiments, the influenza virus comprises a HA antigen, such as HA antigen selected from the group consisting of H1, H2, H3, H5, H6, H7, H9, and H10, or a variant or reassortant thereof. In some embodiments, the influenza virus comprises an NA antigen, such as an NA antigen selected from the group consisting of N1, N2, N3, N7, N8, and N9, or a variant or reassortant thereof. In some embodiments, the influenza virus is selected from the group consisting of H1N1, H1N2, H2N2, H3N2, H3N8, H5N1, H5N9, H6N1, H7N2, H7N3, H7N7, H7N9, H9N2, H10N7, or a variant or reassortant thereof. In some embodiments, the mucosa is selected from the group consisting of nasal mucosa, larynx mucosa, trachea mucosa, bronchi mucosa, lung mucosa, eye mucosa, and combinations thereof. In some embodiments, the full-length antibody is IgG, IgA, IgM, IgE, or IgD.

In some embodiments, there is provided a chimeric protein (e.g., fusion protein) comprising a full-length antibody comprising: a first antibody heavy chain, a second antibody heavy chain, a first antibody light chain, and a second antibody light chain (e.g., a first, second, third, and fourth polypeptide chain, respectively), wherein the antibody specifically binds to a HA protein, wherein the chimeric protein comprises: (a) a first polypeptide chain comprising the first antibody heavy chain fused to a first mucoadhesive peptide fragment; (b) a second polypeptide chain comprising the second antibody heavy chain fused to a second mucoadhesive peptide fragment; (c) a third polypeptide chain comprising the first antibody light chain; and (d) the fourth polypeptide chain comprising a second antibody light chain, wherein the first and second mucoadhesive peptide fragments each comprise about at least about 5 positively charged amino acid residues (e.g., about 5 to about 30 positively charged amino acid residues), wherein the first and second mucoadhesive peptide fragments facilitate attachment of the chimeric protein to a mucosa. In some embodiments, the chimeric protein comprises: (1) a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of any one of SEQ ID NOs: 216, 218-242, and 416-419, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217; (2) a first and a second polypeptide chain each independently having at least about 90% sequence identity to the amino acid sequence of any one of SEQ ID NOs: 243, 245-258, and 422-425, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 244; or (3) a first and a second polypeptide chain each independently having at least about 90% sequence identity to the amino acid sequence of any one of SEQ ID NOs: 448-486, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447.

In some embodiments, there is provided a chimeric protein (e.g., fusion protein) comprising a full-length antibody comprising: a first antibody heavy chain, a second antibody heavy chain, a first antibody light chain, and a second antibody light chain (e.g., a first, second, third, and fourth polypeptide chain, respectively), wherein the antibody specifically binds to a NA protein, wherein the chimeric protein comprises: (a) a first polypeptide chain comprising the first antibody heavy chain fused to a first mucoadhesive peptide fragment; (b) a second polypeptide chain comprising the second antibody heavy chain fused to a second mucoadhesive peptide fragment; (c) a third polypeptide chain comprising the first antibody light chain; and (d) the fourth polypeptide chain comprising a second antibody light chain, wherein the first and second mucoadhesive peptide fragments each comprise about at least about 5 positively charged amino acid residues (e.g., about 5 to about 30 positively charged amino acid residues), wherein the first and second mucoadhesive peptide fragments facilitate attachment of the chimeric protein to a mucosa. In some embodiments, the chimeric protein comprises: (1) a first and a second polypeptide chains each independently having at least about 90% sequence identity (such as at least about n % sequence identity, where n % is selected from 91%, 92%, 93%, 94%, 95%, 96%, 97%, 98%, and 99%) to the amino acid sequence of any one of SEQ ID NOs: 259, 261-274, and 428-431, and a third and a fourth polypeptide chains each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 260; or (2) a first and a second polypeptide chains each independently having at least about 90% sequence identity (such as at least about n % sequence identity, where n % is selected from 91%, 92%, 93%, 94%, 95%, 96%, 97%, 98%, and 99%) to the amino acid sequence of any one of SEQ ID NOs: 275, 277-290, and 434-437, and a third and a fourth polypeptide chains each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 276.

In some embodiments, there is provided a chimeric protein (e.g., fusion protein) comprising: (a) an scFv that specifically binds to a component of an influenza virus or variant thereof; and (b) a mucoadhesive peptide fragment, wherein the mucoadhesive peptide fragment comprises about at least about 5 positively charged amino acid residues (e.g., about 5 to about 30 positively charged amino acid residues), wherein the mucoadhesive peptide fragment facilitates attachment of the chimeric protein to a mucosa. In some embodiments, the chimeric protein comprises a polypeptide comprising: from the N-terminus to the C-terminus: the scFv, an optional peptide linker, and the mucoadhesive peptide fragment. In some embodiments, the scFv comprises from the N-terminus to the C-terminus: $V_H$, an optional linker, and $V_L$. In some embodiments, the scFv comprises from the N-terminus to the C-terminus: $V_L$, an optional linker, and $V_H$. In some embodiments, the chimeric protein further comprises one or more constant domains of an antibody, e.g., $CH_1$, $C_L$, $CH_2$, $CH_3$, and/or $CH_4$. In some embodiments, the chimeric protein further comprises an Fc. In some embodiments, the positively charged amino acid residues are selected from the group consisting of lysine, arginine, histidine, ornithine, and combinations thereof. In some embodiments, the positively charged amino acid residues are lysines. In some embodiments, the mucoadhesive peptide fragment is a polylysine peptide having at least about 5 (e.g., about 5-30 such as 12) lysines (including for example at least about 5 (e.g., about 5-30 such as 12) contiguous lysines). In some embodiments, the positively charged amino acid residues are histidines. In some embodiments, the mucoadhesive peptide fragment is a polyhistidine peptide having at least about 5 (e.g., about 5-30 such as 12) histidines (including for example at least about 5 (e.g., about 5-30 such as 12) contiguous histidines). In some embodiments, the positively charged amino acid residues are arginines. In some embodiments, the mucoadhesive peptide fragment is a polyarginine peptide having at least about 5 (e.g., about 5-30 such as 12) arginines (including for example at least about 5 (e.g., about 5-30 such as 12) contiguous arginines). In some embodiments, the positively charged amino acid residues are ornithines. In some embodiments, the mucoadhesive peptide fragment is a polyornithine peptide having at least about 5 (e.g., about 5-30 such as 12) ornithines (including for example at least about 5 (e.g., about 5-30 such as 12) contiguous ornithines). In some embodiments, the positively charged amino acid residues are contiguous with each other. In some embodiments, the positively charged amino acid residues are interspersed with non-positively charged amino acid residues. In some embodiments, the influenza virus is a Type A influenza virus (IAV), a Type B influenza virus (IBV), a Type C influenza virus (ICV), a Type D influenza virus (IDV), or a variant, subtype, or reassortant thereof. In some embodiments, the influenza virus comprises an HA antigen, such as an HA selected from the group consisting of H1, H2, H3, H5, H6, H7, H9, and H10, or a variant or reassortant thereof. In some embodiments, the influenza virus comprises a NA antigen, such as an NA selected from the group consisting of N1, N2, N3, N7, N8, and N9, or a variant or reassortant thereof. In some embodiments, the influenza virus is selected from the group consisting of H1N1, H1N2, H2N2, H3N2, H3N8, H5N1, H5N9, H6N1, H7N2, H7N3, H7N7, H7N9, H9N2, H10N7, or a variant or reassortant thereof. In some embodiments, the component of the influenza virus or variant thereof is a viral surface protein. In some embodiments, the viral surface protein is HA. In some embodiments, the viral surface protein is NA. In some embodiments, the influenza virus or variant thereof causes a respiratory infection. In some embodiments, the mucosa is selected from the group consisting of nasal mucosa, larynx mucosa, trachea mucosa, bronchi mucosa, lung mucosa, eye mucosa, and combinations thereof.

In some embodiments, there is provided a chimeric protein (e.g., fusion protein) comprising: (a) a first scFv and a second scFv that each specifically binds to a component of an influenza virus or a variant thereof; and (b) a first and a second mucoadhesive peptide fragments, wherein the mucoadhesive peptide fragments each comprise at least about 5 positively charged amino acid residues (e.g., about 5 to about 30 positively charged amino acid residues), wherein the mucoadhesive peptide fragments facilitate attachment of the chimeric protein to a mucosa; wherein the chimeric protein comprises: (1) a first polypeptide comprising from the N-terminus to the C-terminus: the first scFv, an optional linker, $CH_2$ domain, $CH_3$ domain, an optional linker, and the first mucoadhesive peptide fragment; and (2)

a second polypeptide comprising from the N-terminus to the C-terminus: the second scFv, an optional linker, $CH_2$ domain, $CH_3$ domain, an optional linker, and the second mucoadhesive peptide fragment. In some embodiments, the first mucoadhesive peptide fragment is identical to the second mucoadhesive peptide fragment. In some embodiments, the first mucoadhesive peptide fragment is different from the second mucoadhesive peptide fragment. In some embodiments, the first scFv and the second scFv specifically bind to the same component of the influenza virus or variant thereof. In some embodiments, the first scFv and the second scFv specifically bind to different variants of the same component, different components of the same influenza virus, or components of different influenza viruses. In some embodiments, the positively charged amino acid residues are selected from the group consisting of lysine, arginine, histidine, ornithine, and combinations thereof. In some embodiments, the positively charged amino acid residues are lysines. In some embodiments, the mucoadhesive peptide fragment is a polylysine peptide having at least about 5 (e.g., about 5-30 such as 12) lysines (including for example at least about 5 (e.g., about 5-30 such as 12) contiguous lysines). In some embodiments, the positively charged amino acid residues are histidines. In some embodiments, the mucoadhesive peptide fragment is a polyhistidine peptide having at least about 5 (e.g., about 5-30 such as 12) histidines (including for example at least about 5 (e.g., about 5-30 such as 12) contiguous histidines). In some embodiments, the positively charged amino acid residues are arginines. In some embodiments, the mucoadhesive peptide fragment is a polyarginine peptide having at least about 5 (e.g., about 5-30 such as 12) arginines (including for example at least about 5 (e.g., about 5-30 such as 12) contiguous arginines). In some embodiments, the positively charged amino acid residues are ornithines. In some embodiments, the mucoadhesive peptide fragment is a polyornithine peptide having at least about 5 (e.g., about 5-30 such as 12) ornithines (including for example at least about 5 (e.g., about 5-30 such as 12) contiguous ornithines). In some embodiments, the positively charged amino acid residues are contiguous with each other. In some embodiments, the positively charged amino acid residues are interspersed with non-positively charged amino acid residues. In some embodiments, the influenza virus is a Type A influenza virus (IAV), a Type B influenza virus (IBV), a Type C influenza virus (ICV), a Type D influenza virus (IDV), or a variant, subtype, or reassortant thereof. In some embodiments, the influenza virus comprises an HA antigen, such as an HA antigen selected from the group consisting of H1, H2, H3, H5, H6, H7, H9, and H10, or a variant or reassortant thereof. In some embodiments, the influenza virus comprises a NA antigen, such as an NA selected from the group consisting of N1, N2, N3, N7, N8, and N9, or a variant or reassortant thereof. In some embodiments, the influenza virus is selected from the group consisting of H1N1, H1N2, H2N2, H3N2, H3N8, H5N1, H5N9, H6N1, H7N2, H7N3, H7N7, H7N9, H9N2, H10N7, or a variant or reassortant thereof. In some embodiments, the component of the influenza virus or variant thereof is a viral surface protein. In some embodiments, the viral surface protein is HA. In some embodiments, the viral surface protein is NA. In some embodiments, the influenza virus or variant thereof causes a respiratory infection. In some embodiments, the mucosa is selected from the group consisting of nasal mucosa, larynx mucosa, trachea mucosa, bronchi mucosa, lung mucosa, eye mucosa, and combinations thereof.

In some embodiments, the half-life of the chimeric protein on the mucosa is at least about n hours, where n hours is selected from 6 hours, 8 hours, 10 hours, 12 hours, 14 hours, 16 hours, 18 hours, 20 hours 22 hours, 24 hours, 30 hours, 36 hours, and 48 hours, or more. In some embodiments, the half-life of the chimeric protein on the mucosa is at least 12 hours. In some embodiments, the half-life of the chimeric protein on the mucosa is at least 24 hours.

The half-life of the chimeric protein on the mucosa may be determined using known in vitro assays in the art. In view of the size and polar properties of the chimeric protein, mucosal (e.g., nasal) absorption of the chimeric protein is minimal because of low membrane permeability of the chimeric protein. However, mucociliary clearance of the chimeric protein may play a role in the half-life of the chimeric proteins. The mucoadhesive peptide fragment can improve the retention time of the chimeric protein on the mucosa. For example, an in vitro model cell system, such as mucosal epithelial cells, may be used to determine the amount of the chimeric protein remaining on cell/mucin surface by FACS or immunofluorescence. As another example, mucosa related components, such as mucin, could be used to incubate with a chimeric protein and determine the amount of the chimeric protein associated with mucin by ELISA. In both methods, for chimeric proteins comprising an IgG, anti-IgG secondary antibodies can be used as a detection probe.

Exemplary chimeric proteins comprising an antibody moiety that specifically binds to a component of an influenza virus or a variant thereof, and a mucoadhesive peptide fragment comprising at least about 5 (e.g., about 5 to about 30 positively charges amino acid residues) positively charged amino acid residues are provided herein. Table 1 provides the sequences of some exemplary chimeric proteins which comprise antibody light chain ("LC") polypeptides as well as antibody heavy chain ("HC") polypeptides fused to mucoadhesive peptide fragments.

TABLE 1

Exemplary anti-influenza chimeric proteins

| Chimeric Protein | Antigen | HC / LC | Sequence (mucoadhesive peptide fragment is underlined) | SEQ ID NO |
|---|---|---|---|---|
| HA1-hIgG-6H | HA | HC | QVQLVESGGGVVQPGRSLRLSCAASGFTFSTYAMHWVRQAPG KGLEWVAVISYDANYKYYADSVKGRFTISRDNSKNTLYLQMNS LRAEDTAVYYCAKDSQLRSLLYFEWLSQGYFDYWGQGTLVTV SSSVFPLAPSSKSTSGGTAALGCLVKDYFPEPVTVSWNSGALTS GVHTFPAVLQSSGLYSLSSVVTVPSSSLGTQTYICNVNHKPSNTK VDKRVEPKSCTCPPCPAPELLGGPSVFLFPPKPKDTLMISRTPEV TCVVVDVSHEDPEVKFNWYVDGVEVHNAKTKPREEQYNSTYR VVSVLTVLHQDWLNGKEYKCKVSNKALPAPIEKTISKAKGQPR EPQVYTLPPSRDELTKNQVSLTCLVKGFYPSDIAVEWESNGQPE | 216 |

TABLE 1-continued

Exemplary anti-influenza chimeric proteins

| Chimeric Protein | Anti-gen | HC / LC | Sequence (mucoadhesive peptide fragment is underlined) | SEQ ID NO |
|---|---|---|---|---|
| | | | NNYKTTPPVLDSDGSFFLYSKLTVDKSRWQQGNVFSCSVMHEA<br>LHNHYTQKSLSLSPGKHHHHHH | |
| | | LC | DIVMTQSPDSLAVSLGERATINCKSSQSVTFNYKNYLAWYQQK<br>PGQPPKLLIYWASTRESGVPDRFSGSGSGTDFTLTISSLQAEDVA<br>VYYCQQHYRTPPTFGQGTKVEIKGQPKANPTVTLFPPSSEELQA<br>NKATLVCLISDFYPGAVTVAWKADGSPVKAGVETTKPSKQSNN<br>KYAASSYLSLTPEQWKSHRSYSCQVTHEGSTVEKTVAPTECS | 217 |
| HA1-hIgG-12H | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKHHHHHHHHHHHH | 218 |
| | | LC | "HA1" LC | 217 |
| HA1-hIgG-30H | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKHHHHHHHHHHHHHHHHHHHHHHHHH<br>HHHHH | 219 |
| | | LC | "HA1" LC | 217 |
| HA1-hIgG-6K | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKKKKKKK | 220 |
| | | LC | "HA1" LC | 217 |
| HA1-hIgG-12K | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKGGGGSKKKKKKKKKKKK | 221 |
| | | LC | "HA1" LC | 217 |
| HA1-hIgG-30K | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKKKKKKKKKKKKKKKKKKKKKKKKKK<br>KKKKK | 222 |
| | | LC | "HA1" LC | 217 |

TABLE 1-continued

| Exemplary anti-influenza chimeric proteins | | | | |
|---|---|---|---|---|
| Chimeric Protein | Anti-gen | HC / LC | Sequence (mucoadhesive peptide fragment is underlined) | SEQ ID NO |
| HA1-hIgG-6R | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKPRRRRRR | 223 |
| | | LC | “HA1” LC | 217 |
| HA1-hIgG-12R | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKRRRRRRRRRRRR | 224 |
| | | LC | “HA1” LC | 217 |
| HA1-hIgG-30R | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKRRRRRRRRRRRRRRRRRRRRRRRRRRR<br>RRR | 225 |
| | | LC | “HA1” LC | 217 |
| HA1-hIgG-6O | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSASVFPLAPSSKSTSGGTAALGCLVKDYFPEPVTVSWNSGALT<br>SGVHTFPAVLQSSGLYSLSSVVTVPSSSLGTQTYICNVNHKPSNT<br>KVDKRVEPKSCTCPPCPAPELLGGPSVFLFPPKPKDTLMISRTPE<br>VTCVVVDVSHEDPEVKFNWYVDGVEVHNAKTKPREEQYNSTY<br>RVVSVLTVLHQDWLNGKEYKCKVSNKALPAPIEKTISKAKGQP<br>REPQVYTLPPSRDELTKNQVSLTCLVKGFYPSDIAVEWESNGQP<br>ENNYKTTPPVLDSDGSFFLYSKLTVDKSRWQQGNVFSCSVMHE<br>ALHNHYTQKSLSLSPGKOOOOOO | 226 |
| | | LC | “HA1” LC | 217 |
| HA1-hIgG-12O | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKPOOOOOOOOOOOO | 227 |
| | | LC | “HA1” LC | 217 |
| HA1-hIgG-30O | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR | 228 |

TABLE 1-continued

| Chimeric Protein | Anti-gen | HC / LC | Sequence (mucoadhesive peptide fragment is underlined) | SEQ ID NO |
|---|---|---|---|---|
| Exemplary anti-influenza chimeric proteins | | | | |
| | | | VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKOOOOOOOOOOOOOOOOOOOOOOOOO<br>OOOOO | |
| | | LC | "HA1" LC | 217 |
| HA1-hIgG-6X-1 | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKHHKKOO | 229 |
| | | LC | "HA1" LC | 217 |
| HA1-hIgG-6X-2 | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKHORKHR | 230 |
| | | LC | "HA1" LC | 217 |
| HA1-hIgG-6X-3 | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKHKRSOH | 231 |
| | | LC | "HA1" LC | 217 |
| HA1-hIgG-6X-4 | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKRRHTHR | 232 |
| | | LC | "HA1" LC | 217 |
| HA1-hIgG-12X-1 | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKHHHKKKRRROOO | 233 |
| | | | "HA1" LC | 217 |
| HA1-hIgG-30X-1 | HA | HC | QVQLVESGGGVVQPGRSLRLSCAASGFTFSTYAMHWVRQAPG<br>KGLEWVAVISYDANYKYYADSVKGRFTISRDNSKNTLYLQMNS | 234 |

TABLE 1-continued

| Exemplary anti-influenza chimeric proteins | | | | |
|---|---|---|---|---|
| Chimeric Protein | Anti-gen | HC / LC | Sequence (mucoadhesive peptide fragment is underlined) | SEQ ID NO |
| | | | LRAEDTAVYYCAKDSQLRSLLYFEWLSQGYFDYWGQGTLVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKHKROHKROHKROHKROHKROHKROHK<br>ROHK | |
| | | LC | "HA1" LC | 217 |
| HA1-hIgG-12X-2 | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKHHOAKKRCOOQH | 236 |
| | | LC | "HA1" LC | 217 |
| HA1-hIgG-30X-2 | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKKOHRSOKRHTORHKAHORKCKROKQR<br>KHOS | 237 |
| | | LC | "HA1" LC | 217 |
| HA1-hIgG-12X-3 | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKHRKOORKHHRKK | 239 |
| | | LC | "HA1" LC | 217 |
| HA1-hIgG-30X-3 | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKKKROSRRHOTOOHHAROKHCKHROQR<br>HKKS | 240 |
| | | LC | "HA1" LC | 217 |
| HA1-hIgG-12X-4 | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR | 241 |

TABLE 1-continued

| Exemplary anti-influenza chimeric proteins | | | | |
|---|---|---|---|---|
| Chimeric Protein | Anti-gen | HC / LC | Sequence (mucoadhesive peptide fragment is underlined) | SEQ ID NO |
| | | | EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKKRAHQKCQRKSH | |
| | | LC | "HA1" LC | 217 |
| HA1-hIgG-30X-4 | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSVFPLAPSSKSTSGGTAALGCLVKDYFPEPVTVSWNSGALTSG<br>VHTFPAVLQSSGLYSLSSVVTVPSSSLGTQTYICNVNHKPSNTKV<br>DKRVEPKSCTCPPCPAPELLGGPSVFLFPPKPKDTLMISRTPEVTC<br>VVVDVSHEDPEVKFNWYVDGVEVHNAKTKPREEQYNSTYRVV<br>SVLTVLHQDWLNGKEYKCKVSNKALPAPIEKTISKAKGQPREPQ<br>VYTLPPSRDELTKNQVSLTCLVKGFYPSDIAVEWESNGQPENNY<br>KTTPPVLDSDGSFFLYSKLTVDKSRWQQGNVFSCSVMHEALHN<br>HYTQKSLSLSPGKHRKQQHRSQQKTRRRAHRQCHHHSRHQTH<br>R | 242 |
| | | LC | "HA1" LC | 217 |
| HA1-hIgG-5H | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSTCPPCPAPELLGGPSVFLFPPKPKDTLMISRTPEVTCVVVDVS<br>HEDPEVKFNWYVDGVEVHNAKTKPREEQYNSTYRVVSVLTVL<br>HQDWLNGKEYKCKVSNKALPAPIEKTISKAKGQPREPQVYTLPP<br>SRDELTKNQVSLTCLVKGFYPSDIAVEWESNGQPENNYKTTPPV<br>LDSDGSFFLYSKLTVDKSRWQQGNVFSCSVMHEALHNHYTQKS<br>LSLSPGKHHHHH | 416 |
| | | LC | "HA1" LC | 217 |
| HA1-hIgG-7X-1 | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSTCPPCPAPELLGGPSVFLFPPKPKDTLMISRTPEVTCVVVDVS<br>HEDPEVKFNWYVDGVEVHNAKTKPREEQYNSTYRVVSVLTVL<br>HQDWLNGKEYKCKVSNKALPAPIEKTISKAKGQPREPQVYTLPP<br>SRDELTKNQVSLTCLVKGFYPSDIAVEWESNGQPENNYKTTPPV<br>LDSDGSFFLYSKLTVDKSRWQQGNVFSCSVMHEALHNHYTQKS<br>LSLSPGKKKKGKKK | 417 |
| | | LC | "HA1" LC | 217 |
| HA1-hIgG-12X-7 | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSTCPPCPAPELLGGPSVFLFPPKPKDTLMISRTPEVTCVVVDVS<br>HEDPEVKFNWYVDGVEVHNAKTKPREEQYNSTYRVVSVLTVL<br>HQDWLNGKEYKCKVSNKALPAPIEKTISKAKGQPREPQVYTLPP<br>SRDELTKNQVSLTCLVKGFYPSDIAVEWESNGQPENNYKTTPPV<br>LDSDGSFFLYSKLTVDKSRWQQGNVFSCSVMHEALHNHYTQKS<br>LSLSPGKKKAHHGKKAHHV | 418 |
| | | LC | "HA1" LC | 217 |
| HA1-hIgG-12X-8 | HA | HC | QVQLVESGGGVVQPGRSLRLSCAASGFTFSTYAMHWVRQAPG<br>KGLEWVAVISYDANYKYYADSVKGRFTISRDNSKNTLYLQMNS<br>LRAEDTAVYYCAKDSQLRSLLYFEWLSQGYFDYWGQGTLVTV<br>SSTCPPCPAPELLGGPSVFLFPPKPKDTLMISRTPEVTCVVVDVS<br>HEDPEVKFNWYVDGVEVHNAKTKPREEQYNSTYRVVSVLTVL<br>HQDWLNGKEYKCKVSNKALPAPIEKTISKAKGQPREPQVYTLPP<br>SRDELTKNQVSLTCLVKGFYPSDIAVEWESNGQPENNYKTTPPV<br>LDSDGSFFLYSKLTVDKSRWQQGNVFSCSVMHEALHNHYTQKS<br>LSLSPGKKKARRGKKARRV | 419 |
| | | LC | "HA1" LC | 217 |
| HA2-hIgG-6H | HA | HC | EVQLVESGAEVKKPGSSVKVSCRASGTFYKYAINWVRQAPGQG<br>LEWMGGIIPFFGTTNYAQKFQGRLTITADGSTNTAYMQLDSLRS<br>EDTAVYYCAGPSITESHYCLDCAAKDYYYGLDVWGQGTTVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKHHHHHH | 243 |

TABLE 1-continued

Exemplary anti-influenza chimeric proteins

| Chimeric Protein | Anti-gen | HC / LC | Sequence (mucoadhesive peptide fragment is underlined) | SEQ ID NO |
|---|---|---|---|---|
| | | LC | QSVLTQPPSASGTPGQSVTISCSGSRSNIGGNTVNWYQHLPGMA<br>PKLLIYSSNQRSSGVPDRFSGSKSGTSASLAISGLQSEDDADYYC<br>ASWDDSLNGVVFGGGTKLTVLGGQPKAAPSVTLFPPSSEELQA<br>NKATLVCLISDFYPGAVTVAWKADSSPVKAGVETTTPSKQSNN<br>KYAASSYLSLTPEQWKSHRSYSCQVTHEGSTVEKTVAPTECS | 244 |
| HA2-hIgG-12H | HA | HC | EVQLVESGAEVKKPGSSVKVSCRASGTFYKYAINWVRQAPGQG<br>LEWMGGIIPFFGTTNYAQKFQGRLTITADGSTNTAYMQLDSLRS<br>EDTAVYYCAGPSITESHYCLDCAAKDYYYGLDVWGQGTTVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKHHHHHHHHHHHH | 245 |
| | | LC | "HA2" LC | 244 |
| HA2-hIgG-30H | HA | HC | EVQLVESGAEVKKPGSSVKVSCRASGTFYKYAINWVRQAPGQG<br>LEWMGGIIPFFGTTNYAQKFQGRLTITADGSTNTAYMQLDSLRS<br>EDTAVYYCAGPSITESHYCLDCAAKDYYYGLDVWGQGTTVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKHHHHHHHHHHHHHHHHHHHHHHHHH<br>HHHHH | 246 |
| | | LC | "HA2" LC | 244 |
| HA2-hIgG-6K | HA | HC | EVQLVESGAEVKKPGSSVKVSCRASGTFYKYAINWVRQAPGQG<br>LEWMGGIIPFFGTTNYAQKFQGRLTITADGSTNTAYMQLDSLRS<br>EDTAVYYCAGPSITESHYCLDCAAKDYYYGLDVWGQGTTVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKKKKKKK | 247 |
| | | LC | "HA2" LC | 244 |
| HA2-hIgG-12K | HA | HC | EVQLVESGAEVKKPGSSVKVSCRASGTFYKYAINWVRQAPGQG<br>LEWMGGIIPFFGTTNYAQKFQGRLTITADGSTNTAYMQLDSLRS<br>EDTAVYYCAGPSITESHYCLDCAAKDYYYGLDVWGQGTTVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKGGGGSKKKKKKKKKKKK | 248 |
| | | LC | "HA2" LC | 244 |
| HA2-hIgG-30K | HA | HC | EVQLVESGAEVKKPGSSVKVSCRASGTFYKYAINWVRQAPGQG<br>LEWMGGIIPFFGTTNYAQKFQGRLTITADGSTNTAYMQLDSLRS<br>EDTAVYYCAGPSITESHYCLDCAAKDYYYGLDVWGQGTTVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKKKKKKKKKKKKKKKKKKKKKKKKKK<br>KKKKK | 249 |
| | | LC | "HA2" LC | 244 |

TABLE 1-continued

Exemplary anti-influenza chimeric proteins

| Chimeric Protein | Anti-gen | HC / LC | Sequence (mucoadhesive peptide fragment is underlined) | SEQ ID NO |
|---|---|---|---|---|
| HA2-hIgG-6R | HA | HC | EVQLVESGAEVKKPGSSVKVSCRASGTFYKYAINWVRQAPGQG<br>LEWMGGIIPFFGTTNYAQKFQGRLTITADGSTNTAYMQLDSLRS<br>EDTAVYYCAGPSITESHYCLDCAAKDYYYGLDVWGQGTTVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKRRRRRR | 250 |
| | | LC | "HA2" LC | 244 |
| HA2-hIgG-12R | HA | HC | EVQLVESGAEVKKPGSSVKVSCRASGTFYKYAINWVRQAPGQG<br>LEWMGGIIPFFGTTNYAQKFQGRLTITADGSTNTAYMQLDSLRS<br>EDTAVYYCAGPSITESHYCLDCAAKDYYYGLDVWGQGTTVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKRRRRRRRRRRRR | 251 |
| | | LC | "HA2" LC | 244 |
| HA2-hIgG-30R | HA | HC | EVQLVESGAEVKKPGSSVKVSCRASGTFYKYAINWVRQAPGQG<br>LEWMGGIIPFFGTTNYAQKFQGRLTITADGSTNTAYMQLDSLRS<br>EDTAVYYCAGPSITESHYCLDCAAKDYYYGLDVWGQGTTVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKRRRRRRRRRRRRRRRRRRRRRRRRRRR<br>RRR | 252 |
| | | LC | "HA2" LC | 244 |
| HA2-hIgG-6O | HA | HC | EVQLVESGAEVKKPGSSVKVSCRASGTFYKYAINWVRQAPGQG<br>LEWMGGIIPFFGTTNYAQKFQGRLTITADGSTNTAYMQLDSLRS<br>EDTAVYYCAGPSITESHYCLDCAAKDYYYGLDVWGQGTTVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKOOOOOO | 253 |
| | | LC | "HA2" LC | 244 |
| HA2-hIgG-12O | HA | HC | EVQLVESGAEVKKPGSSVKVSCRASGTFYKYAINWVRQAPGQG<br>LEWMGGIIPFFGTTNYAQKFQGRLTITADGSTNTAYMQLDSLRS<br>EDTAVYYCAGPSITESHYCLDCAAKDYYYGLDVWGQGTTVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKOOOOOOOOOOOO | 254 |
| | | LC | "HA2" LC | 244 |
| HA2-hIgG-30O | HA | HC | EVQLVESGAEVKKPGSSVKVSCRASGTFYKYAINWVRQAPGQG<br>LEWMGGIIPFFGTTNYAQKFQGRLTITADGSTNTAYMQLDSLRS<br>EDTAVYYCAGPSITESHYCLDCAAKDYYYGLDVWGQGTTVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR | 255 |

TABLE 1-continued

| Chimeric Protein | Antigen | HC / LC | Sequence (mucoadhesive peptide fragment is underlined) | SEQ ID NO |
|---|---|---|---|---|
| Exemplary anti-influenza chimeric proteins | | | | |
| | | | EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKOOOOOOOOOOOOOOOOOOOOOOOOO<br>OOOOO | |
| | | LC | "HA2" LC | 244 |
| HA2-hIgG-6X-7 | HA | HC | EVQLVESGAEVKKPGSSVKVSCRASGTFYKYAINWVRQAPGQG<br>LEWMGGIIPFFGTTNYAQKFQGRLTITADGSTNTAYMQLDSLRS<br>EDTAVYYCAGPSITESHYCLDCAAKDYYYGLDVWGQGTTVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKKKOORR | 256 |
| | | LC | "HA2" LC | 244 |
| HA2-hIgG-12X-5 | HA | HC | EVQLVESGAEVKKPGSSVKVSCRASGTFYKYAINWVRQAPGQG<br>LEWMGGIIPFFGTTNYAQKFQGRLTITADGSTNTAYMQLDSLRS<br>EDTAVYYCAGPSITESHYCLDCAAKDYYYGLDVWGQGTTVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKKKRROOHHHRRR | 257 |
| | | LC | "HA2" LC | 244 |
| HA2-hIgG-30X-1 | HA | HC | EVQLVESGAEVKKPGSSVKVSCRASGTFYKYAINWVRQAPGQG<br>LEWMGGIIPFFGTTNYAQKFQGRLTITADGSTNTAYMQLDSLRS<br>EDTAVYYCAGPSITESHYCLDCAAKDYYYGLDVWGQGTTVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKHKROHKROHKROHKROHKROHKROHK<br>ROHK | 258 |
| | | LC | "HA2" LC | 244 |
| HA2-hIgG-5H | HA | HC | EVQLVESGAEVKKPGSSVKVSCRASGTFYKYAINWVRQAPGQG<br>LEWMGGIIPFFGTTNYAQKFQGRLTITADGSTNTAYMQLDSLRS<br>EDTAVYYCAGPSITESHYCLDCAAKDYYYGLDVWGQGTTVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKHHHHH | 422 |
| | | LC | "HA2" LC | 244 |
| HA2-hIgG-7X-1 | HA | HC | EVQLVESGAEVKKPGSSVKVSCRASGTFYKYAINWVRQAPGQG<br>LEWMGGIIPFFGTTNYAQKFQGRLTITADGSTNTAYMQLDSLRS<br>EDTAVYYCAGPSITESHYCLDCAAKDYYYGLDVWGQGTTVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKKKKGKKK | 423 |
| | | LC | "HA2" LC | 244 |

TABLE 1-continued

Exemplary anti-influenza chimeric proteins

| Chimeric Protein | Anti-gen | HC / LC | Sequence (mucoadhesive peptide fragment is underlined) | SEQ ID NO |
|---|---|---|---|---|
| HA2-hIgG-12X-7 | HA | HC | EVQLVESGAEVKKPGSSVKVSCRASGTFYKYAINWVRQAPGQG<br>LEWMGGIIPFFGTTNYAQKFQGRLTITADGSTNTAYMQLDSLRS<br>EDTAVYYCAGPSITESHYCLDCAAKDYYYGLDVWGQGTTVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKKKAHHGKKAHHV | 424 |
| | | LC | "HA2" LC | 244 |
| HA2-hIgG-12X-8 | HA | HC | EVQLVESGAEVKKPGSSVKVSCRASGTFYKYAINWVRQAPGQG<br>LEWMGGIIPFFGTTNYAQKFQGRLTITADGSTNTAYMQLDSLRS<br>EDTAVYYCAGPSITESHYCLDCAAKDYYYGLDVWGQGTTVTV<br>SSSVFPLAPSSKSTSGGTAALGCLVKDYFPEPVTVSWNSGALTS<br>GVHTFPAVLQSSGLYSLSSVVTVPSSSLGTQTYICNVNHKPSNTK<br>VDKRVEPKSCTCPPCPAPELLGGPSVFLFPPKPKDTLMISRTPEV<br>TCVVVDVSHEDPEVKFNWYVDGVEVHNAKTKPREEQYNSTYR<br>VVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGKKKARRGKKARRV | 425 |
| | | LC | "HA2" LC | 244 |
| HA15-hIgG-5H | HA | HC | QVQLVQSGAEVKKPGSSVKVSCKSSGGTSNNYAISWVRQAPGQ<br>GLDWMGGISPIFGSTAYAQKFQGRVTISADIFSNTA YMELNSLTS<br>EDTAVYFCARHGNYYYYSGMDVWGQGTTVTVSSSVFPLAPSS<br>KSTSGGTAALGCLVKDYFPEPVTVSWNSGALTSGVHTFPAVLQ<br>SSGLYSLSSVVTVPSSSLGTQTYICNVNHKPSNTKVDKRVEPKSC<br>TCPPCPAPELLGGPSVFLFPPKPKDTLMISRTPEVTCVVVDVSHE<br>DPEVKFNWYVDGVEVHNAKTKPREEQYNSTYRVVSVLTVLHQ<br>DWLNGKEYKCKVSNKALPAPIEKTISKAKGQPREPQVYTLPPSR<br>DELTKNQVSLTCLVKGFYPSDIAVEWESNGQPENNYKTTPPVLD<br>SDGSFFLYSKLTVDKSRWQQGNVFSCSVMHEALHNHYTQKSLS<br>LSPGKHHHHH | 448 |
| | | LC | QSALTQPPAVSGTPGQRVTISCSGSDSNIGRRSVNWYQQFPGTA<br>PKLLIYSNDQRPSVVPDRFSGSKSGTSASLAISGLQSEDEAEYYC<br>AAWDDSLKGAVFGGGTQLTVLGQPKANPTVTLFPPSSEELQAN<br>KATLVCLISDFYPGAVTVAWKADGSPVKAGVETTKPSKQSNNK<br>YAASSYLSLTPEQWKSHRSYSCQVTHEGSTVEKTVAPTECS | 447 |
| HA15-hIgG-6H | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKHHHHHH | 449 |
| | | LC | "HA15" LC | 447 |
| HA15-hIgG-12H | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKHHHHHHHHHHHH | 450 |
| | | LC | "HA15" LC | 447 |
| HA15-hIgG-30H | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP | 451 |

TABLE 1-continued

Exemplary anti-influenza chimeric proteins

| Chimeric Protein | Anti-gen | HC / LC | Sequence (mucoadhesive peptide fragment is underlined) | SEQ ID NO |
|---|---|---|---|---|
| | | | EVKFNWYVDGVEVHNAKTKPREEQYNSTYRVVSVLTVLHQDW | |
| | | | LNGKEYKCKVSNKALPAPIEKTISKAKGQPREPQVYTLPPSRDEL | |
| | | | TKNQVSLTCLVKGFYPSDIAVEWESNGQPENNYKTTPPVLDSDG | |
| | | | SFFLYSKLTVDKSRWQQGNVFSCSVMHEALHNHYTQKSLSLSP | |
| | | | GKHHHHHHHHHHHHHHHHHHHHHHHHHHHHHH | |
| | | LC | “HA15” LC | 447 |
| HA15-hIgG-6K | HA | HC | QVQLVQSGAEVKKPGSSVKVSCKSSGGTSNNYAISWVRQAPGQ | 452 |
| | | | GLDWMGGISPIFGSTAYAQKFQGRVTISADIFSNTAYMELNSLTS | |
| | | | EDTAVYFCARHGNYYYYSGMDVWGQGTTVTVSSSVFPLAPSSK | |
| | | | STSGGTAALGCLVKDYFPEPVTVSWNSGALTSGVHTFPAVLQSS | |
| | | | GLYSLSSVVTVPSSSLGTQTYICNVNHKPSNTKVDKRVEPKSCTC | |
| | | | PPCPAPELLGGPSVFLFPPKPKDTLMISRTPEVTCVVVDVSHEDP | |
| | | | EVKFNWYVDGVEVHNAKTKPREEQYNSTYRVVSVLTVLHQDW | |
| | | | LNGKEYKCKVSNKALPAPIEKTISKAKGQPREPQVYTLPPSRDEL | |
| | | | TKNQVSLTCLVKGFYPSDIAVEWESNGQPENNYKTTPPVLDSDG | |
| | | | SFFLYSKLTVDKSRWQQGNVFSCSVMHEALHNHYTQKSLSLSP | |
| | | | GKKKKKKK | |
| | | LC | “HA15” LC | 447 |
| HA15-hIgG-12K | HA | HC | QVQLVQSGAEVKKPGSSVKVSCKSSGGTSNNYAISWVRQAPGQ | 453 |
| | | | GLDWMGGISPIFGSTAYAQKFQGRVTISADIFSNTAYMELNSLTS | |
| | | | EDTAVYFCARHGNYYYYSGMDVWGQGTTVTVSSSVFPLAPSSK | |
| | | | STSGGTAALGCLVKDYFPEPVTVSWNSGALTSGVHTFPAVLQSS | |
| | | | GLYSLSSVVTVPSSSLGTQTYICNVNHKPSNTKVDKRVEPKSCTC | |
| | | | PPCPAPELLGGPSVFLFPPKPKDTLMISRTPEVTCVVVDVSHEDP | |
| | | | EVKFNWYVDGVEVHNAKTKPREEQYNSTYRVVSVLTVLHQDW | |
| | | | LNGKEYKCKVSNKALPAPIEKTISKAKGQPREPQVYTLPPSRDEL | |
| | | | TKNQVSLTCLVKGFYPSDIAVEWESNGQPENNYKTTPPVLDSDG | |
| | | | SFFLYSKLTVDKSRWQQGNVFSCSVMHEALHNHYTQKSLSLSP | |
| | | | GGGGSKKKKKKKKKKKKK | |
| | | LC | “HA15” LC | 447 |
| HA15-hIgG-30K | HA | HC | QVQLVQSGAEVKKPGSSVKVSCKSSGGTSNNYAISWVRQAPGQ | 454 |
| | | | GLDWMGGISPIFGSTAYAQKFQGRVTISADIFSNTAYMELNSLTS | |
| | | | EDTAVYFCARHGNYYYYSGMDVWGQGTTVTVSSSVFPLAPSSK | |
| | | | STSGGTAALGCLVKDYFPEPVTVSWNSGALTSGVHTFPAVLQSS | |
| | | | GLYSLSSVVTVPSSSLGTQTYICNVNHKPSNTKVDKRVEPKSCTC | |
| | | | PPCPAPELLGGPSVFLFPPKPKDTLMISRTPEVTCVVVDVSHEDP | |
| | | | EVKFNWYVDGVEVHNAKTKPREEQYNSTYRVVSVLTVLHQDW | |
| | | | LNGKEYKCKVSNKALPAPIEKTISKAKGQPREPQVYTLPPSRDEL | |
| | | | TKNQVSLTCLVKGFYPSDIAVEWESNGQPENNYKTTPPVLDSDG | |
| | | | SFFLYSKLTVDKSRWQQGNVFSCSVMHEALHNHYTQKSLSLSP | |
| | | | GKKKKKKKKKKKKKKKKKKKKKKKKKKKKKKK | |
| | | LC | “HA15” LC | 447 |
| HA15-hIgG-6R | HA | HC | QVQLVQSGAEVKKPGSSVKVSCKSSGGTSNNYAISWVRQAPGQ | 455 |
| | | | GLDWMGGISPIFGSTAYAQKFQGRVTISADIFSNTAYMELNSLTS | |
| | | | EDTAVYFCARHGNYYYYSGMDVWGQGTTVTVSSSVFPLAPSSK | |
| | | | STSGGTAALGCLVKDYFPEPVTVSWNSGALTSGVHTFPAVLQSS | |
| | | | GLYSLSSVVTVPSSSLGTQTYICNVNHKPSNTKVDKRVEPKSCTC | |
| | | | PPCPAPELLGGPSVFLFPPKPKDTLMISRTPEVTCVVVDVSHEDP | |
| | | | EVKFNWYVDGVEVHNAKTKPREEQYNSTYRVVSVLTVLHQDW | |
| | | | LNGKEYKCKVSNKALPAPIEKTISKAKGQPREPQVYTLPPSRDEL | |
| | | | TKNQVSLTCLVKGFYPSDIAVEWESNGQPENNYKTTPPVLDSDG | |
| | | | SFFLYSKLTVDKSRWQQGNVFSCSVMHEALHNHYTQKSLSLSP | |
| | | | GKRRRRRR | |
| | | LC | “HA15” LC | 447 |
| HA15-hIgG-12R | HA | HC | QVQLVQSGAEVKKPGSSVKVSCKSSGGTSNNYAISWVRQAPGQ | 456 |
| | | | GLDWMGGISPIFGSTAYAQKFQGRVTISADIFSNTAYMELNSLTS | |
| | | | EDTAVYFCARHGNYYYYSGMDVWGQGTTVTVSSSVFPLAPSSK | |
| | | | STSGGTAALGCLVKDYFPEPVTVSWNSGALTSGVHTFPAVLQSS | |
| | | | GLYSLSSVVTVPSSSLGTQTYICNVNHKPSNTKVDKRVEPKSCTC | |
| | | | PPCPAPELLGGPSVFLFPPKPKDTLMISRTPEVTCVVVDVSHEDP | |
| | | | EVKFNWYVDGVEVHNAKTKPREEQYNSTYRVVSVLTVLHQDW | |
| | | | LNGKEYKCKVSNKALPAPIEKTISKAKGQPREPQVYTLPPSRDEL | |
| | | | TKNQVSLTCLVKGFYPSDIAVEWESNGQPENNYKTTPPVLDSDG | |
| | | | SFFLYSKLTVDKSRWQQGNVFSCSVMHEALHNHYTQKSLSLSP | |
| | | | GKRRRRRRRRRRRR | |
| | | LC | “HA15” LC | 447 |

TABLE 1-continued

Exemplary anti-influenza chimeric proteins

| Chimeric Protein | Anti-gen | HC / LC | Sequence (mucoadhesive peptide fragment is underlined) | SEQ ID NO |
|---|---|---|---|---|
| HA15-hIgG-30R | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKRRRRRRRRRRRRRRRRRRRRRRRRRRRRRR | 457 |
| | | LC | "HA15" LC | 447 |
| HA15-hIgG-6O | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKOOOOOO | 458 |
| | | LC | "HA15" LC | 447 |
| HA15-hIgG-12O | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKOOOOOOOOOOOO | 459 |
| | | LC | HA15 LC | 447 |
| HA15-hIgG-30O | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKOOOOOOOOOOOOOOOOOOOOOOOOOOOOOO | 460 |
| | | LC | "HA15" LC | 447 |
| HA15-hIgG-6X-1 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKHHKKOO | 461 |
| | | LC | "HA15" LC | 447 |
| HA15-hIgG-6X-2 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW | 462 |

TABLE 1-continued

Exemplary anti-influenza chimeric proteins

| Chimeric Protein | Anti-gen | HC / LC | Sequence (mucoadhesive peptide fragment is underlined) | SEQ ID NO |
|---|---|---|---|---|
| | | | LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKHORKHR | |
| | | LC | "HA15" LC | 447 |
| HA15-hIgG-6X-3 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKHKRSOH | 463 |
| | | LC | "HA15" LC | 447 |
| HA15-hIgG-6X-4 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKRRHTHR | 464 |
| | | LC | "HA15" LC | 447 |
| HA15-hIgG-6X-5 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKKKHHRR | 465 |
| | | LC | "HA15" LC | 447 |
| HA15-hIgG-6X-6 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKOORRHH | 466 |
| | | LC | "HA15" LC | 447 |
| HA15-hIgG-6X-7 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKKKOORR | 467 |
| | | LC | "HA15" LC | 447 |
| HA15-hIgG-7X-1 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK | 468 |

TABLE 1-continued

| Exemplary anti-influenza chimeric proteins | | | | |
|---|---|---|---|---|
| Chimeric Protein | Anti-gen | HC / LC | Sequence (mucoadhesive peptide fragment is underlined) | SEQ ID NO |
| | | | STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKKKKGKKK | |
| | | LC | "HA15" LC | 447 |
| HA15-hIgG-12X-1 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKHHHKKKRRROOO | 469 |
| | | LC | "HA15" LC | 447 |
| HA15-hIgG-12X-2 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKHHOAKKRCOOQH | 470 |
| | | LC | "HA15" LC | 447 |
| HA15-hIgG-12X-3 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKHRKOORKHHRKK | 471 |
| | | LC | "HA15" LC | 447 |
| HA15-hIgG-12X-4 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKKRAHOKCORKSH | 472 |
| | | LC | "HA15" LC | 447 |
| HA15-hIgG-12X-5 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKKKRROOHHHRRR | 473 |
| | | LC | "HA15" LC | 447 |

TABLE 1-continued

| Exemplary anti-influenza chimeric proteins | | | | |
|---|---|---|---|---|
| Chimeric Protein | Anti-gen | HC / LC | Sequence (mucoadhesive peptide fragment is underlined) | SEQ ID NO |
| HA15-hIgG-12X-6 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKOOORRRKKKHHH | 474 |
| | | LC | "HA15" LC | 447 |
| HA15-hIgG-12X-7 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKKKAHHGKKAHHV | 475 |
| | | LC | "HA15" LC | 447 |
| HA15-hIgG-12X-8 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKKKARRGKKARRV | 476 |
| | | LC | "HA15" LC | 447 |
| HA15-hIgG-30X-1 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSASVFPLAPSS<br>KSTSGGTAALGCLVKDYFPEPVTVSWNSGALTSGVHTFPAVLQS<br>SGLYSLSSVVTVPSSSLGTQTYICNVNHKPSNTKVDKRVEPKSCT<br>CPPCPAPELLGGPSVFLFPPKPKDTLMISRTPEVTCVVVDVSHED<br>PEVKFNWYVDGVEVHNAKTKPREEQYNSTYRVVSVLTVLHQD<br>WLNGKEYKCKVSNKALPAPIEKTISKAKGQPREPQVYTLPPSRD<br>ELTKNQVSLTCLVKGFYPSDIAVEWESNGQPENNYKTTPPVLDS<br>DGSFFLYSKLTVDKSRWQQGNVFSCSVMHEALHNHYTQKSLSL<br>SPGKKHKROHKROHKROHKROHKROHKROHKROHK | 477 |
| | | LC | "HA15" LC | 447 |
| HA15-hIgG-30X-2 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKKOHRSOKRHTORHKAHORKCKROKQRKHOS | 478 |
| | | LC | "HA15" LC | 447 |
| HA15-hIgG-30X-3 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL | 479 |

TABLE 1-continued

Exemplary anti-influenza chimeric proteins

| Chimeric Protein | Anti-gen | HC / LC | Sequence (mucoadhesive peptide fragment is underlined) | SEQ ID NO |
|---|---|---|---|---|
| | | | TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKKKROSRRHOTOOHHAROKHCKHROTRHKKS | |
| | | LC | "HA15" LC | 447 |
| HA15-hIgG-30X-4 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSVFPLAPSSKS<br>TSGGTAALGCLVKDYFPEPVTVSWNSGALTSGVHTFPAVLQSSG<br>LYSLSSVVTVPSSSLGTQTYICNVNHKPSNTKVDKRVEPKSCTCP<br>PCPAPELLGGPSVFLFPPKPKDTLMISRTPEVTCVVVDVSHEDPE<br>VKFNWYVDGVEVHNAKTKPREEQYNSTYRVVSVLTVLHQDWL<br>NGKEYKCKVSNKALPAPIEKTISKAKGQPREPQVYTLPPSRDELT<br>KNQVSLTCLVKGFYPSDIAVEWESNGQPENNYKTTPPVLDSDGS<br>FFLYSKLTVDKSRWQQGNVFSCSVMHEALHNHYTQKSLSLSPG<br>KHRKQOHRSOOKTRRRAHROCHHHSRHOTHR | 480 |
| | | LC | "HA15" LC | 447 |
| HA15-hIgG-35X-1 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKGRHKAKNHIRRPKSRWKKWHKYRKVHRHKVHKGRR | 481 |
| | | LC | "HA15" LC | 447 |
| HA15-hIgG-40X-2 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKWRKVHHYKKQHKNRAHGKLKLRAKIHQRSRMHGKQKHYH<br>R | 482 |
| | | LC | "HA15" LC | 447 |
| HA15-hIgG-42X-1 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKAHHKCRRGHKQKILHRRPHKFHRWKRVHKGRHGKKHRRH<br>KHR | 483 |
| | | LC | "HA15" LC | 447 |
| HA15-hIgG-45X-1 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKQHRGKAKYHRTHHVKKQRHGRKNHKVHRHARKFHKIRRL<br>KCHKKH | 484 |
| | | LC | "HA15" LC | 447 |

TABLE 1-continued

| Exemplary anti-influenza chimeric proteins | | | | |
|---|---|---|---|---|
| Chimeric Protein | Anti-gen | HC / LC | Sequence (mucoadhesive peptide fragment is underlined) | SEQ ID NO |
| HA15-hIgG-50X-1 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKHNKRFKKGRHVRHSRHKSHRRTHKYHHWRHYRKVHRCKK<br>AHKSHHRVHHK | 485 |
| | | LC | "HA15" LC | 447 |
| HA15-hIgG-50X-2 | HA | HC | QVQLVQSGAEVKKPGSSVKVSCKSSGGTSNNYAISWVRQAPGQ<br>GLDWMGGISPIFGSTAYAQKFQGRVTISADIFSNTAYMELNSLTS<br>EDTAVYFCARHGNYYYYSGMDVWGQGTTVTVSSSVFPLAPSSK<br>STSGGTAALGCLVKDYFPEPVTVSWNSGALTSGVHTFPAVLQSS<br>GLYSLSSVVTVPSSSLGTQTYICNVNHKPSNTKVDKRVEPKSCTC<br>PPCPAPELLGGPSVFLFPPKPKDTLMISRTPEVTCVVVDVSHEDP<br>EVKFNWYVDGVEVHNAKTKPREEQYNSTYRVVSVLTVLHQDW<br>LNGKEYKCKVSNKALPAPIEKTISKAKGQPREPQVYTLPPSRDEL<br>TKNQVSLTCLVKGFYPSDIAVEWESNGQPENNYKTTPPVLDSDG<br>SFFLYSKLTVDKSRWQQGNVFSCSVMHEALHNHYTQKSLSLSP<br>GKAHGRPHOFKROCKAHOVKHILKRTOSHOYKOVHORNKOAO<br>KMRKIRGGHK | 486 |
| | | LC | "HA15" LC | 447 |
| NA1-hIgG-6H | NA | HC | QVQLQESGPGLVRPSETLSLTCTVSGDSIGGSYWNWIRQPPGKG<br>LQWIGYIYYTGITNYNPSLKSRVTMSLDTSKNQISLKMDSVTAA<br>DTALYFCARGDYSGYDRDVQVELMDVWGKGTTVTVSSSVFPL<br>APSSKSTSGGTAALGCLVKDYFPEPVTVSWNSGALTSGVHTFPA<br>VLQSSGLYSLSSVVTVPSSSLGTQTYICNVNHKPSNTKVDKRVE<br>PKSCTCPPCPAPELLGGPSVFLFPPKPKDTLMISRTPEVTCVVVD<br>VSHEDPEVKFNWYVDGVEVHNAKTKPREEQYNSTYRVVSVLT<br>VLHQDWLNGKEYKCKVSNKALPAPIEKTISKAKGQPREPQVYT<br>LPPSRDELTKNQVSLTCLVKGFYPSDIAVEWESNGQPENNYKTT<br>PPVLDSDGSFFLYSKLTVDKSRWQQGNVFSCSVMHEALHNHYT<br>QKSLSLSPGKHHHHHH | 259 |
| | | LC | DIQMTQSPSSLSASVRDKVTFVCRASQTISIFLNWYQHKPGEAPK<br>LLIYAASRLQSGVPSRFSGSGSGTDFTLTISGLQPEDFATYYCQQ<br>SYSAPWTFGQGTKVEIKGQPKANPTVTLFPPSSEELQANKATLV<br>CLISDFYPGAVTVAWKADGSPVKAGVETTKPSKQSNNKYAASS<br>YLSLTPEQWKSHRSYSCQVTHEGSTVEKTVAPTECS | 260 |
| NA1-hIgG-12H | NA | HC | QVQLQESGPGLVRPSETLSLTCTVSGDSIGGSYWNWIRQPPGKG<br>LOWIGYIYYTGITNYNPSLKSRVTMSLDTSKNQISLKMDSVTAA<br>DTALYFCARGDYSGYDRDVQVELMDVWGKGTTVTVSSSVFPL<br>APSSKSTSGGTAALGCLVKDYFPEPVTVSWNSGALTSGVHTFPA<br>VLQSSGLYSLSSVVTVPSSSLGTQTYICNVNHKPSNTKVDKRVE<br>PKSCTCPPCPAPELLGGPSVFLFPPKPKDTLMISRTPEVTCVVVD<br>VSHEDPEVKFNWYVDGVEVHNAKTKPREEQYNSTYRVVSVLT<br>VLHQDWLNGKEYKCKVSNKALPAPIEKTISKAKGQPREPQVYT<br>LPPSRDELTKNQVSLTCLVKGFYPSDIAVEWESNGQPENNYKTT<br>PPVLDSDGSFFLYSKLTVDKSRWQQGNVFSCSVMHEALHNHYT<br>QKSLSLSPGKHHHHHHHHHHHH | 261 |
| | | LC | "NA1" LC | 260 |
| NA1-hIgG-30H | NA | HC | QVQLQESGPGLVRPSETLSLTCTVSGDSIGGSYWNWIRQPPGKG<br>LOWIGYIYYTGITNYNPSLKSRVTMSLDTSKNQISLKMDSVTAA<br>DTALYFCARGDYSGYDRDVQVELMDVWGKGTTVTVSSSVFPL<br>APSSKSTSGGTAALGCLVKDYFPEPVTVSWNSGALTSGVHTFPA<br>VLQSSGLYSLSSVVTVPSSSLGTQTYICNVNHKPSNTKVDKRVE<br>PKSCTCPPCPAPELLGGPSVFLFPPKPKDTLMISRTPEVTCVVVD<br>VSHEDPEVKFNWYVDGVEVHNAKTKPREEQYNSTYRVVSVLT<br>VLHQDWLNGKEYKCKVSNKALPAPIEKTISKAKGQPREPQVYT<br>LPPSRDELTKNQVSLTCLVKGFYPSDIAVEWESNGQPENNYKTT<br>PPVLDSDGSFFLYSKLTVDKSRWQQGNVFSCSVMHEALHNHYT<br>QKSLSLSPGKHHHHHHHHHHHHHHHHHHHHHHHHHHHHHH | 262 |
| | | LC | "NA1" LC | 260 |
| NA1-hIgG-6K | NA | HC | QVQLQESGPGLVRPSETLSLTCTVSGDSIGGSYWNWIRQPPGKG<br>LOWIGYIYYTGITNYNPSLKSRVTMSLDTSKNQISLKMDSVTAA<br>DTALYFCARGDYSGYDRDVQVELMDVWGKGTTVTVSSSVFPL | 263 |

TABLE 1-continued

Exemplary anti-influenza chimeric proteins

| Chimeric Protein | Anti-gen | HC / LC | Sequence (mucoadhesive peptide fragment is underlined) | SEQ ID NO |
|---|---|---|---|---|
| | | | APSSKSTSGGTAALGCLVKDYFPEPVTVSWNSGALTSGVHTFPA<br>VLQSSGLYSLSSVVTVPSSSLGTQTYICNVNHKPSNTKVDKRVE<br>PKSCTCPPCPAPELLGGPSVFLFPPKPKDTLMISRTPEVTCVVVD<br>VSHEDPEVKFNWYVDGVEVHNAKTKPREEQYNSTYRVVSVLT<br>VLHQDWLNGKEYKCKVSNKALPAPIEKTISKAKGQPREPQVYT<br>LPPSRDELTKNQVSLTCLVKGFYPSDIAVEWESNGQPENNYKTT<br>PPVLDSDGSFFLYSKLTVDKSRWQQGNVFSCSVMHEALHNHYT<br>QKSLSLSPGKKKKKKK | |
| | | LC | "NA1" LC | 260 |
| NA1-hIgG-12K | NA | HC | QVQLQESGPGLVRPSETLSLTCTVSGDSIGGSYWNWIRQPPGKG<br>LQWIGYIYYTGITNYNPSLKSRVTMSLDTSKNQISLKMDSVTAA<br>DTALYFCARGDYSGYDRDVQVELMDVWGKGTTVTVSSSVFPL<br>APSSKSTSGGTAALGCLVKDYFPEPVTVSWNSGALTSGVHTFPA<br>VLQSSGLYSLSSVVTVPSSSLGTQTYICNVNHKPSNTKVDKRVE<br>PKSCTCPPCPAPELLGGPSVFLFPPKPKDTLMISRTPEVTCVVVD<br>VSHEDPEVKFNWYVDGVEVHNAKTKPREEQYNSTYRVVSVLT<br>VLHQDWLNGKEYKCKVSNKALPAPIEKTISKAKGQPREPQVYT<br>LPPSRDELTKNQVSLTCLVKGFYPSDIAVEWESNGQPENNYKTT<br>PPVLDSDGSFFLYSKLTVDKSRWQQGNVFSCSVMHEALHNHYT<br>QKSLSLSPGKGGGGSKKKKKKKKKKKK | 264 |
| | | LC | "NA1" LC | 260 |
| NA1-hIgG-30K | NA | HC | QVQLQESGPGLVRPSETLSLTCTVSGDSIGGSYWNWIRQPPGKG<br>LQWIGYIYYTGITNYNPSLKSRVTMSLDTSKNQISLKMDSVTAA<br>DTALYFCARGDYSGYDRDVQVELMDVWGKGTTVTVSSSVFPL<br>APSSKSTSGGTAALGCLVKDYFPEPVTVSWNSGALTSGVHTFPA<br>VLQSSGLYSLSSVVTVPSSSLGTQTYICNVNHKPSNTKVDKRVE<br>PKSCTCPPCPAPELLGGPSVFLFPPKPKDTLMISRTPEVTCVVVD<br>VSHEDPEVKFNWYVDGVEVHNAKTKPREEQYNSTYRVVSVLT<br>VLHQDWLNGKEYKCKVSNKALPAPIEKTISKAKGQPREPQVYT<br>LPPSRDELTKNQVSLTCLVKGFYPSDIAVEWESNGQPENNYKTT<br>PPVLDSDGSFFLYSKLTVDKSRWQQGNVFSCSVMHEALHNHYT<br>QKSLSLSPGKKKKKKKKKKKKKKKKKKKKKKKKKKKKKK | 265 |
| | | LC | "NA1" LC | 260 |
| NA1-hIgG-6R | NA | HC | QVQLQESGPGLVRPSETLSLTCTVSGDSIGGSYWNWIRQPPGKG<br>LQWIGYIYYTGITNYNPSLKSRVTMSLDTSKNQISLKMDSVTAA<br>DTALYFCARGDYSGYDRDVQVELMDVWGKGTTVTVSSSVFPL<br>APSSKSTSGGTAALGCLVKDYFPEPVTVSWNSGALTSGVHTFPA<br>VLQSSGLYSLSSVVTVPSSSLGTQTYICNVNHKPSNTKVDKRVE<br>PKSCTCPPCPAPELLGGPSVFLFPPKPKDTLMISRTPEVTCVVVD<br>VSHEDPEVKFNWYVDGVEVHNAKTKPREEQYNSTYRVVSVLT<br>VLHQDWLNGKEYKCKVSNKALPAPIEKTISKAKGQPREPQVYT<br>LPPSRDELTKNQVSLTCLVKGFYPSDIAVEWESNGQPENNYKTT<br>PPVLDSDGSFFLYSKLTVDKSRWQQGNVFSCSVMHEALHNHYT<br>QKSLSLSPGKRRRRRR | 266 |
| | | LC | "NA1" LC | 260 |
| NA1-hIgG-12R | NA | HC | QVQLQESGPGLVRPSETLSLTCTVSGDSIGGSYWNWIRQPPGKG<br>LQWIGYIYYTGITNYNPSLKSRVTMSLDTSKNQISLKMDSVTAA<br>DTALYFCARGDYSGYDRDVQVELMDVWGKGTTVTVSSSVFPL<br>APSSKSTSGGTAALGCLVKDYFPEPVTVSWNSGALTSGVHTFPA<br>VLQSSGLYSLSSVVTVPSSSLGTQTYICNVNHKPSNTKVDKRVE<br>PKSCTCPPCPAPELLGGPSVFLFPPKPKDTLMISRTPEVTCVVVD<br>VSHEDPEVKFNWYVDGVEVHNAKTKPREEQYNSTYRVVSVLT<br>VLHQDWLNGKEYKCKVSNKALPAPIEKTISKAKGQPREPQVYT<br>LPPSRDELTKNQVSLTCLVKGFYPSDIAVEWESNGQPENNYKTT<br>PPVLDSDGSFFLYSKLTVDKSRWQQGNVFSCSVMHEALHNHYT<br>QKSLSLSPGKRRRRRRRRRRRR | 267 |
| | | LC | "NA1" LC | 260 |
| NA1-hIgG-30R | NA | HC | QVQLQESGPGLVRPSETLSLTCTVSGDSIGGSYWNWIRQPPGKG<br>LQWIGYIYYTGITNYNPSLKSRVTMSLDTSKNQISLKMDSVTAA<br>DTALYFCARGDYSGYDRDVQVELMDVWGKGTTVTVSSSVFPL<br>APSSKSTSGGTAALGCLVKDYFPEPVTVSWNSGALTSGVHTFPA<br>VLQSSGLYSLSSVVTVPSSSLGTQTYICNVNHKPSNTKVDKRVE<br>PKSCTCPPCPAPELLGGPSVFLFPPKPKDTLMISRTPEVTCVVVD<br>VSHEDPEVKFNWYVDGVEVHNAKTKPREEQYNSTYRVVSVLT<br>VLHQDWLNGKEYKCKVSNKALPAPIEKTISKAKGQPREPQVYT<br>LPPSRDELTKNQVSLTCLVKGFYPSDIAVEWESNGQPENNYKTT<br>PPVLDSDGSFFLYSKLTVDKSRWQQGNVFSCSVMHEALHNHYT<br>QKSLSLSPGKRRRRRRRRRRRRRRRRRRRRRRRRRRRRRR | 268 |
| | | LC | "NA1" LC | 260 |

TABLE 1-continued

Exemplary anti-influenza chimeric proteins

| Chimeric Protein | Antigen | HC / LC | Sequence (mucoadhesive peptide fragment is underlined) | SEQ ID NO |
|---|---|---|---|---|
| NA1-hIgG-6O | NA | HC | QVQLQESGPGLVRPSETLSLTCTVSGDSIGGSYWNWIRQPPGKG LQWIGYIYYTGITNYNPSLKSRVTMSLDTSKNQISLKMDSVTAA DTALYFCARGDYSGYDRDVQVELMDVWGKGTTVTVSSSVFPL APSSKSTSGGTAALGCLVKDYFPEPVTVSWNSGALTSGVHTFPA VLQSSGLYSLSSVVTVPSSSLGTQTYICNVNHKPSNTKVDKRVE PKSCTCPPCPAPELLGGPSVFLFPPKPKDTLMISRTPEVTCVVVD VSHEDPEVKFNWYVDGVEVHNAKTKPREEQYNSTYRVVSVLT VLHQDWLNGKEYKCKVSNKALPAPIEKTISKAKGQPREPQVYT LPPSRDELTKNQVSLTCLVKGFYPSDIAVEWESNGQPENNYKTT PPVLDSDGSFFLYSKLTVDKSRWQQGNVFSCSVMHEALHNHYT QKSLSLSPGKOOOOOO | 269 |
| | | LC | "NA1" LC | 260 |
| NA1-hIgG-12O | NA | HC | QVQLQESGPGLVRPSETLSLTCTVSGDSIGGSYWNWIRQPPGKG LOWIGYIYYTGITNYNPSLKSRVTMSLDTSKNQISLKMDSVTAA DTALYFCARGDYSGYDRDVQVELMDVWGKGTTVTVSSSVFPL APSSKSTSGGTAALGCLVKDYFPEPVTVSWNSGALTSGVHTFPA VLQSSGLYSLSSVVTVPSSSLGTQTYICNVNHKPSNTKVDKRVE PKSCTCPPCPAPELLGGPSVFLFPPKPKDTLMISRTPEVTCVVVD VSHEDPEVKFNWYVDGVEVHNAKTKPREEQYNSTYRVVSVLT VLHQDWLNGKEYKCKVSNKALPAPIEKTISKAKGQPREPQVYT LPPSRDELTKNQVSLTCLVKGFYPSDIAVEWESNGQPENNYKTT PPVLDSDGSFFLYSKLTVDKSRWQQGNVFSCSVMHEALHNHYT QKSLSLSPGKOOOOOOOOOOOO | 270 |
| | | LC | "NA1" LC | 260 |
| NA1-hIgG-30O | NA | HC | QVQLQESGPGLVRPSETLSLTCTVSGDSIGGSYWNWIRQPPGKG LOWIGYIYYTGITNYNPSLKSRVTMSLDTSKNQISLKMDSVTAA DTALYFCARGDYSGYDRDVQVELMDVWGKGTTVTVSSSVFPL APSSKSTSGGTAALGCLVKDYFPEPVTVSWNSGALTSGVHTFPA VLQSSGLYSLSSVVTVPSSSLGTQTYICNVNHKPSNTKVDKRVE PKSCTCPPCPAPELLGGPSVFLFPPKPKDTLMISRTPEVTCVVVD VSHEDPEVKFNWYVDGVEVHNAKTKPREEQYNSTYRVVSVLT VLHQDWLNGKEYKCKVSNKALPAPIEKTISKAKGQPREPQVYT LPPSRDELTKNQVSLTCLVKGFYPSDIAVEWESNGQPENNYKTT PPVLDSDGSFFLYSKLTVDKSRWQQGNVFSCSVMHEALHNHYT QKSLSLSPGKGOOOOOOOOOOOOOOOOOOOOOOOOOOOOOO | 271 |
| | | LC | "NA1" LC | 260 |
| NA1-hIgG-6X-5 | NA | HC | QVQLQESGPGLVRPSETLSLTCTVSGDSIGGSYWNWIRQPPGKG LQWIGYIYYTGITNYNPSLKSRVTMSLDTSKNQISLKMDSVTAA DTALYFCARGDYSGYDRDVQVELMDVWGKGTTVTVSSSVFPL APSSKSTSGGTAALGCLVKDYFPEPVTVSWNSGALTSGVHTFPA VLQSSGLYSLSSVVTVPSSSLGTQTYICNVNHKPSNTKVDKRVE PKSCTCPPCPAPELLGGPSVFLFPPKPKDTLMISRTPEVTCVVVD VSHEDPEVKFNWYVDGVEVHNAKTKPREEQYNSTYRVVSVLT VLHQDWLNGKEYKCKVSNKALPAPIEKTISKAKGQPREPQVYT LPPSRDELTKNQVSLTCLVKGFYPSDIAVEWESNGQPENNYKTT PPVLDSDGSFFLYSKLTVDKSRWQQGNVFSCSVMHEALHNHYT QKSLSLSPGKKKHHRR | 272 |
| | | LC | "NA1" LC | 260 |
| NA1-hIgG-12X-5 | NA | HC | QVQLQESGPGLVRPSETLSLTCTVSGDSIGGSYWNWIRQPPGKG LQWIGYIYYTGITNYNPSLKSRVTMSLDTSKNQISLKMDSVTAA DTALYFCARGDYSGYDRDVQVELMDVWGKGTTVTVSSSVFPL APSSKSTSGGTAALGCLVKDYFPEPVTVSWNSGALTSGVHTFPA VLQSSGLYSLSSVVTVPSSSLGTQTYICNVNHKPSNTKVDKRVE PKSCTCPPCPAPELLGGPSVFLFPPKPKDTLMISRTPEVTCVVVD VSHEDPEVKFNWYVDGVEVHNAKTKPREEQYNSTYRVVSVLT VLHQDWLNGKEYKCKVSNKALPAPIEKTISKAKGQPREPQVYT LPPSRDELTKNQVSLTCLVKGFYPSDIAVEWESNGQPENNYKTT PPVLDSDGSFFLYSKLTVDKSRWQQGNVFSCSVMHEALHNHYT QKSLSLSPGKKKRROOHHRRR | 273 |
| | | LC | "NA1" LC | 260 |
| NA1-hIgG-30X-1 | NA | HC | QVQLQESGPGLVRPSETLSLTCTVSGDSIGGSYWNWIRQPPGKG LQWIGYIYYTGITNYNPSLKSRVTMSLDTSKNQISLKMDSVTAA DTALYFCARGDYSGYDRDVQVELMDVWGKGTTVTVSSSVFPL APSSKSTSGGTAALGCLVKDYFPEPVTVSWNSGALTSGVHTFPA VLQSSGLYSLSSVVTVPSSSLGTQTYICNVNHKPSNTKVDKRVE PKSCTCPPCPAPELLGGPSVFLFPPKPKDTLMISRTPEVTCVVVD VSHEDPEVKFNWYVDGVEVHNAKTKPREEQYNSTYRVVSVLT | 274 |

TABLE 1-continued

Exemplary anti-influenza chimeric proteins

| Chimeric Protein | Anti-gen | HC / LC | Sequence (mucoadhesive peptide fragment is underlined) | SEQ ID NO |
|---|---|---|---|---|
| | | | VLHQDWLNGKEYKCKVSNKALPAPIEKTISKAKGQPREPQVYT<br>LPPSRDELTKNQVSLTCLVKGFYPSDIAVEWESNGQPENNYKTT<br>PPVLDSDGSFFLYSKLTVDKSRWQQGNVFSCSVMHEALHNHYT<br>QKSLSLSPGKHKROHKROHKROHKROHKROHKROHKROHK | |
| | | LC | "NA1" LC | 260 |
| NA1-hIgG-5H | NA | HC | QVQLQESGPGLVRPSETLSLTCTVSGDSIGGSYWNWIRQPPGKG<br>LQWIGYIYYTGITNYNPSLKSRVTMSLDTSKNQISLKMDSVTAA<br>DTALYFCARGDYSGYDRDVQVELMDVWGKGTTVTVSSSVFPL<br>APSSKSTSGGTAALGCLVKDYFPEPVTVSWNSGALTSGVHTFPA<br>VLQSSGLYSLSSVVTVPSSSLGTQTYICNVNHKPSNTKVDKRVEP<br>KSCTCPPCPAPELLGGPSVFLFPPKPKDTLMISRTPEVTCVVVDV<br>SHEDPEVKFNWYVDGVEVHNAKTKPREEQYNSTYRVVSVLTVL<br>HQDWLNGKEYKCKVSNKALPAPIEKTISKAKGQPREPQVYTLPP<br>SRDELTKNQVSLTCLVKGFYPSDIAVEWESNGQPENNYKTTPPV<br>LDSDGSFFLYSKLTVDKSRWQQGNVFSCSVMHEALHNHYTQKS<br>LSLSPGKHHHHH | 428 |
| | | LC | "NA1" LC | 260 |
| NA1-hIgG-7X-1 | NA | HC | QVQLQESGPGLVRPSETLSLTCTVSGDSIGGSYWNWIRQPPGKG<br>LQWIGYIYYTGITNYNPSLKSRVTMSLDTSKNQISLKMDSVTAA<br>DTALYFCARGDYSGYDRDVQVELMDVWGKGTTVTVSSSVFPL<br>APSSKSTSGGTAALGCLVKDYFPEPVTVSWNSGALTSGVHTFPA<br>VLQSSGLYSLSSVVTVPSSSLGTQTYICNVNHKPSNTKVDKRVEP<br>KSCTCPPCPAPELLGGPSVFLFPPKPKDTLMISRTPEVTCVVVDV<br>SHEDPEVKFNWYVDGVEVHNAKTKPREEQYNSTYRVVSVLTVL<br>HQDWLNGKEYKCKVSNKALPAPIEKTISKAKGQPREPQVYTLPP<br>SRDELTKNQVSLTCLVKGFYPSDIAVEWESNGQPENNYKTTPPV<br>LDSDGSFFLYSKLTVDKSRWQQGNVFSCSVMHEALHNHYTQKS<br>LSLSPGKKKKGKKK | 429 |
| | | LC | "NA1" LC | 260 |
| NA1-hIgG-12X-7 | NA | HC | QVQLQESGPGLVRPSETLSLTCTVSGDSIGGSYWNWIRQPPGKG<br>LQWIGYIYYTGITNYNPSLKSRVTMSLDTSKNQISLKMDSVTAA<br>DTALYFCARGDYSGYDRDVQVELMDVWGKGTTVTVSSSVFPL<br>APSSKSTSGGTAALGCLVKDYFPEPVTVSWNSGALTSGVHTFPA<br>VLQSSGLYSLSSVVTVPSSSLGTQTYICNVNHKPSNTKVDKRVEP<br>KSCTCPPCPAPELLGGPSVFLFPPKPKDTLMISRTPEVTCVVVDV<br>SHEDPEVKFNWYVDGVEVHNAKTKPREEQYNSTYRVVSVLTVL<br>HQDWLNGKEYKCKVSNKALPAPIEKTISKAKGQPREPQVYTLPP<br>SRDELTKNQVSLTCLVKGFYPSDIAVEWESNGQPENNYKTTPPV<br>LDSDGSFFLYSKLTVDKSRWQQGNVFSCSVMHEALHNHYTQKS<br>LSLSPGKKKAHHGKKAHHV | 430 |
| | | LC | "NA1" LC | 260 |
| NA1-hIgG-12X-8 | NA | HC | QVQLQESGPGLVRPSETLSLTCTVSGDSIGGSYWNWIRQPPGKG<br>LQWIGYIYYTGITNYNPSLKSRVTMSLDTSKNQISLKMDSVTAA<br>DTALYFCARGDYSGYDRDVQVELMDVWGKGTTVTVSSSVFPL<br>APSSKSTSGGTAALGCLVKDYFPEPVTVSWNSGALTSGVHTFPA<br>VLQSSGLYSLSSVVTVPSSSLGTQTYICNVNHKPSNTKVDKRVEP<br>KSCTCPPCPAPELLGGPSVFLFPPKPKDTLMISRTPEVTCVVVDV<br>SHEDPEVKFNWYVDGVEVHNAKTKPREEQYNSTYRVVSVLTVL<br>HQDWLNGKEYKCKVSNKALPAPIEKTISKAKGQPREPQVYTLPP<br>SRDELTKNQVSLTCLVKGFYPSDIAVEWESNGQPENNYKTTPPV<br>LDSDGSFFLYSKLTVDKSRWQQGNVFSCSVMHEALHNHYTQKS<br>LSLSPGKKKARRGKKARRV | 431 |
| | | LC | "NA1" LC | 260 |
| NA2-hIgG-6H | NA | HC | EVQLVQSGAEVKKPGSSVKVSCKASGYTFINHALSWVRQAPGQ<br>GLEWVGGIIPIFGLAKYGQKFQDRVTITADESTKTAYMDLRSLR<br>SDDTAVYYCARDTVAVYEDFDWSSPYFFYMDVWGKGTTVTVS<br>SSVFPLAPSSKSTSGGTAALGCLVKDYFPEPVTVSWNSGALTSG<br>VHTFPAVLQSSGLYSLSSVVTVPSSSLGTQTYICNVNHKPSNTKV<br>DKRVEPKSCTCPPCPAPELLGGPSVFLFPPKPKDTLMISRTPEVTC<br>VVVDVSHEDPEVKFNWYVDGVEVHNAKTKPREEQYNSTYRVV<br>SVLTVLHQDWLNGKEYKCKVSNKALPAPIEKTISKAKGQPREPQ<br>VYTLPPSRDELTKNQVSLTCLVKGFYPSDIAVEWESNGQPENNY<br>KTTPPVLDSDGSFFLYSKLTVDKSRWQQGNVFSCSVMHEALHN<br>HYTQKSLSLSPGKHHHHHH | 275 |
| | | LC | EIVLTQSPATLSLFPGERATLSCRASQSAGSKSLAWYQHKVGQP<br>PRLLINGASSRATGIPDRESGSGSGPDFNLTISRLEPEDFAVYYCQ<br>RYGTSLVTFGGGTKVEIKGQPKANPTVTLFPPSSEELQANKATL<br>VCLISDFYPGAVTVAWKADGSPVKAGVETTKPSKQSNNKYAAS<br>SYLSLTPEQWKSHRSYSCQVTHEGSTVEKTVAPTECS | 276 |

TABLE 1-continued

| Exemplary anti-influenza chimeric proteins | | | | |
|---|---|---|---|---|
| Chimeric Protein | Anti-gen | HC / LC | Sequence (mucoadhesive peptide fragment is underlined) | SEQ ID NO |
| NA2-hIgG-12H | NA | HC | EVQLVQSGAEVKKPGSSVKVSCKASGYTFINHALSWVRQAPGQ<br>GLEWVGGIIPIFGLAKYGQKFQDRVTITADESTKTAYMDLRSLR<br>SDDTAVYYCARDTVAVYEDFDWSSPYFFYMDVWGKGTTVTVS<br>SSVFPLAPSSKSTSGGTAALGCLVKDYFPEPVTVSWNSGALTSG<br>VHTFPAVLQSSGLYSLSSVVTVPSSSLGTQTYICNVNHKPSNTKV<br>DKRVEPKSCTCPPCPAPELLGGPSVFLFPPKPKDTLMISRTPEVTC<br>VVVDVSHEDPEVKFNWYVDGVEVHNAKTKPREEQYNSTYRVV<br>SVLTVLHQDWLNGKEYKCKVSNKALPAPIEKTISKAKGQPREPQ<br>VYTLPPSRDELTKNQVSLTCLVKGFYPSDIAVEWESNGQPENNY<br>KTTPPVLDSDGSFFLYSKLTVDKSRWQQGNVFSCSVMHEALHN<br>HYTQKSLSLSPGKHHHHHHHHHHHH | 277 |
| | | LC | "NA2" LC | 276 |
| NA2-hIgG-30H | NA | HC | EVQLVQSGAEVKKPGSSVKVSCKASGYTFINHALSWVRQAPGQ<br>GLEWVGGIIPIFGLAKYGQKFQDRVTITADESTKTAYMDLRSLR<br>SDDTAVYYCARDTVAVYEDFDWSSPYFFYMDVWGKGTTVTVS<br>SSVFPLAPSSKSTSGGTAALGCLVKDYFPEPVTVSWNSGALTSG<br>VHTFPAVLQSSGLYSLSSVVTVPSSSLGTQTYICNVNHKPSNTKV<br>DKRVEPKSCTCPPCPAPELLGGPSVFLFPPKPKDTLMISRTPEVTC<br>VVVDVSHEDPEVKFNWYVDGVEVHNAKTKPREEQYNSTYRVV<br>SVLTVLHQDWLNGKEYKCKVSNKALPAPIEKTISKAKGQPREPQ<br>VYTLPPSRDELTKNQVSLTCLVKGFYPSDIAVEWESNGQPENNY<br>KTTPPVLDSDGSFFLYSKLTVDKSRWQQGNVFSCSVMHEALHN<br>HYTQKSLSLSPGKHHHHHHHHHHHHHHHHHHHHHHHHHHHH<br>HH | 278 |
| | | LC | "NA2" LC | 276 |
| NA2-hIgG-6K | NA | HC | EVQLVQSGAEVKKPGSSVKVSCKASGYTFINHALSWVRQAPGQ<br>GLEWVGGIIPIFGLAKYGQKFQDRVTITADESTKTAYMDLRSLR<br>SDDTAVYYCARDTVAVYEDFDWSSPYFFYMDVWGKGTTVTVS<br>SSVFPLAPSSKSTSGGTAALGCLVKDYFPEPVTVSWNSGALTSG<br>VHTFPAVLQSSGLYSLSSVVTVPSSSLGTQTYICNVNHKPSNTKV<br>DKRVEPKSCTCPPCPAPELLGGPSVFLFPPKPKDTLMISRTPEVTC<br>VVVDVSHEDPEVKFNWYVDGVEVHNAKTKPREEQYNSTYRVV<br>SVLTVLHQDWLNGKEYKCKVSNKALPAPIEKTISKAKGQPREPQ<br>VYTLPPSRDELTKNQVSLTCLVKGFYPSDIAVEWESNGQPENNY<br>KTTPPVLDSDGSFFLYSKLTVDKSRWQQGNVFSCSVMHEALHN<br>HYTQKSLSLSPGKKKKKKK | 279 |
| | | LC | "NA2" LC | 276 |
| NA2-hIgG-12K | NA | HC | EVQLVQSGAEVKKPGSSVKVSCKASGYTFINHALSWVRQAPGQ<br>GLEWVGGIIPIFGLAKYGQKFQDRVTITADESTKTAYMDLRSLR<br>SDDTAVYYCARDTVAVYEDFDWSSPYFFYMDVWGKGTTVTVS<br>SSVFPLAPSSKSTSGGTAALGCLVKDYFPEPVTVSWNSGALTSG<br>VHTFPAVLQSSGLYSLSSVVTVPSSSLGTQTYICNVNHKPSNTKV<br>DKRVEPKSCTCPPCPAPELLGGPSVFLFPPKPKDTLMISRTPEVTC<br>VVVDVSHEDPEVKFNWYVDGVEVHNAKTKPREEQYNSTYRVV<br>SVLTVLHQDWLNGKEYKCKVSNKALPAPIEKTISKAKGQPREPQ<br>VYTLPPSRDELTKNQVSLTCLVKGFYPSDIAVEWESNGQPENNY<br>KTTPPVLDSDGSFFLYSKLTVDKSRWQQGNVFSCSVMHEALHN<br>HYTQKSLSLSPGKGGGGSKKKKKKKKKKKK | 280 |
| | | LC | "NA2" LC | 276 |
| NA2-hIgG-30K | NA | HC | EVQLVQSGAEVKKPGSSVKVSCKASGYTFINHALSWVRQAPGQ<br>GLEWVGGIIPIFGLAKYGQKFQDRVTITADESTKTAYMDLRSLR<br>SDDTAVYYCARDTVAVYEDFDWSSPYFFYMDVWGKGTTVTVS<br>SSVFPLAPSSKSTSGGTAALGCLVKDYFPEPVTVSWNSGALTSG<br>VHTFPAVLQSSGLYSLSSVVTVPSSSLGTQTYICNVNHKPSNTKV<br>DKRVEPKSCTCPPCPAPELLGGPSVFLFPPKPKDTLMISRTPEVTC<br>VVVDVSHEDPEVKFNWYVDGVEVHNAKTKPREEQYNSTYRVV<br>SVLTVLHQDWLNGKEYKCKVSNKALPAPIEKTISKAKGQPREPQ<br>VYTLPPSRDELTKNQVSLTCLVKGFYPSDIAVEWESNGQPENNY<br>KTTPPVLDSDGSFFLYSKLTVDKSRWQQGNVFSCSVMHEALHN<br>HYTQKSLSLSPGKKKKKKKKKKKKKKKKKKKKKKKKKKKKK<br>KK | 281 |
| | | LC | "NA2" LC | 276 |
| NA2-hIgG-6R | NA | HC | EVQLVQSGAEVKKPGSSVKVSCKASGYTFINHALSWVRQAPGQ<br>GLEWVGGIIPIFGLAKYGQKFQDRVTITADESTKTAYMDLRSLR<br>SDDTAVYYCARDTVAVYEDFDWSSPYFFYMDVWGKGTTVTVS<br>SSVFPLAPSSKSTSGGTAALGCLVKDYFPEPVTVSWNSGALTSG<br>VHTFPAVLQSSGLYSLSSVVTVPSSSLGTQTYICNVNHKPSNTKV<br>DKRVEPKSCTCPPCPAPELLGGPSVFLFPPKPKDTLMISRTPEVTC | 282 |

TABLE 1-continued

Exemplary anti-influenza chimeric proteins

| Chimeric Protein | Anti-gen | HC / LC | Sequence (mucoadhesive peptide fragment is underlined) | SEQ ID NO |
|---|---|---|---|---|
| | | | VVVDVSHEDPEVKFNWYVDGVEVHNAKTKPREEQYNSTYRVV<br>SVLTVLHQDWLNGKEYKCKVSNKALPAPIEKTISKAKGQPREPQ<br>VYTLPPSRDELTKNQVSLTCLVKGFYPSDIAVEWESNGQPENNY<br>KTTPPVLDSDGSFFLYSKLTVDKSRWQQGNVFSCSVMHEALHN<br>HYTQKSLSLSPGKRRRRRR | |
| | | LC | "NA2" LC | 276 |
| NA2-hIgG-12R | NA | HC | EVQLVQSGAEVKKPGSSVKVSCKASGYTFINHALSWVRQAPGQ<br>GLEWVGGIIPIFGLAKYGQKFQDRVTITADESTKTAYMDLRSLR<br>SDDTAVYYCARDTVAVYEDFDWSSPYFFYMDVWGKGTTVTVS<br>SSVFPLAPSSKSTSGGTAALGCLVKDYFPEPVTVSWNSGALTSG<br>VHTFPAVLQSSGLYSLSSVVTVPSSSLGTQTYICNVNHKPSNTKV<br>DKRVEPKSCTCPPCPAPELLGGPSVFLFPPKPKDTLMISRTPEVTC<br>VVVDVSHEDPEVKFNWYVDGVEVHNAKTKPREEQYNSTYRVV<br>SVLTVLHQDWLNGKEYKCKVSNKALPAPIEKTISKAKGQPREPQ<br>VYTLPPSRDELTKNQVSLTCLVKGFYPSDIAVEWESNGQPENNY<br>KTTPPVLDSDGSFFLYSKLTVDKSRWQQGNVFSCSVMHEALHN<br>HYTQKSLSLSPGKRRRRRRRRRRRR | 283 |
| | | LC | "NA2" LC | 276 |
| NA2-hIgG-30R | NA | HC | EVQLVQSGAEVKKPGSSVKVSCKASGYTFINHALSWVRQAPGQ<br>GLEWVGGIIPIFGLAKYGQKFQDRVTITADESTKTAYMDLRSLR<br>SDDTAVYYCARDTVAVYEDFDWSSPYFFYMDVWGKGTTVTVS<br>SSVFPLAPSSKSTSGGTAALGCLVKDYFPEPVTVSWNSGALTSG<br>VHTFPAVLQSSGLYSLSSVVTVPSSSLGTQTYICNVNHKPSNTKV<br>DKRVEPKSCTCPPCPAPELLGGPSVFLFPPKPKDTLMISRTPEVTC<br>VVVDVSHEDPEVKFNWYVDGVEVHNAKTKPREEQYNSTYRVV<br>SVLTVLHQDWLNGKEYKCKVSNKALPAPIEKTISKAKGQPREPQ<br>VYTLPPSRDELTKNQVSLTCLVKGFYPSDIAVEWESNGQPENNY<br>KTTPPVLDSDGSFFLYSKLTVDKSRWQQGNVFSCSVMHEALHN<br>HYTQKSLSLSPGKRRRRRRRRRRRRRRRRRRRRRRRRRRRRRR | 284 |
| | | LC | "NA2" LC | 276 |
| NA2-hIgG-6O | NA | HC | EVQLVQSGAEVKKPGSSVKVSCKASGYTFINHALSWVRQAPGQ<br>GLEWVGGIIPIFGLAKYGQKFQDRVTITADESTKTAYMDLRSLR<br>SDDTAVYYCARDTVAVYEDFDWSSPYFFYMDVWGKGTTVTVS<br>SSVFPLAPSSKSTSGGTAALGCLVKDYFPEPVTVSWNSGALTSG<br>VHTFPAVLQSSGLYSLSSVVTVPSSSLGTQTYICNVNHKPSNTKV<br>DKRVEPKSCTCPPCPAPELLGGPSVFLFPPKPKDTLMISRTPEVTC<br>VVVDVSHEDPEVKFNWYVDGVEVHNAKTKPREEQYNSTYRVV<br>SVLTVLHQDWLNGKEYKCKVSNKALPAPIEKTISKAKGQPREPQ<br>VYTLPPSRDELTKNQVSLTCLVKGFYPSDIAVEWESNGQPENNY<br>KTTPPVLDSDGSFFLYSKLTVDKSRWQQGNVFSCSVMHEALHN<br>HYTQKSLSLSPGKOOOOOO | 285 |
| | | LC | "NA2" LC | 276 |
| NA2-hIgG-12O | NA | HC | EVQLVQSGAEVKKPGSSVKVSCKASGYTFINHALSWVRQAPGQ<br>GLEWVGGIIPIFGLAKYGQKFQDRVTITADESTKTAYMDLRSLR<br>SDDTAVYYCARDTVAVYEDFDWSSPYFFYMDVWGKGTTVTVS<br>SSVFPLAPSSKSTSGGTAALGCLVKDYFPEPVTVSWNSGALTSG<br>VHTFPAVLQSSGLYSLSSVVTVPSSSLGTQTYICNVNHKPSNTKV<br>DKRVEPKSCTCPPCPAPELLGGPSVFLFPPKPKDTLMISRTPEVTC<br>VVVDVSHEDPEVKFNWYVDGVEVHNAKTKPREEQYNSTYRVV<br>SVLTVLHQDWLNGKEYKCKVSNKALPAPIEKTISKAKGQPREPQ<br>VYTLPPSRDELTKNQVSLTCLVKGFYPSDIAVEWESNGQPENNY<br>KTTPPVLDSDGSFFLYSKLTVDKSRWQQGNVFSCSVMHEALHN<br>HYTQKSLSLSPGKOOOOOOOOOOOO | 286 |
| | | LC | "NA2" LC | 276 |
| NA2-hIgG-30O | NA | HC | EVQLVQSGAEVKKPGSSVKVSCKASGYTFINHALSWVRQAPGQ<br>GLEWVGGIIPIFGLAKYGQKFQDRVTITADESTKTAYMDLRSLR<br>SDDTAVYYCARDTVAVYEDFDWSSPYFFYMDVWGKGTTVTVS<br>SSVFPLAPSSKSTSGGTAALGCLVKDYFPEPVTVSWNSGALTSG<br>VHTFPAVLQSSGLYSLSSVVTVPSSSLGTQTYICNVNHKPSNTKV<br>DKRVEPKSCTCPPCPAPELLGGPSVFLFPPKPKDTLMISRTPEVTC<br>VVVDVSHEDPEVKFNWYVDGVEVHNAKTKPREEQYNSTYRVV<br>SVLTVLHQDWLNGKEYKCKVSNKALPAPIEKTISKAKGQPREPQ<br>VYTLPPSRDELTKNQVSLTCLVKGFYPSDIAVEWESNGQPENNY<br>KTTPPVLDSDGSFFLYSKLTVDKSRWQQGNVFSCSVMHEALHN<br>HYTQKSLSLSPGKOOOOOOOOOOOOOOOOOOOOOOOOOOOO<br>OO | 287 |
| | | LC | "NA2" LC | 276 |

TABLE 1-continued

Exemplary anti-influenza chimeric proteins

| Chimeric Protein | Antigen | HC / LC | Sequence (mucoadhesive peptide fragment is underlined) | SEQ ID NO |
|---|---|---|---|---|
| NA2-hIgG-6X-6 | NA | HC | EVQLVQSGAEVKKPGSSVKVSCKASGYTFINHALSWVRQAPGQ<br>GLEWVGGIIPIFGLAKYGQKFQDRVTITADESTKTAYMDLRSLR<br>SDDTAVYYCARDTVAVYEDFDWSSPYFFYMDVWGKGTTVTVS<br>SSVFPLAPSSKSTSGGTAALGCLVKDYFPEPVTVSWNSGALTSG<br>VHTFPAVLQSSGLYSLSSVVTVPSSSLGTQTYICNVNHKPSNTKV<br>DKRVEPKSCTCPPCPAPELLGGPSVFLFPPKPKDTLMISRTPEVTC<br>VVVDVSHEDPEVKFNWYVDGVEVHNAKTKPREEQYNSTYRVV<br>SVLTVLHQDWLNGKEYKCKVSNKALPAPIEKTISKAKGQPREPQ<br>VYTLPPSRDELTKNQVSLTCLVKGFYPSDIAVEWESNGQPENNY<br>KTTPPVLDSDGSFFLYSKLTVDKSRWQQGNVFSCSVMHEALHN<br>HYTQKSLSLSPGKOORRHH | 288 |
| | | LC | "NA2" LC | 276 |
| NA2-hIgG-12X-6 | NA | HC | EVQLVQSGAEVKKPGSSVKVSCKASGYTFINHALSWVRQAPGQ<br>GLEWVGGIIPIFGLAKYGQKFQDRVTITADESTKTAYMDLRSLR<br>SDDTAVYYCARDTVAVYEDFDWSSPYFFYMDVWGKGTTVTVS<br>SSVFPLAPSSKSTSGGTAALGCLVKDYFPEPVTVSWNSGALTSG<br>VHTFPAVLQSSGLYSLSSVVTVPSSSLGTQTYICNVNHKPSNTKV<br>DKRVEPKSCTCPPCPAPELLGGPSVFLFPPKPKDTLMISRTPEVTC<br>VVVDVSHEDPEVKFNWYVDGVEVHNAKTKPREEQYNSTYRVV<br>SVLTVLHQDWLNGKEYKCKVSNKALPAPIEKTISKAKGQPREPQ<br>VYTLPPSRDELTKNQVSLTCLVKGFYPSDIAVEWESNGQPENNY<br>KTTPPVLDSDGSFFLYSKLTVDKSRWQQGNVFSCSVMHEALHN<br>HYTQKSLSLSPGKOOORRRKKKHHH | 289 |
| | | LC | "NA2" LC | 276 |
| NA2-hIgG-30X-1 | NA | HC | EVQLVQSGAEVKKPGSSVKVSCKASGYTFINHALSWVRQAPGQ<br>GLEWVGGIIPIFGLAKYGQKFQDRVTITADESTKTAYMDLRSLR<br>SDDTAVYYCARDTVAVYEDFDWSSPYFFYMDVWGKGTTVTVS<br>SSVFPLAPSSKSTSGGTAALGCLVKDYFPEPVTVSWNSGALTSG<br>VHTFPAVLQSSGLYSLSSVVTVPSSSLGTQTYICNVNHKPSNTKV<br>DKRVEPKSCTCPPCPAPELLGGPSVFLFPPKPKDTLMISRTPEVTC<br>VVVDVSHEDPEVKFNWYVDGVEVHNAKTKPREEQYNSTYRVV<br>SVLTVLHQDWLNGKEYKCKVSNKALPAPIEKTISKAKGQPREPQ<br>VYTLPPSRDELTKNQVSLTCLVKGFYPSDIAVEWESNGQPENNY<br>KTTPPVLDSDGSFFLYSKLTVDKSRWQQGNVFSCSVMHEALHN<br>HYTQKSLSLSPGKKROHKROHKROHKROHKROHKROHK | 290 |
| | | LC | "NA2" LC | 276 |
| NA2-hIgG-5H | NA | HC | EVQLVESGAEVKKPGSSVKVSCRASGTFYKYAINWVRQAPGQG<br>LEWMGGIIPFFGTTNYAQKFQGRLTITADGSTNTAYMQLDSLRS<br>EDTAVYYCAGPSITESHYCLDCAAKDYYYGLDVWGQGTTVTVS<br>SSVFPLAPSSKSTSGGTAALGCLVKDYFPEPVTVSWNSGALTSG<br>VHTFPAVLQSSGLYSLSSVVTVPSSSLGTQTYICNVNHKPSNTKV<br>DKRVEPKSCTCPPCPAPELLGGPSVFLFPPKPKDTLMISRTPEVTC<br>VVVDVSHEDPEVKFNWYVDGVEVHNAKTKPREEQYNSTYRVV<br>SVLTVLHQDWLNGKEYKCKVSNKALPAPIEKTISKAKGQPREPQ<br>VYTLPPSRDELTKNQVSLTCLVKGFYPSDIAVEWESNGQPENNY<br>KTTPPVLDSDGSFFLYSKLTVDKSRWQQGNVFSCSVMHEALHN<br>HYTQKSLSLSPGKHHHHH | 434 |
| | | LC | "NA2" LC | 276 |
| NA2-hIgG-7X-1 | NA | HC | EVQLVESGAEVKKPGSSVKVSCRASGTFYKYAINWVRQAPGQG<br>LEWMGGIIPFFGTTNYAQKFQGRLTITADGSTNTAYMQLDSLRS<br>EDTAVYYCAGPSITESHYCLDCAAKDYYYGLDVWGQGTTVTVS<br>SSVFPLAPSSKSTSGGTAALGCLVKDYFPEPVTVSWNSGALTSG<br>VHTFPAVLQSSGLYSLSSVVTVPSSSLGTQTYICNVNHKPSNTKV<br>DKRVEPKSCTCPPCPAPELLGGPSVFLFPPKPKDTLMISRTPEVTC<br>VVVDVSHEDPEVKFNWYVDGVEVHNAKTKPREEQYNSTYRVV<br>SVLTVLHQDWLNGKEYKCKVSNKALPAPIEKTISKAKGQPREPQ<br>VYTLPPSRDELTKNQVSLTCLVKGFYPSDIAVEWESNGQPENNY<br>KTTPPVLDSDGSFFLYSKLTVDKSRWQQGNVFSCSVMHEALHN<br>HYTQKSLSLSPGKKKKGKKK | 435 |
| | | LC | "NA2" LC | 276 |
| NA2-hIgG-12X-7 | NA | HC | EVQLVESGAEVKKPGSSVKVSCRASGTFYKYAINWVRQAPGQG<br>LEWMGGIIPFFGTTNYAQKFQGRLTITADGSTNTAYMQLDSLRS<br>EDTAVYYCAGPSITESHYCLDCAAKDYYYGLDVWGQGTTVTVS<br>SSVFPLAPSSKSTSGGTAALGCLVKDYFPEPVTVSWNSGALTSG<br>VHTFPAVLQSSGLYSLSSVVTVPSSSLGTQTYICNVNHKPSNTKV<br>DKRVEPKSCTCPPCPAPELLGGPSVFLFPPKPKDTLMISRTPEVTC<br>VVVDVSHEDPEVKFNWYVDGVEVHNAKTKPREEQYNSTYRVV | 436 |

TABLE 1-continued

Exemplary anti-influenza chimeric proteins

| Chimeric Protein | Anti-gen | HC / LC | Sequence (mucoadhesive peptide fragment is underlined) | SEQ ID NO |
|---|---|---|---|---|
| | | | SVLTVLHQDWLNGKEYKCKVSNKALPAPIEKTISKAKGQPREPQ VYTLPPSRDELTKNQVSLTCLVKGFYPSDIAVEWESNGQPENNY KTTPPVLDSDGSFFLYSKLTVDKSRWQQGNVFSCSVMHEALHN HYTQKSLSLSPGK<u>KKAHHGKKAHHV</u> | |
| | | LC | "NA2" LC | 276 |
| NA2-hIgG-12X-8 | NA | HC | EVQLVESGAEVKKPGSSVKVSCRASGTFYKYAINWVRQAPGQG LEWMGGIIPFFGTTNYAQKFQGRLTITADGSTNTAYMQLDSLRS EDTAVYYCAGPSITESHYCLDCAAKDYYYGLDVWGQGTTVTVS SSVFPLAPSSKSTSGGTAALGCLVKDYFPEPVTVSWNSGALTSG VHTFPAVLQSSGLYSLSSVVTVPSSSLGTQTYICNVNHKPSNTKV DKRVEPKSCTCPPCPAPELLGGPSVFLFPPKPKDTLMISRTPEVTC VVVDVSHEDPEVKFNWYVDGVEVHNAKTKPREEQYNSTYRVV SVLTVLHQDWLNGKEYKCKVSNKALPAPIEKTISKAKGQPREPQ VYTLPPSRDELTKNQVSLTCLVKGFYPSDIAVEWESNGQPENNY KTTPPVLDSDGSFFLYSKLTVDKSRWQQGNVFSCSVMHEALHN HYTQKSLSLSPGK<u>KKARRGKKARRV</u> | 437 |
| | | LC | "NA2" LC | 276 |

Additional chimeric proteins comprising any of the anti-influenza virus (e.g., anti-HA or anti-NA) antibody moieties or variants thereof, the mucoadhesive peptide fragments, and/or linkers provided herein are also contemplated. It should be understood that various other chimeric proteins comprising anti-influenza virus antibody moieties or variants known in the art fused with any of the mucoadhesive peptide fragments and/or linkers provided herein may be encompassed by the scope of this invention.

In some embodiments, the chimeric protein comprises an anti-HA antibody moiety and one or more of the mucoadhesive peptide fragments described herein. In some embodiments, the chimeric protein comprises a first and a second polypeptide chain each independently comprising a heavy chain of a full-length anti-HA antibody, and a third and fourth polypeptide chain each independently comprising a light chain of a full-length anti-HA antibody, such as any of the chimeric proteins provided in Table 1 above, e.g., HA1-hIgG-6H; HA1-hIgG-12H; HA1-hIgG-30H; HA1-hIgG-6K; HA1-hIgG-12K; HA1-hIgG-30K; HA1-hIgG-6R; HA1-hIgG-12R; HA1-hIgG-30R; HA1-hIgG-60; HA1-hIgG-120; HA1-hIgG-300; HA1-hIgG-6X-1; HA1-hIgG-6X-2; HA1-hIgG-6X-3; HA1-hIgG-6X-4; HA1-hIgG-12X-1; HA1-hIgG-30X-1; HA1-hIgG-6X-2; HA1-hIgG-12X-2; HA1-hIgG-30X-2; HA1-hIgG-6X-3; HA1-hIgG-12X-3; HA1-hIgG-30X-3; HA1-hIgG-12X-4; HA1-hIgG-30X-4; HA2-hIgG-6H; HA2-hIgG-12H; HA2-hIgG-30H; HA2-hIgG-6K; HA2-hIgG-12K; HA2-hIgG-30K; HA2-hIgG-6R; HA2-hIgG-12R; HA2-hIgG-30R; HA2-hIgG-60; HA2-hIgG-120; HA2-hIgG-300; HA2-hIgG-6X-7; HA2-hIgG-12X-5; HA2-hIgG-30X-1; HA1-hIgG-5H; HA1-hIgG-7X-1; HA1-hIgG-12X-7; HA1-hIgG-12X-8; HA2-hIgG-5H; HA2-hIgG-7X-1; HA2-hIgG-12X-7; HA2-hIgG-12X-8; HA15-hIgG-5H; HA15-hIgG-6H; HA15-hIgG-12H; HA15-hIgG-30H; HA15-hIgG-6K; HA15-hIgG-12K; HA15-hIgG-30K; HA15-hIgG-6R; HA15-hIgG-12R; HA15-hIgG-30R; HA15-hIgG-60; HA15-hIgG-120; HA15-hIgG-300; HA15-hIgG-6X-1; HA15-hIgG-6X-2; HA15-hIgG-6X-3; HA15-hIgG-6X-4; HA15-hIgG-6X-5; HA15-hIgG-6X-6; HA15-hIgG-6X-7; HA15-hIgG-7X-1; HA15-hIgG-12X-1; HA15-hIgG-12X-2; HA15-hIgG-12X-3; HA15-hIgG-12X-4; HA15-hIgG-12X-5; HA15-hIgG-12X-6; HA15-hIgG-12X-7; HA15-hIgG-12X-8; HA15-hIgG-30X-1; HA15-hIgG-30X-2; HA15-hIgG-30X-3; HA15-hIgG-30X-4; HA15-hIgG-35X-1; HA15-hIgG-40X-2; HA15-hIgG-42X-1; HA15-hIgG-45X-1; HA15-hIgG-50X-1; and HA15-hIgG-50X-2.

In some embodiments, the chimeric protein comprises a heavy chain (HC) polypeptide comprising the amino acid sequence of any one of SEQ ID NOs: 414, 420, and 446, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of any one of SEQ ID NOs: 414, 420, and 446, and a light chain (LC) polypeptide comprising the amino acid sequence of any one of SEQ ID NOs: 217, 244, and 447, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of any one of SEQ ID NOs: 217, 244, and 447.

In some embodiments, the chimeric protein comprises an HC polypeptide comprising the amino acid sequence of SEQ ID NO: 414, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 414, and an LC polypeptide comprising the amino acid sequence of SEQ ID NO: 217, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217.

In some embodiments, the chimeric protein comprises an HC polypeptide comprising the amino acid sequence of SEQ ID NO: 420, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 420, and an LC polypeptide comprising the amino acid sequence of SEQ ID NO: 244, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 244.

In some embodiments, the chimeric protein comprises an HC polypeptide comprising the amino acid sequence of SEQ ID NO: 446, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 446, and an LC polypeptide comprising the amino acid sequence of SEQ ID NO: 447, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of any one of SEQ ID NOs: 216, 218-234, 236, 237, 239-242, and 416-419, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of any one of SEQ ID NOs: 216, 218-234, 236, 237, 239-242, and 416-419, and a third and a fourth polypeptide chain each having the amino acid sequence of SEQ ID NO: 217.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 216, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 216, and a third and a fourth polypeptide chain each having the amino acid sequence of SEQ ID NO: 217. In some embodiments, the chimeric protein is HA1-hIgG-6H, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 218, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 218, and a third and a fourth polypeptide chain each having the amino acid sequence of SEQ ID NO: 217. In some embodiments, the chimeric protein is HA1-hIgG-12H, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 219, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 219, and a third and a fourth polypeptide chain each having the amino acid sequence of SEQ ID NO: 217. In some embodiments, the chimeric protein is HA1-hIgG-30H, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 220, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 220, and a third and a fourth polypeptide chain each having the amino acid sequence of SEQ ID NO: 217. In some embodiments, the chimeric protein is HA1-hIgG-6K, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 221, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 221, and a third and a fourth polypeptide chain each having the amino acid sequence of SEQ ID NO: 217. In some embodiments, the chimeric protein is HA1-hIgG-12K, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 222, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 222, and a third and a fourth polypeptide chain each having the amino acid sequence of SEQ ID NO: 217. In some embodiments, the chimeric protein is HA1-hIgG-30K, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 223, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 223, and a third and a fourth polypeptide chain each having the amino acid sequence of SEQ ID NO: 217. In some embodiments, the chimeric protein is HA1-hIgG-6R, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 224, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 224, and a third and a fourth polypeptide chain each having the amino acid sequence of SEQ ID NO: 217. In some embodiments, the chimeric protein is HA1-hIgG-12R, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 225, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 225, and a third and a fourth polypeptide chain each having the amino acid sequence of SEQ ID NO: 217. In some embodiments, the chimeric protein is HA1-hIgG-30R, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 226, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 226, and a third and a fourth polypeptide chain each having the amino acid sequence of SEQ ID NO: 217. In some embodiments, the chimeric protein is HA1-hIgG-60, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 227, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 227, and a third and a fourth polypeptide chain each having the amino acid sequence of SEQ ID NO: 217. In some embodiments, the chimeric protein is HA1-hIgG-120, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 228, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 228, and a third and a fourth polypeptide chain each having the amino acid sequence of SEQ ID NO: 217. In some embodiments, the chimeric protein is HA1-hIgG-300, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 229, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 229, and a third and a fourth polypeptide chain each having the amino acid sequence of SEQ ID NO: 217. In some embodiments, the chimeric protein is HA1-hIgG-6X-1, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 230, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 230, and a third and a fourth polypeptide chain each having the amino acid sequence of SEQ ID NO: 217. In some embodiments, the chimeric protein is HA1-hIgG-6X-2, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 231, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 231, and a third and a fourth polypeptide chain each having the amino acid sequence of SEQ ID NO: 217. In some embodiments, the chimeric protein is HA1-hIgG-6X-3, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 232, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 232, and a third and a fourth polypeptide chain each having the amino acid sequence of SEQ ID NO: 217. In some embodiments, the chimeric protein is HA1-hIgG-6X-4, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 233, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 233, and a third and a fourth polypeptide chain each having the amino acid sequence of SEQ ID NO: 217. In some embodiments, the chimeric protein is HA1-hIgG-12X-1, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 234, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 234, and a third and a fourth polypeptide chain each having the amino acid sequence of SEQ ID NO: 217. In some embodiments, the chimeric protein is HA1-hIgG-30X-1, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 236, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 236, and a third and a fourth polypeptide chain each having the amino acid sequence of SEQ ID NO: 217. In some embodiments, the chimeric protein is HA1-hIgG-12X-2, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 237, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 237, and a third and a fourth polypeptide chain each having the amino acid sequence of SEQ ID NO: 217. In some embodiments, the chimeric protein is HA1-hIgG-30X-2, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 239, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 239, and a third and a fourth polypeptide chain each having the amino acid sequence of SEQ ID NO: 217. In some embodiments, the chimeric protein is HA1-hIgG-12X-3, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 240, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 240, and a third and a fourth polypeptide chain each having the amino acid sequence of SEQ ID NO: 217. In some embodiments, the chimeric protein is HA1-hIgG-30X-3, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 241, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 241, and a third and a fourth polypeptide chain each having the amino acid sequence of SEQ ID NO: 217. In some embodiments, the chimeric protein is HA1-hIgG-12X-4, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 242, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 242, and a third and a fourth polypeptide chain each having the amino acid sequence of SEQ ID NO: 217. In some embodiments, the chimeric protein is HA1-hIgG-30X-4, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 416, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 416, and a third and a fourth polypeptide chain each having the amino acid sequence of SEQ ID NO: 217. In some embodiments, the chimeric protein is HA1-hIgG-5H, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 417, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 417, and a third and a fourth polypeptide chain each having the amino acid sequence of SEQ ID NO: 217. In some embodiments, the chimeric protein is HA1-hIgG-7X-1, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 418, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 418, and a third and a fourth polypeptide chain each having the amino acid sequence of SEQ ID NO: 217. In some embodiments, the chimeric protein is HA1-hIgG-12X-7, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 419, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 217. In some embodiments, the chimeric protein comprises a first and a second polypeptide chain each independently having the amino acid sequence of SEQ ID NO: 419, and a third and a fourth polypeptide chain each having the amino acid sequence of SEQ ID NO: 217. In some embodiments, the chimeric protein is HA1-hIgG-12X-8, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of any one of SEQ ID NOs: 243, 245-258, and 422-425, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 244. In some embodiments, the chimeric protein comprises a first and a second polypeptide chain each independently having the amino acid sequence of any one of SEQ ID NOs: 243, 245-258, and 422-425, and a third and a fourth polypeptide chain each having the amino acid sequence of SEQ ID NO: 244.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 243, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 244. In some embodiments, the chimeric protein comprises a first and a second polypeptide chain each independently having the amino acid sequence of SEQ ID NO: 243, and a third and a fourth polypeptide chain each having the amino acid sequence of SEQ ID NO: 244. In some embodiments, the chimeric protein is HA2-hIgG-6H, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 245, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 244. In some embodiments, the chimeric protein comprises a first and a second polypeptide chain each independently having the amino acid sequence of SEQ ID NO: 245, and a third and a fourth polypeptide chain each having the amino acid sequence of SEQ ID NO: 244. In some embodiments, the chimeric protein is HA2-hIgG-12H, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 246, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 244. In some embodiments, the chimeric protein comprises a first and a second polypeptide chain each independently having the amino acid sequence of SEQ ID NO: 246, and a third and a fourth polypeptide chain each having the amino acid sequence of SEQ ID NO: 244. In some embodiments, the chimeric protein is HA2-hIgG-30H, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 247, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 244. In some embodiments, the chimeric protein comprises a first and a second polypeptide chain each independently having the amino acid sequence of SEQ ID NO: 247, and a third and a fourth polypeptide chain each having the amino acid sequence of SEQ ID NO: 244. In some embodiments, the chimeric protein is HA2-hIgG-6K, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 248, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 244. In some embodiments, the chimeric protein comprises a first and a second polypeptide chain each independently having the amino acid sequence of SEQ ID NO: 248, and a third and a fourth polypeptide chain each having the amino acid sequence of SEQ ID NO: 244. In some embodiments, the chimeric protein is HA2-hIgG-12K, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 249, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 244. In some embodiments, the chimeric protein comprises a first and a second polypeptide chain each independently having the amino acid sequence of SEQ ID NO: 249, and a third and a fourth polypeptide chain each having the amino acid sequence of SEQ ID NO: 244. In some embodiments, the chimeric protein is HA2-hIgG-30K, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 250, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 244. In some embodiments, the chimeric protein comprises a first and a second polypeptide chain each independently having the amino acid sequence of SEQ ID NO: 250, and a third and a fourth polypeptide chain each having the amino acid sequence of SEQ ID NO: 244. In some embodiments, the chimeric protein is HA2-hIgG-6R, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 251, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 244. In some embodiments, the chimeric protein comprises a first and a second polypeptide chain each independently having the amino acid sequence of SEQ ID NO: 251, and a third and a fourth polypeptide chain each having the amino acid sequence of SEQ ID NO: 244. In some embodiments, the chimeric protein is HA2-hIgG-12R, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 252, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 244. In some embodiments, the chimeric protein comprises a first and a second polypeptide chain each independently having the amino acid sequence of SEQ ID NO: 252, and a third and a fourth polypeptide chain each having the amino acid sequence of SEQ ID NO: 244. In some embodiments, the chimeric protein is HA2-hIgG-30R, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 253, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 244. In some embodiments, the chimeric protein comprises a first and a second polypeptide chain each independently having the amino acid sequence of SEQ ID NO: 253, and a third and a fourth polypeptide chain each having the amino acid sequence of SEQ ID NO: 244. In some embodiments, the chimeric protein is HA2-hIgG-60, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 254, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 244. In some embodiments, the chimeric protein comprises a first and a second polypeptide chain each independently having the amino acid sequence of SEQ ID NO: 254, and a third and a fourth polypeptide chain each having the amino acid sequence of SEQ ID NO: 244. In some embodiments, the chimeric protein is HA2-hIgG-120, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 255, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 244. In some embodiments, the chimeric protein comprises a first and a second polypeptide chain each independently having the amino acid sequence of SEQ ID NO: 255, and a third and a fourth polypeptide chain each having the amino acid sequence of SEQ ID NO: 244. In some embodiments, the chimeric protein is HA2-hIgG-300, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 256, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 244. In some embodiments, the chimeric protein comprises a first and a second polypeptide chain each independently having the amino acid sequence of SEQ ID NO: 256, and a third and a fourth polypeptide chain each having the amino acid sequence of SEQ ID NO: 244. In some embodiments, the chimeric protein is HA2-hIgG-6X-7, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 257, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 244. In some embodiments, the chimeric protein comprises a first and a second polypeptide chain each independently having the amino acid sequence of SEQ ID NO: 257, and a third and a fourth polypeptide chain each having the amino acid sequence of SEQ ID NO: 244. In some embodiments, the chimeric protein is HA2-hIgG-12X-5, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 258, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 244. In some embodiments, the chimeric protein comprises a first and a second polypeptide chain each independently having the amino acid sequence of SEQ ID NO: 258, and a third and a fourth polypeptide chain each having the amino acid sequence of SEQ ID NO: 244. In some embodiments, the chimeric protein is HA2-hIgG-30X-1, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 422, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 244. In some embodiments, the chimeric protein comprises a first and a second polypeptide chain each independently having the amino acid sequence of SEQ ID NO: 422, and a third and a fourth polypeptide chain each having the amino acid sequence of SEQ ID NO: 244. In some embodiments, the chimeric protein is HA2-hIgG-5H, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 423, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 244. In some embodiments, the chimeric protein comprises a first and a second polypeptide chain each independently having the amino acid sequence of SEQ ID NO: 423, and a third and a fourth polypeptide chain each having the amino acid sequence of SEQ ID NO: 244. In some embodiments, the chimeric protein is HA2-hIgG-7X-1, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 424, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 244. In some embodiments, the chimeric protein comprises a first and a second polypeptide chain each independently having the amino acid sequence of SEQ ID NO: 424, and a third and a fourth polypeptide chain each having the amino acid sequence of SEQ ID NO: 244. In some embodiments, the chimeric protein is HA2-hIgG-12X-7, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 425, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 244. In some embodiments, the chimeric protein comprises a first and a second polypeptide chain each independently having the amino acid sequence of SEQ ID NO: 425, and a third and a fourth polypeptide chain each having the amino acid sequence of SEQ ID NO: 244. In some embodiments, the chimeric protein is HA2-hIgG-12X-8, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of any one of SEQ ID NOs: 448-486, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of any one of SEQ ID NOs: 448-486, and a third and a fourth polypeptide chain each having the amino acid sequence of SEQ ID NO: 447.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 448, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 448, and a third and a fourth polypeptide chain each having the amino acid sequence of SEQ ID NO: 447. In some embodiments, the chimeric protein is HA15-hIgG-5H, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 449, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 449, and a third and a fourth polypeptide chain each having the amino acid sequence of SEQ ID NO: 447. In some embodiments, the chimeric protein is HA15-hIgG-6H, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 450, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 450, and a third and a fourth polypeptide chain each having the amino acid sequence of SEQ ID NO: 447. In some embodiments, the chimeric protein is HA15-hIgG-12H, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 451, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 451, and a third and a fourth polypeptide chain each having the amino acid sequence of SEQ ID NO: 447. In some embodiments, the chimeric protein is HA15-hIgG-30H, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 452, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 452, and a third and a fourth polypeptide chain each having the amino acid sequence of SEQ ID NO: 447. In some embodiments, the chimeric protein is HA15-hIgG-6K, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 453, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 453, and a third and a fourth polypeptide chain each having the amino acid sequence of SEQ ID NO: 447. In some embodiments, the chimeric protein is HA15-hIgG-12K, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 454, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 454, and a third and a fourth polypeptide chain each having the amino acid sequence of SEQ ID NO: 447. In some embodiments, the chimeric protein is HA15-hIgG-30K, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 455, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 455, and a third and a fourth polypeptide chain each having the amino acid sequence of SEQ ID NO: 447. In some embodiments, the chimeric protein is HA15-hIgG-6R, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 456, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 456, and a third and a fourth polypeptide chain each having the amino acid sequence of SEQ ID NO: 447. In some embodiments, the chimeric protein is HA15-hIgG-12R, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 457, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 457, and a third and a fourth polypeptide chain each having the amino acid sequence of SEQ ID NO: 447. In some embodiments, the chimeric protein is HA15-hIgG-30R, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 458, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 458, and a third and a fourth polypeptide chain each having the amino acid sequence of SEQ ID NO: 447. In some embodiments, the chimeric protein is HA15-hIgG-60, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 459, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 459, and a third and a fourth polypeptide chain each having the amino acid sequence of SEQ ID NO: 447. In some embodiments, the chimeric protein is HA15-hIgG-120, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 460, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 460, and a third and a fourth polypeptide chain each having the amino acid sequence of SEQ ID NO: 447. In some embodiments, the chimeric protein is HA15-hIgG-300, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 461, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 461, and a third and a fourth polypeptide chain each having the amino acid sequence of SEQ ID NO: 447. In some embodiments, the chimeric protein is HA15-hIgG-6X-1, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 462, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 462, and a third and a fourth polypeptide chain each having the amino acid sequence of SEQ ID NO: 447. In some embodiments, the chimeric protein is HA15-hIgG-6X-2, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 463, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 463, and a third and a fourth polypeptide chain each having the amino acid sequence of SEQ ID NO: 447. In some embodiments, the chimeric protein is HA15-hIgG-6X-3, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 464, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 464, and a third and a fourth polypeptide chain each having the amino acid sequence of SEQ ID NO: 447. In some embodiments, the chimeric protein is HA15-hIgG-6X-4, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 465, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 465, and a third and a fourth polypeptide chain each having the amino acid sequence of SEQ ID NO: 447. In some embodiments, the chimeric protein is HA15-hIgG-6X-5, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 466, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 466, and a third and a fourth polypeptide chain each having the amino acid sequence of SEQ ID NO: 447. In some embodiments, the chimeric protein is HA15-hIgG-6X-6, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 467, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 467, and a third and a fourth polypeptide chain each having the amino acid sequence of SEQ ID NO: 447. In some embodiments, the chimeric protein is HA15-hIgG-6X-7, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 468, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 468, and a third and a fourth polypeptide chain each having the amino acid sequence of SEQ ID NO: 447. In some embodiments, the chimeric protein is HA15-hIgG-7X-1, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 469, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 469, and a third and a fourth polypeptide chain each having the amino acid sequence of SEQ ID NO: 447. In some embodiments, the chimeric protein is HA15-hIgG-12X-1, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 470, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 470, and a third and a fourth polypeptide chain each having the amino acid sequence of SEQ ID NO: 447. In some embodiments, the chimeric protein is HA15-hIgG-12X-2, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 471, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 471, and a third and a fourth polypeptide chain each having the amino acid sequence of SEQ ID NO: 447. In some embodiments, the chimeric protein is HA15-hIgG-12X-3, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 472, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 472, and a third and a fourth polypeptide chain each having the amino acid sequence of SEQ ID NO: 447. In some embodiments, the chimeric protein is HA15-hIgG-12X-4, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 473, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 473, and a third and a fourth polypeptide chain each having the amino acid sequence of SEQ ID NO: 447. In some embodiments, the chimeric protein is HA15-hIgG-12X-5, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 474, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 474, and a third and a fourth polypeptide chain each having the amino acid sequence of SEQ ID NO: 447. In some embodiments, the chimeric protein is HA15-hIgG-12X-6, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 475, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 475, and a third and a fourth polypeptide chain each having the amino acid sequence of SEQ ID NO: 447. In some embodiments, the chimeric protein is HA15-hIgG-12X-7, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 476, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 476, and a third and a fourth polypeptide chain each having the amino acid sequence of SEQ ID NO: 447. In some embodiments, the chimeric protein is HA15-hIgG-12X-8, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 477, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 477, and a third and a fourth polypeptide chain each having the amino acid sequence of SEQ ID NO: 447. In some embodiments, the chimeric protein is HA15-hIgG-30X-1, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 478, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 478, and a third and a fourth polypeptide chain each having the amino acid sequence of SEQ ID NO: 447. In some embodiments, the chimeric protein is HA15-hIgG-30X-2, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 479, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 479, and a third and a fourth polypeptide chain each having the amino acid sequence of SEQ ID NO: 447. In some embodiments, the chimeric protein is HA15-hIgG-30X-3, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 480, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 480, and a third and a fourth polypeptide chain each having the amino acid sequence of SEQ ID NO: 447. In some embodiments, the chimeric protein is HA15-hIgG-30X-4, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 481, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 481, and a third and a fourth polypeptide chain each having the amino acid sequence of SEQ ID NO: 447. In some embodiments, the chimeric protein is HA15-hIgG-35X-1, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 482, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 482, and a third and a fourth polypeptide chain each having the amino acid sequence of SEQ ID NO: 447. In some embodiments, the chimeric protein is HA15-hIgG-40X-2, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 483, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 483, and a third and a fourth polypeptide chain each having the amino acid sequence of SEQ ID NO: 447. In some embodiments, the chimeric protein is HA15-hIgG-42X-1, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 484, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 484, and a third and a fourth polypeptide chain each having the amino acid sequence of SEQ ID NO: 447. In some embodiments, the chimeric protein is HA15-hIgG-45X-1, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 485, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 485, and a third and a fourth polypeptide chain each having the amino acid sequence of SEQ ID NO: 447. In some embodiments, the chimeric protein is HA15-hIgG-50X-1, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 486, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 447. In some embodiments, the chimeric protein comprises a first and a second polypeptide chain each independently having the amino acid sequence of SEQ ID NO: 486, and a third and a fourth polypeptide chain each having the amino acid sequence of SEQ ID NO: 447. In some embodiments, the chimeric protein is HA15-hIgG-50X-2, as described in Table 1.

In some embodiments, the chimeric protein comprises a first and a second polypeptide chain each independently comprising a $V_H$ of a full-length anti-NA antibody, and a third and fourth polypeptide chain each independently comprising a $V_L$ of a full-length anti-NA antibody, such as any of the chimeric proteins provided in Table 1 above, e.g., NA1-hIgG-6H; NA1-hIgG-12H; NA1-hIgG-30H; NA1-hIgG-6K; NA1-hIgG-12K; NA1-hIgG-30K; NA1-hIgG-6R; NA1-hIgG-12R; NA1-hIgG-30R; NA1-hIgG-60; NA1-hIgG-120; NA1-hIgG-300; NA1-hIgG-6X-5; NA1-hIgG-12X-5; NA1-hIgG-30X-1; NA2-hIgG-6H; NA2-hIgG-12H; NA2-hIgG-30H; NA2-hIgG-6K; NA2-hIgG-12K; NA2-hIgG-30K; NA2-hIgG-6R; NA2-hIgG-12R; NA2-hIgG-30R; NA2-hIgG-60; NA2-hIgG-120; NA2-hIgG-300; NA2-hIgG-6X-6; NA2-hIgG-12X-6; NA2-hIgG-30X-1; NA1-hIgG-5H; NA1-hIgG-7X-1; NA1-hIgG-12X-7; NA1-hIgG-12X-8; NA2-hIgG-5H; NA2-hIgG-7X-1; NA2-hIgG-12X-7; and NA2-hIgG-12X-8.

In some embodiments, the chimeric protein comprises an HC polypeptide comprising the amino acid sequence of SEQ ID NO: 426 or 432, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 426 or 432, an LC polypeptide comprising the amino acid sequence of SEQ ID NO: 260 or 276, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 260 or 276.

In some embodiments, the chimeric protein comprises an HC polypeptide comprising the amino acid sequence of SEQ ID NO: 426, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 426, and an LC polypeptide comprising the amino acid sequence of SEQ ID NO: 260, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 260.

In some embodiments, the chimeric protein comprises an HC polypeptide comprising the amino acid sequence of SEQ ID NO: 432, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 432, and an LC polypeptide comprising the amino acid sequence of SEQ ID NO: 276, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 276.

In some embodiments, the chimeric protein comprises a first and a second polypeptide chains each independently having at least about 90% sequence identity (such as at least about n % sequence identity, where n % is selected from 91%, 92%, 93%, 94%, 95%, 96%, 97%, 98%, and 99%) to the amino acid sequence of any one of SEQ ID NOs: 259, 261-274, and 428-431, and a third and a fourth polypeptide chains each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 260. In some embodiments, the chimeric protein comprises a first and a second polypeptide chains each independently having the amino acid sequence of any one of SEQ ID NOs: 259, 261-274, and 428-431, and a third and a fourth polypeptide chains each having the amino acid sequence of SEQ ID NO: 260.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 259, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 260. In some embodiments, the chimeric protein comprises a first and a second polypeptide chain each independently having the amino acid sequence of SEQ ID NO: 259, and a third and a fourth polypeptide chain each having the amino acid sequence of SEQ ID NO: 260. In some embodiments, the chimeric protein is NA1-hIgG-6H, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 261, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 260. In some embodiments, the chimeric protein comprises a first and a second polypeptide chain each independently having the amino acid sequence of SEQ ID NO: 261, and a third and a fourth polypeptide chain each having the amino acid sequence of SEQ ID NO: 260. In some embodiments, the chimeric protein is NA1-hIgG-12H, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 262, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 260. In some embodiments, the chimeric protein comprises a first and a second polypeptide chain each independently having the amino acid sequence of SEQ ID NO: 262, and a third and a fourth polypeptide chain each having the amino acid sequence of SEQ ID NO: 260. In some embodiments, the chimeric protein is NA1-hIgG-30H, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 263, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 260. In some embodiments, the chimeric protein comprises a first and a second polypeptide chain each independently having the amino acid sequence of SEQ ID NO: 263, and a third and a fourth polypeptide chain each having the amino acid sequence of SEQ ID NO: 260. In some embodiments, the chimeric protein is NA1-hIgG-6K, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 264, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 260. In some embodiments, the chimeric protein comprises a first and a second polypeptide chain each independently having the amino acid sequence of SEQ ID NO: 264, and a third and a fourth polypeptide chain each having the amino acid sequence of SEQ ID NO: 260. In some embodiments, the chimeric protein is NA1-hIgG-12K, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 265, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 260. In some embodiments, the chimeric protein comprises a first and a second polypeptide chain each independently having the amino acid sequence of SEQ ID NO: 265, and a third and a fourth polypeptide chain each having the amino acid sequence of SEQ ID NO: 260. In some embodiments, the chimeric protein is NA1-hIgG-30K, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 266, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 260. In some embodiments, the chimeric protein comprises a first and a second polypeptide chain each independently having the amino acid sequence of SEQ ID NO: 266, and a third and a fourth polypeptide chain each having the amino acid sequence of SEQ ID NO: 260. In some embodiments, the chimeric protein is NA1-hIgG-6R, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 267, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 260. In some embodiments, the chimeric protein comprises a first and a second polypeptide chain each independently having the amino acid sequence of SEQ ID NO: 267, and a third and a fourth polypeptide chain each having the amino acid sequence of SEQ ID NO: 260. In some embodiments, the chimeric protein is NA1-hIgG-12R, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 268, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 260. In some embodiments, the chimeric protein comprises a first and a second polypeptide chain each independently having the amino acid sequence of SEQ ID NO: 268, and a third and a fourth polypeptide chain each having the amino acid sequence of SEQ ID NO: 260. In some embodiments, the chimeric protein is NA1-hIgG-30R, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 269, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 260. In some embodiments, the chimeric protein comprises a first and a second polypeptide chain each independently having the amino acid sequence of SEQ ID NO: 269, and a third and a fourth polypeptide chain each having the amino acid sequence of SEQ ID NO: 260. In some embodiments, the chimeric protein is NA1-hIgG-60, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 270, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 260. In some embodiments, the chimeric protein comprises a first and a second polypeptide chain each independently having the amino acid sequence of SEQ ID NO: 270, and a third and a fourth polypeptide chain each having the amino acid sequence of SEQ ID NO: 260. In some embodiments, the chimeric protein is NA1-hIgG-120, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 271, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 260. In some embodiments, the chimeric protein comprises a first and a second polypeptide chain each independently having the amino acid sequence of SEQ ID NO: 271, and a third and a fourth polypeptide chain each having the amino acid sequence of SEQ ID NO: 260. In some embodiments, the chimeric protein is NA1-hIgG-300, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 272, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 260. In some embodiments, the chimeric protein comprises a first and a second polypeptide chain each independently having the amino acid sequence of SEQ ID NO: 272, and a third and a fourth polypeptide chain each having the amino acid sequence of SEQ ID NO: 260. In some embodiments, the chimeric protein is NA1-hIgG-6X-5, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 273, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 260. In some embodiments, the chimeric protein comprises a first and a second polypeptide chain each independently having the amino acid sequence of SEQ ID NO: 273, and a third and a fourth polypeptide chain each having the amino acid sequence of SEQ ID NO: 260. In some embodiments, the chimeric protein is NA1-hIgG-12X-5, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 274, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 260. In some embodiments, the chimeric protein comprises a first and a second polypeptide chain each independently having the amino acid sequence of SEQ ID NO: 274, and a third and a fourth polypeptide chain each having the amino acid sequence of SEQ ID NO: 260. In some embodiments, the chimeric protein is NA1-hIgG-30X-1, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 428, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 260. In some embodiments, the chimeric protein comprises a first and a second polypeptide chain each independently having the amino acid sequence of SEQ ID NO: 428, and a third and a fourth polypeptide chain each having the amino acid sequence of SEQ ID NO: 260. In some embodiments, the chimeric protein is NA1-hIgG-5H, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 429, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 260. In some embodiments, the chimeric protein comprises a first and a second polypeptide chain each independently having the amino acid sequence of SEQ ID NO: 429, and a third and a fourth polypeptide chain each having the amino acid sequence of SEQ ID NO: 260. In some embodiments, the chimeric protein is NA1-hIgG-7X-1, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 430, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 260. In some embodiments, the chimeric protein comprises a first and a second polypeptide chain each independently having the amino acid sequence of SEQ ID NO: 430, and a third and a fourth polypeptide chain each having the amino acid sequence of SEQ ID NO: 260. In some embodiments, the chimeric protein is NA1-hIgG-12X-7, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 431, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 260. In some embodiments, the chimeric protein comprises a first and a second polypeptide chain each independently having the amino acid sequence of SEQ ID NO: 431, and a third and a fourth polypeptide chain each having the amino acid sequence of SEQ ID NO: 260. In some embodiments, the chimeric protein is NA1-hIgG-12X-8, as described in Table 1.

In some embodiments, the chimeric protein comprises a first and a second polypeptide chains each independently having at least about 90% sequence identity (such as at least about n % sequence identity, where n % is selected from 91%, 92%, 93%, 94%, 95%, 96%, 97%, 98%, and 99%) to the amino acid sequence of any one of SEQ ID NOs: 275, 277-290 and 434-437, and a third and a fourth polypeptide chains each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 276. In some embodiments, the chimeric protein comprises a first and a second polypeptide chains each independently having the amino acid sequence of any one of SEQ ID NOs: 275, 277-290, and 434-437, and a third and a fourth polypeptide chains each having the amino acid sequence of SEQ ID NO: 276.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 275, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 276. In some embodiments, the chimeric protein comprises a first and a second polypeptide chain each independently having the amino acid sequence of SEQ ID NO: 275, and a third and a fourth polypeptide chain each having the amino acid sequence of SEQ ID NO: 276. In some embodiments, the chimeric protein is NA2-hIgG-6H, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 277, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 276. In some embodiments, the chimeric protein comprises a first and a second polypeptide chain each independently having the amino acid sequence of SEQ ID NO: 277, and a third and a fourth polypeptide chain each having the amino acid sequence of SEQ ID NO: 276. In some embodiments, the chimeric protein is NA2-hIgG-12H, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 278, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 276. In some embodiments, the chimeric protein comprises a first and a second polypeptide chain each independently having the amino acid sequence of SEQ ID NO: 278, and a third and a fourth polypeptide chain each having the amino acid sequence of SEQ ID NO: 276. In some embodiments, the chimeric protein is NA2-hIgG-30H, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 279, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 276. In some embodiments, the chimeric protein comprises a first and a second polypeptide chain each independently having the amino acid sequence of SEQ ID NO: 279, and a third and a fourth polypeptide chain each having the amino acid sequence of SEQ ID NO: 276. In some embodiments, the chimeric protein is NA2-hIgG-6K, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 280, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 276. In some embodiments, the chimeric protein comprises a first and a second polypeptide chain each independently having the amino acid sequence of SEQ ID NO: 280, and a third and a fourth polypeptide chain each having the amino acid sequence of SEQ ID NO: 276. In some embodiments, the chimeric protein is NA2-hIgG-12K, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 281, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 276. In some embodiments, the chimeric protein comprises a first and a second polypeptide chain each independently having the amino acid sequence of SEQ ID NO: 281, and a third and a fourth polypeptide chain each having the amino acid sequence of SEQ ID NO: 276. In some embodiments, the chimeric protein is NA2-hIgG-30K, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 282, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 276. In some embodiments, the chimeric protein comprises a first and a second polypeptide chain each independently having the amino acid sequence of SEQ ID NO: 282, and a third and a fourth polypeptide chain each having the amino acid sequence of SEQ ID NO: 276. In some embodiments, the chimeric protein is NA2-hIgG-6R, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 283, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 276. In some embodiments, the chimeric protein comprises a first and a second polypeptide chain each independently having the amino acid sequence of SEQ ID NO: 283, and a third and a fourth polypeptide chain each having the amino acid sequence of SEQ ID NO: 276. In some embodiments, the chimeric protein is NA2-hIgG-12R, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 284, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 276. In some embodiments, the chimeric protein comprises a first and a second polypeptide chain each independently having the amino acid sequence of SEQ ID NO: 284, and a third and a fourth polypeptide chain each having the amino acid sequence of SEQ ID NO: 276. In some embodiments, the chimeric protein is NA2-hIgG-30R, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 285, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 276. In some embodiments, the chimeric protein comprises a first and a second polypeptide chain each independently having the amino acid sequence of SEQ ID NO: 285, and a third and a fourth polypeptide chain each having the amino acid sequence of SEQ ID NO: 276. In some embodiments, the chimeric protein is NA2-hIgG-60, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 286, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 276. In some embodiments, the chimeric protein comprises a first and a second polypeptide chain each independently having the amino acid sequence of SEQ ID NO: 286, and a third and a fourth polypeptide chain each having the amino acid sequence of SEQ ID NO: 276. In some embodiments, the chimeric protein is NA2-hIgG-120, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 287, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 276. In some embodiments, the chimeric protein comprises a first and a second polypeptide chain each independently having the amino acid sequence of SEQ ID NO: 287, and a third and a fourth polypeptide chain each having the amino acid sequence of SEQ ID NO: 276. In some embodiments, the chimeric protein is NA2-hIgG-300, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 288, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 276. In some embodiments, the chimeric protein comprises a first and a second polypeptide chain each independently having the amino acid sequence of SEQ ID NO: 288, and a third and a fourth polypeptide chain each having the amino acid sequence of SEQ ID NO: 276. In some embodiments, the chimeric protein is NA2-hIgG-6X-6, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 289, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 276. In some embodiments, the chimeric protein comprises a first and a second polypeptide chain each independently having the amino acid sequence of SEQ ID NO: 289, and a third and a fourth polypeptide chain each having the amino acid sequence of SEQ ID NO: 276. In some embodiments, the chimeric protein is NA2-hIgG-12X-6, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 290, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 276. In some embodiments, the chimeric protein comprises a first and a second polypeptide chain each independently having the amino acid sequence of SEQ ID NO: 290, and a third and a fourth polypeptide chain each having the amino acid sequence of SEQ ID NO: 276. In some embodiments, the chimeric protein is NA2-hIgG-30X-1, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 434, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 276. In some embodiments, the chimeric protein comprises a first and a second polypeptide chain each independently having the amino acid sequence of SEQ ID NO: 434, and a third and a fourth polypeptide chain each having the amino acid sequence of SEQ ID NO: 276. In some embodiments, the chimeric protein is NA2-hIgG-5H, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 435, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 276. In some embodiments, the chimeric protein comprises a first and a second polypeptide chain each independently having the amino acid sequence of SEQ ID NO: 435, and a third and a fourth polypeptide chain each having the amino acid sequence of SEQ ID NO: 276. In some embodiments, the chimeric protein is NA2-hIgG-7X-1, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 436, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 276. In some embodiments, the chimeric protein comprises a first and a second polypeptide chain each independently having the amino acid sequence of SEQ ID NO: 436, and a third and a fourth polypeptide chain each having the amino acid sequence of SEQ ID NO: 276. In some embodiments, the chimeric protein is NA2-hIgG-12X-7, as described in Table 1.

In some embodiments, the chimeric protein comprises a first and a second polypeptide chain each independently having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 437, and a third and a fourth polypeptide chain each having at least about 90% sequence identity (such as at least about n % sequence identity, where n % is selected from 91%, 92%, 93%, 94%, 95%, 96%, 97%, 98%, and 99%) to the amino acid sequence of SEQ ID NO: 276. In some embodiments, the chimeric protein comprises a first and a second polypeptide chain each independently having the amino acid sequence of SEQ ID NO: 437, and a third and a fourth polypeptide chain each having the amino acid sequence of SEQ ID NO: 276. In some embodiments, the chimeric protein is NA2-hIgG-12X-8, as described in Table 1.

Without being bound by any theory or hypothesis, influenza virus infection occurs mainly through respiratory droplets and possible airborne transmission. Upper respiratory surfaces are the dominant and initial sites for influenza virus infection. The nasal epithelium produces a physical glycoprotein barrier to inhaled particles including allergens and pathogens, preventing penetration to the epithelial surface of mucosal tissues. One major component of the mucosal layer of nasal and respiratory tract are mucins, a family of large glycoproteins that coat the surface of the respiratory epithelium. Mucins, the primary non-aqueous component of mucus, are a complex and heterogeneous structure, which carry a highly negative charge. The inventors of the present application, in some embodiments, engineered a tail comprising at least 5 positively charged amino acids (e.g., lysines, histidines, arginines, ornithines, or combinations thereof) which, when covalently linked to an antibody or antibody moiety, confers to the conjugate (i.e., chimeric protein) positive charges. The antibody with its positively charged tail can form a layer of influenza-binding antibody that can line the nasal/respiratory tract and prevent the virus from binding to the viral receptor-expressing epithelial cells. A positively charged antibody could also bind the phospholipid bilayer of cell membranes, also negatively charged. This "sticky" property of polymeric positively charged amino acid chain imparts to the antibody a longer half-life in the respiratory mucosal epithelium, providing a lengthened period of protection. Therefore, the engineered antibody-mucoadhesive polymer conjugate can function as a neutralizing antibody, which can block influenza viral entry into the cells of the respiratory cavity, even if the virus might penetrate the mucosal barrier and reach viral receptor-positive epithelial cells. In other embodiments, the positively charged mucoadhesive amino acids can be interspersed with non-positively charged amino acids without disrupting the mucoadhesive properties of the chimeric protein. Furthermore, the chimeric protein may be expressed as a fusion protein, or the mucoadhesive peptide fragment may be chemically conjugated to antibodies.

The different aspects and embodiments are discussed in various sections below in further detail.

A. Anti-Influenza Antibody Moieties

The chimeric proteins described herein comprise an antibody moiety that specifically binds to a component of an influenza virus (including influenza virus variants), e.g., a HA or NA influenza viral surface protein. Contemplated antibody moieties include, for example, scFv, Fab, Fc fusion protein (e.g., scFv-Fc), full-length antibodies, and multi-specific antibodies.

In some embodiments, the antibody moiety comprises one or more (e.g., 2, 3, 4 or more) polypeptide chains. These one or more polypeptide chains may be bound together, for example, via a disulfide bond (i.e., S—S bond) or multimerization domains.

In some embodiments, the antibody moiety is a full-length antibody or any suitable antigen binding fragments thereof. In some embodiments, the antibody moiety is a full-length antibody. In some embodiments, the antibody moiety is selected from the group consisting of an IgG, an IgA, an IgM, and an IgD. In some embodiments, the antibody moiety is an antigen-binding fragment selected from the group consisting of a Fab, a Fab', a $(Fab')_2$, an Fv, a single chain Fv (scFv), an scFv-Fc, a disulfide stabilized Fv fragment (dsFv), a $(dsFv)_2$, an scFv dimer, a domain antibody, a camelized single domain antibody, a bivalent domain antibody, a minibody, and a $V_HH$. In some embodiments, the antibody moiety is an animal, human, humanized, camelid, or chimeric antibody or an antigen-binding fragment thereof.

In some embodiments, the antibody moiety comprises a scFv. In some embodiments, the antibody moiety is a scFv. In some embodiments, the antibody moiety is a scFv-Fc fusion protein. In some embodiments, the antibody moiety is a scFv-$CH_3$ fusion protein. In some embodiments, the scFv comprises a $V_H$ fused to a $V_L$ via a flexible peptide linker, such as $(GGGS)_n$, or similar peptides disclosed in Table 9, SEQ ID NOs: 343-348. In some embodiments, the scFv comprises a $V_L$ fused to a $V_H$ via a peptide linker.

In humans, IgA is the major antibody isotype secreted in the upper airways; its presence there correlates with resistance to infection by some respiratory viruses, such as influenza viruses or variants thereof. Antibody delivery to the upper airway mucosal surface, mimicking naturally secreted antibody, can prevent virus from reaching its target or directly neutralize infectious virus, and may prove a very useful strategy for prophylaxis. Indeed, antibodies have been shown to provide protection of the respiratory tract from viral infection when given prophylactically. IgA antibodies have a unique structure and glycosylation pattern that enables binding to mucin molecules in the airway epithelium, resulting in extension of their half-lives in the mucosa. While secretory IgA antibodies are more efficient than IgG antibodies in providing effective viral protection, IgG antibodies have a well-established modality for large-scale manufacturing and characterization, both of which are essential for providing an affordable and scalable source of antibodies for a prophylactic approach.

In some embodiments, the antibody moiety comprises a purification tag, e.g., a His tag, such as DYKDDDDKHHHHHH (Flag-His(6), SEQ ID NO: 342).

In some embodiments, the influenza virus or variant thereof causes respiratory infections.

The component of the influenza virus or variant thereof can be a protein-based molecule, or a non-protein-based molecule (e.g., oligosaccharide). In some embodiments, the component is a glycoprotein.

The component of the influenza virus or variant thereof may be a surface molecule on the influenza virus. For example, the component may be a glycoprotein on the surface of the influenza virus. In some embodiments, the component is a capsid protein, an envelope protein, or a viral membrane fusion protein. In some embodiments, the component is a lipopolysaccharide (LPS). In some embodiments, the component is a viral surface protein or fragment thereof. In some embodiments, the viral surface protein is I-A. In some embodiments, the viral surface protein is NA.

Exemplary influenza viruses and antibody moieties are further described below.

Influenza

The chimeric proteins of the present invention comprise an antibody moiety that specifically binds to a component of an influenza virus or a variant thereof.

In some embodiments, the influenza virus is a Type A influenza virus (IAV), a Type B influenza virus (IBV), a Type C influenza virus (ICV), a Type D influenza virus (IDV), or a variant, subtype, or reassortant thereof. In some embodiments, the influenza virus comprises a HA antigen, such as an HA antigen selected from the group consisting of H1, H2, H3, H5, H6, H7, H9, and H10, or a variant or reassortant thereof. In some embodiments, the influenza virus comprises a NA antigen, such as an NA antigen selected from the group consisting of N1, N2, N3, N7, N8, and N9, or a variant or reassortant thereof. In some embodiments, the influenza virus is selected from the group consisting of H1N1, H1N2, H2N2, H3N2, H3N8, H5N1, H5N9, H6N1, H7N2, H7N3, H7N7, H7N9, H9N2, H10N7, or a variant or reassortant thereof.

In some embodiments, the antibody moiety specifically binds to a component, e.g., HA protein or NA protein, on the surface of an influenza virus or a variant thereof. In some embodiment, the antibody moiety is derived from a subneutralizing or non-neutralizing antibody for a virulent influenza virus or variant thereof.

Influenza viruses are a group of related, yet antigenically and genetically diverse viruses that cause diseases in mammals and birds. In humans, influenza viruses cause respiratory tract infections that can range from mild to lethal. The most common symptoms include: a sudden onset of fever, cough (usually dry), headache, muscle and joint pain, severe malaise (feeling unwell), sore throat and a runny nose. The incubation period of influenza varies between one to four days, with symptoms appearing about two days following exposure to the influenza virus. Complications of influenza viruses can cause pneumonia (either direct viral pneumonia or secondary bacterial pneumonia) and bronchitis (either direct viral bronchitis or secondary bacterial bronchitis).

There are four type of influenza viruses: types A (IAV), B (IBV), C (ICV), and D (IDV). Of the four types of influenza virus, three types (A, B and C) affect humans. Influenza type A viruses, also referred to herein as "influenza A" are the most virulent human pathogens and cause the most severe disease. Influenza A viruses can be categorized based on the different subtypes of major viral surface proteins present, HA and NA. At present, there are 18 different HAs and 11 different NAs present among various influenza A viral strains, resulting in various subtype or strain combinations of the viral surface proteins (e.g., H1N1, H5N1). Type B influenza virus does not usually cause as severe disease as does type A influenza virus, and is more commonly seen in children, long-term care facilities, college campuses, and military camps. Influenza C virus generally causes a mild respiratory illness.

Influenza A and B viruses continuously evolve, generating new variants, a phenomenon known as antigenic drift. Consequently, antibodies produced in response to past viruses may be poorly- or non-protective against new drifted viruses. Therefore, a new vaccine may need to be produced every year against viruses that are predicted to emerge. Tables 2A and 2B show exemplary influenza A (Table 2A) and influenza B (Table 2B) antigens from the 2019 flu season. Table 3 shows exemplary influenza antigens from various flu seasons.

TABLE 2A

Exemplary influenza A HA and NA antigens from the 2019 flu season

| Name; Antigen | Sequence | SEQ ID NO |
|---|---|---|
| >QHA30968A/ Yokosuka/ NHRC_OID_FD X70722/2019 2019/04/17 HA | MKTIIALSCILCLVFAQKIPGNDNSTATLCLGHHAVPNGTIVKTITDDRIEVTN ATELVQNSSIGEICDSPHQILDGENCTLIDALLGDPQCDGFQNKKWDLFVERN KAYSNCYPYDVPDYASLRSLVASSGTLEFNNESFNWAGVTQNGTSSSCIRGS KSSFFSRLNWLTHLNSKYPALNVTMPNNEQFDKLYIWGVHHPGTDKDQISLY AQSSGRITVSTKRSQQAVIPNIGSRPRIRDIPSRISIYWTIVKPGDILLINSTGNLI APRGYFKIRSGKSSIMRSDAPIGKCKSECITPNGSIPNDKPFQNVNRITYGACP RYVKQSTLKLATGMRNVPERQTRGIFGAIAGFIENGWEGLVDGWYGFRHQN SEGRGQAADLKSTQAAIDQINGKLNRLIGKTNEKFHQIEKEFSEVEGRIQDLE KYVEDTKIDLWSYNAELLVALENQHTIDLTDSEMNKLFEKTKKQLRENAED MGNGCFKIYHKCDNACMGSIRNGTYDHNVYRDEALNNRFQIKGVELKSGY KDWILWISFAISCFLLCVVLLGFIMWACQKGNIRCNICI | 326 |
| >QHA30980A/ Yokosuka/ NHRC_OID_FD X70778/2019 2019/05/30 NA | MNPNQKIITIGSICMTIGMANLILQIGNIISIWVSHSIQIGNQSQIETCNKSVITYE NNTWVNQTYVNISNTNSAARQSVASVKLAGNSSLCPVSGWAIYSKDNSVRI GSKGDVFVIREPFISCSPLECRTFFLTQGALLNDKHSNGTIKDRSPYRTLMSCPI GEVPSPYNSRFESVAWSASACHDGTNWLTIGVSGPDSGAVAVLKYNGIITDTI KSWRNNILRTQESECACVNGSCFTIMTDGPSDGQASYKIFRIEKGKIIKSVEM KAPNYHYEECSCYPDSSEITCVCRDNWHGSNRPWVSFNQNLEYQMGYICSG VFGDNPRPNDKTGSCGPVSSNGANGVKGFAFKYGNGVWIGRTKSISSRKGFE MIWDPNGWTGTDNKFSKKQDIVGINEWSGYSGSFVQHPELTGLNCIRPCFW VELIRGRPEENTIWTSGSSISFCGVDSDIVGWSWPDGAELPFTIDK | 327 |
| >QFG38740A/ Thailand/ TM-5434_51/ 2019 2019/04/01 HA | VFAQKIPGNDNSTATLCLGHHAVPNGTIVKTITNDRIEVTNATELVQNSSIGEI CDSPHLILDGKNCTLIDALLGDPQCDGFQNKKWDLFVERSKAYSNCYPYDVP DYASLRSLVASSGTLEFNNESFNWTGVKQNGTSSACIRKSSSSFFSRLNWLTH LNYTYPALNVTMPNNEQFDKLYIWGVHHPGTDKDQIFLYAQSSGRITVSTKR SQQTVIPNIGSRPRIRDIPSRISIYWTIVKPGDILLINSTGNLIAPRGYFKIQSGKS SIMRSDAPIGKCKSECITPNGSIPNDKPFQNVNRITYGTCPRYVKHSTLKLATG MRNVPEKQTRGIFGAIAGFIENGWEGMVDGWYGFRHQNSEGRGQAADLKS TQAAIDQINGKLNRLIGKTNEKFHQIEKEFSEVEGRIQDLEKYVEDTKIDLWS YNAELLVALENQHTIDLTDSEMNKLFEKTKKQLRENAEDMGNGCFKIYHKC DNACIGSIRNGTYDHNVYRDEALNNRFQIKGVELKSGYKDWILWISFAISCFL LCVALLGFIMWACQKGN | 328 |
| >QFP41505A/ Thailand/ TM-5434_51/ 2019 2019/04/01 NA | SLTISTICFFMQIAILITTVTLHFKQYEFNSPPNNQVMLCEPTIIERNITEIVYLTN TTIEKEICLKPAEYRNWSKPQCGITGFAPFSKDNSIRLSAGGDIWVTREPYVSC DPDKCYQFALGQGTTLNNVHSNNTVRDRTPYRTLLMNELGVPFHLGTKQVC MAWSSSSCHDGKAWLHVCITGDDKNATASFIYNGRLVDSVVSWSKDILRTQ ESECVCINGTCTVVMTDGNATGKADTKILFIEEGKIVHTSKLSGSAQHVEECS CYPRYPGVRCVCRDNWKGSNRPIVDINIKDHSIVSSYVCSGLVGDTPRKSDSS SSSHCLNPNNEEGGHGVKGWAFDDGNDVWMGRTINETSRLGYETFKVVEG WSNSKSKLQINRQVIVDRGDRSGYSGIFSVEGKSCINRCFYVELIRGRKEETE VLWTSNSIVVFCGTSGTYGT | 329 |
| >QDC19555A/ Germany/94 96/2019 2019/04/03 HA | MKTIIALSCILCLVFAQKIPGNDNSTATLCLGHHAVPNGTIVKTITNDRIEVTN ATELVQNSSIGEICDSPHQILDGENCTLIDALLGDPQCDGFQNKKWDLFVERN KAYSNCYPYDVPDYASLRSLVASSGTLEFNNESFNWAGVTQNGTSSSCIRGS KSSFFSRLNWLTHLNSKYPALNVTMPNNEQFDKLYIWGVHHPGTDKDQTSL YAQSSGRITVSTKRSQQAVIPNIGSRPRIRDIPSRISIYWTIVKPGDILLINSTGNL IAPRGYFKIRSGKSSIMKSDAPIGKCKSECITPNGSIPNDKPFQNVNRITYGACP | 330 |

TABLE 2A-continued

| Exemplary influenza A HA and NA antigens from the 2019 flu season | | |
|---|---|---|
| Name; Antigen | Sequence | SEQ ID NO |
| | RYVKQSTLKLATGMRNVPEKQTRGIFGAIAGFIENGWEGLVDGWYGFRHQN SEGRGQAADLKSTQAAIDQINGKLNRLIGKTNEKFHQIEKEFSEVEGRIQDLE KYVEDTKIDLWSYNAELLVALENQHTIDLTDSEMNKLFEKTKKQLRENAED MGNGCFKIYHKCDNACMGSIRNGTYDHNVYRDEALNNRFQIKGVELKSGY KDWILWISFAISCFLLCVVLLGFIMWACQKGNIRCNICI | |
| >QDC19627A/ Germany/94 96/2019 2019/04/03 NA | MNPNQKIITISSVSLTISTICFFMQIAILITTVTLHFKQYEFNPPPNNQVMLCEPT HIERNITEIVYLTNTTIEREICPKPAEYRNWSKPQCGITGFAPFSKDNSIRLSAGG DIWVTREPYVSCDPDKCYQFALGQGTTINNVHSNNTARDRTPHRTLLMSELG VPFHLGTKQVCIAWSSSSCHDGKAWLHVCITGDDKNATASFIYNGRLVDSV VSWSKDILRTQESECVCINGTCTVVMTDGNATGKADTKILFIEEGKIVHTSKL SGSAQHVEECSCYPRYPGVRCVCRDNWKGSNRPIVDINIKDHSIVSSYVCSGL VGDTPRKTDSSSSSHCLNPNNEKGGHGVKGWAFDDGNDVWMGRTINETSR LGYETFKVVEGWSNSKSKLQINRQVIVDRGDRSGYSGIFSVEGKSCINRCFYV ELIRGRKEETEVLWTSNSIVVFCGTSGTYGTGSWPDGADLNLMHI | 331 |
| >QIA57890A/ Delaware/ 55/2019 2019/12/11 NA | MNPNQKIITIGSICMTIGTANLILQIGNIISIWVSHSIQIGNQSQIETCNKSVITYE NNTWVNQTFVNISNTNSAARQSVASVKLAGNSSLCPVSGWAIYSKDNSVRIG SKGDVFVIREPFISCSPLECRTFFLTQGALLNDKHSNGTIKDRSPYRTLMSCPIG EVPSPYNSRFESVAWSASACHDGTNWLTIGISGPDSGAVAVLKYNGIITDTIK SWRNKILRTQESECACVNGSCFTIMTDGPSDGQASYKIFRIEKGKIIKSVEMK APNYHYEECSCYPDSSEITCVCRDNWHGSNRPWVSFNQNLEYQMGYICSGV FGDNPRPNDKTGSCGPVSSNGANGVKGFSFKYGNGVWIGRTKSISSRKGFEM IWDPNGWTGTDNKFSKKQDIVGINEWSGYSGSFVQHPELTGLNCIRPCFWVE LIRGRPEENTIWTSGSSISFCGVDSDIVGWSWPDGAELPFTIDK | 332 |
| >QIA57903A/ Delaware/ 56/2019 2019/12/12 NA | MNPNQKIITIGSICMTIGMANLILQIGNIISIWVSHSIQTGNQSQIETCNKNVITY ENNTWVNQTYVNISNTNSAARQSVASVKLAGNSSLCPVSGWAIYSKDNSVRI GSKGDVFVIREPFISCSPLECRTFFLTQGALLNDKHSNGTIKDRSPYRTLMSCPI GEVPSPYNSRFESVAWSASACHDGTNWLTIGISGPDSGAVAVLKYNGIITDTI KSWRNNILRTQESECACVNGSCFTMMTDGPSDGQASYKIFRIEKGKIIKSVEM KAPNYHYEECSCYPDSSEITCVCRDNWHGSNRPWVSFNQNLEYQMGYICSG VFGDNPRPNDKTGSCGPVSSNGANGVKGFSFKYGNGVWIGRTKSISSRKGFE MIWDPNGWTGTDNKFSKKQDIVGINEWSGYSGSFVQHPELTGLNCIRPCFW VELIRGRPEENTIWTSGSSISFCGVDSDIVGWSWPDGAELPFTIDK | 333 |

TABLE 2B

| Exemplary influenza B HA and NA antigens from the 2019 flu season | | |
|---|---|---|
| Name; Antigen | Sequence | SEQ ID NO |
| >QJA11920B/ Alabama/07/ 2020 2020/02/21 HA | MKAIIVLLMVVTSNADRICTGITSSNSPHVVKTATQGEVNVTGVIPLTTTPTKS HFANLKGTETRGKLCPKCLNCTDLDVALGRPKCTGKIPSARVSILHEVRPVTS GCFPIMHDRTKIRQLPNLLRGYEHVRLSTHNVINAEGAPGGPYKIGTSGSCPNI TNGNGFFATMAWAVPDKNKTATNPLTIEVPYVCTEGEDQITVWGFHSDNET QMAKLYGDSKPQKFTSSANGVTTHYVSQIGGFPNQTEDGGLPQSGRIVVDY MVQKSGKTGTITYQRGILLPQKVWCAXGRSKVIKGSLPLIGEADCLHEKYGG LNKSKPYYTGEHAKAIGNCPIWVKTPLKLANGTKYRPPAKLLKERGFFGAIA GFLEGGWEGMIAGWHGYTSHGAHGVAVAADLKSTQEAINKITKNLNSLSEL EVKNLQRLSGAMDELHNEILELDEKVDDLRADTISSQIELAVLLSNEGIINSED EHLLALERKLKKMLGPSAVEIGNGCFETKHKCNQTCLDKIAAGTFDAGEFSL PTFDSLNITAASLNDDGLDNHTILLYYSTAASSLAVTLMIAIFVVYMVSRDNV SCSICL | 334 |
| >QJA11911B/ Alabama/07/ 2020 2020/02/21 NA | MLPSTIQTLTLFLTSGGVLLSLYVSASLSYLLYSDILLKFSPTEITAPTMPLDCA NASNVQAVNRSATKGVILLLPEPEWTYPRLSCPGSTFQKALLISPHRFGETKG NSAPLIIREPFVACGPNECKHEALTHYAAQPGGYYNGTRGDRNKLRHLISVK LGKIPTVENSIFHMAAWSGSACHDGKEWTYIGVDGPDNNALLKIKYGEAYT DTYHSYANNILRTQESACNCIGGNCYLMITDGSXSGVSECRFLKIREGRIIKEI FPTGRVKHTEECTCGFASNKTIECACRDNRYTAKRPFVKLNVETDTAEIRLM CTDTYLDTPRPNDGSITGPCESDGDKGSGGIKGGFVHQRMKSKIGRWYSRTM SQTERMGMGLYVKYGGDPWADSDALAFSGVMVSMKEPGWYSFGFEIKDK KCDVPCIGIEMVHDGGKETWHSAATAIYCLMGSGQLLWDTVTGVDMAL | 335 |
| >QGT76054B/ China/b45/ 2019 2019/ 01/08 | MKAIIVLLMVVTSNADRICTGITSSNSPHVVKTATQGEVNVTGVIPLTTTPTKS HFANLKGTETRGKLCPKCLNCTDLDVALGRPKCTGKIPSARVSILHEVRPVTS GCFPIMHDRTKIRQLPNLLRGYEHVRLSTHNVINAEDAPGGPYKIGTSGSCPNI TNGNGFFATMAWAVPKNDKNKTATNPLTIEVPYICTEGEDQITVWGFHSDN | 336 |

TABLE 2B-continued

Exemplary influenza B HA and NA antigens from the 2019 flu season

| Name; Antigen | Sequence | SEQ ID NO |
|---|---|---|
| HA | ETQMAKLYGDSKPQKFTSSANGVTTHYVSQIGGFPNQTEDGGLPQSGRIVVD<br>YMVQKSGKTGTITYQRGILLPQKVWCASGRSKVIKGSLPLIGEADCLHEKYG<br>GLNKSKPYYTGEHAKAIGNCPIWVKTPLKLANGTKYRPPAKLLKERGFFGAI<br>AGFLEGGWEGMIAGWHGYTSHGAHGIAVAADLKSTQEAINKITKNLNSLSE<br>LEVKNLQRLSGAMDELHNEILELDEKVDDLRADTISSQIELAVLLSNEGIINSE<br>DEHLLALERKLKKMLGPSAVEIGNGCFETKHKCNQTCLDRIAAGTFDAGEFS<br>LPTFDSLNITAASLNDDGLDNHTILLYYSTAASSLAVTLMIAIFVVYMVSRDN<br>VSCSICL | |
| >QGT76183B/ China/b45/ 2019 2019/ 01/08 NA | MLPSTIQTLTLFLTSGGVLLSLYVSASLSYLLYSDILLKFSPTEITAPTMPLDCA<br>NASNVQAVNRSATKGATLLLPEPEWTYPRLSCPGSTFQKALLISPHRFGETKG<br>NSAPLIIREPFVACGPNECKHEALTHYAAQPGGYYNGTRGDRNKLRHLISVK<br>LGKIPTVENSIFHMAAWSGSACHDGKEWTYIGVDGPDNNALLKVKYGEAYT<br>DTYHSYANNILRTQESACNCIGGNCYLMITDGSASGVSECRFLKIREGRIIKEI<br>FPTGRVKHTEECTCGFASNKTIECACRDNRYTAKRPFVKLNVETDTAEIRLM<br>CTDTYLDTPRPNDGSITGPCESDGDEGSGGIKGGFVHQRMKSKIGRWYSRTM<br>SKTERMGMGLYVKYGGDPWADSDALVFSGVMISMKEPGWYSFGFEIKDKK<br>CDVPCIGIEMVHDGGKETWHSAATAIYCLMGSGQLLWDTVTGVDMAL | 337 |
| >QDX11011B/ Japan/9830/ 2019 2019/ 05/22 HA | MKAIIVLLMVVTSNADRICTGITSSNSPHVVKTATQGEVNVTGVIPLTTTPTKS<br>HFANLKGTETRGKLCPKCLNCTDLDVALGRPKCTGKIPSARVSILHEVRPVTS<br>GCFPIMHDRTKIRQLPNILRGYEHVRLSTHNVINAEDAPGRPYEIGTSGSCPNI<br>TNGNGFFATMAWAVPKNKTATNPLTIEVPYICTEGEDQITVWGFHSDNETQ<br>MAKLYGDSKPQKFTSSANGVTTHYVSQIGGFPNQTEDGGLPQSGRIVVDYM<br>VQKSGKTGTITYQRGILLPQKVWCASGRSKVIKGSLPLIGEADCLHEKYGGL<br>NKSKPYYTGEHAKAIGNCPIWVKTPLKLANGTKYRPPAKLLKERGFFGAIAG<br>FLEGGWEGMIAGWHGYTSHGAHGVAVAADLKSTQEAINKITKNLNSLSELE<br>VKNLQRLSGAMDELHNEILELDEKVDDLRADTISSQIELAVLLSNEGIINSEDE<br>HLLALERKLKKMLGPSAVEIGNGCFETKHKCNQTCLDRIAAGTFDAGEFSLP<br>TFDSLNITAASLNDDGLDNHTILLYYSTAASSLAVTLMIAIFVVYMVSRDNVS<br>CSICL | 338 |
| >QDX11015B/ Japan/9830/ 2019 2019/ 05/22 NA | MLPSTIQTLTLFLTSGGVLLSLYVSASLSYLLYSDILLKFSPTEITAPTMPLDCA<br>NASNVQAVNRSATKGVTLLLPEPEWTYPRLSCPGSTFQKALLISPHRFGETKG<br>NSAPLIIREPFVACGPNECKHEALTHYAAQPGGYYNGTRGDRNKLRHLISVK<br>LGKIPTVENSIFHMAAWSGSACHDGKEWTYIGVDGPDNNALLKVKYGEAYT<br>DTYHSYANNILRTQESACNCIGGNCYLMITDGSASGVSECRFLKIREGRIIKEI<br>FPTGRVKHTEECTCGFASNKTIECACRDNKYTAKRPFVKLNVETDTAEIRLM<br>CTDTYLDTPRPNDGSITGPCESDGDKGSGGIKGGFVHQRMKSKIGRWYSRTM<br>SKTERMGMGLYVKYGGDPWADSDALTFSGVMVSMKEPGWYSFGFEIKDKK<br>CDVPCIGIEMVHDGGKETWHSAATAIYCLMGSGQLLWDTVTGVDMAL | 339 |
| >QDA45896B/ Moscow/2/ 2019 2019/ 02/22 HA | MKAIIVLLMVVTSNADRICTGITSSNSPHVVKTATQGEVNVTGVIPLTTTPTKS<br>HFANLKGTETRGKLCPKCLNCTDLDVALGRPKCTGKIPSARVSILHEVKPVTS<br>GCFPIMHDRTKIRQLPNLLRGYEHVRLSTHNVINAEGAPGGPYKIGTSGSCPNI<br>TNGNGFFATMAWAVPDKNKTATNPLTIEVPYICTEGEDQITVWGFHSDNETQ<br>MAKLYGDSKPQKFTSSANGVTTHYVSQIGGFPNQTEDGGLPQSGRIVVDYM<br>VQKSGKTGTITYQRGILLPQKVWCASGRSKVIKGSLPLIGEADCLHEKYGGL<br>NKSKPYYTGEHAKAIGNCPIWVKTPLKLANGTKYRPPAKLLKERGFFGAIAG<br>FLEGGWEGMIAGWHGYTSHGAHGVAVAADLKSTQEAINKITKNLNSLSELE<br>VKNLQRLSGAMDELHNEILELDEKVDDLRADTISSQIELAVLLSNEGIINSEDE<br>HLLALERKLKKMLGPSAVEIGNGCFETKHKCNQTCLDKIAAGTFDAGEFSLP<br>TFDSLNITAASLNDDGLDNHTILLYYSTAASSLAVTLMIAIFVVYMVSRDNVS<br>CSICL | 340 |
| >QDA45899B/ Moscow/2/ 2019 2019/ 02/22 NA | MLPSTIQTLTLFLTSGGVLLSLYVSASLSYLLYSDILLKFSPTEITAPTMPLDCA<br>NASNVQAVNRSATKGVTLLLPEPEWTYPRLSCPGSTFQKALLISPHRFGETKG<br>NSAPLIIREPFVACGPNECKHEALTHYAAQPGGYYNGTRGDRNKLRHLISVK<br>LGKIPTVENSIFHMAAWSGSACHDGKEWTYIGVDGPDNNALLKVKYGEAYT<br>DTYHSYANNILRTQESACNCIGGNCYLMITDGSASGVSECRFLKIREGRIIKEI<br>FPTGRVKHTEECTCGFASNKTIECACRDNRYTAKRPFVKLNVETDTAEIRLM<br>CTDTYLDTPRPNDGSITGPCESDGDKGSGGIKGGFVHQRMKSKIGRWYSRTM<br>SKTERMGMGLYVKYGGDPWADSNALAFSGVMISMKEPGWYSFGFEIKDKK<br>CDVPCIGIEMVHDGGKETWHSAATAIYCLMGSGQLLWDTVTGVDMAL | 341 |

TABLE 3

Exemplary influenza A HA and NA antigens from various flu seasons

| Name; Antigen | Sequence | SEQ ID NO |
|---|---|---|
| >AB745403.1/ H1N1 A/ Tottori/ YK041/2011 | AGSGIIISDTPVHDCNTTCQTPKGAINTSLPFQNIHPITIGKCPKYVKSTKLRLA TGLRNVPSIQSRGLFGAIAGFIEGGWTGMVDGWYGYHHQNEQGSGYAADLK STQNAIDKITNKVNSVIEKMNTQFTAVGKEFNHLEKRIENLNKKVDDGFLDI WTYNAELLVLLENERTLDYHDSNVKNLYEKVRNQLKNNAKEIGNGCFEFYH KCDNTCMESVKNGTYDYPKYSEEAKLNREEIDGVKLESTRIYQIL | 421 |
| >4058_A/H3A/ (H3N2 Victoria/3/ 1975) | RTGKSSIMRSDAPIGTCSSECITPNGSIPNDKPFQNVNKITYGACPKYVKQNTL KLATGMRNVPEKQTRGIFGAIAGFIENGWEGMIDGWYGFRHQNSEGTGQAA DLKSTQAAIDQINGKLNRVIEKTNEKFHQIEKEFSEVEGRIQDLEKYVEDTKID LWSYNAELLVALENQHTIDLTDSEMNKLFEKTRRQLRENAEDMGNGCFKIY HKCDNACIGSIRNGTYDHDVYRDEALNNRFQIKGVELKSGYKDWI | 427 |
| >O56140/H5 (H5N1 A/Hong Kong/156/97) | STIMKSELEYGNCNTKCQTPMGAINSSMPFHNIHPLTIGECPKYVKSNRLVLA TGLRNTPQRERRRKKRGLFGAIAGFIEGGWQGMVDGWYGYHHSNEQGSGY AADKESTQKAIDGVTNKVNSIINKMNTQFEAVGREFNNLERRIENLNKKMED GFLDVWTYNAELLVLMENERTLDFHDSNVKNLYDKVRLQLRDNAKELGNG CFEFYHKCDNECMESVKNGTYDYPQYSEEARLNREEISGVKLESMGTYQIL | 444 |
| >ARM59253/ H7 (H9N2 A/ Egypt/ZU65/ 2016) | LSGESHGRILKTDLNSGNCVVQCQTEKGGLNSTLPFHNISKYAFGDCPKYIGV KSLKLAIGLRNVPARSSRGLFGAIAGFIEGGWPGLVAGWYGFQHSNDQGVG MAADRDSTQKAVDKITSKVNNIVDKMNKQYEIIDHEFSEVETRLNMINNKID DQIQDVWAYNAELLVLLENQKTLDEHDANVNNLYNKVKRALGSNAMEDG KGCFELYHKCDDQCMETIRNGTYNRRKYMEESRLGRQKIEGVKLESEGTYKIL | 495 |

Exemplary antibodies against the HA antigen (e.g., human and animal HA antigen) of influenza virus are known in the art, including, for example, FI6V3, F045-092, mAb35490, KPF1, H1H14611N2, FluA-20, H5.28, H5.31, H7-200, 12mab, mAb14303, VIS410, FluAB_MLNS, D7, AT10_004, CR8001, and CR9114 reported in U.S. Pat. Nos. 10,815,294, 9,605,053, 11,168,129, 11,230,593, 9,611,317, 9,718,874, US 2021/0171612, US 2021/0371505, US 2021/0252150, PCT/US2020/017889, PCT/CN2020/071524, PCT/EP2020/062160, CN111704665 and PCT/EP2012/063637 which are incorporated by reference in their entirety. Exemplary antibodies against the NA protein of influenza virus (e.g., in humans and animals) are also known in the art, including, for example, 1G05, 2E01, IF2, 1F4, 1092A9, 1092B6, 3C05, SEQ 42-43, SEQ 40-41, SEQ 44-45, 2D04, 1D05, 1G03, and 2B04, reported in U.S. Pat. No. 10,079,518, US 2021/0047389, US 2021/0002354, PCT/US2021/016879, and PCT/US2020/035323, which are incorporated by reference in their entirety. Exemplary human antibody sequences against HA and NA of various influenza viruses or variants thereof are shown in Tables 4A-4B, respectively. Exemplary animal anti-HA antibody sequences are shown in Table 6. Exemplary animal anti-NA antibodies targeting the NA protein of zoonotic IAV strain H7N9 have been published in the literature (D3 and 7H2, Xiong, et al., Emerging Microbes & Infections 9(1):78-87 (2020)). Additionally, a camelid antibody directed to another zoonotic strain, IAV H5N1 (N1-$V_H$H, Cardoso, et al. Journal of Virology, 88(15): 8278-96 (2014)) has been described.

New antibodies may be developed against a component (e.g., antibodies against HA and NA antigens, such as human or animal HA and NA antigens) of an influenza virus or variant thereof using art-known techniques, and the variable region sequences of such antibodies, or a fragment thereof, may be used as the antibody moiety of a chimeric protein of the present disclosure. In some embodiments, the influenza virus is a known influenza virus. In some embodiments, the influenza virus is a variant of a known influenza virus. In some embodiments, the influenza virus is a future influenza virus. In some embodiments, the influenza virus is a variant of a future influenza virus.

In some embodiments, the antibody moiety is a derivative of any one of the antibodies against the HA or NA protein of an influenza virus or variant thereof described herein. In some embodiments, the antibodies that compete with any of these art-recognized antibodies for binding to the HA protein or NA of an influenza virus or variant thereof can be used.

HA is the main target of neutralizing antibodies that are induced by infection of an individual by an influenza virus or variant thereof or vaccination against an influenza virus or variant thereof. HA directs the binding the influenza virus to cells with sialic acid on the membranes, such as cells in the upper respiratory tract, e.g., cells of the nasal cavity, the larynx, trachea, bronchi or lung. In addition, HA is responsible for the fusion of the influenza viral envelope with the endosome membrane, allowing the capsid and viral genome to enter and infect the host.

HA is a homotrimeric integral membrane glycoprotein, composed of three identical monomers, each made of an intact HA0 single polypeptide chain comprising HA1 and HA2 regions linked by two disulfide bridges. Each HA2 region adopts an α-helical coiled coil structure and primarily forms the "stem" region of HA, while the HA1 region is a small globular domain comprising a combination of a/P structures ("head" region of HA). The globular HA head region facilitates binding to viral receptors expressed on host cells, which are typically sialic acid-containing glycoproteins, gangliosides, or glycolipid ("sialic acid receptors"), while the HA stem mediates the subsequent fusion between the viral and cellular membranes. While the highly variable and immunodominant HA globular head domain undergoes constant antigenic drift, the HA stem region is fairly conserved among influenza subtypes. Current influenza vaccines generally induce an immune response against the HA head region. (see, e.g., Kirkpatrick et al., *Nat Sci Rep,* 8:10432 (2018)). Therefore, a particular influenza vaccine usually confers protection for no more than a few years and annual re-development of influenza vaccines is required.

Recently, a new class of influenza-neutralizing antibodies that target conserved sites in the HA stem were developed as influenza virus therapeutics. These antibodies targeting the stem region of HA are usually broader neutralizing compared to antibodies targeting the head region of HA. An overview over broadly neutralizing influenza A antibodies is provided in *Corti* and Lanzavecchia, *Annu Rev Immunol,* 31:705-742 (2013).

The other major surface glycoprotein of influenza A and B viruses is NA, which is absent in influenza C virus. NA is a receptor-destroying enzyme that is responsible for cleaving terminal sialic acid residues from N-linked glycans present on cell surfaces and progeny virions. This activity is important for releasing incoming influenza viruses trapped by glycans of host natural defense proteins on mucosal surfaces, and for releasing of nascent influenza viruses budding from infected host cells. Anti-NA antibodies can block this cleavage activity by directly binding to the enzymatic active site of NA or by sterically hindering interactions between NA and its substrate.

NA is a homotetrameric transmembrane glycoprotein made of four identical subunits. NA protein is made of four main regions: a cytoplasmic tail domain, a hydrophobic transmembrane domain, a stalk region, and a globular head domain containing the enzyme active site. The structure of each NA individual subunit consists of six topologically identical 4-stranded antiparallel β-sheets arranged. The enzyme active site (19 amino acids) is located at the center of each subunit. The active site is a deep pocket made of amino acids that are highly conserved in all strains of influenza virus. Antibody-binding sites are located on the surface loops that surround the enzyme active site. Additional description of NA can be found in, for example, Jagadesh et al., *Arch Virol,* 161:2087-2094 (2016). As described above, influenza viruses can mutate the antigenic sites in HA (particularly in the HA stem region) at a high rate, whereas NA has been shown to exhibit a slower antigenic drift, resulting in a broader cross-reactivity of anti-NA antibodies compared with that of anti-HA antibodies.

In some embodiments, provided herein is a chimeric protein comprising an antibody or an antigen binding fragment thereof that binds an epitope on HA or NA on the surface of an influenza virus or variant thereof. In some embodiments, the antibody or an antigen binding fragment thereof binds an epitope on HA. In some embodiments, the HA epitope is from an HA antigen, such as an HA antigen of the HA1, HA2, HA3, HA4, HA5, HA6, HA7, HA8, HA9, HA10, HA11, HA12, HA13, HA14, HA15, HA16, HA17, or HA18 subtype, or a combination thereof. In some embodiments, the antibody or an antigen binding fragment thereof binds an epitope on two or more HA subtypes (e.g., HA1, HA2, HA3, HA4, HA5, HA6, HA7, HA8, HA9, HA10, HA11, HA12, HA13, HA14, HA15, HA16, HA17, HA18). In some embodiments, the antibody or an antigen binding fragment thereof binds an epitope on NA. In some embodiments, the NA epitope is from an NA antigen, such as an NA antigen of the N1, N2, N3, N4, N5, N6, N7, N8, N9, N10, or N11 subtype, or a combination thereof. In some embodiments, the antibody or an antigen binding fragment thereof binds an epitope on two or more NA types (e.g., N1, N2, N3, N4, N5, N6, N7, N8, N9, N10, N11). In some embodiments, the chimeric protein treats or prevents infection by two or more types of influenza virus, e.g., H1N1, H1N2, H2N2, H3N2, H3N8, H5N1, H5N9, H6N1, H7N2, H7N3, H7N7, H7N9, H9N2, H10N7, or variants or reassortants thereof.

Anti-HA and Anti-NA Antibodies and Antigen Binding Fragments Thereof

The present application provides chimeric proteins comprising antibodies or antigen binding fragments thereof that specifically bind to a HA or NA surface protein of an influenza virus (including influenza virus variants) (also referred to as "anti-HA or anti-NA antibodies"). The anti-HA and NA antibodies described herein can be of any suitable full-length antibody or antigen-binding fragment format. Any of the anti-HA or anti-NA antibodies or antigen binding fragments thereof may be used as the antibody moiety in a chimeric protein described herein, or the anti-HA or anti-NA antibody moiety in an anti-HA or anti-NA antibody construct described herein.

In some embodiments, the anti-HA or anti-NA antibody is a full-length antibody or an immunoglobulin derivative. In some embodiments, the anti-HA or anti-NA antibody is an IgG, an IgA, an IgD, an IgE, or an IgM. Full-length antibodies comprise two heavy chains and two light chains. IgG, IgA, and IgD's heavy chains each comprise $V_H$, $CH_1$, $CH_2$, and $CH_3$, while IgM and IgE's heavy chains each comprise the additional $CH_4$, with pairs of the $CH_2CH_3$ fragment or the $CH_2CH_3CH_4$ fragment forming the Fc domain. Light chains each comprise $V_L$ and $C_L$. $V_H$ and $V_L$ pair up to form a variable region of an antibody, while $CH_1$ and $C_L$ pair up as a part of the constant region of an antibody. The complete constant region of a full-length antibody comprises two $CH_1$—$C_L$ pairs and one pair of the $CH_2CH_3$ fragment or the $CH_2CH_3CH_4$ fragment.

In some embodiments, the anti-HA or anti-NA antibody is an antigen-binding fragment, for example, an antigen-binding fragment selected from the group consisting of a Fab, a Fab', a F(ab')2, an Fv fragment, a disulfide stabilized Fv fragment (dsFv), a $(dsFv)_2$, an scFv dimer, a domain antibody, a bivalent domain antibody, a single-chain Fv (scFv), a scFv-Fc fusion protein, and a minibody (i.e., a scFv-CH3 fusion protein). In some embodiments, the anti-HA or anti-NA antibody is a scFv. In some embodiments, the anti-HA or anti-NA antibody is a fusion protein comprising a scFv fused to an Fc region. In some embodiments, the anti-HA or anti-NA antibody is a fusion protein comprising a scFv fused to a $CH_3$ domain.

In some embodiments, the anti-HA or anti-NA antibody is chimeric, animal, human, partially humanized, fully humanized, or semi-synthetic. In some embodiments, the anti-HA or anti-NA antibody is a semi-synthetic antibody comprising fully human sequences and one or more synthetic regions. In some embodiments, the synthetic HC-CDR3 is from about 5 to about 19 (such as about n, where n is selected from 5, 6, 7, 8, 9, 10, 11, 12, 13, 14, 15, 16, 17, 18, and 19) amino acids in length. In some embodiments, the anti-HA or anti-NA antibody is a semi-synthetic antibody comprising human CDRs and non-human framework sequences. Non-human framework sequences include, in some embodiments, any sequence that can be used for generating synthetic heavy and/or light chain variable regions using one or more human CDR sequences as described herein, including, e.g., mammals, such as mouse, rat, rabbit, pig, bovine (e.g., cow, bull, buffalo), deer, sheep, goat, chicken, cat, dog, ferret, primate (e.g., marmoset, rhesus monkey), etc. In some embodiments, the anti-HA or anti-NA antibody is generated by grafting one or more human CDR sequences as described herein onto a non-human framework sequence (e.g., a mouse or chicken framework sequence).

The anti-HA or anti-NA antibody, in some embodiments, comprises specific sequences or certain variants of such sequences. In some embodiments, the amino acid substitutions in the variant sequences do not substantially reduce the ability of the anti-HA or anti-NA antibody to specifically recognize an HA protein or an NA protein, respectively, of an influenza virus or variant thereof. For example, alterations that do not substantially reduce HA or NA binding affinity may be made. Alterations that substantially improve HA or NA binding affinity or affect some other property, such as specificity and/or cross-reactivity with related variants of the HA or NA protein, are also contemplated.

Exemplary human antibody sequences are shown in Tables 4A-4B, and exemplary animal antibody sequences are shown in Table 6.

Exemplary Human Anti-HA Antibodies

In some embodiments, there is provided a chimeric protein comprising an anti-HA antibody or antigen binding fragment thereof (e.g., an anti-HA antibody moiety) that specifically binds to a human HA antigen. In some embodiments, the anti-HA antibody or antigen fragment thereof is a human anti-HA antibody or antigen fragment thereof.

Exemplary anti-HA antibodies are provided in Table 4A.

TABLE 4A

CDR and $V_H$/$V_L$ sequences of exemplary human anti-HA antibodies

| Antibody code | Antibody Name | Target strain | Sequence | Type | SEQ ID NO |
|---|---|---|---|---|---|
| HA1 Reference: WO2013011347 | FI6V3 | IAV group 1 and 2: H1, H5, H9, H3, H7 | QVQLVESGGGVVQPGRSLRLSCAASGFTFSTYAMHWVRQAPGKGLEWVAVISYDANYKYYADSVKGRFTISRDNSKNTLYLQMNSLRAEDTAVYYCAKDSQLRSLLYFEWLSQGYFDYWGQGTLVTVSS | $V_H$ | 76 |
| | | IAV group 1: H1, H5, H9 | DIVMTQSPDSLAVSLGERATINCKSSQSVTFNYKNYLAWYQQKPGQPPKLLIYWASTRESGVPDRFSGSGSGTDFTLTISSLQAEDVAVYYCQQHYRTPPTFGQGTKVEIK | $V_L$ | 77 |
| | | IAV group 2: H3, H7 | GFTFSTYA | HC-CDR1 | 1 |
| | | | ISYDANYK | HC-CDR2 | 2 |
| | | | AKDSQLRSLLYFEWLSQGYFDY | HC-CDR3 | 3 |
| | | | QSVTFNYKNY | LC-CDR1 | 4 |
| | | | WAS | LC-CDR2 | |
| | | | QQHYRTPPT | LC-CDR3 | 6 |
| HA2 Reference: WO2012029997 | F045-092 | IAV group 1: H1, H3 | EVQLVESGAEVKKPGSSVKVSCRASGTFYKYAINWVRQAPGQGLEWMGGIIPFFGTTNYAQKFQGRLTITADGSTNTAYMQLDSLRSEDTAVYYCAGPSITESHYCLDCAAKDYYYGLDVWGQGTTVTVSS | $V_H$ | 78 |
| | | | QSVLTQPPSASGTPGQSVTISCSGSRSNIGGNTVNWYQHLPGMAPKLLIYSSNQRSSGVPDRFSGSKSGTSASLAISGLQSEDDADYYCASWDDSLNGVVFGGGTKLTVLG | $V_L$ | 79 |
| | | | KYAIN | HC-CDR1 | 7 |
| | | | GIIPFFGTTNYAQKFQG | HC-CDR2 | 8 |
| | | | PSITESHYCLDCAAKDYYYGLDV | HC-CDR3 | 9 |
| | | | SGSRSNIGGNTVN | LC-CDR1 | 235 |
| | | | SSNQRSS | LC-CDR2 | 238 |
| | | | ASWDDSLNG | LC-CDR3 | 415 |
| HA3 Reference: WO2021086899 | mAb35490 | IBV | EVQLVESGGDLVQPGGSLRLSCAASGFTVSSNYMSWVRQVPGKGLDWVSVTYSGGNTYYADSVKGRFTISRHNSKNTLYLQMNSLRIEDTAVYYCATVPSFHGMDVWGQGTTVTVSS | $V_H$ | 80 |
| | | | DIQMTQSPSSLSASVGDRVTITCRASQSISSYLNWYQQKPGKAPKLLIYAASSLQSGVPSRFSGSGSGTDFTLTISSLQPEDFATYYCQQSYSTPPITFGQGTRLEIK | $V_L$ | 81 |
| | | | GFTVSSNY | HC-CDR1 | 10 |
| | | | TYSGGNT | HC-CDR2 | 11 |
| | | | ATVPSFHGMDV | HC-CDR3 | 12 |
| | | | QSISSY | LC-CDR1 | 13 |
| | | | AAS | LC-CDR2 | |
| | | | QQSYSTPPIT | LC-CDR3 | 15 |
| HA4 Reference: WO2018213097 | KPF1 | IAV group 1: H1 | EVQLLESGGGLVQPGGSLRISCAASGSTFGDFAMSWVRQSPGRGLEWVSVTSAGGDRTYYADSVKGRFTISRDNSKNTLYLQMNSLRGEDTAMYYCARLDSSGFHYGRPGRNWGQGTLVTVSS | $V_H$ | 82 |
| | | | DIQMTHSPPSLSASVGDRITITCQASQDISYYLIWYQQKPGKAPKPLIYDASNLEAGVPSRFSASGSGTDFTLTISSLQPEDLATYYCQQYKSLPYTFGQGTKLEIK | $V_L$ | 83 |

TABLE 4A-continued

CDR and $V_H$/$V_L$ sequences of exemplary human anti-HA antibodies

| Antibody code | Antibody Name | Target strain | Sequence | Type | SEQ ID NO |
|---|---|---|---|---|---|
| | | | GSTFGDFA | HC-CDR1 | 16 |
| | | | TSAGGDRT | HC-CDR2 | 17 |
| | | | ARLDSSGFHYGRPGRN | HC-CDR3 | 18 |
| | | | QDISYY | LC-CDR1 | 19 |
| | | | DAS | LC-CDR2 | |
| | | | QQYKSLPYT | LC-CDR3 | 21 |
| HA5 Reference: WO2019147867 | H1H14611 N2 | IAV group 2: H3, H4, H10, H14, H15 | EVQLVESGGGLVKPGGSLRLSCAASGFTFSGFSMNWVRQVPGKGLEWVSSISTSGNYMYYADSVKGRFTISRDNAKKSFSLQMNSLRAEDSAIYYCARGGGYNWNLFDYWGQGSLVTVSS | $V_H$ | 84 |
| | | | EIVLTQSPGTLSLSPGERATLSCRASQSLNSNYLAWYQQKPGQAPRLLIYGASSRATGIPDRFSGSGSGTDFTLTITRLESEDFAVYYCQQYGNSPLTFGGGTKVEIK | $V_L$ | 85 |
| | | | GFTFSGFS | HC-CDR1 | 22 |
| | | | ISTSGNYM | HC-CDR2 | 23 |
| | | | ARGGGYNWNLFDY | HC-CDR3 | 24 |
| | | | QSLNSNY | LC-CDR1 | 25 |
| | | | GAS | LC-CDR2 | |
| | | | QQYGNSPLT | LC-CDR3 | 27 |
| HA6 Reference: WO2020041540 | FluA-20 | Pan IAV | QVQLQESGPGLVKPSETLSLTCSVSGVSVTSDIYYWTWIRQPPGKGLEWIGYIFYNGDTNYNPSLKSRVTMSIDTSKNEFSLRLTSVTAADTAVYFCARGTEDLGYCSSGSCPNHWGQGTLVTVSS | $V_H$ | 86 |
| | | | DIQMTQSPSSLSASIGDRVTITCRPSQNIRSFLNWFQHKPGKAPKLLIYAASNLQSGVPSRFSGSGSGTEFTLTIRSLQPEDFATYYCQQSYNTPPTFGQGTKVEIK | $V_L$ | 87 |
| | | | GVSVTSDIYY | HC-CDR1 | 28 |
| | | | IFYNGDT | HC-CDR2 | 29 |
| | | | ARGTEDLGYCSSGSCPNH | HC-CDR3 | 30 |
| | | | QNIRSF | LC-CDR1 | 31 |
| | | | AAS | LC-CDR2 | |
| | | | QQSYNTPPT | LC-CDR3 | 33 |
| HA7 Reference: WO2020041540 | H5.28 | Pan IAV | EVQLVESGGGLVQPGGSLRLSCAASGFTFSTYWMTWVRQAPGKGLEWVANINQDGGEKYFVDSVKGRFTISRDNAKNSLFLQMNTLRAEDTAVYYCARGFLERLLLGRQGAYYYGMDVWGQGTTVTVSS | $V_H$ | 88 |
| | | | DIQMTQSPSSLSASVGDRVSMTCRASQIISSSLNWYQQKPGKAPKLLIYAASNLQSGVPSRFSGSGSGTDFTLTISSLQPEDFATYYCQQSYSTPPELTFGGGTKVEIK | $V_L$ | 89 |
| | | | GFTFSTYW | HC-CDR1 | 34 |
| | | | INQDGGEK | HC-CDR2 | 35 |
| | | | ARGFLERLLLGRQGAYYYGMDV | HC-CDR3 | 36 |
| | | | QIISSS | LC-CDR1 | 37 |
| | | | AAS | LC-CDR2 | |
| | | | QQSYSTPPELT | LC-CDR3 | 39 |
| HA8 Reference: WO2020041540 | H5.31 | Pan IAV | EVQLVQSGGGLVQPGGSLRLSCEASRFTSSSYWITWVRQAPGKGLEWVANIKQDGSEKYFVDSVKGRFTISRDNASNSLYLQMSSLRAEDTAVYYCARGFLERLLLGRQGAYYYGMDVWGQGTTVTVSS | $V_H$ | 90 |
| | | | DIQMTQSPSSLSASVGDRVTMTCRASQSISSSLNWYQQKPGKAPKLLIYAASNLQSGVPSRFSGSGSGTDFTLTISSLQPEDFATYYCQQSYTMPPELTFGGGTKVQIK | $V_L$ | 91 |
| | | | RFTSSSYW | HC-CDR1 | 40 |
| | | | IKQDGSEK | HC-CDR2 | 41 |
| | | | ARGFLERLLLGRQGAYYYGMDV | HC-CDR3 | 42 |
| | | | QSISSS | LC-CDR1 | 43 |
| | | | AAS | LC-CDR2 | |
| | | | QQSYTMPPELT | LC-CDR3 | 45 |

TABLE 4A-continued

CDR and $V_H$/$V_L$ sequences of exemplary human anti-HA antibodies

| Antibody code | Antibody Name | Target strain | Sequence | Type | SEQ ID NO |
|---|---|---|---|---|---|
| HA9 Reference: WO2020041540 | H7-200 | Pan IAV | QVQLVESGPGLVKPSQTLSLTCTVSGGSIN SSHSFWSWIRQPAGKGLEWIGRIYSTGNSN YNPSLKSRVTISLDTSKNQFSLKLSSVTAA DTAVYYCARESLWNPDYYYYMDVWGKG TLVTVSS | $V_H$ | 92 |
| | | | DIVMTQSPSSLSASVGDRVTITCRASQSFSS HLNWYQQKPGRAPDLLIYAASSLHSGVPS RFSGSGSGTDFTLTISSLQPEDFAVYYCQQS YSVPYTFGQGTKLQIK | $V_L$ | 93 |
| | | | GGSINSSHSF | HC-CDR1 | 46 |
| | | | IYSTGNS | HC-CDR2 | 47 |
| | | | ARESLWNPDYYYYMDV | HC-CDR3 | 48 |
| | | | QSFSSH | LC-CDR1 | 49 |
| | | | AAS | LC-CDR2 | |
| | | | QQSYSVPYT | LC-CDR3 | 51 |
| HA10 Reference: WO2020143799 | 12mab | IAV group 1: H1 IAV group 2: H3, H4, H7, H10, H14, H15 | EVQLVESGGGLVQPGGSLRLSCAASGFTFS TYNMNWVRQAPGKGLEWLSYISTSSNTIY YADSVKGRFTISRDNAKNSLFLQMNSLRD EDTAVYYCARDRGCSSTNCYVVGYYFYG MDVWGQGTTVTVSS | $V_H$ | 94 |
| | | | DIQMTQSPSSVSASVGDRVTITCRASQGISS YLAWYQLKPGRAPKLLIYGATRLQSGVPS RFSGSGSGTDFTLTISGLQPEDFATYHCQQ ADSFPLTFGQGTRLEIK | $V_L$ | 95 |
| | | | GFTFSTYN | HC-CDR1 | 52 |
| | | | ISTSSNTI | HC-CDR2 | 53 |
| | | | ARDRGCSSTNCYVVGYYFYGMDV | HC-CDR3 | 54 |
| | | | QGISSY | LC-CDR1 | 55 |
| | | | GAT | LC-CDR2 | |
| | | | QQADSFPLT | LC-CDR3 | 57 |
| HA11 Reference: WO2020167919 | mAb14303 | IAV H1 | QVHLVQSGPEVKKPGSSVKVSCKASGVTFI SHAISWVRQAPGQGLEWVGGIIAIFGTTNY AQKFQGRVTVTTDKSTNTVYMELSRLRSE DTAIYYCARGETYYEGNFDFWGQGTLVTV SS | $V_H$ | 96 |
| | | | DIQMTQSPSSLSASVGDRVTITCRASQSISS YLNWYQQKPGKAPKLLIYAASSLQSGVPS RFSGSGSGTDFTLTISSLQPEDFATYYCQQS YSTPPITFGQGTRLEIK | $V_L$ | 97 |
| | | | GVTFISHA | HC-CDR1 | 58 |
| | | | IIAIFGTT | HC-CDR2 | 59 |
| | | | ARGETYYEGNFDF | HC-CDR3 | 60 |
| | | | QSISSY | LC-CDR1 | 61 |
| | | | AAS | LC-CDR2 | |
| | | | QQSYSTPPIT | LC-CDR3 | 63 |
| HA12 Reference: WO2020198329 | VIS410 | IAV: H1N1, H1N2, H2N2, H3N2, H5N1, H6N1, H7N2, H7N3, H7N7, H7N9, H9N2, H10N7 | QVQLLETGGGLVKPGQSLKLSCAASGFTFT SYAMHWVRQPPGKGLEWVAVVSYDGNY KYYADSVQGRFTISRDNSKNTLYLQMNSL RAEDTAVYYCAKDSRLRSLLYFEWLSQGY FNPWGQGTTLTVSS | $V_H$ | 98 |
| | | | DIQMTQSPSSLSASVGDRVTITCRSSQSITF DYKNYLAWYQQKPGKAPKLLIYWGSYLE SGVPSRFSGSGSGTDFTLTISSLQPEDFATY YCQQHYRTPPSFGQGTKVEIK | $V_L$ | 99 |
| | | | SYAMH | HC-CDR1 | 64 |
| | | | VVSYDGNYKYYADSVQG | HC-CDR2 | 65 |
| | | | DSRLRSLLYFEWLSQGYFNP | HC-CDR3 | 66 |
| | | | WGSYLES | LC-CDR1 | 67 |
| | | | QQHYRTPPS | LC-CDR2 | 68 |
| | | | QSITFDYKNYLA | LC-CDR3 | 69 |
| HA13 Reference: WO2020221908 | FluAB_ML NS | IAV: H1N1 | QVQLQQSGPGLVKPSQTLSLTCAISGDSVS SYNAVWNWIRQSPSRGLEWLGRTYYRSG WYNDYAESVKSRITINPDTSKNQFSLQLNS VTPEDTAVYYCARSGHITVFGVNVDAFDM WGQGTMVTVSS | $V_H$ | 100 |
| | | | DIQMTQSPSSLSASVGDRVTITCRTSQSLSS YTHWYQQKPGKAPKLLIYAASSRGSGVPS RFSGSGSGTDFTLTISSLQPEDFATYYCQQS RTFGQGTKVEIK | $V_L$ | 101 |

TABLE 4A-continued

CDR and $V_H$/$V_L$ sequences of exemplary human anti-HA antibodies

| Antibody code | Antibody Name | Target strain | Sequence | Type | SEQ ID NO |
|---|---|---|---|---|---|
| | | | SYNAVWN | HC-CDR1 | 70 |
| | | | RTYYRSGWYNDYAESVKS | HC-CDR2 | 71 |
| | | | SGHITVFGVNVDAFDM | HC-CDR3 | 72 |
| | | | RTSQSLSSYTH | LC-CDR1 | 73 |
| | | | AASSRGS | LC-CDR2 | 74 |
| | | | QQSRT | LC-CDR3 | 75 |
| HA14 Reference: CN111704665 | D7 | IAV group 1: H2 IAV group 2: H3 | PDSVIRTQQRQTTMESVLSWVFLVAILQGE VQLVESGGDLVKPGGSLRLSCVASGFTFSD FDMSWVRQAPGKGLQWVAAIAYDGSSTY YTDAVKGRFTISRDNARNTVYLQMDNSLR AEDTAVYYCASPTTVPTIDWFYYWGQGTL VTVS | $V_H$ | 102 |
| | | | MLWIPGSTGEAVMTQTPLSLAVTPGELATI SCRANQSLLRSDGKSYLWYLQKPGPQTPR PLIYEASKRFSGVSGRFSGSGTDFTKITRVE ADEVGYYCQQGLHFPPFQGTKVEI | $V_L$ | 103 |
| HA15 Reference: WO13007770 | CR9114 | IAV group 1 H1, H2, H5, H6, H8, H9 IAV group 2: H3, H4, H7, H10 | QVQLVQSGAEVKKPGSSVKVSCKSSGGTS NNYAISWVRQAPGQGLDWMGGISPIFGST AYAQKFQGRVTISADIFSNTAYMELNSLTS EDTAVYFCARHGNYYYYSGMDVWGQGT TVTVSS | $V_H$ | 438 |
| | | | QSALTQPPAVSGTPGQRVTISCSGSDSNIGR RSVNWYQQFPGTAPKLLIYSNDQRPSVVP DRFSGSKSGTSASLAISGLQSEDEAEYYCA AWDDSLKGAVFGGGTQLTVL | $V_L$ | 442 |
| | | | GGTSNNYA | HC-CDR1 | 439 |
| | | | ISPIFGST | HC-CDR2 | 440 |
| | | | ARHGNYYYYSGMDV | HC-CDR3 | 441 |
| | | | DSNIGRRS | LC-CDR1 | 443 |
| | | | SND | LC-CDR2 | |
| | | | AAWDDSLKGAV | LC-CDR3 | 445 |
| HA16 Reference: WO17123685 | MEDI8852 | Pan IAV | QVQLQQSGPGLVKPSQTLSLTCAISGDSVS SYNAVWNWIRQSPSRGLEWLGRTYYRSG WYNDYAESVKSRITINPDTSKNQFSLQLNS VTPEDTAVYYCARSGHITVFGVNVDAFDM WGQGTMVTVSS | $V_H$ | 487 |
| | | | DIQMTQSPSSLSASVGDRVTITCRTSQSLSS YTHWYQQKPGKAPKLLIYAASSRGSGVPS RFSGSGSGTDFTLTISSLQPEDFATYYCQQS RTFGQGTKVEIK | $V_L$ | 491 |
| | | | SYAMH | HC-CDR1 | 488 |
| | | | VVSYDGNYKYYADSVQG | HC-CDR2 | 489 |
| | | | DSRLRSLLYFEWLSQGYFNP | HC-CDR3 | 490 |
| | | | WGSYLES | LC-CDR1 | 492 |
| | | | QQHYRTPPS | LC-CDR2 | 493 |
| | | | QSITFDYKNYLA | LC-CDR3 | 494 |

In some embodiments, the anti-HA antibody or antigen binding fragment thereof comprises an HC-CDR1, HC-CDR2, HC-CDR3, LC-CDR1, LC-CDR2, and LC-CDR3 of any one of antibodies HA1-HA16 of Table 4A. In some embodiments, the anti-HA antibody or antigen binding fragment thereof comprises a $V_H$ and $V_L$ of any one of antibodies HA1-HA16 of Table 4A. In some embodiments, the anti-HA antibody or antigen binding fragment thereof comprises an HC-CDR1, HC-CDR2, HC-CDR3, LC-CDR1, LC-CDR2, and LC-CDR3 of antibody HA1 of Table 4A. In some embodiments, the anti-HA antibody or antigen binding fragment thereof comprises a $V_H$ and $V_L$ of antibody HA1 of Table 4A. In some embodiments, the anti-HA antibody or antigen binding fragment thereof comprises an HC-CDR1, HC-CDR2, HC-CDR3, LC-CDR1, LC-CDR2, and LC-CDR3 of antibody HA2 of Table 4A. In some embodiments, the anti-HA antibody or antigen binding fragment thereof comprises a $V_H$ and $V_L$ of antibody HA2 of Table 4A. In some embodiments, the anti-HA antibody or antigen binding fragment thereof comprises an HC-CDR1, HC-CDR2, HC-CDR3, LC-CDR1, LC-CDR2, and LC-CDR3 of antibody HA15 of Table 4A. In some embodiments, the anti-HA antibody or antigen binding fragment thereof comprises a $V_H$ and $V_L$ of antibody HA15 of Table 4A.

In some embodiments, the anti-HA antibody or antigen binding fragment thereof comprises: i) a $V_H$ comprising an HC-CDR1 comprising the amino acid sequence of SEQ ID NO: 1, or a variant thereof comprising up to about 5 (such as about n, where n is selected from 1, 2, 3, 4, and 5) amino acid substitutions, an HC-CDR2 comprising the amino acid sequence of SEQ ID NO: 2, or a variant thereof comprising up to about 5 (such as about n, where n is selected from 1, 2, 3, 4, and 5) amino acid substitutions, and an HC-CDR3 comprising the amino acid sequence of SEQ ID NO: 3, or a variant thereof comprising up to about 5 (such as about n, where n is selected from 1, 2, 3, 4, and 5) amino acid substitutions; and ii) a $V_L$ Comprising an LC-CDR1 comprising the amino acid sequence of SEQ ID NO: 4, or a variant thereof comprising up to about 5 (such as about n, where n is selected from 1, 2, 3, 4, and 5) amino acid substitutions, an LC-CDR2 comprising the amino acid sequence of WAS, or a variant thereof comprising about 1 or about 2 amino acid substitutions, and an LC-CDR3 comprising the amino acid sequence of SEQ ID NO: 6, or a variant thereof comprising up to about 5 (such as about n, where n is selected from 1, 2, 3, 4, and 5) amino acid substitutions. In some embodiments, the anti-HA antibody or antigen binding fragment thereof comprises i) a $V_H$ comprising an HC-CDR1 comprising the amino acid sequence of SEQ ID NO: 1, an HC-CDR2 comprising the amino acid sequence of SEQ ID NO: 2, and an HC-CDR3 comprising the amino acid sequence of SEQ ID NO: 3; and ii) a $V_L$ comprising an LC-CDR1 comprising the amino acid sequence of SEQ ID NO: 4, an LC-CDR2 comprising the amino acid sequence of WAS, and an LC-CDR3 comprising the amino acid sequence of SEQ ID NO: 6.

In some embodiments, the anti-HA antibody or antigen binding fragment thereof comprises a $V_H$ comprising the amino acid sequences of SEQ ID NOs: 1, 2, and 3; and a $V_L$ comprising the amino acid sequences of WAS and SEQ ID NOs: 4 and 6. In some embodiments, the anti-HA antibody or antigen binding fragment thereof comprises a $V_H$ comprising an HC-CDR1, an HC-CDR2, and an HC-CDR3 of the amino acid sequence of SEQ ID NO: 76 and a $V_L$ comprising an LC-CDR1, an LC-CDR2, and an LC-CDR3 of the amino acid sequence of SEQ ID NO: 77. In some embodiments, the anti-HA antibody or antigen binding fragment thereof comprises a $V_H$ comprising the amino acid sequence of SEQ ID NO: 76, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 76, and a $V_L$ comprising the amino acid sequence of SEQ ID NO: 77, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 77.

In some embodiments, the anti-HA antibody or antigen binding fragment thereof comprises: i) a $V_H$ comprising an HC-CDR1 comprising the amino acid sequence of SEQ ID NO: 7, or a variant thereof comprising up to about 5 (such as about n, where n is selected from 1, 2, 3, 4, and 5) amino acid substitutions, an HC-CDR2 comprising the amino acid sequence of SEQ ID NO: 8, or a variant thereof comprising up to about 5 (such as about n, where n is selected from 1, 2, 3, 4, and 5) amino acid substitutions, and an HC-CDR3 comprising the amino acid sequence of SEQ ID NO: 9, or a variant thereof comprising up to about 5 (such as about n, where n is selected from 1, 2, 3, 4, and 5) amino acid substitutions; and ii) a $V_L$ Comprising an LC-CDR1 comprising the amino acid sequence of SEQ ID NO: 235, or a variant thereof comprising up to about 5 (such as about n, where n is selected from 1, 2, 3, 4, and 5) amino acid substitutions, an LC-CDR2 comprising the amino acid sequence of SEQ ID NO: 238, or a variant thereof comprising up to about 3 (such as about any of 1, 2, or 3) amino acid substitutions, and an LC-CDR3 comprising the amino acid sequence of SEQ ID NO: 415, or a variant thereof comprising up to about 5 (such as about n, where n is selected from 1, 2, 3, 4, and 5) amino acid substitutions. In some embodiments, the anti-HA antibody or antigen binding fragment thereof comprises i) a $V_H$ comprising an HC-CDR1 comprising the amino acid sequence of SEQ ID NO: 7, an HC-CDR2 comprising the amino acid sequence of SEQ ID NO: 8, and an HC-CDR3 comprising the amino acid sequence of SEQ ID NO: 9; and ii) a $V_L$ comprising an LC-CDR1 comprising the amino acid sequence of SEQ ID NO: 235, an LC-CDR2 comprising the amino acid sequence of SEQ ID NO: 238, and an LC-CDR3 comprising the amino acid sequence of SEQ ID NO: 415.

In some embodiments, the anti-HA antibody or antigen binding fragment thereof comprises a $V_H$ comprising the amino acid sequences of SEQ ID NOs: 7, 8, and 9; and a $V_L$ comprising the amino acid sequences of SEQ ID NOs: 235, 238, and 415. In some embodiments, the anti-HA antibody or antigen binding fragment thereof comprises a $V_H$ comprising an HC-CDR1, an HC-CDR2, and an HC-CDR3 of the amino acid sequence of SEQ ID NO: 78 and a $V_L$ comprising an LC-CDR1, an LC-CDR2, and an LC-CDR3 of the amino acid sequence of SEQ ID NO: 79. In some embodiments, the anti-HA antibody or antigen binding fragment thereof comprises a $V_H$ comprising the amino acid sequence of SEQ ID NO: 78, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 78, and a $V_L$ comprising the amino acid sequence of SEQ ID NO: 79, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 79.

In some embodiments, the anti-HA antibody or antigen binding fragment thereof comprises: i) a $V_H$ comprising an HC-CDR1 comprising the amino acid sequence of SEQ ID NO: 10, or a variant thereof comprising up to about 5 (such as about n, where n is selected from 1, 2, 3, 4, and 5) amino acid substitutions, an HC-CDR2 comprising the amino acid sequence of SEQ ID NO: 11, or a variant thereof comprising up to about 5 (such as about n, where n is selected from 1, 2, 3, 4, and 5) amino acid substitutions, and an HC-CDR3 comprising the amino acid sequence of SEQ ID NO: 12, or a variant thereof comprising up to about 5 (such as about n, where n is selected from 1, 2, 3, 4, and 5) amino acid substitutions; and ii) a $V_L$ Comprising an LC-CDR1 comprising the amino acid sequence of SEQ ID NO: 13, or a variant thereof comprising up to about 5 (such as about n, where n is selected from 1, 2, 3, 4, and 5) amino acid substitutions, an LC-CDR2 comprising the amino acid sequence of AAS, or a variant thereof comprising about 1 or about 2 amino acid substitutions, and an LC-CDR3 comprising the amino acid sequence of SEQ ID NO: 15, or a variant thereof comprising up to about 5 (such as about n, where n is selected from 1, 2, 3, 4, and 5) amino acid substitutions. In some embodiments, the anti-HA antibody or antigen binding fragment thereof comprises i) a $V_H$ comprising an HC-CDR1 comprising the amino acid sequence of SEQ ID NO: 10, an HC-CDR2 comprising the amino acid sequence of SEQ ID NO: 11, and an HC-CDR3 comprising the amino acid sequence of SEQ ID NO: 12; and ii) a $V_L$ comprising an LC-CDR1 comprising the amino acid sequence of SEQ ID NO: 13, an LC-CDR2 comprising the amino acid sequence of AAS, and an LC-CDR3 comprising the amino acid sequence of SEQ ID NO: 15.

In some embodiments, the anti-HA antibody or antigen binding fragment thereof comprises a $V_H$ comprising the amino acid sequences of SEQ ID NOs: 10, 11, and 12; and a $V_L$ comprising the amino acid sequences of AAS and SEQ ID NOs: 13 and 15. In some embodiments, the anti-HA antibody or antigen binding fragment thereof comprises a $V_H$ comprising an HC-CDR1, an HC-CDR2, and an HC-CDR3 of the amino acid sequence of SEQ ID NO: 80 and a $V_L$ comprising an LC-CDR1, an LC-CDR2, and an LC-CDR3 of the amino acid sequence of SEQ ID NO: 81. In some embodiments, the anti-HA antibody or antigen binding fragment thereof comprises a $V_H$ comprising the amino acid sequence of SEQ ID NO: 80, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 80, and a $V_L$ comprising the amino acid sequence of SEQ ID NO: 81, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 81.

In some embodiments, the anti-HA antibody or antigen binding fragment thereof comprises: i) a $V_H$ comprising an HC-CDR1 comprising the amino acid sequence of SEQ ID NO: 16, or a variant thereof comprising up to about 5 (such as about n, where n is selected from 1, 2, 3, 4, and 5) amino acid substitutions, an HC-CDR2 comprising the amino acid sequence of SEQ ID NO: 17, or a variant thereof comprising up to about 5 (such as about n, where n is selected from 1, 2, 3, 4, and 5) amino acid substitutions, and an HC-CDR3 comprising the amino acid sequence of SEQ ID NO: 18, or a variant thereof comprising up to about 5 (such as about n, where n is selected from 1, 2, 3, 4, and 5) amino acid substitutions; and ii) a $V_L$ Comprising an LC-CDR1 comprising the amino acid sequence of SEQ ID NO: 19, or a variant thereof comprising up to about 5 (such as about n, where n is selected from 1, 2, 3, 4, and 5) amino acid substitutions, an LC-CDR2 comprising the amino acid sequence of DAS, or a variant thereof comprising about 1 or about 2 amino acid substitutions, and an LC-CDR3 comprising the amino acid sequence of SEQ ID NO: 21, or a variant thereof comprising up to about 5 (such as about n, where n is selected from 1, 2, 3, 4, and 5) amino acid substitutions. In some embodiments, the anti-HA antibody or antigen binding fragment thereof comprises i) a $V_H$ comprising an HC-CDR1 comprising the amino acid sequence of SEQ ID NO: 16, an HC-CDR2 comprising the amino acid sequence of SEQ ID NO: 17, and an HC-CDR3 comprising the amino acid sequence of SEQ ID NO: 18; and ii) a $V_L$ comprising an LC-CDR1 comprising the amino acid sequence of SEQ ID NO: 19, an LC-CDR2 comprising the amino acid sequence of DAS, and an LC-CDR3 comprising the amino acid sequence of SEQ ID NO: 21.

In some embodiments, the anti-HA antibody or antigen binding fragment thereof comprises a $V_H$ comprising the amino acid sequences of SEQ ID NOs: 16, 17, and 18; and a $V_L$ comprising the amino acid sequences of DAS and SEQ ID NOs: 19 and 21. In some embodiments, the anti-HA antibody or antigen binding fragment thereof comprises a $V_H$ comprising an HC-CDR1, an HC-CDR2, and an HC-CDR3 of the amino acid sequence of SEQ ID NO: 82 and a $V_L$ comprising an LC-CDR1, an LC-CDR2, and an LC-CDR3 of the amino acid sequence of SEQ ID NO: 83. In some embodiments, the anti-HA antibody or antigen binding fragment thereof comprises a $V_H$ comprising the amino acid sequence of SEQ ID NO: 82, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 82, and a $V_L$ comprising the amino acid sequence of SEQ ID NO: 83, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 83.

In some embodiments, the anti-HA antibody or antigen binding fragment thereof comprises: i) a $V_H$ comprising an HC-CDR1 comprising the amino acid sequence of SEQ ID NO: 22, or a variant thereof comprising up to about 5 (such as about n, where n is selected from 1, 2, 3, 4, and 5) amino acid substitutions, an HC-CDR2 comprising the amino acid sequence of SEQ ID NO: 23, or a variant thereof comprising up to about 5 (such as about n, where n is selected from 1, 2, 3, 4, and 5) amino acid substitutions, and an HC-CDR3 comprising the amino acid sequence of SEQ ID NO: 24, or a variant thereof comprising up to about 5 (such as about n, where n is selected from 1, 2, 3, 4, and 5) amino acid substitutions; and ii) a $V_L$ Comprising an LC-CDR1 comprising the amino acid sequence of SEQ ID NO: 25, or a variant thereof comprising up to about 5 (such as about n, where n is selected from 1, 2, 3, 4, and 5) amino acid substitutions, an LC-CDR2 comprising the amino acid sequence of GAS, or a variant thereof comprising about 1 or about 2 amino acid substitutions, and an LC-CDR3 comprising the amino acid sequence of SEQ ID NO: 27, or a variant thereof comprising up to about 5 (such as about n, where n is selected from 1, 2, 3, 4, and 5) amino acid substitutions. In some embodiments, the anti-HA antibody or antigen binding fragment thereof comprises i) a $V_H$ comprising an HC-CDR1 comprising the amino acid sequence of SEQ ID NO: 22, an HC-CDR2 comprising the amino acid sequence of SEQ ID NO: 23, and an HC-CDR3 comprising the amino acid sequence of SEQ ID NO: 24; and ii) a $V_L$ comprising an LC-CDR1 comprising the amino acid sequence of SEQ ID NO: 25, an LC-CDR2 comprising the amino acid sequence of GAS, and an LC-CDR3 comprising the amino acid sequence of SEQ ID NO: 27.

In some embodiments, the anti-HA antibody or antigen binding fragment thereof comprises a $V_H$ comprising the amino acid sequences of SEQ ID NOs: 22, 23, and 24; and a $V_L$ comprising the amino acid sequences of GAS and SEQ ID NOs: 25 and 27. In some embodiments, the anti-HA antibody or antigen binding fragment thereof comprises a $V_H$ comprising an HC-CDR1, an HC-CDR2, and an HC-CDR3 of the amino acid sequence of SEQ ID NO: 84 and a $V_L$ comprising an LC-CDR1, an LC-CDR2, and an LC-CDR3 of the amino acid sequence of SEQ ID NO: 85. In some embodiments, the anti-HA antibody or antigen binding fragment thereof comprises a $V_H$ comprising the amino acid sequence of SEQ ID NO: 84, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 84, and a $V_L$ comprising the amino acid sequence of SEQ ID NO: 85, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 85.

In some embodiments, the anti-HA antibody or antigen binding fragment thereof comprises: i) a $V_H$ comprising an HC-CDR1 comprising the amino acid sequence of SEQ ID NO: 28, or a variant thereof comprising up to about 5 (such as about n, where n is selected from 1, 2, 3, 4, and 5) amino acid substitutions, an HC-CDR2 comprising the amino acid sequence of SEQ ID NO: 29, or a variant thereof comprising up to about 5 (such as about n, where n is selected from 1, 2, 3, 4, and 5) amino acid substitutions, and an HC-CDR3 comprising the amino acid sequence of SEQ ID NO: 30, or a variant thereof comprising up to about 5 (such as about n, where n is selected from 1, 2, 3, 4, and 5) amino acid substitutions; and ii) a $V_L$ Comprising an LC-CDR1 comprising the amino acid sequence of SEQ ID NO: 31, or a variant thereof comprising up to about 5 (such as about n, where n is selected from 1, 2, 3, 4, and 5) amino acid substitutions, an LC-CDR2 comprising the amino acid sequence of AAS, or a variant thereof comprising about 1 or about 2 amino acid substitutions, and an LC-CDR3 comprising the amino acid sequence of SEQ ID NO: 33, or a variant thereof comprising up to about 5 (such as about n, where n is selected from 1, 2, 3, 4, and 5) amino acid substitutions. In some embodiments, the anti-HA antibody or antigen binding fragment thereof comprises i) a $V_H$ Comprising an HC-CDR1 comprising the amino acid sequence of SEQ ID NO: 28, an HC-CDR2 comprising the amino acid sequence of SEQ ID NO: 29, and an HC-CDR3 comprising the amino acid sequence of SEQ ID NO: 30; and ii) a $V_L$ comprising an LC-CDR1 comprising the amino acid sequence of SEQ ID NO: 31, an LC-CDR2 comprising the amino acid sequence of AAS, and an LC-CDR3 comprising the amino acid sequence of SEQ ID NO: 33.

In some embodiments, the anti-HA antibody or antigen binding fragment thereof comprises a $V_H$ comprising the amino acid sequences of SEQ ID NOs: 28, 29, and 30; and a $V_L$ comprising the amino acid sequences of AAS and SEQ ID NOs: 31 and 33. In some embodiments, the anti-HA antibody or antigen binding fragment thereof comprises a $V_H$ comprising an HC-CDR1, an HC-CDR2, and an HC-CDR3 of the amino acid sequence of SEQ ID NO: 86 and a $V_L$ comprising an LC-CDR1, an LC-CDR2, and an LC-CDR3 of the amino acid sequence of SEQ ID NO: 87. In some embodiments, the anti-HA antibody or antigen binding fragment thereof comprises a $V_H$ comprising the amino acid sequence of SEQ ID NO: 86, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 86, and a $V_L$ comprising the amino acid sequence of SEQ ID NO: 87, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 87.

In some embodiments, the anti-HA antibody or antigen binding fragment thereof comprises: i) a $V_H$ comprising an HC-CDR1 comprising the amino acid sequence of SEQ ID NO: 34, or a variant thereof comprising up to about 5 (such as about n, where n is selected from 1, 2, 3, 4, and 5) amino acid substitutions, an HC-CDR2 comprising the amino acid sequence of SEQ ID NO: 35, or a variant thereof comprising up to about 5 (such as about n, where n is selected from 1, 2, 3, 4, and 5) amino acid substitutions, and an HC-CDR3 comprising the amino acid sequence of SEQ ID NO: 36, or a variant thereof comprising up to about 5 (such as about n, where n is selected from 1, 2, 3, 4, and 5) amino acid substitutions; and ii) a $V_L$ Comprising an LC-CDR1 comprising the amino acid sequence of SEQ ID NO: 37, or a variant thereof comprising up to about 5 (such as about n, where n is selected from 1, 2, 3, 4, and 5) amino acid substitutions, an LC-CDR2 comprising the amino acid sequence of AAS, or a variant thereof comprising about 1 or about 2 amino acid substitutions, and an LC-CDR3 comprising the amino acid sequence of SEQ ID NO: 39, or a variant thereof comprising up to about 5 (such as about n, where n is selected from 1, 2, 3, 4, and 5) amino acid substitutions. In some embodiments, the anti-HA antibody or antigen binding fragment thereof comprises i) a $V_H$ comprising an HC-CDR1 comprising the amino acid sequence of SEQ ID NO: 34, an HC-CDR2 comprising the amino acid sequence of SEQ ID NO: 35, and an HC-CDR3 comprising the amino acid sequence of SEQ ID NO: 36; and ii) a $V_L$ comprising an LC-CDR1 comprising the amino acid sequence of SEQ ID NO: 37, an LC-CDR2 comprising the amino acid sequence of AAS, and an LC-CDR3 comprising the amino acid sequence of SEQ ID NO: 39.

In some embodiments, the anti-HA antibody or antigen binding fragment thereof comprises a $V_H$ comprising the amino acid sequences of SEQ ID NOs: 34, 35, and 36; and a $V_L$ comprising the amino acid sequences of AAS and SEQ ID NOs: 37 and 39. In some embodiments, the anti-HA antibody or antigen binding fragment thereof comprises a $V_H$ comprising an HC-CDR1, an HC-CDR2, and an HC-CDR3 of the amino acid sequence of SEQ ID NO: 88 and a $V_L$ comprising an LC-CDR1, an LC-CDR2, and an LC-CDR3 of the amino acid sequence of SEQ ID NO: 89. In some embodiments, the anti-HA antibody or antigen binding fragment thereof comprises a $V_H$ comprising the amino acid sequence of SEQ ID NO: 88, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 88, and a $V_L$ comprising the amino acid sequence of SEQ ID NO: 89, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 89.

In some embodiments, the anti-HA antibody or antigen binding fragment thereof comprises: i) a $V_H$ comprising an HC-CDR1 comprising the amino acid sequence of SEQ ID NO: 40, or a variant thereof comprising up to about 5 (such as about n, where n is selected from 1, 2, 3, 4, and 5) amino acid substitutions, an HC-CDR2 comprising the amino acid sequence of SEQ ID NO: 41, or a variant thereof comprising up to about 5 (such as about n, where n is selected from 1, 2, 3, 4, and 5) amino acid substitutions, and an HC-CDR3 comprising the amino acid sequence of SEQ ID NO: 42, or a variant thereof comprising up to about 5 (such as about n, where n is selected from 1, 2, 3, 4, and 5) amino acid substitutions; and ii) a $V_L$ Comprising an LC-CDR1 comprising the amino acid sequence of SEQ ID NO: 43, or a variant thereof comprising up to about 5 (such as about n, where n is selected from 1, 2, 3, 4, and 5) amino acid substitutions, an LC-CDR2 comprising the amino acid sequence of AAS, or a variant thereof comprising about 1 or about 2 amino acid substitutions, and an LC-CDR3 comprising the amino acid sequence of SEQ ID NO: 45, or a variant thereof comprising up to about 5 (such as about n, where n is selected from 1, 2, 3, 4, and 5) amino acid substitutions. In some embodiments, the anti-HA antibody or antigen binding fragment thereof comprises i) a $V_H$ comprising an HC-CDR1 comprising the amino acid sequence of SEQ ID NO: 40, an HC-CDR2 comprising the amino acid sequence of SEQ ID NO: 41, and an HC-CDR3 comprising the amino acid sequence of SEQ ID NO: 42; and ii) a $V_L$ comprising an LC-CDR1 comprising the amino acid sequence of SEQ ID NO: 43, an LC-CDR2 comprising the amino acid sequence of AAS, and an LC-CDR3 comprising the amino acid sequence of SEQ ID NO: 45.

In some embodiments, the anti-HA antibody or antigen binding fragment thereof comprises a $V_H$ comprising the amino acid sequences of SEQ ID NOs: 40, 41, and 42; and a $V_L$ comprising the amino acid sequences of AAS and SEQ ID NOs: 43 and 45. In some embodiments, the anti-HA antibody or antigen binding fragment thereof comprises a $V_H$ comprising an HC-CDR1, an HC-CDR2, and an HC-CDR3 of the amino acid sequence of SEQ ID NO: 90 and a $V_L$ comprising an LC-CDR1, an LC-CDR2, and an LC-CDR3 of the amino acid sequence of SEQ ID NO: 91. In some embodiments, the anti-HA antibody or antigen binding fragment thereof comprises a $V_H$ comprising the amino acid sequence of SEQ ID NO: 90, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 90, and a $V_L$ comprising the amino acid sequence of SEQ ID NO: 91, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 91.

In some embodiments, the anti-HA antibody or antigen binding fragment thereof comprises: i) a $V_H$ comprising an HC-CDR1 comprising the amino acid sequence of SEQ ID NO: 46, or a variant thereof comprising up to about 5 (such as about n, where n is selected from 1, 2, 3, 4, and 5) amino acid substitutions, an HC-CDR2 comprising the amino acid sequence of SEQ ID NO: 47, or a variant thereof comprising up to about 5 (such as about n, where n is selected from 1, 2, 3, 4, and 5) amino acid substitutions, and an HC-CDR3 comprising the amino acid sequence of SEQ ID NO: 48, or a variant thereof comprising up to about 5 (such as about n, where n is selected from 1, 2, 3, 4, and 5) amino acid substitutions; and ii) a $V_L$ Comprising an LC-CDR1 comprising the amino acid sequence of SEQ ID NO: 49, or a variant thereof comprising up to about 5 (such as about n, where n is selected from 1, 2, 3, 4, and 5) amino acid substitutions, an LC-CDR2 comprising the amino acid sequence of AAS, or a variant thereof comprising about 1 or about 2 amino acid substitutions, and an LC-CDR3 comprising the amino acid sequence of SEQ ID NO: 51, or a variant thereof comprising up to about 5 (such as about n, where n is selected from 1, 2, 3, 4, and 5) amino acid substitutions. In some embodiments, the anti-HA antibody or antigen binding fragment thereof comprises i) a $V_H$ comprising an HC-CDR1 comprising the amino acid sequence of SEQ ID NO: 46, an HC-CDR2 comprising the amino acid sequence of SEQ ID NO: 47, and an HC-CDR3 comprising the amino acid sequence of SEQ ID NO: 48; and ii) a $V_L$ comprising an LC-CDR1 comprising the amino acid sequence of SEQ ID NO: 49, an LC-CDR2 comprising the amino acid sequence of AAS, and an LC-CDR3 comprising the amino acid sequence of SEQ ID NO: 51.

In some embodiments, the anti-HA antibody or antigen binding fragment thereof comprises a $V_H$ comprising the amino acid sequences of SEQ ID NOs: 46, 47, and 48; and a $V_L$ comprising the amino acid sequences of AAS and SEQ ID NOs: 49 and 51. In some embodiments, the anti-HA antibody or antigen binding fragment thereof comprises a $V_H$ comprising an HC-CDR1, an HC-CDR2, and an HC-CDR3 of the amino acid sequence of SEQ ID NO: 92 and a $V_L$ comprising an LC-CDR1, an LC-CDR2, and an LC-CDR3 of the amino acid sequence of SEQ ID NO: 93. In some embodiments, the anti-HA antibody or antigen binding fragment thereof comprises a $V_H$ comprising the amino acid sequence of SEQ ID NO: 92, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 92, and a $V_L$ comprising the amino acid sequence of SEQ ID NO: 93, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 93.

In some embodiments, the anti-HA antibody or antigen binding fragment thereof comprises: i) a $V_H$ comprising an HC-CDR1 comprising the amino acid sequence of SEQ ID NO: 52, or a variant thereof comprising up to about 5 (such as about n, where n is selected from 1, 2, 3, 4, and 5) amino acid substitutions, an HC-CDR2 comprising the amino acid sequence of SEQ ID NO: 53, or a variant thereof comprising up to about 5 (such as about n, where n is selected from 1, 2, 3, 4, and 5) amino acid substitutions, and an HC-CDR3 comprising the amino acid sequence of SEQ ID NO: 54, or a variant thereof comprising up to about 5 (such as about n, where n is selected from 1, 2, 3, 4, and 5) amino acid substitutions; and ii) a $V_L$ Comprising an LC-CDR1 comprising the amino acid sequence of SEQ ID NO: 55, or a variant thereof comprising up to about 5 (such as about n, where n is selected from 1, 2, 3, 4, and 5) amino acid substitutions, an LC-CDR2 comprising the amino acid sequence of GAT, or a variant thereof comprising about 1 or about 2 amino acid substitutions, and an LC-CDR3 comprising the amino acid sequence of SEQ ID NO: 57, or a variant thereof comprising up to about 5 (such as about n, where n is selected from 1, 2, 3, 4, and 5) amino acid substitutions. In some embodiments, the anti-HA antibody or antigen binding fragment thereof comprises i) a $V_H$ comprising an HC-CDR1 comprising the amino acid sequence of SEQ ID NO: 52, an HC-CDR2 comprising the amino acid sequence of SEQ ID NO: 53, and an HC-CDR3 comprising the amino acid sequence of SEQ ID NO: 54; and ii) a $V_L$ comprising an LC-CDR1 comprising the amino acid sequence of SEQ ID NO: 55, an LC-CDR2 comprising the amino acid sequence of GAT, and an LC-CDR3 comprising the amino acid sequence of SEQ ID NO: 57.

In some embodiments, the anti-HA antibody or antigen binding fragment thereof comprises a $V_H$ comprising the amino acid sequences of SEQ ID NOs: 52, 53, and 54; and a $V_L$ comprising the amino acid sequences of GAT and SEQ ID NOs: 55 and 57. In some embodiments, the anti-HA antibody or antigen binding fragment thereof comprises a $V_H$ comprising an HC-CDR1, an HC-CDR2, and an HC-CDR3 of the amino acid sequence of SEQ ID NO: 94 and a $V_L$ comprising an LC-CDR1, an LC-CDR2, and an LC-CDR3 of the amino acid sequence of SEQ ID NO: 95. In some embodiments, the anti-HA antibody or antigen binding fragment thereof comprises a $V_H$ comprising the amino acid sequence of SEQ ID NO: 94, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 94, and a $V_L$ comprising the amino acid sequence of SEQ ID NO: 95, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 95.

In some embodiments, the anti-HA antibody or antigen binding fragment thereof comprises: i) a $V_H$ comprising an HC-CDR1 comprising the amino acid sequence of SEQ ID NO: 58, or a variant thereof comprising up to about 5 (such as about n, where n is selected from 1, 2, 3, 4, and 5) amino acid substitutions, an HC-CDR2 comprising the amino acid sequence of SEQ ID NO: 59, or a variant thereof comprising up to about 5 (such as about n, where n is selected from 1, 2, 3, 4, and 5) amino acid substitutions, and an HC-CDR3 comprising the amino acid sequence of SEQ ID NO: 60, or a variant thereof comprising up to about 5 (such as about n, where n is selected from 1, 2, 3, 4, and 5) amino acid substitutions; and ii) a $V_L$ comprising an LC-CDR1 comprising the amino acid sequence of SEQ ID NO: 61, or a variant thereof comprising up to about 5 (such as about n, where n is selected from 1, 2, 3, 4, and 5) amino acid substitutions, an LC-CDR2 comprising the amino acid sequence of AAS, or a variant thereof comprising about 1 or about 2 amino acid substitutions, and an LC-CDR3 comprising the amino acid sequence of SEQ ID NO: 63, or a variant thereof comprising up to about 5 (such as about n, where n is selected from 1, 2, 3, 4, and 5) amino acid substitutions. In some embodiments, the anti-HA antibody or antigen binding fragment thereof comprises i) a $V_H$ comprising an HC-CDR1 comprising the amino acid sequence of SEQ ID NO: 58, an HC-CDR2 comprising the amino acid sequence of SEQ ID NO: 59, and an HC-CDR3 comprising the amino acid sequence of SEQ ID NO: 60; and ii) a $V_L$ comprising an LC-CDR1 comprising the amino acid sequence of SEQ ID NO: 61, an LC-CDR2 comprising the amino acid sequence of AAS, and an LC-CDR3 comprising the amino acid sequence of SEQ ID NO: 63.

In some embodiments, the anti-HA antibody or antigen binding fragment thereof comprises a $V_H$ comprising the amino acid sequences of SEQ ID NOs: 58, 59, and 60; and a $V_L$ comprising the amino acid sequences of AAS and SEQ ID NOs: 61 and 63. In some embodiments, the anti-HA antibody or antigen binding fragment thereof comprises a $V_H$ comprising an HC-CDR1, an HC-CDR2, and an HC-CDR3 of the amino acid sequence of SEQ ID NO: 96 and a $V_L$ comprising an LC-CDR1, an LC-CDR2, and an LC-CDR3 of the amino acid sequence of SEQ ID NO: 97. In some embodiments, the anti-HA antibody or antigen binding fragment thereof comprises a $V_H$ comprising the amino acid sequence of SEQ ID NO: 96, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 96, and a $V_L$ comprising the amino acid sequence of SEQ ID NO: 97, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 97.

In some embodiments, the anti-HA antibody or antigen binding fragment thereof comprises: i) a $V_H$ comprising an HC-CDR1 comprising the amino acid sequence of SEQ ID NO: 64, or a variant thereof comprising up to about 5 (such as about n, where n is selected from 1, 2, 3, 4, and 5) amino acid substitutions, an HC-CDR2 comprising the amino acid sequence of SEQ ID NO: 65, or a variant thereof comprising up to about 5 (such as about n, where n is selected from 1, 2, 3, 4, and 5) amino acid substitutions, and an HC-CDR3 comprising the amino acid sequence of SEQ ID NO: 66, or a variant thereof comprising up to about 5 (such as about n, where n is selected from 1, 2, 3, 4, and 5) amino acid substitutions; and ii) a $V_L$ Comprising an LC-CDR1 comprising the amino acid sequence of SEQ ID NO: 67, or a variant thereof comprising up to about 5 (such as about n, where n is selected from 1, 2, 3, 4, and 5) amino acid substitutions, an LC-CDR2 comprising the amino acid sequence of SEQ ID NO: 68, or a variant thereof comprising up to about 3 (such as about any of 1, 2, or 3) amino acid substitutions, and an LC-CDR3 comprising the amino acid sequence of SEQ ID NO: 69, or a variant thereof comprising up to about 5 (such as about n, where n is selected from 1, 2, 3, 4, and 5) amino acid substitutions. In some embodiments, the anti-HA antibody or antigen binding fragment thereof comprises i) a $V_H$ comprising an HC-CDR1 comprising the amino acid sequence of SEQ ID NO: 64, an HC-CDR2 comprising the amino acid sequence of SEQ ID NO: 65, and an HC-CDR3 comprising the amino acid sequence of SEQ ID NO: 66; and ii) a $V_L$ comprising an LC-CDR1 comprising the amino acid sequence of SEQ ID NO: 67, an LC-CDR2 comprising the amino acid sequence of SEQ ID NO: 68, and an LC-CDR3 comprising the amino acid sequence of SEQ ID NO: 69.

In some embodiments, the anti-HA antibody or antigen binding fragment thereof comprises a $V_H$ comprising the amino acid sequences of SEQ ID NOs: 64, 65, and 66; and a $V_L$ comprising the amino acid sequences of SEQ ID NOs: 67, 68, and 69. In some embodiments, the anti-HA antibody or antigen binding fragment thereof comprises a $V_H$ Comprising an HC-CDR1, an HC-CDR2, and an HC-CDR3 of the amino acid sequence of SEQ ID NO: 98 and a $V_L$ comprising an LC-CDR1, an LC-CDR2, and an LC-CDR3 of the amino acid sequence of SEQ ID NO: 99. In some embodiments, the anti-HA antibody or antigen binding fragment thereof comprises a $V_H$ comprising the amino acid sequence of SEQ ID NO: 98, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 98, and a $V_L$ comprising the amino acid sequence of SEQ ID NO: 99, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 99.

In some embodiments, the anti-HA antibody or antigen binding fragment thereof comprises: i) a $V_H$ comprising an HC-CDR1 comprising the amino acid sequence of SEQ ID NO: 70, or a variant thereof comprising up to about 5 (such as about n, where n is selected from 1, 2, 3, 4, and 5) amino acid substitutions, an HC-CDR2 comprising the amino acid sequence of SEQ ID NO: 71, or a variant thereof comprising up to about 5 (such as about n, where n is selected from 1, 2, 3, 4, and 5) amino acid substitutions, and an HC-CDR3 comprising the amino acid sequence of SEQ ID NO: 72, or a variant thereof comprising up to about 5 (such as about n, where n is selected from 1, 2, 3, 4, and 5) amino acid substitutions; and ii) a $V_L$ Comprising an LC-CDR1 comprising the amino acid sequence of SEQ ID NO: 73, or a variant thereof comprising up to about 5 (such as about n, where n is selected from 1, 2, 3, 4, and 5) amino acid substitutions, an LC-CDR2 comprising the amino acid sequence of SEQ ID NO: 74, or a variant thereof comprising up to about 3 (such as about any of 1, 2, or 3) amino acid substitutions, and an LC-CDR3 comprising the amino acid sequence of SEQ ID NO: 75, or a variant thereof comprising up to about 5 (such as about n, where n is selected from 1, 2, 3, 4, and 5) amino acid substitutions. In some embodiments, the anti-HA antibody or antigen binding fragment thereof comprises i) a $V_H$ comprising an HC-CDR1 comprising the amino acid sequence of SEQ ID NO: 70, an HC-CDR2 comprising the amino acid sequence of SEQ ID NO: 71, and an HC-CDR3 comprising the amino acid sequence of SEQ ID NO: 72; and ii) a $V_L$ comprising an LC-CDR1 comprising the amino acid sequence of SEQ ID NO: 73, an LC-CDR2 comprising the amino acid sequence of SEQ ID NO: 74, and an LC-CDR3 comprising the amino acid sequence of SEQ ID NO: 75.

In some embodiments, the anti-HA antibody or antigen binding fragment thereof comprises a $V_H$ comprising the amino acid sequences of SEQ ID NOs: 70, 71, and 72; and a $V_L$ comprising the amino acid sequences of SEQ ID NOs: 73, 74, and 75. In some embodiments, the anti-HA antibody or antigen binding fragment thereof comprises a $V_H$ Comprising an HC-CDR1, an HC-CDR2, and an HC-CDR3 of the amino acid sequence of SEQ ID NO: 100 and a $V_L$ comprising an LC-CDR1, an LC-CDR2, and an LC-CDR3 of the amino acid sequence of SEQ ID NO: 101. In some embodiments, the anti-HA antibody or antigen binding fragment thereof comprises a $V_H$ comprising the amino acid sequence of SEQ ID NO: 100, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 100, and a $V_L$ comprising the amino acid sequence of SEQ ID NO: 101, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 101.

In some embodiments, the anti-HA antibody or antigen binding fragment thereof comprises a $V_H$ comprising an HC-CDR1, an HC-CDR2, and an HC-CDR3 of the amino acid sequence of SEQ ID NO: 102 and a $V_L$ comprising an LC-CDR1, an LC-CDR2, and an LC-CDR3 of the amino acid sequence of SEQ ID NO: 103. In some embodiments, the anti-HA antibody or antigen binding fragment thereof comprises a $V_H$ Comprising the amino acid sequence of SEQ ID NO: 102, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 102, and a $V_L$ comprising the amino acid sequence of SEQ ID NO: 103, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 103.

In some embodiments, the anti-HA antibody or antigen binding fragment thereof comprises: i) a $V_H$ comprising an HC-CDR1 comprising the amino acid sequence of SEQ ID NO: 439, or a variant thereof comprising up to about 5 (such as about n, where n is selected from 1, 2, 3, 4, and 5) amino acid substitutions, an HC-CDR2 comprising the amino acid sequence of SEQ ID NO: 440, or a variant thereof comprising up to about 5 (such as about n, where n is selected from 1, 2, 3, 4, and 5) amino acid substitutions, and an HC-CDR3 comprising the amino acid sequence of SEQ ID NO: 441, or a variant thereof comprising up to about 5 (such as about n, where n is selected from 1, 2, 3, 4, and 5) amino acid substitutions; and ii) a $V_L$ comprising an LC-CDR1 comprising the amino acid sequence of SEQ ID NO: 443, or a variant thereof comprising up to about 5 (such as about n, where n is selected from 1, 2, 3, 4, and 5) amino acid substitutions, an LC-CDR2 comprising the amino acid sequence of SND, or a variant thereof comprising about 1 or about 2 amino acid substitutions, and an LC-CDR3 comprising the amino acid sequence of SEQ ID NO: 445, or a variant thereof comprising up to about 5 (such as about n, where n is selected from 1, 2, 3, 4, and 5) amino acid substitutions. In some embodiments, the anti-HA antibody or antigen binding fragment thereof comprises i) a $V_H$ comprising an HC-CDR1 comprising the amino acid sequence of SEQ ID NO: 439, an HC-CDR2 comprising the amino acid sequence of SEQ ID NO: 440, and an HC-CDR3 comprising the amino acid sequence of SEQ ID NO: 441; and ii) a $V_L$ comprising an LC-CDR1 comprising the amino acid sequence of SEQ ID NO: 443, an LC-CDR2 comprising the amino acid sequence of SND, and an LC-CDR3 comprising the amino acid sequence of SEQ ID NO: 445.

In some embodiments, the anti-HA antibody or antigen binding fragment thereof comprises a $V_H$ comprising the amino acid sequences of SEQ ID NOs: 439, 440, and 441; and a $V_L$ comprising the amino acid sequences of SND and SEQ ID NOs: 443 and 445. In some embodiments, the anti-HA antibody or antigen binding fragment thereof comprises a $V_H$ comprising an HC-CDR1, an HC-CDR2, and an HC-CDR3 of the amino acid sequence of SEQ ID NO: 438 and a $V_L$ comprising an LC-CDR1, an LC-CDR2, and an LC-CDR3 of the amino acid sequence of SEQ ID NO: 442. In some embodiments, the anti-HA antibody or antigen binding fragment thereof comprises a $V_H$ comprising the amino acid sequence of SEQ ID NO: 438, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 438, and a $V_L$ comprising the amino acid sequence of SEQ ID NO: 442, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 442.

In some embodiments, the anti-HA antibody or antigen binding fragment thereof comprises: i) a $V_H$ comprising an HC-CDR1 comprising the amino acid sequence of SEQ ID NO: 488, or a variant thereof comprising up to about 5 (such as about n, where n is selected from 1, 2, 3, 4, and 5) amino acid substitutions, an HC-CDR2 comprising the amino acid sequence of SEQ ID NO: 489, or a variant thereof comprising up to about 5 (such as about n, where n is selected from 1, 2, 3, 4, and 5) amino acid substitutions, and an HC-CDR3 comprising the amino acid sequence of SEQ ID NO: 490, or a variant thereof comprising up to about 5 (such as about n, where n is selected from 1, 2, 3, 4, and 5) amino acid substitutions; and ii) a $V_L$ comprising an LC-CDR1 comprising the amino acid sequence of SEQ ID NO: 492, or a variant thereof comprising up to about 5 (such as about n, where n is selected from 1, 2, 3, 4, and 5) amino acid substitutions, an LC-CDR2 comprising the amino acid sequence of SEQ ID NO: 493, or a variant thereof comprising up to about 3 (such as about any of 1, 2, or 3) amino acid substitutions, and an LC-CDR3 comprising the amino acid sequence of SEQ ID NO: 493, or a variant thereof comprising up to about 5 (such as about n, where n is selected from 1, 2, 3, 4, and 5) amino acid substitutions. In some embodiments, the anti-HA antibody or antigen binding fragment thereof comprises i) a $V_H$ comprising an HC-CDR1 comprising the amino acid sequence of SEQ ID NO: 488, an HC-CDR2 comprising the amino acid sequence of SEQ ID NO: 489, and an HC-CDR3 comprising the amino acid sequence of SEQ ID NO: 490; and ii) a $V_L$ comprising an LC-CDR1 comprising the amino acid sequence of SEQ ID NO: 492, an LC-CDR2 comprising the amino acid sequence of SEQ ID NO: 493, and an LC-CDR3 comprising the amino acid sequence of SEQ ID NO: 494.

In some embodiments, the anti-HA antibody or antigen binding fragment thereof comprises a $V_H$ comprising the amino acid sequences of SEQ ID NOs: 488, 489, and 490; and a $V_L$ comprising the amino acid sequences of SEQ ID NOs: 492, 493, and 494. In some embodiments, the anti-HA antibody or antigen binding fragment thereof comprises a $V_H$ comprising an HC-CDR1, an HC-CDR2, and an HC-CDR3 of the amino acid sequence of SEQ ID NO: 487 and a $V_L$ comprising an LC-CDR1, an LC-CDR2, and an LC-CDR3 of the amino acid sequence of SEQ ID NO: 491. In some embodiments, the anti-HA antibody or antigen binding fragment thereof comprises a $V_H$ comprising the amino acid sequence of SEQ ID NO: 487, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 487, and a $V_L$ comprising the amino acid sequence of SEQ ID NO: 491, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 491.

In some embodiments, the anti-HA antibody or antigen binding fragment thereof specifically binds to the HA protein of an influenza virus or a variant thereof. In some embodiments, the anti-HA antibody or antigen binding fragment thereof specifically binds to the HA1 region (e.g., the globular "head" region) of the HA protein. In some embodiments, the binding of the anti-HA antibody or antigen binding fragment thereof to the HA1 region of the HA protein prevents binding of an influenza virus or variant thereof to a sialic acid receptor. In some embodiments, the anti-HA antibody or antigen binding fragment thereof specifically binds to the HA2 region (e.g., the "stem" region) of the HA protein. In some embodiments, binding of the anti-HA antibody or antigen binding fragment thereof to the HA2 region of the HA protein prevents fusion of an influenza virus or variant thereof viral membrane with that of a host cell. In some embodiments, the anti-HA antibody or antigen binding fragment thereof is a neutralizing antibody.

In some embodiments, the anti-HA antibody or antigen binding fragment thereof specifically binds to the HA protein of an influenza virus or variant thereof with a $K_D$ of no more than about any one of 100 nM, 50 nM, 20 nM, 10 nM, 5 nM, 4 nM, 3 nM, 2 nM, 1 nM, 0.75 nM, 0.5 nM, 0.2 nM, 0.1 nM, 0.05 nM, 0.01 nM, or less, including any values and ranges in between these values. In some embodiments, the anti-HA antibody or antigen binding fragment thereof specifically binds to the HA protein of an influenza virus or variant thereof with a $K_D$ of about any one of 0.01 nM to 0.1 nM, 0.1 nM to 1 nM, 1 nM to 5 nM, 5 nM to 10 nM, 10 nM-100 nM, 0.01 nM to 1 nM, 0.5 nM to 10 nM, 0.1 nM to 1 nM, 0.1 nM to 10 nM, or 0.01 nM to 100 nM.

In some embodiments, the antibody moiety can be an anti-HA antibody that competes for binding to an HA protein of an influenza virus or variant thereof with a second anti-HA antibody according to any of the anti-HA antibodies described herein. In some embodiments, the anti-HA antibody can bind to the same, or substantially the same, epitope as the second anti-HA antibody. In some embodiments, binding of the anti-HA antibody to an HA protein of an influenza virus or variant thereof can inhibit the binding of a second anti-HA antibody to the same HA protein of an influenza virus or variant by at least about 70% (such as by at least about any of 75%, 80%, 85%, 90%, 95%, 98% or 99%), or vice versa. In some embodiments, the anti-HA antibody and the second anti-HA antibody can cross-compete for binding to the HA protein of an influenza virus or variant, i.e., each of the anti-HA antibody moieties can compete with the other for binding to the HA protein of an influenza virus or variant.

Exemplary Human Anti-NA Antibodies

In some embodiments, there is provided a chimeric protein comprising an anti-NA antibody or antigen binding fragment thereof (e.g., an anti-NA antibody moiety) that specifically binds to a human NA antigen. In some embodiments, the anti-HA antibody or antigen fragment thereof is a human anti-NA antibody or antigen fragment thereof.

Exemplary anti-NA antibodies are provided in Table 4B.

TABLE 4B

CDR and VH/VL sequences of exemplary human anti-NA antibodies

| Antibody code | Antibody Name | Target strain | Sequence | Type | SEQ ID NO |
|---|---|---|---|---|---|
| NA1 Reference: WO2021158960 | 1G05 | IBV | QVQLQESGPGLVRPSETLSLTCTVSGDSIG GSYWNWIRQPPGKGLQWIGYIYYTGITNY NPSLKSRVTMSLDTSKNQISLKMDSVTAA DTALYFCARGDYSGYDRDVQVELMDVW GKGTTVTVSS | $V_H$ | 188 |
| | | | DIQMTQSPSSLSASVRDKVTFVCRASQTISI FLNWYQHKPGEAPKLLIYAASRLQSGVPS RFSGSGSGTDFTLTISGLQPEDFATYYCQQS YSAPWTFGQGTKVEIK | $V_L$ | 189 |
| | | | GDSIGGSY | HC-CDR1 | 104 |
| | | | IYYTGIT | HC-CDR2 | 105 |
| | | | ARGDYSGYDRDVQVELMDV | HC-CDR3 | 106 |
| | | | QTISIF | LC-CDR1 | 107 |
| | | | AAS | LC-CDR2 | |
| | | | QQSYSAPWT | LC-CDR3 | 109 |

TABLE 4B-continued

CDR and VH/VL sequences of exemplary human anti-NA antibodies

| Antibody code | Antibody Name | Target strain | Sequence | Type | SEQ ID NO |
|---|---|---|---|---|---|
| NA2 Reference: WO2021158960 | 2E01 | IBV | EVQLVESGAEVKKPGSSVKVSCRASGTFY KYAINWVRQAPGQGLEWMGGIIPFFGTTN YAQKFQGRLTITADGSTNTAYMQLDSLRS EDTAVYYCAGPSITESHYCLDCAAKDYYY GLDVWGQGTTVTVSS | $V_H$ | 190 |
| | | | QSVLTQPPSASGTPGQSVTISCSGSRSNIGG NTVNWYQHLPGMAPKLLIYSSNQRSSGVP DRFSGSKSGTSASLAISGLQSEDDADYYCA SWDDSLNGVVFGGGTKLTVLG | $V_L$ | 191 |
| | | | GYTFINHA | HC-CDR1 | 110 |
| | | | IIPIFGLA | HC-CDR2 | 111 |
| | | | ARDTVAVYEDFDWSSPYFFYMDV | HC-CDR3 | 112 |
| | | | QSAGSKS | LC-CDR1 | 113 |
| | | | GAS | LC-CDR2 | |
| | | | QRYGTSLVT | LC-CDR3 | 115 |
| NA3 Reference: WO2018187706 | IF2 | IBV: Victoria, Yamagata lineages | QVHLQQSGPEVARPGASVKLSCKASGYTF TDYYLNWVKQRPRQGLEWIGQIHPGSTNT YYNEKFKGKATLTADKSSSTAYMQLSSLT FEDSAVYFCAISLGDGYYVYAMVCWGQG TAVTVSS | $V_H$ | 192 |
| | | | DIVMTQSQKFMSTSVGDRVSVTCKASQNV VTNVVWYQQKPGQSPKPLIYSASYRYSGV PDRFTGSGSGTDFTLTISNV | $V_L$ | 193 |
| | | | GYTFTDYY | HC-CDR1 | 116 |
| | | | IHPGSTNT | HC-CDR2 | 117 |
| | | | AISLGDGYYVYAMVC | HC-CDR3 | 118 |
| | | | QNVVTN | LC-CDR1 | 119 |
| | | | SAS | LC-CDR2 | |
| | | | QQYHSYPFT | LC-CDR3 | 121 |
| NA4 Reference: WO2018187706 | IF4 | IBV: Victoria, Yamagata lineages | QVHLQQSGSELRSPGSSVKLSCKDFDSEVF PIVYMRWIRQKPGHGFEWIGDILPSFGRTIY GEKFEDKATLDADTVSNTAYLELNSLTSE DSAIYYCARGDHGNWLAYWGQGTLVTVS A | $V_H$ | 194 |
| | | | DIVMTQSHKFMSTSVGDRVTITCKASQDV STNVAWYQQKPGQSPKLLIYWASTRHTGV PNRFTGIISGTDYTLTISSVQAEDRALYYCQ QHYSAPWTFGGGTKLEIK | $V_L$ | 195 |
| | | | DSEVFPIVY | HC-CDR1 | 122 |
| | | | ILPSFGRT | HC-CDR2 | 123 |
| | | | ARGDHGNWLAY | HC-CDR3 | 124 |
| | | | QDVSTN | LC-CDR1 | 125 |
| | | | WAS | LC-CDR2 | |
| | | | QQHYSAPWT | LC-CDR3 | 127 |
| NA5 Reference: WO2019213384 | 1092A9 | IBV | EVQLLQSGGGLVQPGGSLRLSCAASGLTFS GYAMSWVRQVPGKGPECVSGIIASGGSTY FADSVKGRFTISRDNSKNTLDLEMNSLRAE DTAVYYCAQHTKSHYYSGMGVWGQGTT VTVSS | $V_H$ | 196 |
| | | | DIQMTQSPSSLSASVGDRVTITCQASQDISN YLNWYQQRPGKAPKLLIYDAANLETGVPS RFSGSGSATQFTFTISGLQPEDFATYYCQQ YDNLPLTFGGGTKVEIK | $V_L$ | 197 |
| | | | GLTFSGYA | HC-CDR1 | 128 |
| | | | IIASGGST | HC-CDR2 | 129 |
| | | | AQHTKSHYYSGMGV | HC-CDR3 | 130 |
| | | | QDISNY | LC-CDR1 | 131 |
| | | | DAA | LC-CDR2 | |
| | | | QQYDNLPLT | LC-CDR3 | 133 |
| NA6 Reference: WO2019213384 | 1092B6 | IBV | QVQLVQSGAEVRKPGASVKVSCKVSRYNI IELSMDWVRQAPGKGLEWMGGIDPDDSER IYAQKLQGRVTMTEDTSTDTAYMELSGLR SEDTAIYYCAAARRPIRGEYHYALDVWGQ GTAVTVSS | $V_H$ | 198 |
| | | | EIVLTQSPGTLSLSPGERATLSCRASQSVSS SYLGWYQQKPGQAPRLLIYRASSRATGIPH RFSGSGSGTEFTLTITRLEPEDFA VYYCHH YAKVFGQGTKVEIK | $V_L$ | 199 |
| | | | RYNIIELS | HC-CDR1 | 134 |
| | | | IDPDDSER | HC-CDR2 | 135 |

TABLE 4B-continued

CDR and VH/VL sequences of exemplary human anti-NA antibodies

| Antibody code | Antibody Name | Target strain | Sequence | Type | SEQ ID NO |
|---|---|---|---|---|---|
| | | | AAARRPIRGEYHYALDV | HC-CDR3 | 136 |
| | | | QSVSSSY | LC-CDR1 | 137 |
| | | | RAS | LC-CDR2 | |
| | | | HHYAKV | LC-CDR3 | 139 |
| NA7 Reference: WO2020251834 | 3C05 | IAV | QVQLQQWGAGLLKPSETLSLTCAVYGGSFGGYYWNWIRQPPGKGLEWIGEINHSGSTNYNPSLKSRVTLSVDTSKNQVSLNVSSVTAADTAVYYCARGRGGYATYYYYYYVDVWGKGTTVTVSS | $V_H$ | 200 |
| | | | EIVLTQSPATLSLSPGERATLSCRASQSVSSYLAWYQQKPGQAPRLLIYDASKRATGIPARFSGSGSGTDFTLTISSLEPEDFAVYYCQQRSNWLTFGGGTKVELE | $V_L$ | 201 |
| | | | GGSFGGYY | HC-CDR1 | 140 |
| | | | INHSGST | HC-CDR2 | 141 |
| | | | ARGRGGYATYYYYYYVDV | HC-CDR3 | 142 |
| | | | QSVSSY | LC-CDR1 | 143 |
| | | | DAS | LC-CDR2 | |
| | | | QQRSNWLT | LC-CDR3 | 145 |
| NA8 Reference: WO2020243572 | SEQ 42-43 | pan-NA | EVQLVESGGRVVRPGGSLRLSCAASGFTFDDYGMSWVRQPPGKGLEFVSGLNWNGDITAFTDSVKGRETISRDNVKSSLYLQMNSLRADDTAFYYCARVRTWGDYTTGEEIINSWYFDLWGRGTLVTVSS | $V_H$ | 202 |
| | | | DIQLTQSPSFLSASVGDRVTITCRASQDISSYLAWYQQKPGNAPKVLIYAASLLSGVPSRFSAFGSGTEFTLTISSLQPEDFATYYCQHLKSYPLETFGPGTKVDIK | $V_L$ | 203 |
| | | | GFTFDDYGM | HC-CDR1 | 146 |
| | | | LNWNGDITA | HC-CDR2 | 147 |
| | | | TWGEYTTREEPINSWY | HC-CDR3 | 148 |
| | | | DISSFL | LC-CDR1 | 149 |
| | | | SLL | LC-CDR2 | |
| | | | LNSYPLETF | LC-CDR3 | 151 |
| NA9 Reference: WO2020243572 | SEQ 40-41 | pan-NA | EVQLVESGGRVVRPGGSLRLSCAASGFTFDDYGMSWVRQAPGKGLEFVSGLNWNGDITAFTDSVKGRETISRDNAKSSLYLQMNSLRADDTAFYYCARVRTWGEYTTREEPIHSWYFDLWGRGTLVTVSS | $V_H$ | 204 |
| | | | DIQLTQSPSFLSASVGDRVTITCRASQDISSYLAWYQQKPGNAPKLLIYAASLLSGVPSRFSAFGSGTEFTLTISSLQPEDFATYYCQHLKSYPLETFGPGTKVDIK | $V_L$ | 205 |
| | | | GFTFDDYGM | HC-CDR1 | 152 |
| | | | LNWNGDITA | HC-CDR2 | 153 |
| | | | TWGDYTTGEEIINSWY | HC-CDR3 | 154 |
| | | | DISSYL | LC-CDR1 | 155 |
| | | | SLL | LC-CDR2 | |
| | | | LKSYPLETF | LC-CDR3 | 157 |
| NA10 Reference: WO2020243572 | SEQ 44-45 | pan-NA | EVQLVESGGRALRPGGSLRLSCAASGFKFDDYAMSWVRQVPGKGLEFVSGLNWNGDITAYTDSVKGRETVSRDNAKNSLYLHINSPKPEDTALYYCARTSSWGDYTRGPEPKITWYFDLWGRGTLVTVSS | $V_H$ | 206 |
| | | | DIQLTQSPSFLSASVGDRITITCRASQGIDGYLAWYQQRPGKAPNLLIYAASLLSGVPSRFSGSGYGTEFTLTISSLQPEDFATYYCQHLDSYPLETFGPGTKVDIK | $V_L$ | 207 |
| | | | GFKFDDYAM | HC-CDR1 | 158 |
| | | | LNWNGDITA | HC-CDR2 | 159 |
| | | | SWGDYTRGPEPKITWY | HC-CDR3 | 160 |
| | | | GIDGYL | LC-CDR1 | 161 |
| | | | SLL | LC-CDR2 | |
| | | | LDSYPLETF | LC-CDR3 | 163 |
| NA11 Reference: WO2019169231 | 2D04 | IAV: N1, N2, N3, N4, N5, N6, N7, N8, N9, | EVQLVESGGGLVKPGQSLRLSCAASGFTFTNAWMSWVRQAPGKGLEWVGRIKTKTEGETVDYAAPVKGRITISRDDSKNMVYLQLKSLKIEDAAVYYCTTGLTRSSLGGFVDYWGPGTLVTVSS | $V_H$ | 208 |

TABLE 4B-continued

CDR and VH/VL sequences of exemplary human anti-NA antibodies

| Antibody code | Antibody Name | Target strain | Sequence | Type | SEQ ID NO |
|---|---|---|---|---|---|
| | | N10, N11 | DIVMTQSPDSLTVSLGERATINCRSSQTVLS SSNNENFLAWYQQKSGQPPNLLIYWASTR ASGVPDRFSGSGSGTDFTLTISSLQTEDVA VYYCLQYLTTPRTFGQGTKVEIK | $V_L$ | 209 |
| | | | NAWMS | HC-CDR1 | 164 |
| | | | RIKTKTEGETVDYAAPVKG | HC-CDR2 | 165 |
| | | | TTGLTRSSLGGFVDY | HC-CDR3 | 166 |
| | | | RSSQTVLSSSNNENFLA | LC-CDR1 | 167 |
| | | | WASTRAS | LC-CDR2 | 168 |
| | | | LQYLTTPRT | LC-CDR3 | 169 |
| NA12 Reference: WO2019169231 | 1D05 | IAV: N1, N2, N3, N4, N5, N6, N7, N8, N9, | VQLVESGGGLVKPGGSLRLSCAASGFTFSD YYMSWIRQAPGKGLEWISYISSSSTYTDYA DSVKGRFTVSRDNAKNSLYLQMNNLRAE DTAVYYCATVADTAYSRGRPQITHFDNW GQGTLVTVSS | $V_H$ | 210 |
| | | N10, N11 | SYELTQPPSMSVSPGQTATITCFGDKLGEK YAYWYQQKPGQSPLLVIYQDTKRPSGIPER FSGSNSGNTATLTISGTQAMDEADYYCQT WDSTLVFFGGGTKLTVL | $V_L$ | 211 |
| | | | DYYMS | HC-CDR1 | 170 |
| | | | YISSSSTYTDYADSVKG | HC-CDR2 | 171 |
| | | | ATVADTAYSRGRPQITHEDN | HC-CDR3 | 172 |
| | | | FGDKLGEKYAY | LC-CDR1 | 173 |
| | | | QDTKRPS | LC-CDR2 | 174 |
| | | | QTWDSTLVF | LC-CDR3 | 175 |
| NA13 Reference: WO2019169231 | 1G03 | IAV: N1, N2, N3, N4, N5, N6, N7, N8, N9, | VQLVESGGGVVQPGGSLRLSCAVSGLTIN DLVIHWVRQPPDKGLEWVAVMGYDGGN KDYAESVKGRFSISGDNPQNTLYLQINSLR VEDTAVYYCARASYFGELRDEYYSFAMD VWGQGTTVTVSS | $V_H$ | 212 |
| | | N10, N11 | EIVLTQSPGTLSLSPGERGTLSCRASQSVSR SYLAWYQQKPGQAPRLLIYGASSRATGIPD RFSGSGSGTDFTLTISRLEPEDFALYYCQLY GTSPPYTFGQGTKVEIK | $V_L$ | 213 |
| | | | DLVIH | HC-CDR1 | 176 |
| | | | VMGYDGGNKDYAESVKG | HC-CDR2 | 177 |
| | | | ARASYFGELRDEYYSFAMDV | HC-CDR3 | 178 |
| | | | RASQSVSRSYLA | LC-CDR1 | 179 |
| | | | GASSRAT | LC-CDR2 | 180 |
| | | | QLYGTSPPYT | LC-CDR3 | 181 |
| NA14 Reference: WO2019169231 | 2B04 | IAV: N1, N2, N3, N4, N5, N6, N7, N8, N9, | EVQLVESGGGLVKPGGSLRLSCAASGFTVS NAWMSWVRQAPGKGLEWVGRIKKESEGG TIDYGAPVKGRFTISRDESKNILYLHMKSLI TDDTAVYYCTIPNPQIVVVTTTPHSHWGQ GTLVTVSS | $V_H$ | 214 |
| | | N10, N11 | SYELTQPPSVSVAPGKTARITCGGNNIGSK NVHWYQQKPGQAPVLVIYYDSDRPSAIPE RFSGSNSGNTATLTISRVEAGDEADYYCQV WDSSSDHWVFGGGTKLAVL | $V_L$ | 215 |
| | | | NAWMS | HC-CDR1 | 182 |
| | | | RIKKESEGGTIDYGAPVKG | HC-CDR2 | 183 |
| | | | TIPNPQIVVVTTTPHSH | HC-CDR3 | 184 |
| | | | GGNNIGSKNVH | LC-CDR1 | 185 |
| | | | YDSDRPS | LC-CDR2 | 186 |
| | | | QVWDSSSDHWV | LC-CDR3 | 187 |

In some embodiments, the anti-NA antibody or antigen binding fragment thereof comprises an HC-CDR1, HC-CDR2, HC-CDR3, LC-CDR1, LC-CDR2, and LC-CDR3 of any one of antibodies NA1-NA14 of Table 4B. In some embodiments, the anti-NA antibody or antigen binding fragment thereof comprises a $V_H$ and $V_L$ of any one of antibodies NA1-NA14 of Table 4B. In some embodiments, the anti-NA antibody or antigen binding fragment thereof comprises an HC-CDR1, HC-CDR2, HC-CDR3, LC-CDR1, LC-CDR2, and LC-CDR3 of antibody NA1 of Table 4B. In some embodiments, the anti-NA antibody or antigen binding fragment thereof comprises a $V_H$ and $V_L$ of antibody NA1 of Table 4B. In some embodiments, the anti-NA antibody or antigen binding fragment thereof comprises an HC-CDR1, HC-CDR2, HC-CDR3, LC-CDR1, LC-CDR2, and LC-CDR3 of antibody NA2 of Table 4B. In some embodiments, the anti-NA antibody or antigen binding fragment thereof comprises a $V_H$ and $V_L$ of antibody NA2 of Table 4B.

In some embodiments, the anti-NA antibody or antigen binding fragment thereof comprises: i) a $V_H$ comprising an HC-CDR1 comprising the amino acid sequence of SEQ ID NO: 104, or a variant thereof comprising up to about 5 (such as about n, where n is selected from 1, 2, 3, 4, and 5) amino acid substitutions, an HC-CDR2 comprising the amino acid sequence of SEQ ID NO: 105, or a variant thereof comprising up to about 5 (such as about n, where n is selected from 1, 2, 3, 4, and 5) amino acid substitutions, and an HC-CDR3 comprising the amino acid sequence of SEQ ID NO: 106, or a variant thereof comprising up to about 5 (such as about n, where n is selected from 1, 2, 3, 4, and 5) amino acid substitutions; and ii) a $V_L$ comprising an LC-CDR1 comprising the amino acid sequence of SEQ ID NO: 107, or a variant thereof comprising up to about 5 (such as about n, where n is selected from 1, 2, 3, 4, and 5) amino acid substitutions, an LC-CDR2 comprising the amino acid sequence of AAS, or a variant thereof comprising about 1 or about 2 amino acid substitutions, and an LC-CDR3 comprising the amino acid sequence of SEQ ID NO: 109, or a variant thereof comprising up to about 5 (such as about n, where n is selected from 1, 2, 3, 4, and 5) amino acid substitutions. In some embodiments, the anti-NA antibody or antigen binding fragment thereof comprises i) a $V_H$ comprising an HC-CDR1 comprising the amino acid sequence of SEQ ID NO: 104, an HC-CDR2 comprising the amino acid sequence of SEQ ID NO: 105, and an HC-CDR3 comprising the amino acid sequence of SEQ ID NO: 106; and ii) a $V_L$ comprising an LC-CDR1 comprising the amino acid sequence of SEQ ID NO: 107, an LC-CDR2 comprising the amino acid sequence of AAS, and an LC-CDR3 comprising the amino acid sequence of SEQ ID NO: 109.

In some embodiments, the anti-NA antibody or antigen binding fragment thereof comprises a $V_H$ comprising the amino acid sequences of SEQ ID NOs: 104, 105, and 106; and a $V_L$ comprising the amino acid sequences of AAS and SEQ ID NOs: 107 and 109. In some embodiments, the anti-NA antibody or antigen binding fragment thereof comprises a $V_H$ comprising an HC-CDR1, an HC-CDR2, and an HC-CDR3 of the amino acid sequence of SEQ ID NO: 188 and a $V_L$ comprising an LC-CDR1, an LC-CDR2, and an LC-CDR3 of the amino acid sequence of SEQ ID NO: 189. In some embodiments, the anti-NA antibody or antigen binding fragment thereof comprises a $V_H$ comprising the amino acid sequence of SEQ ID NO: 188, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 188, and a $V_L$ comprising the amino acid sequence of SEQ ID NO: 189, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 189.

In some embodiments, the anti-NA antibody or antigen binding fragment thereof comprises: i) a $V_H$ comprising an HC-CDR1 comprising the amino acid sequence of SEQ ID NO: 110, or a variant thereof comprising up to about 5 (such as about n, where n is selected from 1, 2, 3, 4, and 5) amino acid substitutions, an HC-CDR2 comprising the amino acid sequence of SEQ ID NO: 111, or a variant thereof comprising up to about 5 (such as about n, where n is selected from 1, 2, 3, 4, and 5) amino acid substitutions, and an HC-CDR3 comprising the amino acid sequence of SEQ ID NO: 112, or a variant thereof comprising up to about 5 (such as about n, where n is selected from 1, 2, 3, 4, and 5) amino acid substitutions; and ii) a $V_L$ comprising an LC-CDR1 comprising the amino acid sequence of SEQ ID NO: 113, or a variant thereof comprising up to about 5 (such as about n, where n is selected from 1, 2, 3, 4, and 5) amino acid substitutions, an LC-CDR2 comprising the amino acid sequence of GAS, or a variant thereof comprising about 1 or about 2 amino acid substitutions, and an LC-CDR3 comprising the amino acid sequence of SEQ ID NO: 115, or a variant thereof comprising up to about 5 (such as about n, where n is selected from 1, 2, 3, 4, and 5) amino acid substitutions. In some embodiments, the anti-NA antibody or antigen binding fragment thereof comprises i) a $V_H$ comprising an HC-CDR1 comprising the amino acid sequence of SEQ ID NO: 110, an HC-CDR2 comprising the amino acid sequence of SEQ ID NO: 111, and an HC-CDR3 comprising the amino acid sequence of SEQ ID NO: 112; and ii) a $V_L$ comprising an LC-CDR1 comprising the amino acid sequence of SEQ ID NO: 113, an LC-CDR2 comprising the amino acid sequence of GAS, and an LC-CDR3 comprising the amino acid sequence of SEQ ID NO: 115.

In some embodiments, the anti-NA antibody or antigen binding fragment thereof comprises a $V_H$ comprising the amino acid sequences of SEQ ID NOs: 110, 111, and 112; and a $V_L$ comprising the amino acid sequences of GAS and SEQ ID NOs: 113 and 115. In some embodiments, the anti-NA antibody or antigen binding fragment thereof comprises a $V_H$ comprising an HC-CDR1, an HC-CDR2, and an HC-CDR3 of the amino acid sequence of SEQ ID NO: 190 and a $V_L$ comprising an LC-CDR1, an LC-CDR2, and an LC-CDR3 of the amino acid sequence of SEQ ID NO: 191. In some embodiments, the anti-NA antibody or antigen binding fragment thereof comprises a $V_H$ comprising the amino acid sequence of SEQ ID NO: 190, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 190, and a $V_L$ comprising the amino acid sequence of SEQ ID NO: 191, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 191.

In some embodiments, the anti-NA antibody or antigen binding fragment thereof comprises: i) a $V_H$ comprising an HC-CDR1 comprising the amino acid sequence of SEQ ID NO: 116, or a variant thereof comprising up to about 5 (such as about n, where n is selected from 1, 2, 3, 4, and 5) amino acid substitutions, an HC-CDR2 comprising the amino acid sequence of SEQ ID NO: 117, or a variant thereof comprising up to about 5 (such as about n, where n is selected from 1, 2, 3, 4, and 5) amino acid substitutions, and an HC-CDR3 comprising the amino acid sequence of SEQ ID NO: 118, or a variant thereof comprising up to about 5 (such as about n, where n is selected from 1, 2, 3, 4, and 5) amino acid substitutions; and ii) a $V_L$ comprising an LC-CDR1 comprising the amino acid sequence of SEQ ID NO: 119, or a variant thereof comprising up to about 5 (such as about n, where n is selected from 1, 2, 3, 4, and 5) amino acid substitutions, an LC-CDR2 comprising the amino acid sequence of SAS, or a variant thereof comprising about 1 or about 2 amino acid substitutions, and an LC-CDR3 comprising the amino acid sequence of SEQ ID NO: 121, or a variant thereof comprising up to about 5 (such as about n, where n is selected from 1, 2, 3, 4, and 5) amino acid substitutions. In some embodiments, the anti-NA antibody or antigen binding fragment thereof comprises i) a $V_H$ comprising an HC-CDR1 comprising the amino acid sequence of SEQ ID NO: 116, an HC-CDR2 comprising the amino acid sequence of SEQ ID NO: 117, and an HC-CDR3 comprising the amino acid sequence of SEQ ID NO: 118; and ii) a $V_L$ comprising an LC-CDR1 comprising the amino acid sequence of SEQ ID NO: 119, an LC-CDR2 comprising the amino acid sequence of SAS, and an LC-CDR3 comprising the amino acid sequence of SEQ ID NO: 121.

In some embodiments, the anti-NA antibody or antigen binding fragment thereof comprises a $V_H$ comprising the amino acid sequences of SEQ ID NOs: 116, 117, and 118; and a $V_L$ comprising the amino acid sequences of SAS and SEQ ID NOs: 119 and 121. In some embodiments, the anti-NA antibody or antigen binding fragment thereof comprises a $V_H$ comprising an HC-CDR1, an HC-CDR2, and an HC-CDR3 of the amino acid sequence of SEQ ID NO: 192 and a $V_L$ comprising an LC-CDR1, an LC-CDR2, and an LC-CDR3 of the amino acid sequence of SEQ ID NO: 193. In some embodiments, the anti-NA antibody or antigen binding fragment thereof comprises a $V_H$ comprising the amino acid sequence of SEQ ID NO: 192, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 192, and a $V_L$ comprising the amino acid sequence of SEQ ID NO: 193, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 193.

In some embodiments, the anti-NA antibody or antigen binding fragment thereof comprises: i) a $V_H$ comprising an HC-CDR1 comprising the amino acid sequence of SEQ ID NO: 122, or a variant thereof comprising up to about 5 (such as about n, where n is selected from 1, 2, 3, 4, and 5) amino acid substitutions, an HC-CDR2 comprising the amino acid sequence of SEQ ID NO: 123, or a variant thereof comprising up to about 5 (such as about n, where n is selected from 1, 2, 3, 4, and 5) amino acid substitutions, and an HC-CDR3 comprising the amino acid sequence of SEQ ID NO: 124, or a variant thereof comprising up to about 5 (such as about n, where n is selected from 1, 2, 3, 4, and 5) amino acid substitutions; and ii) a $V_L$ comprising an LC-CDR1 comprising the amino acid sequence of SEQ ID NO: 125, or a variant thereof comprising up to about 5 (such as about n, where n is selected from 1, 2, 3, 4, and 5) amino acid substitutions, an LC-CDR2 comprising the amino acid sequence of WAS, or a variant thereof comprising about 1 or about 2 amino acid substitutions, and an LC-CDR3 comprising the amino acid sequence of SEQ ID NO: 127, or a variant thereof comprising up to about 5 (such as about n, where n is selected from 1, 2, 3, 4, and 5) amino acid substitutions. In some embodiments, the anti-NA antibody or antigen binding fragment thereof comprises i) a $V_H$ comprising an HC-CDR1 comprising the amino acid sequence of SEQ ID NO: 122, an HC-CDR2 comprising the amino acid sequence of SEQ ID NO: 123, and an HC-CDR3 comprising the amino acid sequence of SEQ ID NO: 124; and ii) a $V_L$ comprising an LC-CDR1 comprising the amino acid sequence of SEQ ID NO: 125, an LC-CDR2 comprising the amino acid sequence of WAS, and an LC-CDR3 comprising the amino acid sequence of SEQ ID NO: 127.

In some embodiments, the anti-NA antibody or antigen binding fragment thereof comprises a $V_H$ comprising the amino acid sequences of SEQ ID NOs: 122, 123, and 124; and a $V_L$ comprising the amino acid sequences of WAS and SEQ ID NOs: 125 and 127. In some embodiments, the anti-NA antibody or antigen binding fragment thereof comprises a $V_H$ comprising an HC-CDR1, an HC-CDR2, and an HC-CDR3 of the amino acid sequence of SEQ ID NO: 194 and a $V_L$ comprising an LC-CDR1, an LC-CDR2, and an LC-CDR3 of the amino acid sequence of SEQ ID NO: 195. In some embodiments, the anti-NA antibody or antigen binding fragment thereof comprises a $V_H$ comprising the amino acid sequence of SEQ ID NO: 194, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 194, and a $V_L$ comprising the amino acid sequence of SEQ ID NO: 195, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 195.

In some embodiments, the anti-NA antibody or antigen binding fragment thereof comprises: i) a $V_H$ comprising an HC-CDR1 comprising the amino acid sequence of SEQ ID NO: 128, or a variant thereof comprising up to about 5 (such as about n, where n is selected from 1, 2, 3, 4, and 5) amino acid substitutions, an HC-CDR2 comprising the amino acid sequence of SEQ ID NO: 129, or a variant thereof comprising up to about 5 (such as about n, where n is selected from 1, 2, 3, 4, and 5) amino acid substitutions, and an HC-CDR3 comprising the amino acid sequence of SEQ ID NO: 130, or a variant thereof comprising up to about 5 (such as about n, where n is selected from 1, 2, 3, 4, and 5) amino acid substitutions; and ii) a $V_L$ comprising an LC-CDR1 comprising the amino acid sequence of SEQ ID NO: 131, or a variant thereof comprising up to about 5 (such as about n, where n is selected from 1, 2, 3, 4, and 5) amino acid substitutions, an LC-CDR2 comprising the amino acid sequence DAA, or a variant thereof comprising about 1 or about 2 amino acid substitutions, and an LC-CDR3 comprising the amino acid sequence of SEQ ID NO: 133, or a variant thereof comprising up to about 5 (such as about n, where n is selected from 1, 2, 3, 4, and 5) amino acid substitutions. In some embodiments, the anti-NA antibody or antigen binding fragment thereof comprises i) a $V_H$ comprising an HC-CDR1 comprising the amino acid sequence of SEQ ID NO: 128, an HC-CDR2 comprising the amino acid sequence of SEQ ID NO: 129, and an HC-CDR3 comprising the amino acid sequence of SEQ ID NO: 130; and ii) a $V_L$ comprising an LC-CDR1 comprising the amino acid sequence of SEQ ID NO: 131, an LC-CDR2 comprising the amino acid sequence of DAA, and an LC-CDR3 comprising the amino acid sequence of SEQ ID NO: 133.

In some embodiments, the anti-NA antibody or antigen binding fragment thereof comprises a $V_H$ comprising the amino acid sequences of SEQ ID NOs: 128, 129, and 130; and a $V_L$ comprising the amino acid sequences of DAA and SEQ ID NOs: 131 and 133. In some embodiments, the anti-NA antibody or antigen binding fragment thereof comprises a $V_H$ comprising an HC-CDR1, an HC-CDR2, and an HC-CDR3 of the amino acid sequence of SEQ ID NO: 196 and a $V_L$ comprising an LC-CDR1, an LC-CDR2, and an LC-CDR3 of the amino acid sequence of SEQ ID NO: 197. In some embodiments, the anti-NA antibody or antigen binding fragment thereof comprises a $V_H$ comprising the amino acid sequence of SEQ ID NO: 196, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 196, and a $V_L$ comprising the amino acid sequence of SEQ ID NO: 197, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 197.

In some embodiments, the anti-NA antibody or antigen binding fragment thereof comprises: i) a $V_H$ comprising an HC-CDR1 comprising the amino acid sequence of SEQ ID NO: 134, or a variant thereof comprising up to about 5 (such as about n, where n is selected from 1, 2, 3, 4, and 5) amino acid substitutions, an HC-CDR2 comprising the amino acid sequence of SEQ ID NO: 135, or a variant thereof comprising up to about 5 (such as about n, where n is selected from 1, 2, 3, 4, and 5) amino acid substitutions, and an HC-CDR3 comprising the amino acid sequence of SEQ ID NO: 136, or a variant thereof comprising up to about 5 (such as about n, where n is selected from 1, 2, 3, 4, and 5) amino acid substitutions; and ii) a $V_L$ comprising an LC-CDR1 comprising the amino acid sequence of SEQ ID NO: 137, or a variant thereof comprising up to about 5 (such as about n, where n is selected from 1, 2, 3, 4, and 5) amino acid substitutions, an LC-CDR2 comprising the amino acid sequence of RAS, or a variant thereof comprising about 1 or about 2 amino acid substitutions, and an LC-CDR3 comprising the amino acid sequence of SEQ ID NO: 139, or a variant thereof comprising up to about 5 (such as about n, where n is selected from 1, 2, 3, 4, and 5) amino acid substitutions. In some embodiments, the anti-NA antibody or antigen binding fragment thereof comprises i) a $V_H$ comprising an HC-CDR1 comprising the amino acid sequence of SEQ ID NO: 134, an HC-CDR2 comprising the amino acid sequence of SEQ ID NO: 135, and an HC-CDR3 comprising the amino acid sequence of SEQ ID NO: 136; and ii) a $V_L$ comprising an LC-CDR1 comprising the amino acid sequence of SEQ ID NO: 137, an LC-CDR2 comprising the amino acid sequence of RAS, and an LC-CDR3 comprising the amino acid sequence of SEQ ID NO: 139.

In some embodiments, the anti-NA antibody or antigen binding fragment thereof comprises a $V_H$ comprising the amino acid sequences of SEQ ID NOs: 134, 135, and 136; and a $V_L$ comprising the amino acid sequences of RAS and SEQ ID NOs: 137 and 139. In some embodiments, the anti-NA antibody or antigen binding fragment thereof comprises a $V_H$ comprising an HC-CDR1, an HC-CDR2, and an HC-CDR3 of the amino acid sequence of SEQ ID NO: 198 and a $V_L$ comprising an LC-CDR1, an LC-CDR2, and an LC-CDR3 of the amino acid sequence of SEQ ID NO: 199. In some embodiments, the anti-NA antibody or antigen binding fragment thereof comprises a $V_H$ comprising the amino acid sequence of SEQ ID NO: 198, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 198, and a $V_L$ comprising the amino acid sequence of SEQ ID NO: 199, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 199.

In some embodiments, the anti-NA antibody or antigen binding fragment thereof comprises: i) a $V_H$ comprising an HC-CDR1 comprising the amino acid sequence of SEQ ID NO: 140, or a variant thereof comprising up to about 5 (such as about n, where n is selected from 1, 2, 3, 4, and 5) amino acid substitutions, an HC-CDR2 comprising the amino acid sequence of SEQ ID NO: 141, or a variant thereof comprising up to about 5 (such as about n, where n is selected from 1, 2, 3, 4, and 5) amino acid substitutions, and an HC-CDR3 comprising the amino acid sequence of SEQ ID NO: 142, or a variant thereof comprising up to about 5 (such as about n, where n is selected from 1, 2, 3, 4, and 5) amino acid substitutions; and ii) a $V_L$ comprising an LC-CDR1 comprising the amino acid sequence of SEQ ID NO: 143, or a variant thereof comprising up to about 5 (such as about n, where n is selected from 1, 2, 3, 4, and 5) amino acid substitutions, an LC-CDR2 comprising the amino acid sequence of DAS, or a variant thereof comprising about 1 or about 2 amino acid substitutions, and an LC-CDR3 comprising the amino acid sequence of SEQ ID NO: 145, or a variant thereof comprising up to about 5 (such as about n, where n is selected from 1, 2, 3, 4, and 5) amino acid substitutions. In some embodiments, the anti-NA antibody or antigen binding fragment thereof comprises i) a $V_H$ comprising an HC-CDR1 comprising the amino acid sequence of SEQ ID NO: 140, an HC-CDR2 comprising the amino acid sequence of SEQ ID NO: 141, and an HC-CDR3 comprising the amino acid sequence of SEQ ID NO: 142; and ii) a $V_L$ comprising an LC-CDR1 comprising the amino acid sequence of SEQ ID NO: 143, an LC-CDR2 comprising the amino acid sequence of DAS, and an LC-CDR3 comprising the amino acid sequence of SEQ ID NO: 145.

In some embodiments, the anti-NA antibody or antigen binding fragment thereof comprises a $V_H$ comprising the amino acid sequences of SEQ ID NOs: 140, 141, and 142; and a $V_L$ comprising the amino acid sequences of DAS and SEQ ID NOs: 143 and 145. In some embodiments, the anti-NA antibody or antigen binding fragment thereof comprises a $V_H$ comprising an HC-CDR1, an HC-CDR2, and an HC-CDR3 of the amino acid sequence of SEQ ID NO: 200 and a $V_L$ comprising an LC-CDR1, an LC-CDR2, and an LC-CDR3 of the amino acid sequence of SEQ ID NO: 201. In some embodiments, the anti-NA antibody or antigen binding fragment thereof comprises a $V_H$ comprising the amino acid sequence of SEQ ID NO: 200, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 200, and a $V_L$ comprising the amino acid sequence of SEQ ID NO: 201, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 201.

In some embodiments, the anti-NA antibody or antigen binding fragment thereof comprises: i) a $V_H$ comprising an HC-CDR1 comprising the amino acid sequence of SEQ ID NO: 146, or a variant thereof comprising up to about 5 (such as about n, where n is selected from 1, 2, 3, 4, and 5) amino acid substitutions, an HC-CDR2 comprising the amino acid sequence of SEQ ID NO: 147, or a variant thereof comprising up to about 5 (such as about n, where n is selected from 1, 2, 3, 4, and 5) amino acid substitutions, and an HC-CDR3 comprising the amino acid sequence of SEQ ID NO: 148, or a variant thereof comprising up to about 5 (such as about n, where n is selected from 1, 2, 3, 4, and 5) amino acid substitutions; and ii) a $V_L$ comprising an LC-CDR1 comprising the amino acid sequence of SEQ ID NO: 149, or a variant thereof comprising up to about 5 (such as about n, where n is selected from 1, 2, 3, 4, and 5) amino acid substitutions, an LC-CDR2 comprising the amino acid sequence of SLL, or a variant thereof comprising about 1 or about 2 amino acid substitutions, and an LC-CDR3 comprising the amino acid sequence of SEQ ID NO: 151, or a variant thereof comprising up to about 5 (such as about n, where n is selected from 1, 2, 3, 4, and 5) amino acid substitutions. In some embodiments, the anti-NA antibody or antigen binding fragment thereof comprises i) a $V_H$ comprising an HC-CDR1 comprising the amino acid sequence of SEQ ID NO: 146, an HC-CDR2 comprising the amino acid sequence of SEQ ID NO: 147, and an HC-CDR3 comprising the amino acid sequence of SEQ ID NO: 148; and ii) a $V_L$ comprising an LC-CDR1 comprising the amino acid sequence of SEQ ID NO: 149, an LC-CDR2 comprising the amino acid sequence of SLL, and an LC-CDR3 comprising the amino acid sequence of SEQ ID NO: 151.

In some embodiments, the anti-NA antibody or antigen binding fragment thereof comprises a $V_H$ comprising the amino acid sequences of SEQ ID NOs: 146, 147, and 148; and a $V_L$ comprising the amino acid sequences of SLL and SEQ ID NOs: 149 and 151. In some embodiments, the anti-NA antibody or antigen binding fragment thereof comprises a $V_H$ comprising an HC-CDR1, an HC-CDR2, and an HC-CDR3 of the amino acid sequence of SEQ ID NO: 202 and a $V_L$ comprising an LC-CDR1, an LC-CDR2, and an LC-CDR3 of the amino acid sequence of SEQ ID NO: 203. In some embodiments, the anti-NA antibody or antigen binding fragment thereof comprises a $V_H$ comprising the amino acid sequence of SEQ ID NO: 202, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 202, and a $V_L$ comprising the amino acid sequence of SEQ ID NO: 203, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 203.

In some embodiments, the anti-NA antibody or antigen binding fragment thereof comprises: i) a $V_H$ comprising an HC-CDR1 comprising the amino acid sequence of SEQ ID NO: 152, or a variant thereof comprising up to about 5 (such as about n, where n is selected from 1, 2, 3, 4, and 5) amino acid substitutions, an HC-CDR2 comprising the amino acid sequence of SEQ ID NO: 153, or a variant thereof comprising up to about 5 (such as about n, where n is selected from 1, 2, 3, 4, and 5) amino acid substitutions, and an HC-CDR3 comprising the amino acid sequence of SEQ ID NO: 154, or a variant thereof comprising up to about 5 (such as about n, where n is selected from 1, 2, 3, 4, and 5) amino acid substitutions; and ii) a $V_L$ comprising an LC-CDR1 comprising the amino acid sequence of SEQ ID NO: 155, or a variant thereof comprising up to about 5 (such as about n, where n is selected from 1, 2, 3, 4, and 5) amino acid substitutions, an LC-CDR2 comprising the amino acid sequence of SLL, or a variant thereof comprising about 1 or about 2 amino acid substitutions, and an LC-CDR3 comprising the amino acid sequence of SEQ ID NO: 157, or a variant thereof comprising up to about 5 (such as about n, where n is selected from 1, 2, 3, 4, and 5) amino acid substitutions. In some embodiments, the anti-NA antibody or antigen binding fragment thereof comprises i) a $V_H$ comprising an HC-CDR1 comprising the amino acid sequence of SEQ ID NO: 152, an HC-CDR2 comprising the amino acid sequence of SEQ ID NO: 153, and an HC-CDR3 comprising the amino acid sequence of SEQ ID NO: 154; and ii) a $V_L$ comprising an LC-CDR1 comprising the amino acid sequence of SEQ ID NO: 155, an LC-CDR2 comprising the amino acid sequence of SLL, and an LC-CDR3 comprising the amino acid sequence of SEQ ID NO: 157.

In some embodiments, the anti-NA antibody or antigen binding fragment thereof comprises a $V_H$ comprising the amino acid sequences of SEQ ID NOs: 152, 153, and 154; and a $V_L$ comprising the amino acid sequences of SLL and SEQ ID NOs: 155 and 157. In some embodiments, the anti-NA antibody or antigen binding fragment thereof comprises a $V_H$ comprising an HC-CDR1, an HC-CDR2, and an HC-CDR3 of the amino acid sequence of SEQ ID NO: 204 and a $V_L$ comprising an LC-CDR1, an LC-CDR2, and an LC-CDR3 of the amino acid sequence of SEQ ID NO: 205. In some embodiments, the anti-NA antibody or antigen binding fragment thereof comprises a $V_H$ comprising the amino acid sequence of SEQ ID NO: 204, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 204, and a $V_L$ comprising the amino acid sequence of SEQ ID NO: 205, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 205.

In some embodiments, the anti-NA antibody or antigen binding fragment thereof comprises: i) a $V_H$ comprising an HC-CDR1 comprising the amino acid sequence of SEQ ID NO: 158, or a variant thereof comprising up to about 5 (such as about n, where n is selected from 1, 2, 3, 4, and 5) amino acid substitutions, an HC-CDR2 comprising the amino acid sequence of SEQ ID NO: 159, or a variant thereof comprising up to about 5 (such as about n, where n is selected from 1, 2, 3, 4, and 5) amino acid substitutions, and an HC-CDR3 comprising the amino acid sequence of SEQ ID NO: 160, or a variant thereof comprising up to about 5 (such as about n, where n is selected from 1, 2, 3, 4, and 5) amino acid substitutions; and ii) a $V_L$ comprising an LC-CDR1 comprising the amino acid sequence of SEQ ID NO: 161, or a variant thereof comprising up to about 5 (such as about n, where n is selected from 1, 2, 3, 4, and 5) amino acid substitutions, an LC-CDR2 comprising the amino acid sequence of SLL, or a variant thereof comprising about 1 or about 2 amino acid substitutions, and an LC-CDR3 comprising the amino acid sequence of SEQ ID NO: 163, or a variant thereof comprising up to about 5 (such as about n, where n is selected from 1, 2, 3, 4, and 5) amino acid substitutions. In some embodiments, the anti-NA antibody or antigen binding fragment thereof comprises i) a $V_H$ comprising an HC-CDR1 comprising the amino acid sequence of SEQ ID NO: 158, an HC-CDR2 comprising the amino acid sequence of SEQ ID NO: 159, and an HC-CDR3 comprising the amino acid sequence of SEQ ID NO: 160; and ii) a $V_L$ comprising an LC-CDR1 comprising the amino acid sequence of SEQ ID NO: 161, an LC-CDR2 comprising the amino acid sequence of SLL, and an LC-CDR3 comprising the amino acid sequence of SEQ ID NO: 163.

In some embodiments, the anti-NA antibody or antigen binding fragment thereof comprises a $V_H$ comprising the amino acid sequences of SEQ ID NOs: 158, 159, and 160; and a $V_L$ comprising the amino acid sequences of SLL and SEQ ID NOs: 161 and 163. In some embodiments, the anti-NA antibody or antigen binding fragment thereof comprises a $V_H$ comprising an HC-CDR1, an HC-CDR2, and an HC-CDR3 of the amino acid sequence of SEQ ID NO: 206 and a $V_L$ comprising an LC-CDR1, an LC-CDR2, and an LC-CDR3 of the amino acid sequence of SEQ ID NO: 207. In some embodiments, the anti-NA antibody or antigen binding fragment thereof comprises a $V_H$ comprising the amino acid sequence of SEQ ID NO: 206, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 206, and a $V_L$ comprising the amino acid sequence of SEQ ID NO: 207, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 207.

In some embodiments, the anti-NA antibody or antigen binding fragment thereof comprises: i) a $V_H$ comprising an HC-CDR1 comprising the amino acid sequence of SEQ ID NO: 164, or a variant thereof comprising up to about 5 (such as about n, where n is selected from 1, 2, 3, 4, and 5) amino acid substitutions, an HC-CDR2 comprising the amino acid sequence of SEQ ID NO: 165, or a variant thereof comprising up to about 5 (such as about n, where n is selected from 1, 2, 3, 4, and 5) amino acid substitutions, and an HC-CDR3 comprising the amino acid sequence of SEQ ID NO: 166, or a variant thereof comprising up to about 5 (such as about n, where n is selected from 1, 2, 3, 4, and 5) amino acid substitutions; and ii) a $V_L$ comprising an LC-CDR1 comprising the amino acid sequence of SEQ ID NO: 167, or a variant thereof comprising up to about 5 (such as about n, where n is selected from 1, 2, 3, 4, and 5) amino acid substitutions, an LC-CDR2 comprising the amino acid sequence of SEQ ID NO: 168, or a variant thereof comprising up to about 3 (such as about any of 1, 2, or 3) amino acid substitutions, and an LC-CDR3 comprising the amino acid sequence of SEQ ID NO: 169, or a variant thereof comprising up to about 5 (such as about n, where n is selected from 1, 2, 3, 4, and 5) amino acid substitutions. In some embodiments, the anti-NA antibody or antigen binding fragment thereof comprises i) a $V_H$ comprising an HC-CDR1 comprising the amino acid sequence of SEQ ID NO: 164, an HC-CDR2 comprising the amino acid sequence of SEQ ID NO: 165, and an HC-CDR3 comprising the amino acid sequence of SEQ ID NO: 166; and ii) a $V_L$ comprising an LC-CDR1 comprising the amino acid sequence of SEQ ID NO: 167, an LC-CDR2 comprising the amino acid sequence of SEQ ID NO: 168, and an LC-CDR3 comprising the amino acid sequence of SEQ ID NO: 169.

In some embodiments, the anti-NA antibody or antigen binding fragment thereof comprises a $V_H$ comprising the amino acid sequences of SEQ ID NOs: 164, 165, and 166; and a $V_L$ comprising the amino acid sequences of SEQ ID NOs: 167, 168, and 169. In some embodiments, the anti-NA antibody or antigen binding fragment thereof comprises a $V_H$ comprising an HC-CDR1, an HC-CDR2, and an HC-CDR3 of the amino acid sequence of SEQ ID NO: 208 and a $V_L$ comprising an LC-CDR1, an LC-CDR2, and an LC-CDR3 of the amino acid sequence of SEQ ID NO: 209. In some embodiments, the anti-NA antibody or antigen binding fragment thereof comprises a $V_H$ comprising the amino acid sequence of SEQ ID NO: 208, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 208, and a $V_L$ comprising the amino acid sequence of SEQ ID NO: 209, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 209.

In some embodiments, the anti-NA antibody or antigen binding fragment thereof comprises: i) a $V_H$ comprising an HC-CDR1 comprising the amino acid sequence of SEQ ID NO: 170, or a variant thereof comprising up to about 5 (such as about n, where n is selected from 1, 2, 3, 4, and 5) amino acid substitutions, an HC-CDR2 comprising the amino acid sequence of SEQ ID NO: 171, or a variant thereof comprising up to about 5 (such as about n, where n is selected from 1, 2, 3, 4, and 5) amino acid substitutions, and an HC-CDR3 comprising the amino acid sequence of SEQ ID NO: 172, or a variant thereof comprising up to about 5 (such as about n, where n is selected from 1, 2, 3, 4, and 5) amino acid substitutions; and ii) a $V_L$ comprising an LC-CDR1 comprising the amino acid sequence of SEQ ID NO: 173, or a variant thereof comprising up to about 5 (such as about n, where n is selected from 1, 2, 3, 4, and 5) amino acid substitutions, an LC-CDR2 comprising the amino acid sequence of SEQ ID NO: 174, or a variant thereof comprising up to about 3 (such as about any of 1, 2, or 3) amino acid substitutions, and an LC-CDR3 comprising the amino acid sequence of SEQ ID NO: 175, or a variant thereof comprising up to about 5 (such as about n, where n is selected from 1, 2, 3, 4, and 5) amino acid substitutions. In some embodiments, the anti-NA antibody or antigen binding fragment thereof comprises i) a $V_H$ comprising an HC-CDR1 comprising the amino acid sequence of SEQ ID NO: 170, an HC-CDR2 comprising the amino acid sequence of SEQ ID NO: 171, and an HC-CDR3 comprising the amino acid sequence of SEQ ID NO: 172; and ii) a $V_L$ comprising an LC-CDR1 comprising the amino acid sequence of SEQ ID NO: 173, an LC-CDR2 comprising the amino acid sequence of SEQ ID NO: 174, and an LC-CDR3 comprising the amino acid sequence of SEQ ID NO: 175.

In some embodiments, the anti-NA antibody or antigen binding fragment thereof comprises a $V_H$ comprising the amino acid sequences of SEQ ID NOs: 170, 171, and 172; and a $V_L$ comprising the amino acid sequences of SEQ ID NOs: 173, 174, and 175. In some embodiments, the anti-NA antibody or antigen binding fragment thereof comprises a $V_H$ comprising an HC-CDR1, an HC-CDR2, and an HC-CDR3 of the amino acid sequence of SEQ ID NO: 210 and a $V_L$ comprising an LC-CDR1, an LC-CDR2, and an LC-CDR3 of the amino acid sequence of SEQ ID NO: 211. In some embodiments, the anti-NA antibody or antigen binding fragment thereof comprises a $V_H$ comprising the amino acid sequence of SEQ ID NO: 210, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 210, and a $V_L$ comprising the amino acid sequence of SEQ ID NO: 211, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 211.

In some embodiments, the anti-NA antibody or antigen binding fragment thereof comprises: i) a $V_H$ comprising an HC-CDR1 comprising the amino acid sequence of SEQ ID NO: 176, or a variant thereof comprising up to about 5 (such as about n, where n is selected from 1, 2, 3, 4, and 5) amino acid substitutions, an HC-CDR2 comprising the amino acid sequence of SEQ ID NO: 177, or a variant thereof comprising up to about 5 (such as about n, where n is selected from 1, 2, 3, 4, and 5) amino acid substitutions, and an HC-CDR3 comprising the amino acid sequence of SEQ ID NO: 178, or a variant thereof comprising up to about 5 (such as about n, where n is selected from 1, 2, 3, 4, and 5) amino acid substitutions; and ii) a $V_L$ comprising an LC-CDR1 comprising the amino acid sequence of SEQ ID NO: 179, or a variant thereof comprising up to about 5 (such as about n, where n is selected from 1, 2, 3, 4, and 5) amino acid substitutions, an LC-CDR2 comprising the amino acid sequence of SEQ ID NO: 180, or a variant thereof comprising up to about 3 (such as about any of 1, 2, or 3) amino acid substitutions, and an LC-CDR3 comprising the amino acid sequence of SEQ ID NO: 181, or a variant thereof comprising up to about 5 (such as about n, where n is selected from 1, 2, 3, 4, and 5) amino acid substitutions. In some embodiments, the anti-NA antibody or antigen binding fragment thereof comprises i) a $V_H$ comprising an HC-CDR1 comprising the amino acid sequence of SEQ ID NO: 176, an HC-CDR2 comprising the amino acid sequence of SEQ ID NO: 177, and an HC-CDR3 comprising the amino acid sequence of SEQ ID NO: 178; and ii) a $V_L$ comprising an LC-CDR1 comprising the amino acid sequence of SEQ ID NO: 179, an LC-CDR2 comprising the amino acid sequence of SEQ ID NO: 180, and an LC-CDR3 comprising the amino acid sequence of SEQ ID NO: 181.

In some embodiments, the anti-NA antibody or antigen binding fragment thereof comprises a $V_H$ comprising the amino acid sequences of SEQ ID NOs: 176, 177, and 178; and a $V_L$ comprising the amino acid sequences of SEQ ID NOs: 179, 180, and 181. In some embodiments, the anti-NA antibody or antigen binding fragment thereof comprises a $V_H$ comprising an HC-CDR1, an HC-CDR2, and an HC-CDR3 of the amino acid sequence of SEQ ID NO: 212 and a $V_L$ comprising an LC-CDR1, an LC-CDR2, and an LC-CDR3 of the amino acid sequence of SEQ ID NO: 213. In some embodiments, the anti-NA antibody or antigen binding fragment thereof comprises a $V_H$ comprising the amino acid sequence of SEQ ID NO: 212, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 212, and a $V_L$ comprising the amino acid sequence of SEQ ID NO: 213, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 213.

In some embodiments, the anti-NA antibody or antigen binding fragment thereof comprises: i) a $V_H$ comprising an HC-CDR1 comprising the amino acid sequence of SEQ ID NO: 182, or a variant thereof comprising up to about 5 (such as about n, where n is selected from 1, 2, 3, 4, and 5) amino acid substitutions, an HC-CDR2 comprising the amino acid sequence of SEQ ID NO: 183, or a variant thereof comprising up to about 5 (such as about n, where n is selected from 1, 2, 3, 4, and 5) amino acid substitutions, and an HC-CDR3 comprising the amino acid sequence of SEQ ID NO: 184, or a variant thereof comprising up to about 5 (such as about n, where n is selected from 1, 2, 3, 4, and 5) amino acid substitutions; and ii) a $V_L$ comprising an LC-CDR1 comprising the amino acid sequence of SEQ ID NO: 185, or a variant thereof comprising up to about 5 (such as about n, where n is selected from 1, 2, 3, 4, and 5) amino acid substitutions, an LC-CDR2 comprising the amino acid sequence of SEQ ID NO: 186, or a variant thereof comprising up to about 3 (such as about any of 1, 2, or 3) amino acid substitutions, and an LC-CDR3 comprising the amino acid sequence of SEQ ID NO: 187, or a variant thereof comprising up to about 5 (such as about n, where n is selected from 1, 2, 3, 4, and 5) amino acid substitutions. In some embodiments, the anti-NA antibody or antigen binding fragment thereof comprises i) a $V_H$ comprising an HC-CDR1 comprising the amino acid sequence of SEQ ID NO: 182, an HC-CDR2 comprising the amino acid sequence of SEQ ID NO: 183, and an HC-CDR3 comprising the amino acid sequence of SEQ ID NO: 184; and ii) a $V_L$ comprising an LC-CDR1 comprising the amino acid sequence of SEQ ID NO: 185, an LC-CDR2 comprising the amino acid sequence of SEQ ID NO: 186, and an LC-CDR3 comprising the amino acid sequence of SEQ ID NO: 187.

In some embodiments, the anti-NA antibody or antigen binding fragment thereof comprises a $V_H$ comprising the amino acid sequences of SEQ ID NOs: 182, 183, and 184; and a $V_L$ comprising the amino acid sequences of SEQ ID NOs: 185, 186, and 187. In some embodiments, the anti-NA antibody or antigen binding fragment thereof comprises a $V_H$ comprising an HC-CDR1, an HC-CDR2, and an HC-CDR3 of the amino acid sequence of SEQ ID NO: 214 and a $V_L$ comprising an LC-CDR1, an LC-CDR2, and an LC-CDR3 of the amino acid sequence of SEQ ID NO: 215. In some embodiments, the anti-NA antibody or antigen binding fragment thereof comprises a $V_H$ comprising the amino acid sequence of SEQ ID NO: 214, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 214, and a $V_L$ comprising the amino acid sequence of SEQ ID NO: 215, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 215.

In some embodiments, the anti-NA antibody or antigen binding fragment thereof specifically binds to the NA protein of an influenza virus or a variant thereof. In some embodiments, the anti-NA antibody prevents the cleavage of terminal sialic acid residues from N-linked glycans present on host cell surfaces and progeny virions of the influenza virus or variant thereof. In some embodiments, the anti-NA antibody or antigen binding fragment thereof specifically binds to the enzymatic active site of the NA protein. In some embodiments, binding of the enzymatic active site of the NA protein by the anti-NA antibody prevents the cleavage of terminal sialic acid residues from N-linked glycans present on host cell surfaces and progeny In some embodiments, the anti-NA antibody or antigen binding fragment thereof specifically binds to the NA protein of an influenza virus or variant thereof with a $K_D$ of no more than about any one of 100 nM, 50 nM, 20 nM, 10 nM, 5 nM, 4 nM, 3 nM, 2 nM, 1 nM, 0.75 nM, 0.5 nM, 0.2 nM, 0.1 nM, 0.05 nM, 0.01 nM, or less, including any values and ranges in between these values. In some embodiments, the anti-NA antibody or antigen binding fragment thereof specifically binds to the NA protein of an influenza virus or variant thereof with a $K_D$ of about any one of 0.01 nM to 0.1 nM, 0.1 nM to 1 nM, 1 nM to 5 nM, 5 nM to 10 nM, 10 nM-100 nM, 0.01 nM to 1 nM, 0.5 nM to 10 nM, 0.1 nM to 1 nM, 0.1 nM to 10 nM, or 0.01 nM to 100 nM.

In some embodiments, the antibody moiety can be an anti-NA antibody that competes for binding to an NA protein of an influenza virus or variant thereof with a second anti-NA antibody, according to any of the anti-NA antibodies described herein. In some embodiments, the anti-NA antibody can bind to the same, or substantially the same, epitope as the second anti-NA antibody. In some embodiments, binding of the anti-NA antibody to an NA protein of an influenza virus or variant thereof can inhibit the binding of a second anti-NA antibody to the same NA protein of an influenza virus or variant by at least about 70% (such as by at least n %, where n % is selected from 75%, 80%, 85%, 90%, 95%, 98%, and 99%), or vice versa. In some embodiments, the anti-NA antibody and the second anti-NA antibody can cross-compete for binding to the NA protein of an influenza virus or variant, i.e., each of the anti-NA antibody moieties can compete with the other for binding to the NA protein of an influenza virus or variant.

Exemplary Animal Anti-HA and Anti-NA Antibodies

In some embodiments, there is provided a chimeric protein comprising an animal anti-HA or an animal anti-NA antibody or antigen binding fragment thereof (e.g., an animal anti-HA or an animal anti-NA antibody moiety) that specifically binds to an animal HA or NA antigen, respectively.

Exemplary animal HA and NA antigens are provided in Table 5 below.

TABLE 5

Exemplary animal HA and NA antigens

| Antigen;<br>Animal;<br>Reference;<br>Strain | Sequence | SEQ ID NO |
|---|---|---|
| HA;<br>Bird;<br>QDX47284.1;<br>H3N8 | MKTIIVLSYLFCLALSQDYSENNNSTATLCLGHHAVPNGTVVKTITDDQI<br>EVTNATELVQSSSTGKICNNPHRILDGRDCTLIDALLGDPHCDVFQDETW<br>DLYVERSSAFSNCYPYDVPDYASLRSLVASSGTLEFITEGFTWTGVTQNG<br>GSSACKRGPASGFFSRLNWLTKSGSAYPVLNVTMPNNDNFDKLYVWGV<br>HHPSTNQEQTNLYVQASGRVTVSTRKSQQTIIPNIGSRPWVRGQSGRISIY<br>WTIVKPGDVLVINSNGNLIAPRGYFKMRTGKSSIMRSDAPIDTCISECITPN<br>GSIPNDKPFQNVNKITYGACPKYVKQSTLKLATGMRNVPEKQTRGLFGA<br>IAGFIENGWEGMIDGWYGFRHQNSEGTGQAADLKSTQAAIDQINGKLNR<br>VIEKTNEKFHQIEKEFSEVEGRIQDLEKYVEDTKIDLWSYNAELLVALEN<br>QHTIDLTDSEMNKLFEKTRRQLRENAEDMGNGCFKIYHKCDNACIESIRN<br>GTYDHDIYRDEALNNRFQIKGVELKSGYKDWILWISFAISCFLLCVVLLG<br>FIMWACQRGNIRCNICI | 349 |
| NA;<br>Bird;<br>QDX47725.1;<br>H3N8 | MNPNQKIITIGSICMAIGIMSLVLQIGNIISIWVSHSIQTESKSPETCNQSVIT<br>YENNTWVNQTYLNISNTNLIVEQIVAPVTLAGNSSLCPISGWAIYSKDNGI<br>RIGSKGDVFVIREPFISCSHLECRTFFLTQGALLNDKHSNGTVKDRSPYRT<br>LMSCPVGEAPSPYNSRFESVAWSASACHDGISWLTIGISGPDNGAVAVLK<br>YNGIITDTVKSWRNNILRTQESECACINGSCFTIMTDGPSNGQASYKIFKIE<br>KGKVVKSVELNAPNYHYEECSCYPDASEVMCVCRDNWHGSNRPWVSF<br>NQDLEYQIGYICSGVFGDNPRPNDGTGSCGPVSSNGAYGVKGFSFRYGN<br>GVWIGRTKSTSSRSGFEMIWDPNGWTETDNSFSVKQDIVAITDWSGYSG<br>SFVQHPELTGLDCVRPCFWVELIRGRPKENTIWTSGSSISFCGVNSDTVG<br>WSWPDGAELPFTIDK | 350 |
| HA;<br>Cat;<br>AFI61906.1;<br>H3N2 | MRTVIALSYIFCLAFGQNLKGNENNAATLCLGHHAVPNGTMVKTITSDQI<br>EVTNATEQVQNSSTGKICNNPHKILDGRDCTLIDALLGDPHCDVFQNET<br>WDLFVERSNAFSNCYPYDVQDYASLRSIVASSGTLEFITEGFTWAGVTQN<br>GGSGACKRGPANGFFSRLNWLTKSGNTYQVLNVTMPNNNNFDKLYIWG<br>VHHPSTNQEQTSLYIQASGRVTVSTRRSKQTIILNIESRPLVRCQSGRISVY<br>WTIVKPGVILVINSNGNLIAPRGYFKMHIGKSTIMRSDAPVDTCISECITPN<br>GSIPNEKPFQNVNKITYGACPKYVKQNTLKLSTGMRNVPERQTRGLFGAI<br>AGFIENGWEGMVDGWYGFRHQNSEGTGQAADLKSTQAAIDQINGKLNR<br>VIEKTNEKFHQIEKEFSEVEGRIQDLERYVEDTKVDLWSYNAELLVALEN<br>QNTIDLTDSEMNKLFEKTRRQLRENAEDMGNGCFKIYHKCDNACIESIRN<br>GTYDHNIYRDEAVNNRFQIKGVELKSGYKDLILWISFAISCFLLCVVLLGF<br>IMWACQRGNIRCNICI | 351 |
| NA;<br>Cat;<br>ANW47171.1;<br>H3N2 | MNPNQKIIAIGSVSLIIATVCFLLQIAILATNVTLYFKQNECNIPSNSQVVPC<br>KPIIIERNITEVVYLNNTTIEKEIYSVVLEYRNWSKPQCQITGFAPFSKDNSI<br>RLSAGGDIWVTREPYVSCDPSKCYQFALGQGTTLNNKHSNGTIHDRISHR<br>TLLMNELGVPFHLGTKQVCIAWSSSSCHDGKAWLHVCVTGDDKNATAS<br>FVYNGMLVDSIGSWSRNILRTQESECVCINGTCTVVMTDGSASGRADTRI<br>LFIREGKIVHISPLSGSAQHIEECSCYPRYPNVRCVCRDNWKGSNRPVIDI<br>NMADYSIDSSYVCSGLVGDTPRNDDSFSSSNCRDPNNERGNPGVKGWAF<br>DNENDVWMGRTISKDLRSGYETFKVIGCRTTANSKSQVNRQVIVDNNN<br>WSGYSGIFSVEGKSCVNRCFYVELIRGGPQETRVWWTSNSIVVFCGTSGT<br>YGAGSWPDGANINFMPI | 352 |
| HA;<br>Dog;<br>QBQ33923.2;<br>H3N2 | MKTVIALSYIFCLAFGQNLLGNENNAATLCLGHHAVPNGTMVKTITDDQ<br>IEVTNATELVQNSSTGKICNNPHKILDGRDCTLIDALLGDPHCDVFQNET<br>WDLFVERSNAFSNCYPYDVPDYASLRSIVASSGTLEFITEGFTWAGVTQN<br>GGSGACKRGPANSFFSRLNWLTKSGNTYPVLNVTMPNNNNFDKLYIWG<br>VHHPSTDQEQTSLYIQASGRVTVSTRKSQQTIIPNIGSRPLVRGQSGRISVY<br>WTIVEPGDILVINSNGNLIAPRGYFKMHIGKSSIMRSDAPIDTCISECITPNG<br>SIPTEKPFQNVNKITYGACPKYVKQNTLKLATGMRNVPERQTRGLFGAX<br>AGFIENGWEGMVDGWYGFRHQNSEGTGQAADLKSTQAAIDQINGKLNR<br>VIEKTNEKFHQIEKEFSEVEGRIQDLERYVEDTKIDLWSYNAELLVALEN<br>QNTIDLTDSEMNKLFEKTRRQLRENAEDMGNGCFKIYHKCDNACIESIRN<br>GTYDHNIYRDEAVNNRFQIKGVELKSGYKDWILWISFAISCFLLCVVLLG<br>FIMWACQRGNIRCNICI | 353 |
| NA;<br>Dog;<br>QBQ33992.2;<br>H3N2 | MNPNQKIIAIGSVSLAIATVCFLLQIATLATTVTLYFKQNECNIPSNSQIVP<br>CKPIIIERNITEVVHLNNTTIEKEIYSVVLEYRNWSKPQCQITGFAPFSKDN<br>SIRLSAGGDIWVTREPYVSCDPSKCYQFALGQGTTLNNKHSNSTIHDRTS<br>YRTLLMNELGVPXHLGTKQVCIAWSSSSCHDGKAWLHVCVTGDDRNAT<br>ASFVYNGMLVDSIGSWSRNILRTQESECVCINGTCTVVMTDGSASGKAD<br>TRILFIKEGKIIHISPLSGSAQHIEECSCYPQYPNVRCVCRDNWKGSNRPVI<br>DINMADYNINSSYVCSGLVGDTPRNDDSSSSSNCKDPNNERGNPGVKGW | 354 |

TABLE 5-continued

Exemplary animal HA and NA antigens

| Antigen; Animal; Reference; Strain | Sequence | SEQ ID NO |
|---|---|---|
| | AFDNDNDVWMGRTISKDLRSGYETFKVIGGWTTANSKSQVNRQVIVDN | |
| | NNWSGYSGIFSVEGKSCVNRCFYVELIRGGPQETRVWWTSNSIVVFCGTS | |
| | GTYGTGSWPDGANINFMPI | |
| NA; | MNPNQKIITIGTASLGILIINVILHVVSIIVTVLVLNNNETGLNCKGTIIREY | 355 |
| Horse; | NETVRVEKITQWHNTSAIKYIERPPNEYYMNNTEPLCEAQGFAPFSKDNG | |
| AIZ95447.1; | IRIGSRGHVFVIREPFVSCSPSECRTFFLTQGSLLNDKHSNGTVKDRSPYRT | |
| H3N8 | LMSVKIGQSPNVYQARFESVAWSATACHDGKKWMTIGVTGPDNQAIAV | |
| | VNYGGIPVDIINSWEGDILRTQESSCTCIKGNCYWVMTDGPANRQAKYRI | |
| | FKAKDGRVIGQTDISFNGGHIEECSCYPNEGKVECICRDNWTGTNRPILVI | |
| | SSDLSYTVGYLCAGIPTDTPRGEDSQFTGSCTSPLGNKGYGVKGFGFRQG | |
| | TDVWAGRTISRTSRSRFEIIKIRNGWTQNSKDQIRRQVIIDDPNWSGYSGS | |
| | FTLPVELTKKGCLVPCFWVEMIRGKPEETTIWTSSSSIVMCGVDHKIASW | |
| | SWHDGAILPFDIDKM | |
| HA; | MKTTTIFIFILLTHWAYSQNPISNNNTATLCLGHHAVANGTLVKTISDDQI | 356 |
| Horse; | EVTNATELVQSISMGKICNNSYRILDGRNCTLIDAMLGDPHCDVFQYEN | |
| AXQ87682.1; | WDLFIERSSAFSNCYPYDIPDYASLRSIVASSGTLEFTAEGFTWTGVTQNG | |
| H3N8 | RSGACKRGSTDSFFSRLNWLTKSGNSYPTLNVTMPNNKNFDKLYIWGIH | |
| | HPSSNQEQTKLYIQGSGRVTVSTKRSQQTIIPNIGSRPWVRGQSGRISIYW | |
| | TIVKPGDILMINSNGNLVAPRGYFKLKTGKSSVMRSDVPIDICVSECITPN | |
| | GSISNDKPFQNVNKVTYGKCPKYIRQNTLKLATGMRNVPEKQIRGIFGAI | |
| | AGFIENGWEGMVDGWYGFRYQNSEGTGQAADLKSTQTAIDQINEKLNR | |
| | VIERTNEKFHQIEKEFSEVEGRIQDLEKYVEDTKIDLWSYNAELLVALEN | |
| | QHTIDLTDAEMNKLFEKTRRQLRENAEDMGGGCFKIYHKCDNACIGSIR | |
| | NGTYDHYIYRDEALNNRFQIKGVELKSGYKDWILWISFAISCFLICVVLL | |
| | GFIMWACQKGNIRCNICI | |
| HA; | MKAILLVLLYTFVPTNADTLCIGYHANNSTDTVDTILERNVTVTHSVNLL | 357 |
| Pig; | EDKHNGRLCKLGGIAPLHLGKCNIAGWLLGNPECESLFTVSSWSYIVETS | |
| AEA29582.1; | NSYNGTCYPGDFINYEELREQLSSVSSFERFEIFPKASSWPNHETNKGVTA | |
| H1N1 | ACSHAGTKSFYRNLIWLVKKGNSYPNISKSYFNNKGNEVLVLWGIHHPS | |
| | TNNDQQTLYQNADTYVFVGTSKYNKKFKPEIAIRPKVRDQEGRMNYYW | |
| | TLVEPGDKITFEATGNLVVPRYAFAMERNAGSGIIISDTPVHDCNTTCQTP | |
| | KGAINTSLPFQNIHPTTIGKCPKYVKSTKLRLATGLRNVPSIQSRGLFGAIA | |
| | GFIEGGWTGMVDGWYGYHHQNEQGSGYAADQKSTQNAIDGITNKVNS | |
| | VIEKMNTQFTAVGKEFNHLEKRIENLNKKVDDGFLDVWTYNAELLILLE | |
| | NERTLDFHDSNVKNLYEKARRQLKNNAKEIGNGCFEFYHKCDNACMES | |
| | VKNGTYDYPKYSEESRLNREEISGVKLDSTRIYQILAIYSTVASSSVLLVS | |
| | LGAISFWMCSNGSLQCRICI | |
| NA; | MNTNQRIITIGTVCLTVGIISLLLQIGNIVSLWISHSIQTGGKNHTEMCNKN | 358 |
| Pig; | VITYVNNTWVNRTYVNISNTKIVNVQDVVSVILTGNSSLCPISGWAIYSK | |
| AHB21162.1; | DNSIRIGSKGDIFVIREPFISCSHLECRTFFLTQGALLNDKHSNGTVKDRSP | |
| H1N1 | YRTLMSCPIGEAPSPYNSRFESVAWSASACHDGMGWLTIGISGPDNGAV | |
| | AVLKYNGIITDTIKSWRNKILRTQESECVCMNGSCFTVLTDGPSNGQASY | |
| | KIFKMEKGKIIKSIELDAPNYHYEECSCYPDAGKVMCVCRDNWHASNRP | |
| | WVSFDQNLDYQIGYICSGVFGDNPRSNDGKGNCGPVHSNGANGVKGFS | |
| | YRYGNGVWIGRTKSINSRSGFEMIWDPNGWTGTDSSFSMKQDIIALTDW | |
| | SGYSGSFVQHPELTGMNCIRPCFWVELIRGQPKENTIWASGSSISFCGVN | |
| | GETASWSWPDGADLPFTIDK | |

Exemplary animal HA and NA antigens, such as SEQ ID NOs: 349-358 of Table 5, may be bound (e.g., targeted) by a chimeric protein described herein (e.g., a chimeric protein comprising an antibody moiety that specifically binds to an animal HA protein or an animal NA protein of an influenza virus or a variant thereof). It should be understood that the chimeric proteins of the present invention may bind additional animal HA and NA influenza antigens and variants thereof, such as known animal HA and NA influenza antigen or variants thereof, or future animal HA and NA influenza antigen or variants thereof, all of which are encompassed by the scope of the present invention.

Exemplary animal anti-HA antibodies are provided in Table 6.

TABLE 6

CDR and VH/VL sequences of exemplary animal anti-HA antibodies

| Antibody Name; Reference; Target Species; Ab Source | Target Strain | Sequence | Type | SEQ ID NO |
|---|---|---|---|---|
| G126; QJD38416 QJD38411; Swine; Rabbit | H1 | QSLEESGGDLVKPGASLTLTCTASGFSFSSSYWICWVRQAPGKGLEWIACIYAGSSGSAYFASWAKGRFTISETSSTTVTLQMTSLTAADTATYFCARAPSYTYGYAGYAYAYSYYFNLWGPGTLVTVSS | $V_H$ | 383 |
| | | VMTQTPASVEVTMGGTVTINCQASQSINNELCWYQQKPGQRPKLLIYDASDLASGVPSRFKGSGSGTEFTLTISDLECADAATYYCQQDYSTNNVDNLFGGGTEVVVK | $V_L$ | 384 |
| | | SGFSFSSSY | HC-CDR1 | 359 |
| | | LEWIACIYAGSSGSAYF | HC-CDR2 | 360 |
| | | APSYTYGYAGYAYAYSYYEN | HC-CDR3 | 361 |
| | | QSINN | LC-CDR1 | 362 |
| | | PKLLYDASDLA | LC-CDR2 | 363 |
| | | DYSTNN | LC-CDR3 | 364 |
| FY-UCA-VH; ANT83586 ANT83603; Pan_IAV; Human | H5 | QVQLQQSGPGLVKPSQTLSLTCAISGDSVSSNNAVWNWIRQSPSRGLEWLGRTYYRSKWYNDYAESVKSRITINPDTSKNQFSLQLNSVTPEDTAVYYCARSGHITVFGVNVDAFDMWGQGTMVTVSS | $V_H$ | 385 |
| | | DIQMTQSPSSLSASVGDRVTITCRTSQSLSSYTHWYQQKPGKAPKLLIYAASSRGSGVPSRFSGSGSGTDFTLTISSLQPEDFATYYCQQSRTFGQGTKVEIK | $V_L$ | 386 |
| | | SNNAVWN | HC-CDR1 | 365 |
| | | RTYYRSKWYNDYAESVKS | HC-CDR2 | 366 |
| | | SGHITVFGVNVDAFDM | HC-CDR3 | 367 |
| | | TRSQSLSSYLH | LC-CDR1 | 368 |
| | | AASSLQS | LC-CDR2 | 369 |
| | | QQSRT | LC-CDR3 | 370 |
| AT10_004; WO10130636; Cat; Human | H1 | EVQLVESGGGLIQPGGSLRLSCAASGFTVSSNYVSWVRQAPGKGLEWLSLIYTGGTTYYADSVKGRFTISRDNSKNTVFLQMNSLRAEDAAMYYCARVSALRFLQWPNYAMDV | $V_H$ | 387 |
| | H3 | QSALTQPASVSGSPGRSITISCSGTRSDVGGHNYVSWYQQHPGKAPKLMIYEVSHRPSGVSNRFSGSKSGSTASLTISGLQSEDEADYYCSSYTGEGPLGV | $V_L$ | 388 |
| | H5 | LIYTGGTTYYADSVKG | HC-CDR1 | 371 |
| | | VSALRFLQWPNYAMDV | HC-CDR2 | 372 |
| | | SGTRSDVGGHNYVS | HC-CDR3 | 373 |
| | | EVSHRPS | LC-CDR1 | 374 |
| | | SSYTGEGPLGV | LC-CDR2 | 375 |
| | | SYWMS | LC-CDR3 | 376 |
| CR8001; WO13081463; Bird/Pig; Human | H1 | QVQLVQSGAEVRKPGASVKVSCKASGYTFTRHGISWVRQAPGQGLEWMGWISAYTGDTDYAQKFQGRVTMTTDTSTNTAYMELRSLRSDDAAVYYCARLRLQGEVVVPPSQSNWFDPWGQGTLVTVSS | $V_H$ | 389 |
| | H3 | EIVLTQSPATLSLYPGERATLSCRASQSVSRYLAWYQQKPGQAPRLLIYDASNRATGIPARFSGSGSGTDFTLTISSLEPEDFAVYYCCDRQQRSNWLKITFGQGTRLEIKGTV | $V_L$ | 390 |
| | H5 | RHGIS | HC-CDR1 | 377 |
| | H7 | WISAYTGDTDYAQKFQG | HC-CDR2 | 378 |
| | H9 | GWGAVTSPFDF | HC-CDR3 | 379 |
| | | GWGAVTSPFDF | LC-CDR1 | 380 |
| | | DASNRAT | LC-CDR2 | 381 |
| | | QQRSNWLK | LC-CDR3 | 382 |

In some embodiments, the antibody moiety of a chimeric protein comprises animal anti-HA or anti-NA antibody or antigen binding fragment thereof that comprises an HC-CDR1, HC-CDR2, HC-CDR3, LC-CDR1, LC-CDR2, and LC-CDR3 of any one of the antibodies of Table 6. In some embodiments, the antibody moiety comprises an animal anti-HA antibody or antigen binding fragment thereof that comprises a $V_H$ and $V_L$ of any one of the antibodies of Table 6.

In some embodiments, the antibody moiety comprises an animal anti-HA antibody or antigen binding fragment thereof comprising: i) a $V_H$ comprising an HC-CDR1 comprising the amino acid sequence of SEQ ID NO: 359, or a variant thereof comprising up to about 5 (such as about n, where n is selected from 1, 2, 3, 4, and 5) amino acid substitutions, an HC-CDR2 comprising the amino acid sequence of SEQ ID NO: 360, or a variant thereof comprising up to about 5 (such as about n, where n is selected from 1, 2, 3, 4, and 5) amino acid substitutions, and an HC-CDR3 comprising the amino acid sequence of SEQ ID NO: 361, or a variant thereof comprising up to about 5 (such as about n, where n is selected from 1, 2, 3, 4, and 5) amino acid substitutions; and ii) a $V_L$ comprising an LC-CDR1 comprising the amino acid sequence of SEQ ID NO: 362, or a variant thereof comprising up to about 5 (such as about n, where n is selected from 1, 2, 3, 4, and 5) amino acid substitutions, an LC-CDR2 comprising the amino acid sequence of SEQ ID NO: 363, or a variant thereof comprising up to about 3 (such as about any of 1, 2, or 3) amino acid substitutions, and an LC-CDR3 comprising the amino acid sequence of SEQ ID NO: 364, or a variant thereof comprising up to about 5 (such as about n, where n is selected from 1, 2, 3, 4, and 5) amino acid substitutions. In some embodiments, the animal anti-HA antibody or antigen binding fragment thereof comprises i) a $V_H$ Comprising an HC-CDR1 comprising the amino acid sequence of SEQ ID NO: 359, an HC-CDR2 comprising the amino acid sequence of SEQ ID NO: 360, and an HC-CDR3 comprising the amino acid sequence of SEQ ID NO: 361; and ii) a $V_L$ comprising an LC-CDR1 comprising the amino acid sequence of SEQ ID NO: 362, an LC-CDR2 comprising the amino acid sequence of SEQ ID NO: 363, and an LC-CDR3 comprising the amino acid sequence of SEQ ID NO: 364.

In some embodiments, the animal anti-HA antibody or antigen binding fragment thereof comprises a $V_H$ comprising the amino acid sequences of SEQ ID NOs: 359, 360, and 361; and a $V_L$ comprising the amino acid sequences of SEQ ID NOs: 362, 363, and 364. In some embodiments, the animal anti-HA antibody or antigen binding fragment thereof comprises a $V_H$ comprising an HC-CDR1, an HC-CDR2, and an HC-CDR3 of the amino acid sequence of SEQ ID NO: 383 and a $V_L$ comprising an LC-CDR1, an LC-CDR2, and an LC-CDR3 of the amino acid sequence of SEQ ID NO: 384. In some embodiments, the anti-HA antibody or antigen binding fragment thereof comprises a $V_H$ comprising the amino acid sequence of SEQ ID NO: 383, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 383, and a $V_L$ comprising the amino acid sequence of SEQ ID NO: 384, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 384.

In some embodiments, the antibody moiety comprises an animal anti-HA antibody or antigen binding fragment thereof comprising: i) a $V_H$ comprising an HC-CDR1 comprising the amino acid sequence of SEQ ID NO: 365, or a variant thereof comprising up to about 5 (such as about n, where n is selected from 1, 2, 3, 4, and 5) amino acid substitutions, an HC-CDR2 comprising the amino acid sequence of SEQ ID NO: 366, or a variant thereof comprising up to about 5 (such as about n, where n is selected from 1, 2, 3, 4, and 5) amino acid substitutions, and an HC-CDR3 comprising the amino acid sequence of SEQ ID NO: 367, or a variant thereof comprising up to about 5 (such as about n, where n is selected from 1, 2, 3, 4, and 5) amino acid substitutions; and ii) a $V_L$ comprising an LC-CDR1 comprising the amino acid sequence of SEQ ID NO: 368, or a variant thereof comprising up to about 5 (such as about n, where n is selected from 1, 2, 3, 4, and 5) amino acid substitutions, an LC-CDR2 comprising the amino acid sequence of SEQ ID NO: 369, or a variant thereof comprising up to about 3 (such as about any of 1, 2, or 3) amino acid substitutions, and an LC-CDR3 comprising the amino acid sequence of SEQ ID NO: 370, or a variant thereof comprising up to about 5 (such as about n, where n is selected from 1, 2, 3, 4, and 5) amino acid substitutions. In some embodiments, the animal anti-HA antibody or antigen binding fragment thereof comprises i) a $V_H$ Comprising an HC-CDR1 comprising the amino acid sequence of SEQ ID NO: 365, an HC-CDR2 comprising the amino acid sequence of SEQ ID NO: 366, and an HC-CDR3 comprising the amino acid sequence of SEQ ID NO: 367; and ii) a $V_L$ comprising an LC-CDR1 comprising the amino acid sequence of SEQ ID NO: 368, an LC-CDR2 comprising the amino acid sequence of SEQ ID NO: 369, and an LC-CDR3 comprising the amino acid sequence of SEQ ID NO: 370.

In some embodiments, the animal anti-HA antibody or antigen binding fragment thereof comprises a $V_H$ comprising the amino acid sequences of SEQ ID NOs: 365, 366, and 367; and a $V_L$ comprising the amino acid sequences of SEQ ID NOs: 368, 369, and 370. In some embodiments, the animal anti-HA antibody or antigen binding fragment thereof comprises a $V_H$ comprising an HC-CDR1, an HC-CDR2, and an HC-CDR3 of the amino acid sequence of SEQ ID NO: 385 and a $V_L$ comprising an LC-CDR1, an LC-CDR2, and an LC-CDR3 of the amino acid sequence of SEQ ID NO: 386. In some embodiments, the anti-HA antibody or antigen binding fragment thereof comprises a $V_H$ comprising the amino acid sequence of SEQ ID NO: 385, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 385, and a $V_L$ comprising the amino acid sequence of SEQ ID NO: 386, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 386.

In some embodiments, the antibody moiety comprises an animal anti-HA antibody or antigen binding fragment thereof comprising: i) a $V_H$ comprising an HC-CDR1 comprising the amino acid sequence of SEQ ID NO: 371, or a variant thereof comprising up to about 5 (such as about n, where n is selected from 1, 2, 3, 4, and 5) amino acid substitutions, an HC-CDR2 comprising the amino acid sequence of SEQ ID NO: 372, or a variant thereof comprising up to about 5 (such as about n, where n is selected from 1, 2, 3, 4, and 5) amino acid substitutions, and an HC-CDR3 comprising the amino acid sequence of SEQ ID NO: 373, or a variant thereof comprising up to about 5 (such as about n, where n is selected from 1, 2, 3, 4, and 5) amino acid substitutions; and ii) a $V_L$ comprising an LC-CDR1 comprising the amino acid sequence of SEQ ID NO: 374, or a variant thereof comprising up to about 5 (such as about n, where n is selected from 1, 2, 3, 4, and 5) amino acid substitutions, an LC-CDR2 comprising the amino acid sequence of SEQ ID NO: 375, or a variant thereof comprising up to about 3 (such as about any of 1, 2, or 3) amino acid substitutions, and an LC-CDR3 comprising the amino acid sequence of SEQ ID NO: 376, or a variant thereof comprising up to about 5 (such as about n, where n is selected from 1, 2, 3, 4, and 5) amino acid substitutions. In some embodiments, the animal anti-HA antibody or antigen binding fragment thereof comprises i) a $V_H$ Comprising an HC-CDR1 comprising the amino acid sequence of SEQ ID NO: 371, an HC-CDR2 comprising the amino acid sequence of SEQ ID NO: 372, and an HC-CDR3 comprising the amino acid sequence of SEQ ID NO: 373; and ii) a $V_L$ comprising an LC-CDR1 comprising the amino acid sequence of SEQ ID NO: 374, an LC-CDR2 comprising the amino acid sequence of SEQ ID NO: 375, and an LC-CDR3 comprising the amino acid sequence of SEQ ID NO: 376.

In some embodiments, the animal anti-HA antibody or antigen binding fragment thereof comprises a $V_H$ comprising the amino acid sequences of SEQ ID NOs: 371, 372, and 373; and a $V_L$ comprising the amino acid sequences of SEQ ID NOs: 374, 375, and 376. In some embodiments, the animal anti-HA antibody or antigen binding fragment thereof comprises a $V_H$ comprising an HC-CDR1, an HC-CDR2, and an HC-CDR3 of the amino acid sequence of SEQ ID NO: 387 and a $V_L$ comprising an LC-CDR1, an LC-CDR2, and an LC-CDR3 of the amino acid sequence of SEQ ID NO: 388. In some embodiments, the anti-HA antibody or antigen binding fragment thereof comprises a $V_H$ comprising the amino acid sequence of SEQ ID NO: 387, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 387, and a VL comprising the amino acid sequence of SEQ ID NO: 388, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 389.

In some embodiments, the antibody moiety comprises an animal anti-HA antibody or antigen binding fragment thereof comprising: i) a $V_H$ comprising an HC-CDR1 comprising the amino acid sequence of SEQ ID NO: 377, or a variant thereof comprising up to about 5 (such as about n, where n is selected from 1, 2, 3, 4, and 5) amino acid substitutions, an HC-CDR2 comprising the amino acid sequence of SEQ ID NO: 378, or a variant thereof comprising up to about 5 (such as about n, where n is selected from 1, 2, 3, 4, and 5) amino acid substitutions, and an HC-CDR3 comprising the amino acid sequence of SEQ ID NO: 379, or a variant thereof comprising up to about 5 (such as about n, where n is selected from 1, 2, 3, 4, and 5) amino acid substitutions; and ii) a $V_L$ comprising an LC-CDR1 comprising the amino acid sequence of SEQ ID NO: 380, or a variant thereof comprising up to about 5 (such as about n, where n is selected from 1, 2, 3, 4, and 5) amino acid substitutions, an LC-CDR2 comprising the amino acid sequence of SEQ ID NO: 381, or a variant thereof comprising up to about 3 (such as about any of 1, 2, or 3) amino acid substitutions, and an LC-CDR3 comprising the amino acid sequence of SEQ ID NO: 382, or a variant thereof comprising up to about 5 (such as about n, where n is selected from 1, 2, 3, 4, and 5) amino acid substitutions. In some embodiments, the animal anti-HA antibody or antigen binding fragment thereof comprises i) a $V_H$ Comprising an HC-CDR1 comprising the amino acid sequence of SEQ ID NO: 377, an HC-CDR2 comprising the amino acid sequence of SEQ ID NO: 378, and an HC-CDR3 comprising the amino acid sequence of SEQ ID NO: 379; and ii) a $V_L$ comprising an LC-CDR1 comprising the amino acid sequence of SEQ ID NO: 380, an LC-CDR2 comprising the amino acid sequence of SEQ ID NO: 381, and an LC-CDR3 comprising the amino acid sequence of SEQ ID NO: 382.

In some embodiments, the animal anti-HA antibody or antigen binding fragment thereof comprises a $V_H$ comprising the amino acid sequences of SEQ ID NOs: 377, 378, and 379; and a $V_L$ comprising the amino acid sequences of SEQ ID NOs: 380, 381, and 382. In some embodiments, the animal anti-HA antibody or antigen binding fragment thereof comprises a $V_H$ comprising an HC-CDR1, an HC-CDR2, and an HC-CDR3 of the amino acid sequence of SEQ ID NO: 389 and a $V_L$ comprising an LC-CDR1, an LC-CDR2, and an LC-CDR3 of the amino acid sequence of SEQ ID NO: 390. In some embodiments, the anti-HA antibody or antigen binding fragment thereof comprises a $V_H$ comprising the amino acid sequence of SEQ ID NO: 389, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 389, and a $V_L$ comprising the amino acid sequence of SEQ ID NO: 390, or a variant thereof comprising at least about 90% sequence identity (such as at least about n % sequence identity, where n % is selected from 91%, 92%, 93%, 94%, 95%, 96%, 97%, 98%, and 99%) to the amino acid sequence of SEQ ID NO: 390.

In some embodiments, the animal anti-HA antibody or antigen binding fragment thereof specifically binds to the HA protein of an influenza virus or a variant thereof. In some embodiments, the animal anti-HA antibody or antigen binding fragment thereof specifically binds to the HA1 region (e.g., the globular "head" region) of the HA protein. In some embodiments, the binding of the animal anti-HA antibody or antigen binding fragment thereof to the HA1 region of the HA protein prevents binding of an influenza virus or variant thereof to a sialic acid receptor. In some embodiments, the animal anti-HA antibody or antigen binding fragment thereof specifically binds to the HA2 region (e.g., the "stem" region) of the HA protein. In some embodiments, binding of the animal anti-HA antibody or antigen binding fragment thereof to the HA2 region of the HA protein prevents fusion of an influenza virus or variant thereof viral membrane with that of a host cell. In some embodiments, the animal anti-HA antibody or antigen binding fragment thereof is a neutralizing antibody.

In some embodiments, the animal anti-HA antibody or antigen binding fragment thereof specifically binds to the HA protein of an influenza virus or variant thereof with a $K_D$ of no more than about n, where n is selected from 100 nM, 50 nM, 20 nM, 10 nM, 5 nM, 4 nM, 3 nM, 2 nM, 1 nM, 0.75 nM, 0.5 nM, 0.2 nM, 0.1 nM, 0.05 nM, and 0.01 nM, or less, including any values and ranges in between these values. In some embodiments, the animal anti-HA antibody or antigen binding fragment thereof specifically binds to the HA protein of an influenza virus or variant thereof with a $K_D$ of about 0.01 nM to about 0.1 nM, about 0.1 nM to about 1 nM, about 1 nM to about 5 nM, about 5 nM to about 10 nM, about 10 nM to about 100 nM, about 0.01 nM to about 1 nM, about 0.5 nM to about 10 nM, about 0.1 nM to about 1 nM, about 0.1 nM to about 10 nM, or about 0.01 nM to about 100 nM.

In some embodiments, the antibody moiety can comprise an animal anti-HA antibody that competes for binding to an HA protein of an influenza virus or variant thereof with a second anti-HA antibody according to any of the anti-HA antibodies described herein. In some embodiments, the animal anti-HA antibody can bind to the same, or substantially the same, epitope as the second anti-HA antibody. In some embodiments, binding of the animal anti-HA antibody to an HA protein of an influenza virus or variant thereof can inhibit the binding of a second animal anti-HA antibody to the same HA protein of an influenza virus or variant by at least about 70% (such as at least about n %, where n % is selected from 75%, 80%, 85%, 90%, 95%, 98%, and 99%), or vice versa. In some embodiments, the animal anti-HA antibody and the second animal anti-HA antibody can cross-compete for binding to the HA protein of an influenza virus or variant, i.e., each of the animal anti-HA antibody moieties can compete with the other for binding to the HA protein of an influenza virus or variant.

Animal anti-NA antibodies or antigen binding fragments thereof are also contemplated. Exemplary animal anti-NA antibodies targeting the NA protein of zoonotic IAV strain H7N9 have been published in the literature (D3 and 7H2, Xiong, et al., *Emerging Microbes & Infections* 9(1):78-87 (2020). Additionally, a camelid antibody directed to another zoonotic strain, IAV H5N1 (N1-$V_H$H, Cardoso, et al. *Journal of Virology,* 88(15):8278-96 (2014)) has been described.

In some embodiments, the animal anti-NA antibody or antigen binding fragment thereof specifically binds to the NA protein of an influenza virus or a variant thereof. In some embodiments, the animal anti-NA antibody prevents the cleavage of terminal sialic acid residues from N-linked glycans present on host cell surfaces and progeny virions of the influenza virus or variant thereof. In some embodiments, the animal anti-NA antibody or antigen binding fragment thereof specifically binds to the enzymatic active site of the NA protein. In some embodiments, binding of the enzymatic active site of the NA protein by the animal anti-NA antibody prevents the cleavage of terminal sialic acid residues from N-linked glycans present on host cell surfaces and progeny.

In some embodiments, the animal anti-NA antibody or antigen binding fragment thereof specifically binds to the NA protein of an influenza virus or variant thereof with a $K_D$ of no more than about n, where n is selected from 100 nM, 50 nM, 20 nM, 10 nM, 5 nM, 4 nM, 3 nM, 2 nM, 1 nM, 0.75 nM, 0.5 nM, 0.2 nM, 0.1 nM, 0.05 nM, and 0.01 nM, or less, including any values and ranges in between these values. In some embodiments, the animal anti-NA antibody or antigen binding fragment thereof specifically binds to the NA protein of an influenza virus or variant thereof with a $K_D$ of about 0.01 nM to about 0.1 nM, about 0.1 nM to about 1 nM, about 1 nM to about 5 nM, about 5 nM to about 10 nM, about 10 nM to about 100 nM, about 0.01 nM to about 1 nM, about 0.5 nM to about 10 nM, about 0.1 nM to about 1 nM, about 0.1 nM to about 10 nM, or about 0.01 nM to about 100 nM.

In some embodiments, the antibody moiety can comprise an animal anti-NA antibody that competes for binding to an NA protein of an influenza virus or variant thereof with a second anti-NA antibody according to any of the anti-NA antibodies described herein. In some embodiments, the animal anti-NA antibody can bind to the same, or substantially the same, epitope as the second anti-NA antibody. In some embodiments, binding of the animal anti-HA antibody to an NA protein of an influenza virus or variant thereof can inhibit the binding of a second animal anti-NA antibody to the same NA protein of an influenza virus or variant by at least about 70% (such as at least about n %, where n % is selected from 75%, 80%, 85%, 90%, 95%, 98%, and 99%), or vice versa. In some embodiments, the animal anti-NA antibody and the second animal anti-NA antibody can cross-compete for binding to the NA protein of an influenza virus or variant, i.e., each of the animal anti-NA antibody moieties can compete with the other for binding to the HA protein of an influenza virus or variant.

B. Fc Region

The antibodies, e.g., the antibody moiety of the chimeric proteins described herein, in some embodiments comprise an Fc region. The term "Fc region," "Fc domain" or "FC" refers to a C-terminal non-antigen binding region of an immunoglobulin heavy chain that contains at least a portion of the constant region. The term includes native Fc regions and variant Fc regions. In some embodiments, a human IgG heavy chain Fc region extends from Cys226 to the carboxyl-terminus of the heavy chain. However, the C-terminal lysine (Lys447) of the Fc region may or may not be present, without affecting the structure or stability of the Fc region. Unless otherwise specified herein, numbering of amino acid residues in the IgG or Fc region is according to the EU numbering system for antibodies, also called the EU index, as described in Kabat et al., Sequences of Proteins of Immunological Interest, 5th Ed. Public Health Service, National Institutes of Health, Bethesda, MD (1991).

In some embodiments, the Fc fragment comprises an immunoglobulin IgG heavy chain constant region comprising a hinge region (starting at Cys226), an IgG CH2 domain and CH3 domain. The term "hinge region" or "hinge sequence" as used herein refers to the amino acid sequence located between the linker and the CH2 domain. In some embodiments, the fusion protein comprises an Fc fragment comprising a hinge region. In some embodiments, the fusion protein comprises an Fc fragment that does not comprise the hinge region.

In some embodiments, the anti-HA or anti-NA antibody comprises an Fc fragment selected from the group consisting of Fc fragments from IgG, IgA, IgD, IgE, IgM, and combinations and hybrids thereof. IgG's, IgA's and IgD's Fc fragments comprise $CH_2$ and $CH_3$, while IgE's and IgM's Fc fragments comprise $CH_2$, $CH_3$, and $CH_4$. In some embodiments, the Fc fragment is derived from a human IgG. In some embodiments, the Fc fragment comprises the Fc region of human $IgG_1$, $IgG_2$, $IgG_3$, IgG4, or a combination or hybrid IgG. In some embodiments, the Fc fragment is an $IgG_1$ Fc fragment. In some embodiments, the Fc fragment comprises the $CH_2$ and $CH_3$ domains of $IgG_1$. In some embodiments, the Fc fragment is an $IgG_4$ Fc fragment. In some embodiments, the Fc fragment comprises the $CH_2$ and $CH_3$ domains of $IgG_4$. $IgG_4$ Fc is known to exhibit less effector activity than $IgG_1$ Fc, and thus may be desirable for some applications. In some embodiments, the Fc fragment is derived from of a mouse immunoglobulin.

In some embodiments, the IgG $CH_2$ domain starts at Ala231. In some embodiments, the $CH_3$ domain starts at Gly341. It is understood that the C-terminus Lys residue of human IgG can be optionally absent. It is also understood that conservative amino acid substitutions of the Fc region without affecting the desired structure and/or stability of Fc is contemplated within the scope of the invention.

In some embodiments of the chimeric proteins disclosed herein, especially the embodiments wherein the chimeric protein comprises an Fc region or a fragment thereof such as $CH_2$, the chimeric protein binds to or recruits a component of the complement system, known as the C1 complex (C1qC1r2C1s2). Such recruitment can initiate a cleavage cascade involving C2, C3, C4, and C5, and subsequently trigger microbial clearance. The microbial clearance can result from the so-called "classical complement pathway," which depends on further downstream complement components, e.g., the membrane attack complex (MAC), thereby killing the microbial targets, e.g., bacterial cells or enveloped viruses. See Mellors et al., 2020. Microbial clearance may also be achieved through a C1- and C4-dependent antiviral mechanism that is independent of downstream complement components. With assistance from C1, which is recruited by Fc or just $CH_2$ (a fragment of Fc), C4 directly inactivates the virus capsid and neutralizes viruses. See Bottermann et al., *Cell Host & Microbe,* 25:617-629 (2019). As used herein, the term "activation of the complement pathway" includes activation of the classical complement pathway and/or the C4-dependent antiviral pathway.

Additionally, anti-HA or anti-NA antibodies comprising any of the Fc variants known in the art, or combinations thereof, are contemplated. In some embodiments, the Fc fragment comprises sequence that has been altered or otherwise changed so that it has enhanced antibody dependent cellular cytotoxicity (ADCC) or complement dependent cytotoxicity (CDC) effector function.

In some embodiments, each chain of the Fc fragment is fused to the same entity. In some embodiments, the anti-HA or anti-NA antibody comprises two identical anti-HA or anti-NA antibody moieties described herein, each fused with one chain of the Fc fragment. In some embodiments, the two chains of the Fc fragment are identical. In some embodiments, the anti-HA or anti-NA antibody comprising the Fc fragment is a homodimer.

In some embodiments, each chain of the Fc fragment is fused to a different entity. In some embodiments, the anti-HA or anti-NA antibody comprises two different anti-HA or anti-NA antibody moieties, each fused to one chain of the Fc fragment. In some embodiments, the two anti-HA or anti-NA antibody moieties are different, but both specifically recognize an HA or NA protein, respectively. In some embodiments, the anti-HA or anti-NA antibody is monovalent, i.e., only one anti-HA or anti-NA antibody moiety is fused to one chain of the Fc fragment, and the second chain of the Fc fragment is not fused to an anti-HA or anti-NA antibody moiety, respectively. In some embodiments, the anti-HA or anti-NA antibody comprising the Fc fragment is a heterodimer.

Heterodimerization of non-identical polypeptides in the anti-HA or anti-NA antibody can be facilitated by methods known in the art, including without limitation, heterodimerization by the knob-into-hole technology. The structure and assembly method of the knob-into-hole technology can be found in, e.g., U.S. Pat. Nos. 5,821,333, 7,642,228, US 2011/0287009, and PCT/US2012/059810, hereby incorporated by reference in their entireties. This technology was developed by introducing a "knob" (or a protuberance) by replacing a small amino acid residue with a large one in the $CH_3$ domain of one Fc and introducing a "hole" (or a cavity) in the $CH_3$ domain of the other Fc by replacing one or more large amino acid residues with smaller ones. In some embodiments, one chain of the Fc fragment in the fusion protein comprises a knob, and the second chain of the Fc fragment comprises a hole.

The preferred residues for the formation of a knob are generally naturally occurring amino acid residues and are preferably selected from arginine (R), phenylalanine (F), tyrosine (Y) and tryptophan (W). Most preferred are tryptophan and tyrosine. In one embodiment, the original residue for the formation of the knob has a small side chain volume, such as alanine, asparagine, aspartic acid, glycine, serine, threonine or valine. Exemplary amino acid substitutions in the $CH_3$ domain for forming the knob include without limitation the T366W, T366Y or F405W substitution.

The preferred residues for the formation of a hole are usually naturally occurring amino acid residues and are preferably selected from alanine (A), serine (S), threonine (T) and valine (V). In one embodiment, the original residue for the formation of the hole has a large side chain volume, such as tyrosine, arginine, phenylalanine or tryptophan. Exemplary amino acid substitutions in the $CH_3$ domain for generating the hole include without limitation the T366S, L368A, F405A, Y407A, Y407T and Y407V substitutions. In certain embodiments, the knob comprises T366W substitution, and the hole comprises the T366S/L368A/Y407V substitutions. It is understood that other modifications to the Fc region known in the art that facilitate heterodimerization are also contemplated and encompassed by the instant application.

C. Variants

In some embodiments, amino acid sequence variants of the anti-HA or anti-NA antibody moieties of the chimeric proteins, and amino acid sequence variants of the chimeric proteins provided herein (e.g., in the peptide linker and/or in the mucoadhesive peptide fragment), are contemplated. For example, it may be desirable to improve the binding affinity and/or other biological properties of the antibody moieties. Amino acid sequence variants of an antibody moiety (e.g., an anti-HA or anti-NA antibody or antigen-binding fragment thereof) may be prepared by introducing appropriate modifications into the nucleotide sequence encoding the antibody moiety, or by peptide synthesis. Such modifications include, for example, deletions from, and/or insertions into and/or substitutions of residues within the amino acid sequences of the antibody moiety (e.g., an anti-HA or anti-NA antibody or antigen-binding fragment thereof). Any combination of deletion, insertion, and substitution can be made to arrive at the final construct, provided that the final construct possesses the desired characteristics, e.g., target-binding.

In some embodiments, variants having one or more amino acid substitutions are provided. Sites of interest for substitutional mutagenesis include the HVRs and FRs of antibody moieties. Amino acid substitutions may be introduced into an antibody moiety of interest (e.g., an anti-HA or anti-NA antibody or antigen-binding fragment thereof) and the products screened for a desired activity, e.g., retained/improved target binding or decreased immunogenicity.

Conservative substitutions are shown in Table B below.

TABLE B

Conservative amino acid substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |

TABLE B-continued

| Conservative amino acid substitutions | | |
|---|---|---|
| Original Residue | Exemplary Substitutions | Preferred Substitutions |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped into different classes according to common side-chain properties:

a. hydrophobic: Norleucine, Met, Ala, Val, Leu, Ile;

b. neutral hydrophilic: Cys, Ser, Thr, Asn, Gln;

c. acidic: Asp, Glu;

d. basic: His, Lys, Arg;

e. residues that influence chain orientation: Gly, Pro;

f. aromatic: Trp, Tyr, Phe.

Non-conservative substitutions will entail exchanging a member of one of these classes for another class.

An exemplary substitutional variant is an affinity matured antibody moiety, which may be conveniently generated, e.g., using phage display-based affinity maturation techniques. Briefly, one or more CDR residues are mutated and the variant antibody moieties displayed on phage and screened for a particular biological activity (e.g., binding affinity). Alterations (e.g., substitutions) may be made in HVRs, e.g., to improve antibody moiety affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or specificity determining residues (SDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).)

In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody moiety variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody moiety to bind antigen. For example, conservative alterations (e.g., conservative substitutions as provided herein) that do not substantially reduce binding affinity may be made in HVRs. Such alterations may be outside of HVR "hotspots" or SDRs. In some embodiments of the variant VH and VL sequences provided above, each HVR either is unaltered, or contains no more than one, two or three amino acid substitutions.

A useful method for identification of residues or regions of an antibody moiety that may be targeted for mutagenesis is called "alanine scanning mutagenesis" as described by Cunningham and Wells *Science,* 244:1081-1085 (1989). In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody moiety with its target is affected. Further substitutions may be introduced at the amino acid locations demonstrating functional sensitivity to the initial substitutions. Alternatively, or additionally, a crystal structure of an antibody moiety-target complex can be determined to identify contact points between the antibody moiety and the target. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody moiety with an N-terminal methionyl residue. Other insertional variants of the antibody moiety include the fusion to the N- or C-terminus of the antibody moiety to an enzyme (e.g., for ADEPT) or a polypeptide which increases the serum half-life of the antibody moiety.

D. Mucoadhesive Peptide Fragments

The chimeric proteins described herein comprise one or more (e.g., 1, 2, 3, 4 or more) mucoadhesive peptide fragments.

In some embodiments, the antibody moiety comprises the same number of polypeptide chains as the number of mucoadhesive peptide fragment(s) in the chimeric protein. In some embodiments, the antibody moiety comprises more polypeptide chains than the number of mucoadhesive peptide fragment(s) in the chimeric protein. In some embodiments, each polypeptide chain of the antibody moiety is coupled to (e.g., fused to) a mucoadhesive peptide fragment. In some embodiments, the antibody moiety comprises polypeptide chains that are not coupled (e.g., fused to) a mucoadhesive peptide fragment.

In some embodiments, the mucoadhesive peptide fragment is fused to any position in the antibody moiety that does not interference with binding of the antibody moiety to the component of an influenza virus or variant thereof. In some embodiments, the mucoadhesive peptide fragment is fused to a site that is distal from the antibody-binding site. In some embodiments, the mucoadhesive peptide fragment is fused to the C-terminus of an antibody heavy chain in the antibody moiety. In some embodiments, the mucoadhesive peptide fragment is fused to the C-terminus of an antibody light chain in the antibody moiety.

In some embodiments, the chimeric protein comprises a single polypeptide chain comprising the antibody moiety and a mucoadhesive peptide fragment.

In some embodiments, the chimeric protein comprises: (a) a first polypeptide comprising a first polypeptide chain of the antibody moiety and a first mucoadhesive peptide fragment; and (b) a second polypeptide comprising a second polypeptide of antibody moiety and a second mucoadhesive peptide fragment. In some embodiments, the antibody moiety further comprises polypeptide chains that are not coupled to (e.g., fused to) a mucoadhesive peptide fragment.

In some embodiments, the mucoadhesive peptide fragments comprises (including for example consisting of or consisting essentially of) about 10 to about 600 amino acid residues (e.g., positively charged amino acid residues plus non-positively charged amino acid residues). In some embodiments, the mucoadhesive peptide fragment comprises (including for example consisting of or consisting essentially of) about 10 to about 20 amino acid residues. In some embodiments, the mucoadhesive peptide fragment comprises (including for example consisting of or consisting essentially of) about 22 to about 30 amino acid residues. In some embodiments, the mucoadhesive peptide fragment comprises (including for example consisting of or consisting essentially of) about 32 to about 40 amino acid residues. In some embodiments, the mucoadhesive peptide fragment comprises (including for example consisting of or consisting essentially of) about 42 to about 50 amino acid residues. In some embodiments, the mucoadhesive peptide fragment comprises (including for example consisting of or consisting essentially of) about 52 to about 60 amino acid residues. In some embodiments, the mucoadhesive peptide fragment comprises (including for example consisting of or consisting essentially of) about 16 to about 50 amino acid residues. In some embodiments, the mucoadhesive peptide fragment comprises (including for example consisting of or consisting essentially of) about 20 to about 44 amino acid residues. In some embodiments, the mucoadhesive peptide fragment comprises (including for example consisting of or consisting essentially of) about 24 to about 40 amino acid residues. In some embodiments, the mucoadhesive peptide fragment comprises (including for example consisting of or consisting essentially of) about 28 to about 36 amino acid residues. In some embodiments, the mucoadhesive peptide fragment comprises (including for example consisting of or consisting essentially of) about n amino acid residues, where n is selected from 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 70, 80, 90, 100, 120, 140, 160, 180, 200, 300, 400, 500, and 600, or more. In some embodiments, the mucoadhesive peptide fragment comprises (including for example consisting of or consisting essentially of) between about n amino acid residues, where n is selected from 10-20, 21-30, 31-40, 41-50, 51-60, 61-70, 71-80, 81-90, 91-100, 101-110, 111-120, 121-130, 131-140, 141-150, 151-160, 161-170, 171-180, 181-190, 191-200, 201-210, 211-220, 221-230, 231-240, 241-250, 251-260, 261-270, 271-280, 281-290, 291-300, 301-310, 311-320, 321-330, 331-340, 341-350, 351-360, 361-370, 371-380, 381-390, 391-400, 401-410, 411-420, 421-430, 431-440, 441-450, 451-460, 461-470, 471-480, 481-490, 491-500, 501-510, 511-520, 521-530, 531-540, 541-550, 551-560, 561-570, 571-580, 581-590, 591-600, 10-30, 10-40, 10-50, 16-30, 16-40, 16-50, 20-40, 20-50, 24-40, 24-50, 30-50-30-60, 10-60, 12-60, and 10-100. In some embodiments, the mucoadhesive peptide fragment comprises (including for example consisting of or consisting essentially of) at least about n amino acid residues, where n is selected from 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 70, 80, 90, 100, 120, 140, 160, 180, 200, 300, 400, 500, and 600, or more. In some embodiments, the mucoadhesive peptide fragment comprises (including for example consisting of or consisting essentially of) no more than about about n amino acid residues, where n is selected from 600, 500, 400, 300, 200, 180, 160, 140, 120, 100, 90, 80, 70, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, and 10.

In some embodiments, the mucoadhesive peptide fragment comprises about 5 to about 300 positively charged amino acid residues. In some embodiments, the mucoadhesive peptide fragment comprises about 5 to about 10 positively charged amino acid residues. In some embodiments, the mucoadhesive peptide fragment comprises about 11 to about 15 positively charged amino acid residues. In some embodiments, the mucoadhesive peptide fragment comprises about 16 to about 20 positively charged amino acid residues. In some embodiments, the mucoadhesive peptide fragment comprises about 21 to about 25 positively charged amino acid residues. In some embodiments, the mucoadhesive peptide fragment comprises about 26 to about 30 positively charged amino acid residues. In some embodiments, the mucoadhesive peptide fragment comprises about 8 to about 25 positively charged amino acid residues. In some embodiments, the mucoadhesive peptide fragment comprises about 10 to about 22 positively charged amino acid residues. In some embodiments, the mucoadhesive peptide fragment comprises about 12 to about 20 positively charged amino acid residues. In some embodiments, the mucoadhesive peptide fragment comprises about 14 to about 18 positively charged amino acid residues. In some embodiments, the mucoadhesive peptide fragment comprises about n positively charged amino acid residues, where n is selected from 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200, 250, and 300, or more. In some embodiments, the mucoadhesive peptide fragment comprises between about n positively charged amino acid residues, where n is selected from 5-10, 11-15, 16-20, 21-25, 26-30, 31-35, 36-40, 41-45, 46-50, 51-55, 56-60, 61-65, 66-70, 71-75, 76-80, 81-85, 86-90, 91-95, 96-100, 101-110, 111-120, 121-130, 131-140, 141-150, 151-160, 161-170, 171-180, 181-190, 191-200, 201-210, 211-220, 221-230, 231-240, 241-250, 251-260, 261-270, 271-280, 281-290, 291-300, 5-15, 5-20, 5-25, 8-15, 8-20, 8-25, 10-20, 10-25, 12-20, 12-25, 15-25, 15-30, 5-30, 6-30, and 5-50. In some embodiments, the mucoadhesive peptide fragment comprises at least about n positively charged amino acid residues, where n is selected from 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, and 300, or more. In some embodiments, the mucoadhesive peptide fragment comprises no more than about n positively charged amino acid residues, where n is selected from 300, 290, 280, 270, 260, 250, 240, 230, 220, 210, 200, 190, 180, 170, 160, 150, 140, 130, 120, 110, 100, 95, 90, 85, 80, 75, 70, 65, 60, 55, 50, 45, 40, 35, 30, 29, 28, 27, 26, 25, 24, 23, 22, 21, 20, 19, 18, 17, 16, 15, 14, 13, 12, 10, 9, 8, 7, 6, and 5.

In some embodiments, the mucoadhesive peptide fragment comprises at least about 5 positively charged amino acid residues (e.g., lysines, arginines, histidines, ornithines, and combinations thereof). In some embodiments, the mucoadhesive peptide fragment comprises at least about 5 positively charged amino acid residues (e.g., lysines, arginines, histidines, ornithines, and combinations thereof). In some embodiments, the mucoadhesive peptide fragment comprises at least about 6 positively charged amino acid residues (e.g., lysines, arginines, histidines, ornithines, and combinations thereof). In some embodiments, the mucoadhesive peptide fragment comprises about 5 to about 50 positively charged amino acid residues (e.g., lysines, arginines, histidines, ornithines, and combinations thereof). In some embodiments, the mucoadhesive peptide fragment comprises about 5 to about 30 positively charged amino acid residues (e.g., lysines, arginines, histidines, ornithines, and combinations thereof). In some embodiments, the mucoadhesive peptide fragment comprises about 5, 6, 12, 18, 24, or 30 positively charged amino acid residues (e.g., lysines, arginines, histidines, ornithines, and combinations thereof).

In some embodiments, the chimeric protein comprises two or more mucoadhesive peptide fragments. In some embodiments, each of the two or more mucoadhesive peptide fragments comprises about 5 to about 300 positively charged amino acid residues. In some embodiments, each of the two or more mucoadhesive peptide fragments comprises about 5 to about 10 positively charged amino acid residues. In some embodiments, each of the two or more mucoadhesive peptide fragments comprises about 11 to about 15 positively charged amino acid residues. In some embodiments, each of the two or more mucoadhesive peptide fragments comprises about 16 to about 20 positively charged amino acid residues. In some embodiments, each of the two or more mucoadhesive peptide fragments comprises about 21 to about 25 positively charged amino acid residues. In some embodiments, each of the two or more mucoadhesive peptide fragments comprises about 26 to about 30 positively charged amino acid residues. In some embodiments, each of the two or more mucoadhesive peptide fragments comprises about 8 to about 25 positively charged amino acid residues. In some embodiments, each of the two or more mucoadhesive peptide fragments comprises about 10 to about 22 positively charged amino acid residues. In some embodiments, each of the two or more mucoadhesive peptide fragments comprises about 12 to about 20 positively charged amino acid residues. In some embodiments, each of the two or more mucoadhesive peptide fragments comprises about 14 to about 18 positively charged amino acid residues. In some embodiments, each of the two or more mucoadhesive peptide fragments comprises about n positively charged amino acid residues, where n is selected from 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200, 250, and 300, or more. In some embodiments, each of the two or more mucoadhesive peptide fragments comprises between about n positively charged amino acid residues, where n is selected from 5-10, 11-15, 16-20, 21-25, 26-30, 31-35, 36-40, 41-45, 46-50, 51-55, 56-60, 61-65, 66-70, 71-75, 76-80, 81-85, 86-90, 91-95, 96-100, 101-110, 111-120, 121-130, 131-140, 141-150, 151-160, 161-170, 171-180, 181-190, 191-200, 201-210, 211-220, 221-230, 231-240, 241-250, 251-260, 261-270, 271-280, 281-290, 291-300, 5-15, 5-20, 5-25, 8-15, 8-20, 8-25, 10-20, 10-25, 12-20, 12-25, 15-25, 15-30, 5-30, 6-30, and 5-50. In some embodiments, each of the two or more mucoadhesive peptide fragments comprises at least about n positively charged amino acid residues, where n is selected from 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, and 300, or more. In some embodiments, each of the two or more mucoadhesive peptide fragments comprises no more than about about n positively charged amino acid residues, where n is selected from 300, 290, 280, 270, 260, 250, 240, 230, 220, 210, 200, 190, 180, 170, 160, 150, 140, 130, 120, 110, 100, 95, 90, 85, 80, 75, 70, 65, 60, 55, 50, 45, 40, 35, 30, 29, 28, 27, 26, 25, 24, 23, 22, 21, 20, 19, 18, 17, 16, 15, 14, 13, 12, 10, 9, 8, 7, 6, and 5.

In some embodiments, the total number of positively charged amino acid residues in the mucoadhesive peptide fragment(s) in the chimeric protein is about 5 to about 600. In some embodiments, the total number of positively charged amino acid residues in the mucoadhesive peptide fragment(s) in the chimeric protein is about 5 to about 20. In some embodiments, the total number of positively charged amino acid residues in the mucoadhesive peptide fragment(s) in the chimeric protein is about 11 to about 30. In some embodiments, the total number of positively charged amino acid residues in the mucoadhesive peptide fragment(s) in the chimeric protein is about 16 to about 40. In some embodiments, the total number of positively charged amino acid residues in the mucoadhesive peptide fragment(s) in the chimeric protein is about 21 to about 50. In some embodiments, the total number of positively charged amino acid residues in the mucoadhesive peptide fragment(s) in the chimeric protein is about 26 to about 60. In some embodiments, the total number of positively charged amino acid residues in the mucoadhesive peptide fragment(s) in the chimeric protein is about 8 to about 50. In some embodiments, the total number of positively charged amino acid residues in the mucoadhesive peptide fragment(s) in the chimeric protein is about 10 to about 44. In some embodiments, the total number of positively charged amino acid residues in the mucoadhesive peptide fragment(s) in the chimeric protein is about 12 to about 40. In some embodiments, the total number of positively charged amino acid residues in the mucoadhesive peptide fragment(s) in the chimeric protein is about 14 to about 36. In some embodiments, the total number of positively charged amino acid residues in the mucoadhesive peptide fragment(s) in the chimeric protein is about n positively charged amino acid residues, where n is selected from 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200, 250, 300, 350, 400, 450, 550, and 600, or more. In some embodiments, the total number of positively charged amino acid residues in the mucoadhesive peptide fragment(s) in the chimeric protein is between about n positively charged amino acid residues, where n is selected from 5-10, 11-15, 16-20, 21-25, 26-30, 31-35, 36-40, 41-45, 46-50, 51-55, 56-60, 61-65, 66-70, 71-75, 76-80, 81-85, 86-90, 91-95, 96-100, 101-110, 111-120, 121-130, 131-140, 141-150, 151-160, 161-170, 171-180, 181-190, 191-200, 201-210, 211-220, 221-230, 231-240, 241-250, 251-160, 261-270, 271-280, 281-290, 291-300, 301-310, 311-320, 321-330, 331-340, 341-350, 351-360, 361-370, 371-380, 381-390, 391-400, 401-410, 411-420, 421-430, 431-440, 441-450, 451-460, 461-470, 471-480, 481-490, 491-500, 501-510, 511-520, 521-530, 531-540, 541-550, 551-560, 561-570, 571-580, 581-590, 591-600, 5-15, 5-20, 5-25, 8-15, 8-20, 8-25, 10-20, 10-25, 12-20, 12-25, 15-25, 15-30, 5-30, 6-30, and 5-50. In some embodiments, the total number of positively charged amino acid residues in the mucoadhesive peptide fragment(s) in the chimeric protein is at least about n positively charged amino acid residues, where n is selected from 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, and 600, or more. In some embodiments, the total number of positively charged amino acid residues in the mucoadhesive peptide fragment(s) in the chimeric protein is no more than about n positively charged amino acid residues, where n is selected from 600, 590, 580, 570, 560, 550, 540, 530, 520, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 95, 90, 85, 80, 75, 70, 65, 60, 55, 50, 45, 40, 35, 30, 29, 28, 27, 26, 25, 24, 23, 22, 21, 20, 19, 18, 17, 16, 15, 14, 13, 12, 10, 9, 8, 7, 6, and 5.

In some embodiments, the number of positively charged amino acid residues in the mucoadhesive peptide fragment(s) per antibody moiety is about 5 to about 30. In some embodiments, the number of positively charged amino acid residues in the mucoadhesive peptide fragment(s) per antibody moiety is about 8 to about 25. In some embodiments, the number of positively charged amino acid residues in the mucoadhesive peptide fragment(s) per antibody moiety is about 10 to about 22. In some embodiments, the number of positively charged amino acid residues in the mucoadhesive peptide fragment(s) per antibody moiety is about 12 to about 20. In some embodiments, the number of positively charged amino acid residues in the mucoadhesive peptide fragment(s) per antibody moiety is about 14 to about 18. In some embodiments, the number of positively charged amino acid residues in the mucoadhesive peptide fragment(s) per antibody moiety is about n positively charged amino acid residues, where n is selected from 5, 6, 7, 8, 9, 10, 11, 12, 13, 14, 15, 16, 17, 18, 19, 20, 21, 22, 23, 24, 25, 26, 27, 28, 29, and 30, or more. In some embodiments, the number of positively charged amino acid residues in the mucoadhesive peptide fragment(s) per antibody moiety is between about about n positively charged amino acid residues, where n is selected from 5-10, 11-15, 16-20, 21-25, 26-30, 5-15, 5-20, 5-25, 8-15, 8-20, 8-25, 10-20, 10-25, 12-20, 12-25, 15-25, 15-30, 5-30, and 6-30. In some embodiments, the number of positively charged amino acid residues in the mucoadhesive peptide fragment(s) per antibody moiety is at least about about n positively charged amino acid residues, where n is selected from 5, 6, 7, 8, 9, 10, 11, 12, 13, 14, 15, 16, 17, 18, 19, 20, 21, 22, 23, 24, 25, and 30, or more. In some embodiments, the number of positively charged amino acid residues in the mucoadhesive peptide fragment(s) per antibody moiety is no more than about n positively charged amino acid residues, where n is selected from 30, 29, 28, 27, 26, 25, 24, 23, 22, 21, 20, 19, 18, 17, 16, 15, 14, 13, 12, 10, 9, 8, 7, 6, and 5.

The mucoadhesive peptide fragment(s) may comprise any suitable positively charged amino acid residues at physiological pH of the mucosa, including naturally occurring and synthetic amino acid residues such as lysine, arginine, histidine, ornithine, and combinations thereof. In some embodiments, the mucoadhesive peptide fragment comprises lysines only. In some embodiments, the mucoadhesive peptide fragment comprises arginines only. In some embodiments, the mucoadhesive peptide fragment comprises histidines only. In some embodiments, the mucoadhesive peptide fragment comprises ornithines only.

In some embodiments, the mucoadhesive peptide fragment comprises both lysines and arginines. In some embodiments, the mucoadhesive peptide fragment comprises an equal number of lysines and arginines. In some embodiments, the mucoadhesive peptide fragment comprises unequal numbers of lysines and arginines. In some embodiments, the mucoadhesive peptide fragment comprises both lysines and histidines. In some embodiments, the mucoadhesive peptide fragment comprises an equal number of lysines and histidines. In some embodiments, the mucoadhesive peptide fragment comprises unequal numbers of lysines and histidines. In some embodiments, the mucoadhesive peptide fragment comprises both lysines and ornithines. In some embodiments, the mucoadhesive peptide fragment comprises an equal number of lysines and ornithines. In some embodiments, the mucoadhesive peptide fragment comprises unequal numbers of lysines and ornithines. In some embodiments, the mucoadhesive peptide fragment comprises both arginines and ornithines. In some embodiments, the mucoadhesive peptide fragment comprises an equal number of arginines and ornithines. In some embodiments, the mucoadhesive peptide fragment comprises an unequal number of arginines and ornithines. In some embodiments, the mucoadhesive peptide fragment comprises both arginines and histidines. In some embodiments, the mucoadhesive peptide fragment comprises an equal number of arginines and histidines. In some embodiments, the mucoadhesive peptide fragment comprises an unequal number of ornithines and histidines. In some embodiments, the mucoadhesive peptide fragment comprises both ornithines and histidines. In some embodiments, the mucoadhesive peptide fragment comprises an equal number of ornithines and histidines. In some embodiments, the mucoadhesive peptide fragment comprises an unequal number of ornithines and histidines. In some embodiments, the mucoadhesive peptide fragment comprises lysines, arginines, and ornithines. In some embodiments, the mucoadhesive peptide fragment comprises an equal number of lysines, arginines, and ornithines. In some embodiments, the mucoadhesive peptide fragment comprises unequal numbers of lysines, arginines, and ornithines. In some embodiments, the mucoadhesive peptide fragment comprises histidines, arginines, and ornithines. In some embodiments, the mucoadhesive peptide fragment comprises an equal number of histidines, arginines, and ornithines. In some embodiments, the mucoadhesive peptide fragment comprises unequal numbers of histidines, arginines, and ornithines. In some embodiments, the mucoadhesive peptide fragment comprises lysines, histidines, and ornithines. In some embodiments, the mucoadhesive peptide fragment comprises an equal number of lysines, histidines, and ornithines. In some embodiments, the mucoadhesive peptide fragment comprises unequal numbers of lysines, histidines, and ornithines. In some embodiments, the mucoadhesive peptide fragment comprises lysines, arginines, and histidines. In some embodiments, the mucoadhesive peptide fragment comprises an equal number of lysines, arginines, and histidines. In some embodiments, the mucoadhesive peptide fragment comprises unequal numbers of lysines, arginines, and histidines. In some embodiments, the mucoadhesive peptide fragment comprises lysines, arginines, histidines, and ornithines. In some embodiments, the mucoadhesive peptide fragment comprises an equal number of lysines, arginines, histidines, and ornithines. In some embodiments, the mucoadhesive peptide fragment comprises unequal numbers of lysines, arginines, histidines, and ornithines. In some embodiments, the mucoadhesive peptide fragment(s) comprises one or more non-naturally occurring amino acid residues that are positively charged at physiological pH of the mucosa.

In some embodiments, the mucoadhesive peptide fragment has an isoelectric point (pI) higher than the pH of the mucosa. The pH values of various mucosa in human are known. For example, the human nasal mucosa may have a pH range of about 5.5 to about 6.5, about 5.5 to about 6.6, about 6.44 to about 6.91, about 6.4 to about 7.9, or about 6.4 to about 6.5. In some examples, the human nasal mucosa may have a pH of about 6.6. In other examples, the human tracheal mucosa may have a pH range of about 6.1 to about 7.9, or a pH of about 6.71. In further examples, the human bronchial mucosa may have a pH range of about 5.7 to about 6.6 or about 7 to about 7.5. In some examples, the human bronchial mucosa may have a pH of about 6.7, about 7.1, about 6.25, about 6.78, or about 6.58. In some examples, the human mucosa may be diseased. In such examples, smokers may have a sputum mucosa pH of about 7.25 or about 6.82. In other examples, patients suffering with chronic bronchitis may have a sputum mucoid pH of about 7.59 and/or a sputum purulent pH of about 7.83. In other examples, patients suffering with rhinitis may have a nasal mucosa pH range of about 7.2 to about 8.3. In other examples still, patients suffering with the common cold may have a mucosa pH range of about 7.2 to about 8.3.

In some embodiments, at nasal pH (e.g., ~6.5), the various properties (e.g., pI, net charge, and molecular weight) of polycationic peptides described herein may be calculated. In some examples, at nasal pH (e.g., ~6.5), the equivalent of a 20-mer polypeptide may be calculated. The 20-mer polypeptide will be linear, and the size of each polypeptide will be proportional to the molecular weight. The pI and molecular weight of various exemplary 20-mer polypeptides at nasal pH were calculated and are listed in Table 7. The interactions between the positively charged polypeptides and mucosal cells or mucin may primarily occur by charge.

TABLE 7

Exemplary amino acid and corresponding 20-mer polypeptides properties at nasal pH

| Amino acid or polypeptide | pI | Net charge | Molecular weight (Da) |
|---|---|---|---|
| Lysine (K) | 8.8 | +1 | 146.2 |
| Arginine (R) | 10.0 | +1 | 174.2 |
| Histidine (H) | 7.2 | +0.5 | 155.2 |
| K-20 | 11.3 | +20 | 2581.5 |
| R-20 | 13.3 | +20 | 3141.8 |
| H-20 | 8.1 | +10 | 2760.8 |

In some embodiments, the pI range of the mucoadhesive peptide fragment is at least about n, where n is selected from 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.5, 12, 12.5, and 13, or more. In some embodiments, the pI range of the mucoadhesive peptide fragment is about 8 to about 14. In some embodiments, the range of pI values of the mucoadhesive peptide fragment is about 8.8 to about 10.0. In some embodiments, the range of pI values of the mucoadhesive peptide fragment is about 11.3 to about 13.3. In some embodiments, the range of pI values of the chimeric protein is at least about n, where n is selected from 8, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.5, 12, 12.5, and 13, or more, including, 8-8.3, 8.3-8.5, 8.5-8.7, 8.7-8.9, 8.9-9.1, 9.1-9.3, 9.3-9.4, 9.4-10, 8-10, 8-9, 9-10, 8-11, 8.5-9.5, 8.76-9.44, 8.77-9.61, and 8.32-9.33.

In some embodiments, the mucoadhesive peptide fragment is a polylysine peptide. In some embodiments, the mucoadhesive peptide fragment is a polylysine peptide having about n contiguous lysines, where n is selected from 5, 6, 7, 8, 9, 10, 11, 12, 13, 14, 15, 16, 17, 18, 19, 20, 21, 22, 23, 24, 25, 26, 27, 28, 29, and 30. In some embodiments, the mucoadhesive peptide fragment is a polylysine peptide having between about n contiguous lysines, where n is selected from 5-10, 10-15, 15-20, 20-25, 25-30, 30-40, 40-50, 5-15, 5-20, 5-25, 8-15, 8-20, 8-25, 10-20, 10-25, 12-20, 12-25, 15-25, 15-30, 5-30, 6-30, and 5-50.

In some embodiments, the mucoadhesive peptide fragment is a polyhistidine peptide. In some embodiments, the mucoadhesive peptide fragment is a polyhistidine peptide having about n contiguous histidines, where n is selected from 5, 6, 7, 8, 9, 10, 11, 12, 13, 14, 15, 16, 17, 18, 19, 20, 21, 22, 23, 24, 25, 26, 27, 28, 29, and 30. In some embodiments, the mucoadhesive peptide fragment is a polyhistidine peptide having between about n contiguous histidines, where n is selected from 5-10, 10-15, 15-20, 20-25, 25-30, 30-40, 40-50, 5-15, 5-20, 5-25, 8-15, 8-20, 8-25, 10-20, 10-25, 12-20, 12-25, 15-25, 15-30, 5-30, 6-30, and 5-50.

In some embodiments, the mucoadhesive peptide fragment is a polyarginine peptide. In some embodiments, the mucoadhesive peptide fragment is a polyarginine peptide having any about n contiguous arginines, where n is selected from 5, 6, 7, 8, 9, 10, 11, 12, 13, 14, 15, 16, 17, 18, 19, 20, 21, 22, 23, 24, 25, 26, 27, 28, 29, and 30. In some embodiments, the mucoadhesive peptide fragment is a polyarginine peptide having between about n contiguous arginines, where n is selected from 5-10, 10-15, 15-20, 20-25, 25-30, 30-40, 40-50, 5-15, 5-20, 5-25, 8-15, 8-20, 8-25, 10-20, 10-25, 12-20, 12-25, 15-25, 15-30, 5-30, 6-30, and 5-50.

In some embodiments, the mucoadhesive peptide fragment is a polyornithine peptide. In some embodiments, the mucoadhesive peptide fragment is a polyornithine peptide having about n contiguous ornithines, where n is selected from 5, 6, 7, 8, 9, 10, 11, 12, 13, 14, 15, 16, 17, 18, 19, 20, 21, 22, 23, 24, 25, 26, 27, 28, 29, and 30. In some embodiments, the mucoadhesive peptide fragment is a polyornithine peptide having between about n contiguous ornithines, where n is selected from 5-10, 10-15, 15-20, 20-25, 25-30, 30-40, 40-50, 5-15, 5-20, 5-25, 8-15, 8-20, 8-25, 10-20, 10-25, 12-20, 12-25, 15-25, 15-30, 5-30, 6-30, and 5-50.

In some embodiments, the mucoadhesive peptide fragment comprises a continuous stretch of positively charged amino acid residues. In some embodiments, the mucoadhesive peptide fragment comprises about n positively charged amino acid residues, such as arginines, histidines, lysines, or ornithines, or combinations thereof, where n is selected from 2, 3, 4, 5, 6, 7, 8, 9, 10, 11, 12, 13, 14, 15, 16, 17, 18, 19, 20, 21, 22, 23, 24, 25, 26, 27, 28, 29, and 30. In some embodiments, the mucoadhesive peptide fragment comprises between n contiguous positively charged amino acid residues, such as arginines, histidines, lysines, or ornithines, or combinations thereof, where n is selected from 2-5, 5-10, 10-15, 15-20, 20-25, 25-30, 30-40, 40-50, 2-15, 2-20, 2-25, 8-15, 8-20, 8-25, 10-20, 10-25, 12-20, 12-25, 15-25, 15-30, 2-30, 6-30, and 2-50. In some embodiments, all positively charged amino acid residues are contiguous with respect to each other.

In some embodiments, the mucoadhesive peptide fragment comprises one or more non-positively charged amino acid residues. In some embodiments, the non-positively charged amino acid residues are non-polar amino acids or polar uncharged amino acids. In some embodiments, the mucoadhesive peptide fragment comprises isoleucine, valine, alanine, tryptophan, leucine, glycine, methionine, proline, phenylalanine, threonine, cysteine, tyrosine, glutamine, serine, asparagine, or combinations thereof. In some embodiments, the mucoadhesive peptide fragment comprises one or more alanine, threonine, cysteine, serine, glutamine, asparagine, or combinations thereof. In some embodiments, the mucoadhesive peptide fragment comprises a combination of one or more isoleucines, valines, alanines, tryptophans, leucines, glycines, methionines, prolines, phenylalanines, threonines, cysteines, tyrosines, glutamines, serines, or asparagines. In some embodiments, the mucoadhesive peptide fragment comprises a combination of one or more alanines, threonines, cysteines, serines, glutamines, or asparagines. In some embodiments, the mucoadhesive peptide fragment(s) comprises one or more non-naturally occurring amino acid residues that are non-positively charged at physiological pH of the mucosa.

In some embodiments, the positively charged amino acid residues are interspersed with non-positively charged amino acid residues. In some embodiments, the positively charged amino acid residues are present in every other position in the mucoadhesive peptide fragment. In some embodiments, the positively charged amino acid residues are present in every third position in the mucoadhesive peptide fragment. In some embodiments, the positively charged amino acid residues are present in every fourth position in the mucoadhesive peptide fragment. In some embodiments, the positively charged amino acid residues are randomly dispersed in the mucoadhesive peptide fragment. In some embodiments, the positive charged residues are present in one or more clusters within the mucoadhesive peptide fragment.

In some embodiments, at least about n % of the amino acid residues in the mucoadhesive peptide fragment are positively charged amino acid residues, where n % is selected from 10%, 20%, 30%, 40%, 50%, 60%, 70%, 80%, 90%, 95%, and 99%, or more. In some embodiments, all amino acid residues in the mucoadhesive peptide fragment are positively charged. In some embodiments, no more than about n % of the amino acid residues in the mucoadhesive peptide fragment are positively charged amino acid residues, where n % is selected from 99%, 95%, 90%, 80%, 70%, 60%, 50%, 40%, 30%, 20%, and 10%. In some embodiments, between about n % of the amino acid residues in the mucoadhesive peptide fragment are positively charged amino acid residues, where n % is selected from 10%-99%, 10%-20%, 20%-30%, 30%-40%, 40%-50%, 50%-60%, 60%-80%, 10%-100%, 10%-30%, 30%-60%, 60%-90%, 20%-50%, and 50%-100%. In some embodiments, at least about 50% of the amino acid residues in the mucoadhesive peptide fragment are positively charged amino acid residues.

In some embodiments, at least about n % of the amino acid residues in the mucoadhesive peptide fragment are non-positively charged amino acid residues, where n % is selected from 1%, 2%, 3%, 4%, 5%, 6%, 7%, 8%, 9%, 10%, 20%, 30%, 40%, and 50%, or more. In some embodiments, all amino acid residues in the mucoadhesive peptide fragment are positively charged. In some embodiments, no more than about n % of the amino acid residues in the mucoadhesive peptide fragment are non-positively charged amino acid residues, where n % is selected from 50%, 40%, 30%, 20%, 10%, 9%, 8%, 7%, 6%, 5%, 4%, 3%, 2%, and 1%. In some embodiments, between about n % of the amino acid residues in the mucoadhesive peptide fragment are non-positively charged amino acid residues, where n % is selected from 1%-5%, 5%-10%, 10%-25%, 25%-50%, 1%-10%, 5%-15%, 10%-20%, 15%-25%, 20%-30%, 25%-35%, 30%-40%, 35%-45%, and 40%-50%. In some embodiments, no more than about 50% of the amino acid residues in the mucoadhesive peptide fragment are non-positively charged amino acid residues.

In some embodiments, the mucoadhesive peptide fragment is no more than about 15 kD. In some embodiments, the mucoadhesive peptide fragment is about 0.5 kD to about 50 kD. In some embodiments, the mucoadhesive peptide fragment is about 0.5 kD to about 15 kD. In some embodiments, the mucoadhesive peptide fragment is about 2 kD to about 12 kD. In some embodiments, the mucoadhesive peptide fragment is about 4 kD to about 10 kD. In some embodiments, the mucoadhesive peptide fragment is about 6 kD to about 14 kD. In some embodiments, the mucoadhesive peptide fragment is about n kD, where n kD is selected from a 0.5 kD, 1 kD, 2 kD, 3 kD, 4 kD, 5 kD, 6 kD, 7 kD, 8 kD, 9 kD, 10 kD, 11 kD, 12 kD, 13 kD, 14 kD, 15 kD, 20 kD, 25 kD, 30 kD, 35 kD, 40 kD, 45 kD, and 50 kD, or more. In some embodiments, the mucoadhesive peptide fragment is between about n kD, where n kD is selected from 0.5-1 kD, 1-2 kD, 2-3 kD, 4-5 kD, 5-6 kD, 6-7 kD, 8-9 kD, 9-10 kD, 10-11 kD, 11-12 kD, 12-13 kD, 13-14 kD, 14-15 kD, 15-20 kD, 20-25 kD, 25-30 kD, 30-35 kD, 35-40 kD, 40-45 kD, 45-50 kD, or more. In some embodiments, the mucoadhesive peptide fragment at least about n kD, where n kD is selected from 0.5 kD, 1 kD, 2 kD, 3 kD, 4 kD, 5 kD, 6 kD, 7 kD, 8 kD, 9 kD, 10 kD, 11 kD, 12 kD, 13 kD, 14 kD, 15 kD, 20 kD, 25 kD, 30 kD, 35 kD, 40 kD, 45 kD, 50 kD, or more. In some embodiments, the mucoadhesive peptide fragment is no more than about n kD, where n kD is selected from 50 kD, 45 kD, 40 kD, 35 kD, 30 kD, 25 kD, 20 kD, 15 kD, 14 kD, 13 kD, 12 kD, 11 kD, 10 kD, 9 kD, 8 kD, 7 kD, 6 kD, 5 kD, 4 kD, 3 kD, 2 kD, 1 kD, and 0.5 kD.

In some embodiments, the mucoadhesive peptide fragment does not facilitate penetration of the chimeric protein into a cell of the mucosa. In some embodiments, the mucoadhesive peptide fragment does not comprises a motif in a cell penetrating peptide. In some embodiments, the mucoadhesive peptide is not a cell penetrating peptide.

In some embodiments, the mucoadhesive peptide fragment is not a histidine tag. In some embodiments, the mucoadhesive peptide fragment is not a peptide consisting of, or consisting essentially of, six histidines.

In some embodiments, the mucoadhesive peptide fragment does not disrupt folding of the chimeric protein within a host cell expressing the chimeric protein. In some embodiments, at least about n % of chimeric protein expressed in a mammalian host cell is properly folded, where n % is selected from 20%, 30%, 40%, 50%, 60%, 70%, 80%, and 90%, or more.

In some embodiments, the mucoadhesive peptide fragment does not block secretion of the chimeric protein from a host cell expressing the chimeric protein. In some embodiments, at least about n % of chimeric protein expressed in a mammalian host cell is secreted, where n % is selected from 20%, 30%, 40%, 50%, 60%, 70%, 80%, and 90%, or more. Without being bound by any theory or hypothesis, proteins with positively charged fragments tend to be trapped in the Golgi apparatus of cells expressing the proteins. The chimeric proteins described herein are readily expressed and secreted by host cells, and do not get trapped in the Golgi apparatus.

In some embodiments, the mucoadhesive peptide fragment does not interfere with the specific binding between the antibody moiety and the component of an influenza virus or variant thereof. In some embodiments, the mucoadhesive peptide fragment reduces binding between the antibody moiety and the component of an influenza virus or variant thereof by no more than about n %, where n % is selected from 50%, 40%, 30%, 20%, and 10%, or less.

Exemplary mucoadhesive peptide fragments for incorporation into a chimeric protein of the present disclosure are provided herein and are shown in Table 8.

TABLE 8

Exemplary mucoadhesive peptides

| Mucoadhesive Peptide Fragment | Percentage Positively Charged AA Residues | Sequence | SEQ ID NO |
|---|---|---|---|
| 5H | 100 | HHHHH | 407 |
| 6H | 100 | HHHHHH | 291 |
| 12H | 100 | HHHHHHHHHHHH | 292 |
| 30H | 100 | HHHHHHHHHHHHHHHHHHHHHHHHHHHHHH | 293 |
| 6K | 100 | KKKKKK | 294 |
| 12K | 100 | KKKKKKKKKKKK | 295 |
| 30K | 100 | KKKKKKKKKKKKKKKKKKKKKKKKKKKKKK | 296 |
| 6R | 100 | RRRRRR | 297 |
| 12R | 100 | RRRRRRRRRRRR | 298 |
| 30R | 100 | RRRRRRRRRRRRRRRRRRRRRRRRRRRRRR | 299 |
| 6O | 100 | OOOOOO | 300 |
| 12O | 100 | OOOOOOOOOOOO | 301 |
| 30O | 100 | OOOOOOOOOOOOOOOOOOOOOOOOOOOOOO | 302 |
| 6X-1 | 100 | HHKKOO | 303 |
| 6X-2 | 100 | HORKHR | 304 |
| 6X-3 | 83.3 | HKRSOH | 305 |
| 6X-4 | 83.3 | RRHTHR | 306 |
| 6X-7 | 100 | KKOORR | 307 |
| 6X-5 | 100 | KKHHRR | 308 |
| 6X-6 | 100 | OORRHH | 309 |
| 7X-1 | 85.7 | KKKGKKK | 408 |
| 12X-1 | 100 | HHHKKKRRROOO | 310 |
| 12X-2 | 75 | HHOAKKRCOOQH | 311 |
| 12X-3 | 100 | HRKOORKHHRKK | 312 |
| 12X-4 | 75 | KRAHOKCORKSH | 313 |
| 12X-5 | 100 | KKRROOHHHRRR | 314 |
| 12X-6 | 100 | OOORRRKKKHHH | 315 |
| 12X-7 | 66.7 | KKAHHGKKAHHV | 409 |
| 12X-8 | 66.7 | KKARRGKKARRV | 410 |
| 12X-9 | 58 | KLIHKKARVRGK | 411 |
| 15X-1 | 60 | ILRRKAHHGKIKKVR | 412 |
| 15X-2 | 57 | GHRVKKAVRHIKRL | 413 |
| 30X-1 | 100 | HKROHKROHKROHKROHKROHKROHKROHK | 316 |
| 30X-2 | 80 | KOHRSOKRHTORHKAHORKCKROKQRKHOS | 317 |

TABLE 8-continued

Exemplary mucoadhesive peptides

| Mucoadhesive Peptide Fragment | Percentage Positively Charged AA Residues | Sequence | SEQ ID NO |
|---|---|---|---|
| 30X-3 | 80 | KKROSRRHOTOOHHAROKHCKHROTRHKKS | 318 |
| 30X-4 | 80 | HRKQOHRSOOKTRRRAHROCHHHSRHOTHR | 319 |
| 35X-1 | 65.7 | GRHKAKNHIRRPKSRWKKWHKYRKVHRHKV HKGRR | 320 |
| 40X-2 | 57.5 | WRKVHHYKKQHKNRAHGKLKLRAKIHQRSR MHGKQKHYHR | 321 |
| 42X-1 | 71.4 | AHHKCRRGHKQKILHRRPHKFHRWKRVHKGR HGKKHRRHKHR | 322 |
| 45X-1 | 67 | QHRGKAKYHRTHHVKKQRHGRKNHKVHRHA RKFHKIRRLKCHKKH | 323 |
| 50X-1 | 70 | HNKRFKKGRHVRHSRHKSHRRTHKYHHWRHYRKVHRC KKAHKSHHRVHHK | 324 |
| 50X-2 | 60 | AHGRPHOFKROCKAHOVKHILKRTOSHOYKOVHQRNKO AOKMRKIRGGHK | 325 |

It should be understood that additional mucoadhesive peptide fragments comprising similar percentages of positively charged and/or non-positively charged amino acid residues are also within the scope of the invention.

In some embodiments, the mucoadhesive peptide fragment comprises an amino acid sequence having at least about 90% sequence identity (such as at least about n % sequence identity, where n % is selected from 91%, 92%, 93%, 94%, 95%, 96%, 97%, 98%, and 99%) to the amino acid sequence of any one of SEQ ID NOs: 291-325 and 407-413. In some embodiments, mucoadhesive peptide fragment comprises the amino acid sequence of any one of SEQ ID NOs: 291-325 and 407-413, or a variant thereof comprising about 1, about 2, or about 3 amino acid substitutions. In some embodiments, the mucoadhesive peptide fragment comprises the amino acid sequence of any one of SEQ ID NOs: 291-325 and 407-413.

E. Linkers

In some aspects, the antibody moiety is linked to the mucoadhesive peptide fragment via a linker (such as a peptide linker, also referred herein as a connecting peptide). In some embodiments, the antibody moiety is not covalently linked to the mucoadhesive peptide fragment. In some embodiments, the mucoadhesive peptide fragment is chemically conjugated to the antibody moiety, i.e., via a chemical linker.

In some embodiments, the peptide linker is located between the antibody moiety and the mucoadhesive peptide fragment of the chimeric protein. In some embodiments, the peptide linker is fused to a polypeptide chain of the antibody moiety. In some embodiments, the linker is fused to the mucoadhesive peptide fragment.

In some embodiments, the mucoadhesive peptide fragment is fused to a polypeptide chain of the antibody moiety via a peptide linker. In some embodiments, the linker is about 1 to 20 amino acid residues. In some embodiments, the linker is a glycine-serine linker. In some embodiments, the linker has the amino acid sequence of GGGGS (SEQ ID NO: 344).

The length, the degree of flexibility and/or other properties of the linker may have some influence on properties, including but not limited to the affinity, specificity or avidity for one or more targets of the fusion protein (e.g., bispecific immune cell engager or engineered receptor) described herein. For example, longer linkers may be selected to ensure that two adjacent binding moieties (e.g., the influenza virus HA or NA protein, or fragment thereof, and the effector protein or fragment thereof) do not sterically interfere with one another. In some embodiments, a linker (such as peptide linker) comprises flexible residues (such as glycine and serine) so that the adjacent binding moieties are free to move relative to each other. For example, a glycine-serine doublet can be a suitable peptide linker. In some embodiments, the linker is a non-peptide linker. In some embodiments, the linker is a peptide linker. In some embodiments, the linker is a non-cleavable linker. In some embodiments, the linker is a cleavable linker.

Other linker considerations include the effect on physical or pharmacokinetic properties of the resulting fusion protein (e.g., bispecific immune cell engager or engineered receptor), such as solubility, lipophilicity, hydrophilicity, hydrophobicity, stability (more or less stable as well as planned degradation), rigidity, flexibility, immunogenicity, modulation of antibody moiety binding, the ability to be incorporated into a micelle or liposome, and the like.

Any one or all of the linkers described herein can be accomplished by any chemical reaction that will bind the two molecules so long as the components or fragments retain their respective activities. This linkage can include many chemical mechanisms, for instance covalent binding, affinity binding, intercalation, coordinate binding and complexation. In some embodiments, the binding is covalent binding. Covalent binding can be achieved either by direct condensation of existing side chains or by the incorporation of external bridging molecules. Many bivalent or polyvalent linking agents are useful in coupling protein molecules, such as an Fc fragment. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents (see Killen and Lindstrom, *Jour. Immun.* 133:1335-2549 (1984); Jansen et al., Immunological Reviews 62:185-216 (1982); and Vitetta et al., *Science* 238:1098 (1987)).

Linkers that can be applied in the present application are described in the literature (see, for example, Ramakrishnan, S. et al., *Cancer Res.* 44:201-208 (1984) describing use of MBS (M-maleimidobenzoyl-N-hydroxysuccinimide ester)). In some embodiments, non-peptide linkers used herein include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat. #21651G); (iv) Sulfo-LC-SPDP (sulfosuccinimidyl 6 [3-(2-pyridyldithio)-propianamide]hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to fusion proteins with different physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form fusion protein with increased stability. Disulfide linkages, are in general, less stable than other linkages because the disulfide linkage is cleaved in vitro, resulting in less fusion protein available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Any one or all of the linkers described herein can be peptide linkers. The peptide linker may have a naturally occurring sequence, or a non-naturally occurring sequence. For example, a sequence derived from the hinge region of heavy chain only antibodies may be used as the linker. See, for example, WO1996/34103.

The peptide linker can be of any suitable length. In some embodiments, the peptide linker is at least about n amino acids (aa) long, where n is selected from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, and 100, or more. In some embodiments, the peptide linker is no more than about n aa long, where n is selected from a 100, 75, 50, 40, 35, 30, 25, 20, 19, 18, 17, 16, 15, 14, 13, 12, 11, 10, 9, 8, 7, 6, and 5, or fewer. In some embodiments, the length of the peptide linker is any of about 1 aa to about 10 aa, about 1 aa to about 20 aa, about 1 aa to about 30 aa, about 5 aa to about 15 aa, about 10 aa to about 25 aa, about 5 aa to about 30 aa, about 10 aa to about 30 aa, about 30 aa to about 50 aa, about 50 aa to about 100 aa, or about 1 aa to about 100 aa.

In some embodiments, the peptide linker is a stable linker, which is not cleavable by a protease. In some embodiments, the peptide linker is cleavable by a protease.

In some embodiments, the peptide linker tends not to adopt a rigid three-dimensional structure, but rather provide flexibility to a polypeptide. In some embodiments, the peptide linker is a flexible linker. Exemplary flexible linkers include glycine polymers $(G)_n$, where n≥1, glycine-serine polymers (including, for example, $GS(GS)_n$, where n≥0 (SEQ ID NO: 345), $(GSGGS)_n$, where n≥1 (SEQ ID NO: 346), $(GGGGS)_n$, where n≥1 (SEQ ID NO: 347), and $(GGGS)_n$, where n≥1 (SEQ ID NO: 348), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine and is much less restricted than residues with longer side chains (see Scheraga, *Rev. Computational Chem.,* 11 173-142 (1992)). The ordinarily skilled artisan will recognize that design of a fusion protein can include linkers that are all or partially flexible, such that the linker can include a flexible linker portion as well as one or more portions that confer less flexible structure to provide a desired fusion protein structure.

Natural linkers adopt various conformations in secondary structure, such as helical, β-strand, coil/bend and turns, to exert their functions. Linkers in an α-helix structure might serve as rigid spacers to effectively separate protein domains, thus reducing their unfavorable interactions. Non-helical linkers with Pro-rich sequence could increase the linker rigidity and function in reducing inter-domain interference.

Additional linkers may be used in the chimeric proteins of the present application for purposes of stability. For example, in some embodiments, the linker stabilizes the chimeric protein. In some embodiments, the linker increases, the serum half-life of the chimeric protein in vivo, the avidity of the chimeric protein to the component of the influenza virus or variant thereof in vitro, the number of chimeric proteins in vitro, and/or the effective amount of the chimeric protein delivered to a nasal cavity in vivo. In some embodiments, the linker comprises an oligomerization or multimerization domain. In some embodiments, the oligomerization or multimerization domain is from a naturally occurring protein. In some embodiments, the oligomerization or multimerization domain is from a non-naturally occurring protein. Exemplary linkers (e.g., peptide linkers and domains to be included in linkers) are shown in Table 9.

TABLE 9

Exemplary peptide linkers and linker domains

| Linker or Multimerization Domain | Cluster | Exemplary Sequence | SEQ ID NO | Reference |
|---|---|---|---|---|
| Immunoglobulin Fc region ($CH_2CH_3$) | Dimer | TCPPCPAPELLGGPSVFLFPPKPKDTLMISRTPE VTCVVVDVSHEDPEVKFNWYVDGVEVHNAK TKPREEQYNSTYRVVSVLTVLHQDWLNGKEY KCKVSNKALPAPIEKTISKAKGQPREPQVYTLP PSRDELTKNQVSLTCLVKGFYPSDIA VEWESN GQPENNYKTTPPVLDSDGSFFLYSKLTVDKSR WQQGNVFSCSVMHEALHNHYTQKSLSLSPGK | 391 | Lobner et al., Immunol. Rev., 270(1)113-31 (2016) |

TABLE 9-continued

| Exemplary peptide linkers and linker domains | | | | |
|---|---|---|---|---|
| Linker or Multimerization Domain | Cluster | Exemplary Sequence | SEQ ID NO | Reference |
| Immunoglobulin Fc region ($CH_2CH_3CH_4$) | Dimer | PPKVSVFVPPRDGFFGNPRKSKLICQATGFSPR QIQVSWLREGKQVGSGVTTDQVQAEAKESGP TTYKVTSTLTIKESDWLSQSMFTCRVDHRGLT FQQNASSMCVPDQDTAIRVFAIPPSFASIFLTKS TKLTCLVTDLTTYDSVTISWTRQNGEAVKTHT NISESHPNATFSAVGEASICEDDWNSGERFTCT VTHTDLPSPLKQTISRPKGVALHRPDVYLLPPA REQLNLRESATITCLVTGFSPADVFVQWMQRG QPLSPEKYVTSAPMPEPQAPGRYFAHSILTVSE EEWNTGETYTCVVAHEALPNRVTERTVDKST GKPTLYNVSLVMSDTAGTCY | 406 | pir\|\|S37768 |
| Immunoglobulin $C_L$ | Dimer (pairing with $CH_1$) | GQPKANPTVTLFPPSSEELQANKATLVCLISDF YPGAVTVAWKADGSPVKAGVETTKPSKQSNN KYAASSYLSLTPEQWKSHRSYSCQVTHEGSTV EKTVAPTECS | 392 | |
| Immunoglobulin $CH_1$ | Dimer (pairing with $C_L$) | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKRV EPKSC | 393 | |
| Immunoglobulin $CH_2$ | Dimer (pairing with $CH_2$) | TCPPCPAPELLGGPSVFLFPPKPKDTLMISRTPE VTCVVVDVSHEDPEVKFNWYVDGVEVHNAK TKPREEQYNSTYRVVSVLTVLHQDWLNGKEY KCKVSNKALPAPIEKTISKAKGQPRE | 394 | |
| Immunoglobulin $CH_3$ | Dimer (pairing with $CH_3$) | PQVYTLPPSRDELTKNQVSLTCLVKGFYPSDIA VEWESNGQPENNYKTTPPVLDSDGSFFLYSKL TVDKSRWQQGNVFSCSVMHEALHNHYTQKSL SLSPGK | 395 | |
| Immunoglobulin $CH_4$ | Dimer (pairing with $CH_4$) | PDVYLLPPAREQLNLRESATITCLVTGFSPADV FVQWMQRGQPLSPEKYVTSAPMPEPQAPGRY FAHSILTVSEEEWNTGETYTCVVAHEALPNRV TERTVDKSTGK | 396 | pir\|\|S37768 |
| Alkaline phosphatase | Dimer | MWWRLWWLLLLLLLLWGSSASAAIIPVEEEN PDFWNREAAEALGAAKKLQPAQTAAKNLIIFL GDGMGVSTVTAARILKGQKKDKLGPEIPLAM DRFPYVALSKTYNVDKHVPDSGATATAYLCG VKGNFQTIGLSAAARFNQCNTTRGNEVISVMN RAKKAGKSVGVVTTTRVQHASPAGTYAHTVN RNWYSDADVPASARQEGCQDIATQLISNMDID VILGGGRKYMFRMGTPDPEYPDDYSQGGTRL DGKNLVQEWLAKRQGARYVWNRTELMQASL DPSVTHLMGLFEPGDMKYEIHRDSTLDPSLME MTEAALRLLSRNPRGFFLFVEGGRIDHGHHES RAYRALTETIMFDDAIERAGQLTSEEDTLSLVT ADHSHVFSFGGYPLRGSSIFGLAPGKARDRKA YTVLLYGNGPGYVLKDGARPDVTESESGSPEY RQQSAVPLDEETHAGEDVAVFARGPQAHLVH GVQEQTFIAHVMAFAACLEPYTACDLAPPAGT TDAAHPGYSRVGAAGRFEQT | 397 | BBD75655.1 |
| Glutathione-s-transferase | Dimer | MKLVGSYTSPFVRKLSILLLEKGITFEFINELPY NADNGVAQFNPLGKVPVLVTEEGECWFDSPII AEYIELMNVAPAMLPRDPLESLRVRKIEALAD GIMDAGLVSVREQARPAAQQSEDELLRQREKI NRSLDVLEGYLVDGTLKTDTVNLATIAIACAV GYLNFRRVAPGWCVDRPHLVKLVENLFSRESF ARTEPPKA | 398 | WP_000779792 |
| bHLH-Leucine Zipper | Trimer | LENHSRRLEMTNKQLWLRIQEL | 399 | Napolitano and Ballabio, J. Cell Sci., 129(13):2475-81 (2016) |
| Leucine/ Isoleucine Zipper | Trimer | LSIIAICLGSLGLILIILLSVVVWKLL | 400 | Branttie and Dutch, J. Gen Virol., 101(5):467-472 (2020) |

TABLE 9-continued

Exemplary peptide linkers and linker domains

| Linker or Multimerization Domain | Cluster | Exemplary Sequence | SEQ ID NO | Reference |
|---|---|---|---|---|
| Collagen-like Peptide | Trimer | GPP(GPP)$_n$, where n ≥ 0 | 401 | Fan et al., FASEB J., 22:3795-3804 (2008). |
| p53 Tetramerization Domain | Tetramer | EYFTLQIRGRERFEMFRELNEALELKDAQAG | 402 | Gencel-Augusto et al., Genes Dev., 34(17-18):1128-1146 (2020) |
| Streptavidin (SA) | Tetramer | MAEAGITGTWYNQLGSTFIVTAGADGALTGT YESAVGNAEGDYVLTGRYDSAPATDGSGTAL GWTVAWKNNYRNAHSATTWSGQYVGGAEA RINTQWLLTSGTTEANAWKSTLVGHDTFTKV KPSAAS | 403 | Chivers et al., Biochem J., 435(Pt 1):55-63 (2011) |
| T4 Fibritin | Trimer | GYIPEAPRDGQAYVRKDGEWVLLSTFL | 404 | Yang et al., J. Virol., 76(9):4634-42 (2002) |
| COMP (cartilage oligomeric matrix protein) | Pentamer | GPQMLRELGETNAALQDVRELLRQQVREITFL KNTVMECDAC | 405 | Holler et al., J. Immunol. Methods, 237:159-173 (2000) |
| Dextramers + SA | 3, 6 or 13 SA per Dextramer | Dextran polymer scaffold | N/A | Dolton et al., Clin. Exp. Immunol., 177(1):47-63 (2014) |
| DMGS + SA | Octamers | Di-maleimide-di-glycine-serine | N/A | Guillaume et al., J. Biol. Chem., 278:P4500-4509 (2003) |
| Linker A | N/A | SRGGGGSGGGGSGGGGSLEMA | 343 | N/A |
| Linker 1 | N/A | GGGGS | 344 | N/A |
| Linker 2 | N/A | GS(GS)$_n$, where n ≥ 0 | 345 | N/A |
| Linker 3 | N/A | (GSGGS)$_n$, where n ≥ 1 | 346 | N/A |
| Linker 4 | N/A | (GGGGS)$_n$, where n ≥ 1 | 347 | N/A |
| Linker 5 | N/A | (GGGS)$_n$, where n ≥ 1 | 348 | N/A |

Any of the linkers described in Table 9 are compatible with the chimeric proteins provided herein. In some embodiments, the mucoadhesive peptide fragment is fused to a polypeptide chain of the target-binding moiety via any of the linkers provided in Table 9, or variants thereof. In some embodiments, the mucoadhesive peptide fragment is fused to a polypeptide chain of the target-binding moiety via a linker comprising at least about 90% sequence identity (such as about n % sequence identity, where n % is selected from 91%, 92%, 93%, 94%, 95%, 96%, 97%, 98%, and 99%) to the amino acid sequence of any one of SEQ ID NOs: 343-348 and 391-406. In some embodiments, the linker comprises the amino acid sequence of any one of SEQ ID NOs: 343-348 and 391-406. It should be understood that the linkers provided in Table 9 are exemplary, and other linkers with similar properties would similarly be compatible with the chimeric proteins provided herein.

In some embodiments, the peptide linker comprises a constant region of a full-length antibody, or a fragment thereof. In some embodiments, the peptide linker comprises the complete constant region of a full-length antibody. In some embodiments wherein the full-length antibody is IgG, IgA, or IgD, the peptide linker comprises the $CH_1$, $CH_2$, and $CH_3$ domains. In some embodiments wherein the full-length antibody is IgE or IgM, the peptide linker comprises the $CH_1$, $CH_2$, $CH_3$, and $CH_4$ domains. In some embodiments, the peptide linker comprises a fragment of a constant region of a full-length antibody. In some embodiments, the peptide linker comprises a $CH_1$ domain or a fragment thereof. In some embodiments, the peptide linker comprises a $CH_2$ domain or a fragment thereof. In some embodiments, the peptide linker comprises a $CH_3$ domain or a fragment thereof. In some embodiments, the peptide linker comprises a $CH_4$ domain or a fragment thereof. In some embodiments, the peptide linker comprises a CL domain or a fragment thereof.

Immunoglobulin Fc regions, or fragments thereof, may be used as the peptide linker or a portion thereof. Fc region may facilitate dimerization and retain antibody-like properties, including physicochemical characteristics for expression, purification and storage, and long serum half-life in vivo. Such properties would be advantageous to the chimeric proteins provided herein. In some embodiments, the peptide linker comprises an Fc region or a fragment thereof. In some embodiments, the Fc region comprises a $CH_2$ and $CH_3$ domain. In some embodiments, the Fc region comprises a $CH_2$, $CH_3$, and $CH_4$ domain.

In some embodiments, the peptide linker comprises an enzymatic tag, such as a detectable enzymatic tag. In some embodiments, the enzymatic tag functions as a dimer. In some embodiments, the enzymatic tag is an alkaline phosphatase. In some embodiments, the enzymatic tag is a glutathione-s-transferase (GST).

Additional peptide linkers or useful domains to be included in linkers described herein may be used to facilitate stable protein:protein interactions in the chimeric proteins of the present invention. In some embodiments, the linker comprises a domain that facilitates protein:protein interactions. In some embodiments, the linker comprises one or more heptad repeats. The term "heptad repeat" as used herein refers to a structural motif that consists of a repeating pattern of seven amino acids. In some embodiments, the heptad repeat comprises the repeating pattern: "H P P H C P C", wherein "H" represents a hydrophobic amino acid residue, "C" typically represents a charged amino acid residue, and "P" represents a polar (hydrophilic) amino acid residue. In some embodiments, the linker comprises the heptad repeats of a basic helix-loop-helix leucine zipper (bZIP) domain. In some embodiments, the linker comprises the heptad repeats of a basic isoleucine bZIP domain. In some embodiments, the heptad repeat forms a protein trimer.

Glycine-X-Y repeats (e.g., $GPP(GPP)_n$, where $n \geq 0$) have been shown not to interfere with the functionality or safety profile of fusion proteins (e.g., chimeric proteins). In some embodiments, the linker comprises one or more $(GPP)_n$, where $n \geq 1$, motifs. In some embodiments, the linker comprises a collagen-like protein. In some embodiments, the collagen-like protein forms a protein trimer.

Other, higher order, multimerization domains may be incorporated in the linkers provided herein. In some embodiments, the multimerization domains may form self-assembling complexes. In some embodiments, the linker comprises an affinity moiety. In some embodiments, the linker comprises a streptavidin (SA) protein. In some embodiments, the streptavidin protein forms a tetramer with biotin molecules. In some embodiments, the linker comprises a dextran scaffold domain. In some embodiments, the linker comprises a SA protein and a dextran scaffold domain. In some embodiments, the linker comprises one or more maleimide polymers (DMGS). In some embodiments, the linker comprises one or more malemide polymers and a SA protein. In some embodiments, the linker comprises a p53 tetramerization domain. In some embodiments, the linker comprises a bacteriophage T7 fibritin protein, or a portion thereof. In some embodiments, the linker comprises the C-terminal 27 amino acids of the bacteriophage T7 fibritin protein. In some embodiments, the C-terminal 27 amino acids of the bacteriophage T7 fibritin protein forms a trimeric complex. In some embodiments, the linker comprises one or more coiled-coil structural domains. In some embodiments, the linker comprises a cartilage oligomeric matrix protein (COMP), or a portion thereof. In some embodiments, the liner comprises a coiled-coil domain of the COMP. In some embodiments, the coiled-coil domain of the COMP forms a pentameric complex.

III. Methods of Prevention and Treatment, Methods of Killing a Virus, Methods of Neutralizing a Virus, Methods of Activating Complement Pathway The present application further provides methods of preventing or treating an infection caused by an influenza virus or variant thereof in an individual, comprising administering to the individual an effective amount of any one of the chimeric proteins described herein, or a cocktail composition of chimeric proteins described herein. In some embodiments, the method comprises administering to the individual a pharmaceutical composition, such as any of the pharmaceutical compositions provided herein, comprising an effective amount of any one of the chimeric proteins described herein, or a cocktail composition of chimeric proteins described herein. In some embodiments, the method is for preventing an infection caused by an influenza virus or variant thereof in an individual (e.g., a human or an animal). In some embodiments, the method is for treating an infection caused by influenza virus or variant thereof in an individual. In some embodiments, the influenza virus comprises an HA antigen, such as an HA antigen selected from the group consisting of H1, H2, H3, H5, H6, H7, H9, and H10, or a variant or reassortant thereof. In some embodiments, the influenza virus comprises an NA antigen, such as an NA antigen selected from the group consisting of N1, N2, N3, N7, N8, and N9, or a variant or reassortant thereof. In some embodiments, the influenza virus is selected from the group consisting of H1N1, H1N2, H2N2, H3N2, H3N8, H5N1, H5N9, H6N1, H7N2, H7N3, H7N7, H7N9, H9N2, H10N7, or a variant or reassortant thereof. In some embodiments, the method is for activation of complement pathway in an individual. In some embodiments, the method is an in vitro method for killing or neutralizing an influenza virus. In some embodiments, the method is for killing or neutralizing an influenza virus in an individual. In some embodiments, the method is for preventing, treating, or reducing infection caused by an influenza virus in an individual, wherein at least one virus is killed or neutralized on the mucosa. Use of the chimeric in prevention or treatment of an infection, for activating the complement pathway, or for killing or neutralizing a virus, and use of the chimeric proteins in the preparation of a medicament for preventing or treating an infection, for activating the complement pathway, or for killing or neutralizing a virus, are also provided. Methods of veterinary use are also contemplated herein.

In some embodiments, there is provided a method of preventing or treating an infection caused by an influenza virus or variant thereof that infects through a mucosa in an individual, comprising administering to the individual an effective amount of a chimeric protein comprising: (a) an antibody moiety that specifically binds to a component of an influenza virus or a variant thereof; and (b) a mucoadhesive peptide fragment comprising at least about 5 positively charged amino acid residues, wherein the mucoadhesive peptide fragment facilitates attachment of the chimeric protein to a mucosa.

In some embodiments, there is provided a method of activating the complement pathway in an individual infected with a virus (e.g., an influenza virus or variant thereof), comprising administering to the individual an effective amount of a chimeric protein comprising administering to the individual an effective amount of a chimeric protein comprising: (a) an antibody moiety that specifically binds to a component of an influenza virus or a variant thereof; and (b) a mucoadhesive peptide fragment comprising at least about 5 positively charged amino acid residues, wherein the mucoadhesive peptide fragment facilitates attachment of the chimeric protein to a mucosa. In some embodiments, at least one virus is killed or neutralized on the mucosa. In some embodiments, the virus is an influenza virus.

In some embodiments, there is provided a method of killing or neutralizing a virus (e.g., an influenza virus or variant thereof) in an individual, comprising administering to the individual an effective amount of a chimeric protein comprising: (a) an antibody moiety that specifically binds to a component of an influenza virus or a variant thereof; and (b) a mucoadhesive peptide fragment comprising at least about 5 positively charged amino acid residues, wherein the mucoadhesive peptide fragment facilitates attachment of the chimeric protein to a mucosa. In some embodiments, at least one virus is killed or neutralized on the mucosa. In some embodiments, the killing or neutralization is via activation of the complement pathway. In some embodiments, the virus is an influenza virus.

In some embodiments, there is provided an in vitro method of killing or neutralizing a virus (e.g., an influenza virus or variant thereof), comprising contacting the virus with a chimeric protein comprising: (a) an antibody moiety that specifically binds to a component of an influenza virus or a variant thereof; and (b) a mucoadhesive peptide fragment comprising at least about 5 positively charged amino acid residues, wherein the mucoadhesive peptide fragment facilitates attachment of the chimeric protein to a mucosa, in the presence of at least one component of the complement system. In some embodiments, the at least one component of the complement system is C1, C4, or membrane attack complex (MAC). In some embodiments, the at least one component of the complement system is CL. In some embodiments, the at least one component of the complement system is C4. In some embodiments, the C4 is involved in the neutralization of the virus. In some embodiments, the at least one component of the complement system is MAC. In some embodiments, the MAC is involved in the killing of the virus. In some embodiments, at least one virus is killed or neutralized on the mucosa. In some embodiments, the killing or neutralization is via activation of the complement pathway. In some embodiments, the virus is an influenza virus.

In some embodiments, there is provided a method of preventing, treating, or reducing infection caused by a virus (e.g., an influenza virus or variant thereof) in an individual, comprising administering to the individual a chimeric protein comprising: (a) an antibody moiety that specifically binds to a component of an influenza virus or a variant thereof; and (b) a mucoadhesive peptide fragment comprising at least about 5 positively charged amino acid residues, wherein the mucoadhesive peptide fragment facilitates attachment of the chimeric protein to a mucosa, wherein at least one virus is killed or neutralized on the mucosa. In some embodiments, the chimeric protein induces an immune response in the individual. In some embodiments, the chimeric protein activates the complement pathway in the individual. In some embodiments, the at least one virus is killed or neutralized on the mucosa via activation of the complement pathway. In some embodiments, the virus is an influenza virus.

In some embodiments, the chimeric protein is administered to the individual before the individual is exposed to the influenza virus or variant thereof. In some embodiments, the chimeric protein is administered to the individual within about any one of n hours from exposure of the individual to the influenza virus or variant thereof, where n hours is selected from 72 hours, 48 hours, 36 hours, 24 hours, 12 hours, 6 hours, 4 hours, or less. In some embodiments, administration of the chimeric protein to the individual protects the individual from infection by the pathogen for about n days, where n is selected from 1, 2, 3, 4, 5, 6, 7, 8, 9, 10, 11, 12, 13, 14, or more. In some embodiments, the chimeric protein is administered topically to the mucosa. In some embodiments, the chimeric protein is administered via a nasal spray, an inhaler, a nebulizer, or an eye drop. In some embodiments, the chimeric protein is administered to both nostrils of the individual. In some embodiments, the chimeric protein is administered once every two days, once daily, or twice daily.

In some embodiments, the individual is a mammal (e.g., human, non-human primate, rat, mouse, cow, horse, pig, sheep, goat, dog, cat, etc.). In some embodiments, the individual is a human. In some embodiments, the individual is a clinical patient, a clinical trial volunteer, an experimental animal, etc. In some embodiments, the individual is younger than about 60 years old (such as younger than about n years old, where n years old is selected from 50, 40, 30, 25, 20, 15, and 10 years old). In some embodiments, the individual is about 60 years old or older (such as older than about n years old, where n years old is selected from 70, 80, 90, and 100 years old). In some embodiments, the individual has not been exposed to the influenza virus or variant thereof. In some embodiments, the individual is diagnosed with influenza, such as H1N1, H1N2, H2N2, H3N2, H3N8, H5N1, H5N9, H6N1, H7N2, H7N3, H7N7, H7N9, H9N2, H10N7, or a variant or reassortant thereof. In some embodiments, the individual is diagnosed with an influenza variant. In some embodiments, the individual is at a risk of developing severe symptoms of the influenza infection. In some embodiments, the individual has an underlying medical condition, such as cardiovascular disease, diabetes, chronic respiratory disease, and/or cancer.

In some embodiments, the method is for preventing or treating infection by one or more influenza variants. In some embodiments, the method prevents or treats infection by a plurality (e.g., 2, 3, 4, 5, 6, 7, 8, 9, 10, or more) of influenza variants.

In some embodiments, there is provided a method of treating or preventing infection of an individual by a plurality of influenza variants, comprising administering to the individual an effective amount of a pharmaceutical composition (e.g., a cocktail composition) comprising a plurality of chimeric proteins, wherein the plurality of chimeric proteins each comprises: (a) an antibody moiety that specifically binds to a component of an influenza virus or a variant thereof; and (b) a mucoadhesive peptide fragment comprising at least about 5 positively charged amino acid residues, wherein the mucoadhesive peptide fragment facilitates attachment of the chimeric protein to a mucosa. In some embodiments, the plurality of chimeric proteins each comprise a different antibody moiety that specifically recognize different influenza variants. In some embodiments, the antibody moiety is derived from a neutralizing antibody that specifically binds to an viral surface protein, such as HA or NA, of an influenza virus, e.g., an anti-HA or anti-NA antibody. For example, the pharmaceutical composition may comprise a cocktail of chimeric proteins each comprising an antibody fragment derived from a different anti-HA or anti-NA antibody described herein or known in the art. In some embodiments, the mucoadhesive peptide fragment comprises at least 5 positively charged amino acid residues interspersed with one or more non-positively charged amino acid residues. In some embodiments, the chimeric protein is administered via a nasal spray.

In some embodiments, there is provided a method of treating or preventing infection of an individual by a plurality of influenza variants, comprising administering to the individual an effective amount of a chimeric protein comprising: (a) an antibody moiety that specifically binds to a component of an influenza virus or a variant thereof; and (b) a mucoadhesive peptide fragment comprising at least about 5 positively charged amino acid residues, wherein the mucoadhesive peptide fragment facilitates attachment of the chimeric protein to a mucosa of the individual. In some embodiments, the antibody moiety is derived from a neutralizing antibody that specifically binds to a HA protein of an influenza virus or variant thereof, e.g., an anti-HA antibody. In some embodiments, the antibody moiety is derived from a neutralizing antibody that specifically binds to a NA protein of an influenza virus or variant thereof, e.g., an anti-NA antibody. In some embodiments, the positively charged amino acid residues are interspersed with non-positively charged amino acid residues. In some embodiments, the chimeric protein is administered via a nasal spray.

In some embodiments, the chimeric protein, e.g., any of the anti-HA or anti-NA chimeric proteins or other constructs of the present application, is administered as a single agent, or in combination with a second, third, or fourth agent (including, e.g., anti-viral drugs, convalescent plasma, anti-inflammatory drugs etc.) to treat the infection, kill the virus, neutralize the virus, and/or activate the complement pathway.

Efficacy of the treatments can be evaluated, for example, by viral load (e.g., via detection of viral DNA), duration of survival, quality of life, viral protein expression and/or activity, detection of serological antibodies against the influenza virus or variant thereof, assessment of respiratory functions, and/or Computerized Tomography (CT) imaging.

IV. Nucleic Acids and Methods of Preparation

Nucleic acid molecules encoding the chimeric proteins described herein are contemplated. In some embodiments, the nucleic acid molecules encode the anti-HA or anti-NA chimeric proteins described herein. In some embodiments, there is provided a nucleic acid (such as an isolated nucleic acid) encoding any of the chimeric proteins described herein. In some embodiments, the nucleic acid (such as an isolated nucleic acid) encodes the complete amino acid sequence or sequences of any of the chimeric proteins described herein. In some embodiments, there is provided a set of nucleic acids (such as a set of isolated nucleic acids) encoding any of the chimeric proteins described herein. For example, different polypeptides of a chimeric protein, such as any of the chimeric proteins described herein, may be encoded by different nucleic acids (such as isolated nucleic acids) within the set of nucleic acids (such as a set of isolated nucleic acids). Nucleic acid molecules may be constructed using recombinant DNA techniques conventional in the art. In some embodiments, a nucleic acid molecule is an expression vector that is suitable for expression in a selected host cell.

Vectors comprising polynucleotides that encode the chimeric proteins described herein are also provided. In some embodiments, the vectors comprise polynucleotides encoding the anti-HA or anti-NA chimeric proteins described herein. In some embodiments, the vectors comprise a nucleic acid encoding any of the chimeric proteins described herein. In some embodiments, a vector comprises a nucleic acid sequence encoding the complete amino acid sequence or sequences of any of the chimeric proteins described herein. In some embodiments, there is provided a set of vectors comprising different nucleic acids encoding different polypeptides of any of the chimeric proteins described herein. Such vectors include, but are not limited to, DNA vectors, phage vectors, viral vectors, retroviral vectors, etc.

In various embodiments, the chimeric proteins described herein may be expressed in prokaryotic cells, such as bacterial cells; or in eukaryotic cells, such as fungal cells (such as yeast cells), plant cells, insect cells, and mammalian cells. In some embodiments, the anti-HA or anti-NA chimeric proteins described herein may be expressed in prokaryotic cells, such as bacterial cells; or in eukaryotic cells, such as fungal cells (such as yeast cells), plant cells, insect cells, and mammalian cells. In some embodiments, a nucleic acid encoding any of the chimeric proteins described herein may be expressed in prokaryotic cells, such as bacterial cells; or in eukaryotic cells, such as fungal cells (such as yeast cells), plant cells, insect cells, and mammalian cells. In some embodiments, a set of nucleic acids encoding any of the chimeric proteins described herein may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells (Crucell); and NSO cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Non-limiting exemplary methods are described, e.g., in Sambrook et al., Molecular Cloning, A Laboratory Manual, $3^{rd}$ ed. Cold Spring Harbor Laboratory Press (2001). Nucleic acids may be transiently or stably transfected in the desired host cells, according to any suitable method.

The invention also provides host cells comprising any of the nucleic acids or vectors described herein. In some embodiments, the invention provides a host cell comprising a chimeric protein described herein. In some embodiments, the invention provides a host cell comprising the anti-HA or anti-NA chimeric proteins described herein. In some embodiments, the invention provides a host cell comprising a nucleic acid encoding any of the chimeric proteins described herein. In some embodiments, the nucleic acid encodes the complete amino acid sequence or sequences of any of the chimeric proteins described herein. In some embodiments, the invention provides a host cell comprising a set of nucleic acids encoding any of the chimeric proteins described herein. In some embodiments, the invention provides a host cell comprising a vector that contains a nucleic acid encoding any of the chimeric proteins described herein. In some embodiments, the vector comprises a nucleic acid sequence encoding the complete amino acid sequence or sequences of any of the chimeric proteins described herein. In some embodiments, the invention provides a host cell comprising a set of vectors comprising different nucleic acids encoding different polypeptides of any of the chimeric proteins described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. Suitable non-mammalian host cells include prokaryotes (such as *E. coli* or *B. subtilis*) and yeast (such as *S. cerevisae, S. pombe*; or *K. lactis*).

The chimeric proteins described herein, the anti-HA or anti-NA chimeric proteins described herein, an isolated nucleic acid encoding any of the chimeric proteins described herein, and/or a set of isolated nucleic acids encoding any of the chimeric proteins described herein may be purified by any suitable method. Such methods include, but are not limited to, the use of affinity matrices or hydrophobic interaction chromatography. Suitable affinity ligands include ligands that bind antibody constant regions. For example, a Protein A, Protein G, Protein A/G, or an antibody affinity column may be used to bind the constant region and to purify a chimeric protein or anti-HA or anti-NA antibody comprising an Fc region. Hydrophobic interactive chromatography, for example, a butyl or phenyl column, may also be suitable for purifying some polypeptides such as antibodies. Ion exchange chromatography (e.g., anion exchange chromatography and/or cation exchange chromatography) may be also suitable for purifying some polypeptides such as antibodies. Mixed-mode chromatography (e.g., reversed phase/anion exchange, reversed phase/cation exchange, hydrophilic interaction/anion exchange, hydrophilic interaction/cation exchange, etc.) may also be suitable for purifying some polypeptides such as antibodies. Many methods of purifying polypeptides are known in the art.

V. Pharmaceutical Compositions, Kits, and Articles of Manufacture

A. Pharmaceutical Composition

One aspect of the present application provides compositions (e.g., pharmaceutical compositions) comprising any one of the chimeric proteins described herein. In some embodiments, the pharmaceutical composition is suitable for nasal administration. In some embodiments, the pharmaceutical composition is suitable for respiratory (e.g., upper respiratory airway) administration. In some embodiments, the pharmaceutical composition is suitable for administration by inhalation. In some embodiments, the pharmaceutical composition is a nasal spray formulation.

In some embodiments, the pharmaceutical composition comprises a pharmaceutically acceptable carrier. In some embodiments, the pharmaceutical composition comprises a citrate-buffered saline carrier. In some embodiments, the pharmaceutical composition comprises a stabilizing agent, a viscosity enhancing agent, a surfactant, and/or a preservative. In some embodiments, the pharmaceutical composition comprises 25 mM citrate buffer, pH 6.5, 100 mM NaCl, 0.1% methionine, 0.02% polysorbate 80, and 0.1% potassium sorbate. In some embodiments, the pharmaceutical composition comprises 25 mM citrate buffer, pH 6.5, 125 mM NaCl, 5% glycerin, 0.1% methionine, 0.02% polysorbate 80, and 0.1% potassium sorbate.

In some embodiments, the pharmaceutical composition comprises a single type of chimeric protein. In some embodiments, the pharmaceutical composition comprises at least two chimeric proteins, wherein the two chimeric proteins have different antibody moieties. In some embodiments, the pharmaceutical composition comprises a plurality (e.g., 2, 3, 4, 5, 6, 7, 8, 9, 10, 15, 20, or more) of chimeric proteins, wherein the antibody moieties of the chimeric proteins are different from each other. In some embodiments, the pharmaceutical composition comprises a cocktail of chimeric proteins that target different component of the same influenza virus and/or the same component of different variants (e.g., strains) of an influenza virus. In some embodiments, the chimeric proteins in the cocktail composition each comprise the same mucoadhesive peptide fragment(s). In some embodiments, the chimeric proteins in the cocktail composition each comprise different mucoadhesive peptide fragment(s).

In some embodiments, the pharmaceutical composition is formulated for topical administration to a mucosa, such as nasal mucosa, larynx mucosa, trachea mucosa, bronchi mucosa, lung mucosa, eye mucosa, and combinations thereof. In some embodiments, the pharmaceutical composition is formulated for administration via a nasal spray, an inhaler, a nebulizer, or an eye drop.

In some embodiments, there is provided a pharmaceutical composition comprising: (a) a chimeric protein comprising an antibody moiety that specifically binds to a component of an influenza virus or a variant thereof, and a mucoadhesive peptide fragment comprising at least about 5 (e.g., about 5 to about 30 such as about 12) positively charged amino acid residues (e.g., lysine, histidine, arginine, ornithine, or combinations thereof), wherein the mucoadhesive peptide fragment facilitates attachment of the chimeric protein to a mucosa, (b) a stabilizing agent that maintains the weak reducing environment in nasal area, (c) a buffering agent, and (d) an osmolality adjusting agent, wherein the pharmaceutical composition has a pH of about 4.5 to about 7.5 (e.g., about 6.0 to about 7.0), and wherein the pharmaceutical composition has an osmolality of about 230 to about 330 Osm/kg (e.g., about 250 to about 300 Osm/kg). In some embodiments, the antibody specifically binds an influenza virus viral surface protein or fragment thereof, and/or an influenza virus variant viral surface protein or fragment thereof. In some embodiments, the viral surface protein is HA. In some embodiments, the viral surface protein is NA. In some embodiments, the antibody moiety is any one of the anti-influenza (e.g., anti-HA or anti-NA) antibody moieties as described in Section II. In some embodiments, the chimeric protein is any one of the chimeric proteins described in Section II. In some embodiments, the positively charged amino acid residues are interspersed with one or more non-positively charged amino acid residues. In some embodiments, the pharmaceutical composition further comprises a viscosity-enhancing agent. In some embodiments, the pharmaceutical composition further comprises a surfactant. In some embodiments, the formulation further comprises a preservative.

In some embodiments, there is provided a pharmaceutical composition for nasal administration comprising: (a) a chimeric protein comprising an antibody moiety that specifically binds to a component of an influenza virus or a variant thereof, and a mucoadhesive peptide fragment comprising at least about 5 (e.g., about 5 to about 30 such as about 12) positively charged amino acid residues (e.g., lysine, histidine, arginine, ornithine, or combinations thereof), wherein the mucoadhesive peptide fragment facilitates attachment of the chimeric protein to a mucosa, (b) a methionine, (c) a buffering agent, (d) an osmolality adjusting agent, (e) a viscosity enhancing agent, (f) a surfactant, and (g) a preservative, wherein the pharmaceutical composition has a pH of about 4.5 to about 7.5 (e.g., about 6.0 to about 7.0), and wherein the pharmaceutical composition has an osmolality of about 230 to about 330 Osm/kg (e.g., about 250 to about 300 Osm/kg). In some embodiments, the antibody specifically binds an influenza virus viral surface protein or fragment thereof, and/or an influenza virus variant viral surface protein or fragment thereof. In some embodiments, the viral surface protein is HA. In some embodiments, the viral surface protein is N A. In some embodiments, the antibody moiety anti-influenza (e.g., anti-HA or anti-NA) antibody moieties as described in Section II. In some embodiments, the chimeric protein is any one of the chimeric proteins described in Section II. In some embodiments, the positively charged amino acid residues are interspersed with one or more non-positively charged amino acid residues.

In some embodiments, there is provided a pharmaceutical composition for nasal administration comprising: (a) a chimeric protein comprising an antibody moiety that specifically binds to a component of an influenza virus or a variant thereof, and a mucoadhesive peptide fragment comprising at least about 5 (e.g., about 5 to about 30 such as about 12) positively charged amino acid residues (e.g., lysine, histidine, arginine, ornithine, or combinations thereof), wherein the mucoadhesive peptide fragment facilitates attachment of the chimeric protein to a mucosa, (b) a methionine, (c) a citrate buffer, and (d) NaCl, wherein the pharmaceutical composition has a pH of about 4.5 to about 7.5 (e.g., about 6.0 to about 7.0), and wherein the pharmaceutical composition has an osmolality of about 230 to about 330 Osm/kg (e.g., about 250 to about 300 Osm/kg). In some embodiments, the antibody specifically binds an influenza virus viral surface protein or fragment thereof, and/or an influenza virus variant viral surface protein or fragment thereof. In some embodiments, the viral surface protein is I A. In some embodiments, the viral surface protein is NA. In some embodiments, the antibody moiety anti-influenza (e.g., anti-HA or anti-NA) antibody moieties as described in Section II. In some embodiments, the chimeric protein is any one of the chimeric proteins described in Section II. In some embodiments, the positively charged amino acid residues are interspersed with one or more non-positively charged amino acid residues. In some embodiments, the pharmaceutical composition further comprises a viscosity-enhancing agent (e.g., glycerin). In some embodiments, the pharmaceutical composition further comprises a surfactant (e.g., polysorbate 80). In some embodiments, the pharmaceutical composition further comprises a preservative (e.g., potassium sorbate).

In some embodiments, there is provided a pharmaceutical composition for nasal administration comprising: (a) a chimeric protein comprising an antibody moiety that specifically binds to a component of an influenza virus or a variant thereof, and a mucoadhesive peptide fragment comprising at least about 5 (e.g., about 5 to about 30 such as about 12) positively charged amino acid residues (e.g., lysine, histidine, arginine, ornithine, or combinations thereof), wherein the mucoadhesive peptide fragment facilitates attachment of the chimeric protein to a mucosa at a concentration of about 0.6 mg/mL to about 1 mg/mL (e.g., about 1 mg/mL to about 3 mg/mL), (b) a methionine at about 0.05% to 0.2% (e.g., about 0.075% to about 0.125%) (w/w), (c) a citrate buffer at about 20 mM to about 50 mM (e.g., about 20 mM to about 30 mM), (d) NaCl at about 100 mM to about 150 mM (e.g., about 110 mM to about 130 mM), (e) glycerin at about 1% to about 10% (e.g., about 2.5% to about 7.5%) (w/w), (f) polysorbate 80 at about 0.01% to about 0.1% (e.g., about 0.01% to about 0.05%) (w/w), and (g) potassium polysorbate at about 0.05% to 0.2% (e.g., about 0.075% to about 0.125%) (w/w), wherein the pharmaceutical composition has a pH of about 4.5 to about 7.5 (e.g., about 6.0 to about 7.0). In some embodiments, the pharmaceutical composition comprises about 25 mM citrate at pH 6.5, about 125 mM NaCl, about 5% glycerin, about 0.1% methionine, about 0.02% polysorbate 80, and about 0.1% potassium sorbate. In some embodiments, the antibody specifically binds an influenza virus viral surface protein or fragment thereof, and/or an influenza virus variant viral surface protein or fragment thereof. In some embodiments, the viral surface protein is HA. In some embodiments, the viral surface protein is NA. In some embodiments, the antibody moiety anti-influenza (e.g., anti-HA or anti-NA) antibody moieties as described in Section II. In some embodiments, the chimeric protein is any one of the chimeric proteins described in Section II. In some embodiments, the positively charged amino acid residues are interspersed with one or more non-positively charged amino acid residues.

In some embodiments, the pharmaceutical composition described herein is for administration via a nasal spray. In some embodiments, the pharmaceutical composition is for prophylactic use. In some embodiments, the pharmaceutical composition maintains the stability (including physical and chemical stability) of the antibody at 37° C. for at least about n days, where n is selected from 1, 2, 3, 4, 5, 6, 7, 8, 9, 10, 11, 12, 13, 14, or more days, including any values and ranges in between these values. In some embodiments, the pharmaceutical composition promotes adhesion of the antibody to a mucosa, such as nasal mucosa. In some embodiments, the pharmaceutical composition prolongs the residence time of the antibody in nostrils and other upper respiratory tract areas, for example, by at least about n compared to the antibody in PBS, where n is selected from 12 hours, 24 hours, 2 days, 3 days, 4 days, 5 days, 6 days, 7 days, 8 days, 9 days, 10 days, or more. In some embodiments, the pharmaceutical composition is neutral and gentle to the nasal surfaces. In some embodiments, the pharmaceutical composition is a solution of the antibody. In some embodiments, the pharmaceutical composition is an aqueous solution.

Nasal spray pharmaceutical composition parameters and excipients have been described, for example, in Kulkami and Shaw, *Inhalation,* 10-11 (2021); Thorat, *Scholars Journal of Applied Medical Sciences* (*SJAMS*), 4(8D):2976-2985 (2016), which are incorporated by reference in their entirety. Commonly used excipients for a nasal spray pharmaceutical composition include, but are not limited to, a tonicity agent or osmolality adjustment agent, buffering agent, purging agent, preservative, surfactant, chelating agent, suspending agent, co-solvent, antioxidant, and humectant. Antibody pharmaceutical compositions for various routes of administration, including nasal pharmaceutical composition, have been described, for example, in Cui Y. et al., *Drug Development and Industrial Pharmacy,* 11:28 (2017), which is incorporated herein by reference. Any excipients compatible with the FDA guideline for nasal spray pharmaceutical composition and/or antibody pharmaceutical composition may be used here.

In some embodiments, the pharmaceutical composition has a pH that is compatible with the nasal environment. The average baseline human nasal pH is about 6.3. The optimal pH of the pharmaceutical composition also depends on factors, including, for example, pI of the antibody (including positively charged mucoadhesive peptide), protein stability, net charge of the antibody, etc. In some embodiments, the pharmaceutical composition has a pH of about 4.5 to about 7.5, such as about n, where n is selected from 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, and 7.5, including any values or ranges in between the values. In some embodiments, the pharmaceutical composition has a pH of between about n, where n is selected from 4.5-5.0, 5.0-5.5, 5.5-6.0, 6.0-6.5, 4.5-5.5, 5.5-6.5, 5.0-6.5, 4.5-6.0, 6.5-7.0, 7.0-7.5, 6.0-7.5, 5.5-7, 6-7, and 6.5-7.5. In some embodiments, the pharmaceutical composition has a pH of about 6.5.

For adjusting and buffering pH value, physiologically acceptable acids, bases, salts, and combinations of these may be used. Suitable excipients for lowering the pH value or as acidic components of a buffer system are strong mineral acids, in particular, sulfuric acid and hydrochloric acid. Moreover, inorganic and organic acids of medium strength as well as acidic salts may be used, for example, phosphoric acid, citric acid, tartaric acid, succinic acid, fumaric acid, methionine, acidic hydrogen phosphates with sodium or potassium, lactic acid, glucuronic acid etc. Suitable for raising the pH value or as basic component for buffer system are, in particular, mineral bases such as sodium hydroxide or other alkali and alkaline earth hydroxides and oxides such as, in particular, magnesium hydroxide and calcium hydroxide, ammonium hydroxide and basic ammonium salts such as ammonium acetate, as well as basic amino acids such as lysine, carbonates such as sodium or magnesium carbonate, sodium hydrogen carbonate, citrates such as sodium citrate etc.

In some embodiments, the pharmaceutical composition comprises a citrate buffer. In some embodiments, the citrate buffer contains citric acid and sodium citrate. The citrate buffer has a pKa of about 6.4. In some embodiments, the citrate buffer is present a concentration of about 20 mM to about 50 mM, such as about n mM, where n is selected from 20, 25, 30, 35, 40, 45, and 50, including any values or ranges in between these values. In some embodiments, the citrate buffer is present a concentration of about between about n mM, where n is selected from 20-30, 30-40, 40-50, 25-50, 25-35, and 25-40. In some embodiments, the pharmaceutical composition comprises a citrate buffer at about 25 mM.

In some embodiments, the pharmaceutical composition comprises a phosphate buffer. The phosphate buffer has a pKa of about 7.2.

In some embodiments, the pharmaceutical composition has an osmolality that is close to the nasal environment. In some embodiments, the pharmaceutical composition has an osmolality that facilitates adhesion of the antibody to a mucosa (e.g., nasal mucosa). In some embodiments, the pharmaceutical composition minimizes penetration of the antibody into blood stream. In some embodiments, the pharmaceutical composition has an osmolality of about 230 Osm/kg to about 330 Osm/kg, such as about n Osm/kg, where n is selected from 230, 240, 250, 260, 270, 280, 290, 300, 310, 320, and 330, including any values or ranges in between these values. In some embodiments, the pharmaceutical composition has an osmolality of between about n Osm/kg, where n is selected from 230-250, 250-270, 270-290, 290-310, 310-330, 230-275, 275-300, 300-330, 230-280, 280-330, and 260-320. In some embodiments, the pharmaceutical composition has an osmolality of about 280 Osm/kg. A skilled person in the art could readily convert these osmolality values to osmolality.

In some embodiments, the pharmaceutical composition comprises an osmolality adjusting agent. Exemplary osmolality adjusting agents or tonicity agents include, but are not limited to, sodium, calcium or magnesium chloride, sulfate or phosphate. In some embodiments, the osmolality adjusting agent is sodium chloride. Calcium and magnesium salts may have a positive or auxiliary influence in the inhalation of active agent solutions, possibly because they themselves counteract the local irritations caused by the administration. Alternatively, physiologically safe organic compounds may be used as the osmolality adjusting agent. Particularly suitable are water-soluble substances with a relatively low molecular weight, for example, with a molecular weight of less than 300 or, better still, less than 200 and with a correspondingly high osmotic activity. Examples for such excipients are sugars and sugar alcohols, in particular, trehalose, mannitol, sorbitol and isomalt.

In some embodiments, the pharmaceutical composition comprises about 100 mM to about 150 mM NaCl, such as about n mM NaCl, where n is selected from 100, 105, 110, 115, 120, 125, 130, 135, 140, 145, and 150, including any values or ranges in between these values. In some embodiments, the pharmaceutical composition comprises between about n nM NaCl, where n is selected from 100-120, 120-140, 100-125, 125-150, 130-150, and 110-130. In some embodiments, the pharmaceutical composition comprises about 125 mM NaCl.

In some embodiments, the pharmaceutical composition comprises one or more stabilizing agents. In some embodiments, the stabilizing agent maintains the weak reducing environment in nasal areas. In some embodiments, the one or more stabilizing agents comprises methionine. In some embodiments, the one or more stabilizing agents comprise glycerin. In some embodiments, the one or more stabilizing agents comprise trehalose, e.g., 10% trehalose. In some embodiments, the pharmaceutical composition comprises about 0.05% to about 0.2% (w/w) methionine, such as about n % (w/w) methionine, where n % (w/w) is selected from 0.05%, 0.06%, 0.07%, 0.08%, 0.09%, 0.1%, 0.11%, 0.12%, 0.13%, 0.14%, 0.15%, 0.16%, 0.17%, 0.18%, 0.19%, and 0.2%, including any values or ranges in between these values. In some embodiments, the pharmaceutical composition comprises between about n % (w/w) methionine, where n % (w/w) is selected from any one of 0.05%-0.1%, 0.75%-1.25%, 0.1%-0.15%, 0.15%-0.2%, 0.1%-0.2%, 0.125-0.175%, 0.8%-1.6%, and 0.5%-0.15%. In some embodiments, the pharmaceutical composition comprises about 0.1% (w/w) methionine.

In some embodiments, the pharmaceutical composition comprises a viscosity-enhancing agent. In some embodiments, the viscosity-enhancing agent is selected from the group consisting of glycerin, dextran and hydroxyethylcellulose. In some embodiments, the viscosity-enhancing agent is glycerin. In some embodiments, the pharmaceutical composition comprises about 1% (w/w) to about 10% (w/w) glycerin, such as about n % (w/w) glycerin, where n % (w/w) is selected from 1%, 2%, 3%, 3%, 4%, 5%, 6%, 7%, 8%, 9%, and 10% (w/w), including any values or ranges in between these values. In some embodiments, the pharmaceutical composition comprises between about n % (w/w) glycerin, where n % (w/w) is selected from 1%-4%, 2%-6%, 3%-7%, 5%-8%, 7%-10%, 2.5%-7.5%, 4%-6%, 1%-2.5%, 2.5%-5%, 5%-7.5%, and 7.5%-10% (w/w). In some embodiments, the pharmaceutical composition comprises about 5% (w/w) glycerin.

In some embodiments, the pharmaceutical composition comprises surfactant. In some embodiments, the surfactant allows the antibody to cross a mucosa (e.g., nasal mucosa) and/or allows absorption of the antibody across the mucosa. Suitable surfactants include, in particular, those that are to be considered safe for oral or nasal inhalation or mucosal administration. Examples of surfactants with particularly good physiological compatibility include tyloxapol, polysorbates (such as polysorbate 20, polysorbate 80), PEG400, PEG3500, polyoxyl 400 stearate, vitamin E-TPGS, and macrogol hydroxystearates such as macrogol-15-hydroxystearate. In some embodiments, the surfactant is polysorbate 80. In some embodiments, the pharmaceutical composition comprises about 0.01% (w/w) to about 0.1% (w/w) polysorbate 80, such as about n % (w/w) polysorbate 80, where n % (w/w) is selected from 0.01%, 0.02%, 0.03%, 0.04%, 0.05%, 0.06%, 0.07%, 0.08%, 0.09%, and 0.1% (w/w), including any values or ranges in between these values. In some embodiments, the pharmaceutical composition comprises between about n % (w/w) polysorbate 80, where n % (w/w) is selected from 0.01%-0.02%, 0.02%-0.05%, 0.05%-0.1%, 0.01%-0.05%, 0.02%-0.04%, 0.04%-0.08%, 0.02%-0.08%, and 0.02%-0.1% (w/w). In some embodiments, the pharmaceutical composition comprises about 0.02% (w/w) polysorbate 80.

In some embodiments, the pharmaceutical composition comprises a preservative. In some embodiments, the preservative maintains sterility of the pharmaceutical composition. Exemplary preservatives include, but are not limited to, benzyl alcohol, benzalkonium chloride, chlorobutanol, methylparaben, phenylethyl alcohol, propylparaben, and potassium sorbate. In some embodiments, the preservative is potassium sorbate. In some embodiments, the pharmaceutical composition comprises about 0.05% to about 0.2% (w/w) potassium polysorbate, such as about any one of 0.05%, 0.06%, 0.07%, 0.08%, 0.09%, 0.1%, 0.11%, 0.12%, 0.13%, 0.14%, 0.15%, 0.16%, 0.17%, 0.18%, 0.19% or 0.2% (w/w), including any values or ranges in between these values. In some embodiments, the pharmaceutical composition comprises about any one of 0.05%-0.1%, 0.75%-1.25%, 0.1%-0.15%, 0.15%-0.2%, 0.1%-0.2%, 0.125-0.175%, 0.8%-1.6%, or 0.5%-0.15% (w/w) potassium sorbate. In some embodiments, the pharmaceutical composition comprises about 0.1% potassium sorbate.

In some embodiments, the antibody is present in the pharmaceutical composition at a concentration of about 0.6 mg/mL to about 6 mg/mL, such as about n mg/mL, where n is selected from 0.6, 0.8, 1, 1.5, 2, 2.5, 3, 3.5, 4, 4.5, 5, 5.5, and, including about any values or ranges in between these values. In some embodiments, the antibody is present in the pharmaceutical composition at a concentration of between about n mg/mL, where n is selected from 0.6-1, 1-2, 2-3, 3-4, 4-5, 5-6, 0.6-2.5, 2.5-5, 2-4, 4-6, 0.6-3, 3-6, and 2-5.

A nasal spray containing IgG antibodies can be used as a complement to vaccines, therapeutics and other preventive measures against the spread of influenza. Human IgG antibody nasal sprays have many advantages. One advantage of using antibodies or chimeric proteins comprising antibodies in a prophylaxis nasal spray is the well-established manufacturing process and scale-up capacity for antibodies. More than two dozen IgG antibodies have been approved by the U.S. Food and Drug Administration (FDA) for human use. The IgG antibody manufacturing process, from cell line development to large-scale bioreactor culture, has been optimized to produce high quality and yield for use in humans. In addition, the effectiveness of IgG antibodies against influenza has already been demonstrated in patients in a therapeutic setting. An IgG in a nasal spray application also has the advantage of a much lower dosage requirement (approximately 10,000 times lower) than an IgG therapeutic. This will significantly lower the cost and make it affordable for wider use. Furthermore, use of a human IgG antibody significantly reduces the risk of immunogenicity, which is an important consideration for a prophylactic nasal spray pharmaceutical composition subject to long-term repeated use. The long-term stability of the modified IgG antibody at room temperature in the nasal spray pharmaceutical composition makes it easy for daily use and storage.

In some embodiments, the pharmaceutical composition (e.g., nasal spray pharmaceutical composition or eye drop pharmaceutical composition) is administered at a dosage of about 0.1 mg to about 1 mg of the antibody, e.g., per nostril or per eye. In some embodiments, about 100 □L of the pharmaceutical composition (e.g., nasal spray pharmaceutical composition or eye drop pharmaceutical composition) is administered at a time, e.g., to both nostrils of an individual (e.g., 100 □L per nostril or per eye).

Suitable pharmaceutical compositions are obtained by mixing the chimeric protein(s), anti-HA or anti-NA antibody or construct described herein having the desired degree of purity with optional pharmaceutically acceptable carriers, excipients or stabilizers (*Remington's Pharmaceutical Sciences* 23rd edition, Adejare, A. Ed. (2020)), in the form of lyophilized pharmaceutical compositions or aqueous solutions. Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The pharmaceutical composition herein may also contain one or more active compounds in addition to the compositions described herein as necessary for the infection being treated, preferably those with complementary activities that do not adversely affect each other. Such molecules are suitably present in combination in amounts that are effective for the purpose intended. The effective amount of such other agents depends on the amount of the composition described herein present in the pharmaceutical composition, the type and severity of infection in the treatment, and other factors discussed above. These are generally used in the same dosages and with administration routes as described herein or from about 1% to about 99% of the heretofore employed dosages.

The pharmaceutical compositions to be used for in vivo administration must be sterile. This is readily accomplished by, e.g., filtration through sterile filtration membranes.

Further provided are methods and use of the pharmaceutical compositions described herein for preventing or treating an infection, e.g., influenza infection.

B. Kits and Articles of Manufacture

In some embodiments, there is provided an article of manufacture comprising materials useful for the prevention or treatment of a microbial infection (e.g., infection by an influenza virus or variant thereof). The article of manufacture can comprise a container and a label or package insert on or associated with the container. Suitable containers include, for example, bottles, vials, syringes, etc. The containers may be formed from a variety of materials such as glass or plastic. Generally, the container holds a composition, which is effective for treating a microbial infection, described herein, and may have a sterile access port. In some embodiments, the article of manufacture is a nasal spray, an inhaler, a nebulizer, or an eye drop. Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating a microbial infection. The label or package insert may further comprise instructions for administering the composition to a patient.

Additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In some embodiments, there is provided an article of manufacture (e.g., a nasal spray) comprising a pharmaceutical composition comprising any one of the chimeric proteins described herein, and a spray device for applying the formulation to a nostril of a subject. In some embodiments, the nasal spray provides a uniform plume with droplets having a diameter of 10 □m or more. In some embodiments, the device sprays a volume of about 100 □L at a time. In some embodiments, the spray device is for an adult patient. In some embodiments, the spray device is for a pediatric patient. In some embodiments, the article of manufacture comprises a single dose of the active agent. In some embodiments, the article of manufacture comprises at least about n doses of the active agent, where n is selected from 2, 5, 10, 20, 30, 40, and 50, or more.

Kits are also provided that are useful for various purposes, e.g., for prevention or treatment of a microbial infection described herein, optionally in combination with the articles of manufacture. Kits of the invention include one or more containers comprising any one of the compositions described herein (or unit dosage form and/or article of manufacture). In some embodiments, the kit further comprises other agents and/or instructions for use in accordance with any of the methods described herein. The kit may further comprise a description of selection of individuals suitable for prevention or treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a chimeric protein comprising: (a) an antibody moiety that specifically binds to a component of an influenza virus or a variant thereof; and (b) a mucoadhesive peptide fragment comprising at least about 5 (e.g., about 5 to about 30 such as about 12) positively charged amino acid residues (e.g., lysine, histidine, arginine, ornithine, or combinations thereof), wherein the mucoadhesive peptide fragment facilitates attachment of the chimeric protein to a mucosa. In some embodiments, the component is a HA or NA viral surface protein.

The kits of the invention are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The containers may be unit doses, bulk packages (e.g., multi-dose packages) or sub-unit doses. Kits may also include multiple unit doses of the pharmaceutical compositions and instructions for use and packaged in quantities sufficient for storage and use in pharmacies, for example, hospital pharmacies and compounding pharmacies.

EXEMPLARY EMBODIMENTS

The following exemplary embodiments are provided herein:

Embodiment 1. A chimeric protein comprising: (a) an antibody moiety that specifically binds to a component of an influenza virus or a variant thereof; and (b) a mucoadhesive peptide fragment comprising at least about 5 positively charged amino acid residues, wherein the mucoadhesive peptide fragment facilitates attachment of the chimeric protein to a mucosa.

Embodiment 2. The chimeric protein of embodiment 1, comprising a single polypeptide chain.

Embodiment 3. The chimeric protein of embodiment 1, comprising two or more polypeptide chains.

Embodiment 4. The chimeric protein of embodiment 3, wherein the chimeric protein comprises two or more mucoadhesive peptide fragments.

Embodiment 5. The chimeric protein of embodiment 4, wherein each of the two or more mucoadhesive peptide fragments comprises at least about 5 positively charged amino acid residues.

Embodiment 6. The chimeric protein of any one of embodiments 1-5, wherein the mucoadhesive peptide fragment comprises at least about 6 positively charged amino acid residues.

Embodiment 7. The chimeric protein of any one of embodiments 1-6, wherein the positively charged amino acid residues are selected from the group consisting of lysine, arginine, histidine, ornithine, and combinations thereof.

Embodiment 8. The chimeric protein of embodiment 7, wherein the positively charged amino acid residues comprise lysines.

Embodiment 9. The chimeric protein of embodiment 8, wherein the mucoadhesive peptide fragment comprises about 5, about 6, about 12, or about 30 lysines.

Embodiment 9a. The chimeric protein of embodiment 9, wherein the mucoadhesive peptide fragment comprises about 5 lysines.

Embodiment 10. The chimeric protein of embodiment 7, wherein the positively charged amino acid residues comprise arginines.

Embodiment 11. The chimeric protein of embodiment 10, wherein the mucoadhesive peptide fragment comprises about 6, about 12, or about 30 arginines.

Embodiment 12. The chimeric protein of embodiment 7, wherein the positively charged amino acid residues comprise histidines.

Embodiment 13. The chimeric protein of embodiment 12, wherein the mucoadhesive peptide fragment comprises about 6, about 12, or about 30 histidines.

Embodiment 14. The chimeric protein of embodiment 7, wherein the positively charged amino acid residues comprise ornithines.

Embodiment 15. The chimeric protein of embodiment 14, wherein the mucoadhesive peptide fragment comprises about 6, about 12, or about 30 ornithines.

Embodiment 16. The chimeric protein of any one of embodiments 1-15, wherein the mucoadhesive peptide fragment comprises at least 5 contiguous positively charged amino acids.

Embodiment 17. The chimeric protein of any one of embodiments 1-15, wherein the positively charged amino acid residues are interspersed with one or more non-positively charged amino acid residues.

Embodiment 18. The chimeric protein of embodiment 17, wherein the non-positively charged amino acid residues are non-polar amino acids or polar uncharged amino acids.

Embodiment 19. The chimeric protein of embodiment 17 or 18, wherein the non-positively charged amino acid residues are selected from the group consisting of isoleucine, valine, alanine, tryptophan, leucine, glycine, methionine, proline, phenylalanine, threonine, cysteine, tyrosine, glutamine, serine, and asparagine, and combinations thereof.

Embodiment 20. The chimeric protein of any one of embodiments 17-19, wherein at least 50% of the amino acid residues in the mucoadhesive peptide fragment are positively charged amino acid residues.

Embodiment 21. The chimeric protein of any one of embodiments 1-20, wherein the mucoadhesive peptide fragment is no more than about 15 kD.

Embodiment 22. The chimeric protein of any one of embodiments 1-21, wherein the mucoadhesive peptide fragment has an isoelectric point (pI) higher than the pH of the mucosa.

Embodiment 23. The chimeric protein of any one of embodiments 1-22, wherein the half-life of the chimeric protein on the mucosa is at least 12 hours.

Embodiment 24. The chimeric protein of any one of embodiments 1-23, wherein the mucoadhesive peptide fragment does not facilitate penetration of the chimeric protein into a cell of the mucosa.

Embodiment 25. The chimeric protein of any one of embodiments 1-24, wherein the mucoadhesive peptide fragment does not disrupt folding of the chimeric protein within a host cell expressing the chimeric protein.

Embodiment 26. The chimeric protein of any one of embodiments 1-25, wherein the mucoadhesive peptide fragment does not block secretion of the chimeric protein from a host cell expressing the chimeric protein.

Embodiment 27. The chimeric protein of any one of embodiments 1-26, wherein the mucoadhesive peptide fragment does not interfere with the binding between the antibody moiety and the component of the influenza virus or variant thereof.

Embodiment 28. The chimeric protein of any one of embodiments 1-27, wherein the mucoadhesive peptide fragment comprises an amino acid sequence of any one of SEQ ID NOs: 291-325 and 407-413, or variants thereof comprising up to about 3 amino acid substitutions.

Embodiment 29. The chimeric protein of any one of embodiments 1-28, wherein the mucoadhesive peptide fragment is fused to the antibody moiety.

Embodiment 30. The chimeric protein of any one of embodiments 1-29, wherein the mucoadhesive peptide fragment is fused to the antibody moiety via a bond.

Embodiment 31. The chimeric protein of any one of embodiments 1-29, wherein the mucoadhesive peptide fragment is fused to the antibody moiety via a peptide linker.

Embodiment 32. The chimeric protein of embodiment 31, wherein the peptide linker comprises one or more oligomerization and/or multimerization domains.

Embodiment 33. The chimeric protein of embodiment 31 or 32, wherein the peptide linker comprises the constant region of a heavy chain of a full-length antibody or a fragment thereof, or the constant region of a light chain of a full-length antibody or a fragment thereof.

Embodiment 34. The chimeric protein of any one of embodiments 31-33, wherein the peptide linker comprises an $CH_1$, $CH_2$, $CH_3$, $CH_4$, and/or $C_L$ domain or fragments thereof.

Embodiment 35. The chimeric protein of any one of embodiments 31-33, wherein the peptide linker comprises an Fc region or a fragment thereof.

Embodiment 36. The chimeric protein of any one of embodiments 31-35, wherein the peptide linker comprises a detectable enzymatic tag, optionally wherein the enzymatic tag is an alkaline phosphatase and/or a glutathione-s-transferase.

Embodiment 37. The chimeric protein of any one of embodiments 31-36, wherein the peptide linker comprises:

(i) a basic helix-loop-helix leucine zipper (bZIP) domain, bZIP isoleucine zipper domain, and/or bZIP-leucine/isoleucine zipper domain;

(ii) a collagen-like peptide;

(iii) a p53 tetramerization domain;

(iv) a streptavidin (SA) protein, optionally wherein the linker further comprises a dextran scaffold or one or more maleimide polymers (DMGS);

(v) a bacteriophage T7 fibritin protein or a portion thereof; and/or (vi) a cartilage oligomeric matrix protein (COMP) protein.

Embodiment 38. The chimeric protein of any one of embodiments 1-37, wherein the antibody moiety is a full-length antibody.

Embodiment 39. The chimeric protein of embodiment 38, wherein the antibody moiety is selected from the group consisting of an IgG, an IgA, an IgM, and an IgD.

Embodiment 40. The chimeric protein of any one of embodiments 1-37, wherein the antibody moiety is an antigen-binding fragment selected from the group consisting of a Fab, a Fab', a $(Fab')_2$, an Fv, a single chain Fv (scFv), an scFv-Fc, a disulfide stabilized Fv fragment (dsFv), a $(dsFv)_2$, an scFv dimer, a domain antibody, a camelized single domain antibody (sdAb), a bivalent domain antibody, a minibody, and a $V_HH$.

Embodiment 41. The chimeric protein of any one of embodiments 1-40, wherein the antibody moiety is animal, human, humanized, camelid, or chimeric.

Embodiment 42. The chimeric protein of any one of embodiments 1-41, wherein the mucoadhesive peptide fragment is fused to a C-terminus of the antibody moiety.

Embodiment 43. The chimeric protein of any one of embodiments 1-39, 41, and 42, wherein the antibody moiety is a full-length antibody, and wherein:

(1) the mucoadhesive peptide fragment is fused to the C-terminus of a heavy chain of the full-length antibody via a first optional peptide linker; and/or (2) the mucoadhesive peptide fragment is fused to the C-terminus of a light chain of the full-length antibody via a second optional peptide linker.

Embodiment 44. The chimeric protein of embodiment 43, wherein the chimeric protein comprises: i) a first and a second polypeptide chain each comprising from the N-terminus to the C-terminus: the heavy chain of the full-length antibody, the first optional peptide linker, and the mucoadhesive peptide fragment; and ii) a third and a fourth polypeptide chain each comprising the light chain of the full-length antibody.

Embodiment 45. The chimeric protein of any one of embodiments 1-44, wherein the influenza virus is a Type A influenza virus (IAV), a Type B influenza virus (IBV), a Type C influenza virus (ICV), a Type D influenza virus (IDV), or a variant, subtype, or reassortant thereof.

Embodiment 46. The chimeric protein of any one of embodiments 1-45, wherein the influenza virus comprises a hemagglutinin (HA) antigen selected from the group consisting of H1, H2, H3, H5, H6, H7, H9, and H10, or a variant or reassortant thereof.

Embodiment 47. The chimeric protein of any one of embodiments 1-46, wherein the influenza virus comprises an neuraminidase (NA) antigen selected from the group consisting of N1, N2, N3, N7, N8, and N9, or a variant or reassortant thereof.

Embodiment 48. The chimeric protein of any one of embodiments 1-47, wherein the influenza virus is selected from the group consisting of H1N1, H1N2, H2N2, H3N2, H3N8, H5N1, H5N9, H6N1, H7N2, H7N3, H7N7, H7N9, H9N2, H10N7, or a variant or reassortant thereof.

Embodiment 49. The chimeric protein of any one of embodiments 1-48, wherein the component of the influenza virus or variant thereof is a viral surface protein or fragment thereof.

Embodiment 50. The chimeric protein of embodiment 49, wherein the viral surface protein is HA.

Embodiment 50a. The chimeric protein of embodiment 50, wherein the chimeric protein comprises:

(i) a heavy chain complementarity determining region (HC-CDR) 1 comprising the amino acid sequence of SEQ ID NO: 1, an HC-CDR2 comprising the amino acid sequence of SEQ ID NO: 2, and an HC-CDR3 comprising the amino acid sequence of SEQ ID NO: 3, a light chain complementarity determining region (LC-CDR) 1 comprising the amino acid sequence of SEQ ID NO: 4, an LC-CDR2 comprising the amino acid sequence of WAS, and an LC-CDR3 comprising the amino acid sequence of SEQ ID NO: 6;

(ii) an HC-CDR1 comprising the amino acid sequence of SEQ ID NO: 7, an HC-CDR2 comprising the amino acid sequence of SEQ ID NO: 8, and an HC-CDR3 comprising the amino acid sequence of SEQ ID NO: 9, an LC-CDR1 comprising the amino acid sequence of SEQ ID NO: 235, an LC-CDR2 comprising the amino acid sequence of SEQ ID NO: 238, and an LC-CDR3 comprising the amino acid sequence of SEQ ID NO: 415; or (iii) an HC-CDR1 comprising the amino acid sequence of SEQ ID NO: 439, an HC-CDR2 comprising the amino acid sequence of SEQ ID NO: 440, and an HC-CDR3 comprising the amino acid sequence of SEQ ID NO: 441, an LC-CDR1 comprising the amino acid sequence of SEQ ID NO: 443, an LC-CDR2 comprising the amino acid sequence of SND, and an LC-CDR3 comprising the amino acid sequence of SEQ ID NO: 445.

Embodiment 50b. The chimeric protein of embodiment 50 or 50a, wherein the chimeric protein comprises:

(i) a heavy chain variable domain ($V_H$) comprising the amino acid sequence of SEQ ID NO: 76, or a variant thereof having at least about 90% sequence identity to the amino acid sequence of SEQ ID NO: 76, and a light chain variable domain ($V_L$) comprising the amino acid sequence of SEQ ID NO: 77, or a variant thereof having at least about 90% sequence identity to the amino acid sequence of SEQ ID NO: 77;

(ii) a $V_H$ comprising the amino acid sequence of SEQ ID NO: 78, or a variant thereof having at least about 90% sequence identity to the amino acid sequence of SEQ ID NO: 78, and a $V_L$ comprising the amino acid sequence of SEQ ID NO: 79, or a variant thereof having at least about 90% sequence identity to the amino acid sequence of SEQ ID NO: 79; or (iii) a $V_H$ comprising the amino acid sequence of SEQ ID NO: 438, or a variant thereof having at least about 90% sequence identity to the amino acid sequence of SEQ ID NO: 438, and a $V_L$ comprising the amino acid sequence of SEQ ID NO: 442, or a variant thereof having at least about 90% sequence identity to the amino acid sequence of SEQ ID NO: 443;

Embodiment 50c. The chimeric protein of any one of embodiments 50-50b, wherein the chimeric protein comprises:

(i) a heavy chain (HC) polypeptide comprising the amino acid sequence of SEQ ID NO: 414, or a variant thereof having at least about 90% sequence identity to the amino acid sequence of SEQ ID NO: 414, and a light chain (LC) polypeptide comprising the amino acid sequence of SEQ ID NO: 217, or a variant thereof having at least about 90% sequence identity to the amino acid sequence of SEQ ID NO: 217;

(ii) an HC polypeptide comprising the amino acid sequence of SEQ ID NO: 420, or a variant thereof having at least about 90% sequence identity to the amino acid sequence of SEQ ID NO: 420, and an LC polypeptide comprising the amino acid sequence of SEQ ID NO: 244, or a variant thereof having at least about 90% sequence identity to the amino acid sequence of SEQ ID NO: 244; or (iii) an HC polypeptide comprising the amino acid sequence of SEQ ID NO: 446, or a variant thereof having at least about 90% sequence identity to the amino acid sequence of SEQ ID NO: 446, and an LC polypeptide comprising the amino acid sequence of SEQ ID NO: 447, or a variant thereof having at least about 90% sequence identity to the amino acid sequence of SEQ ID NO: 447.

Embodiment 51. The chimeric protein of any one of embodiments 50-50c, wherein the chimeric protein comprises:

(i) a first and a second polypeptide chain each independently comprising the amino acid sequence of any one of SEQ ID NOs: 216, 218-234, 236, 237, 239-242, and 416-419, or a variant thereof comprising at least about 90% sequence identity to the amino acid sequence of any one of SEQ ID NOs: 216, 218-234, 236, 237, 239-242, and 416-419, and a third and a fourth polypeptide chain each independently comprising the amino acid sequence of SEQ ID NO: 217, or a variant thereof comprising at least about 90% sequence identity to the amino acid sequence of SEQ ID NO: 217;

(ii) a first and a second polypeptide chain each independently comprising the amino acid sequence of any one of SEQ ID NOs: 243, 245-258, and 422-425, or a variant thereof comprising at least about 90% sequence identity to the amino acid sequence of any one of SEQ ID NOs: 243, 245-258, and 422-425, and a third and a fourth polypeptide chain each independently comprising the amino acid sequence of SEQ ID NO: 244, or a variant thereof comprising at least about 90% sequence identity to the amino acid sequence of SEQ ID NO: 244; or (iii) a first and a second polypeptide chain each independently comprising the amino acid sequence of any one of SEQ ID NOs: 448-468, or a variant thereof comprising at least about 90% sequence identity to the amino acid sequence of any one of SEQ ID NOs: 448-468, and a third and a fourth polypeptide chain each independently comprising the amino acid sequence of SEQ ID NO: 447, or a variant thereof comprising at least about 90% sequence identity to the amino acid sequence of SEQ ID NO: 447.

Embodiment 52. The chimeric protein of embodiment 49, wherein the component of the viral surface protein is NA.

Embodiment 52a. The chimeric protein of embodiment 52, wherein the chimeric protein comprises:

(i) an HC-CDR1 comprising the amino acid sequence of SEQ ID NO: 104, an HC-CDR2 comprising the amino acid sequence of SEQ ID NO: 105, and an HC-CDR3 comprising the amino acid sequence of SEQ ID NO: 106, an LC-CDR1 comprising the amino acid sequence of SEQ ID NO: 107, an LC-CDR2 comprising the amino acid sequence AAS, and an LC-CDR3 comprising the amino acid sequence of SEQ ID NO: 109; or (ii) an HC-CDR1 comprising the amino acid sequence of SEQ ID NO: 110, an HC-CDR2 comprising the amino acid sequence of SEQ ID NO: 111, and an HC-CDR3 comprising the amino acid sequence of SEQ ID NO: 112, an LC-CDR1 comprising the amino acid sequence of SEQ ID NO: 113, an LC-CDR2 comprising the amino acid sequence GAS, and an LC-CDR3 comprising the amino acid sequence of SEQ ID NO: 115.

Embodiment 52b. The chimeric protein of embodiment 52 or 52a, wherein the chimeric protein comprises:

(i) a $V_H$ comprising the amino acid sequence of SEQ ID NO: 188, or a variant thereof having at least about 90% sequence identity to the amino acid sequence of SEQ ID NO: 188, and a $V_L$ comprising the amino acid sequence of SEQ ID NO: 189, or a variant thereof having at least about 90% sequence identity to the amino acid sequence of SEQ ID NO: 189; or (ii) a $V_H$ comprising the amino acid sequence of SEQ ID NO: 190, or a variant thereof having at least about 90% sequence identity to the amino acid sequence of SEQ ID NO: 190, and a $V_L$ comprising the amino acid sequence of SEQ ID NO: 191, or a variant thereof having at least about 90% sequence identity to the amino acid sequence of SEQ ID NO: 191.

Embodiment 52c. The chimeric protein of any one of embodiments 52-52b, wherein the chimeric protein comprises:

(i) an HC polypeptide comprising the amino acid sequence of SEQ ID NO: 426, or a variant thereof having at least about 90% sequence identity to the amino acid sequence of SEQ ID NO: 426, and an LC polypeptide comprising the amino acid sequence of SEQ ID NO: 260, or a variant thereof having at least about 90% sequence identity to the amino acid sequence of SEQ ID NO: 260; or (ii) an HC polypeptide comprising the amino acid sequence of SEQ ID NO: 432, or a variant thereof having at least about 90% sequence identity to the amino acid sequence of SEQ ID NO: 432, and an LC polypeptide comprising the amino acid sequence of SEQ ID NO: 276, or a variant thereof having at least about 90% sequence identity to the amino acid sequence of SEQ ID NO: 276.

Embodiment 53. The chimeric protein of any one of embodiments 52-52c, wherein the chimeric protein comprises:

(i) a first and a second polypeptide chain each independently comprising the amino acid sequence of any one of SEQ ID NOs: 259, 261-274, and 428-431, or a variant thereof comprising at least about 90% sequence identity to the amino acid sequence of any one of SEQ ID NOs: 259, 261-274, and 428-431, and a third and a fourth polypeptide chains each independently comprising the amino acid sequence of SEQ ID NO: 260, or a variant thereof comprising at least about 90% sequence identity to the amino acid sequence of SEQ ID NO: 260; or (ii) a first and a second polypeptide chain each independently comprising the amino acid sequence of any one of SEQ ID NOs: 275, 277-290, and 434-437, or a variant thereof comprising at least about 90% sequence identity to the amino acid sequence of any one of SEQ ID NOs: 275, 277-290, and 434-437, and a third and a fourth polypeptide chains each independently comprising the amino acid sequence of SEQ ID NO: 276, or a variant thereof comprising at least about 90% sequence identity to the amino acid sequence of SEQ ID NO: 276.

Embodiment 54. The chimeric protein of any one of embodiments 1-53, wherein the mucosa is selected from the group consisting of nasal mucosa, larynx mucosa, trachea mucosa, bronchi mucosa, lung mucosa, eye mucosa, and combinations thereof.

Embodiment 55. A pharmaceutical composition comprising the chimeric protein of any one of embodiments 1-54, and a pharmaceutically acceptable carrier.

Embodiment 56. The pharmaceutical composition of embodiment 55, wherein the pharmaceutical composition comprises a plurality of the chimeric proteins, and wherein at least two of the plurality of the chimeric proteins are different from each other.

Embodiment 57. The pharmaceutical composition of embodiment 55 or 56, wherein the pharmaceutically acceptable carrier:

(i) comprises about 0.05% to about 0.2% (w/w) methionine;

(ii) has a pH of about 4.5 to about 7.5;

(iii) comprises about 20 mM to about 50 mM citrate;

(iv) comprises about 100 mM to about 150 mM NaCl;

(v) comprises about 0.01% to about 0.1% (w/w) polysorbate 80;

(vi) comprises about 1% to about 10% (w/w) glycerin; and/or (vii) comprises about 0.05% to about 0.2% (w/w) potassium sorbate.

Embodiment 58. The pharmaceutical composition of any one of embodiments 55-57, wherein the pharmaceutical composition is formulated for intranasal administration, intraocular administration, and/or intrabronchial administration.

Embodiment 59. An isolated nucleic acid or a set of isolated nucleic acids encoding the chimeric protein of any one of embodiments 1-54.

Embodiment 60. A vector or a set of vectors comprising the nucleic acid or the set of nucleic acids of embodiment 59.

Embodiment 61. A host cell comprising the chimeric protein of any one of embodiments 1-54, the nucleic acid or set of nucleic acids of embodiment 59, the vector or set of vectors of embodiment 60.

Embodiment 62. A method of preparing a chimeric protein, comprising:

(a) culturing a host cell of embodiment 61 under a condition effective to express the chimeric protein; and (b) obtaining the expressed chimeric protein from the host cell.

Embodiment 63. A method of preventing or treating an infection caused by an influenza virus or a variant thereof in an individual, comprising administering to the individual an effective amount of the chimeric protein of any one of embodiments 1-54, or the pharmaceutical composition of any one of embodiments 55-58.

Embodiment 64. The method of embodiment 63, wherein the chimeric protein or the pharmaceutical composition is administered to the individual before the individual is exposed to the influenza virus or variant thereof.

Embodiment 65. The method of embodiment 63, wherein the chimeric protein or the pharmaceutical composition is administered to the individual within about 72 hours after the individual is exposed to the influenza virus or variant thereof.

Embodiment 66. The method of any one of embodiments 63-65, wherein the chimeric protein or the pharmaceutical composition is administered topically onto the mucosa.

Embodiment 67. The method of embodiment 66, wherein the chimeric protein or the pharmaceutical composition is administered via a nasal spray, an inhaler, a nebulizer, or an eye drop.

Embodiment 68. The method of any one of embodiments 63-67, wherein the chimeric protein or the pharmaceutical composition is administered once daily.

Embodiment 69. An in vitro method of killing or neutralizing a virus, comprising contacting a virus with the chimeric protein of any one of embodiments 1-54 in the presence of at least one component of the complement system, optionally wherein the at least one component of the complement system is C1, C4, or membrane attack complex (MAC).

Embodiment 70. A method of killing or neutralizing a virus in an individual, comprising administering to the individual an effective amount of the chimeric protein of any one of embodiments 1-54, or the pharmaceutical composition of any one of embodiments 55-58.

Embodiment 71. A method of activating the complement pathway in an individual, comprising administering to the individual an effective amount of the chimeric protein of any one of embodiments 1-54, or the pharmaceutical composition of any one of embodiments 55-58.

Embodiment 72. The method of embodiment 70 or 71, wherein at least one virus is killed or neutralized on the mucosa.

Embodiment 73. A method of preventing, treating, or reducing infection caused by a virus in an individual, comprising administering to the individual an effective amount of the chimeric protein of any one of embodiments 1-54, or the pharmaceutical composition of any one of embodiments 55-58, wherein at least one virus is killed or neutralized on the mucosa.

Embodiment 74. The method of any one of embodiments 63-73, wherein the chimeric protein activates the complement pathway in the individual.

Embodiment 75. The method of any one of embodiments 63-74, wherein the killing or neutralization is via activation of the complement pathway.

Embodiment 76. The method of any one of embodiments 62-75, wherein the virus is an influenza virus.

Embodiment 77. The method of embodiment 76, wherein the influenza virus is selected from the group consisting of a Type A influenza virus (IAV), a Type B influenza virus (IBV), a Type C influenza virus (ICV), a Type D influenza virus (IDV), or a variant, subtype, or reassortant thereof.

Embodiment 78. The method of embodiment 76 or 77, wherein the influenza virus comprises an HA antigen selected from the group consisting of H1, H2, H3, H5, H6, H7, H9, and H10, or a variant or reassortant thereof.

Embodiment 79. The method of any one of embodiments 76-78, wherein the influenza virus comprises an NA antigen selected from the group consisting of N1, N2, N3, N7, N8, and N9, or a variant or reassortant thereof.

Embodiment 80. The method of any one of embodiments 76-79, wherein the influenza virus is selected from the group consisting of H1N1, H1N2, H2N2, H3N2, H3N8, H5N1, H5N9, H6N1, H7N2, H7N3, H7N7, H7N9, H9N2, H10N7, or a variant or reassortant thereof.

Embodiment 81. The chimeric protein of any one of embodiments 1-54, or the pharmaceutical composition of any one of embodiments 55-58, for use in a method of preventing or treating an infection caused by an influenza virus or a variant thereof in an individual, the method comprising administering to the individual an effective amount of the chimeric protein of or the pharmaceutical composition.

Embodiment 82. The chimeric protein or pharmaceutical composition for use of embodiment 81, wherein the chimeric protein or the pharmaceutical composition is administered to the individual before the individual is exposed to the influenza virus or variant thereof.

Embodiment 83. The chimeric protein or pharmaceutical composition for use of embodiment 81, wherein the chimeric protein or the pharmaceutical composition is administered to the individual within about 72 hours after the individual is exposed to the influenza virus or variant thereof.

Embodiment 84. The chimeric protein or pharmaceutical composition for use of any one of embodiments 81-83, wherein the chimeric protein or the pharmaceutical composition is administered topically onto the mucosa.

Embodiment 85. The chimeric protein or pharmaceutical composition for use of embodiment 84, wherein the chimeric protein or the pharmaceutical composition is administered via a nasal spray, an inhaler, a nebulizer, or an eye drop.

Embodiment 86. The chimeric protein or pharmaceutical composition for use of any one of embodiments 81-85, wherein the chimeric protein or the pharmaceutical composition is administered once daily.

Embodiment 87. The chimeric protein of any one of embodiments 1-54, or the pharmaceutical composition of any one of embodiments 55-58, for use in a method of killing or neutralizing a virus in an individual, the method comprising administering to the individual an effective amount of the chimeric protein or the pharmaceutical composition.

Embodiment 88. The chimeric protein of any one of embodiments 1-54, or the pharmaceutical composition of any one of embodiments 55-58, for use in a method of activating the complement pathway in an individual, the method comprising administering to the individual an effective amount of the chimeric protein or the pharmaceutical composition.

Embodiment 89. The chimeric protein or pharmaceutical composition for use of embodiment 87 or 88, wherein at least one virus is killed or neutralized on the mucosa.

Embodiment 90. The chimeric protein of any one of embodiments 1-54, or the pharmaceutical composition of any one of embodiments 55-58, for use in a method of preventing, treating, or reducing infection caused by a virus in an individual, wherein at least one virus is killed or neutralized on the mucosa, the method comprising administering to the individual an effective amount of the chimeric protein or the pharmaceutical composition.

Embodiment 91. The chimeric protein or pharmaceutical composition for use of any one of embodiments 81-90, wherein the chimeric protein activates the complement pathway in the individual.

Embodiment 92. The chimeric protein or pharmaceutical composition for use of any one of embodiments 81-91, wherein the killing or neutralization is via activation of the complement pathway.

Embodiment 93. The chimeric protein or pharmaceutical composition for use of any one of embodiments 81-92, wherein the virus is an influenza virus.

Embodiment 94. The chimeric protein or pharmaceutical composition for use of embodiment 93, wherein the influenza virus is selected from the group consisting of a Type A influenza virus (IAV), a Type B influenza virus (IBV), a Type C influenza virus (ICV), a Type D influenza virus (IDV), or a variant, subtype, or reassortant thereof.

Embodiment 95. The chimeric protein or pharmaceutical composition for use of embodiment 93 or 94, wherein the influenza virus comprises an HA antigen selected from the group consisting of H1, H2, H3, H5, H6, H7, H9, and H10, or a variant or reassortant thereof.

Embodiment 96. The chimeric protein or pharmaceutical composition for use of any one of embodiments 93-95, wherein the influenza virus comprises an NA antigen selected from the group consisting of N1, N2, N3, N7, N8, and N9, or a variant or reassortant thereof.

Embodiment 97. The chimeric protein or pharmaceutical composition for use of any one of embodiments 93-96, wherein the influenza virus is selected from the group consisting of H1N1, H1N2, H2N2, H3N2, H3N8, H5N1, H5N9, H6N1, H7N2, H7N3, H7N7, H7N9, H9N2, H10N7, or a variant or reassortant thereof.

Embodiment 98. The use of chimeric protein of any one of embodiments 1-54, or the pharmaceutical composition of any one of embodiments 55-58, in the manufacture of a medicament for preventing or treating an infection caused by an influenza virus or a variant thereof in an individual.

Embodiment 99. The use according to embodiment 98, wherein the chimeric protein or the pharmaceutical composition is administered to the individual before the individual is exposed to the influenza virus or variant thereof.

Embodiment 100. The use according to embodiment 98, wherein the chimeric protein or the pharmaceutical composition is administered to the individual within about 72 hours after the individual is exposed to the influenza virus or variant thereof.

Embodiment 101. The use according to any one of embodiments 98-100, wherein the chimeric protein or the pharmaceutical composition is administered topically onto the mucosa.

Embodiment 102. The use according to embodiment 101, wherein the chimeric protein or the pharmaceutical composition is administered via a nasal spray, an inhaler, a nebulizer, or an eye drop.

Embodiment 103. The use according to any one of embodiments 98-102, wherein the chimeric protein or the pharmaceutical composition is administered once daily.

Embodiment 104. The use of the chimeric protein of any one of embodiments 1-54, or the pharmaceutical composition of any one of embodiments 55-58, in the manufacture of a medicament for killing or neutralizing a virus in an individual.

Embodiment 105. The use of the chimeric protein of any one of embodiments 1-54, or the pharmaceutical composition of any one of embodiments 55-58, in the manufacture of a medicament for activating the complement pathway in an individual.

Embodiment 106. The c use according to embodiment 104 or 105, wherein at least one virus is killed or neutralized on the mucosa.

Embodiment 107. The use chimeric protein of any one of embodiments 1-54, or the pharmaceutical composition of any one of embodiments 55-58, in the manufacture of a medicament for preventing, treating, or reducing infection caused by a virus in an individual, wherein at least one virus is killed or neutralized on the mucosa.

Embodiment 108. The use according to any one of embodiments 98-107, wherein the chimeric protein activates the complement pathway in the individual.

Embodiment 109. The use according to any one of embodiments 98-108, wherein the killing or neutralization is via activation of the complement pathway.

Embodiment 110. The use according to any one of embodiments 98-109, wherein the virus is an influenza virus.

Embodiment 111. The use according to embodiment 110, wherein the influenza virus is selected from the group consisting of a Type A influenza virus (IAV), a Type B influenza virus (IBV), a Type C influenza virus (ICV), a Type D influenza virus (IDV), or a variant, subtype, or reassortant thereof.

Embodiment 112. The use according to embodiment 110 or 111, wherein the influenza virus comprises an HA antigen selected from the group consisting of H1, H2, H3, H5, H6, H7, H9, and H10, or a variant or reassortant thereof.

Embodiment 113. The use according to any one of embodiments 110-112, wherein the influenza virus comprises an NA antigen selected from the group consisting of N1, N2, N3, N7, N8, and N9, or a variant or reassortant thereof.

Embodiment 114. The use according to any one of embodiments 110-113, wherein the influenza virus is selected from the group consisting of H1N1, H1N2, H2N2, H3N2, H3N8, H5N1, H5N9, H6N1, H7N2, H7N3, H7N7, H7N9, H9N2, H10N7, or a variant or reassortant thereof.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1. Exemplary Anti-HA hIgG Antibodies

Several antibodies directed to the hemagglutinin (HA) protein of influenza types A and B are disclosed in Table 4A, along with their variable region and CDR sequences.

Several animal antibodies directed to the HA protein of influenza types A and B are disclosed in Table 6, along with their variable region and CDR sequences.

Example 2. Exemplary Anti-NA hIgG Antibodies

Several antibodies directed to the neuraminidase (NA) protein of influenza types A and B are disclosed in Table 4B, along with their variable region and CDR sequences.

Antibodies directed to animal NA proteins from influenza type A strains are also disclosed.

Example 3. Characterization of Anti-HA IgG Antibodies

Example 3A. Human Anti-HA Antibodies Bind the IAV HA Glycoprotein

This Example demonstrates that exemplary anti-HA-hIgG antibodies (HA1, HA2, HA15 and the other antibodies from Table 4A) bind to HEK293F cell surface expressed HA when co-expressed with influenza NA and M2 (ion channel) proteins according to McKay et al. *Gene Therapy* 13:715-724 (2006). In that study, the ability to produce lentiviral vectors pseudotyped with fowl plague virus HA was improved by co-expression of influenza virus NA and further improved by co-expressing the Influenza Virus M2 proton channel in transfected HEK293 cells. We first test whether HA expression is easily detected in HEK293F cells transfected with an Influenza Virus type A (IAV) HA and Influenza Virus type B (IVB) NA and Influenza M2 expressed from a eukaryotic expression vector.

HEK293F (FreeStyle™ 293-F Cells, ThermoFisher Scientific) cells are transfected with an expression vector carrying the IAV HA gene, the IBV NA gene and the M2 ion channel gene and a stable cell line is established and designated HEK293-HNM. The HEK293-HNM cells are tested for membrane HA expression. HEK293-HNM cells are harvested and washed with 1% ice-cold BSA in PBS (bovine serum albumin, phosphate buffered saline). The cells (0.1 million for each concentration) are stained for 30 min using the exemplary anti-HA antibodies shown in Table 4A, including HA1, HA2 and HA15, or with negative control antibodies such as anti-PSMA. The cells are then washed three times in 1% ice-cold BSA in PBS, and incubated with 5 μg/mL of goat anti-Human IgG (H+L) secondary antibody (PE/Cy7, Novus Biologicals) for 30 min. The cells are washed three times with 1% ice-cold BSA in PBS and resuspended into 100 μL of washing buffer for flow cytometry analysis. Flow cytometry data are collected using BD FACSCanto™ II system using the FlowJo™ v10.6.1 software package. All the anti-HA antibodies tested detect IAV HA proteins on the surface of HEK293-HNM cells. However, negative control antibodies (anti-PSMA) do not bind (data not shown).

Example 3B. Binding of Chimeric Proteins Comprising Anti-HA-hIgG Human Antibodies to HA The binding of exemplary chimeric proteins comprising anti-HA antibodies (Table 4A), including HA1, HA2, and HA15, to IAV HA are measured by Bio-Layer Interferometry (BLI) on a ForteBio Octet KQ with a Sensor Chip CAP. Binding of the human IgG antibodies is demonstrated using the following protocol: 20 μg/mL biotinylated target HA protein in kinetics buffer (10 mM HEPES pH 7.4, 150 mM NaCl, 3 mM EDTA, 0.05% (v/v) Surfactant P20) is loaded onto a streptavidin biosensor. After washing off excess antigen, anti-HA antibody is added at 10 μg/mL in kinetics buffer for a 300 s period of association and a 300 s period of dissociation.

Example 3C. Characterization of Animal Anti-HA Antibodies

Exemplary animal anti-HA antibodies shown in Table 6 are also characterized using the same methods of Examples 3A-3B. Briefly, the animal anti-HA antibodies are evaluated for binding to the IAV HA glycoproteins, and are able to detect IAV HA proteins on the surface of HEK293-HNM cells. The binding of exemplary animal anti-HA antibodies is measured by BLI on a ForteBio Octet KQ with a Sensor Chip CAP, which shows that the animal anti-HA antibodies are able to bind HA proteins from IAV strains.

Example 4. Characterization of Anti-NA hIgG Antibodies

Example 4A. Human Anti-NA Antibodies Bind the IBV NA Glycoprotein

This Example demonstrates that exemplary anti-NA-hIgG antibodies (NA1, NA2 and the other antibodies from Table 4B) bind to HEK293F cell surface expressed NA when co-expressed with influenza HA and M2 (ion channel) proteins, as cited in the previous Example. We first test whether NA expression is easily detected in HEK293F cells transfected with an Influenza Virus type B (IBV) NA and Influenza Virus type A (IAV)-HA and Influenza M2 expressed from a eukaryotic expression vector.

HEK293F (FreeStyle™ 293-F Cells, ThermoFisher Scientific) cells are transfected with an expression vector carrying the IBV NA gene, the IAV HA gene and the M2 ion channel gene and a stable cell line is established and designated HEK293-HNM. The HEK293-HNM cells are tested for membrane NA expression. HEK293-HNM cells are harvested and washed with 1% ice-cold BSA in PBS. The cells (0.1 million for each concentration) are stained for 30 min using exemplary anti-NA antibodies shown in Table 4B, including NA1 and NA2, or with negative control antibodies such as □PSMA. The cells are then washed three times in 1% ice-cold BSA in PBS, and incubated with 5 μg/ml of goat anti-Human IgG (H+L) secondary antibody (PE/Cy7, Novus Biologicals) for 30 min. The cells are washed three times with 1% ice-cold BSA in PBS and resuspended into 100 μL of washing buffer for flow cytometry analysis. Flow cytometry data are collected using BD FACSCanto™ II system using the FlowJo™ v10.6.1 software package. All of the anti-NA antibodies tested detect IBV NA proteins on the surface of HEK293-HNM cells, however, negative control antibodies (anti-PSMA) do not bind.

Example 4B. Binding of Human Anti-NA-hIgG Antibodies to NA

The binding of exemplary anti-NA antibodies (Table 4B) including NA1 and NA2 to IBV NA is measured by BLI on a ForteBio Octet KQ with a Sensor Chip CAP. Binding of the human IgG antibodies is demonstrated using the following protocol: 20 μg/mL biotinylated target NA protein in kinetics buffer (10 mM HEPES pH 7.4, 150 mM NaCl, 3 mM EDTA, 0.05% (v/v) Surfactant P20) is loaded onto a streptavidin biosensor. After washing off excess antigen, anti-HA antibody is added at 10 μg/mL in kinetics buffer for a 300 s period of association and a 300 s period of dissociation. The association and dissociation graphs confirm binding of the anti-NA antibody to NA proteins from IBV strains.

Example 4C. Characterization of Animal Anti-NA Antibodies

Exemplary animal anti-NA antibodies, targeting the NA protein of zoonotic IAV strain H7N9 have been published in the literature (D3 and 7H2, Xiong, et al., *Emerging Microbes & Infections,* 9(1):78-87 (2020)). Additionally, a camelid antibody directed to another zoonotic strain, IAV H5N1 (N1-$V_H$H, Cardoso, et al. *Journal of Virology,* 88(15):8278-96 (2014)) has been described. Such exemplary animal anti-NA antibodies, and other animal anti-NA antibodies, are also characterized using the same methods of Examples 4A-4B. Briefly, the animal anti-NA antibodies are evaluated for binding to IBV NA glycoproteins and are able to detect IAB-NA proteins on the surface of HEK293-HNM cells. The binding of exemplary animal anti-NA antibodies is measured by BLI on a ForteBio Octet KQ with a Sensor Chip CAP, which shows that the animal anti-NA antibodies are able to bind NA proteins from IBV strains.

Example 5. Blocking of Pseudoviral Infection by Anti-HA IgGs In Vitro

Example 5A. Production of HA-Pseudotyped Lentiviruses

Lentiviruses containing HA, NA and M2 proteins are produced by transfection of IAV HA, IBV NA and M2 expressing HEK293F cells using the lentiviral expression vector pCDH-EF1-MCS (System Biosciences) that carries the HA, NA and M2 expression constructs on a single vector under the control of the E1F promoter. Helper plasmids which encode the proteins required in trans for the production of infectious pseudotyped virus are simultaneously co-transfected.

Concentrated lentiviruses are applied to engineered HEK293-HNM cells in 96-well plates for 48 hours. In some experiments, HEK293-HNM cells are mock-transduced (no DNA added) or transduced with empty lentiviral vectors. Repeat flow cytometry analyses are done on day 5. Transduction efficiencies of HEK cells are assessed by flow cytometry using a goat anti-human PE-conjugated anti-HA antibody (Jackson Immuno, Cat #109-116-097). Flow cytometry data are collected using a BD LSR FORTESSA™ and analyzed using the FlowJo™ v10.6.1 software package (data not shown).

Example 5B. Pseudovirus Blocking Assay

This Example demonstrates that anti-HA IgG antibodies are able to block IAV HA pseudovirus infection in HEK293F cells expressing Influenza type A HA. Briefly, exemplary anti-HA antibodies shown in Table 4A, including HA1, HA2, and HA15 hIgG, are incubated with HA-pseudotyped lentivirus. The pseudotyped virus contains the EF1-α-driven luciferase and GFP reporter genes separated by a P2A self-cleaving peptide. Following a 30 min incubation of the anti-HA hIgG antibody with HA-pseudotyped lentivirus, the lentivirus is added to HEK293-HNM cells expressing IAV HA, IBV NA and M2 proteins. Cells are cultured in 5% $CO_2$ at 37° C. for 48 h. The degree of cellular infection with the pseudotyped virus is determined by detecting the luciferase level of the infected cells (Promega Luciferase Assay) or by detecting GFP-positive cells using fluorescence microscopy. A low quantity of each anti-HA antibody shown in Table 4A, including HA1, HA2, and HA15 human IgG antibody, is a sufficient antibody concentration to completely block the infection of HEK293-HNM cells expressing IAV HA.

Example 5C. Pseudovirus Blocking by Animal Anti-HA Antibodies

Exemplary animal anti-HA antibodies shown in Table 6 are analyzed for the ability to block IAV HA pseudovirus infection using the same methods of Example 5B. A low quantity of each exemplary animal anti-HA antibodies is sufficient to completely block the infection of HEK293-HNM cells expressing IAV.

Example 6. Blocking of Pseudoviral Infection by Anti-NA IgGs In Vitro

Example 6A. Production of NA-Pseudotyped Lentiviruses

Lentiviruses containing HA, NA and M2 proteins are produced by transfection of IAV HA, IBV NA and M2 expressing HEK293F cells using the lentiviral expression vector pCDH-EF1-MCS (System Biosciences) as in the previous Example.

Concentrated lentiviruses are applied to engineered HEK293-HNM cells in 96-well plates for 48 hours. In some experiments, HEK293-HNM cells are mock-transduced (no DNA added) or transduced with empty lentiviral vectors. Repeat flow cytometry analyses are done on day 5. Transduction efficiencies of HEK cells are assessed by flow cytometry using a goat anti-human PE-conjugated anti-HA antibody (Jackson Immuno, 109-116-097). Flow cytometry data are collected using a BD LSR FORTESSA™ and analyzed using the FlowJo™ v10.6.1 software package (data not shown).

Example 6B. Pseudovirus Blocking Assay

This Example demonstrates that anti-NA IgG antibodies are able to block IBV NA pseudovirus infection in HEK293F cells expressing influenza type B NA. Briefly, exemplary anti-NA antibodies shown in Table 4B, including NA1 and NA2 hIgG, are incubated with NA-pseudotyped lentivirus, as in the previous Example. Following a 30 min incubation of the anti-NA hIgG antibody with NA-pseudotyped lentivirus, the lentivirus is added to HEK293-HNM cells expressing influenza proteins. Cells are cultured in 5% CO2 at 37° C. for 48 h. The degree of cellular infection with the pseudotyped virus is determined by detecting the luciferase level of the infected cells or by detecting GFP-positive cells using fluorescence microscopy. A low quantity of NA1 or NA2 human IgG antibody is a sufficient antibody concentration to completely block the infection of HEK293-HNM cells expressing IBV.

Example 6C. Pseudovirus Blocking by Animal Anti-NA Antibodies

Exemplary animal anti-NA antibodies, including those disclosed in Xiong et al., 2020, Cardoso et al., 2014, and Murphy et al., 1972, *N Engl J Med;* 286:1329-1332, and other animal anti-NA antibodies, fused to any of the mucoadhesive peptides disclosed in Table 8, are able to block pseudovirus infection of HEK293-HNM cells in vitro using the methods described in Example 6B.

Example 7. Expression and Purification of Anti-HA Chimeric Mucoadhesive Proteins

Example 7A. Chimeric Proteins Comprising Anti-HA Antibodies and Mucoadhesive Polylysine and Polyhistidine Peptides Chimeric proteins comprising HA1 hIgG, HA2 hIgG, or HA15 hIgG heavy chains fused to various lengths of polylysine or polyhistidine peptide fragments are generated. Specifically, DNA fragments encoding a polylysine-modified HA1, HA2, or HA15 IgG heavy chain (added to the C-terminus of the IgG heavy chain) and an unmodified HA1 or HA2 light chain were cloned into a single mammalian expression vector and used to transfect HEK293F cells as described in the previous Examples. Chimeric proteins HA1-hIgG-12K, HA2-hIgG-12K, and HA15-hIgG-12K were expressed from the transfected HEK293F cells and purified. Additionally, other proteins whose sequences are shown in Table 1 are also generated, including HA1-hIgG-12H, HA2-hIgG-12H and HA15-hIgG-12H.

The chimeric protein HA1-hIgG-12K has two HA1-hIgG heavy chains each fused to a 12 residue polylysine peptide and two unmodified HA1-hIgG light chains. The chimeric protein HA1-hIgG-12H has two HA1-hIgG heavy chains each fused to a 12 residue polyhistidine peptide and two unmodified HA1-hIgG light chains. These polylysine and polyhistidine peptides are examples of mucoadhesive peptide fragments which facilitate the attachment of the exemplary chimeric proteins to the upper respiratory mucosa.

Exemplary chimeric proteins comprising exemplary anti-HA antibodies disclosed in Table 4A with their heavy chains fused to 6K, 12K, or 30K and 6H, 12H, or 30H peptides are also expressed and purified.

Example 7B. Chimeric Proteins Comprising Anti-HA Antibodies with Other Mucoadhesive Polycationic Peptides Additional mucoadhesive chimeric proteins comprising HA1, HA2, or HA15, or any of the other anti-HA antibodies shown in Table 4A fused to other cationic (positively charged) peptides, produced using the cationic amino acids arginine (R) or ornithine (O). The mucoadhesive antibodies with ornithine-containing peptides are produced by a method described in Mordhorst et al., *Angewandte Chemie* 59:21442-21447 (2020). In addition, these cationic peptides have been further modified to contain either all cationic amino acids or cationic amino acids interspersed with neutral amino acids as shown in Table 8.

Exemplary cationic peptides listed in Table 8 include peptides consisting of only K, only H, only R or only O ranging from 5 to 30 residues, mixed cationic peptides consisting of mixtures of K, H, R and O ranging from 6 to 30 amino acids, and cationic plus neutral amino acid peptides from 6 to 30 amino acids. Examples of various HA1, HA2, and HA15 mucoadhesive proteins are listed in Table 1. Other antibodies shown in Table 4A are modified with cationic peptides of Table 8 and are made and tested for expression of anti-HA mucoadhesive chimeric proteins in HEK293F cells as described above.

Example 7C. Chimeric Anti-HA Mucoadhesive Proteins Expressed in HEK293F Cells Vectors comprising DNA fragments encoding the chimeric proteins described in Examples 7A and B are used to transfect host HEK293F cells. After 7 days of culture at 37° C., culture medium is harvested, and the chimeric proteins are isolated or purified from culture supernatants using a HiTrap® Protein A HP column (Cytiva) on an ÄKTA FPLC system (GE Healthcare).

Example 7D. Expression and Purification of Animal Anti-HA Chimeric Proteins

Chimeric proteins comprising exemplary animal anti-HA antibodies shown in Table 6 and polylysine or polyhistidine mucoadhesive peptides (e.g., 6K, 12K, or 30K and 6H, 12H, or 30H) are also produced using the methods of Example 7A. Additional mucoadhesive chimeric proteins comprising any of the exemplary animal anti-HA antibodies shown in Table 6 are fused to other cationic (positively charged) peptides, produced using the cationic amino acids arginine (R) or ornithine (O), according to the methods of Example 7B. The resulting chimeric animal anti-HA mucoadhesive proteins are expressed in HEK293F cells using the methods of Example 7C.

Example 8. Design and Expression of Anti-NA Chimeric Proteins Comprising Mucoadhesive Peptide Fragments

Example 8A. Chimeric Proteins Comprising Anti-NA Antibodies and Mucoadhesive Polylysine and Polyhistidine Peptides Chimeric proteins comprising NA1 hIgG or NA2 hIgG heavy chains fused to various lengths of polylysine or polyhistidine peptide fragments are generated. Specifically, DNA fragments encoding a polylysine-modified NA1 or NA2 IgG heavy chain (added to the C-terminus of the IgG heavy chain) and an unmodified NA1 or NA2 light chain were cloned into a single mammalian expression vector and used to transfect HEK293F cells as described in previous Examples. Chimeric proteins NA1-hIgG-12K and NA2-hIgG-12K were expressed from the transfected HEK293F cells and purified. Additionally, exemplary proteins whose sequences are shown in Table 1 are also generated, including NA1-hIgG-12H and NA2-hIgG-12H.

The chimeric protein NA1-hIgG-12K has two NA1-hIgG heavy chains each fused to a 12 residue polylysine peptide and two unmodified NA1-hIgG light chains. The chimeric protein NA1-hIgG-12H has two NA1-hIgG heavy chains each fused to a 12 residue polyhistidine peptide and two unmodified NA1-hIgG light chains. The polylysine and polyhistidine peptides are Examples of mucoadhesive peptide fragments which facilitate the attachment of the exemplary chimeric proteins to the upper respiratory mucosa.

Exemplary chimeric proteins comprising the anti-NA antibodies disclosed in Table 4B with their heavy chains fused to 6K, 12K, or 30K, and 6H, 12H, or 30H peptides are also expressed and purified.

Example 8B. Chimeric Proteins Comprising Anti-NA Antibodies with Other Mucoadhesive Polycationic Peptides Additional mucoadhesive chimeric proteins comprising NA1 or NA2 and the anti-NA antibodies shown in Table 4B are fused to other cationic (positively charged) peptides, produced using the cationic amino acids arginine (R) or ornithine (O). In addition, these cationic peptides have been further modified to contain either all cationic amino acids or cationic amino acids interspersed with neutral amino acids as shown in Table 8. Exemplary cationic peptides listed in Table 8 include peptides consisting of only K, only H, only R or only O ranging from 5 to 30 residues, mixed cationic peptides consisting of mixtures of K, H, R and O ranging from 6 to 30 amino acids, and cationic plus neutral amino acid peptides from 6 to 30 amino acids.

Examples of various NA mucoadhesive proteins are listed in Table 1. Other antibodies shown in Table 4B are modified with cationic peptides of Table 8 and are made and tested for expression of chimeric mucoadhesive NA proteins in HEK293F cells as described above.

Example 8C. Chimeric Anti-NA Mucoadhesive Proteins Expressed in HEK293F Cells Vectors comprising DNA fragments encoding the chimeric proteins described in Examples 8A and 8B are used to transfect host HEK293F cells. After 7 days of culture at 37° C., culture medium is harvested, and the chimeric proteins are isolated or purified from culture supernatants using a HiTrap® Protein A HP column (Cytiva) on an AKTA FPLC system (GE Healthcare).

Example 8D. Expression and Purification of Animal Anti-NA Chimeric Proteins

Chimeric proteins comprising exemplary animal anti-NA antibodies, including those disclosed in Xiong et al., 2020, Cardoso et al., 2014, and Murphy et al., 1972, *N Engl J Med;* 286:1329-1332, and other animal anti-NA antibodies, and polylysine or polyhistidine mucoadhesive peptides (e.g., 6K, 12K, or 30K, or 6H, 12H, or 30H) are also produced using the methods of Example 8A. Additional mucoadhesive chimeric proteins comprising any of the exemplary animal anti-NA antibodies are fused to other cationic (positively charged) peptides, produced using the cationic amino acids arginine (R) or ornithine (O), according to the methods of Example 8B. The resulting chimeric animal anti-HA mucoadhesive proteins are expressed in HEK293F cells using the methods of Example 8C.

Example 9. Characterization of Anti-HA Chimeric Proteins Comprising Mucoadhesive Peptide Fragments

Example 9A. Non-Specific Cell Surface Binding of Mucoadhesive Chimeric Proteins to Cell Surface Glycoproteins In Vitro This Example demonstrates that exemplary chimeric proteins described in Example 7, including chimeric proteins comprising HA1, HA2, or HA15 hIgG antibodies or the antibodies of Table 4A fused to various cationic or mixed peptides of Table 8, are able to nonspecifically bind to the HEK293F cell surface.

Chimeric proteins comprising hIgG fused to cationic peptides (30 nM) are combined with $2\times10^5$ HEK293F cells which have been transfected to express HA or NA and incubated for 1 h at room temperature (RT). PE-conjugated goat anti-human IgG Fc is added, and the mixture is incubated for another 30 min at RT. Unmodified hIgG is used as a negative control. Cells are washed once with FACS buffer (2% FBS, 2 mM EDTA in 1×DPBS), and the binding of HA1, HA2 or HA15 hIgG chimeric proteins is assessed by flow cytometry. All tested chimeric proteins, including HA1, HA2 and HA15 hIgG and exemplary proteins listed in Table 4A fused to 5, 6, 12, or 30 K, H, R, or O mucoadhesive peptides are able to nonspecifically bind to the HEK293F cell surface, while unmodified hIgGs are not.

Nonspecific binding to the HEK293F cell surface by exemplary chimeric proteins of varying lengths comprising anti-HA hIgG1 antibody fused to peptides with mixed cationic residues or mixed cationic and neutral residues are also tested using the same method as described above. HA1, HA2 and HA15-hIgG-6X, 12X, and 30X chimeric proteins are also able to nonspecifically bind to the HEK293T cell surface. The nonspecific binding is confirmed for chimeric proteins comprising the antibodies or fragments thereof as disclosed in Table 4A fused to mucoadhesive peptides exemplified in Table 8 to HEK293F cells, but not for their unmodified counterparts.

Example 9B. In Vitro Binding of Mucoadhesive Chimeric Proteins to Mucin

Mucin glycoproteins produced by mucus-producing cells in the respiratory epithelium or submucosal glands are the major macromolecular constituent of mucus. Binding to mucin can potentially extend the retention time of an antibody in the mucus of the respiratory tract.

This Example demonstrates that anti-HA mucoadhesive proteins modified at the C termini of their heavy chains with peptides comprising various numbers of cationic residues (peptides as shown in Table 8) have increased binding to mucin compared to unmodified anti-HA antibodies.

To test the ability of the various mucoadhesive chimeric proteins to bind mucin, 96-well plates are coated with 50 μg/mL mucin (Sigma, M3895) for 2 hr at room temperature. The plates are blocked with 3% BSA overnight at 4° C. 5 μg/mL antibodies in 25 mM HEPES (pH 6.5) is added to the plates and incubated for 1 h at room temperature. After a wash with washing buffer (25 mM HEPES, NaCl, pH 6.5), plates are stained with HRP-conjugated goat anti-human IgG and developed using 3,3',5,5'-Tetramethylbenzidine (TMB). Absorbance at an optical density at 450 nm ($OD_{450}$) is measured using a standard plate reader.

Example 9C. Binding of Mucoadhesive hIgG Chimeric Proteins to HA

Figure 2:
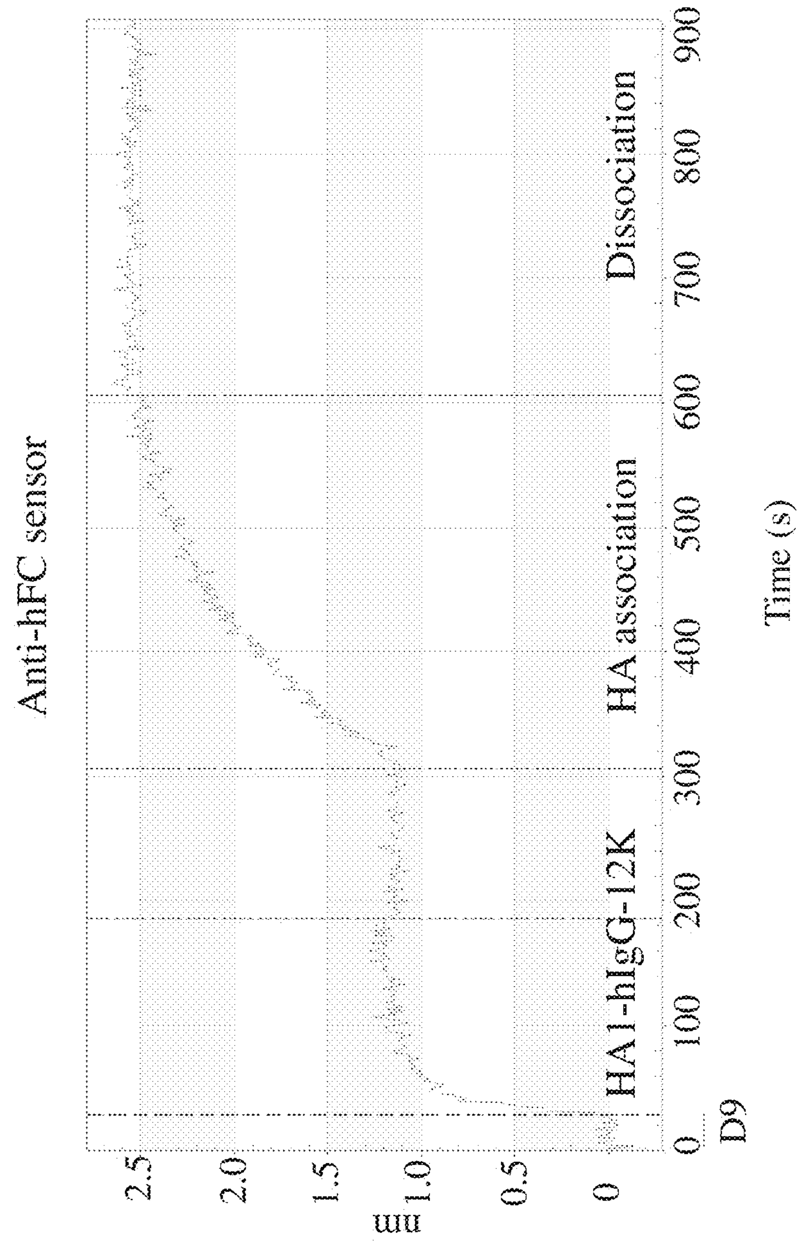
FIG. 2 shows that the exemplary mucoadhesive chimeric human antibody HA2-IgG-12K binds well to hemagglutinin (ECD, His-tagged) from the influenza A H3N2 (A/Aichi/2/1968) strain. Binding was unaffected by the presence of polycationic moieties. All steps were aligned by step sensor location.

To determine whether the binding of the HA1-hIgG-12K chimeric protein to purified HA was unaffected by the mucoadhesive cationic peptide, association of the chimeric protein to HA was examined by BLI. The assay was conducted on a ForteBio Octet KQ with an anti-human IgG (anti-hFC) capture biosensor. Binding of the HA1-hIgG1-12K chimeric protein was measured using the following protocol. 20 μg/mL biotinylated target HA1-hIgG-12K protein in kinetics buffer (10 mM HEPES pH 7.4, 150 mM NaCl, 3 mM EDTA, 0.05% (v/v) Surfactant P20) was loaded onto an anti-hFC capture biosensor. After washing off excess antibody, the HA protein from the H1N1 or H3N2 isolate was added at 10 μg/mL in kinetics buffer for a 300 s period of association and a 300 s period of dissociation. FIGS. 1 and 2 show mucoadhesive chimeric proteins bind well to HA from the H1N1 or H3N2 strain, unaffected by the presence of polycationic moieties.

Other exemplary anti-HA chimeric proteins shown in Table 1 and other anti-HA mucoadhesive chimeric proteins (those comprising any of the other antibodies shown in Table 4A fused to any of the cationic peptides shown in Table 8) are tested for binding to HA using the protocol outlined above, and binding of these exemplary chimeric mucoadhesive proteins to HA is detected. For example, the binding of the HA1-hIgG-12H chimeric protein is tested for binding to HA using the protocol outlined above, and the binding of the HA1-hIgG-12H chimeric mucoadhesive protein to HA is confirmed.

Example 9D. Characterization of Animal Anti-HA Chimeric Proteins Comprising Mucoadhesive Peptide Fragments Exemplary animal anti-HA chimeric proteins comprising mucoadhesive peptide fragments described in Example 7D, including exemplary animal anti-HA antibodies shown in Table 6 fused with any of the mucoadhesive peptide fragments shown in Table 8, are also characterized using the same methods of Examples 9A-9C. Binding of these animal chimeric mucoadhesive proteins to HA is detected using BLI, as above.

Example 10. Characterization of Anti-NA Chimeric Proteins Comprising Mucoadhesive Peptide Fragments

Example 10A. Non-Specific Cell Surface Binding of Mucoadhesive Chimeric Proteins to Cell Surface Glycoproteins In Vitro This Example demonstrates that exemplary chimeric proteins described in previous Examples, including chimeric proteins comprising NA1 or NA2 hIgG antibodies or exemplary antibodies of Table 4B fused to various cationic or mixed peptides of Table 8, are able to nonspecifically bind to the HEK293F cell surface.

Chimeric proteins comprising hIgG fused to cationic peptides (30 nM) are combined with $2\times10^5$ HEK293F cells which have been transfected to express NA and incubated for 1 h at room temperature (RT). PE-conjugated goat anti-human IgG Fc is added, and the mixture is incubated for another 30 min at RT. Unmodified hIgG is used as a negative control. Cells are washed once with FACS buffer (2% FBS, 2 mM EDTA in 1×DPBS), and the binding of NA1 or NA2 hIgG chimeric proteins is assessed by flow cytometry. All tested chimeric proteins, including NA1 and NA2 hIgG and exemplary proteins listed in Table 4B fused to 5, 6, 12, or 30 K, H, R, or O mucoadhesive peptides are able to nonspecifically bind to the HEK293F cell surface, while unmodified hIgGs are not.

Nonspecific binding to the HEK293F cell surface by exemplary chimeric proteins of varying lengths comprising anti-NA hIgG1 antibody fused to peptides with mixed cationic residues or mixed cationic and neutral residues are also tested using the same method as described above. All tested chimeric proteins, including NA1 and NA2 hIgG and exemplary proteins listed in Table 4B fused to 5, 6, 12, or 30 K, H, R, or O mucoadhesive peptides are able to nonspecifically bind to the HEK293F cell surface, while unmodified hIgGs are not.

Example 10B. In Vitro Binding of Mucoadhesive Chimeric Proteins to Mucin

Mucin glycoproteins produced by mucus-producing cells in the respiratory epithelium or submucosal glands are the major macromolecular constituent of mucus. Binding to mucin can potentially extend the retention time of an antibody in the mucus of the respiratory tract.

This Example demonstrates that anti-NA mucoadhesive proteins modified at the C termini of their heavy chains with peptides comprising various numbers of cationic residues (peptides as shown in Table 8) have increased binding to mucin compared to unmodified anti-NA antibodies.

To test the ability of the various mucoadhesive chimeric proteins to bind mucin, 96-well plates are coated with 50 μg/mL mucin (Sigma, M3895) for 2 hrs at room temperature. The plates are blocked with 3% BSA overnight at 4° C. 5 μg/mL antibodies in 25 mM HEPES (pH 6.5) are added to the plates and incubated for 1 h at room temperature. After a wash with washing buffer (25 mM HEPES, 50 mM NaCl, pH 6.5), plates are stained with HRP-conjugated goat anti-human IgG and developed using TMB. Absorbance at $OD_{450}$ is measured.

Example 10C. Binding Affinity of Mucoadhesive hIgG Chimeric Proteins to NA

Figure 3:
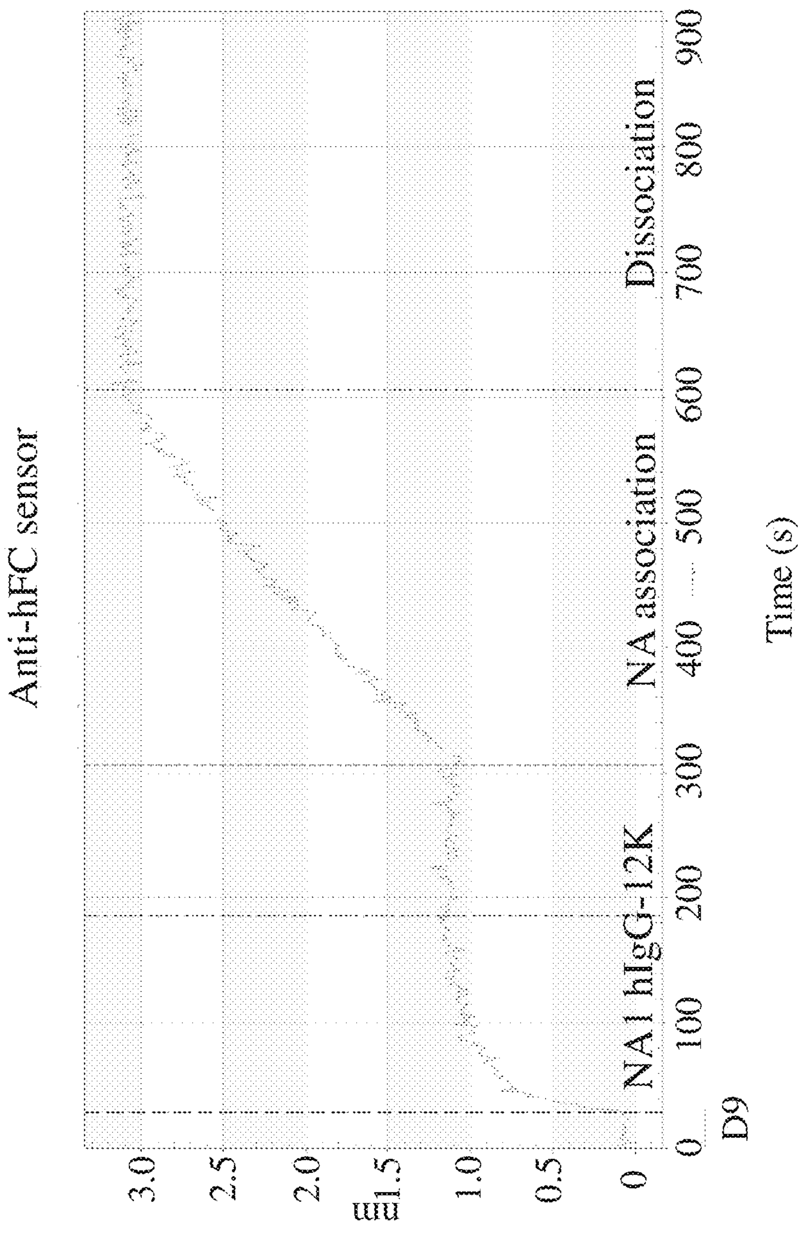
FIG. 3 shows that the exemplary mucoadhesive chimeric human antibody NA1-IgG-12K binds well to the neuraminidase protein (His-tagged) from the influenza B (B/PHUKET/3073/2013) strain. Binding was unaffected by the presence of polycationic moieties. All steps were aligned by step sensor location).

To determine whether the binding of the NA1-hIgG-12K chimeric protein to purified NA was unaffected by presence of the mucoadhesive peptide, association of the chimeric protein to NA was examined by BLI. The assay was conducted on a ForteBio Octet KQ with an anti-hFC capture biosensor Binding of the NA1-hIgG1 chimeric protein was measured using the following protocol. 20 μg/mL biotinylated target NA1-hIgG-12K protein in kinetics buffer (10 mM HEPES pH 7.4, 150 mM NaCl, 3 mM EDTA, 0.05% (v/v) Surfactant P20) was loaded onto an anti-hFC capture biosensor. After washing off excess antibody, the NA protein from an influenza B isolate was added at 10 μg/mL in kinetics buffer for a 300 s period of association and a 300 s period of dissociation. FIG. 3 shows mucoadhesive chimeric protein binds well to NA from the IBV strain, unaffected by the presence of polycationic moieties.

Exemplary chimeric proteins of Table 1 and mucoadhesive variants of proteins in Table 4B are tested for binding to NA using the protocol outlined above and binding of exemplary chimeric mucoadhesive proteins to NA is presented. For example, the binding of the NA1-hIgG-12H chimeric protein is tested for binding to NA using the protocol outlined above, and the binding of the NA2-hIgG-12H chimeric mucoadhesive protein to NA is also confirmed.

Example 10D. Characterization of Animal Anti-NA Chimeric Proteins

Exemplary animal anti-NA chimeric proteins comprising mucoadhesive peptide fragments described in Example 8D, including exemplary animal anti-NA antibodies disclosed in Xiong et al., 2020, Cardoso et al., 2014, and Murphy et al., 1972, and other animal anti-NA antibodies, fused with any of the mucoadhesive peptide fragments shown in Table 8, are also characterized using the same methods of Examples 10A-10C. Binding of these animal chimeric mucoadhesive proteins to NA is detected.

Example 11. Protective Effects of Anti-HA Mucoadhesive Chimeric Proteins in a Mouse Model of Infection

Example 11A. Protective Effects of Human Anti-HA Mucoadhesive Chimeric Protein in a Mouse Model of Infection In a study by Yan et al., *Proc. Nat. Sci. USA,* 115 (5):1081-1086 (2017), it was shown that greater than $10^4$ RNA copies and up to 103 infectious virus particles (per 30 min) are contained in the aerosolized droplets from exhalations of infected persons when speaking.

In the experiments described here, we challenge mice with HA-NA pseudovirus by directly dropping at least $10^6$ pseudovirus particles into the nostrils of the mice. Inhibition of viral infection is achieved by pre-administration of HA1-IgG-12K, HA2-IgG-12K, HA15-IgG-12K, HA15-IgG-6K, HA1-IgG-12H, HA2-IgG-12H, HA15-IgG-12H, or other exemplary mucoadhesive chimeric proteins comprising any of the antibodies disclosed in Table 4A fused with any of the mucoadhesive peptide fragments disclosed in Table 8. Inhibition against this high viral titer shows the promise of a nasal spray protection even in a worst-case scenario and could provide a large cushion of protection in most common situations where a healthy person encounters an infected individual.

To test if chimeric proteins comprising anti-HA antibodies fused to various mucoadhesive or polycationic peptide fragments can block infectious influenza viruses or pseudoviruses in vivo, and to determine the role of the polycationic peptide fragment in the potential blocking of influenza infection, the HA1, HA2, and HA15 hIgG chimeric proteins (sequences shown in Table 1; e.g., HA1-hIgG-12K or HA1-IgG-12H) are compared to the unmodified HA1, HA2 and HA15 hIgG antibodies lacking the C-terminal mucoadhesive peptide modification, respectively, in an in vivo pseudovirus protection assay. Seven groups of 4-week-old young adult CD-1® IGS or BALB/c mice (Charles River) (A1 through A7) are pretreated with an HA1, HA2 or HA15 hIgG chimeric protein (e.g., HA1-IgG-12K or HA1-IgG-12H) or unmodified HA1, HA2 or HA15 hIgG. Doses of 25 μg (A2 and A3), 75 μg (A4 and A5) or 200 g (A6 and A7) per nostril of an HA1, HA2, or HA15 chimeric protein (A2, A4, A6) or an unmodified HA1, HA2, or HA15 antibody (A3, A5, A7) are each delivered to 3 groups of mice through nasal administration. A control group (A1) receives no pretreatment with any antibody.

10 hours after nasal administration of the mucoadhesive proteins or antibodies, all groups are dosed with HA-NA pseudotyped lentivirus. Animals are closely monitored after nasal administration of the pseudovirus; on day 3, day 5 and day 7 following pseudoviral application, bioluminescence and body weight are measured for each mouse. After the day 7 measurement, the lungs are dissected and imaged.

The mice pretreated with each of the HA1, HA2, or HA15 hIgG chimeric proteins tested (e.g., HA1-IgG-12K or HA1-IgG-12H) are free of signs of infection as measured by bioluminescent imaging, whereas the mice receiving the HA1, HA2, or HA15 antibody lacking the polylysine or polyhistidine peptide fragment and the control group with no antibody show obvious signs of infection. The mice pretreated with unmodified HA1, HA2, or HA15 hIgG also show signs of pseudoviral infection in their lung tissues, whereas the mice pretreated with the HA1, HA2 or HA15 hIgG chimeric proteins are free of signs of lung involvement after Day 7.

Each of the HA1, HA2, or HA15 hIgG chimeric proteins when tested (e.g., HA1-hIgG-12K or HA1-IgG-12H) is able to block nasal infection by influenza pseudoviruses in mice, and the polycationic peptide fragments play an essential role in the blocking of infection. Each of the HA1, HA2, or HA15 hIgG chimeric proteins is superior to the unmodified HA1, HA2, or HA15 antibody in protecting mice from virus infection when the chimeric proteins or unmodified antibodies are administered 10 hours prior to virus dosing. Thus, the mucin-binding modification (i.e., addition of the cationic peptide fragment) of the HA1, HA2, and HA15 mucoadhesive chimeric proteins makes it possible for these modified proteins to protect mice against nasal infection by influenza pseudoviruses.

Other anti-HA mucoadhesive chimeric proteins, e.g., those using each of antibodies HA3-HA16 (as disclosed in Table 4A) fused with each mucoadhesive peptide fragment disclosed in Table 8, are also compared to their corresponding unmodified HA antibodies in the mouse nasal infection experiments as described in this Example. The protective effect provided by the mucoadhesive proteins tested and each of the HA3-HA16 chimeric proteins is determined by their ability to block nasal infection by influenza pseudoviruses in mice, compared to their unmodified counterpart antibodies.

Example 11B. Protective Effects of Animal Anti-HA Mucoadhesive Chimeric Protein in a Mouse Model of Infection Chimeric proteins comprising the exemplary animal anti-HA antibodies shown in Table 6 fused with each mucoadhesive peptide fragment disclosed in Table 8 are also characterized for protective effects in a mouse model of influenza pseudovirus infection using the same methods of Example 11A. The protective effect provided by the animal anti-HA chimeric proteins is determined by their ability to block nasal infection by influenza pseudoviruses in mice, compared to their unmodified counterpart antibodies.

Example 12. Protective Effects of Anti-NA Mucoadhesive Chimeric Proteins in a Mouse Model of Infection

Example 12A. Protective Effects of Human Anti-NA Mucoadhesive Chimeric Protein in a Mouse Model of Infection In the experiments described here, we challenge mice with HA-NA pseudovirus by directly dropping at least $10^6$ pseudovirus particles into the nostrils of the mice. Inhibition of viral infection is achieved by pre-administration of NA1-IgG-12K, NA2-IgG-12K, NA1-IgG-12H, NA2-IgG-12H, or other exemplary mucoadhesive chimeric proteins comprising any of the antibodies disclosed in Table 4A against this high viral titer illustrates the promise of a nasal spray protection even in a worst-case scenario and could provide a large cushion of protection in most common situations where a healthy person encounters an infected individual.

To test if chimeric proteins comprising anti-NA fused to various mucoadhesive or polycationic peptide fragments can block infectious influenza viruses or pseudoviruses in vivo, and to determine the role of the polycationic peptide fragment in the potential blocking of influenza infection, the NA1 and NA2 hIgG chimeric proteins (sequences shown in Table 1; e.g., NA1-hIgG-12K or NA1-IgG-12H) are compared to the unmodified NA1 and NA2 antibodies lacking the C-terminal mucoadhesive peptide modification, respectively, in an in vivo pseudovirus protection assay. Seven groups of 4-week-old young adult CD-1® IGS or BALB/c mice (Charles River) (A1 through A7) are pretreated with an NA1 or NA2 hIgG chimeric protein (e.g., NA1-IgG-12K or NA1-IgG-12H) or unmodified NA1 or NA2 hIgG. Doses of 25 μg (A2 and A3), 75 μg (A4 and A5) or 200 μg (A6 and A7) per nostril of an NA1 or NA2 chimeric protein (A2, A4, A6) or an unmodified NA1 or NA2 antibody (A3, A5, A7) are each delivered to 3 groups of mice through nasal administration. A control group (A1) receives no pretreatment with any antibody.

10 hours after nasal administration of the mucoadhesive proteins and unmodified antibodies, all groups are dosed with HA-NA pseudotyped lentivirus. Animals are closely monitored after nasal administration of the pseudovirus; on day 3, day 5 and day 7 following pseudoviral application, bioluminescence and body weight are measured for each mouse. After the day 7 measurement, the lungs are dissected and imaged.

The mice pretreated with each of the NA1 or NA2 hIgG chimeric proteins tested (e.g., NA1-IgG-12K or NA1-IgG-12H) are free of signs of infection as measured by bioluminescent imaging, whereas the mice receiving the NA1 or NA2 antibody lacking the polylysine peptide fragment and the control group with no antibody show obvious signs of infection. The mice pretreated with unmodified NA1 or NA2 hIgG also show signs of pseudoviral infection in their lung tissues, whereas the mice pretreated with the NA1 or NA2 hIgG chimeric proteins are free of signs of lung involvement after Day 7, as measured by bioluminescent imaging.

Each of the NA1 or NA2 hIgG chimeric proteins tested (e.g., NA1-hIgG-12K or NA1-IgG-12H) is tested for the ability to block nasal infection by influenza pseudoviruses in mice; the polycationic peptide fragments play an essential role in such blocking of infection. Each of the NA1 or NA2 hIgG chimeric proteins is superior to the unmodified NA1 or NA2 antibody in protecting mice from virus infection when the chimeric proteins or unmodified antibodies are administered 10 hours prior to virus dosing. Thus, the mucin-binding modification (i.e., addition of the cationic peptide fragment) of the NA1 and NA2 antibodies makes it possible for the modified chimeric proteins to protect mice against nasal infection by influenza pseudoviruses.

Other anti-HA mucoadhesive chimeric proteins, e.g., those using each of antibodies NA3-NA14 (as disclosed in Table 4B) fused with each mucoadhesive peptide fragment disclosed in Table 8, are also compared to their corresponding unmodified NA antibody proteins in the mouse nasal infection experiments as described in this Example. The protective effect provided by the mucoadhesive proteins tested and each of the NA3-NA14 chimeric proteins is determined by their ability to block nasal infection by Influenza pseudoviruses in mice compared to their unmodified counterpart antibodies.

Example 12B. Protective Effects of Animal Anti-NA Mucoadhesive Chimeric Protein in a Mouse Model of Infection Chimeric proteins comprising exemplary animal anti-NA antibodies, including those disclosed in Xiong et al., 2020, Cardoso et al., 2014, and Murphy et al., 1972, and other animal anti-NA antibodies fused with mucoadhesive peptide fragments disclosed in Table 8 are also characterized for protective effects in a mouse model of influenza pseudovirus infection using the same methods as in Example 12A. The protective effect provided by the animal anti-NA chimeric proteins is determined by their ability to block nasal infection by influenza pseudoviruses in mice, compared to their unmodified counterpart antibodies. Antibodies D3 and 7H2 from Xiong, et al. 2020 and N1-$V_H$H from Cardozo, et al. 2014 are tested for their ability to block pseudoviral infection of HEK293-HNM cells as described; in this Example, chimeric mucoadhesive proteins derived from these antibodies (fused to mucoadhesive peptides), along with the unmodified antibodies are tested for their ability to protect mice from pseudoviral infection. Mucoadhesive variants of anti-NA antibodies D3, 7H2, or N1-$V_H$H are capable of protecting mice from pseudoviral infection compared to their unmodified counterparts.

Example 13. Protection from Influenza Pseudoviral Infection by Anti-HA Mucoadhesive Proteins in a Nasal Spray Formulation

Example 13A. Anti-HA-IgG-12K and Anti-HA-IgG-12H Chimeric Proteins Stored in NS Buffer Maintain Binding Affinity to HA Protein An accelerated antibody stability assay is performed to confirm that the formulation buffer does not affect the antigen binding ability of HA1-hIgG when modified with (fused to) the 12K or 12H peptide fragment. Neither does the formulation buffer affect the antigen binding ability of the other exemplary anti-HA chimeric proteins (chimeric proteins comprising any of the antibodies disclosed in Table 4A fused with any of the peptides disclosed in Table 8, other than HA1-hIgG-12K and HA1-IgG-12H). Briefly, HA1-hIgG-12K and HA1-IgG-12H chimeric proteins are stored in NS buffer (25 mM citrate buffer, pH 6.5, 125 mM NaCl, 5% glycerin, 0.1% methionine, 0.02% polysorbate 80, and 0.1% potassium sorbate) at 37° C. over a maximum period of 14 days, which is equivalent to about 1.5 years at 4° C. The binding of HA1-hIgG-12K and HA1-IgG-12H towards antigens is determined using a ForteBio Octet instrument with anti-hFC capture biosensor and the data is acquired by Octet Data Acquisition software 9.0. The binding curves of HA1-hIgG-12K and HA1-IgG-12H in NS buffer at different time points are compared to the binding curve of a sample of the unmodified HA1-hIgG antibody stored in PBS at 4° C. Graphs are obtained which show the binding (association and dissociation) of HA1-hIgG-12K and HA1-IgG-12H to HA protein after storage in the nasal spray formulation for 0, 1, 3, 5 7, or 14 days. The stability of binding to HA of other exemplary anti-HA mucoadhesive chimeric proteins in NS buffer are also tested for up to 14 days at 37° C. Mucoadhesive chimeric proteins stored in NS buffer are able to maintain binding affinity to HA protein as measured in this in vitro assay.

Example 13B. Anti-HA-IgG-12K and Anti-HA-IgG-12H Chimeric Proteins Stored in NS Buffer Maintain Monomeric Form During the 7-day storage period, the degree of aggregation of the HA1-hIgG-12K, HA1-hIgG-12H, or the other exemplary anti-HA chimeric proteins in NS buffer is assayed using size exclusion chromatography (SEC)-HPLC. Briefly, 5 μL of 1 μg/μL antibody in PBS is loaded onto a Waters™ XBridge™ protein BEH 200A SEC column, 3.5 μm, 7.2× 300 mm on an Agilent 1260 Infinity HPLC system. The chimeric proteins are eluted using DPBS (Dulbecco's PBS) buffer, pH 7.0 at a flow rate of 0.5 mL/min. A UV reading of the elution flow is monitored. The elution profiles of the mucoadhesive chimeric proteins and the unmodified antibodies stored for 14 days are compared. The accelerated antibody stability test at 37° C. demonstrates the stability of the modified chimeric proteins in NS formulation buffer, remaining precipitate-free over time.

Example 13C. Anti-HA-IgG-12K and Anti-HA-IgG-12H Chimeric Proteins Stored in NS Buffer Maintain the Ability to Block Sialic Acid Glycan Binding The receptor determinant of influenza A and B viruses are sialic acids, comprised mostly of N-acetyl-neuraminic acid (Neu5Ac). A Neu5Ac (Sigma Aldrich)-coated microplate ELISA assay is used to test antibody blocking ability at varying (antibody) concentrations. HA proteins are incubated with anti-HA1-hIgG-12K or HA1-hIgG-12H chimeric proteins in a series of diluted concentrations for 30 mins. The HA protein and chimeric protein solutions are added into each well of the sialic acid-coated microplate. After 30 mins of incubation, the plate is washed three times in TBST (Tris-Buffered Saline, 0.1% Tween®20). Horseradish peroxidase conjugated (HRP) anti-His Tag (ThermoFisher Scientific) secondary antibody is added to each well for 30 mins, and the plate is washed five times in TBST. Chromogen solution is used as the substrate, and absorbance at 450 nm is measured using a standard microplate reader. HA1-hIgG-12K or HA1-hIgG-12H stored in NS buffer retains the ability to block HA protein binding to sialic acid glycan moieties in vitro. The other exemplary anti-HA chimeric proteins perform similarly in exemplary ELISA assays.

Example 13D. Anti-HA-IgG-12K and Anti-HA-IgG-12H Chimeric Proteins Stored in NS Buffer Maintain the Ability to Block Pseudoviral Infection of HEK-HNM Cells A luciferase assay is performed as described in Example 5. The HA-NA-pseudotyped lentivirus is added into HA1-hIgG-12K, anti-HA-IgG-12H, or the other exemplary anti-HA chimeric proteins in NS buffer for 30 min at room temperature. The mixture is then added into HEK293F-HNM cells (see Materials and Methods) in culture media. The assay is performed using 3.3 nM, 10 nM or 30 nM HA1-12K hIgG or HA1-12H hIgG chimeric protein stored in NS buffer at 37° C. over a period of 7 days. After 48 hours of incubation, the degree of infection is determined by monitoring luciferase levels in infected cells using a Promega Luciferase Assay or imaged for GFP using fluorescence microscopy, demonstrating the protective effects of the mucoadhesive proteins on HEK-293 cell infection.

Example 13E. Protection from Influenza Pseudoviral Infection by Animal Anti-HA Mucoadhesive Proteins in a Nasal Spray Formulation Exemplary animal anti-HA mucoadhesive proteins comprising any of the animal anti-HA antibodies shown in Table 6 are also evaluated for protection from influenza pseudoviral infection using the same methods of Examples 13A-13D. Briefly, an accelerated antibody stability assay is performed using the methods of Example 13A to confirm that the formulation buffer does not affect the antigen binding ability of animal anti-HA mucoadhesive chimeric proteins when modified with (fused to) the mucoadhesive peptide fragments. Animal anti-HA mucoadhesive chimeric proteins stored in NS buffer are able to maintain binding affinity to HA protein as measured in this in vitro assay. The degree of aggregation of the exemplary animal anti-HA chimeric proteins in NS buffer is assayed using SEC-HPLC, using the methods of Example 13B. The modified chimeric proteins in NS formulation buffer remain precipitate-free over time. A Neu5Ac (Sigma Aldrich)-coated microplate ELISA assay is used to test antibody blocking ability at varying (antibody) concentrations, using the same methods of Example 13C, showing that the exemplary animal anti-HA mucoadhesive proteins stored in NS buffer retain the ability to block HA protein binding to sialic acid glycan moieties in vitro. A luciferase assay is performed as described in Example 5, using the methods of Example 13D. The exemplary animal anti-HA chimeric proteins stored in NS buffer maintain the ability to block pseudoviral infection of HEK-HNM cells.

Example 14. In Vitro Characterization of Modified NA Mucoadhesive Proteins in a Nasal Spray Formulation

Example 14A. NA-12K hIgG and NA-12H hIgG Chimeric Proteins Stored in NS Buffer Maintain Binding Affinity to NA Protein An accelerated antibody stability assay is performed to confirm that the formulation buffer does not affect the binding ability of the NA1-hIgG-12K or NA1-hIgG-12H mucoadhesive proteins (or other exemplary chimeric proteins using the antibodies disclosed in Table 4B fused with the peptides disclosed in Table 8) to the NA protein. Briefly, NA1-hIgG-12K chimeric proteins were stored in NS buffer (25 mM citrate buffer, pH 6.5, 125 mM NaCl, 5% glycerin, 0.1% methionine, 0.02% polysorbate 80, and 0.1% potassium sorbate) at 37° C. over a maximum period of 14 days, which is equivalent to about 1.5 years at 4° C. The binding of antibodies towards antigens is determined using a ForteBio Octet instrument with an anti-hFC capture biosensor and the data is acquired by Octet Data Acquisition software 9.0. The binding curves of the mucoadhesive proteins in NS buffer at different time points are compared to the binding curve of a sample of the unmodified NA1-hIgG antibody stored in PBS at 4° C. FIG. 3 shows the binding (association and dissociation) of the NA1-hIgG-12K to NA protein after storage in the nasal spray formulation for 0, 1, 3, 5, 7, or 14 days. The stability of binding to NA of exemplary mucoadhesive proteins derived from the antibodies from Table 4B in NS buffer, including NA1-hIgG-12H, are also tested for up to 14 days at 37° C. Mucoadhesive chimeric proteins stored in NS buffer are able to maintain binding affinity to NA protein as measured in this in vitro assay.

Example 14B. NA1-IgG-12K and NA1-IgG-12H Chimeric Protein Stored in NS Buffer Maintains its Monomeric Form During the 14 day storage period, the degree of aggregation of the NA-IgG-12K hIgG or NA-IgG-12H hIgG protein or exemplary modified antibodies of Table 4B in NS buffer is assayed using SEC-HPLC. Briefly, 5 μL of 1 μg/μL antibody in PBS is loaded onto a Waters™ XBridge™ protein BEH 200 Å SEC column, 3.5 μm, 7.2×300 mm on an Agilent 1260 Infinity HPLC system. The antibody is eluted using DPBS (Dulbecco's PBS) buffer, pH 7.0 at a flow rate of 0.5 mL/min. A UV reading of the elution flow is monitored. The elution profiles of the mucoadhesive proteins and the unmodified antibodies stored for 14 days are compared. The accelerated antibody stability test at 37° C. shows how stable the mucoadhesive proteins in NS formulation buffer remain precipitate-free over time.

Example 14C. Anti-NA-12K hIgG and Anti-NA-12H hIgG Chimeric Proteins Stored in NS Buffer Maintain Ability to Block Sialic Acid Glycan Binding A Neu5Ac (Sigma Aldrich)-coated microplate ELISA assay is used to test antibody blocking ability at varying (antibody) concentrations. NA proteins are incubated with anti-NA-12K hIgG or anti-NA-12H hIgG chimeric proteins in a series of diluted concentrations for 30 mins. The NA protein and antibody solutions are added into each well of the sialic acid-coated microplate. After 30 mins of incubation, the plate is washed three time in TBST (Tris-Buffered Saline, 0.1% Tween®20). HRP anti-His Tag (ThermoFisher Scientific) secondary antibody is added to each well for 30 mins, and the plate is washed five times in TBST.

Chromogen solution is used as the substrate, and absorbance at 450 nm is measured using a standard microplate reader. The NA1-hIgG-12K or NA1-hIgG-12H proteins stored in NS buffer retain the ability to block NA protein binding to sialic acid glycan moieties in vitro. Exemplary mucoadhesive proteins derived from the antibodies of Table 4B perform similarly in comparable ELISA assays.

Example 14D. NA-IgG-12K or NA-IgG-12H Modified Proteins Stored in NS Buffer Maintain the Ability to Block Pseudoviral Infection of HEK-HNM Cells A luciferase assay is performed as described in Example 5. The HA-NA-pseudotyped lentivirus is added into NA1-hIgG-12K or NA1-hIgG-12H proteins (or other exemplary antibodies disclosed in Table 4B fused with the peptides disclosed in Table 8) in NS buffer for 30 min at room temperature. The mixture is then added into HEK293F-HNM cells in culture media. The assay is performed using 3.3 nM, 10 nM or 30 nM NA1-12K hIgG or NA1-12H hIgG chimeric proteins stored in NS buffer at 37° C. over a period of 14 days. After 48 hours of incubation, the degree of infection is determined by monitoring luciferase levels in infected cells using a Promega Luciferase Assay or imaged for GFP using fluorescence microscopy. Exemplary mucoadhesive chimeric proteins from Table 4B in NS buffer are also tested for up to 14 days.

Example 14E. In Vitro Characterization of Modified NA Mucoadhesive Proteins in a Nasal Spray Formulation Exemplary animal anti-NA mucoadhesive proteins comprising any of the animal anti-NA antibodies described in Xiong et al., 2020, Cardoso et al., 2014, and Murphy et al., 1972, and other animal anti-NA antibodies, are also evaluated for protection from influenza pseudoviral infection using the same methods of Examples 14A-14D.

Briefly, an accelerated antibody stability assay is performed using the methods of Example 14A to confirm that the formulation buffer does not affect the antigen binding ability of animal anti-NA mucoadhesive chimeric proteins when modified with (fused to) the mucoadhesive peptide fragments. Animal anti-NA mucoadhesive chimeric proteins stored in NS buffer are able to maintain binding affinity to NA protein as measured in this in vitro assay. The degree of aggregation of the exemplary animal anti-NA chimeric proteins in NS buffer is assayed using SEC-HPLC, using the methods of Example 14B. The modified chimeric proteins in NS formulation buffer remain precipitate-free over time. A Neu5Ac (Sigma Aldrich)-coated microplate ELISA assay is used to test antibody blocking ability at varying (antibody) concentrations, using the same methods of Example 13C, showing that the exemplary animal anti-NA mucoadhesive proteins stored in NS buffer retain the ability to block NA protein binding to sialic acid glycan moieties in vitro. A luciferase assay is performed as described in Example 5, and using the methods of Example 14D. The exemplary animal anti-NA chimeric proteins stored in NS buffer maintain the ability to block pseudoviral infection of HEK-HNM cells.

Example 15. Protection from Pseudoviral Infection by Anti-HA Mucoadhesive Chimeric Proteins in a Nasal Spray Formulation In Vivo

Example 15A. Mucoadhesive Human Anti-HA Chimeric Proteins Stored in NS Buffer Prevent Pseudovirus Infection in a Mouse Model Demonstration of the ability of anti-HA mucoadhesive proteins including HA1-hIgG-12K, HA2-hIgG-12K, HA1-hIgG-12H, HA2-hIgG-12H, and exemplary modified forms of antibodies disclosed in Table 4A stored in NS buffer to prevent HA-NA pseudovirus infection in a mouse model is described in this Example. In experiments conducted previously (not shown), the most effective length of the mucoadhesive amino acid fragments required to effectively adhere the chimeric proteins to the nasal cavity was shown to be 12 residues when chimeric proteins are administered 10 hours prior to pseudoviral administration, as measured by the protective effect in mice.

4-week-old young adult CD-1® IGS or BALB/c mice (Charles River) are nasally administered the HA1-hIgG-12K or HA1-hIgG-12H chimeric protein stored in NS buffer at various concentrations (25 μg to 200 μg total in 20 μL instilled per nostril), with the same amount of unmodified HA1-hIgG in a second group of mice, and NS buffer alone in control mice. 10 hours after chimeric protein or buffer administration, HA-NA pseudovirus is administered to mice intranasally (20 μL instilled per nostril).

The bioluminescent signal in treated mice in both nose and lung areas up to 7 days is monitored in mice following the pseudoviral dosage. Measurement of luciferase activity is used to assess the degree of infection on days 3, 5 and 7. After the day 7 measurement, the lungs are dissected and imaged. Measurement of bioluminescence in the nasal cavity or lung areas demonstrate the protective effects of the HA1-hIgG-12K- or HA1-hIgG-12H-treated mice up to 7 days after the viral dosage and are reflected in these measurements.

Other exemplary anti-HA chimeric proteins using the antibodies disclosed in Table 4A fused with the peptides disclosed in Table 8 are stored in NS buffer and tested in the mouse pseudovirus infection model as described in this Example. The bioluminescent values and imaging results are obtained for each group. Pre-treating mice nasally with HA1-IgG-12K, HA2-IgG-12K, HA1-IgG-12H, HA2-IgG-12H, or the other exemplary anti-HA chimeric proteins in the nasal spray formulation protect the mice against the influenza pseudovirus infection, at least in the nasal cavities or lungs.

Example 15B. In Vivo Protection from Different Influenza Strains in a Mouse Model A series of pseudovirus preparations made from the HA and NA proteins of different strains of influenza viruses (variant HA and NA proteins are listed in Tables 2A-B and 3) are used to infect mice pretreated with anti-HA mucoadhesive chimeric proteins described in Example 15A or unmodified anti-HA antibodies, using the methods described in Example 15A. The protective effects of HA1-hIgG-12K or HA1-hIgG-12H and other exemplary modified chimeric proteins to infection with pseudoviruses prepared from several HA strains are examined. Bioluminescent imaging and measurement of luciferase activity taken from the nasal cavities and lungs of pseudovirus-treated mice are obtained, and the degree of protection provided by the mucoadhesive chimeric proteins is calculated using the methods described in previous Examples. The anti-HA mucoadhesive chimeric proteins tested are able to protect the mice against infection by influenza pseudovirus made with the various HA and NA proteins listed in Tables 2A-B and 3.

Example 15C. Protection from Pseudoviral Infection by Animal Anti-HA Mucoadhesive Chimeric Proteins in a Nasal Spray Formulation In Vivo Exemplary animal anti-HA mucoadhesive proteins comprising any of the animal anti-HA antibodies shown in Table 6, in NS buffer are also evaluated for protection from influenza pseudoviral infection using the methods detailed in Examples 15A-15B. Mucoadhesive animal anti-HA chimeric proteins stored in NS buffer prevent pseudovirus infection in a mouse model, in contrast to their unmodified anti-HA counterparts. The animal anti-HA mucoadhesive chimeric proteins tested are able to protect the mice against infection by influenza pseudovirus made with the various HA and NA proteins listed in Tables 2A-B and 3, as determined using the same methods of Example 15B.

Example 16. Protection from Pseudoviral Infection by Anti-NA Mucoadhesive Chimeric Proteins in a Nasal Spray Formulation In Vivo

Example 16A. Mucoadhesive Human Anti-NA Chimeric Proteins Stored in NS Buffer Prevents Pseudovirus Infection in a Mouse Model Demonstration of the ability of anti-NA mucoadhesive proteins including modified NA1-IgG-12K, NA2-IgG-12K, NA1-IgG-12H, NA2-IgG-12H, and exemplary modified forms of antibodies disclosed in Table 4A stored in NS buffer to prevent HA-NA pseudovirus infection in a mouse model is described in this Example. 4-week-old young adult CD-1® IGS or BALB/c mice (Charles River) are nasally administered the NA1-hIgG1-12K chimeric protein stored in NS buffer at various concentrations (25 μg to 200 μg total in 20 μL instilled per nostril), with the same amount of unmodified NA1-hIgG in a second group of mice, and NS buffer alone in control mice. 10 hours after chimeric protein or buffer administration, HA-NA pseudovirus is administered to mice intranasally (20 μL instilled per nostril).

The bioluminescent signal in treated mice in both the nose and lung areas up to 7 days is monitored in mice following the pseudoviral dosage. Measurement of luciferase activity is used to assess the degree of infection on days 3, 5 and 7. After the day 7 measurement, the lungs are dissected and imaged. Measurement of bioluminescence in the nasal cavity or lung areas demonstrate the protective effects of the NA1-hIgG1-12K or NA1-hIgG1-12H antibody-treated mice up to 7 days after the viral dosage and are reflected in these measurements.

Other exemplary anti-NA chimeric proteins using the antibodies disclosed in Table 4B fused with the peptides disclosed in Table 8 are stored in NS buffer and tested in the mouse pseudovirus infection model as described in this Example. The bioluminescent values and imaging results are obtained for each group. Pre-treating mice nasally with NA1-IgG-12K, NA2-IgG-12K, NA1-IgG-12H, NA2-IgG-12H, or the other exemplary anti-NA chimeric proteins in the nasal spray formulation protect the mice against the influenza pseudovirus infection, at least in the nasal cavities or lungs.

Example 16B. In Vivo Protection from Different Influenza Strains in a Mouse Model A series of pseudovirus preparations made from the HA and NA proteins of different strains of influenza viruses (variant HA and NA proteins are listed in Tables 2A-B and 3) are used to infect mice pretreated with anti-NA mucoadhesive chimeric proteins or unmodified anti-NA antibodies as described in Example 15A. The protective effects of NA1-hIgG-12K or NA1-hIgG-12H and the other exemplary chimeric proteins against infection with pseudoviruses prepared from several NA strains are examined. Measurements of luciferase activity taken from the nasal cavities and lungs of pseudovirus-infected mice are obtained, and the degree of protection provided by the mucoadhesive chimeric proteins is calculated using the methods described in previous examples.

Example 16C. Protection from Pseudoviral Infection by Animal Anti-NA Mucoadhesive Chimeric Proteins in a Nasal Spray Formulation In Vivo Exemplary animal anti-NA mucoadhesive proteins comprising any of the animal anti-NA antibodies disclosed in Xiong et al., 2020, Cardoso et al., 2014, and Murphy et al., 1972, or other animal anti-NA antibodies, in NS buffer are also evaluated for protection from influenza pseudoviral infection using the methods of Examples 16A-16B. Mucoadhesive animal anti-NA chimeric proteins stored in NS buffer prevent pseudovirus infection in a mouse model, in contrast to their unmodified counterparts. The animal anti-NA mucoadhesive chimeric proteins tested are able to protect the mice against infection by influenza pseudovirus made with the various HA and NA proteins listed in Tables 2A-B and 3, as determined using the same methods of Example 16B.

Example 17. Protective Effect and In Vivo Characterization of Anti-Canine HA Mucoadhesive Chimeric Proteins in a Nasal Spray Formulation Using a Mouse Model The incidence of canine influenza (CIV) has become a concern for pet owners, dog breeders and veterinary practitioners in the North America and China over the past several years (Li et al. Viruses. 2021 Nov. 15; 13(11):2279). Two of the canine influenza virus strains circulating in China and in North America are of avian origin (H3N2); additionally, an American strain (H3N8), is of equine origin (Parrish and Voorhees, Vet Clin North Am Small Anim Pract. 2019 July; 49(4):643-649). All are highly contagious, transmitted from dog to dog, and though often resulting in asymptomatic or mild indications, can cause more severe disease resulting in tracheal bronchitis, pneumonia or death. Influenza virus infections have been most notably found in birds and pigs, but are also found in domestic cats, and horses and in wild animals such as bats and seals.

To investigate the feasibility of a mucoadhesive antibody which could be administered in a veterinary setting, we used antibodies based on an endemic strain of canine influenza in the US, H3N2. Monoclonal antibody D7 (Xie et al., Veterinary Research 46:33 (2015)) was identified as a neutralizing antibody providing protection against CIV H3N2 virus stains Canine/Jiangsu/06/2010 (JS/10) and A/Canine/Guangdong/12/2012 (GD/12).

Using the methods described in Examples 11 and 15, a mucoadhesive chimeric protein comprising the D7 monoclonal antibody fused to a polylysine peptide fragment, D7-IgG-12K, or fused to a polyhistidine peptide fragment, D7-IgG-12H, is produced in HEK293F cells (as described in Example 7) and used to determine the protective effect in mice from canine influenza pseudovirus infection. Pseudovirus particles decorated with the CIV HA3 and N2 proteins are prepared according to Example 5.

Using methods described in Xie et al., the mucoadhesive chimeric protein D7-IgG-12K, D7-IgG-12H, or unmodified D7 antibody in NS buffer is instilled in the nasal passages of CD1 or Balb/c mice at various concentrations (25 μg to 200 μg total in 20 μL instilled per nostril) and the HA3-NA2 pseudovirus is introduced 10 hours later. The mice are monitored for weight and luciferase activity, measured on Day 3, 5 and 7. Demonstration of a protective effect of the D7-IgG-12K or D7-IgG-12H mucoadhesive chimeric protein compared to unmodified antibody are provided by the measurement of luciferase activity in the nasal cavities and lungs of mice challenged with pseudovirus. D7-IgG-12K or D7-IgG-12H protects mice against CIV pseudovirus infection.

Other mucoadhesive chimeric proteins comprising D7-IgG fused to the peptides disclosed in Table 8 are also generated and tested to be protective against CIV pseudovirus infection in mice.

Example 18. Various Peptide Linker Fragments as an Optional Part of the Mucoadhesive Chimeric Proteins In some instances, it may be necessary to stabilize the mucoadhesive chimeric proteins, with the inclusion of peptide linker fragments, to increase the protein half-life or increase the avidity or number of mucoadhesive proteins in vitro to more easily detect or measure the signal or in vivo to increase the effective amount being delivered to the nasal cavity in a single dose. For this purpose, various types of peptide linker fragments, especially oligomerization or multimerization domains from natural proteins, are used in various embodiments of the mucoadhesive chimeric proteins. In the previous Examples of this application, mucoadhesive modifications of full-length antibodies are described in detail as the main possible embodiments and are tested for functionality. In those embodiments, the peptide linker fragments comprise the complete constant region of a full-length antibody's heavy chain, which is composed of $CH_1$, $CH_2$, and $CH_3$ if the antibody is IgG, IgA, or IgD, or $CH_1$, $CH_2$, $CH_3$, and $CH_4$ if the antibody is IgE or IgM. In other embodiments of mucoadhesive chimeric proteins, the peptide linker fragments can comprise only parts of the constant region of a full-length antibody's heavy chain or a part of the constant region of an antibody's light chain, e.g., $CH_1$, $CH_2$, $CH_3$, and $CH_4$, and/or $C_L$. Some exemplary chimeric proteins comprise Immunoglobulin Fc regions as the peptide linker fragments or a part of the peptide linker fragments, which are comprised of $CH_2$ and $CH_3$ domains or $CH_2$, $CH_3$, and $CH_4$ domains. Fc regions act as dimerizing agents and retain some antibody-like properties, such as good physicochemical characteristics for expression, purification and storage, and long serum half-life in vivo see, Lobner et al., Immunol. Rev., 270(1)113-31 (2016). Exemplary sequences of Fc as well as $CH_1$, $CH_2$, $CH_3$, and $CH_4$, and $C_L$ are shown in Table 9.

Other possible peptide linker fragments or useful domains to be included in peptide linker fragments which can be used to induce stable protein:protein interactions in the mucoadhesive chimeric proteins are shown in Table 9, and include the detectable enzymatic tags alkaline phosphatase and glutathione-s-transferase (GST), both functioning as dimers. In particular, alkaline phosphatase (513 amino acids (aa)) dimerization contacts are formed by patches of discrete aa sequences from at N-terminus: aa27-42, aa68-76, aa83-85, aa94-98 and aa103-105; and the C-terminus: 382-391 and 397-410. GST (217aa) homodimerizes as two monomers: monomer 1 (aal-84): monomer 2 (aa85-217). Alkaline phosphate and GST fusion proteins are highly soluble, easily detected using their enzymatic functions, and they do not seem to interfere with the fusion partner's activity. The enzymatic domains and protein interaction domains are embodied in the whole molecule.

In Table 9, we list exemplary full-length linkers or protein:protein interaction domains which are able to induce multimerization in their fusion partners and may also serve to increase the overall strength or avidity of binding. One often-used example includes the heptad repeats of the basic helix-loop-helix leucine zipper domains (bZIP) or isoleucine zipper domains, which form stable protein trimers see, Napolitano and Ballabio, *J. Cell Sci.,* 129(13):2475-81 (2016); and Branttie and Dutch, *J. Gen Virol.,* 101(5):467-472 (2020). Collagen-like proteins form trimers of great binding strength due to the presence of repeated Glycine-X-Y repeats $(GPP)_n$ and have been shown not to interfere with the fusion protein's functionality or safety profile see, (Fan et al., *FASEB J.,* 22:3795-3804 (2008). Higher order multimerization domains have been used extensively as well; the streptavidin protein is able to tightly bind biotin molecules forming tetrameric units that are easily detectable see Chivers et al., *Biochem J.,* 435(Pt 1):55-63 (2011). However, the streptavidin fusion moiety is large, and perhaps too bulky for some applications; the p53 tetramerization domain is only 31 amino acids long see, Gencel-Augusto et al., *Genes Dev.,* 34(17-18):1128-1146 (2020). The C-terminal 27 amino acids of the bacteriophage T7 fibritin protein (also called folden; see, Yang et al., *J. Virol.,* 76(9):4634-42 (2002)) forms stable soluble trimeric complexes. The coiled-coil domain of the COMP protein (cartilage oligomeric matrix protein, see Holler et al., *J. Immunol. Methods,* 237:159-173 (2000)) is able to form self-assembling pentameric complexes. Further protein-protein interaction domains can be found in the literature and higher-order complexes can be formed using dextran scaffolds or maleimide polymers (DMGS) (see Dolton et al., *Clin. Exp. Immunol.*, 177(1):47-63 (2014); and Guillaume et al., *J. Biol. Chem.*, 278: P4500-4509 (2003).

Example 19. Anti-HA Mucoadhesive Chimeric Proteins Comprising Various Peptide Linker Fragments In addition to the exemplary anti-HA mucoadhesive chimeric proteins described in previous Examples in this application, other exemplary anti-HA chimeric proteins are generated using the variable regions of any of the antibodies disclosed in Table 4A, including HA1, HA2, and other human anti-HA antibodies, as well as animal anti-HA antibodies disclosed in Table 6, and other animal anti-HA antibodies, to fuse with any of the linkers or domains disclosed in Table 9, and further fused with any of the mucoadhesive peptides disclosed in Table 8. These other exemplary anti-HA mucoadhesive chimeric proteins are tested for various functions and capabilities as described in previous Examples. They specifically bind to the HA antigens, nonspecifically bind to mucin, and block influenza pseudovirus infection and real virus infection in vitro and in vivo.

Example 20. Anti-NA Mucoadhesive Chimeric Proteins Comprising Various Peptide Linker Fragments In addition to the exemplary anti-NA mucoadhesive chimeric proteins described in previous Examples in this application, other exemplary anti-NA chimeric proteins are generated using the variable regions of any of the antibodies disclosed in Table 4B, including NA1, NA2, and other human anti-NA antibodies, as well as animal anti-NA antibodies including those disclosed in Xiong et al., 2020, Cardoso et al., 2014, and Murphy et al., 1972, and other animal anti-NA antibodies, to fuse with any of the linkers or domains disclosed in Table 9, and further fused with any of the mucoadhesive peptides disclosed in Table 8. These other exemplary anti-NA mucoadhesive chimeric proteins are tested for various functions and capabilities as described in previous Examples. They specifically bind to the NA antigens, nonspecifically bind to mucin, and block influenza pseudovirus infection and real virus infection in vitro and in vivo.

Example 21. Production of HA-Pseudotyped Lentiviruses

Lentiviruses containing HA, NA and M2 proteins were produced by transfection of HA, NA and M2 expressing HEK293T cells (HEK293-HNM cells) using the lentiviral expression vector pCDH-EF1-MCS (System Biosciences) that carries the HA, NA and M2 expression constructs on a single vector under the control of the E1Fa promoter. A transgene that carries GFP and luciferase markers was also introduced into the lentiviral vector. Helper plasmids which encode the proteins required in trans for the production of infectious pseudotyped virus were simultaneously co-transfected. To evaluate the functional titer of the lentivirus produced, concentrated lentiviruses were applied to HEK293-HNM cells in 96-well plates for 48 hours. Control groups included mock-transduced (no DNA added) HEK293-HNM cells or HEK293-HNM cells transduced with empty lentiviral vectors. Flow cytometry analyses were done on day 3. Transduction efficiencies of the HEK293-HNM cells were assessed by measuring the GFP signal with flow cytometry. Flow cytometry data were collected using a BD LSR FORTESSA™ and analyzed using the FlowJo™ v10.6.1 software package, and pseudoviral titers of greater than $1\times10^6$ H3N2 pseudovirus per mL were achieved (data not shown).

Example 22. Expression and Purification of Anti-HA Chimeric Mucoadhesive Proteins Chimeric proteins comprising HA1 hIgG or HA15 hIgG heavy chains fused to various lengths of polylysine peptide fragments were generated. Specifically, DNA fragments encoding a polylysine-modified HA1 or HA15 IgG heavy chain (added to the C-terminus of the IgG heavy chain) and an unmodified HA1 or HA15 light chain were cloned into a single mammalian expression vector and used to transfect HEK293T cells as described in the previous Examples. Chimeric proteins HA1-hIgG-12K and HA15-hIgG-6K and HA15-hIgG-12K were expressed from the transfected HEK293T cells and purified.

The chimeric protein HA1-hIgG-12K has two HA1-hIgG heavy chains each fused to a 12-residue polylysine peptide and two unmodified HA1-hIgG light chains. The chimeric proteins HA15-hIgG-6K and HA15-hIgG-12K have two HA1-hIgG heavy chains each fused to a 6 or 12-residue polylysine peptide and two unmodified HA1-hIgG light chains. These polylysine peptides are examples of mucoadhesive peptide fragments which facilitate the attachment of the exemplary chimeric proteins to the upper respiratory mucosa.

Example 23. Characterization of Anti-HA Chimeric Proteins Comprising Mucoadhesive Peptide Fragments

Example 23A. In Vitro Binding of Mucoadhesive Chimeric Proteins to Mucin

This Example demonstrates that anti-HA mucoadhesive proteins modified at the C termini of their heavy chains with peptides comprising various numbers of cationic residues (peptides as shown in Table 8) have increased binding to mucin compared to unmodified anti-HA antibodies.

Figure 4:
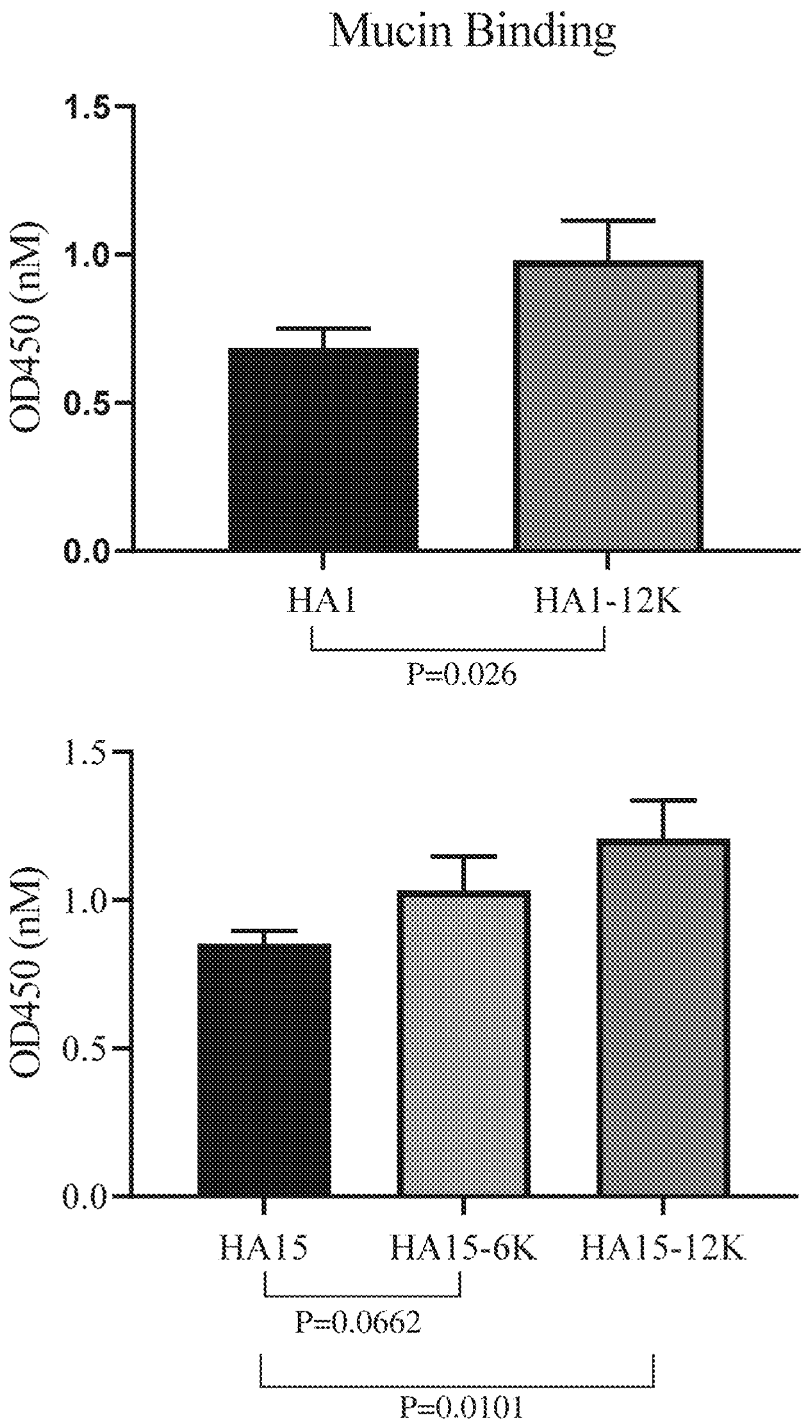
FIG. 4 shows that modified chimeric human antibodies HA1-IgG-12K and HA15-IgG-12K bind mucin in vitro significantly better than their unmodified counterparts. HRP-anti-human IgG fluorescence at 450 nM measures the binding of HA-IgG mucoadhesive antibodies compared to HA-IgG antibodies alone.

To test the ability of the anti-HA-IgG mucoadhesive chimeric proteins to bind mucin, 96-well plates were coated with 50 μg/mL mucin (Sigma, M3895) for 2 hr at room temperature. The plates were blocked with 3% BSA overnight at 4° C. 5 μg/mL anti-HA1-IgG-12K, anti-HA15-IgG-6K or anti-HA15-IgG-12K chimeric antibodies in 25 mM HEPES (pH 6.5) was added and the plates were incubated for an hour at room temperature. After a wash with washing buffer (25 mM HEPES, mM NaCl, pH 6.5), plates were stained with HRP-conjugated goat anti-human IgG and developed using 3,3',5,5'-Tetramethylbenzidine (TMB). Absorbance at an optical density at 450 nm ($OD_{450}$) was measured using a standard plate reader. FIG. 4 shows that the addition of either the 6K or 12K cationic moiety significantly increased the antibody binding to mucin-coated plates compared to antibodies that lack mucoadhesive peptides.

Figure 5A:
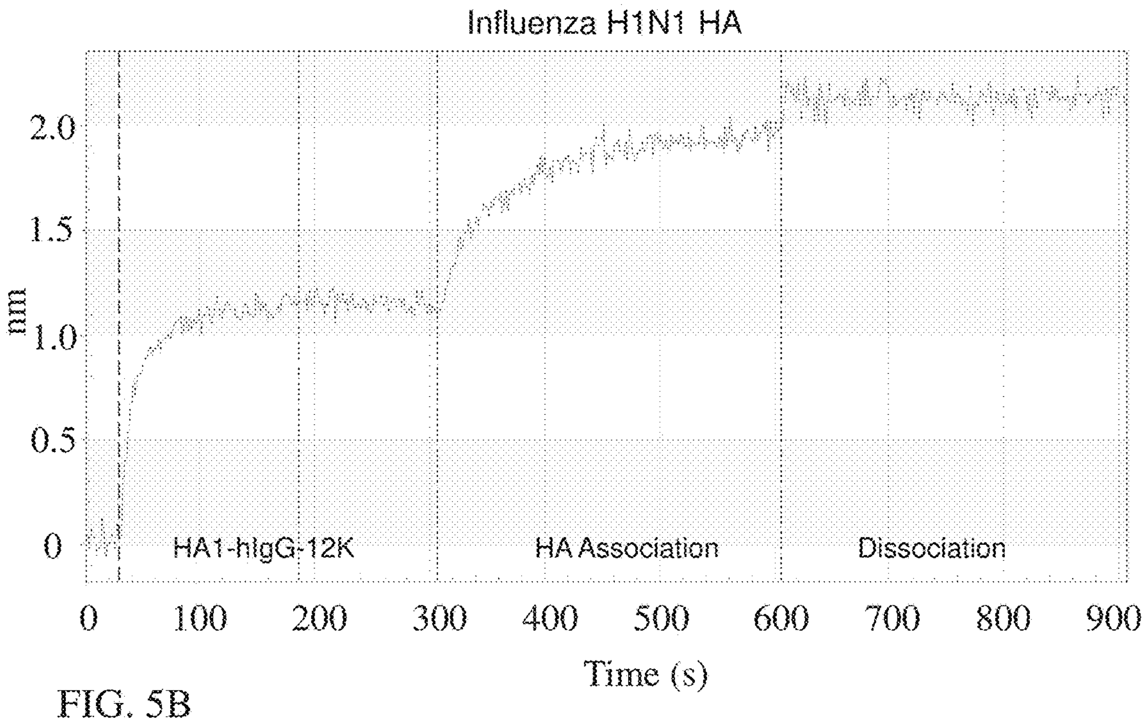
FIGS. 5A-5B show the association of the chimeric antibodies to HA examined by BLI using a ForteBio Octet KQ with a with an anti-hFC capture biosensor. Influenza A H1N1 (A/Wisconsin/588/2019)/(A/Victoria/2570/2019) His-tagged HA protein binding was unaffected by the presence of the cationic peptides of HA-1-IgG (FIG. 5A) and HA15-IgG (FIG. 5B) mucoadhesive antibodies.
Figure 5B:
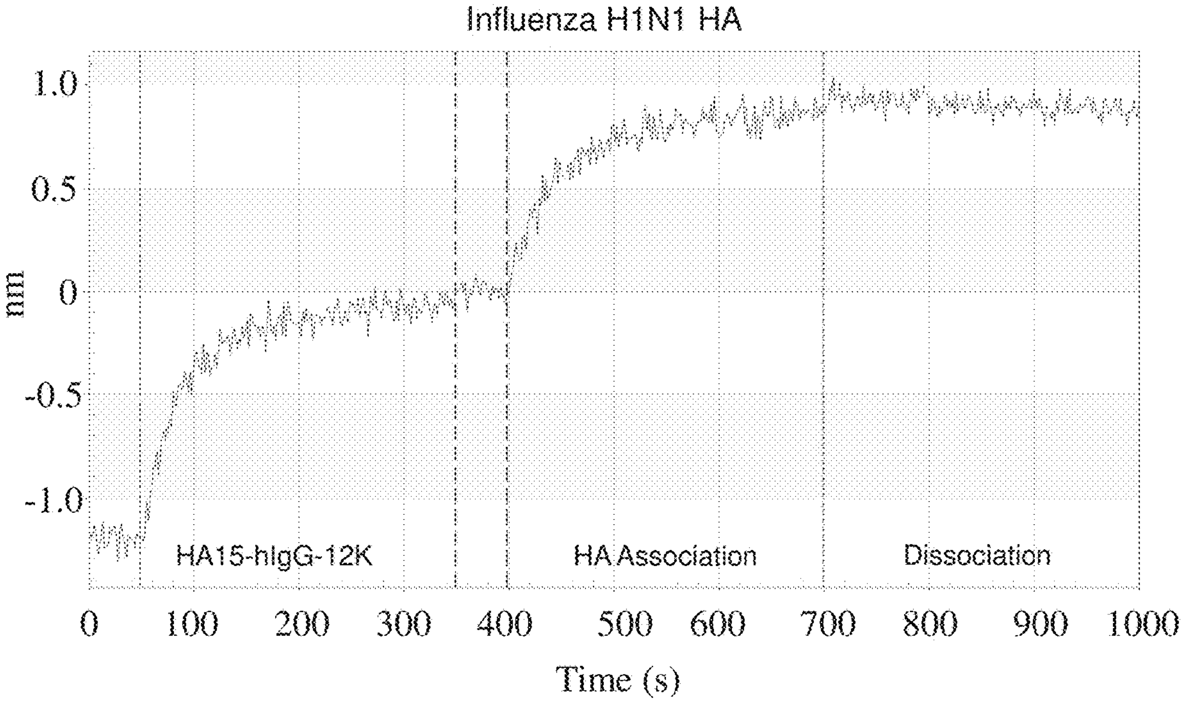
Figure 6A:
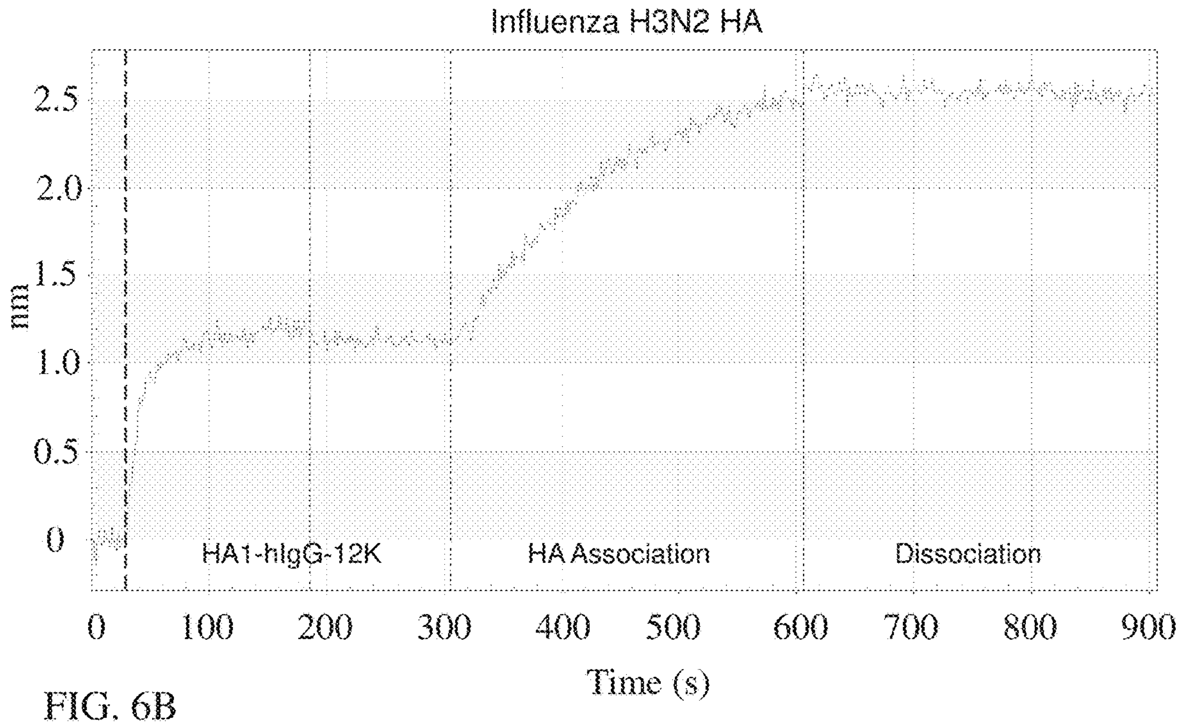
FIGS. 6A-6B show the association of the chimeric antibodies to HA examined by BLI using a ForteBio Octet KQ with a with an anti-hFC capture biosensor. Influenza A H3N2 (A/Aichi/2/1968) His-tagged HA antigen binding was unaffected by the presence of the cationic peptides of HA-1-IgG (FIG. 6A) and HA15-IgG (FIG. 6B) mucoadhesive antibodies.
Figure 6B:
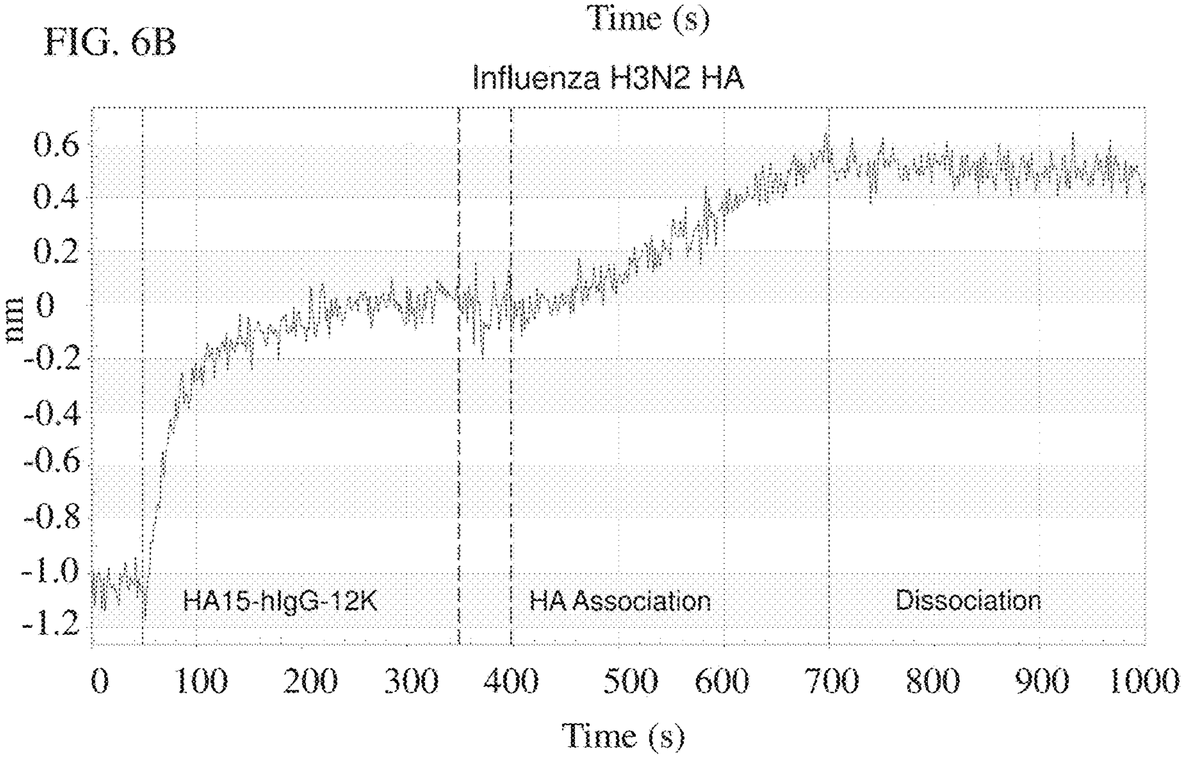

Example 23B. Binding of Human Anti-HA-hIgG Human Chimeric Mucoadhesive Antibodies to HA To determine whether the binding of the HA1-hIgG-12K chimeric protein to purified HA was unaffected by the mucoadhesive cationic peptide, association of the chimeric protein to HA was examined by BLI. The binding of exemplary anti-HA chimeric antibodies HA1 and HA15, to H1N1 or H3N2 HA was measured by Bio-Layer Interferometry (BLI) on a ForteBio Octet KQ with an anti-human IgG (anti-hFC) Capture biosensor. Binding of the human IgG antibodies was demonstrated using the following protocol: 20 μg/mL biotinylated anti-HA1-IgG-12K or anti-HA15-IgG-12K protein in kinetics buffer (10 mM HEPES pH 7.4, 150 mM NaCl, 3 mM EDTA, 0.05% (v/v) Surfactant P20) was loaded onto an anti-hFC biosensor. After washing off excess antibody, the sensor tips were dipped into 10 μg/mL of His-tagged H1N1 (A/Wisconsin/588/2019)/(A/Victoria/2570/2019) hemagglutinin proteins (SinoBiological Cat. 40787-V08H) in kinetics buffer for a 300 s period of association and a 300 s period of dissociation. The association and dissociation graphs were generated using Octet Data Acquisition Software v9, and the robust binding to H1N1 hemagglutinin protein was confirmed. Binding of anti-HA1-IgG-12K (FIG. 5A and FIG. 6A) and anti-HA15-IgG-12K (FIGS. 5B and 6B) chimeric mucoadhesive proteins also showed strong binding to HA from the H3N2 (A/Aichi/2/1968) strain using His-tagged H3N2 HA (Sino-Biological Cat. 11707-V08H) as the binding partner; binding was unaffected by the presence of polycationic moieties.

Example 24. Neutralization of Pseudoviral Infection by Anti-HA Mucoadhesive Chimeric Proteins In Vitro This Example demonstrates that anti-HA IgG mucoadhesive chimeric antibodies are able to block H1N1 and H3N2 pseudovirus infection in HEK293F cells. Briefly, exemplary anti-HA antibodies HA1-IgG-12K and HA15-hIgG-12K, were serially diluted (400, 100, 25, 6.25, 1.5625, 0.0977, 0.0244, 0.0061, 0 nM) and were then incubated with HA-pseudotyped lentivirus. The pseudotyped virus contains the EF1-α-driven luciferase and GFP reporter genes separated by a P2A self-cleaving peptide. Following a 30 min incubation of the anti-HA hIgG antibody with H1N1 or H3N2 pseudotyped lentivirus (H1N1 at 1 μL/well, H3N2 at 0.5 μl/well), the incubated antibody and lentivirus solution was added to $1\times10^6$ HEK293F cells. The cells were cultured in 5% $CO_2$ at 37° C. for 48 h. The degree of cellular infection with the pseudotyped virus was determined by detecting the luciferase level of the infected cells (Promega Luciferase Assay).

Figure 7A:
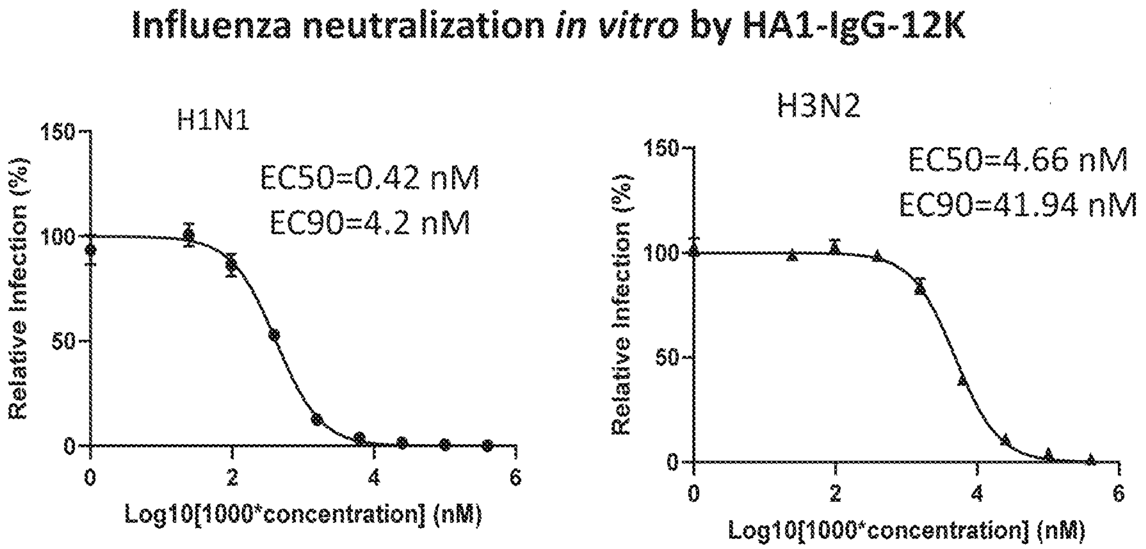
FIGS. 7A-7B show the in vitro neutralization of pseudoviral infection of HEK293F cells using luciferase bioluminescence. The relative infection value determined with the intensity of bioluminescence indicates that the virus infection level of the transduced cells is inhibited by HA1-IgG-12K (FIG. 7A) and HA15-IgG-12K (FIG. 7B) mucoadhesive antibody binding to H1N1 (left panels) or H3N2 (right panels) pseudovirus.
Figure 7B:
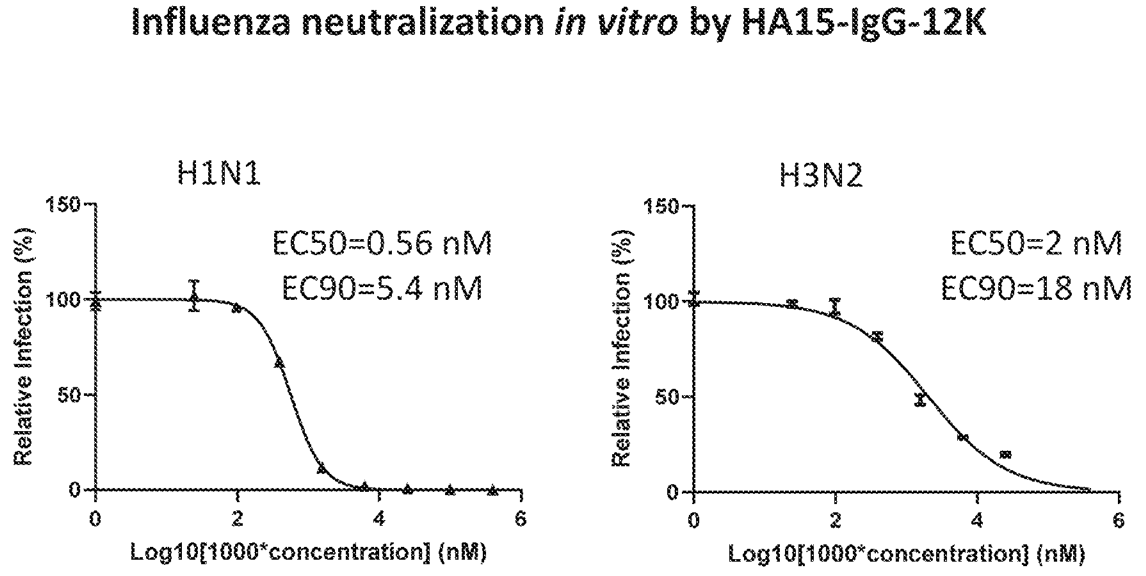

FIG. 7A and FIG. 7B demonstrate that a low quantity of anti-HA antibody HA1-IgG-12K (FIG. 7A) or HA15-IgG-12K (FIG. 7B) was a sufficient antibody concentration to completely block the infection of HEK293F cells, shown by the attenuation of the luciferase signal. The EC50 and EC90 values were calculated for each assay.

Figure 9A:
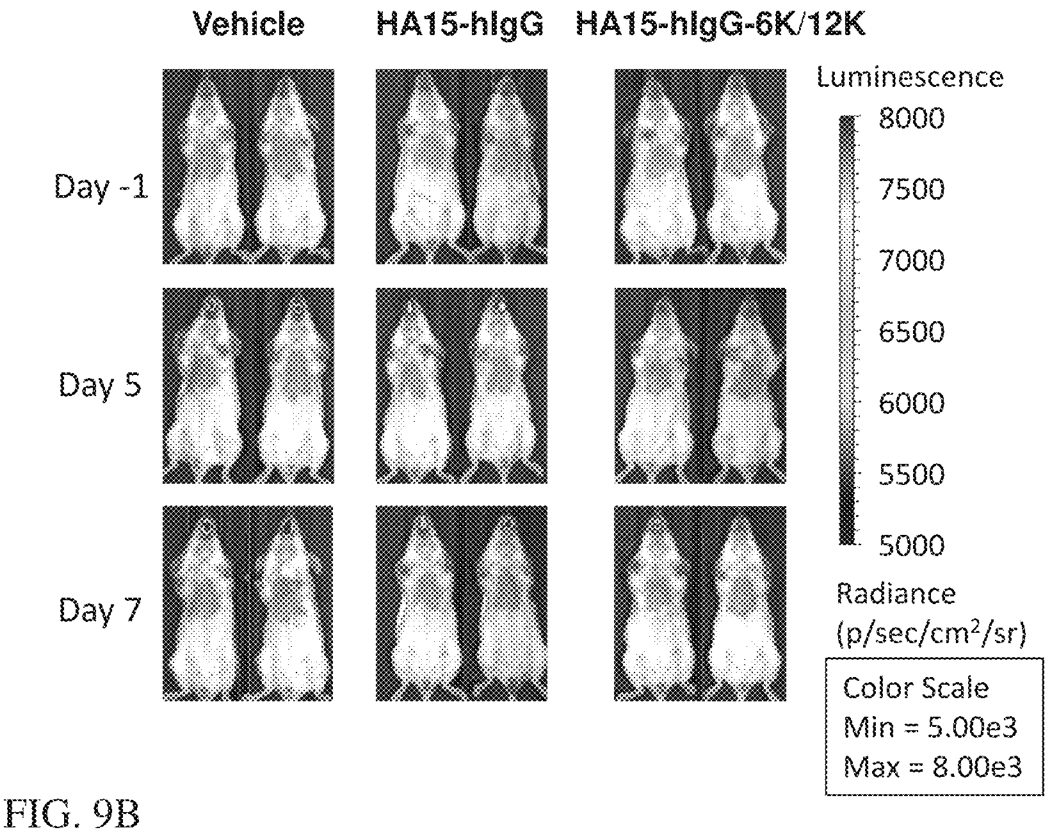
FIGS. 9A-9B show the neutralization of pseudoviral infection in a mouse model. H3N2 pseudovirus infection is attenuated by pretreatment with mucoadhesive HA15-IgG-6K/HA15-IgG-12K antibody compared to unmodified HA15-IgG antibody or pretreatment without antibody (Vehicle). Bioluminescent imaging of mice (FIG. 9A) and corresponding graph (FIG. 9B) shows protection by HA15-IgG-6K/12K antibodies from pseudoviral infection on Day 5 and Day 7 post pretreatment (Day-1).
Figure 9B:
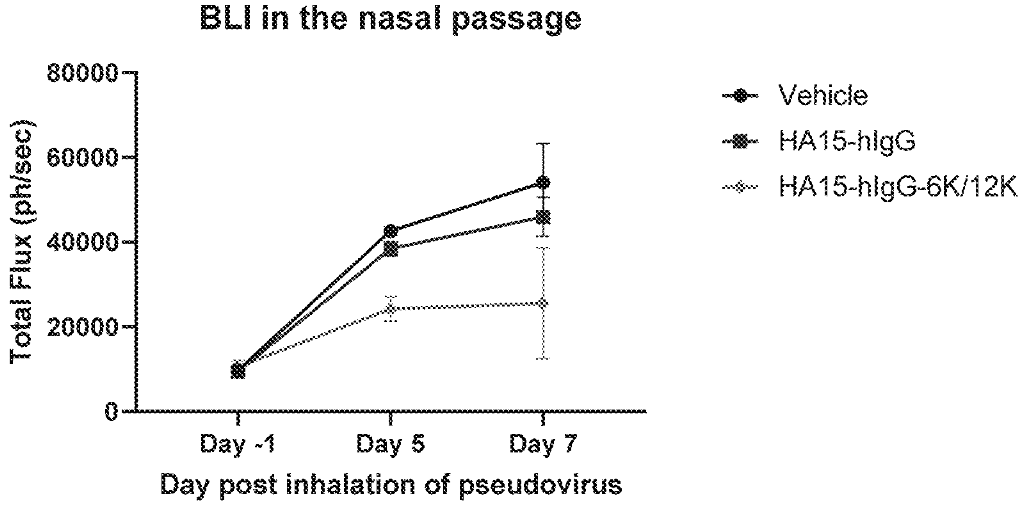

Example 25. Protective Effects of Anti-HA Mucoadhesive Chimeric Proteins in a Mouse Model of Infection The protective effects of human anti-HA1-IgG or anti-HA15-IgG mucoadhesive chimeric protein in a mouse model of infection was clearly demonstrated for both of the mucoadhesive HA1 and HA15 antibodies. In the experiments described here, mice were challenged mice H3N2 influenza pseudovirus by directly dropping at least $2.0\times10^5$ particles into the nostrils of the mice. Inhibition of viral infection was achieved by pre-administration of HA15-IgG-6K and HA15-IgG-12K, or HA15-IgG antibody with no mucoadhesive fragment. Enhancement of protection by HA15-IgG-6K and HA15-IgG-12K compared with HA15-IgG antibody illustrates the advantage of adding mucoadhesive fragment, as shown in FIGS. 9A-9B.

To test if chimeric proteins comprising anti-HA1 antibodies fused to a 12K mucoadhesive polycationic peptide fragment could block infectious influenza viruses or pseudoviruses in vivo, the HA hIgG chimeric protein (sequence shown in Table 1; e.g., HA1-IgG-12K) was tested in an in vivo pseudovirus protection assay. 6-week-old young adult BALB/c mice (Jackson Labs) were pretreated with HA1-IgG-12K chimeric protein. Doses of 100 μg per each nostril were delivered to the mice through nasal administration. A control group received no pretreatment with any antibody (denoted "Vehicle").

Figure 8A:
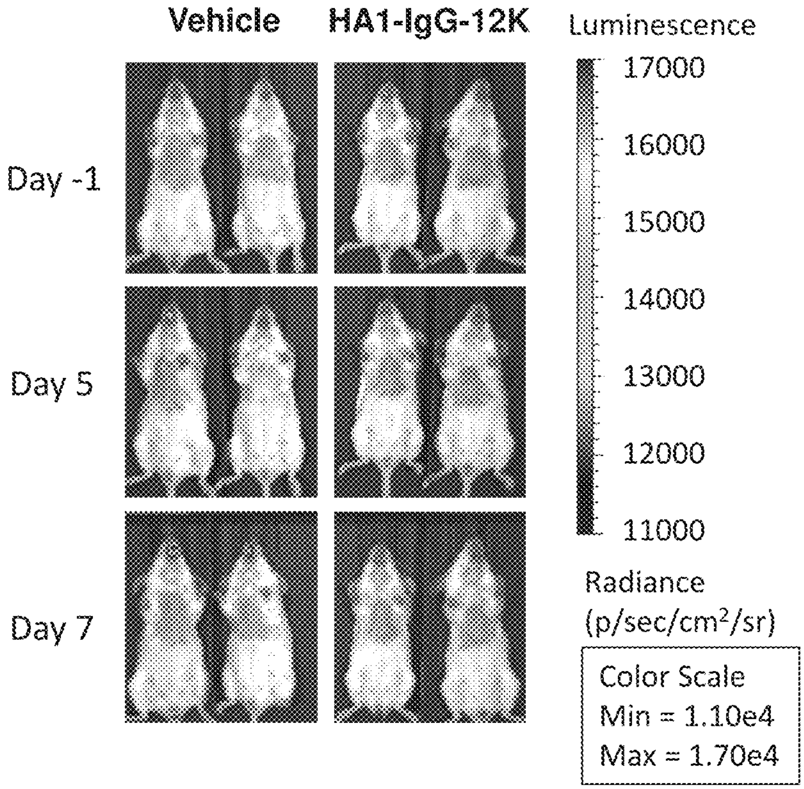
FIGS. 8A-8B show the neutralization of pseudoviral infection in a mouse model. H3N2 pseudovirus infection is attenuated by pretreatment with mucoadhesive HA1-IgG-12K antibody compared to pretreatment without antibody (Vehicle). Bioluminescent imaging of mice (FIG. 8A) and corresponding graph (FIG. 8B) shows protection by HA1-IgG-12K antibody from pseudoviral infection on Day 5 and Day 7 post pretreatment (Day-1).
Figure 8B:
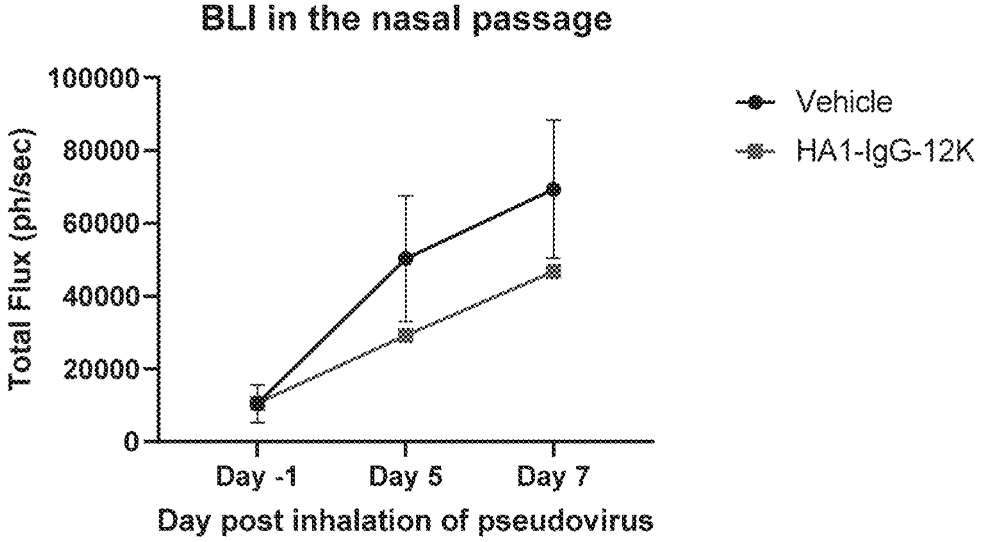

10 hours after nasal administration of the mucoadhesive proteins/antibodies, both groups of mice were dosed with H3N2 pseudotyped lentivirus. Animals were closely monitored after nasal administration of the pseudovirus; on day 5 and day 7 following pseudoviral application, bioluminescence and body weight were measured for each mouse. FIG. 8A shows bioluminescent imaging of the mice before pseudoviral dosing (Day-1) and on Days 5 and 7 after dosing. FIG. 8B is a graph representing the luminescence values for each group. Mice receiving pretreatment with HA-IgG-12K chimeric mucoadhesive proteins show a significant reduction of luminescence compared to unpretreated mice on Days 5 and 7 indicating a resistance to pseudoviral infection.

In another experiment, an HA15-hIgG mucoadhesive chimeric protein mixture (sequences shown in Table 1; e.g., HA15-hIgG-6K and HA15-hIgG-12K) were compared to the unmodified HA15-hIgG antibody lacking the C-terminal mucoadhesive peptide modification, in an in vivo pseudovirus protection assay. Seven groups of 4-week-old young adult BALB/c mice (Jackson Labs) were pretreated with HA15-hIgG-6K and HA15-hIgG-12K chimeric protein mix (50/50) or unmodified HA15-hIgG. Doses of 100 μg per nostril were delivered to 2 groups of mice through nasal administration. A control group received no pretreatment with any antibody ("Vehicle"). 10 hours after nasal administration of the mucoadhesive proteins or antibodies, all groups are dosed with H3N2 pseudotyped lentivirus as in the previous example. FIG. 9A shows the bioluminescence imaging for each mouse and FIG. 9B depicts the corresponding values as a graph. This Example demonstrates the protective effect of the mucoadhesive moiety in protecting mice from pseudoviral infection. Compared to "Vehicle" and HA15-IgG with no modification, the mice pretreated with HA15-IgG-12K show a significant resistance to pseudoviral infection. Enhancement of protection by HA15-IgG-6K and HA15-IgG-12K compared with unmodified HA15-IgG antibody shows the advantage of adding mucoadhesive fragment and the role the cationic moiety plays in resisting infection.

Example 26. HA or NA Mucoadhesive Chimeric Proteins Activate Complement Pathway to Induce Virolysis

Example 26A. HA or NA Mucoadhesive Chimeric Proteins Activate Complement Pathway The complement pathway is an important aspect of innate immunity. Activation of the complement pathway induces vital host responses to protect against acute, chronic, and recurrent viral infections (Huber et al., 2006; Mellors et al, 2020). Virus opsonization can be induced by complement pathway activation, wherein the opsonization of the viral surface can lead to the aggregation of the viruses, as well as phagocytosis of these viruses (due to complement receptors on phagocytic cells) and virolysis (Mellors et al., 2020). Therefore, HA or NA mucoadhesive chimeric proteins are tested for their ability to activate the complement pathway, and subsequently kill Influenza pseudovirus. This Example demonstrates that HA or NA mucoadhesive chimeric proteins (HA1-hIgG-12K, HA2-hIgG-12K, HA15-hIgG-12K, NA1-hIgG-12K, NA2-hIgG-12K, or any mucoadhesive chimeric protein listed in Table 1) bind HA or NA and trigger the complement pathway.

Briefly, a complement pathway assay is performed (using a $CH_{50}$ Functional Test Kit; CTK-907, Creative Biolabs) with some modifications. Plasma with normal complement activity is used as a positive control, and plasma with low complement activity is used as a negative control. In this assay, complement in serum samples and control samples is first activated. HA1-hIgG-12K, HA2-hIgG-12K, HA15-IgG-12K, HA1-hIgG-12H, HA2-hIgG-12H, HA15-IgG-12H, NA1-IgG-12K, NA2-IgG-12K, NA1-IgG-12H and NA2-hIgG-12H (separately) are incubated with the HA or NA protein if the Influenza A strain and complement immunoassay reagents including antibody to TCC (terminal complement complexes) and purified human complement proteins (Cat. #A3724; Quidel). Following a 5 min incubation, erythrocytes are added to the HA- or NA-hIgG-12K proteins, complement, and HA or NA protein mixture, and were further incubated at 37° C. for 25 min, then centrifuged at 400×g for 5 min. The supernatant is analyzed at $OD_{415}$ to detect hemoglobin release.

HA-IgG-12K and NA-hIgG-12K chimeric proteins activate the complement pathway. The results demonstrate the ability of HA or NA mucoadhesive chimeric proteins to bind the Influenza virus HA protein in vitro and induce complement pathway activation.

Example 26B. HA Mucoadhesive Chimeric Protein can Kill Influenza Pseudovirus Via Complement Pathway Activation This Example demonstrates that HA1-, HA2-, HA15-hIgG-12K or NA1-NA2-hIgG-12K (or any of the mucoadhesive chimeric peptides listed in Table1) chimeric proteins kills Influenza pseudovirus by activating the complement pathway. Plasma comprises complement molecules or white blood cells that can produce complement molecules.

HA1-hIgG-12K, HA2-hIgG-12K, HA15-hIgG-12K, NA1-hIgG-12K, NA2-hIgG-12K chimeric proteins are incubated with pseudotyped lentivirus expressing the HA, NA and M2 proteins of the Influenza A strain according to the method described in Example 21. The pseudotyped virus contains the EF1-α-driven luciferase reporter gene. The incubated HA- or NA-hIgG-12K/pseudovirus mixture is added to serially diluted human complement IgG/IgM (Cat. #340105, Pel Freez Biologicals). Following a 3 h incubation of the HA- or NA-hIgG-12K chimeric protein with pseudotyped lentivirus and complement, the incubated solution is added to HEK293T-HNM cells. Cells are cultured in 5% $CO_2$ at 37° C. for 48 h. The degree of cellular infection with the pseudotyped virus is determined by detecting the luciferase level of the infected cells (Promega Luciferase Assay). HA1-hIgG-12K, HA2-hIgG-12K, HA15-hIgG-12K, NA1-hIgG-12K, NA2-hIgG-12K chimeric proteins activate the complement pathway, thereby killing pseudovirus expressing the Influenza A HA or NA protein which leads to lower pseudoviral infection of HEK293T-HMN cells as determined by the fluctuation in luciferase luminescence.

Taken together, these results show that HA or NA mucoadhesive chimeric proteins activate the complement pathway and induce virolysis of Influenza A pseudovirus.

Example 26C. HA or NA Mucoadhesive Chimeric Peptides Kill Influenza Virus in Plasma HA or NA mucoadhesive chimeric proteins are evaluated to assess whether they can bind and kill Influenza virus, using "capture and kill" assays in plasma. Plasma comprises complement molecules or white blood cells that can produce complement molecules.

Influenza pseudovirus viruses are incubated with plasma mixed with various HA mucoadhesive chimeric proteins (e.g., HA1-hIgG-12K, HA2-hIgG-12K, A HA15-hIgG-12K, NA1-hIgG-12K, NA2-hIgG-12K separately) or control plasma (e.g., plasma that was not mixed with HA or NA mucoadhesive chimeric proteins) for 72 h at 37° C. After 72 h, the cultures are analyzed for HA or NA protein concentration. Production of HA or NA protein in the absence of anti-HA-hIgG mucoadhesive peptides in the plasma is designated as 100%.

Plasma mixed with various HA- or NA-hIgG mucoadhesive chimeric proteins have decreased HA or NA protein concentration compared to the control plasma. The results demonstrate that HA- and NA-hIgG mucoadhesive chimeric peptides kill influenza pseudoviruses in plasma.

Example 27. ACE2 Mucoadhesive Chimeric Proteins with Various Positively Charged Mucoadhesive Peptide Fragments Bind Mucin In Vitro The mucin-binding ability of mucoadhesive chimeric proteins with various positively charged mucoadhesive peptide fragments was tested.

For this Example, a set of chimeric proteins were designed and generated to target a different viral antigen, SARS-CoV-2 spike protein's Si subunit. These chimeric proteins, "ACE2-Fc1 mucoadhesive chimeric proteins", are composed of a fragment of SARS-CoV-2 Si's receptor ACE2 (amino acids 19-740 of human ACE2, i.e., SEQ ID NO: 496) whose C-terminus was fused to the N-terminus of IgG's CH1+Fc fragment (CH1, SEQ ID NO: 393; $CH_2$—$CH_3$, SEQ ID NO: 391), which was in turn fused to the N-terminus of various mucoadhesive peptides to generate various ACE740-Fc1 mucoadhesive chimeric proteins. These chimeric proteins bear mucoadhesive peptides with a mixture of positively and non-positively charged amino acids of varying lengths. For example, mucoadhesive peptides as short as five amino acids (HHHHH, SEQ ID NO: 407) or six amino acids (HHHHHH, SEQ ID NO: 291) were tested, as well as peptides with positively charged amino acids other than lysine. In addition, mucoadhesive peptides with fewer than 5 consecutive positively charged amino acids were analyzed, such as peptides bearing two to three consecutive positively charged amino acids interspersed with a non-positively charged amino acid (KKKGKKK, SEQ ID NO: 408; KKAHHGKKAHHV, SEQ ID NO: 409; and KKARRGKKARRV, SEQ ID NO: 410).

Figure 10:
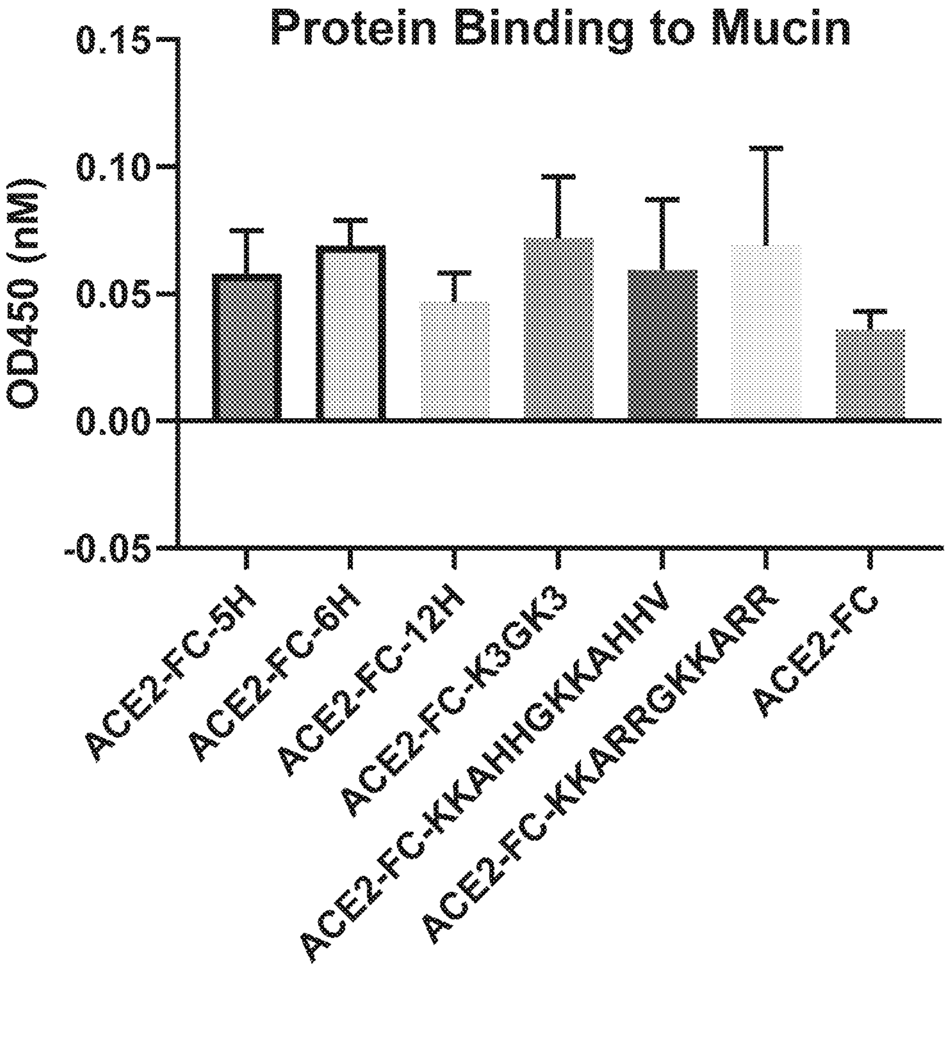
FIG. 10 demonstrates that the addition of various mucoadhesive peptides increases the attraction of a different viral antigen-binding chimeric protein ACE2-Fc1 to mucin proteins. An ELISA assay using mucin-coated plates was conducted to compare the mucin-binding ability of various ACE2-Fc1 mucoadhesive chimeric proteins to that of ACE2-Fc1 without mucoadhesive peptide. Binding was detected using horseradish peroxidase (HRP)-conjugated goat anti-human IgG and staining was detected at $OD_{450}$.

The mucin-binding ability of various ACE740-Fc1 mucoadhesive chimeric proteins was analyzed using the method described in Example 9B. Briefly, mucin-coated plates were blocked overnight in BSA, washed, and 0.5 μg/well of ACE740-Fc1 mucoadhesive chimeric protein was added to the plate. The plates were stained with HRP-conjugated goat-anti-human IgG and tested for HRP activity. FIG. 10 shows significant mucin binding for all tested ACE740-Fc1 mucoadhesive chimeric proteins, greater than ACE2-Fc1 protein lacking a positively charged mucoadhesive peptide.

Although this Example shows mucin binding results of mucoadhesive chimeric proteins targeting a different viral antigen, the ability of the various positively charged mucoadhesive peptides to increase mucin-binding capability of chimeric proteins is expected to be a conserved property of the mucoadhesive chimeric proteins comprising anti-influenza antibody moieties as well.

SEQUENCE LISTING

| SEQ ID NO | Sequence | Description |
|---|---|---|
| 1 | GFTFSTYA | HA1 HC-CDR1 |
| 2 | ISYDANYK | HA1 HC-CDR2 |
| 3 | AKDSQLRSLLYFEWLSQGYFDY | HA1 HC-CDR3 |
| 4 | QSVTFNYKNY | HA1 LC-CDR1 |
| 5 | | |
| 6 | QQHYRTPPT | HA1 LC-CDR3 |
| 7 | KYAIN | HA2 HC-CDR1 |
| 8 | GIIPFFGTTNYAQKFQG | HA2 HC-CDR2 |
| 9 | PSITESHYCLDCAAKDYYYGLDV | HA2 HC-CDR3 |
| 10 | GFTVSSNY | HA3 HC-CDR1 |
| 11 | TYSGGNT | HA3 HC-CDR2 |
| 12 | ATVPSFHGMDV | HA3 HC-CDR3 |
| 13 | QSISSY | HA3 LC-CDR1 |
| 14 | | |
| 15 | QQSYSTPPIT | HA3 LC-CDR3 |
| 16 | GSTFGDFA | HA4 HC-CDR1 |
| 17 | TSAGGDRT | HA4 HC-CDR2 |
| 18 | ARLDSSGFHYGRPGRN | HA4 HC-CDR3 |
| 19 | QDISYY | HA4 LC-CDR1 |
| 20 | | |
| 21 | QQYKSLPYT | HA4 LC-CDR3 |
| 22 | GFTFSGFS | HA5 HC-CDR1 |
| 23 | ISTSGNYM | HA5 HC-CDR2 |
| 24 | ARGGGYNWNLFDY | HA5 HC-CDR3 |
| 25 | QSLNSNY | HA5 LC-CDR1 |
| 26 | | |
| 27 | QQYGNSPLT | HA5 LC-CDR3 |
| 28 | GVSVTSDIYY | HA6 HC-CDR1 |
| 29 | IFYNGDT | HA6 HC-CDR2 |
| 30 | ARGTEDLGYCSSGSCPNH | HA6 HC-CDR3 |
| 31 | QNIRSF | HA6 LC-CDR1 |
| 32 | | |
| 33 | QQSYNTPPT | HA6 LC-CDR3 |
| 34 | GFTFSTYW | HA7 HC-CDR1 |
| 35 | INQDGGEK | HA7 HC-CDR2 |
| 36 | ARGFLERLLLGRQGAYYYGMDV | HA7 HC-CDR3 |
| 37 | QIISSS | HA7 LC-CDR1 |
| 38 | | |

-continued

SEQUENCE LISTING

| SEQ ID NO | Sequence | Description |
|---|---|---|
| 39 | QQSYSTPPELT | HA7 LC-CDR3 |
| 40 | RFTSSSYW | HA8 HC-CDR1 |
| 41 | IKQDGSEK | HA8 HC-CDR2 |
| 42 | ARGFLERLLLGRQGAYYYGMDV | HA8 HC-CDR3 |
| 43 | QSISSS | HA8-LC-CDR1 |
| 44 | | |
| 45 | QQSYTMPPELT | HA8 LC-CDR3 |
| 46 | GGSINSSHSF | HA9 HC-CDR1 |
| 47 | IYSTGNS | HA9 HC-CDR2 |
| 48 | ARESLWNPDYYYYMDV | HA9 HC-CDR3 |
| 49 | QSFSSH | HA9 LC-CDR1 |
| 50 | | |
| 51 | QQSYSVPYT | HA9 LC-CDR3 |
| 52 | GFTFSTYN | HA10 HC-CDR1 |
| 53 | ISTSSNTI | HA10 HC-CDR2 |
| 54 | ARDRGCSSTNCYVVGYYFYGMDV | HA10 HC-CDR3 |
| 55 | QGISSY | HA10 LC-CDR1 |
| 56 | | |
| 57 | QQADSFPLT | HA10 LC-CDR3 |
| 58 | GVTFISHA | HA11 HC-CDR1 |
| 59 | IIAIFGTT | HA11 HC-CDR2 |
| 60 | ARGETYYEGNFDF | HA11 HC-CDR3 |
| 61 | QSISSY | HA11 LC-CDR1 |
| 62 | | |
| 63 | QQSYSTPPIT | HA11 LC-CDR3 |
| 64 | SYAMH | HA12 HC-CDR1 |
| 65 | VVSYDGNYKYYADSVQG | HA12 HC-CDR2 |
| 66 | DSRLRSLLYFEWLSQGYFNP | HA12 HC-CDR3 |
| 67 | WGSYLES | HA12 LC-CDR1 |
| 68 | QQHYRTPPS | HA12 LC-CDR2 |
| 69 | QSITFDYKNYLA | HA12 LC-CDR3 |
| 70 | SYNAVWN | HA13 HC-CDR1 |
| 71 | RTYYRSGWYNDYAESVKS | HA13 HC-CDR2 |
| 72 | SGHITVFGVNVDAFDM | HA13 HC-CDR3 |
| 73 | RTSQSLSSYTH | HA13 LC-CDR1 |

-continued

SEQUENCE LISTING

| SEQ ID NO | Sequence | Description |
|---|---|---|
| 74 | AASSRGS | HA13 LC-CDR2 |
| 75 | QQSRT | HA13 LC-CDR3 |
| 76 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSS | HA1 $V_H$ |
| 77 | DIVMTQSPDSLAVSLGERATINCKSSQSVTFNYKNYLAWYQQKPGQPPKLL IYWASTRESGVPDRFSGSGSGTDFTLTISSLQAEDVAVYYCQQHYRTPPTFG QGTKVEIK | HA1 $V_L$ |
| 78 | EVQLVESGAEVKKPGSSVKVSCRASGTFYKYAINWVRQAPGQGLEWMGG IIPFFGTTNYAQKFQGRLTITADGSTNTAYMQLDSLRSEDTAVYYCAGPSIT ESHYCLDCAAKDYYYGLDVWGQGTTVTVSS | HA2 $V_H$ |
| 79 | QSVLTQPPSASGTPGQSVTISCSGSRSNIGGNTVNWYQHLPGMAPKLLIYSS NQRSSGVPDRFSGSKSGTSASLAISGLQSEDDADYYCASWDDSLNGVVFG GGTKLTVLG | HA2 $V_L$ |
| 80 | EVQLVESGGDLVQPGGSLRLSCAASGFTVSSNYMSWVRQVPGKGLDWVS VTYSGGNTYYADSVKGRFTISRHNSKNTLYLQMNSLRIEDTAVYYCATVPS FHGMDVWGQGTTVTVSS | HA3 $V_H$ |
| 81 | DIQMTQSPSSLSASVGDRVTITCRASQSISSYLNWYQQKPGKAPKLLIYAAS SLQSGVPSRFSGSGSGTDFTLTISSLQPEDFATYYCQQSYSTPPITFGQGTRL EIK | HA3 $V_L$ |
| 82 | EVQLLESGGGLVQPGGSLRISCAASGSTFGDFAMSWVRQSPGRGLEWVSV TSAGGDRTYYADSVKGRFTISRDNSKNTLYLQMNSLRGEDTAMYYCARL DSSGFHYGRPGRNWGQGTLVTVSS | HA4 $V_H$ |
| 83 | DIQMTHSPPSLSASVGDRITITCQASQDISYYLIWYQQKPGKAPKPLIYDASN LEAGVPSRFSASGSGTDFTLTISSLQPEDLATYYCQQYKSLPYTFGQGTKLEI K | HA4 $V_L$ |
| 84 | EVQLVESGGGLVKPGGSLRLSCAASGFTFSGFSMNWVRQVPGKGLEWVSS ISTSGNYMYYADSVKGRFTISRDNAKKSFSLQMNSLRAEDSAIYYCARGGG YNWNLFDYWGQGSLVTVSS | HA5 $V_H$ |
| 85 | EIVLTQSPGTLSLSPGERATLSCRASQSLNSNYLAWYQQKPGQAPRLLIYGA SSRATGIPDRFSGSGSGTDFTLTITRLESEDFAVYYCQQYGNSPLTFGGGTK VEIK | HA5 $V_L$ |
| 86 | QVQLQESGPGLVKPSETLSLTCSVSGVSVTSDIYYWTWIRQPPGKGLEWIG YIFYNGDTNYNPSLKSRVTMSIDTSKNEFSLRLTSVTAADTAVYFCARGTE DLGYCSSGSCPNHWGQGTLVTVSS | HA6 $V_H$ |
| 87 | DIQMTQSPSSLSASIGDRVTITCRPSQNIRSFLNWFQHKPGKAPKLLIYAASN LQSGVPSRFSGSGSGTEFTLTIRSLQPEDFATYYCQQSYNTPPTFGQGTKVEI K | HA6 $V_L$ |
| 88 | EVQLVESGGGLVQPGGSLRLSCAASGFTFSTYWMTWVRQAPGKGLEWVA NINQDGGEKYFVDSVKGRFTISRDNAKNSLFLQMNTLRAEDTAVYYCARG FLERLLLGRQGAYYYGMDVWGQGTTVTVSS | HA7 $V_H$ |
| 89 | DIQMTQSPSSLSASVGDRVSMTCRASQIISSSLNWYQQKPGKAPKLLIYAAS NLQSGVPSRFSGSGSGTDFTLTISSLQPEDFATYYCQQSYSTPPELTFGGGTK VEIK | HA7 $V_L$ |
| 90 | EVQLVQSGGGLVQPGGSLRLSCEASRFTSSSYWITWVRQAPGKGLEWVAN IKQDGSEKYFVDSVKGRFTISRDNASNSLYLQMSSLRAEDTAVYYCARGFL ERLLLGRQGAYYYGMDVWGQGTTVTVSS | HA8 $V_H$ |
| 91 | DIQMTQSPSSLSASVGDRVTMTCRASQSISSSLNWYQQKPGKAPKLLIYAA SNLQSGVPSRFSGSGSGTDFTLTISSLQPEDFATYYCQQSYTMPPELTFGGG TKVQIK | HA8 $V_L$ |
| 92 | QVQLVESGPGLVKPSQTLSLTCTVSGGSINSSHSFWSWIRQPAGKGLEWIG RIYSTGNSNYNPSLKSRVTISLDTSKNQFSLKLSSVTAADTAVYYCARESLW NPDYYYYMDVWGKGTLVTVSS | HA9 $V_H$ |

-continued

SEQUENCE LISTING

| SEQ ID NO | Sequence | Description |
|---|---|---|
| 93 | DIVMTQSPSSLSASVGDRVTITCRASQSFSSHLNWYQQKPGRAPDLLIYAAS SLHSGVPSRFSGSGSGTDFTLTISSLQPEDFAVYYCQQSYSVPYTFGQGTKL QIK | HA9 $V_L$ |
| 94 | EVQLVESGGGLVQPGGSLRLSCAASGFTFSTYNMNWVRQAPGKGLEWLS YISTSSNTIYYADSVKGRFTISRDNAKNSLFLQMNSLRDEDTAVYYCARDR GCSSTNCYVVGYYFYGMDVWGQGTTVTVSS | HA10 $V_H$ |
| 95 | DIQMTQSPSSVSASVGDRVTITCRASQGISSYLAWYQLKPGRAPKLLIYGAT RLQSGVPSRFSGSGSGTDFTLTISGLQPEDFATYHCQQADSFPLTFGQGTRL EIK | HA10 $V_L$ |
| 96 | QVHLVQSGPEVKKPGSSVKVSCKASGVTFISHAISWVRQAPGQGLEWVGG IIAIFGTTNYAQKFQGRVTVTTDKSTNTVYMELSRLRSEDTAIYYCARGETY YEGNFDFWGQGTLVTVSS | HA11 $V_H$ |
| 97 | DIQMTQSPSSLSASVGDRVTITCRASQSISSYLNWYQQKPGKAPKLLIYAAS SLQSGVPSRFSGSGSGTDFTLTISSLQPEDFATYYCQQSYSTPPITFGQGTRL EIK | HA11 $V_L$ |
| 98 | QVQLLETGGGLVKPGQSLKLSCAASGFTFTSYAMHWVRQPPGKGLEWVA VVSYDGNYKYYADSVQGRFTISRDNSKNTLYLQMNSLRAEDTAVYYCAK DSRLRSLLYFEWLSQGYFNPWGQGTTLTVSS | HA12 $V_H$ |
| 99 | DIQMTQSPSSLSASVGDRVTITCRSSQSITFDYKNYLAWYQQKPGKAPKLLI YWGSYLESGVPSRFSGSGSGTDFTLTISSLQPEDFATYYCQQHYRTPPSFGQ GTKVEIK | HA12 $V_L$ |
| 100 | QVQLQQSGPGLVKPSQTLSLTCAISGDSVSSYNAVWNWIRQSPSRGLEWLG RTYYRSGWYNDYAESVKSRITINPDTSKNQFSLQLNSVTPEDTAVYYCARS GHITVFGVNVDAFDMWGQGTMVTVSS | HA13 $V_H$ |
| 101 | DIQMTQSPSSLSASVGDRVTITCRTSQSLSSYTHWYQQKPGKAPKLLIYAAS SRGSGVPSRFSGSGSGTDFTLTISSLQPEDFATYYCQQSRTFGQGTKVEIK | HA13 $V_L$ |
| 102 | PDSVIRTQQRQTTMESVLSWVFLVAILQGEVQLVESGGDLVKPGGSLRLSC VASGFTFSDFDMSWVRQAPGKGLQWVAAIAYDGSSTYYTDAVKGRFTISR DNARNTVYLQMDNSLRAEDTAVYYCASPTTVPTIDWFYYWGQGTLVTVS | HA14 $V_H$ |
| 103 | MLWIPGSTGEAVMTQTPLSLAVTPGELATISCRANQSLLRSDGKSYLWYLQ KPGPQTPRPLIYEASKRFSGVSGRFSGSGTDFTKITRVEADEVGYYCQQGLH FPPFQGTKVEI | HA14 $V_L$ |
| 104 | GDSIGGSY | NA1 HC-CDR1 |
| 105 | IYYTGIT | NA1 HC-CDR2 |
| 106 | ARGDYSGYDRDVQVELMDV | NA1 HC-CDR3 |
| 107 | QTISIF | NA1 LC-CDR1 |
| 108 | | |
| 109 | QQSYSAPWT | NA1 LC-CDR3 |
| 110 | GYTFINHA | NA2 HC-CDR1 |
| 111 | IIPIFGLA | NA2 HC-CDR2 |
| 112 | ARDTVAVYEDFDWSSPYFFYMDV | NA2 HC-CDR3 |
| 113 | QSAGSKS | NA2 LC-CDR1 |
| 114 | | |
| 115 | QRYGTSLVT | NA2 LC-CDR3 |
| 116 | GYTFTDYY | NA3 HC-CDR1 |
| 117 | IHPGSTNT | NA3 HC-CDR2 |
| 118 | AISLGDGYYVYAMVC | NA3 HC-CDR3 |

-continued

SEQUENCE LISTING

| SEQ ID NO | Sequence | Description |
|---|---|---|
| 119 | QNVVTN | NA3 LC-CDR1 |
| 120 | | |
| 121 | QQYHSYPFT | NA3 LC-CDR3 |
| 122 | DSEVFPIVY | NA4 HC-CDR1 |
| 123 | ILPSFGRT | NA4 HC-CDR2 |
| 124 | ARGDHGNWLAY | NA4 HC-CDR3 |
| 125 | QDVSTN | NA4 LC-CDR1 |
| 126 | | |
| 127 | QQHYSAPWT | NA4 LC-CDR3 |
| 128 | GLTFSGYA | NA5 HC-CDR1 |
| 129 | IIASGGST | NA5 HC-CDR2 |
| 130 | AQHTKSHYYSGMGV | NA5 HC-CDR3 |
| 131 | QDISNY | NA5 LC-CDR1 |
| 132 | | |
| 133 | QQYDNLPLT | NA5 LC-CDR3 |
| 134 | RYNIIELS | NA6 HC-CDR1 |
| 135 | IDPDDSER | NA6 HC-CDR2 |
| 136 | AAARRPIRGEYHYALDV | NA6 HC-CDR3 |
| 137 | QSVSSSY | NA6 LC-CDR1 |
| 138 | | |
| 139 | HHYAKV | NA6 LC-CDR3 |
| 140 | GGSFGGYY | NA7 HC-CDR1 |
| 141 | INHSGST | NA7 HC-CDR2 |
| 142 | ARGRGGYATYYYYYYVDV | NA7 HC-CDR3 |
| 143 | QSVSSY | NA7 LC-CDR1 |
| 144 | | |
| 145 | QQRSNWLT | NA7 LC-CDR3 |
| 146 | GFTFDDYGM | NA8 HC-CDR1 |
| 147 | LNWNGDITA | NA8 HC-CDR2 |
| 148 | TWGEYTTREEPINSWY | NA8 HC-CDR3 |
| 149 | DISSFL | NA8 LC-CDR1 |
| 150 | | |
| 151 | LNSYPLETF | NA8 LC-CDR3 |
| 152 | GFTFDDYGM | NA9 HC-CDR1 |
| 153 | LNWNGDITA | NA9 HC-CDR2 |
| 154 | TWGDYTTGEEIINSWY | NA9 HC-CDR3 |
| 155 | DISSYL | NA9 LC-CDR1 |

-continued

SEQUENCE LISTING

| SEQ ID NO | Sequence | Description |
|---|---|---|
| 156 | | |
| 157 | LKSYPLETF | NA9 LC-CDR3 |
| 158 | GFKFDDYAM | NA10 HC-CDR1 |
| 159 | LNWNGDITA | NA10 HC-CDR2 |
| 160 | SWGDYTRGPEPKITWY | NA10 HC-CDR3 |
| 161 | GIDGYL | NA10 LC-CDR1 |
| 162 | | |
| 163 | LDSYPLETF | NA10 LC-CDR3 |
| 164 | NAWMS | NA11 HC-CDR1 |
| 165 | RIKTKTEGETVDYAAPVKG | NA11 HC-CDR2 |
| 166 | TTGLTRSSLGGFVDY | NA11 HC-CDR3 |
| 167 | RSSQTVLSSSNNENFLA | NA11 LC-CDR1 |
| 168 | WASTRAS | NA11 LC-CDR2 |
| 169 | LQYLTTPRT | NA11 LC-CDR3 |
| 170 | DYYMS | NA12 HC-CDR1 |
| 171 | YISSSSTYTDYADSVKG | NA12 HC-CDR2 |
| 172 | ATVADTAYSRGRPQITHFDN | NA12 HC-CDR3 |
| 173 | FGDKLGEKYAY | NA12 LC-CDR1 |
| 174 | QDTKRPS | NA12 LC-CDR2 |
| 175 | QTWDSTLVF | NA12 LC-CDR3 |
| 176 | DLVIH | NA13 HC-CDR1 |
| 177 | VMGYDGGNKDYAESVKG | NA13 HC-CDR2 |
| 178 | ARASYFGELRDEYYSFAMDV | NA13 HC-CDR3 |
| 179 | RASQSVSRSYLA | NA13 LC-CDR1 |
| 180 | GASSRAT | NA13 LC-CDR2 |
| 181 | QLYGTSPPYT | NA13 LC-CDR3 |
| 182 | NAWMS | NA14 HC-CDR1 |
| 183 | RIKKESEGGTIDYGAPVKG | NA14 HC-CDR2 |
| 184 | TIPNPQIVVVTTTPHSH | NA14 HC-CDR3 |
| 185 | GGNNIGSKNVH | NA14 LC-CDR1 |
| 186 | YDSDRPS | NA14 LC-CDR2 |
| 187 | QVWDSSSDHWV | NA14 LC-CDR3 |
| 188 | QVQLQESGPGLVRPSETLSLTCTVSGDSIGGSYWNWIRQPPGKGLQWIGYI YYTGITNYNPSLKSRVTMSLDTSKNQISLKMDSVTAADTALYFCARGDYS GYDRDVQVELMDVWGKGTTVTVSS | NA1 $V_H$ |
| 189 | DIQMTQSPSSLSASVRDKVTFVCRASQTISIFLNWYQHKPGEAPKLLIYAAS RLQSGVPSRFSGSGSGTDFTLTISGLQPEDFATYYCQQSYSAPWTFGQGTK VEIK | NA1 $V_L$ |

-continued

SEQUENCE LISTING

| SEQ ID NO | Sequence | Description |
|---|---|---|
| 190 | EVQLVQSGAEVKKPGSSVKVSCKASGYTFINHALSWVRQAPGQGLEWVG GIIPIFGLAKYGQKFQDRVTITADESTKTAYMDLRSLRSDDTAVYYCARDT VAVYEDFDWSSPYFFYMDVWGKGTTVTVSS | NA2 $V_H$ |
| 191 | EIVLTQSPATLSLFPGERATLSCRASQSAGSKSLAWYQHKVGQPPRLLINGA SSRATGIPDRFSGSGSGPDFNLTISRLEPEDFAVYYCQRYGTSLVTFGGGTK VEIK | NA2 $V_L$ |
| 192 | QVHLQQSGPEVARPGASVKLSCKASGYTFTDYYLNWVKQRPRQGLEWIG QIHPGSTNTYYNEKFKGKATLTADKSSSTAYMQLSSLTFEDSAVYFCAISLG DGYYVYAMVCWGQGTAVTVSS | NA3 $V_H$ |
| 193 | DIVMTQSQKFMSTSVGDRVSVTCKASQNVVTNVVWYQQKPGQSPKPLIYS ASYRYSGVPDRFTGSGSGTDFTLTISNV | NA3 $V_L$ |
| 194 | QVHLQQSGSELRSPGSSVKLSCKDFDSEVFPIVYMRWIRQKPGHGFEWIGDI LPSFGRTIYGEKFEDKATLDADTVSNTAYLELNSLTSEDSAIYYCARGDHG NWLAYWGQGTLVTVSA | NA4 $V_H$ |
| 195 | DIVMTQSHKFMSTSVGDRVTITCKASQDVSTNVAWYQQKPGQSPKLLIYW ASTRHTGVPNRFTGIISGTDYTLTISSVQAEDRALYYCQQHYSAPWTFGGG TKLEIK | NA4 $V_L$ |
| 196 | EVQLLQSGGGLVQPGGSLRLSCAASGLTFSGYAMSWVRQVPGKGPECVSG IIASGGSTYFADSVKGRFTISRDNSKNTLDLEMNSLRAEDTAVYYCAQHTK SHYYSGMGVWGQGTTVTVSS | NA5 $V_H$ |
| 197 | DIQMTQSPSSLSASVGDRVTITCQASQDISNYLNWYQQRPGKAPKLLIYDA ANLETGVPSRFSGSGSATQFTFTISGLQPEDFATYYCQQYDNLPLTFGGGTK VEIK | NA5 $V_L$ |
| 198 | QVQLVQSGAEVRKPGASVKVSCKVSRYNIIELSMDWVRQAPGKGLEWMG GIDPDDSERIYAQKLQGRVTMTEDTSTDTAYMELSGLRSEDTAIYYCAAAR RPIRGEYHYALDVWGQGTAVTVSS | NA6 $V_H$ |
| 199 | EIVLTQSPGTLSLSPGERATLSCRASQSVSSSYLGWYQQKPGQAPRLLIYRA SSRATGIPHRFSGSGSGTEFTLTITRLEPEDFAVYYCHHYAKVFGQGTKVEI K | NA6 $V_L$ |
| 200 | QVQLQQWGAGLLKPSETLSLTCAVYGGSFGGYYWNWIRQPPGKGLEWIG EINHSGSTNYNPSLKSRVTLSVDTSKNQVSLNVSSVTAADTAVYYCARGRG GYATYYYYYYVDVWGKGTTVTVSS | NA7 $V_H$ |
| 201 | EIVLTQSPATLSLSPGERATLSCRASQSVSSYLAWYQQKPGQAPRLLIYDAS KRATGIPARFSGSGSGTDFTLTISSLEPEDFAVYYCQQRSNWLTFGGGTKVE LE | NA7 $V_L$ |
| 202 | EVQLVESGGRVVRPGGSLRLSCAASGFTFDDYGMSWVRQPPGKGLEFVSG LNWNGDITAFTDSVKGRETISRDNVKSSLYLQMNSLRADDTAFYYCARVR TWGDYTTGEEIINSWYFDLWGRGTLVTVSS | NA8 $V_H$ |
| 203 | DIQLTQSPSFLSASVGDRVTITCRASQDISSYLAWYQQKPGNAPKVLIYAAS LLSGVPSRFSAFGSGTEFTLTISSLQPEDFATYYCQHLKSYPLETFGPGTKVD IK | NA8 $V_L$ |
| 204 | EVQLVESGGRVVRPGGSLRLSCAASGFTFDDYGMSWVRQAPGKGLEFVSG LNWNGDITAFTDSVKGRETISRDNAKSSLYLQMNSLRADDTAFYYCARVR TWGEYTTREEPIHSWYFDLWGRGTLVTVSS | NA9 $V_H$ |
| 205 | DIQLTQSPSFLSASVGDRVTITCRASQDISSYLAWYQQKPGNAPKLLIYAAS LLSGVPSRFSAFGSGTEFTLTISSLQPEDFATYYCQHLKSYPLETFGPGTKVD IK | NA9 $V_L$ |
| 206 | EVQLVESGGRALRPGGSLRLSCAASGFKFDDYAMSWVRQVPGKGLEFVSG LNWNGDITAYTDSVKGRETVSRDNAKNSLYLHINSPKPEDTALYYCARTSS WGDYTRGPEPKITWYFDLWGRGTLVTVSS | NA10 $V_H$ |
| 207 | DIQLTQSPSFLSASVGDRITITCRASQGIDGYLAWYQQRPGKAPNLLIYAAS LLSGVPSRFSGSGYGTEFTLTISSLQPEDFATYYCQHLDSYPLETFGPGTKV DIK | NA10 $V_L$ |

-continued

SEQUENCE LISTING

| SEQ ID NO | Sequence | Description |
|---|---|---|
| 208 | EVQLVESGGGLVKPGQSLRLSCAASGFTFTNAWMSWVRQAPGKGLEWVG RIKTKTEGETVDYAAPVKGRITISRDDSKNMVYLQLKSLKIEDAAVYYCTT GLTRSSLGGFVDYWGPGTLVTVSS | NA11 $V_H$ |
| 209 | DIVMTQSPDSLTVSLGERATINCRSSQTVLSSSNNENFLAWYQQKSGQPPN LLIYWASTRASGVPDRFSGSGSGTDFTLTISSLQTEDVAVYYCLQYLTTPRT FGQGTKVEIK | NA11 $V_L$ |
| 210 | VQLVESGGGLVKPGGSLRLSCAASGFTFSDYYMSWIRQAPGKGLEWISYIS SSSTYTDYADSVKGRFTVSRDNAKNSLYLQMNNLRAEDTAVYYCATVAD TAYSRGRPQITHFDNWGQGTLVTVSS | NA12 $V_H$ |
| 211 | SYELTQPPSMSVSPGQTATITCFGDKLGEKYAYWYQQKPGQSPLLVIYQDT KRPSGIPERFSGSNSGNTATLTISGTQAMDEADYYCQTWDSTLVFFGGGTK LTVL | NA12 $V_L$ |
| 212 | VQLVESGGGVVQPGGSLRLSCAVSGLTINDLVIHWVRQPPDKGLEWVAV MGYDGGNKDYAESVKGRFSISGDNPQNTLYLQINSLRVEDTAVYYCARAS YFGELRDEYYSFAMDVWGQGTTVTVSS | NA13 $V_H$ |
| 213 | EIVLTQSPGTLSLSPGERGTLSCRASQSVSRSYLAWYQQKPGQAPRLLIYGA SSRATGIPDRFSGSGSGTDFTLTISRLEPEDFALYYCQLYGTSPPYTFGQGTK VEIK | NA13 $V_L$ |
| 214 | EVQLVESGGGLVKPGGSLRLSCAASGFTVSNAWMSWVRQAPGKGLEWVG RIKKESEGGTIDYGAPVKGRFTISRDESKNILYLHMKSLITDDTAVYYCTIPN PQIVVVTTTPHSHWGQGTLVTVSS | NA14 $V_H$ |
| 215 | SYELTQPPSVSVAPGKTARITCGGNNIGSKNVHWYQQKPGQAPVLVIYYDS DRPSAIPERFSGSNSGNTATLTISRVEAGDEADYYCQVWDSSSDHWVFGGG TKLAVL | NA14 $V_L$ |
| 216 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKHHHH HH | HA1-hIgG-6H (HA1-hIgG heavy chain (HC) fused to 6H) |
| 217 | DIVMTQSPDSLAVSLGERATINCKSSQSVTFNYKNYLAWYQQKPGQPPKLL IYWASTRESGVPDRFSGSGSGTDFTLTISSLQAEDVAVYYCQQHYRTPPTFG QGTKVEIKGQPKANPTVTLFPPSSEELQANKATLVCLISDFYPGAVTVAWK ADGSPVKAGVETTKPSKQSNNKYAASSYLSLTPEQWKSHRSYSCQVTHEG STVEKTVAPTECS | HA1 light chain (LC) |
| 218 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKHHHH HHHHHHHH | HA1-hIgG-12H (HA1-hIgG HC fused to 12H) |
| 219 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKHHHH HHHHHHHHHHHHHHHHHHHHHHHHHH | HA1-hIgG-30H (HA1-IgG HC fused to 30H) |

SEQUENCE LISTING

| SEQ ID NO | Sequence | Description |
|---|---|---|
| 220 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKKKKK KK | HA1-hIgG-6K (HA1-IgG HC fused to 6K) |
| 221 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKGGGG SKKKKKKKKKKKK | HA1-hIgG-12K (HA1-IgG HC fused to 12K) |
| 222 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKKKKK KKKKKKKKKKKKKKKKKKKKKKKKK | HA1-hIgG-30K (HA1-IgG HC fused to 30K) |
| 223 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKRRRR RR | HA1-hIgG-6R (HA1-IgG HC fused to 6R) |
| 224 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKRRRR RRRRRRRR | HA1-hIgG-12R (HA1-IgG HC fused to 12R) |
| 225 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKRRRR RRRRRRRRRRRRRRRRRRRRRRRRR | HA1-hIgG-30R (HA1-IgG HC fused to 30R) |
| 226 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY | HA1-hIgG-6O (HA1-IgG HC fused to 6O) |

-continued

SEQUENCE LISTING

| SEQ ID NO | Sequence | Description |
|---|---|---|
| | RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKOOOO OO | |
| 227 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKOOOO OOOOOOOO | HA1-hIgG-120 (HA1-IgG HC fused to 120) |
| 228 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKOOOO OOOOOOOOOOOOOOOOOOOOOOOOOO | HA1-hIgG-300 (HA1-IgG HC fused to 300) |
| 229 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKHHKK OO | HA1-hIgG-6X-1 (HA1-IgG HC fused to HHKKQQ) |
| 230 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKHORK HR | HA1-hIgG-6X-2 (HA1-IgG HC fused to HQRKHR) |
| 231 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKHKRS OH | HA1-hIgG-6X-3 (HA1-IgG HC fused to HKRSQH) |
| 232 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKRRHT HR | HA1-hIgG-6X-4 (HA1-IgG HC fused to RRHTHR) |
| 233 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD | HA1-hIgG-12X-1 (HA1-IgG HC |

-continued

SEQUENCE LISTING

| SEQ ID NO | Sequence | Description |
|---|---|---|
| | SQLRSLLYFEWLSQGYFDYWGQGTLVTVSSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKHHHK KKRRROOO | fused to HHHKKKRRRO OO) |
| 234 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKHKRO HKROHKROHKROHKROHKROHKROHK | HA1-hIgG-30X-1 (HA-IgG HC fused to HKROHKROHK ROHKROHKRO HKROHKROHK) |
| 235 | SGSRSNIGGNTVN | HA2 LC-CDR1 |
| 236 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKHHQA KKRCQQQH | HA1-hIgG-12X-2 (HA1-IgG HC fused to HHOAKKRCOO QH) |
| 237 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKKOHR SOKRHTORHKAHORKCKROKORKHOS | HA1-hIgG-30X-2 (HA1-IgG HC fused to KOHRSOKRHTO RHKAHORKCK ROKQRKHOS) |
| 238 | SSNQRSS | HA2 LC-CDR2 |
| 239 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKHRKO ORKHHRKK | HA1-hIgG-12X-3 (HA1-IgG HC fused to HRKOORKHHR KK) |
| 240 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKKKRO SRRHOTOOHHAROKHCKHROQRHKKS | HA1-hIgG-30X-3 HA1-IgG HC fused to KKROSRRHOTO OHHAROKHCK HROQRHKKS |
| 241 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY | HA1-hIgG-12X-4 (HA1-IgG HC fused to KRAHOKCORKS H) |

-continued

SEQUENCE LISTING

| SEQ ID NO | Sequence | Description |
|---|---|---|
| | RVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSD<br>GSFFLYSKLTVDKSRWQQGNVFSCSVMHEALHNHYTQKSLSLSPGKKRAH<br>OKCORKSH | |
| 242 | QVQLVESGGGVVQPGRSLRLSCAASGFTFSTYAMHWVRQAPGKGLEWVA<br>VISYDANYKYYADSVKGRFTISRDNSKNTLYLQMNSLRAEDTAVYYCAKD<br>SQLRSLLYFEWLSQGYFDYWGQGTLVTVSSSVFPLAPSSKSTSGGTAALGC<br>LVKDYFPEPVTVSWNSGALTSGVHTFPAVLQSSGLYSLSSVVTVPSSSLGT<br>QTYICNVNHKPSNTKVDKRVEPKSCTCPPCPAPELLGGPSVFLFPPKPKDTL<br>MISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSD<br>GSFFLYSKLTVDKSRWQQGNVFSCSVMHEALHNHYTQKSLSLSPGKHRKQ<br>OHRSOOKTRRRAHROCHHHSRHOTHR | HA1-hIgG-30X-4<br>(HA1-IgG HC<br>fused to<br>HRKQOHRSOO<br>KTRRRAHROCH<br>HHSRHOTHR) |
| 243 | EVQLVESGAEVKKPGSSVKVSCRASGTFYKYAINWVRQAPGQGLEWMGG<br>IIPFFGTTNYAQKFQGRLTITADGSTNTAYMQLDSLRSEDTAVYYCAGPSIT<br>ESHYCLDCAAKDYYYGLDVWGQGTTVTVSSSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCTCPPCPAPELLGGPSVFLFPPKPKDTL<br>MISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSD<br>GSFFLYSKLTVDKSRWQQGNVFSCSVMHEALHNHYTQKSLSLSPGKHHHH<br>HH | HA2-hIgG-6H<br>(HA2-IgG HC<br>fused to 6H) |
| 244 | QSVLTQPPSASGTPGQSVTISCSGSRSNIGGNTVNWYQHLPGMAPKLLIYSS<br>NQRSSGVPDRFSGSKSGTSASLAISGLQSEDDADYYCASWDDSLNGVVFG<br>GGTKLTVLGGQPKAAPSVTLFPPSSEELQANKATLVCLISDFYPGAVTVAW<br>KADSSPVKAGVETTTPSKQSNNKYAASSYLSLTPEQWKSHRSYSCQVTHE<br>GSTVEKTVAPTECS | HA2 LC |
| 245 | EVQLVESGAEVKKPGSSVKVSCRASGTFYKYAINWVRQAPGQGLEWMGG<br>IIPFFGTTNYAQKFQGRLTITADGSTNTAYMQLDSLRSEDTAVYYCAGPSIT<br>ESHYCLDCAAKDYYYGLDVWGQGTTVTVSSSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCTCPPCPAPELLGGPSVFLFPPKPKDTL<br>MISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSD<br>GSFFLYSKLTVDKSRWQQGNVFSCSVMHEALHNHYTQKSLSLSPGKHHHH<br>HHHHHHHH | HA2-hIgG-12H<br>(HA2-IgG HC<br>fused to 12H) |
| 246 | EVQLVESGAEVKKPGSSVKVSCRASGTFYKYAINWVRQAPGQGLEWMGG<br>IIPFFGTTNYAQKFQGRLTITADGSTNTAYMQLDSLRSEDTAVYYCAGPSIT<br>ESHYCLDCAAKDYYYGLDVWGQGTTVTVSSSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCTCPPCPAPELLGGPSVFLFPPKPKDTL<br>MISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSD<br>GSFFLYSKLTVDKSRWQQGNVFSCSVMHEALHNHYTQKSLSLSPGKHHHH<br>HHHHHHHHHHHHHHHHHHHHHHHHHH | HA2-hIgG-30H<br>(HA2-IgG HC<br>fused to 30H) |
| 247 | EVQLVESGAEVKKPGSSVKVSCRASGTFYKYAINWVRQAPGQGLEWMGG<br>IIPFFGTTNYAQKFQGRLTITADGSTNTAYMQLDSLRSEDTAVYYCAGPSIT<br>ESHYCLDCAAKDYYYGLDVWGQGTTVTVSSSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCTCPPCPAPELLGGPSVFLFPPKPKDTL<br>MISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSD<br>GSFFLYSKLTVDKSRWQQGNVFSCSVMHEALHNHYTQKSLSLSPGKKKKK<br>KK | HA2-hIgG-6K<br>(HA2-IgG HC<br>fused to 6K) |
| 248 | EVQLVESGAEVKKPGSSVKVSCRASGTFYKYAINWVRQAPGQGLEWMGG<br>IIPFFGTTNYAQKFQGRLTITADGSTNTAYMQLDSLRSEDTAVYYCAGPSIT<br>ESHYCLDCAAKDYYYGLDVWGQGTTVTVSSSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCTCPPCPAPELLGGPSVFLFPPKPKDTL<br>MISRTPEVTCVVVDVSHEDPEVKFNWYVDGVEVHNAKTKPREEQYNSTY | HA2-hIgG-12K<br>(HA2-IgG HC<br>fused to 12K) |

-continued

SEQUENCE LISTING

| SEQ ID NO | Sequence | Description |
| --- | --- | --- |
| | RVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSD<br>GSFFLYSKLTVDKSRWQQGNVFSCSVMHEALHNHYTQKSLSLSPGKGGGG<br>SKKKKKKKKKKKK | |
| 249 | EVQLVESGAEVKKPGSSVKVSCRASGTFYKYAINWVRQAPGQGLEWMGG<br>IIPFFGTTNYAQKFQGRLTITADGSTNTAYMQLDSLRSEDTAVYYCAGPSIT<br>ESHYCLDCAAKDYYYGLDVWGQGTTVTVSSSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCTCPPCPAPELLGGPSVFLFPPKPKDTL<br>MISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSD<br>GSFFLYSKLTVDKSRWQQGNVFSCSVMHEALHNHYTQKSLSLSPGKKKKK<br>KKKKKKKKKKKKKKKKKKKKKKKKK | HA2-hIgG-30K<br>(HA2-IgG HC<br>fused to 30K) |
| 250 | EVQLVESGAEVKKPGSSVKVSCRASGTFYKYAINWVRQAPGQGLEWMGG<br>IIPFFGTTNYAQKFQGRLTITADGSTNTAYMQLDSLRSEDTAVYYCAGPSIT<br>ESHYCLDCAAKDYYYGLDVWGQGTTVTVSSSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCTCPPCPAPELLGGPSVFLFPPKPKDTL<br>MISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSD<br>GSFFLYSKLTVDKSRWQQGNVFSCSVMHEALHNHYTQKSLSLSPGKRRRR<br>RR | HA2-hIgG-6R<br>(HA2-IgG HC<br>fused to 6R) |
| 251 | EVQLVESGAEVKKPGSSVKVSCRASGTFYKYAINWVRQAPGQGLEWMGG<br>IIPFFGTTNYAQKFQGRLTITADGSTNTAYMQLDSLRSEDTAVYYCAGPSIT<br>ESHYCLDCAAKDYYYGLDVWGQGTTVTVSSSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCTCPPCPAPELLGGPSVFLFPPKPKDTL<br>MISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSD<br>GSFFLYSKLTVDKSRWQQGNVFSCSVMHEALHNHYTQKSLSLSPGKRRRR<br>RRRRRRRR | HA2-hIgG-12R<br>(HA2-IgG HC<br>fused to 12R) |
| 252 | EVQLVESGAEVKKPGSSVKVSCRASGTFYKYAINWVRQAPGQGLEWMGG<br>IIPFFGTTNYAQKFQGRLTITADGSTNTAYMQLDSLRSEDTAVYYCAGPSIT<br>ESHYCLDCAAKDYYYGLDVWGQGTTVTVSSSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCTCPPCPAPELLGGPSVFLFPPKPKDTL<br>MISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSD<br>GSFFLYSKLTVDKSRWQQGNVFSCSVMHEALHNHYTQKSLSLSPGKRRRR<br>RRRRRRRRRRRRRRRRRRRRRRRRR | HA2-hIgG-30R<br>(HA2-IgG HC<br>fused to 30R) |
| 253 | EVQLVESGAEVKKPGSSVKVSCRASGTFYKYAINWVRQAPGQGLEWMGG<br>IIPFFGTTNYAQKFQGRLTITADGSTNTAYMQLDSLRSEDTAVYYCAGPSIT<br>ESHYCLDCAAKDYYYGLDVWGQGTTVTVSSSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCTCPPCPAPELLGGPSVFLFPPKPKDTL<br>MISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSD<br>GSFFLYSKLTVDKSRWQQGNVFSCSVMHEALHNHYTQKSLSLSPGKCOOO<br>OOO | HA2-hIgG-6O<br>(HA2-IgG HC<br>fused to 6O) |
| 254 | EVQLVESGAEVKKPGSSVKVSCRASGTFYKYAINWVRQAPGQGLEWMGG<br>IIPFFGTTNYAQKFQGRLTITADGSTNTAYMQLDSLRSEDTAVYYCAGPSIT<br>ESHYCLDCAAKDYYYGLDVWGQGTTVTVSSSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCTCPPCPAPELLGGPSVFLFPPKPKDTL<br>MISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSD<br>GSFFLYSKLTVDKSRWQQGNVFSCSVMHEALHNHYTQKSLSLSPGKCOOO<br>OOOOOOOOO | HA2-hIgG-12O<br>(HA2-IgG HC<br>fused to 12O) |
| 255 | EVQLVESGAEVKKPGSSVKVSCRASGTFYKYAINWVRQAPGQGLEWMGG<br>IIPFFGTTNYAQKFQGRLTITADGSTNTAYMQLDSLRSEDTAVYYCAGPSIT | HA2-hIgG-30O<br>(HA2-IgG HC |

-continued

SEQUENCE LISTING

| SEQ ID NO | Sequence | Description |
|---|---|---|
| | ESHYCLDCAAKDYYYGLDVWGQGTTVTVSSSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKOOOO OOOOOOOOOOOOOOOOOOOOOOOOOO | fused to 300) |
| 256 | EVQLVESGAEVKKPGSSVKVSCRASGTFYKYAINWVRQAPGQGLEWMGG IIPFFGTTNYAQKFQGRLTITADGSTNTAYMQLDSLRSEDTAVYYCAGPSIT ESHYCLDCAAKDYYYGLDVWGQGTTVTVSSSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKKKOO RR | HA2-hIgG-6X-7 (HA2-IgG HC fused to KKOORR) |
| 257 | EVQLVESGAEVKKPGSSVKVSCRASGTFYKYAINWVRQAPGQGLEWMGG IIPFFGTTNYAQKFQGRLTITADGSTNTAYMQLDSLRSEDTAVYYCAGPSIT ESHYCLDCAAKDYYYGLDVWGQGTTVTVSSSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKKKRR OOHHHRRR | HA2-hIgG-12X-5 (HA2-IgG HC fused to HHHRRR) |
| 258 | EVQLVESGAEVKKPGSSVKVSCRASGTFYKYAINWVRQAPGQGLEWMGG IIPFFGTTNYAQKFQGRLTITADGSTNTAYMQLDSLRSEDTAVYYCAGPSIT ESHYCLDCAAKDYYYGLDVWGQGTTVTVSSSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKHKRO HKROHKROHKROHKROHKROHKROHK | HA2-hIgG-30X-1 (HA2-IgG HC fused to HKROHKROHK ROHKROHKRO HKROHKROHK) |
| 259 | QVQLQESGPGLVRPSETLSLTCTVSGDSIGGSYWNWIRQPPGKGLQWIGYI YYTGITNYNPSLKSRVTMSLDTSKNQISLKMDSVTAADTALYFCARGDYS GYDRDVQVELMDVWGKGTTVTVSSSVFPLAPSSKSTSGGTAALGCLVKD YFPEPVTVSWNSGALTSGVHTFPAVLQSSGLYSLSSVVTVPSSSLGTQTYIC NVNHKPSNTKVDKRVEPKSCTCPPCPAPELLGGPSVFLFPPKPKDTLMISRT PEVTCVVVDVSHEDPEVKFNWYVDGVEVHNAKTKPREEQYNSTYRVVSV LTVLHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFFLY SKLTVDKSRWQQGNVFSCSVMHEALHNHYTQKSLSLSPGKHHHHHH | NA1-hIgG-6H (NA1-IgG HC fused to 6H) |
| 260 | DIQMTQSPSSLSASVRDKVTFVCRASQTISIFLNWYQHKPGEAPKLLIYAAS RLQSGVPSRFSGSGSGTDFTLTISGLQPEDFATYYCQQSYSAPWTFGQGTK VEIKGQPKANPTVTLFPPSSEELQANKATLVCLISDFYPGAVTVAWKADGS PVKAGVETTKPSKQSNNKYAASSYLSLTPEQWKSHRSYSCQVTHEGSTVE KTVAPTECS | NA1 LC |
| 261 | QVQLQESGPGLVRPSETLSLTCTVSGDSIGGSYWNWIRQPPGKGLQWIGYI YYTGITNYNPSLKSRVTMSLDTSKNQISLKMDSVTAADTALYFCARGDYS GYDRDVQVELMDVWGKGTTVTVSSSVFPLAPSSKSTSGGTAALGCLVKD YFPEPVTVSWNSGALTSGVHTFPAVLQSSGLYSLSSVVTVPSSSLGTQTYIC NVNHKPSNTKVDKRVEPKSCTCPPCPAPELLGGPSVFLFPPKPKDTLMISRT PEVTCVVVDVSHEDPEVKFNWYVDGVEVHNAKTKPREEQYNSTYRVVSV LTVLHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFFLY SKLTVDKSRWQQGNVFSCSVMHEALHNHYTQKSLSLSPGKHHHHHHHHH HHH | NA1-hIgG-12H (NA1-IgG HC fused to 12H) |
| 262 | QVQLQESGPGLVRPSETLSLTCTVSGDSIGGSYWNWIRQPPGKGLQWIGYI YYTGITNYNPSLKSRVTMSLDTSKNQISLKMDSVTAADTALYFCARGDYS GYDRDVQVELMDVWGKGTTVTVSSSVFPLAPSSKSTSGGTAALGCLVKD YFPEPVTVSWNSGALTSGVHTFPAVLQSSGLYSLSSVVTVPSSSLGTQTYIC | NA1-hIgG-30H (NA1-IgG HC fused to 30H) |

-continued

SEQUENCE LISTING

| SEQ ID NO | Sequence | Description |
|---|---|---|
| | NVNHKPSNTKVDKKVEPKSCRSLVPRGSSGHHHHHHHHHHHHHHHHHH<br>HHHHHHHHHHH | |
| 263 | QVQLQESGPGLVRPSETLSLTCTVSGDSIGGSYWNWIRQPPGKGLQWIGYI<br>YYTGITNYNPSLKSRVTMSLDTSKNQISLKMDSVTAADTALYFCARGDYS<br>GYDRDVQVELMDVWGKGTTVTVSSSVFPLAPSSKSTSGGTAALGCLVKD<br>YFPEPVTVSWNSGALTSGVHTFPAVLQSSGLYSLSSVVTVPSSSLGTQTYIC<br>NVNHKPSNTKVDKRVEPKSCTCPPCPAPELLGGPSVFLFPPKPKDTLMISRT<br>PEVTCVVVDVSHEDPEVKFNWYVDGVEVHNAKTKPREEQYNSTYRVVSV<br>LTVLHQDWLNGKEYKCKVSNKALPAPIEKTISKAKGQPREPQVYTLPPSRD<br>ELTKNQVSLTCLVKGFYPSDIAVEWESNGQPENNYKTTPPVLDSDGSFFLY<br>SKLTVDKSRWQQGNVFSCSVMHEALHNHYTQKSLSLSPGKKKKKKK | NA1-hIgG-6K (NA1-IgG HC fused to 6K) |
| 264 | QVQLQESGPGLVRPSETLSLTCTVSGDSIGGSYWNWIRQPPGKGLQWIGYI<br>YYTGITNYNPSLKSRVTMSLDTSKNQISLKMDSVTAADTALYFCARGDYS<br>GYDRDVQVELMDVWGKGTTVTVSSSVFPLAPSSKSTSGGTAALGCLVKD<br>YFPEPVTVSWNSGALTSGVHTFPAVLQSSGLYSLSSVVTVPSSSLGTQTYIC<br>NVNHKPSNTKVDKRVEPKSCTCPPCPAPELLGGPSVFLFPPKPKDTLMISRT<br>PEVTCVVVDVSHEDPEVKFNWYVDGVEVHNAKTKPREEQYNSTYRVVSV<br>LTVLHQDWLNGKEYKCKVSNKALPAPIEKTISKAKGQPREPQVYTLPPSRD<br>ELTKNQVSLTCLVKGFYPSDIAVEWESNGQPENNYKTTPPVLDSDGSFFLY<br>SKLTVDKSRWQQGNVFSCSVMHEALHNHYTQKSLSLSPGKGGGGSKKKK<br>KKKKKKKK | NA1-hIgG-12K (NA1-IgG HC fused to 12K) |
| 265 | QVQLQESGPGLVRPSETLSLTCTVSGDSIGGSYWNWIRQPPGKGLQWIGYI<br>YYTGITNYNPSLKSRVTMSLDTSKNQISLKMDSVTAADTALYFCARGDYS<br>GYDRDVQVELMDVWGKGTTVTVSSSVFPLAPSSKSTSGGTAALGCLVKD<br>YFPEPVTVSWNSGALTSGVHTFPAVLQSSGLYSLSSVVTVPSSSLGTQTYIC<br>NVNHKPSNTKVDKRVEPKSCTCPPCPAPELLGGPSVFLFPPKPKDTLMISRT<br>PEVTCVVVDVSHEDPEVKFNWYVDGVEVHNAKTKPREEQYNSTYRVVSV<br>LTVLHQDWLNGKEYKCKVSNKALPAPIEKTISKAKGQPREPQVYTLPPSRD<br>ELTKNQVSLTCLVKGFYPSDIAVEWESNGQPENNYKTTPPVLDSDGSFFLY<br>SKLTVDKSRWQQGNVFSCSVMHEALHNHYTQKSLSLSPGKKKKKKKKKK<br>KKKKKKKKKKKKKKKKKKKK | NA1-hIgG-30K (NA1-IgG HC fused to 30K) |
| 266 | QVQLQESGPGLVRPSETLSLTCTVSGDSIGGSYWNWIRQPPGKGLQWIGYI<br>YYTGITNYNPSLKSRVTMSLDTSKNQISLKMDSVTAADTALYFCARGDYS<br>GYDRDVQVELMDVWGKGTTVTVSSSVFPLAPSSKSTSGGTAALGCLVKD<br>YFPEPVTVSWNSGALTSGVHTFPAVLQSSGLYSLSSVVTVPSSSLGTQTYIC<br>NVNHKPSNTKVDKRVEPKSCTCPPCPAPELLGGPSVFLFPPKPKDTLMISRT<br>PEVTCVVVDVSHEDPEVKFNWYVDGVEVHNAKTKPREEQYNSTYRVVSV<br>LTVLHQDWLNGKEYKCKVSNKALPAPIEKTISKAKGQPREPQVYTLPPSRD<br>ELTKNQVSLTCLVKGFYPSDIAVEWESNGQPENNYKTTPPVLDSDGSFFLY<br>SKLTVDKSRWQQGNVFSCSVMHEALHNHYTQKSLSLSPGKRRRRRR | NA1-hIgG-6R (NA1-IgG HC fused to 6R) |
| 267 | QVQLQESGPGLVRPSETLSLTCTVSGDSIGGSYWNWIRQPPGKGLQWIGYI<br>YYTGITNYNPSLKSRVTMSLDTSKNQISLKMDSVTAADTALYFCARGDYS<br>GYDRDVQVELMDVWGKGTTVTVSSSVFPLAPSSKSTSGGTAALGCLVKD<br>YFPEPVTVSWNSGALTSGVHTFPAVLQSSGLYSLSSVVTVPSSSLGTQTYIC<br>NVNHKPSNTKVDKRVEPKSCTCPPCPAPELLGGPSVFLFPPKPKDTLMISRT<br>PEVTCVVVDVSHEDPEVKFNWYVDGVEVHNAKTKPREEQYNSTYRVVSV<br>LTVLHQDWLNGKEYKCKVSNKALPAPIEKTISKAKGQPREPQVYTLPPSRD<br>ELTKNQVSLTCLVKGFYPSDIAVEWESNGQPENNYKTTPPVLDSDGSFFLY<br>SKLTVDKSRWQQGNVFSCSVMHEALHNHYTQKSLSLSPGKRRRRRRRRRR<br>RR | NA1-hIgG-12R (NA1-IgG HC fused to 12R) |
| 268 | QVQLQESGPGLVRPSETLSLTCTVSGDSIGGSYWNWIRQPPGKGLQWIGYI<br>YYTGITNYNPSLKSRVTMSLDTSKNQISLKMDSVTAADTALYFCARGDYS<br>GYDRDVQVELMDVWGKGTTVTVSSSVFPLAPSSKSTSGGTAALGCLVKD<br>YFPEPVTVSWNSGALTSGVHTFPAVLQSSGLYSLSSVVTVPSSSLGTQTYIC<br>NVNHKPSNTKVDKRVEPKSCTCPPCPAPELLGGPSVFLFPPKPKDTLMISRT<br>PEVTCVVVDVSHEDPEVKFNWYVDGVEVHNAKTKPREEQYNSTYRVVSV<br>LTVLHQDWLNGKEYKCKVSNKALPAPIEKTISKAKGQPREPQVYTLPPSRD<br>ELTKNQVSLTCLVKGFYPSDIAVEWESNGQPENNYKTTPPVLDSDGSFFLY<br>SKLTVDKSRWQQGNVFSCSVMHEALHNHYTQKSLSLSPGKRRRRRRRRRR<br>RRRRRRRRRRRRRRRRRRRR | NA1-hIgG-30R (NA1-IgG HC fused to 30R) |
| 269 | QVQLQESGPGLVRPSETLSLTCTVSGDSIGGSYWNWIRQPPGKGLQWIGYI<br>YYTGITNYNPSLKSRVTMSLDTSKNQISLKMDSVTAADTALYFCARGDYS<br>GYDRDVQVELMDVWGKGTTVTVSSSVFPLAPSSKSTSGGTAALGCLVKD<br>YFPEPVTVSWNSGALTSGVHTFPAVLQSSGLYSLSSVVTVPSSSLGTQTYIC<br>NVNHKPSNTKVDKRVEPKSCTCPPCPAPELLGGPSVFLFPPKPKDTLMISRT | NA1-hIgG-6O (NA1-IgG HC fused to 6O) |

-continued

SEQUENCE LISTING

| SEQ ID NO | Sequence | Description |
|---|---|---|
| | PEVTCVVVDVSHEDPEVKFNWYVDGVEVHNAKTKPREEQYNSTYRVVSV<br>LTVLHQDWLNGKEYKCKVSNKALPAPIEKTISKAKGQPREPQVYTLPPSRD<br>ELTKNQVSLTCLVKGFYPSDIAVEWESNGQPENNYKTTPPVLDSDGSFFLY<br>SKLTVDKSRWQQGNVFSCSVMHEALHNHYTQKSLSLSPGKOOOOOO | |
| 270 | QVQLQESGPGLVRPSETLSLTCTVSGDSIGGSYWNWIRQPPGKGLQWIGYI<br>YYTGITNYNPSLKSRVTMSLDTSKNQISLKMDSVTAADTALYFCARGDYS<br>GYDRDVQVELMDVWGKGTTVTVSSSVFPLAPSSKSTSGGTAALGCLVKD<br>YFPEPVTVSWNSGALTSGVHTFPAVLQSSGLYSLSSVVTVPSSSLGTQTYIC<br>NVNHKPSNTKVDKRVEPKSCTCPPCPAPELLGGPSVFLFPPKPKDTLMISRT<br>PEVTCVVVDVSHEDPEVKFNWYVDGVEVHNAKTKPREEQYNSTYRVVSV<br>LTVLHQDWLNGKEYKCKVSNKALPAPIEKTISKAKGQPREPQVYTLPPSRD<br>ELTKNQVSLTCLVKGFYPSDIAVEWESNGQPENNYKTTPPVLDSDGSFFLY<br>SKLTVDKSRWQQGNVFSCSVMHEALHNHYTQKSLSLSPGKOOOOOOOOO<br>OOO | NA1-hIgG-12O<br>(NA1-IgG HC<br>fused to 12O) |
| 271 | QVQLQESGPGLVRPSETLSLTCTVSGDSIGGSYWNWIRQPPGKGLQWIGYI<br>YYTGITNYNPSLKSRVTMSLDTSKNQISLKMDSVTAADTALYFCARGDYS<br>GYDRDVQVELMDVWGKGTTVTVSSSVFPLAPSSKSTSGGTAALGCLVKD<br>YFPEPVTVSWNSGALTSGVHTFPAVLQSSGLYSLSSVVTVPSSSLGTQTYIC<br>NVNHKPSNTKVDKRVEPKSCTCPPCPAPELLGGPSVFLFPPKPKDTLMISRT<br>PEVTCVVVDVSHEDPEVKFNWYVDGVEVHNAKTKPREEQYNSTYRVVSV<br>LTVLHQDWLNGKEYKCKVSNKALPAPIEKTISKAKGQPREPQVYTLPPSRD<br>ELTKNQVSLTCLVKGFYPSDIAVEWESNGQPENNYKTTPPVLDSDGSFFLY<br>SKLTVDKSRWQQGNVFSCSVMHEALHNHYTQKSLSLSPGKQQOOOOOOO<br>OOOOOOOOOOOOOOOOOOOOO | NA1-hIgG-3OO<br>(NA1-IgG HC<br>fused to 3OO) |
| 272 | QVQLQESGPGLVRPSETLSLTCTVSGDSIGGSYWNWIRQPPGKGLQWIGYI<br>YYTGITNYNPSLKSRVTMSLDTSKNQISLKMDSVTAADTALYFCARGDYS<br>GYDRDVQVELMDVWGKGTTVTVSSSVFPLAPSSKSTSGGTAALGCLVKD<br>YFPEPVTVSWNSGALTSGVHTFPAVLQSSGLYSLSSVVTVPSSSLGTQTYIC<br>NVNHKPSNTKVDKRVEPKSCTCPPCPAPELLGGPSVFLFPPKPKDTLMISRT<br>PEVTCVVVDVSHEDPEVKFNWYVDGVEVHNAKTKPREEQYNSTYRVVSV<br>LTVLHQDWLNGKEYKCKVSNKALPAPIEKTISKAKGQPREPQVYTLPPSRD<br>ELTKNQVSLTCLVKGFYPSDIAVEWESNGQPENNYKTTPPVLDSDGSFFLY<br>SKLTVDKSRWQQGNVFSCSVMHEALHNHYTQKSLSLSPGKKKHHRR | NA1-hIgG-6X-5<br>(NA1-IgG HC<br>fused to<br>KKHHRR) |
| 273 | QVQLQESGPGLVRPSETLSLTCTVSGDSIGGSYWNWIRQPPGKGLQWIGYI<br>YYTGITNYNPSLKSRVTMSLDTSKNQISLKMDSVTAADTALYFCARGDYS<br>GYDRDVQVELMDVWGKGTTVTVSSSVFPLAPSSKSTSGGTAALGCLVKD<br>YFPEPVTVSWNSGALTSGVHTFPAVLQSSGLYSLSSVVTVPSSSLGTQTYIC<br>NVNHKPSNTKVDKRVEPKSCTCPPCPAPELLGGPSVFLFPPKPKDTLMISRT<br>PEVTCVVVDVSHEDPEVKFNWYVDGVEVHNAKTKPREEQYNSTYRVVSV<br>LTVLHQDWLNGKEYKCKVSNKALPAPIEKTISKAKGQPREPQVYTLPPSRD<br>ELTKNQVSLTCLVKGFYPSDIAVEWESNGQPENNYKTTPPVLDSDGSFFLY<br>SKLTVDKSRWQQGNVFSCSVMHEALHNHYTQKSLSLSPGKKKRROOHHH<br>RRR | NA1-hIgG-12X-5<br>(NA1-IgG HC<br>fused to<br>KKRROOHHHR<br>RR) |
| 274 | QVQLQESGPGLVRPSETLSLTCTVSGDSIGGSYWNWIRQPPGKGLQWIGYI<br>YYTGITNYNPSLKSRVTMSLDTSKNQISLKMDSVTAADTALYFCARGDYS<br>GYDRDVQVELMDVWGKGTTVTVSSSVFPLAPSSKSTSGGTAALGCLVKD<br>YFPEPVTVSWNSGALTSGVHTFPAVLQSSGLYSLSSVVTVPSSSLGTQTYIC<br>NVNHKPSNTKVDKRVEPKSCTCPPCPAPELLGGPSVFLFPPKPKDTLMISRT<br>PEVTCVVVDVSHEDPEVKFNWYVDGVEVHNAKTKPREEQYNSTYRVVSV<br>LTVLHQDWLNGKEYKCKVSNKALPAPIEKTISKAKGQPREPQVYTLPPSRD<br>ELTKNQVSLTCLVKGFYPSDIAVEWESNGQPENNYKTTPPVLDSDGSFFLY<br>SKLTVDKSRWQQGNVFSCSVMHEALHNHYTQKSLSLSPGKHKROHKROH<br>KROHKROHKROHKROHKROHK | NA1-hIgG-30X-1<br>(NA1-IgG HC<br>fused to<br>HKROHKROHK<br>ROHKROHKRO<br>HKROHKROHK) |
| 275 | EVQLVQSGAEVKKPGSSVKVSCKASGYTFINHALSWVRQAPGQGLEWVG<br>GIIPIFGLAKYGQKFQDRVTITADESTKTAYMDLRSLRSDDTAVYYCARDT<br>VAVYEDFDWSSPYFFYMDVWGKGTTVTVSSSVFPLAPSSKSTSGGTAALG<br>CLVKDYFPEPVTVSWNSGALTSGVHTFPAVLQSSGLYSLSSVVTVPSSSLGT<br>QTYICNVNHKPSNTKVDKRVEPKSCTCPPCPAPELLGGPSVFLFPPKPKDTL<br>MISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSD<br>GSFFLYSKLTVDKSRWQQGNVFSCSVMHEALHNHYTQKSLSLSPGKHHHH<br>HH | NA2-hIgG-6H<br>(NA2-IgG HC<br>fused to 6H) |
| 276 | EIVLTQSPATLSLFPGERATLSCRASQSAGSKSLAWYQHKVGQPPRLLINGA<br>SSRATGIPDRFSGSGSGPDFNLTISRLEPEDFAVYYCQRYGTSLVTFGGGTK | NA2 LC |

SEQUENCE LISTING

| SEQ ID NO | Sequence | Description |
|---|---|---|
| | VEIKGQPKANPTVTLFPPSSEELQANKATLVCLISDFYPGAVTVAWKADGS PVKAGVETTKPSKQSNNKYAASSYLSLTPEQWKSHRSYSCQVTHEGSTVE KTVAPTECS | |
| 277 | EVQLVQSGAEVKKPGSSVKVSCKASGYTFINHALSWVRQAPGQGLEWVG GIIPIFGLAKYGQKFQDRVTITADESTKTAYMDLRSLRSDDTAVYYCARDT VAVYEDFDWSSPYFFYMDVWGKGTTVTVSSSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKHHHH HHHHHHHH | NA2-hIgG-12H (NA2-IgG HC fused to 12H) |
| 278 | EVQLVQSGAEVKKPGSSVKVSCKASGYTFINHALSWVRQAPGQGLEWVG GIIPIFGLAKYGQKFQDRVTITADESTKTAYMDLRSLRSDDTAVYYCARDT VAVYEDFDWSSPYFFYMDVWGKGTTVTVSSSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKHHHH HHHHHHHHHHHHHHHHHHHHHHHHHH | NA2-hIgG-30H (NA2-IgG HC fused to 30H) |
| 279 | EVQLVQSGAEVKKPGSSVKVSCKASGYTFINHALSWVRQAPGQGLEWVG GIIPIFGLAKYGQKFQDRVTITADESTKTAYMDLRSLRSDDTAVYYCARDT VAVYEDFDWSSPYFFYMDVWGKGTTVTVSSSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKKKKK KK | NA2-hIgG-6K (NA2-IgG HC fused to 6K) |
| 280 | EVQLVQSGAEVKKPGSSVKVSCKASGYTFINHALSWVRQAPGQGLEWVG GIIPIFGLAKYGQKFQDRVTITADESTKTAYMDLRSLRSDDTAVYYCARDT VAVYEDFDWSSPYFFYMDVWGKGTTVTVSSSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKGGGG SKKKKKKKKKKK | NA2-hIgG-12K (NA2-IgG HC fused to 12K) |
| 281 | EVQLVQSGAEVKKPGSSVKVSCKASGYTFINHALSWVRQAPGQGLEWVG GIIPIFGLAKYGQKFQDRVTITADESTKTAYMDLRSLRSDDTAVYYCARDT VAVYEDFDWSSPYFFYMDVWGKGTTVTVSSSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKKKKK KKKKKKKKKKKKKKKKKKKKKKKKK | NA2-hIgG-30K (NA2-IgG HC fused to 30K) |
| 282 | EVQLVQSGAEVKKPGSSVKVSCKASGYTFINHALSWVRQAPGQGLEWVG GIIPIFGLAKYGQKFQDRVTITADESTKTAYMDLRSLRSDDTAVYYCARDT VAVYEDFDWSSPYFFYMDVWGKGTTVTVSSASVFPLAPSSKSTSGGTAAL GCLVKDYFPEPVTVSWNSGALTSGVHTFPAVLQSSGLYSLSSVVTVPSSSL GTQTYICNVNHKPSNTKVDKRVEPKSCTCPPCPAPELLGGPSVFLFPPKPKD TLMISRTPEVTCVVVDVSHEDPEVKFNWYVDGVEVHNAKTKPREEQYNST YRVVSVLTVLHQDWLNGKEYKCKVSNKALPAPIEKTISKAKGQPREPQVY TLPPSRDELTKNQVSLTCLVKGFYPSDIAVEWESNGQPENNYKTTPPVLDS DGSFFLYSKLTVDKSRWQQGNVFSCSVMHEALHNHYTQKSLSLSPGKRRR RRR | NA2-hIgG-6R (NA2-IgG HC fused to 6R) |
| 283 | EVQLVQSGAEVKKPGSSVKVSCKASGYTFINHALSWVRQAPGQGLEWVG GIIPIFGLAKYGQKFQDRVTITADESTKTAYMDLRSLRSDDTAVYYCARDT VAVYEDFDWSSPYFFYMDVWGKGTTVTVSSSVFPLAPSSKSTSGGTAALG | NA2-hIgG-12R (NA2-IgG HC fused to 12R) |

-continued

SEQUENCE LISTING

| SEQ ID NO | Sequence | Description |
|---|---|---|
| | CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKRRRR RRRRRRRR | |
| 284 | EVQLVQSGAEVKKPGSSVKVSCKASGYTFINHALSWVRQAPGQGLEWVG GIIPIFGLAKYGQKFQDRVTITADESTKTAYMDLRSLRSDDTAVYYCARDT VAVYEDFDWSSPYFFYMDVWGKGTTVTVSSSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKRRRR RRRRRRRRRRRRRRRRRRRRRRRRRR | NA2-hIgG-30R (NA2-IgG HC fused to 30R) |
| 285 | EVQLVQSGAEVKKPGSSVKVSCKASGYTFINHALSWVRQAPGQGLEWVG GIIPIFGLAKYGQKFQDRVTITADESTKTAYMDLRSLRSDDTAVYYCARDT VAVYEDFDWSSPYFFYMDVWGKGTTVTVSSSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKOOOO OO | NA2-hIgG-6O (NA2-IgG HC fused to 6O) |
| 286 | EVQLVQSGAEVKKPGSSVKVSCKASGYTFINHALSWVRQAPGQGLEWVG GIIPIFGLAKYGQKFQDRVTITADESTKTAYMDLRSLRSDDTAVYYCARDT VAVYEDFDWSSPYFFYMDVWGKGTTVTVSSSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKOOOO OOOOOOOO | NA2-hlgG-12O (NA2-IgG HC fused to 12O) |
| 287 | EVQLVQSGAEVKKPGSSVKVSCKASGYTFINHALSWVRQAPGQGLEWVG GIIPIFGLAKYGQKFQDRVTITADESTKTAYMDLRSLRSDDTAVYYCARDT VAVYEDFDWSSPYFFYMDVWGKGTTVTVSSSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKOOOO OOOOOOOOOOOOOOOOOOOOOOOOOO | NA2-hIgG-30O (NA2-IgG HC fused to 30O) |
| 288 | EVQLVQSGAEVKKPGSSVKVSCKASGYTFINHALSWVRQAPGQGLEWVG GIIPIFGLAKYGQKFQDRVTITADESTKTAYMDLRSLRSDDTAVYYCARDT VAVYEDFDWSSPYFFYMDVWGKGTTVTVSSVFPLAPSSKSTSGGTAALGC LVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKOORR HH | NA2-hIgG-6X-6 (NA2-IgG HC fused to OORRHH) |
| 289 | EVQLVQSGAEVKKPGSSVKVSCKASGYTFINHALSWVRQAPGQGLEWVG GIIPIFGLAKYGQKFQDRVTITADESTKTAYMDLRSLRSDDTAVYYCARDT VAVYEDFDWSSPYFFYMDVWGKGTTVTVSSSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKOOOR RRKKKHHH | NA2-hIgG-12X-6 (NA2-IgG HC fused to OOORRRKKKH HH) |

-continued

SEQUENCE LISTING

| SEQ ID NO | Sequence | Description |
|---|---|---|
| 290 | EVQLVQSGAEVKKPGSSVKVSCKASGYTFINHALSWVRQAPGQGLEWVG GIIPIFGLAKYGQKFQDRVTITADESTKTAYMDLRSLRSDDTAVYYCARDT VAVYEDFDWSSPYFFYMDVWGKGTTVTVSSASVFPLAPSSKSTSGGTAAL GCLVKDYFPEPVTVSWNSGALTSGVHTFPAVLQSSGLYSLSSVVTVPSSSL GTQTYICNVNHKPSNTKVDKRVEPKSCTCPPCPAPELLGGPSVFLFPPKPKD TLMISRTPEVTCVVVDVSHEDPEVKFNWYVDGVEVHNAKTKPREEQYNST YRVVSVLTVLHQDWLNGKEYKCKVSNKALPAPIEKTISKAKGQPREPQVY TLPPSRDELTKNQVSLTCLVKGFYPSDIAVEWESNGQPENNYKTTPPVLDS DGSFFLYSKLTVDKSRWQQGNVFSCSVMHEALHNHYTQKSLSLSPGKHKR OHKROHKROHKROHKROHKROHKROHK | NA2-hIgG-30X-1 (NA2-IgG HC fused to HKROHKROHK ROHKROHKRO HKROHKROHK) |
| 291 | HHHHHH | 6H |
| 292 | HHHHHHHHHHHH | 12H |
| 293 | HHHHHHHHHHHHHHHHHHHHHHHHHHHHHH | 30H |
| 294 | KKKKKK | 6K |
| 295 | KKKKKKKKKKKK | 12K |
| 296 | KKKKKKKKKKKKKKKKKKKKKKKKKKKKKK | 30K |
| 297 | RRRRRR | 6R |
| 298 | RRRRRRRRRRRR | 12R |
| 299 | RRRRRRRRRRRRRRRRRRRRRRRRRRRRRR | 30R |
| 300 | OOOOOO | 6O |
| 301 | OOOOOOOOOOOO | 12O |
| 302 | OOOOOOOOOOOOOOOOOOOOOOOOOOOOOO | 30O |
| 303 | HHKKOO | 6X-1 |
| 304 | HORKHR | 6X-2 |
| 305 | HKRSOH | 6X-3 |
| 306 | RRHTHR | 6X-4 |
| 307 | KKOORR | 6X-7 |
| 308 | KKHHRR | 6X-5 |
| 309 | OORRHH | 6X-6 |
| 310 | HHHKKKRRROOO | 12X-1 |
| 311 | HHOAKKRCOOOH | 12X-2 |
| 312 | HRKQQRKHHRKK | 12X-3 |
| 313 | KRAHOKCORKSH | 12X-4 |
| 314 | KKRROOHHHRRR | 12X-5 |
| 315 | OOORRRKKKHHH | 12X-6 |
| 316 | HKROHKROHKROHKROHKROHKROHKROHK | 30X-1 |
| 317 | KOHRSOKRHTORHKAHORKCKROKORKHOS | 30X-2 |
| 318 | KKROSRRHOTOOHHAROKHCKHROTRHKKS | 30X-3 |
| 319 | HRKOOHRSOOKTRRRAHROCHHHSRHOTHR | 30X-4 |
| 320 | GRHKAKNHIRRPKSRWKKWHKYRKVHRHKVHKGRR | 35X-1 |
| 321 | WRKVHHYKKQHKNRAHGKLKLRAKIHQRSRMHGKQKHYHR | 40X-2 |

-continued

SEQUENCE LISTING

| SEQ ID NO | Sequence | Description |
|---|---|---|
| 322 | AHHKCRRGHKQKILHRRPHKFHRWKRVHKGRHGKKHRRHKHR | 42X-1 |
| 323 | QHRGKAKYHRTHHVKKQRHGRKNHKVHRHARKFHKIRRLKCHKKH | 45X-1 |
| 324 | HNKRFKKGRHVRHSRHKSHRRTHKYHHWRHYRKVHRCKKAHKSHHRVH HK | 50X-1 |
| 325 | AHGRPHQFKRQCKAHQVKHILKRTQSHQYKQVHQRNKQAQKMRKIRGG HK | 50X-2 |
| 326 | MKTIIALSCILCLVFAQKIPGNDNSTATLCLGHHAVPNGTIVKTITDDRIEVT NATELVQNSSIGEICDSPHQILDGENCTLIDALLGDPQCDGFQNKKWDLFVE RNKAYSNCYPYDVPDYASLRSLVASSGTLEFNNESFNWAGVTQNGTSSSCI RGSKSSFFSRLNWLTHLNSKYPALNVTMPNNEQFDKLYIWGVHHPGTDKD QISLYAQSSGRITVSTKRSQQAVIPNIGSRPRIRDIPSRISIYWTIVKPGDILLIN STGNLIAPRGYFKIRSGKSSIMRSDAPIGKCKSECITPNGSIPNDKPFQNVNRI TYGACPRYVKQSTLKLATGMRNVPERQTRGIFGAIAGFIENGWEGLVDGW YGFRHQNSEGRGQAADLKSTQAAIDQINGKLNRLIGKTNEKFHQIEKEFSE VEGRIQDLEKYVEDTKIDLWSYNAELLVALENQHTIDLTDSEMNKLFEKTK KQLRENAEDMGNGCFKIYHKCDNACMGSIRNGTYDHNVYRDEALNNRFQ IKGVELKSGYKDWILWISFAISCFLLCVVLLGFIMWACQKGNIRCNICI | >QHA30968A/ Yokosuka/NHRC_ QID_FDX70722/ 2019 2019 Apr. 17 |
| 327 | MNPNQKIITIGSICMTIGMANLILQIGNIISIWVSHSIQIGNQSQIETCNKSVIT YENNTWVNQTYVNISNTNSAARQSVASVKLAGNSSLCPVSGWAIYSKDNS VRIGSKGDVFVIREPFISCSPLECRTFFLTQGALLNDKHSNGTIKDRSPYRTL MSCPIGEVPSPYNSRFESVAWSASACHDGTNWLTIGVSGPDSGAVAVLKY NGIITDTIKSWRNNILRTQESECACVNGSCFTIMTDGPSDGQASYKIFRIEKG KIIKSVEMKAPNYHYEECSCYPDSSEITCVCRDNWHGSNRPWVSFNQNLEY QMGYICSGVFGDNPRPNDKTGSCGPVSSNGANGVKGFAFKYGNGVWIGR TKSISSRKGFEMIWDPNGWTGTDNKFSKKQDIVGINEWSGYSGSFVQHPEL TGLNCIRPCFWVELIRGRPEENTIWTSGSSISFCGVDSDIVGWSWPDGAELP FTIDK | >QHA30980A/ Yokosuka/NHRC_ QID_FDX70778/ 2019 2019 May 30 |
| 328 | VFAQKIPGNDNSTATLCLGHHAVPNGTIVKTITNDRIEVTNATELVQNSSIG EICDSPHLILDGKNCTLIDALLGDPQCDGFQNKKWDLFVERSKAYSNCYPY DVPDYASLRSLVASSGTLEFNNESFNWTGVKQNGTSSACIRKSSSSFFSRLN WLTHLNYTYPALNVTMPNNEQFDKLYIWGVHHPGTDKDQIFLYAQSSGRI TVSTKRSQQTVIPNIGSRPRIRDIPSRISIYWTIVKPGDILLINSTGNLIAPRGYF KIQSGKSSIMRSDAPIGKCKSECITPNGSIPNDKPFQNVNRITYGTCPRYVKH STLKLATGMRNVPEKQTRGIFGAIAGFIENGWEGMVDGWYGFRHQNSEGR GQAADLKSTQAAIDQINGKLNRLIGKTNEKFHQIEKEFSEVEGRIQDLEKYV EDTKIDLWSYNAELLVALENQHTIDLTDSEMNKLFEKTKKQLRENAEDMG NGCFKIYHKCDNACIGSIRNGTYDHNVYRDEALNNRFQIKGVELKSGYKD WILWISFAISCFLLCVALLGFIMWACQKGN | >QFG38740A/ Thailand/TM- 5434_51/2019 2019 Apr. 01 |
| 329 | SLTISTICFFMQIAILITTVTLHFKQYEFNSPPNNQVMLCEPTIIERNITEIVYLT NTTIEKEICLKPAEYRNWSKPQCGITGFAPFSKDNSIRLSAGGDIWVTREPY VSCDPDKCYQFALGQGTTLNNVHSNNTVRDRTPYRTLLMNELGVPFHLGT KQVCMAWSSSSCHDGKAWLHVCITGDDKNATASFIYNGRLVDSVVSWSK DILRTQESECVCINGTCTVVMTDGNATGKADTKILFIEEGKIVHTSKLSGSA QHVEECSCYPRYPGVRCVCRDNWKGSNRPIVDINIKDHSIVSSYVCSGLVG DTPRKSDSSSSSHCLNPNNEEGGHGVKGWAFDDGNDVWMGRTINETSRLG YETFKVVEGWSNSKSKLQINRQVIVDRGDRSGYSGIFSVEGKSCINRCFYVE LIRGRKEETEVLWTSNSIVVFCGTSGTYGT | >QFP41505A/ Thailand/TM- 5434_51/2019 2019 Apr. 01 |
| 330 | MKTIIALSCILCLVFAQKIPGNDNSTATLCLGHHAVPNGTIVKTITNDRIEVT NATELVQNSSIGEICDSPHQILDGENCTLIDALLGDPQCDGFQNKKWDLFVE RNKAYSNCYPYDVPDYASLRSLVASSGTLEFNNESFNWAGVTQNGTSSSCI RGSKSSFFSRLNWLTHLNSKYPALNVTMPNNEQFDKLYIWGVHHPGTDKD QTSLYAQSSGRITVSTKRSQQAVIPNIGSRPRIRDIPSRISIYWTIVKPGDILLI NSTGNLIAPRGYFKIRSGKSSIMKSDAPIGKCKSECITPNGSIPNDKPFQNVN RITYGACPRYVKQSTLKLATGMRNVPEKQTRGIFGAIAGFIENGWEGLVDG WYGFRHQNSEGRGQAADLKSTQAAIDQINGKLNRLIGKTNEKFHQIEKEFS EVEGRIQDLEKYVEDTKIDLWSYNAELLVALENQHTIDLTDSEMNKLFEKT KKQLRENAEDMGNGCFKIYHKCDNACMGSIRNGTYDHNVYRDEALNNRF QIKGVELKSGYKDWILWISFAISCFLLCVVLLGFIMWACQKGNIRCNICI | >QDC19555A/ Germany/9496/ 2019 2019 Apr. 03 |
| 331 | MNPNQKIITISSVSLTISTICFFMQIAILITTVTLHFKQYEFNPPPNNQVMLCEP TIIERNITEIVYLTNTTIEREICPKPAEYRNWSKPQCGITGFAPFSKDNSIRLSA GGDIWVTREPYVSCDPDKCYQFALGQGTTINNVHSNNTARDRTPHRTLLM SELGVPFHLGTKQVCIAWSSSSCHDGKAWLHVCITGDDKNATASFIYNGRL VDSVVSWSKDILRTQESECVCINGTCTVVMTDGNATGKADTKILFIEEGKI | >QDC19627A/ Germany/9496/ 2019 2019 Apr. 03 |

-continued

SEQUENCE LISTING

| SEQ ID NO | Sequence | Description |
|---|---|---|
| | VHTSKLSGSAQHVEECSCYPRYPGVRCVCRDNWKGSNRPIVDINIKDHSIV<br>SSYVCSGLVGDTPRKTDSSSSSHCLNPNNEKGGHGVKGWAFDDGNDVWM<br>GRTINETSRLGYETFKVVEGWSNSKSKLQINRQVIVDRGDRSGYSGIFSVEG<br>KSCINRCFYVELIRGRKEETEVLWTSNSIVVFCGTSGTYGTGSWPDGADLN<br>LMHI | |
| 332 | MNPNQKIITIGSICMTIGTANLILQIGNIISIWVSHSIQIGNQSQIETCNKSVITY<br>ENNTWVNQTFVNISNTNSAARQSVASVKLAGNSSLCPVSGWAIYSKDNSV<br>RIGSKGDVFVIREPFISCSPLECRTFFLTQGALLNDKHSNGTIKDRSPYRTLM<br>SCPIGEVPSPYNSRFESVAWSASACHDGTNWLTIGISGPDSGAVAVLKYNGI<br>ITDTIKSWRNKILRTQESECACVNGSCFTIMTDGPSDGQASYKIFRIEKGKII<br>KSVEMKAPNYHYEECSCYPDSSEITCVCRDNWHGSNRPWVSFNQNLEYQ<br>MGYICSGVFGDNPRPNDKTGSCGPVSSNGANGVKGFSFKYGNGVWIGRTK<br>SISSRKGFEMIWDPNGWTGTDNKFSKKQDIVGINEWSGYSGSFVQHPELTG<br>LNCIRPCFWVELIRGRPEENTIWTSGSSISFCGVDSDIVGWSWPDGAELPFTI<br>DK | >QIA57890A/<br>Delaware/55/2019<br>2019 Dec. 11 |
| 333 | MNPNQKIITIGSICMTIGMANLILQIGNIISIWVSHSIQTGNQSQIETCNKNVIT<br>YENNTWVNQTYVNISNTNSAARQSVASVKLAGNSSLCPVSGWAIYSKDNS<br>VRIGSKGDVFVIREPFISCSPLECRTFFLTQGALLNDKHSNGTIKDRSPYRTL<br>MSCPIGEVPSPYNSRFESVAWSASACHDGTNWLTIGISGPDSGAVAVLKYN<br>GIITDTIKSWRNNILRTQESECACVNGSCFTMMTDGPSDGQASYKIFRIEKG<br>KIIKSVEMKAPNYHYEECSCYPDSSEITCVCRDNWHGSNRPWVSFNQNLEY<br>QMGYICSGVFGDNPRPNDKTGSCGPVSSNGANGVKGFSFKYGNGVWIGRT<br>KSISSRKGFEMIWDPNGWTGTDNKFSKKQDIVGINEWSGYSGSFVQHPELT<br>GLNCIRPCFWVELIRGRPEENTIWTSGSSISFCGVDSDIVGWSWPDGAELPF<br>TIDK | >QIA57903A/<br>Delaware/56/2019<br>2019 Dec. 12 |
| 334 | MKAIIVLLMVVTSNADRICTGITSSNSPHVVKTATQGEVNVTGVIPLTTTPT<br>KSHFANLKGTETRGKLCPKCLNCTDLDVALGRPKCTGKIPSARVSILHEVR<br>PVTSGCFPIMHDRTKIRQLPNLLRGYEHVRLSTHNVINAEGAPGGPYKIGTS<br>GSCPNITNGNGFFATMAWAVPDKNKTATNPLTIEVPYVCTEGEDQITVWG<br>FHSDNETQMAKLYGDSKPQKFTSSANGVTTHYVSQIGGFPNQTEDGGLPQ<br>SGRIVVDYMVQKSGKTGTITYQRGILLPQKVWCAXGRSKVIKGSLPLIGEA<br>DCLHEKYGGLNKSKPYYTGEHAKAIGNCPIWVKTPLKLANGTKYRPPAKL<br>LKERGFFGAIAGFLEGGWEGMIAGWHGYTSHGAHGVAVAADLKSTQEAI<br>NKITKNLNSLSELEVKNLQRLSGAMDELHNEILELDEKVDDLRADTISSQIE<br>LAVLLSNEGIINSEDEHLLALERKLKKMLGPSAVEIGNGCFETKHKCNQTC<br>LDKIAAGTFDAGEFSLPTFDSLNITAASLNDDGLDNHTILLYYSTAASSLAV<br>TLMIAIFVVYMVSRDNVSCSICL | >QJA11920B/<br>Alabama/07/2020<br>2020 Feb. 21 |
| 335 | MLPSTIQTLTLFLTSGGVLLSLYVSASLSYLLYSDILLKFSPTEITAPTMPLDC<br>ANASNVQAVNRSATKGVILLLPEPEWTYPRLSCPGSTFQKALLISPHRFGET<br>KGNSAPLIIREPFVACGPNECKHEALTHYAAQPGGYYNGTRGDRNKLRHLI<br>SVKLGKIPTVENSIFHMAAWSGSACHDGKEWTYIGVDGPDNNALLKIKYG<br>EAYTDTYHSYANNILRTQESACNCIGGNCYLMITDGSXSGVSECRFLKIREG<br>RIIKEIFPTGRVKHTEECTCGFASNKTIECACRDNRYTAKRPFVKLNVETDT<br>AEIRLMCTDTYLDTPRPNDGSITGPCESDGDKGSGGIKGGFVHQRMKSKIG<br>RWYSRTMSQTERMGMGLYVKYGGDPWADSDALAFSGVMVSMKEPGWY<br>SFGFEIKDKKCDVPCIGIEMVHDGGKETWHSAATAIYCLMGSGQLLWDTV<br>TGVDMAL | >QJA11911B/<br>Alabama/07/2020<br>2020 Feb. 21 |
| 336 | MKAIIVLLMVVTSNADRICTGITSSNSPHVVKTATQGEVNVTGVIPLTTTPT<br>KSHFANLKGTETRGKLCPKCLNCTDLDVALGRPKCTGKIPSARVSILHEVR<br>PVTSGCFPIMHDRTKIRQLPNLLRGYEHVRLSTHNVINAEDAPGGPYKIGTS<br>GSCPNITNGNGFFATMAWAVPKNDKNKTATNPLTIEVPYICTEGEDQITVW<br>GFHSDNETQMAKLYGDSKPQKFTSSANGVTTHYVSQIGGFPNQTEDGGLP<br>QSGRIVVDYMVQKSGKTGTITYQRGILLPQKVWCASGRSKVIKGSLPLIGE<br>ADCLHEKYGGLNKSKPYYTGEHAKAIGNCPIWVKTPLKLANGTKYRPPAK<br>LLKERGFFGAIAGFLEGGWEGMIAGWHGYTSHGAHGIAVAADLKSTQEAI<br>NKITKNLNSLSELEVKNLQRLSGAMDELHNEILELDEKVDDLRADTISSQIE<br>LAVLLSNEGIINSEDEHLLALERKLKKMLGPSAVEIGNGCFETKHKCNQTC<br>LDRIAAGTFDAGEFSLPTFDSLNITAASLNDDGLDNHTILLYYSTAASSLAV<br>TLMIAIFVVYMVSRDNVSCSICL | >QGT76054B/<br>China/b45/2019<br>2019 Jan. 08 |
| 337 | MLPSTIQTLTLFLTSGGVLLSLYVSASLSYLLYSDILLKFSPTEITAPTMPLDC<br>ANASNVQAVNRSATKGATLLLPEPEWTYPRLSCPGSTFQKALLISPHRFGE<br>TKGNSAPLIIREPFVACGPNECKHEALTHYAAQPGGYYNGTRGDRNKLRHL<br>ISVKLGKIPTVENSIFHMAAWSGSACHDGKEWTYIGVDGPDNNALLKVKY<br>GEAYTDTYHSYANNILRTQESACNCIGGNCYLMITDGSASGVSECRFLKIRE<br>GRIIKEIFPTGRVKHTEECTCGFASNKTIECACRDNRYTAKRPFVKLNVETD | >QGT76183B/<br>China/b45/2019<br>2019 Jan. 08 |

-continued

SEQUENCE LISTING

| SEQ ID NO | Sequence | Description |
|---|---|---|
| | TAEIRLMCTDTYLDTPRPNDGSITGPCESDGDEGSGGIKGGFVHQRMKSKI GRWYSRTMSKTERMGMGLYVKYGGDPWADSDALVFSGVMISMKEPGW YSFGFEIKDKKCDVPCIGIEMVHDGGKETWHSAATAIYCLMGSGQLLWDT VTGVDMAL | |
| 338 | MKAIIVLLMVVTSNADRICTGITSSNSPHVVKTATQGEVNVTGVIPLTTTPT KSHFANLKGTETRGKLCPKCLNCTDLDVALGRPKCTGKIPSARVSILHEVR PVTSGCFPIMHDRTKIRQLPNILRGYEHVRLSTHNVINAEDAPGRPYEIGTSG SCPNITNGNGFFATMAWAVPKNKTATNPLTIEVPYICTEGEDQITVWGFHS DNETQMAKLYGDSKPQKFTSSANGVTTHYVSQIGGFPNQTEDGGLPQSGRI VVDYMVQKSGKTGTITYQRGILLPQKVWCASGRSKVIKGSLPLIGEADCLH EKYGGLNKSKPYYTGEHAKAIGNCPIWVKTPLKLANGTKYRPPAKLLKER GFFGAIAGFLEGGWEGMIAGWHGYTSHGAHGVAVAADLKSTQEAINKITK NLNSLSELEVKNLQRLSGAMDELHNEILELDEKVDDLRADTISSQIELAVLL SNEGIINSEDEHLLALERKLKKMLGPSAVEIGNGCFETKHKCNQTCLDRIAA GTFDAGEFSLPTFDSLNITAASLNDDGLDNHTILLYYSTAASSLAVTLMIAIF VVYMVSRDNVSCSICL | >QDX11011B/ Japan/9830/2019 2019 May 22 |
| 339 | MLPSTIQTLTLFLTSGGVLLSLYVSASLSYLLYSDILLKFSPTEITAPTMPLDC ANASNVQAVNRSATKGVTLLLPEPEWTYPRLSCPGSTFQKALLISPHRFGE TKGNSAPLIIREPFVACGPNECKHEALTHYAAQPGGYYNGTRGDRNKLRHL ISVKLGKIPTVENSIFHMAAWSGSACHDGKEWTYIGVDGPDNNALLKVKY GEAYTDTYHSYANNILRTQESACNCIGGNCYLMITDGSASGVSECRFLKIRE GRIIKEIFPTGRVKHTEECTCGFASNKTIECACRDNKYTAKRPFVKLNVETD TAEIRLMCTDTYLDTPRPNDGSITGPCESDGDKGSGGIKGGFVHQRMKSKI GRWYSRTMSKTERMGMGLYVKYGGDPWADSDALTFSGVMVSMKEPGW YSFGFEIKDKKCDVPCIGIEMVHDGGKETWHSAATAIYCLMGSGQLLWDT VTGVDMAL | >QDX11015B/ Japan/9830/2019 2019 May 22 |
| 340 | MKAIIVLLMVVTSNADRICTGITSSNSPHVVKTATQGEVNVTGVIPLTTTPT KSHFANLKGTETRGKLCPKCLNCTDLDVALGRPKCTGKIPSARVSILHEVK PVTSGCFPIMHDRTKIRQLPNLLRGYEHVRLSTHNVINAEGAPGGPYKIGTS GSCPNITNGNGFFATMAWAVPDKNKTATNPLTIEVPYICTEGEDQITVWGF HSDNETQMAKLYGDSKPQKFTSSANGVTTHYVSQIGGFPNQTEDGGLPQS GRIVVDYMVQKSGKTGTITYQRGILLPQKVWCASGRSKVIKGSLPLIGEAD CLHEKYGGLNKSKPYYTGEHAKAIGNCPIWVKTPLKLANGTKYRPPAKLL KERGFFGAIAGFLEGGWEGMIAGWHGYTSHGAHGVAVAADLKSTQEAIN KITKNLNSLSELEVKNLQRLSGAMDELHNEILELDEKVDDLRADTISSQIEL AVLLSNEGIINSEDEHLLALERKLKKMLGPSAVEIGNGCFETKHKCNQTCL DKIAAGTFDAGEFSLPTFDSLNITAASLNDDGLDNHTILLYYSTAASSLAVT LMIAIFVVYMVSRDNVSCSICL | >QDA45896B/ Moscow/2/2019 2019 Feb. 22 |
| 341 | MLPSTIQTLTLFLTSGGVLLSLYVSASLSYLLYSDILLKFSPTEITAPTMPLDC ANASNVQAVNRSATKGVTLLLPEPEWTYPRLSCPGSTFQKALLISPHRFGE TKGNSAPLIIREPFVACGPNECKHEALTHYAAQPGGYYNGTRGDRNKLRHL ISVKLGKIPTVENSIFHMAAWSGSACHDGKEWTYIGVDGPDNNALLKVKY GEAYTDTYHSYANNILRTQESACNCIGGNCYLMITDGSASGVSECRFLKIRE GRIIKEIFPTGRVKHTEECTCGFASNKTIECACRDNRYTAKRPFVKLNVETD TAEIRLMCTDTYLDTPRPNDGSITGPCESDGDKGSGGIKGGFVHQRMKSKI GRWYSRTMSKTERMGMGLYVKYGGDPWADSNALAFSGVMISMKEPGW YSFGFEIKDKKCDVPCIGIEMVHDGGKETWHSAATAIYCLMGSGQLLWDT VTGVDMAL | >QDA45899B/ Moscow/2/2019 2019 Feb. 22 |
| 342 | DYKDDDDKHHHHHH | Flag-His(6) purification tag |
| 343 | SRGGGGSGGGGSGGGGSLEMA | Linker A |
| 344 | GGGGS | Linker 1 |
| 345 | GS(GS)$_n$, where n ≥ 0 | Linker 2 |
| 346 | (GSGGS)$_n$, where n ≥ 1 | Linker 3 |
| 347 | (GGGGS)$_n$, where n ≥ 1 | Linker 4 |
| 348 | (GGGS)$_n$, where n ≥ 1 | Linker 5 |
| 349 | MKTIIVLSYLFCLALSQDYSENNNSTATLCLGHHAVPNGTVVKTITDDQIEV TNATELVQSSSTGKICNNPHRILDGRDCTLIDALLGDPHCDVFQDETWDLY VERSSAFSNCYPYDVPDYASLRSLVASSGTLEFITEGFTWTGVTQNGGSSA CKRGPASGFFSRLNWLTKSGSAYPVLNVTMPNNDNFDKLYVWGVHHPST NQEQTNLYVQASGRVTVSTRKSQQTIIPNIGSRPWVRGQSGRISIYWTIVKP | QDX47284.1 |

-continued

SEQUENCE LISTING

| SEQ ID NO | Sequence | Description |
|---|---|---|
| | GDVLVINSNGNLIAPRGYFKMRTGKSSIMRSDAPIDTCISECITPNGSIPNDK PFQNVNKITYGACPKYVKQSTLKLATGMRNVPEKQTRGLFGAIAGFIENG WEGMIDGWYGFRHQNSEGTGQAADLKSTQAAIDQINGKLNRVIEKTNEKF HQIEKEFSEVEGRIQDLEKYVEDTKIDLWSYNAELLVALENQHTIDLTDSE MNKLFEKTRRQLRENAEDMGNGCFKIYHKCDNACIESIRNGTYDHDIYRD EALNNRFQIKGVELKSGYKDWILWISFAISCFLLCVVLLGFIMWACQRGNI RCNICI | |
| 350 | MNPNQKIITIGSICMAIGIMSLVLQIGNIISIWVSHSIQTESKSHPETCNQSVIT YENNTWVNQTYLNISNTNLIVEQIVAPVTLAGNSSLCPISGWAIYSKDNGIR IGSKGDVFVIREPFISCSHLECRTFFLTQGALLNDKHSNGTVKDRSPYRTLM SCPVGEAPSPYNSRFESVAWSASACHDGISWLTIGISGPDNGAVAVLKYNGI ITDTVKSWRNNILRTQESECACINGSCFTIMTDGPSNGQASYKIFKIEKGKV VKSVELNAPNYHYEECSCYPDASEVMCVCRDNWHGSNRPWVSFNQDLEY QIGYICSGVFGDNPRPNDGTGSCGPVSSNGAYGVKGFSFRYGNGVWIGRTK STSSRSGFEMIWDPNGWTETDNSFSVKQDIVAITDWSGYSGSFVQHPELTG LDCVRPCFWVELIRGRPKENTIWTSGSSISFCGVNSDTVGWSWPDGAELPF TIDK | QDX47725.1 |
| 351 | MRTVIALSYIFCLAFGQNLKGNENNAATLCLGHHAVPNGTMVKTITSDQIE VTNATEQVQNSSTGKICNNPHKILDGRDCTLIDALLGDPHCDVFQNETWDL FVERSNAFSNCYPYDVQDYASLRSIVASSGTLEFITEGFTWAGVTQNGGSG ACKRGPANGFFSRLNWLTKSGNTYQVLNVTMPNNNNFDKLYIWGVHHPS TNQEQTSLYIQASGRVTVSTRRSKQTIILNIESRPLVRCQSGRISVYWTIVKP GVILVINSNGNLIAPRGYFKMHIGKSTIMRSDAPVDTCISECITPNGSIPNEKP FQNVNKITYGACPKYVKQNTLKLSTGMRNVPERQTRGLFGAIAGFIENGW EGMVDGWYGFRHQNSEGTGQAADLKSTQAAIDQINGKLNRVIEKTNEKFH QIEKEFSEVEGRIQDLERYVEDTKVDLWSYNAELLVALENQNTIDLTDSEM NKLFEKTRRQLRENAEDMGNGCFKIYHKCDNACIESIRNGTYDHNIYRDEA VNNRFQIKGVELKSGYKDLILWISFAISCFLLCVVLLGFIMWACQRGNIRCN ICI | AFI61906.1 |
| 352 | MNPNQKIIAIGSVSLIIATVCFLLQIAILATNVTLYFKQNECNIPSNSQVVPCK PIIIERNITEVVYLNNTTIEKEIYSVVLEYRNWSKPQCQITGFAPFSKDNSIRL SAGGDIWVTREPYVSCDPSKCYQFALGQGTTLNNKHSNGTIHDRISHRTLL MNELGVPFHLGTKQVCIAWSSSSCHDGKAWLHVCVTGDDKNATASFVYN GMLVDSIGSWSRNILRTQESECVCINGTCTVVMTDGSASGRADTRILFIREG KIVHISPLSGSAQHIEECSCYPRYPNVRCVCRDNWKGSNRPVIDINMADYSI DSSYVCSGLVGDTPRNDDSFSSSNCRDPNNERGNPGVKGWAFDNENDVW MGRTISKDLRSGYETFKVIGCRTTANSKSQVNRQVIVDNNNWSGYSGIFSV EGKSCVNRCFYVELIRGGPQETRVWWTSNSIVVFCGTSGTYGAGSWPDGA NINFMPI | ANW47171.1 |
| 353 | MKTVIALSYIFCLAFGQNLLGNENNAATLCLGHHAVPNGTMVKTITDDQIE VTNATELVQNSSTGKICNNPHKILDGRDCTLIDALLGDPHCDVFQNETWDL FVERSNAFSNCYPYDVPDYASLRSIVASSGTLEFITEGFTWAGVTQNGGSG ACKRGPANSFFSRLNWLTKSGNTYPVLNVTMPNNNNFDKLYIWGVHHPST DQEQTSLYIQASGRVTVSTRKSQQTIIPNIGSRPLVRGQSGRISVYWTIVEPG DILVINSNGNLIAPRGYFKMHIGKSSIMRSDAPIDTCISECITPNGSIPTEKPFQ NVNKITYGACPKYVKQNTLKLATGMRNVPERQTRGLFGAXAGFIENGWE GMVDGWYGFRHQNSEGTGQAADLKSTQAAIDQINGKLNRVIEKTNEKFH QIEKEFSEVEGRIQDLERYVEDTKIDLWSYNAELLVALENQNTIDLTDSEM NKLFEKTRRQLRENAEDMGNGCFKIYHKCDNACIESIRNGTYDHNIYRDEA VNNRFQIKGVELKSGYKDWILWISFAISCFLLCVVLLGFIMWACQRGNIRC NICI | QBQ33923.2 |
| 354 | MNPNQKIIAIGSVSLAIATVCFLLQIATLATTVTLYFKQNECNIPSNSQIVPCK PIIIERNITEVVHLNNTTIEKEIYSVVLEYRNWSKPQCQITGFAPFSKDNSIRL SAGGDIWVTREPYVSCDPSKCYQFALGQGTTLNNKHSNSTIHDRTSYRTLL MNELGVPXHLGTKQVCIAWSSSSCHDGKAWLHVCVTGDDRNATASFVYN GMLVDSIGSWSRNILRTQESECVCINGTCTVVMTDGSASGKADTRILFIKEG KIIHISPLSGSAQHIEECSCYPQYPNVRCVCRDNWKGSNRPVIDINMADYNI NSSYVCSGLVGDTPRNDDSSSSSNCKDPNNERGNPGVKGWAFDNDNDVW MGRTISKDLRSGYETFKVIGGWTTANSKSQVNRQVIVDNNNWSGYSGIFSV EGKSCVNRCFYVELIRGGPQETRVWWTSNSIVVFCGTSGTYGTGSWPDGA NINFMPI | QBQ33992.2 |
| 355 | MNPNQKIITIGTASLGILIINVILHVVSIIVTVLVLNNNETGLNCKGTIIREYNE TVRVEKITQWHNTSAIKYIERPPNEYYMNNTEPLCEAQGFAPFSKDNGIRIG SRGHVFVIREPFVSCSPSECRTFFLTQGSLLNDKHSNGTVKDRSPYRTLMSV KIGQSPNVYQARFESVAWSATACHDGKKWMTIGVTGPDNQAIAVVNYGG IPVDIINSWEGDILRTQESSCTCIKGNCYWVMTDGPANRQAKYRIFKAKDG RVIGQTDISFNGGHIEECSCYPNEGKVECICRDNWTGTNRPILVISSDLSYTV | AIZ95447.1 |

-continued

SEQUENCE LISTING

| SEQ ID NO | Sequence | Description |
|---|---|---|
| | GYLCAGIPTDTPRGEDSQFTGSCTSPLGNKGYGVKGFGFRQGTDVWAGRTI SRTSRSRFEIIKIRNGWTQNSKDQIRRQVIIDDPNWSGYSGSFTLPVELTKKG CLVPCFWVEMIRGKPEETTIWTSSSSIVMCGVDHKIASWSWHDGAILPFDID KM | |
| 356 | MKTTTIFIFILLTHWAYSQNPISNNNTATLCLGHHAVANGTLVKTISDDQIE VTNATELVQSISMGKICNNSYRILDGRNCTLIDAMLGDPHCDVFQYENWD LFIERSSAFSNCYPYDIPDYASLRSIVASSGTLEFTAEGFTWTGVTQNGRSGA CKRGSTDSFFSRLNWLTKSGNSYPTLNVTMPNNKNEDKLYIWGIHHPSSNQ EQTKLYIQGSGRVTVSTKRSQQTIIPNIGSRPWVRGQSGRISIYWTIVKPGDI LMINSNGNLVAPRGYFKLKTGKSSVMRSDVPIDICVSECITPNGSISNDKPF QNVNKVTYGKCPKYIRQNTLKLATGMRNVPEKQIRGIFGAIAGFIENGWEG MVDGWYGFRYQNSEGTGQAADLKSTQTAIDQINEKLNRVIERTNEKFHQI EKEFSEVEGRIQDLEKYVEDTKIDLWSYNAELLVALENQHTIDLTDAEMNK LFEKTRRQLRENAEDMGGGCFKIYHKCDNACIGSIRNGTYDHYIYRDEALN NRFQIKGVELKSGYKDWILWISFAISCFLICVVLLGFIMWACQKGN IRCNICI | AXQ87682.1 |
| 357 | MKAILLVLLYTFVPTNADTLCIGYHANNSTDTVDTILERNVTVTHSVNLLE DKHNGRLCKLGGIAPLHLGKCNIAGWLLGNPECESLFTVSSWSYIVETSNS YNGTCYPGDFINYEELREQLSSVSSFERFEIFPKASSWPNHETNKGVTAACS HAGTKSFYRNLIWLVKKGNSYPNISKSYFNNKGNEVLVLWGIHHPSTNND QQTLYQNADTYVFVGTSKYNKKFKPEIAIRPKVRDQEGRMNYYWTLVEPG DKITFEATGNLVVPRYAFAMERNAGSGIIISDTPVHDCNTTCQTPKGAINTS LPFQNIHPTTIGKCPKYVKSTKLRLATGLRNVPSIQSRGLFGAIAGFIEGGWT GMVDGWYGYHHQNEQGSGYAADQKSTQNAIDGITNKVNSVIEKMNTQFT AVGKEFNHLEKRIENLNKKVDDGFLDVWTYNAELLILLENERTLDFHDSN VKNLYEKARRQLKNNAKEIGNGCFEFYHKCDNACMESVKNGTYDYPKYS EESRLNREEISGVKLDSTRIYQILAIYSTVASSSVLLVSLGAISFWMCSNGSL QCRICI | AEA29582.1 |
| 358 | MNTNQRIITIGTVCLTVGIISLLLQIGNIVSLWISHSIQTGGKNHTEMCNKNVI TYVNNTWVNRTYVNISNTKIVNVQDVVSVILTGNSSLCPISGWAIYSKDNSI RIGSKGDIFVIREPFISCSHLECRTFFLTQGALLNDKHSNGTVKDRSPYRTLM SCPIGEAPSPYNSRFESVAWSASACHDGMGWLTIGISGPDNGAVAVLKYNG IITDTIKSWRNKILRTQESECVCMNGSCFTVLTDGPSNGQASYKIFKMEKGK IIKSIELDAPNYHYEECSCYPDAGKVMCVCRDNWHASNRPWVSFDQNLDY QIGYICSGVFGDNPRSNDGKGNCGPVHSNGANGVKGFSYRYGNGVWIGRT KSINSRSGFEMIWDPNGWTGTDSSFSMKQDIIALTDWSGYSGSFVQHPELT GMNCIRPCFWVELIRGQPKENTIWASGSSISFCGVNGETASWSWPDGADLP FTIDK | AHB21162.1 |
| 359 | SGFSFSSSY | G126 HC-CDR1 |
| 360 | LEWIACIYAGSSGSAYF | G126 HC-CDR2 |
| 361 | APSYTYGYAGYAYAYSYYFN | G126 HC-CDR3 |
| 362 | QSINN | G126 LC-CDR1 |
| 363 | PKLLYDASDLA | G126 LC-CDR2 |
| 364 | DYSTNN | G126 LC-CDR3 |
| 365 | SNNAVWN | FY-UCA-VH HC-CDR1 |
| 366 | RTYYRSKWYNDYAESVKS | FY-UCA-VH HC-CDR2 |
| 367 | SGHITVFGVNVDAFDM | FY-UCA-VH HC-CDR3 |
| 368 | TRSQSLSSYLH | FY-UCA-VH LC-CDR1 |
| 369 | AASSLQS | FY-UCA-VH LC-CDR2 |
| 370 | QQSRT | FY-UCA-VH LC-CDR3 |

-continued

SEQUENCE LISTING

| SEQ ID NO | Sequence | Description |
|---|---|---|
| 371 | LIYTGGTTYYADSVKG | AT10_004 HC-CDR1 |
| 372 | VSALRFLQWPNYAMDV | AT10_004 HC-CDR2 |
| 373 | SGTRSDVGGHNYVS | AT10_004 HC-CDR3 |
| 374 | EVSHRPS | AT10_004 LC-CDR1 |
| 375 | SSYTGEGPLGV | AT10_004 LC-CDR2 |
| 376 | SYWMS | AT10_004 LC-CDR3 |
| 377 | RHGIS | CR8001 HC-CDR1 |
| 378 | WISAYTGDTDYAQKFQG | CR8001 HC-CDR2 |
| 379 | GWGAVTSPFDF | CR8001 HC-CDR3 |
| 380 | GWGAVTSPFDF | CR8001 LC-CDR1 |
| 381 | DASNRAT | CR8001 LC-CDR2 |
| 382 | QQRSNWLK | CR8001 LC-CDR3 |
| 383 | QSLEESGGDLVKPGASLTLTCTASGFSFSSSYWICWVRQAPGKGLEWIACI YAGSSGSAYFASWAKGRFTISETSSTTVTLQMTSLTAADTATYFCARAPSY TYGYAGYAYAYSYYFNLWGPGTLVTVSS | G126 $V_H$ |
| 384 | VMTQTPASVEVTMGGTVTINCQASQSINNELCWYQQKPGQRPKLLIYDAS DLASGVPSRFKGSGSGTEFTLTISDLECADAATYYCQQDYSTNNVDNLFGG GTEVVVK | G126 $V_L$ |
| 385 | QVQLQQSGPGLVKPSQTLSLTCAISGDSVSSNNAVWNWIRQSPSRGLEWLG RTYYRSKWYNDYAESVKSRITINPDTSKNQFSLQLNSVTPEDTAVYYCARS GHITVFGVNVDAFDMWGQGTMVTVSS | FY-UCA-VH $V_H$ |
| 386 | DIQMTQSPSSLSASVGDRVTITCRTSQSLSSYTHWYQQKPGKAPKLLIYAAS SRGSGVPSRFSGSGSGTDFTLTISSLQPEDFATYYCQQSRTFGQGTKVEIK | FY-UCA-VH $V_L$ |
| 387 | EVQLVESGGGLIQPGGSLRLSCAASGFTVSSNYVSWVRQAPGKGLEWLSLI YTGGTTYYADSVKGRFTISRDNSKNTVFLQMNSLRAEDAAMYYCARVSA LRFLQWPNYAMDV | AT10_004 $V_H$ |
| 388 | QSALTQPASVSGSPGRSITISCSGTRSDVGGHNYVSWYQQHPGKAPKLMIY EVSHRPSGVSNRFSGSKSGSTASLTISGLQSEDEADYYCSSYTGEGPLGV | AT10_004 $V_L$ |
| 389 | QVQLVQSGAEVRKPGASVKVSCKASGYTFTRHGISWVRQAPGQGLEWMG WISAYTGDTDYAQKFQGRVTMTTDTSTNTAYMELRSLRSDDAAVYYCAR LRLQGEVVVPPSQSNWFDPWGQGTLVTVSS | CR8001 $V_H$ |
| 390 | EIVLTQSPATLSLYPGERATLSCRASQSVSRYLAWYQQKPGQAPRLLIYDAS NRATGIPARFSGSGSGTDFTLTISSLEPEDFAVYYCCDRQQRSNWLKITFGQ GTRLEIKGTV | CR8001 $V_L$ |
| 391 | TCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVS NKALPAPIEKTISKAKGQPREPQVYTLPPSRDELTKNQVSLTCLVKGFYPSD IAVEWESNGQPENNYKTTPPVLDSDGSFFLYSKLTVDKSRWQQGNVFSCS VMHEALHNHYTQKSLSLSPGK | Immunoglobulin Fc ($CH_2CH_3$) |

SEQUENCE LISTING

| SEQ ID NO | Sequence | Description |
|---|---|---|
| 392 | GQPKANPTVTLFPPSSEELQANKATLVCLISDFYPGAVTVAWKADGSPVKA GVETTKPSKQSNNKYAASSYLSLTPEQWKSHRSYSCQVTHEGSTVEKTVA PTECS | Immunoglobulin $C_L$ |
| 393 | ASTKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKRVEPKSC | Immunoglobulin $CH_1$ |
| 394 | TCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVS NKALPAPIEKTISKAKGQPRE | Immunoglobulin $CH_2$ |
| 395 | PQVYTLPPSRDELTKNQVSLTCLVKGFYPSDIAVEWESNGQPENNYKTTPP VLDSDGSFFLYSKLTVDKSRWQQGNVFSCSVMHEALHNHYTQKSLSLSPG K | Immunoglobulin $CH_3$ |
| 396 | PDVYLLPPAREQLNLRESATITCLVTGFSPADVFVQWMQRGQPLSPEKYVT SAPMPEPQAPGRYFAHSILTVSEEEWNTGETYTCVVAHEALPNRVTERTVD KSTGK | Immunoglobulin $CH_4$ |
| 397 | MWWRLWWLLLLLLLLWGSSASAAIIPVEEENPDFWNREAAEALGAAKKL QPAQTAAKNLIIFLGDGMGVSTVTAARILKGQKKDKLGPEIPLAMDRFPYV ALSKTYNVDKHVPDSGATATAYLCGVKGNFQTIGLSAAARFNQCNTTRGN EVISVMNRAKKAGKSVGVVTTTRVQHASPAGTYAHTVNRNWYSDADVPA SARQEGCQDIATQLISNMDIDVILGGGRKYMFRMGTPDPEYPDDYSQGGTR LDGKNLVQEWLAKRQGARYVWNRTELMQASLDPSVTHLMGLFEPGDMK YEIHRDSTLDPSLMEMTEAALRLLSRNPRGFFLFVEGGRIDHGHHESRAYR ALTETIMEDDAIERAGQLTSEEDTLSLVTADHSHVFSFGGYPLRGSSIFGLAP GKARDRKAYTVLLYGNGPGYVLKDGARPDVTESESGSPEYRQQSAVPLDE ETHAGEDVAVFARGPQAHLVHGVQEQTFIAHVMAFAACLEPYTACDLAPP AGTTDAAHPGYSRVGAAGRFEQT | Alkaline phosphatase |
| 398 | MKLVGSYTSPFVRKLSILLLEKGITFEFINELPYNADNGVAQFNPLGKVPVL VTEEGECWFDSPIIAEYIELMNVAPAMLPRDPLESLRVRKIEALADGIMDAG LVSVREQARPAAQQSEDELLRQREKINRSLDVLEGYLVDGTLKTDTVNLA TIAIACAVGYLNFRRVAPGWCVDRPHLVKLVENLFSRESFARTEPPKA | Glutathione-s-transferase |
| 399 | LENHSRRLEMTNKQLWLRIQEL | bHLH-leucine zipper |
| 400 | LSIIAICLGSLGLILIILLSVVVWKLL | Leucine/isoleucine zipper |
| 401 | GPP(GPP)$_n$, where n ≥ 0 | Collagen-like peptide |
| 402 | EYFTLQIRGRERFEMFRELNEALELKDAQAG | p53 tetramerization domain |
| 403 | MAEAGITGTWYNQLGSTFIVTAGADGALTGTYESAVGNAEGDYVLTGRY DSAPATDGSGTALGWTVAWKNNYRNAHSATTWSGQYVGGAEARINTQW LLTSGTTEANAWKSTLVGHDTFTKVKPSAAS | Streptavidin (SA) |
| 404 | GYIPEAPRDGQAYVRKDGEWVLLSTFL | T4 fibritin |
| 405 | GPQMLRELGETNAALQDVRELLRQQVREITFLKNTVMECDAC | COMP (cartilage oligomeric matrix protein) |
| 406 | PPKVSVFVPPRDGFFGNPRKSKLICQATGFSPRQIQVSWLREGKQVGSGVTT DQVQAEAKESGPTTYKVTSTLTIKESDWLSQSMFTCRVDHRGLTFQQNASS MCVPDQDTAIRVFAIPPSFASIFLTKSTKLTCLVTDLTTYDSVTISWTRQNGE AVKTHTNISESHPNATFSAVGEASICEDDWNSGERFTCTVTHTDLPSPLKQT ISRPKGVALHRPDVYLLPPAREQLNLRESATITCLVTGFSPADVFVQWMQR GQPLSPEKYVTSAPMPEPQAPGRYFAHSILTVSEEEWNTGETYTCVVAHEA LPNRVTERTVDKSTGKPTLYNVSLVMSDTAGTCY | Immunoglobulin Fc ($CH_2CH_3CH_4$) |
| 407 | HHHHH | 5H |
| 408 | KKKGKKK | 7X-1 |
| 409 | KKAHHGKKAHHV | 12X-7 |

-continued

SEQUENCE LISTING

| SEQ ID NO | Sequence | Description |
|---|---|---|
| 410 | KKARRGKKARRV | 12X-8 |
| 411 | KLIHKKARVRGK | 12x-9 |
| 412 | ILRRKAHHGKIKKVR | 15X-1 |
| 413 | GHRVKKAVRHIKRL | 15X-2 |
| 414 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSTCPPCPAPELLGGPSVFLFPPK PKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREP QVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK | HA1-hIgG heavy chain (HC) |
| 415 | ASWDDSLNG | HA2 LC-CDR3 |
| 416 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSTCPPCPAPELLGGPSVFLFPPK PKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREP QVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK HHHHH | HA1-hIgG-5H (HA1-IgG HC fused to 5H) |
| 417 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSTCPPCPAPELLGGPSVFLFPPK PKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREP QVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK KKKGKKK | HA1-hIgG-7X-1 (HA1-IgG HC fused to KKKGKKK) |
| 418 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSTCPPCPAPELLGGPSVFLFPPK PKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREP QVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK KKAHHGKKAHHV | HA1-hIgG-12X-7 (HA1-IgG HC fused to KKAHHGKKAH HV) |
| 419 | QVQLVESGGGVVQPGRSLRLSCAASGFTFSTYAMHWVRQAPGKGLEWVA VISYDANYKYYADSVKGRFTISRDNSKNTLYLQMNSLRAEDTAVYYCAKD SQLRSLLYFEWLSQGYFDYWGQGTLVTVSSTCPPCPAPELLGGPSVFLFPPK PKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREP QVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK KKARRGKKARRV | HA1-hIgG-12X-8 (HA1-IgG HC fused to KKARRGKKAR RV) |
| 420 | EVQLVESGAEVKKPGSSVKVSCRASGTFYKYAINWVRQAPGQGLEWMGG IIPFFGTTNYAQKFQGRLTITADGSTNTAYMQLDSLRSEDTAVYYCAGPSIT ESHYCLDCAAKDYYYGLDVWGQGTTVTVSSSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGK | HA2-hIgG heavy chain (HC) |
| 421 | AGSGIIISDTPVHDCNTTCQTPKGAINTSLPFQNIHPITIGKCPKYVKSTKLRL ATGLRNVPSIQSRGLFGAIAGFIEGGWTGMVDGWYGYHHQNEQGSGYAA DLKSTQNAIDKITNKVNSVIEKMNTQFTAVGKEFNHLEKRIENLNKKVDDG FLDIWTYNAELLVLLENERTLDYHDSNVKNLYEKVRNQLKNNAKEIGNGC FEFYHKCDNTCMESVKNGTYDYPKYSEEAKLNREEIDGVKLESTRIYQIL | H1 (H1N1 A/Tottori/YK041/ 2011) AB745403.1 |
| 422 | EVQLVESGAEVKKPGSSVKVSCRASGTFYKYAINWVRQAPGQGLEWMGG IIPFFGTTNYAQKFQGRLTITADGSTNTAYMQLDSLRSEDTAVYYCAGPSIT ESHYCLDCAAKDYYYGLDVWGQGTTVTVSSSVFPLAPSSKSTSGGTAALG | HA2-hIgG-5H (HA2-IgG HC fused to 5H) |

SEQUENCE LISTING

| SEQ ID NO | Sequence | Description |
|---|---|---|
| | CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKHHHH H | |
| 423 | EVQLVESGAEVKKPGSSVKVSCRASGTFYKYAINWVRQAPGQGLEWMGG IIPFFGTTNYAQKFQGRLTITADGSTNTAYMQLDSLRSEDTAVYYCAGPSIT ESHYCLDCAAKDYYYGLDVWGQGTTVTVSSSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKKKKG KKK | HA2-hIgG-7X-1 (HA2-IgG HC fused to KKKGKKK) |
| 424 | EVQLVESGAEVKKPGSSVKVSCRASGTFYKYAINWVRQAPGQGLEWMGG IIPFFGTTNYAQKFQGRLTITADGSTNTAYMQLDSLRSEDTAVYYCAGPSIT ESHYCLDCAAKDYYYGLDVWGQGTTVTVSSSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKKKAH HGKKAHHV | HA2-hIgG-12X-7 (HA2-IgG HC fused to KKAHHGKKAH HV) |
| 425 | EVQLVESGAEVKKPGSSVKVSCRASGTFYKYAINWVRQAPGQGLEWMGG IIPFFGTTNYAQKFQGRLTITADGSTNTAYMQLDSLRSEDTAVYYCAGPSIT ESHYCLDCAAKDYYYGLDVWGQGTTVTVSSSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKKKAR RGKKARRV | HA2-hIgG-12X-8 (HA2-IgG HC fused to KKARRGKKAR RV) |
| 426 | QVQLQESGPGLVRPSETLSLTCTVSGDSIGGSYWNWIRQPPGKGLQWIGYI YYTGITNYNPSLKSRVTMSLDTSKNQISLKMDSVTAADTALYFCARGDYS GYDRDVQVELMDVWGKGTTVTVSSSVFPLAPSSKSTSGGTAALGCLVKD YFPEPVTVSWNSGALTSGVHTFPAVLQSSGLYSLSSVVTVPSSSLGTQTYIC NVNHKPSNTKVDKRVEPKSCTCPPCPAPELLGGPSVFLFPPKPKDTLMISRT PEVTCVVVDVSHEDPEVKFNWYVDGVEVHNAKTKPREEQYNSTYRVVSV LTVLHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFFLY SKLTVDKSRWQQGNVFSCSVMHEALHNHYTQKSLSLSPGK | NA1-hIgG heavy chain (HC) |
| 427 | RTGKSSIMRSDAPIGTCSSECITPNGSIPNDKPFQNVNKITYGACPKYVKQNT LKLATGMRNVPEKQTRGIFGAIAGFIENGWEGMIDGWYGFRHQNSEGTGQ AADLKSTQAAIDQINGKLNRVIEKTNEKFHQIEKEFSEVEGRIQDLEKYVED TKIDLWSYNAELLVALENQHTIDLTDSEMNKLFEKTRRQLRENAEDMGNG CFKIYHKCDNACIGSIRNGTYDHDVYRDEALNNRFQIKGVELKSGYKDWI | H3N2A/ Victoria/3/1975 4058 |
| 428 | QVQLQESGPGLVRPSETLSLTCTVSGDSIGGSYWNWIRQPPGKGLQWIGYI YYTGITNYNPSLKSRVTMSLDTSKNQISLKMDSVTAADTALYFCARGDYS GYDRDVQVELMDVWGKGTTVTVSSSVFPLAPSSKSTSGGTAALGCLVKD YFPEPVTVSWNSGALTSGVHTFPAVLQSSGLYSLSSVVTVPSSSLGTQTYIC NVNHKPSNTKVDKRVEPKSCTCPPCPAPELLGGPSVFLFPPKPKDTLMISRT PEVTCVVVDVSHEDPEVKFNWYVDGVEVHNAKTKPREEQYNSTYRVVSV LTVLHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFFLY SKLTVDKSRWQQGNVFSCSVMHEALHNHYTQKSLSLSPGKHHHHH | NA1-hIgG-5H (NA1-IgG HC fused to 5H) |
| 429 | QVQLQESGPGLVRPSETLSLTCTVSGDSIGGSYWNWIRQPPGKGLQWIGYI YYTGITNYNPSLKSRVTMSLDTSKNQISLKMDSVTAADTALYFCARGDYS GYDRDVQVELMDVWGKGTTVTVSSSVFPLAPSSKSTSGGTAALGCLVKD YFPEPVTVSWNSGALTSGVHTFPAVLQSSGLYSLSSVVTVPSSSLGTQTYIC NVNHKPSNTKVDKRVEPKSCTCPPCPAPELLGGPSVFLFPPKPKDTLMISRT PEVTCVVVDVSHEDPEVKFNWYVDGVEVHNAKTKPREEQYNSTYRVVSV | NA1-hIgG-7X-1 (NA1-IgG HC fused to KKKGKKK) |

-continued

SEQUENCE LISTING

| SEQ ID NO | Sequence | Description |
|---|---|---|
| | LTVLHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFFLY SKLTVDKSRWQQGNVFSCSVMHEALHNHYTQKSLSLSPGKKKKGKKK | |
| 430 | QVQLQESGPGLVRPSETLSLTCTVSGDSIGGSYWNWIRQPPGKGLQWIGYI YYTGITNYNPSLKSRVTMSLDTSKNQISLKMDSVTAADTALYFCARGDYS GYDRDVQVELMDVWGKGTTVTVSSSVFPLAPSSKSTSGGTAALGCLVKD YFPEPVTVSWNSGALTSGVHTFPAVLQSSGLYSLSSVVTVPSSSLGTQTYIC NVNHKPSNTKVDKRVEPKSCTCPPCPAPELLGGPSVFLFPPKPKDTLMISRT PEVTCVVVDVSHEDPEVKFNWYVDGVEVHNAKTKPREEQYNSTYRVVSV LTVLHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFFLY SKLTVDKSRWQQGNVFSCSVMHEALHNHYTQKSLSLSPGKKKAHHGKKA HHV | NA1-hIgG-12X-7 (NA1-IgG HC fused to KKAHHGKKAH HV) |
| 431 | QVQLQESGPGLVRPSETLSLTCTVSGDSIGGSYWNWIRQPPGKGLQWIGYI YYTGITNYNPSLKSRVTMSLDTSKNQISLKMDSVTAADTALYFCARGDYS GYDRDVQVELMDVWGKGTTVTVSSSVFPLAPSSKSTSGGTAALGCLVKD YFPEPVTVSWNSGALTSGVHTFPAVLQSSGLYSLSSVVTVPSSSLGTQTYIC NVNHKPSNTKVDKRVEPKSCTCPPCPAPELLGGPSVFLFPPKPKDTLMISRT PEVTCVVVDVSHEDPEVKFNWYVDGVEVHNAKTKPREEQYNSTYRVVSV LTVLHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFFLY SKLTVDKSRWQQGNVFSCSVMHEALHNHYTQKSLSLSPGKKKARRGKKA RRV | NA1-hIgG-12X-8 (NA1-IgG HC fused to KKARRGKKAR RV) |
| 432 | EVQLVQSGAEVKKPGSSVKVSCKASGYTFINHALSWVRQAPGQGLEWVG GIIPIFGLAKYGQKFQDRVTITADESTKTAYMDLRSLRSDDTAVYYCARDT VAVYEDFDWSSPYFFYMDVWGKGTTVTVSSSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGK | NA2-hIgG heavy chain (HC) |
| 433 | RTGKSSIMRSDAPIGTCSSECITPNGSIPNDKPFQNVNKITYGACPKYVKQNT LKLATGMRNVPEKQTRGIFGAIAGFIENGWEGMIDGWYGFRHQNSEGTGQ AADLKSTQAAIDQINGKLNRVIEKTNEKFHQIEKEFSEVEGRIQDLEKYVED TKIDLWSYNAELLVALENQHTIDLTDSEMNKLFEKTRRQLRENAEDMGNG CFKIYHKCDNACIGSIRNGTYDHDVYRDEALNNRFQIKGVELKSGYKDWI | H3 (H3N2A/ Victoria/3/1975) 4058_A |
| 434 | EVQLVESGAEVKKPGSSVKVSCRASGTFYKYAINWVRQAPGQGLEWMGG IIPFFGTTNYAQKFQGRLTITADGSTNTAYMQLDSLRSEDTAVYYCAGPSIT ESHYCLDCAAKDYYYGLDVWGQGTTVTVSSSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKHHHH H | NA2-hIgG-5H (NA2-IgG HC fused to 5H) |
| 435 | EVQLVESGAEVKKPGSSVKVSCRASGTFYKYAINWVRQAPGQGLEWMGG IIPFFGTTNYAQKFQGRLTITADGSTNTAYMQLDSLRSEDTAVYYCAGPSIT ESHYCLDCAAKDYYYGLDVWGQGTTVTVSSSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKKKKG KKK | NA2-hIgG-7X-1 (NA2-IgG HC fused to KKKGKKK) |
| 436 | EVQLVESGAEVKKPGSSVKVSCRASGTFYKYAINWVRQAPGQGLEWMGG IIPFFGTTNYAQKFQGRLTITADGSTNTAYMQLDSLRSEDTAVYYCAGPSIT ESHYCLDCAAKDYYYGLDVWGQGTTVTVSSSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL | NA2-hIgG-12X-7 (NA2-IgG HC fused to KKAHHGKKAH HV) |

| SEQUENCE LISTING | | |
|---|---|---|
| SEQ ID NO | Sequence | Description |
| | MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKKKAH HGKKAHHV | |
| 437 | EVQLVESGAEVKKPGSSVKVSCRASGTFYKYAINWVRQAPGQGLEWMGG IIPFFGTTNYAQKFQGRLTITADGSTNTAYMQLDSLRSEDTAVYYCAGPSIT ESHYCLDCAAKDYYYGLDVWGQGTTVTVSSSVFPLAPSSKSTSGGTAALG CLVKDYFPEPVTVSWNSGALTSGVHTFPAVLQSSGLYSLSSVVTVPSSSLGT QTYICNVNHKPSNTKVDKRVEPKSCTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGKKKAR RGKKARRV | NA2-hIgG-12X-8 (NA2-IgG HC fused to KKARRGKKAR RV) |
| 438 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSS | HA15 $V_H$ |
| 439 | GGTSNNYA | HA15 HC-CDR1 |
| 440 | ISPIFGST | HA15 HC-CDR2 |
| 441 | ARHGNYYYYSGMDV | HA15 HC-CDR3 |
| 442 | QSALTQPPAVSGTPGQRVTISCSGSDSNIGRRSVNWYQQFPGTAPKLLIYSN DQRPSVVPDRFSGSKSGTSASLAISGLQSEDEAEYYCAAWDDSLKGAVFGG GTQLTVL | HA15 VL |
| 443 | DSNIGRRS | HA15 LC-CDR1 |
| 444 | STIMKSELEYGNCNTKCQTPMGAINSSMPFHNIHPLTIGECPKYVKSNRLVL ATGLRNTPQRERRRKKRGLFGAIAGFIEGGWQGMVDGWYGYHHSNEQGS GYAADKESTQKAIDGVTNKVNSIINKMNTQFEAVGREFNNLERRIENLNKK MEDGFLDVWTYNAELLVLMENERTLDFHDSNVKNLYDKVRLQLRDNAK ELGNGCFEFYHKCDNECMESVKNGTYDYPQYSEEARLNREEISGVKLESM GTYQIL | H5 (H5N1A/ Hong Kong/156/97) Q56140 |
| 445 | AAWDDSLKGAV | HA15 LC-CDR3 |
| 446 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGK | HA15-hIgG heavy chain (HC) |
| 447 | QSALTQPPAVSGTPGQRVTISCSGSDSNIGRRSVNWYQQFPGTAPKLLIYSN DQRPSVVPDRFSGSKSGTSASLAISGLQSEDEAEYYCAAWDDSLKGAVFGG GTQLTVLGQPKANPTVTLFPPSSEELQANKATLVCLISDFYPGAVTVAWKA DGSPVKAGVETTKPSKQSNNKYAASSYLSLTPEQWKSHRSYSCQVTHEGS TVEKTVAPTECS | HA15-hIgG light chain (LC) |
| 448 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGKHHHHH | HA15-hIgG-5H (HA15-IgG HC fused to 5H) |
| 449 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC | HA15-hIgG-6H (HA15-IgG HC fused to 6H) |

SEQUENCE LISTING

| SEQ ID NO | Sequence | Description |
|---|---|---|
| | VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGKHHHHHH | |
| 450 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGKHHHHHHHHHHHH | HA15-hIgG-12H (HA15-IgG HC fused to 12H) |
| 451 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGKHHHHHHHHHHHHH HHHHHHHHHHHHHHHHH | HA15-hIgG-30H (HA15-IgG HC fused to 30H) |
| 452 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGKKKKKKK | HA15-hIgG-6K (HA15-IgG HC fused to 6K) |
| 453 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGGGGSKKKKKKKKK KKK | HA15-hIgG-12K (HA15-IgG HC fused to 12K) |
| 454 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGKKKKKKKKKKKKK KKKKKKKKKKKKKKKKK | HA15-hIgG-30K (HA15-IgG HC fused to 30K) |
| 455 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGKRRRRRR | HA15-hIgG-6R (HA15-IgG HC fused to 6R) |
| 456 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC | HA15-hIgG-12R (HA15-IgG HC fused to 12R) |

-continued

SEQUENCE LISTING

| SEQ ID NO | Sequence | Description |
|---|---|---|
| | VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGKRRRRRRRRRRRR | |
| 457 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGKRRRRRRRRRRRRR RRRRRRRRRRRRRRRRR | HA15-hIgG-30R (HA15-IgG HC fused to 30R) |
| 458 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGKOOOOOO | HA15-hIgG-6O (HA15-IgG HC fused to 6O) |
| 459 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGKOOOOOOOOOOOO | HA15-hIgG-12O (HA15-IgG HC fused to 12O) |
| 460 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGKOOOOOOOOOOOOO OOOOOOOOOOOOOOOOO | HA15-hIgG-30O (HA15-IgG HC fused to 30O) |
| 461 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGKHHKKOO | HA15-hIgG-6X-1 (HA15-IgG HC fused to HHKKOO) |
| 462 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGKHQRKHR | HA15-hIgG-6X-2 (HA15-IgG HC fused to HORKHR) |
| 463 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC VVVDVSHEDPEVKFNWYVDGVEVHNAKTKPREEQYNSTYRVVSVLTVLH | HA15-hIgG-6X-3 (HA15-IgG HC fused to HKRSOH) |

-continued

SEQUENCE LISTING

| SEQ ID NO | Sequence | Description |
|---|---|---|
| | QDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTV<br>DKSRWQQGNVFSCSVMHEALHNHYTQKSLSLSPGKHKRSOH | |
| 464 | QVQLVQSGAEVKKPGSSVKVSCKSSGGTSNNYAISWVRQAPGQGLDWMG<br>GISPIFGSTAYAQKFQGRVTISADIFSNTAYMELNSLTSEDTAVYFCARHGN<br>YYYYSGMDVWGQGTTVTVSSSVFPLAPSSKSTSGGTAALGCLVKDYFPEP<br>VTVSWNSGALTSGVHTFPAVLQSSGLYSLSSVVTVPSSSLGTQTYICNVNH<br>KPSNTKVDKRVEPKSCTCPPCPAPELLGGPSVFLFPPKPKDTLMISRTPEVTC<br>VVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTV<br>DKSRWQQGNVFSCSVMHEALHNHYTQKSLSLSPGKRRHTHR | HA15-hIgG-6X-4<br>(HA15-IgG HC<br>fused to<br>RRHTHR) |
| 465 | QVQLVQSGAEVKKPGSSVKVSCKSSGGTSNNYAISWVRQAPGQGLDWMG<br>GISPIFGSTAYAQKFQGRVTISADIFSNTAYMELNSLTSEDTAVYFCARHGN<br>YYYYSGMDVWGQGTTVTVSSSVFPLAPSSKSTSGGTAALGCLVKDYFPEP<br>VTVSWNSGALTSGVHTFPAVLQSSGLYSLSSVVTVPSSSLGTQTYICNVNH<br>KPSNTKVDKRVEPKSCTCPPCPAPELLGGPSVFLFPPKPKDTLMISRTPEVTC<br>VVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTV<br>DKSRWQQGNVFSCSVMHEALHNHYTQKSLSLSPGKKKHHRR | HA15-hIgG-6X-5<br>(HA15-IgG HC<br>fused to<br>KKHHRR) |
| 466 | QVQLVQSGAEVKKPGSSVKVSCKSSGGTSNNYAISWVRQAPGQGLDWMG<br>GISPIFGSTAYAQKFQGRVTISADIFSNTAYMELNSLTSEDTAVYFCARHGN<br>YYYYSGMDVWGQGTTVTVSSSVFPLAPSSKSTSGGTAALGCLVKDYFPEP<br>VTVSWNSGALTSGVHTFPAVLQSSGLYSLSSVVTVPSSSLGTQTYICNVNH<br>KPSNTKVDKRVEPKSCTCPPCPAPELLGGPSVFLFPPKPKDTLMISRTPEVTC<br>VVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTV<br>DKSRWQQGNVFSCSVMHEALHNHYTQKSLSLSPGKOORRHH | HA15-hIgG-6X-6<br>(HA15-IgG HC<br>fused to<br>OORRHH) |
| 467 | QVQLVQSGAEVKKPGSSVKVSCKSSGGTSNNYAISWVRQAPGQGLDWMG<br>GISPIFGSTAYAQKFQGRVTISADIFSNTAYMELNSLTSEDTAVYFCARHGN<br>YYYYSGMDVWGQGTTVTVSSSVFPLAPSSKSTSGGTAALGCLVKDYFPEP<br>VTVSWNSGALTSGVHTFPAVLQSSGLYSLSSVVTVPSSSLGTQTYICNVNH<br>KPSNTKVDKRVEPKSCTCPPCPAPELLGGPSVFLFPPKPKDTLMISRTPEVTC<br>VVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTV<br>DKSRWQQGNVFSCSVMHEALHNHYTQKSLSLSPGKKKOORR | HA15-hIgG-6X-7<br>(HA15-IgG HC<br>fused to<br>KKOORR) |
| 468 | QVQLVQSGAEVKKPGSSVKVSCKSSGGTSNNYAISWVRQAPGQGLDWMG<br>GISPIFGSTAYAQKFQGRVTISADIFSNTAYMELNSLTSEDTAVYFCARHGN<br>YYYYSGMDVWGQGTTVTVSSSVFPLAPSSKSTSGGTAALGCLVKDYFPEP<br>VTVSWNSGALTSGVHTFPAVLQSSGLYSLSSVVTVPSSSLGTQTYICNVNH<br>KPSNTKVDKRVEPKSCTCPPCPAPELLGGPSVFLFPPKPKDTLMISRTPEVTC<br>VVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTV<br>DKSRWQQGNVFSCSVMHEALHNHYTQKSLSLSPGKKKKGKKK | HA15-hIgG-7X-1<br>(HA15-IgG HC<br>fused to<br>KKKGKKK) |
| 469 | QVQLVQSGAEVKKPGSSVKVSCKSSGGTSNNYAISWVRQAPGQGLDWMG<br>GISPIFGSTAYAQKFQGRVTISADIFSNTAYMELNSLTSEDTAVYFCARHGN<br>YYYYSGMDVWGQGTTVTVSSSVFPLAPSSKSTSGGTAALGCLVKDYFPEP<br>VTVSWNSGALTSGVHTFPAVLQSSGLYSLSSVVTVPSSSLGTQTYICNVNH<br>KPSNTKVDKRVEPKSCTCPPCPAPELLGGPSVFLFPPKPKDTLMISRTPEVTC<br>VVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTV<br>DKSRWQQGNVFSCSVMHEALHNHYTQKSLSLSPGKHHHKKKRRROOO | HA15-hIgG-12X-<br>1<br>(HA15-IgG HC<br>fused to<br>HHHKKKRRRO<br>OO) |
| 470 | QVQLVQSGAEVKKPGSSVKVSCKSSGGTSNNYAISWVRQAPGQGLDWMG<br>GISPIFGSTAYAQKFQGRVTISADIFSNTAYMELNSLTSEDTAVYFCARHGN<br>YYYYSGMDVWGQGTTVTVSSSVFPLAPSSKSTSGGTAALGCLVKDYFPEP<br>VTVSWNSGALTSGVHTFPAVLQSSGLYSLSSVVTVPSSSLGTQTYICNVNH<br>KPSNTKVDKRVEPKSCTCPPCPAPELLGGPSVFLFPPKPKDTLMISRTPEVTC<br>VVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTV<br>DKSRWQQGNVFSCSVMHEALHNHYTQKSLSLSPGKHHQAKKRCOOQH | HA15-hlgG-12X-<br>2<br>(HA15-IgG HC<br>fused to<br>HHQAKKRCOO<br>QH) |

-continued

SEQUENCE LISTING

| SEQ ID NO | Sequence | Description |
|---|---|---|
| 471 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGKHRKQQRKHHRKK | HA15-hIgG-12X-3 (HA15-IgG HC fused to HRKOORKHHRKK) |
| 472 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGKKRAHOKOQRKSH | HA15-hIgG-12X-4 (HA15-IgG HC fused to KRAHOKCORKSH) |
| 473 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGKKKRROOHHHRRR | HA15-hIgG-12X-5 (HA15-IgG HC fused to KKRROOHHHRRR) |
| 474 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGKOOORRRKKKHHH | HA15-hIgG-12X-6 (HA15-IgG HC fused to OOORRRKKKHHH) |
| 475 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGKKKAHHGKKAHHV | HA15-hIgG-12X-7 HA15 IgG HC fused to KKAHHGKKAHHV |
| 476 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGKKKARRGKKARRV | HA15-hlgG-12X-8 (HA15-IgG HC fused to KKARRGKKARRV) |
| 477 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSASVFPLAPSSKSTSGGTAALGCLVKDYFPE PVTVSWNSGALTSGVHTFPAVLQSSGLYSLSSVVTVPSSSLGTQTYICNVN HKPSNTKVDKRVEPKSCTCPPCPAPELLGGPSVFLFPPKPKDTLMISRTPEV TCVVVDVSHEDPEVKFNWYVDGVEVHNAKTKPREEQYNSTYRVVSVLTV LHQDWLNGKEYKCKVSNKALPAPIEKTISKAKGQPREPQVYTLPPSRDELT KNQVSLTCLVKGFYPSDIAVEWESNGQPENNYKTTPPVLDSDGSFFLYSKL TVDKSRWQQGNVFSCSVMHEALHNHYTQKSLSLSPGKKHKROHKROHKR OHKROHKROHKROHKROHK | HA15-hIgG-30X-1 (HA15-IgG HC fused to HKROHKROHKROHKROHKROHKROHKROHK) |

-continued

SEQUENCE LISTING

| SEQ ID NO | Sequence | Description |
|---|---|---|
| 478 | QVQLVQSGAEVKKPGSSVKVSCKSSGGTSNNYAISWVRQAPGQGLDWMG<br>GISPIFGSTAYAQKFQGRVTISADIFSNTAYMELNSLTSEDTAVYFCARHGN<br>YYYYSGMDVWGQGTTVTVSSSVFPLAPSSKSTSGGTAALGCLVKDYFPEP<br>VTVSWNSGALTSGVHTFPAVLQSSGLYSLSSVVTVPSSSLGTQTYICNVNH<br>KPSNTKVDKRVEPKSCTCPPCPAPELLGGPSVFLFPPKPKDTLMISRTPEVTC<br>VVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTV<br>DKSRWQQGNVFSCSVMHEALHNHYTQKSLSLSPGKKOHRSOKRHTORHK<br>AHORKCKROKORKHOS | HA15-hIgG-30X-<br>2<br>(HA15-IgG HC<br>fused to<br>KOHRSOKRHTO<br>RHKAHORKCK<br>ROKORKHOS) |
| 479 | QVQLVQSGAEVKKPGSSVKVSCKSSGGTSNNYAISWVRQAPGQGLDWMG<br>GISPIFGSTAYAQKFQGRVTISADIFSNTAYMELNSLTSEDTAVYFCARHGN<br>YYYYSGMDVWGQGTTVTVSSSVFPLAPSSKSTSGGTAALGCLVKDYFPEP<br>VTVSWNSGALTSGVHTFPAVLQSSGLYSLSSVVTVPSSSLGTQTYICNVNH<br>KPSNTKVDKRVEPKSCTCPPCPAPELLGGPSVFLFPPKPKDTLMISRTPEVTC<br>VVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTV<br>DKSRWQQGNVFSCSVMHEALHNHYTQKSLSLSPGKKKROSRRHOTOOHH<br>AROKHCKHROTRHKKS | HA15-hIgG-30X-<br>3<br>(HA15-IgG HC<br>fused to<br>KKROSRRHOTO<br>OHHAROKHCK<br>HROTRHKKS) |
| 480 | QVQLVQSGAEVKKPGSSVKVSCKSSGGTSNNYAISWVRQAPGQGLDWMG<br>GISPIFGSTAYAQKFQGRVTISADIFSNTAYMELNSLTSEDTAVYFCARHGN<br>YYYYSGMDVWGQGTTVTVSSSVFPLAPSSKSTSGGTAALGCLVKDYFPEPV<br>TVSWNSGALTSGVHTFPAVLQSSGLYSLSSVVTVPSSSLGTQTYICNVNHK<br>PSNTKVDKRVEPKSCTCPPCPAPELLGGPSVFLFPPKPKDTLMISRTPEVTCV<br>VVDVSHEDPEVKFNWYVDGVEVHNAKTKPREEQYNSTYRVVSVLTVLHQ<br>DWLNGKEYKCKVSNKALPAPIEKTISKAKGQPREPQVYTLPPSRDELTKNQ<br>VSLTCLVKGFYPSDIAVEWESNGQPENNYKTTPPVLDSDGSFFLYSKLTVD<br>KSRWQQGNVFSCSVMHEALHNHYTQKSLSLSPGKHRKQOHRSOOKTRRR<br>AHROCHHHSRHOTHR | HA15-hIgG-30X-<br>4<br>(HA15-IgG HC<br>fused to<br>HRKQOHRSOO<br>KTRRRAHROCH<br>HHSRHOTHR) |
| 481 | QVQLVQSGAEVKKPGSSVKVSCKSSGGTSNNYAISWVRQAPGQGLDWMG<br>GISPIFGSTAYAQKFQGRVTISADIFSNTAYMELNSLTSEDTAVYFCARHGN<br>YYYYSGMDVWGQGTTVTVSSSVFPLAPSSKSTSGGTAALGCLVKDYFPEP<br>VTVSWNSGALTSGVHTFPAVLQSSGLYSLSSVVTVPSSSLGTQTYICNVNH<br>KPSNTKVDKRVEPKSCTCPPCPAPELLGGPSVFLFPPKPKDTLMISRTPEVTC<br>VVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTV<br>DKSRWQQGNVFSCSVMHEALHNHYTQKSLSLSPGKGRHKAKNHIRRPKSR<br>WKKWHKYRKVHRHKVHKGRR | HA15-hIgG-35X-<br>1<br>(HA15-IgG HC<br>fused to<br>GRHKAKNHIRR<br>PKSRWKKWHK<br>YRKVHRHKVH<br>KGRR) |
| 482 | QVQLVQSGAEVKKPGSSVKVSCKSSGGTSNNYAISWVRQAPGQGLDWMG<br>GISPIFGSTAYAQKFQGRVTISADIFSNTAYMELNSLTSEDTAVYFCARHGN<br>YYYYSGMDVWGQGTTVTVSSSVFPLAPSSKSTSGGTAALGCLVKDYFPEP<br>VTVSWNSGALTSGVHTFPAVLQSSGLYSLSSVVTVPSSSLGTQTYICNVNH<br>KPSNTKVDKRVEPKSCTCPPCPAPELLGGPSVFLFPPKPKDTLMISRTPEVTC<br>VVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTV<br>DKSRWQQGNVFSCSVMHEALHNHYTQKSLSLSPGKWRKVHHYKKQHKN<br>RAHGKLKLRAKIHQRSRMHGKQKHYHR | HA15-hIgG-40X-<br>2<br>(HA15-IgG HC<br>fused to<br>WRKVHHYKKQ<br>HKNRAHGKLK<br>LRAKIHQRSRM<br>HGKQKHYHR) |
| 483 | QVQLVQSGAEVKKPGSSVKVSCKSSGGTSNNYAISWVRQAPGQGLDWMG<br>GISPIFGSTAYAQKFQGRVTISADIFSNTAYMELNSLTSEDTAVYFCARHGN<br>YYYYSGMDVWGQGTTVTVSSSVFPLAPSSKSTSGGTAALGCLVKDYFPEP<br>VTVSWNSGALTSGVHTFPAVLQSSGLYSLSSVVTVPSSSLGTQTYICNVNH<br>KPSNTKVDKRVEPKSCTCPPCPAPELLGGPSVFLFPPKPKDTLMISRTPEVTC<br>VVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKN<br>QVSLTCLVKGFYPSDIAVEWESNGQPENNYKTTPPVLDSDGSFFLYSKLTV<br>DKSRWQQGNVFSCSVMHEALHNHYTQKSLSLSPGKAHHKCRRGHKQKIL<br>HRRPHKFHRWKRVHKGRHGKKHRRHKHR | HA15-hIgG-42X-<br>1<br>(HA15-IgG HC<br>fused to<br>AHHKCRRGHK<br>QKILHRRPHKF<br>HRWKRVHKGR<br>HGKKHRRHKH<br>R) |
| 484 | QVQLVQSGAEVKKPGSSVKVSCKSSGGTSNNYAISWVRQAPGQGLDWMG<br>GISPIFGSTAYAQKFQGRVTISADIFSNTAYMELNSLTSEDTAVYFCARHGN<br>YYYYSGMDVWGQGTTVTVSSSVFPLAPSSKSTSGGTAALGCLVKDYFPEP<br>VTVSWNSGALTSGVHTFPAVLQSSGLYSLSSVVTVPSSSLGTQTYICNVNH<br>KPSNTKVDKRVEPKSCTCPPCPAPELLGGPSVFLFPPKPKDTLMISRTPEVTC<br>VVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKN | HA15-hIgG-45X-<br>1<br>(HA15-IgG HC<br>fused to<br>QHRGKAKYHR<br>THHVKKQRHG<br>RKNHKVHRHA |

-continued

SEQUENCE LISTING

| SEQ ID NO | Sequence | Description |
|---|---|---|
| | QVSLTCLVKGFYPSDIAVEWESNGQPENNYKTTPPVLDSDGSFFLYSKLTV DKSRWQQGNVFSCSVMHEALHNHYTQKSLSLSPGKQHRGKAKYHRTHHV KKQRHGRKNHKVHRHARKFHKIRRLKCHKKH | RKFHKIRRLKC HKKH) |
| 485 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGKHNKRFKKGRHVRHS RHKSHRRTHKYHHWRHYRKVHRCKKAHKSHHRVHHK | HA15-hIgG-50X-1 HA15-IgG HC fused to HNKRFKKGRH VRHSRHKSHRR THKYHHWRHY RKVHRCKKAH KSHHRVHHK) |
| 486 | QVQLVQSGAEVKKPGSSVKVSCKSSGGTSNNYAISWVRQAPGQGLDWMG GISPIFGSTAYAQKFQGRVTISADIFSNTAYMELNSLTSEDTAVYFCARHGN YYYYSGMDVWGQGTTVTVSSSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCTCPPCPAPELLGGPSVFLFPPKPKDTLMISRTPEVTC VVVDVSHEDPEVKFNWYVDGVEVHNAKTKPREEQYNSTYRVVSVLTVLH QDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTV DKSRWQQGNVFSCSVMHEALHNHYTQKSLSLSPGKAHGRPHOFKROCKA HOVKHILKRTOSHOYKOVHORNKOAOKMRKIRGGHK | HA15-hIgG-50X-2 (HA15-IgG HC fused to AHGRPHOFKRO CKAHOVKHILK RTOSHOYKOVH QRNKOAOKMR KIRGGHK) |
| 487 | QVQLLETGGGLVKPGQSLKLSCAASGFTFTSYAMHWVRQPPGKGLEWVA VVSYDGNYKYYADSVQGRFTISRDNSKNTLYLQMNSLRAEDTAVYYCAK DSRLRSLLYFEWLSQGYFNPWGQGTTLTVSS | HA16-IgG $V_H$ |
| 488 | SYAMH | HA16-IgG HC-CDR1 |
| 489 | VVSYDGNYKYYADSVQG | HA16-IgG HC-CDR2 |
| 490 | DSRLRSLLYFEWLSQGYFNP | HA16-IgG HC-CDR3 |
| 491 | DIQMTQSPSSLSASVGDRVTITCRSSQSITFDYKNYLAWYQQKPGKAPKLLI YWGSYLESGVPSRFSGSGSGTDFTLTISSLQPEDFATYYCQQHYRTPPSFGQ GTKVEIK | HA16-IgG $V_L$ |
| 492 | WGSYLES | HA16-IgG LC-CDR1 |
| 493 | QQHYRTPPS | HA16-IgG LC-CDR2 |
| 494 | QSITFDYKNYLA | HA16-IgG LC-CDR3 |
| 495 | LSGESHGRILKTDLNSGNCVVQCQTEKGGLNSTLPFHNISKYAFGDCPKYIG VKSLKLAIGLRNVPARSSRGLFGAIAGFIEGGWPGLVAGWYGFQHSNDQG VGMAADRDSTQKAVDKITSKVNNIVDKMNKQYEIIDHEFSEVETRLNMIN NKIDDQIQDVWAYNAELLVLLENQKTLDEHDANVNNLYNKVKRALGSNA MEDGKGCFELYHKCDDQCMETIRNGTYNRRKYMEESRLGRQKIEGVKLES EGTYKIL | H7 (H9N2A/ Egypt/ZU65/ 2016) ARM59253 |
| 496 | STIEEQAKTFLDKFNHEAEDLFYQSSLASWNYNTNITEENVQNMNNAGDK WSAFLKEQSTLAQMYPLQEIQNLTVKLQLQALQQNGSSVLSEDKSKRLNTI LNTMSTIYSTGKVCNPDNPQECLLLEPGLNEIMANSLDYNERLWAWESWR SEVGKQLRPLYEEYVVLKNEMARANHYEDYGDYWRGDYEVNGVDGYDY SRGQLIEDVEHTFEEIKPLYEHLHAYVRAKLMNAYPSYISPIGCLPAHLLGD MWGRFWTNLYSLTVPFGQKPNIDVTDAMVDQAWDAQRIFKEAEKFFVSV GLPNMTQGFWENSMLTDPGNVQKAVCHPTAWDLGKGDFRILMCTKVTM DDFLTAHHEMGHIQYDMAYAAQPFLLRNGANEGFHEAVGEIMSLSAATPK HLKSIGLLSPDFQEDNETEINFLLKQALTIVGTLPFTYMLEKWRWMVFKGEI PKDQWMKKWWEMKREIVGVVEPVPHDETYCDPASLFHVSNDYSFIRYYT RTLYQFQFQEALCQAAKHEGPLHKCDISNSTEAGQKLFNMLRLGKSEPWT LALENVVGAKNMNVRPLLNYFEPLFTWLKDQNKNSFVGWSTDWSPYADQ | ACE740 aa 19-740 of full-length human ACE2 protein |

-continued

| SEQUENCE LISTING | |
|---|---|
| SEQ ID NO Sequence | Description |
| SIKVRISLKSALGDKAYEWNDNEMYLFRSSVAYAMRQYFLKVKNQMILFG EEDVRVANLKPRISFNFFVTAPKNVSDIIPRTEVEKAIRMSRSRINDAFRLND NSLEFLGIQPTLGPPNQPPVS | |

SEQUENCE LISTING

Sequence total quantity: 496
SEQ ID NO: 1 moltype = AA length = 8
FEATURE Location/Qualifiers
source 1..8
mol_type = protein
organism = synthetic construct
SEQUENCE: 1
GFTFSTYA 8

SEQ ID NO: 2 moltype = AA length = 8
FEATURE Location/Qualifiers
source 1..8
mol_type = protein
organism = synthetic construct
SEQUENCE: 2
ISYDANYK 8

SEQ ID NO: 3 moltype = AA length = 22
FEATURE Location/Qualifiers
source 1..22
mol_type = protein
organism = synthetic construct
SEQUENCE: 3
AKDSQLRSLL YFEWLSQGYF DY 22

SEQ ID NO: 4 moltype = AA length = 10
FEATURE Location/Qualifiers
source 1..10
mol_type = protein
organism = synthetic construct
SEQUENCE: 4
QSVTFNYKNY 10

SEQ ID NO: 5 moltype = length =
SEQUENCE: 5
000

SEQ ID NO: 6 moltype = AA length = 9
FEATURE Location/Qualifiers
source 1..9
mol_type = protein
organism = synthetic construct
SEQUENCE: 6
QQHYRTPPT 9

SEQ ID NO: 7 moltype = AA length = 5
FEATURE Location/Qualifiers
source 1..5
mol_type = protein
organism = synthetic construct
SEQUENCE: 7
KYAIN 5

SEQ ID NO: 8 moltype = AA length = 17
FEATURE Location/Qualifiers
source 1..17
mol_type = protein
organism = synthetic construct
SEQUENCE: 8
GIIPFFGTTN YAQKFQG 17

SEQ ID NO: 9 moltype = AA length = 23
FEATURE Location/Qualifiers

```
source                  1..23
                        mol_type = protein
                        organism = synthetic construct
SEQUENCE: 9
PSITESHYCL DCAAKDYYYG LDV                                       23

SEQ ID NO: 10           moltype = AA  length = 8
FEATURE                 Location/Qualifiers
source                  1..8
                        mol_type = protein
                        organism = synthetic construct
SEQUENCE: 10
GFTVSSNY                                                        8

SEQ ID NO: 11           moltype = AA  length = 7
FEATURE                 Location/Qualifiers
source                  1..7
                        mol_type = protein
                        organism = synthetic construct
SEQUENCE: 11
TYSGGNT                                                         7

SEQ ID NO: 12           moltype = AA  length = 11
FEATURE                 Location/Qualifiers
source                  1..11
                        mol_type = protein
                        organism = synthetic construct
SEQUENCE: 12
ATVPSFHGMD V                                                    11

SEQ ID NO: 13           moltype = AA  length = 6
FEATURE                 Location/Qualifiers
source                  1..6
                        mol_type = protein
                        organism = synthetic construct
SEQUENCE: 13
QSISSY                                                          6

SEQ ID NO: 14           moltype =   length =
SEQUENCE: 14
000

SEQ ID NO: 15           moltype = AA  length = 10
FEATURE                 Location/Qualifiers
source                  1..10
                        mol_type = protein
                        organism = synthetic construct
SEQUENCE: 15
QQSYSTPPIT                                                      10

SEQ ID NO: 16           moltype = AA  length = 8
FEATURE                 Location/Qualifiers
source                  1..8
                        mol_type = protein
                        organism = synthetic construct
SEQUENCE: 16
GSTFGDFA                                                        8

SEQ ID NO: 17           moltype = AA  length = 8
FEATURE                 Location/Qualifiers
source                  1..8
                        mol_type = protein
                        organism = synthetic construct
SEQUENCE: 17
TSAGGDRT                                                        8

SEQ ID NO: 18           moltype = AA  length = 16
FEATURE                 Location/Qualifiers
source                  1..16
                        mol_type = protein
                        organism = synthetic construct
SEQUENCE: 18
ARLDSSGFHY GRPGRN                                               16

SEQ ID NO: 19           moltype = AA  length = 6
FEATURE                 Location/Qualifiers
source                  1..6
                        mol_type = protein
                        organism = synthetic construct
```

```
SEQUENCE: 19
QDISYY                                                                  6

SEQ ID NO: 20           moltype =   length =
SEQUENCE: 20
000

SEQ ID NO: 21           moltype = AA  length = 9
FEATURE                 Location/Qualifiers
source                  1..9
                        mol_type = protein
                        organism = synthetic construct
SEQUENCE: 21
QQYKSLPYT                                                               9

SEQ ID NO: 22           moltype = AA  length = 8
FEATURE                 Location/Qualifiers
source                  1..8
                        mol_type = protein
                        organism = synthetic construct
SEQUENCE: 22
GFTFSGFS                                                                8

SEQ ID NO: 23           moltype = AA  length = 8
FEATURE                 Location/Qualifiers
source                  1..8
                        mol_type = protein
                        organism = synthetic construct
SEQUENCE: 23
ISTSGNYM                                                                8

SEQ ID NO: 24           moltype = AA  length = 13
FEATURE                 Location/Qualifiers
source                  1..13
                        mol_type = protein
                        organism = synthetic construct
SEQUENCE: 24
ARGGGYNWNL FDY                                                          13

SEQ ID NO: 25           moltype = AA  length = 7
FEATURE                 Location/Qualifiers
source                  1..7
                        mol_type = protein
                        organism = synthetic construct
SEQUENCE: 25
QSLNSNY                                                                 7

SEQ ID NO: 26           moltype =   length =
SEQUENCE: 26
000

SEQ ID NO: 27           moltype = AA  length = 9
FEATURE                 Location/Qualifiers
source                  1..9
                        mol_type = protein
                        organism = synthetic construct
SEQUENCE: 27
QQYGNSPLT                                                               9

SEQ ID NO: 28           moltype = AA  length = 10
FEATURE                 Location/Qualifiers
source                  1..10
                        mol_type = protein
                        organism = synthetic construct
SEQUENCE: 28
GVSVTSDIYY                                                              10

SEQ ID NO: 29           moltype = AA  length = 7
FEATURE                 Location/Qualifiers
source                  1..7
                        mol_type = protein
                        organism = synthetic construct
SEQUENCE: 29
IFYNGDT                                                                 7

SEQ ID NO: 30           moltype = AA  length = 18
FEATURE                 Location/Qualifiers
source                  1..18
                        mol_type = protein
```

```
                       organism = synthetic construct
SEQUENCE: 30
ARGTEDLGYC SSGSCPNH                                            18

SEQ ID NO: 31          moltype = AA  length = 6
FEATURE                Location/Qualifiers
source                 1..6
                       mol_type = protein
                       organism = synthetic construct
SEQUENCE: 31
QNIRSF                                                         6

SEQ ID NO: 32          moltype =   length =
SEQUENCE: 32
000

SEQ ID NO: 33          moltype = AA  length = 9
FEATURE                Location/Qualifiers
source                 1..9
                       mol_type = protein
                       organism = synthetic construct
SEQUENCE: 33
QQSYNTPPT                                                      9

SEQ ID NO: 34          moltype = AA  length = 8
FEATURE                Location/Qualifiers
source                 1..8
                       mol_type = protein
                       organism = synthetic construct
SEQUENCE: 34
GFTFSTYW                                                       8

SEQ ID NO: 35          moltype = AA  length = 8
FEATURE                Location/Qualifiers
source                 1..8
                       mol_type = protein
                       organism = synthetic construct
SEQUENCE: 35
INQDGGEK                                                       8

SEQ ID NO: 36          moltype = AA  length = 22
FEATURE                Location/Qualifiers
source                 1..22
                       mol_type = protein
                       organism = synthetic construct
SEQUENCE: 36
ARGFLERLLL GRQGAYYYGM DV                                       22

SEQ ID NO: 37          moltype = AA  length = 6
FEATURE                Location/Qualifiers
source                 1..6
                       mol_type = protein
                       organism = synthetic construct
SEQUENCE: 37
QIISSS                                                         6

SEQ ID NO: 38          moltype =   length =
SEQUENCE: 38
000

SEQ ID NO: 39          moltype = AA  length = 11
FEATURE                Location/Qualifiers
source                 1..11
                       mol_type = protein
                       organism = synthetic construct
SEQUENCE: 39
QQSYSTPPEL T                                                   11

SEQ ID NO: 40          moltype = AA  length = 8
FEATURE                Location/Qualifiers
source                 1..8
                       mol_type = protein
                       organism = synthetic construct
SEQUENCE: 40
RFTSSSYW                                                       8

SEQ ID NO: 41          moltype = AA  length = 8
FEATURE                Location/Qualifiers
source                 1..8
```

```
                         mol_type = protein
                         organism = synthetic construct
SEQUENCE: 41
IKQDGSEK                                                          8

SEQ ID NO: 42            moltype = AA  length = 22
FEATURE                  Location/Qualifiers
source                   1..22
                         mol_type = protein
                         organism = synthetic construct
SEQUENCE: 42
ARGFLERLLL GRQGAYYYGM DV                                          22

SEQ ID NO: 43            moltype = AA  length = 6
FEATURE                  Location/Qualifiers
source                   1..6
                         mol_type = protein
                         organism = synthetic construct
SEQUENCE: 43
QSISSS                                                            6

SEQ ID NO: 44            moltype =   length =
SEQUENCE: 44
000

SEQ ID NO: 45            moltype = AA  length = 11
FEATURE                  Location/Qualifiers
source                   1..11
                         mol_type = protein
                         organism = synthetic construct
SEQUENCE: 45
QQSYTMPPEL T                                                      11

SEQ ID NO: 46            moltype = AA  length = 10
FEATURE                  Location/Qualifiers
source                   1..10
                         mol_type = protein
                         organism = synthetic construct
SEQUENCE: 46
GGSINSSHSF                                                        10

SEQ ID NO: 47            moltype = AA  length = 7
FEATURE                  Location/Qualifiers
source                   1..7
                         mol_type = protein
                         organism = synthetic construct
SEQUENCE: 47
IYSTGNS                                                           7

SEQ ID NO: 48            moltype = AA  length = 16
FEATURE                  Location/Qualifiers
source                   1..16
                         mol_type = protein
                         organism = synthetic construct
SEQUENCE: 48
ARESLWNPDY YYYMDV                                                 16

SEQ ID NO: 49            moltype = AA  length = 6
FEATURE                  Location/Qualifiers
source                   1..6
                         mol_type = protein
                         organism = synthetic construct
SEQUENCE: 49
QSFSSH                                                            6

SEQ ID NO: 50            moltype =   length =
SEQUENCE: 50
000

SEQ ID NO: 51            moltype = AA  length = 9
FEATURE                  Location/Qualifiers
source                   1..9
                         mol_type = protein
                         organism = synthetic construct
SEQUENCE: 51
QQSYSVPYT                                                         9

SEQ ID NO: 52            moltype = AA  length = 8
FEATURE                  Location/Qualifiers
```

```
source                 1..8
                       mol_type = protein
                       organism = synthetic construct
SEQUENCE: 52
GFTFSTYN                                                     8

SEQ ID NO: 53          moltype = AA  length = 8
FEATURE                Location/Qualifiers
source                 1..8
                       mol_type = protein
                       organism = synthetic construct
SEQUENCE: 53
ISTSSNTI                                                     8

SEQ ID NO: 54          moltype = AA  length = 23
FEATURE                Location/Qualifiers
source                 1..23
                       mol_type = protein
                       organism = synthetic construct
SEQUENCE: 54
ARDRGCSSTN CYVVGYYFYG MDV                                    23

SEQ ID NO: 55          moltype = AA  length = 6
FEATURE                Location/Qualifiers
source                 1..6
                       mol_type = protein
                       organism = synthetic construct
SEQUENCE: 55
QGISSY                                                       6

SEQ ID NO: 56          moltype =   length =
SEQUENCE: 56
000

SEQ ID NO: 57          moltype = AA  length = 9
FEATURE                Location/Qualifiers
source                 1..9
                       mol_type = protein
                       organism = synthetic construct
SEQUENCE: 57
QQADSFPLT                                                    9

SEQ ID NO: 58          moltype = AA  length = 8
FEATURE                Location/Qualifiers
source                 1..8
                       mol_type = protein
                       organism = synthetic construct
SEQUENCE: 58
GVTFISHA                                                     8

SEQ ID NO: 59          moltype = AA  length = 8
FEATURE                Location/Qualifiers
source                 1..8
                       mol_type = protein
                       organism = synthetic construct
SEQUENCE: 59
IIAIFGTT                                                     8

SEQ ID NO: 60          moltype = AA  length = 13
FEATURE                Location/Qualifiers
source                 1..13
                       mol_type = protein
                       organism = synthetic construct
SEQUENCE: 60
ARGETYYEGN FDF                                               13

SEQ ID NO: 61          moltype = AA  length = 6
FEATURE                Location/Qualifiers
source                 1..6
                       mol_type = protein
                       organism = synthetic construct
SEQUENCE: 61
QSISSY                                                       6

SEQ ID NO: 62          moltype =   length =
SEQUENCE: 62
000

SEQ ID NO: 63          moltype = AA  length = 10
```

```
FEATURE                 Location/Qualifiers
source                  1..10
                        mol_type = protein
                        organism = synthetic construct
SEQUENCE: 63
QQSYSTPPIT                                                      10

SEQ ID NO: 64           moltype = AA  length = 5
FEATURE                 Location/Qualifiers
source                  1..5
                        mol_type = protein
                        organism = synthetic construct
SEQUENCE: 64
SYAMH                                                           5

SEQ ID NO: 65           moltype = AA  length = 17
FEATURE                 Location/Qualifiers
source                  1..17
                        mol_type = protein
                        organism = synthetic construct
SEQUENCE: 65
VVSYDGNYKY YADSVQG                                              17

SEQ ID NO: 66           moltype = AA  length = 20
FEATURE                 Location/Qualifiers
source                  1..20
                        mol_type = protein
                        organism = synthetic construct
SEQUENCE: 66
DSRLRSLLYF EWLSQGYFNP                                           20

SEQ ID NO: 67           moltype = AA  length = 7
FEATURE                 Location/Qualifiers
source                  1..7
                        mol_type = protein
                        organism = synthetic construct
SEQUENCE: 67
WGSYLES                                                         7

SEQ ID NO: 68           moltype = AA  length = 9
FEATURE                 Location/Qualifiers
source                  1..9
                        mol_type = protein
                        organism = synthetic construct
SEQUENCE: 68
QQHYRTPPS                                                       9

SEQ ID NO: 69           moltype = AA  length = 12
FEATURE                 Location/Qualifiers
source                  1..12
                        mol_type = protein
                        organism = synthetic construct
SEQUENCE: 69
QSITFDYKNY LA                                                   12

SEQ ID NO: 70           moltype = AA  length = 7
FEATURE                 Location/Qualifiers
source                  1..7
                        mol_type = protein
                        organism = synthetic construct
SEQUENCE: 70
SYNAVWN                                                         7

SEQ ID NO: 71           moltype = AA  length = 18
FEATURE                 Location/Qualifiers
source                  1..18
                        mol_type = protein
                        organism = synthetic construct
SEQUENCE: 71
RTYYRSGWYN DYAESVKS                                             18

SEQ ID NO: 72           moltype = AA  length = 16
FEATURE                 Location/Qualifiers
source                  1..16
                        mol_type = protein
                        organism = synthetic construct
SEQUENCE: 72
SGHITVFGVN VDAFDM                                               16
```

```
SEQ ID NO: 73          moltype = AA  length = 11
FEATURE                Location/Qualifiers
source                 1..11
                       mol_type = protein
                       organism = synthetic construct
SEQUENCE: 73
RTSQSLSSYT H                                                  11

SEQ ID NO: 74          moltype = AA  length = 7
FEATURE                Location/Qualifiers
source                 1..7
                       mol_type = protein
                       organism = synthetic construct
SEQUENCE: 74
AASSRGS                                                       7

SEQ ID NO: 75          moltype = AA  length = 5
FEATURE                Location/Qualifiers
source                 1..5
                       mol_type = protein
                       organism = synthetic construct
SEQUENCE: 75
QQSRT                                                         5

SEQ ID NO: 76          moltype = AA  length = 129
FEATURE                Location/Qualifiers
source                 1..129
                       mol_type = protein
                       organism = synthetic construct
SEQUENCE: 76
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSS                                                     129

SEQ ID NO: 77          moltype = AA  length = 111
FEATURE                Location/Qualifiers
source                 1..111
                       mol_type = protein
                       organism = synthetic construct
SEQUENCE: 77
DIVMTQSPDS LAVSLGERAT INCKSSQSVT FNYKNYLAWY QQKPGQPPKL LIYWASTRES  60
GVPDRFSGSG SGTDFTLTIS SLQAEDVAVY YCQQHYRTPP TFGQGTKVEI K           111

SEQ ID NO: 78          moltype = AA  length = 131
FEATURE                Location/Qualifiers
source                 1..131
                       mol_type = protein
                       organism = synthetic construct
SEQUENCE: 78
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS S                                                  131

SEQ ID NO: 79          moltype = AA  length = 111
FEATURE                Location/Qualifiers
source                 1..111
                       mol_type = protein
                       organism = synthetic construct
SEQUENCE: 79
QSVLTQPPSA SGTPGQSVTI SCSGSRSNIG GNTVNWYQHL PGMAPKLLIY SSNQRSSGVP  60
DRFSGSKSGT SASLAISGLQ SEDDADYYCA SWDDSLNGVV FGGGTKLTVL G           111

SEQ ID NO: 80          moltype = AA  length = 117
FEATURE                Location/Qualifiers
source                 1..117
                       mol_type = protein
                       organism = synthetic construct
SEQUENCE: 80
EVQLVESGGD LVQPGGSLRL SCAASGFTVS SNYMSWVRQV PGKGLDWVSV TYSGGNTYYA  60
DSVKGRFTIS RHNSKNTLYL QMNSLRIEDT AVYYCATVPS FHGMDVWGQG TTVTVSS     117

SEQ ID NO: 81          moltype = AA  length = 108
FEATURE                Location/Qualifiers
source                 1..108
                       mol_type = protein
                       organism = synthetic construct
SEQUENCE: 81
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPPITFG QGTRLEIK              108
```

```
SEQ ID NO: 82          moltype = AA  length = 123
FEATURE                Location/Qualifiers
source                 1..123
                       mol_type = protein
                       organism = synthetic construct
SEQUENCE: 82
EVQLLESGGG LVQPGGSLRI SCAASGSTFG DFAMSWVRQS PGRGLEWVSV TSAGGDRTYY  60
ADSVKGRFTI SRDNSKNTLY LQMNSLRGED TAMYYCARLD SSGFHYGRPG RNWGQGTLVT  120
VSS                                                               123

SEQ ID NO: 83          moltype = AA  length = 107
FEATURE                Location/Qualifiers
source                 1..107
                       mol_type = protein
                       organism = synthetic construct
SEQUENCE: 83
DIQMTHSPPS LSASVGDRIT ITCQASQDIS YYLIWYQQKP GKAPKPLIYD ASNLEAGVPS  60
RFSASGSGTD FTLTISSLQP EDLATYYCQQ YKSLPYTFGQ GTKLEIK               107

SEQ ID NO: 84          moltype = AA  length = 120
FEATURE                Location/Qualifiers
source                 1..120
                       mol_type = protein
                       organism = synthetic construct
SEQUENCE: 84
EVQLVESGGG LVKPGGSLRL SCAASGFTFS GFSMNWVRQV PGKGLEWVSS ISTSGNYMYY  60
ADSVKGRFTI SRDNAKKSFS LQMNSLRAED SAIYYCARGG GYNWNLFDYW GQGSLVTVSS  120

SEQ ID NO: 85          moltype = AA  length = 108
FEATURE                Location/Qualifiers
source                 1..108
                       mol_type = protein
                       organism = synthetic construct
SEQUENCE: 85
EIVLTQSPGT LSLSPGERAT LSCRASQSLN SNYLAWYQQK PGQAPRLLIY GASSRATGIP  60
DRFSGSGSGT DFTLTITRLE SEDFAVYYCQ QYGNSPLTFG GGTKVEIK              108

SEQ ID NO: 86          moltype = AA  length = 126
FEATURE                Location/Qualifiers
source                 1..126
                       mol_type = protein
                       organism = synthetic construct
SEQUENCE: 86
QVQLQESGPG LVKPSETLSL TCSVSGVSVT SDIYYWTWIR QPPGKGLEWI GYIFYNGDTN  60
YNPSLKSRVT MSIDTSKNEF SLRLTSVTAA DTAVYFCARG TEDLGYCSSG SCPNHWGQGT  120
LVTVSS                                                            126

SEQ ID NO: 87          moltype = AA  length = 107
FEATURE                Location/Qualifiers
source                 1..107
                       mol_type = protein
                       organism = synthetic construct
SEQUENCE: 87
DIQMTQSPSS LSASIGDRVT ITCRPSQNIR SFLNWFQHKP GKAPKLLIYA ASNLQSGVPS  60
RFSGSGSGTE FTLTIRSLQP EDFATYYCQQ SYNTPPTFGQ GTKVEIK               107

SEQ ID NO: 88          moltype = AA  length = 129
FEATURE                Location/Qualifiers
source                 1..129
                       mol_type = protein
                       organism = synthetic construct
SEQUENCE: 88
EVQLVESGGG LVQPGGSLRL SCAASGFTFS TYWMTWVRQA PGKGLEWVAN INQDGGEKYF  60
VDSVKGRFTI SRDNAKNSLF LQMNTLRAED TAVYYCARGF LERLLLGRQG AYYYGMDVWG  120
QGTTVTVSS                                                         129

SEQ ID NO: 89          moltype = AA  length = 109
FEATURE                Location/Qualifiers
source                 1..109
                       mol_type = protein
                       organism = synthetic construct
SEQUENCE: 89
DIQMTQSPSS LSASVGDRVS MTCRASQIIS SSLNWYQQKP GKAPKLLIYA ASNLQSGVPS  60
RFSGSGSGTD FTLTISSLQP EDFATYYCQQ SYSTPPELTF GGGTKVEIK             109

SEQ ID NO: 90          moltype = AA  length = 129
FEATURE                Location/Qualifiers
source                 1..129
```

```
                        mol_type = protein
                        organism = synthetic construct
SEQUENCE: 90
EVQLVQSGGG LVQPGGSLRL SCEASRFTSS SYWITWVRQA PGKGLEWVAN IKQDGSEKYF  60
VDSVKGRFTI SRDNASNSLY LQMSSLRAED TAVYYCARGF LERLLLGRQG AYYYGMDVWG  120
QGTTVTVSS                                                          129

SEQ ID NO: 91           moltype = AA  length = 109
FEATURE                 Location/Qualifiers
source                  1..109
                        mol_type = protein
                        organism = synthetic construct
SEQUENCE: 91
DIQMTQSPSS LSASVGDRVT MTCRASQSIS SSLNWYQQKP GKAPKLLIYA ASNLQSGVPS  60
RFSGSGSGTD FTLTISSLQP EDFATYYCQQ SYTMPPELTF GGGTKVQIK             109

SEQ ID NO: 92           moltype = AA  length = 124
FEATURE                 Location/Qualifiers
source                  1..124
                        mol_type = protein
                        organism = synthetic construct
SEQUENCE: 92
QVQLVESGPG LVKPSQTLSL TCTVSGGSIN SSHSFWSWIR QPAGKGLEWI GRIYSTGNSN  60
YNPSLKSRVT ISLDTSKNQF SLKLSSVTAA DTAVYYCARE SLWNPDYYYY MDVWGKGTLV  120
TVSS                                                               124

SEQ ID NO: 93           moltype = AA  length = 107
FEATURE                 Location/Qualifiers
source                  1..107
                        mol_type = protein
                        organism = synthetic construct
SEQUENCE: 93
DIVMTQSPSS LSASVGDRVT ITCRASQSFS SHLNWYQQKP GRAPDLLIYA ASSLHSGVPS  60
RFSGSGSGTD FTLTISSLQP EDFAVYYCQQ SYSVPYTFGQ GTKLQIK                107

SEQ ID NO: 94           moltype = AA  length = 130
FEATURE                 Location/Qualifiers
source                  1..130
                        mol_type = protein
                        organism = synthetic construct
SEQUENCE: 94
EVQLVESGGG LVQPGGSLRL SCAASGFTFS TYNMNWVRQA PGKGLEWLSY ISTSSNTIYY  60
ADSVKGRFTI SRDNAKNSLF LQMNSLRDED TAVYYCARDR GCSSTNCYVV GYYFYGMDVW  120
GQGTTVTVSS                                                         130

SEQ ID NO: 95           moltype = AA  length = 107
FEATURE                 Location/Qualifiers
source                  1..107
                        mol_type = protein
                        organism = synthetic construct
SEQUENCE: 95
DIQMTQSPSS VSASVGDRVT ITCRASQGIS SYLAWYQLKP GRAPKLLIYG ATRLQSGVPS  60
RFSGSGSGTD FTLTISGLQP EDFATYHCQQ ADSFPLTFGQ GTRLEIK                107

SEQ ID NO: 96           moltype = AA  length = 120
FEATURE                 Location/Qualifiers
source                  1..120
                        mol_type = protein
                        organism = synthetic construct
SEQUENCE: 96
QVHLVQSGPE VKKPGSSVKV SCKASGVTFI SHAISWVRQA PGQGLEWVGG IIAIFGTTNY  60
AQKFQGRVTV TTDKSTNTVY MELSRLRSED TAIYYCARGE TYYEGNFDFW GQGTLVTVSS  120

SEQ ID NO: 97           moltype = AA  length = 108
FEATURE                 Location/Qualifiers
source                  1..108
                        mol_type = protein
                        organism = synthetic construct
SEQUENCE: 97
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPPITFG QGTRLEIK               108

SEQ ID NO: 98           moltype = AA  length = 129
FEATURE                 Location/Qualifiers
source                  1..129
                        mol_type = protein
                        organism = synthetic construct
SEQUENCE: 98
QVQLLETGGG LVKPGQSLKL SCAASGFTFT SYAMHWVRQP PGKGLEWVAV VSYDGNYKYY  60
```

```
ADSVQGRFTI SRDNSKNTLY LQMNSLRAED TAVYYCAKDS RLRSLLYFEW LSQGYFNPWG  120
QGTTLTVSS                                                         129

SEQ ID NO: 99          moltype = AA  length = 111
FEATURE                Location/Qualifiers
source                 1..111
                       mol_type = protein
                       organism = synthetic construct
SEQUENCE: 99
DIQMTQSPSS LSASVGDRVT ITCRSSQSIT FDYKNYLAWY QQKPGKAPKL LIYWGSYLES  60
GVPSRFSGSG SGTDFTLTIS SLQPEDFATY YCQQHYRTPP SFGQGTKVEI K          111

SEQ ID NO: 100         moltype = AA  length = 128
FEATURE                Location/Qualifiers
source                 1..128
                       mol_type = protein
                       organism = synthetic construct
SEQUENCE: 100
QVQLQQSGPG LVKPSQTLSL TCAISGDSVS SYNAVWNWIR QSPSRGLEWL GRTYYRSGWY  60
NDYAESVKSR ITINPDTSKN QFSLQLNSVT PEDTAVYYCA RSGHITVFGV NVDAFDMWGQ  120
GTMVTVSS                                                          128

SEQ ID NO: 101         moltype = AA  length = 103
FEATURE                Location/Qualifiers
source                 1..103
                       mol_type = protein
                       organism = synthetic construct
SEQUENCE: 101
DIQMTQSPSS LSASVGDRVT ITCRTSQSLS SYTHWYQQKP GKAPKLLIYA ASSRGSGVPS  60
RFSGSGSGTD FTLTISSLQP EDFATYYCQQ SRTFGQGTKV EIK                   103

SEQ ID NO: 102         moltype = AA  length = 150
FEATURE                Location/Qualifiers
source                 1..150
                       mol_type = protein
                       organism = synthetic construct
SEQUENCE: 102
PDSVIRTQQR QTTMESVLSW VFLVAILQGE VQLVESGGDL VKPGGSLRLS CVASGFTFSD  60
FDMSWVRQAP GKGLQWVAAI AYDGSSTYYT DAVKGRFTIS RDNARNTVYL QMDNSLRAED  120
TAVYYCASPT TVPTIDWFYY WGQGTLVTVS                                  150

SEQ ID NO: 103         moltype = AA  length = 114
FEATURE                Location/Qualifiers
source                 1..114
                       mol_type = protein
                       organism = synthetic construct
SEQUENCE: 103
MLWIPGSTGE AVMTQTPLSL AVTPGELATI SCRANQSLLR SDGKSYLWYL QKPGPQTPRP  60
LIYEASKRFS GVSGRFSGSG TDFTKITRVE ADEVGYYCQQ GLHFPPFQGT KVEI        114

SEQ ID NO: 104         moltype = AA  length = 8
FEATURE                Location/Qualifiers
source                 1..8
                       mol_type = protein
                       organism = synthetic construct
SEQUENCE: 104
GDSIGGSY                                                          8

SEQ ID NO: 105         moltype = AA  length = 7
FEATURE                Location/Qualifiers
source                 1..7
                       mol_type = protein
                       organism = synthetic construct
SEQUENCE: 105
IYYTGIT                                                           7

SEQ ID NO: 106         moltype = AA  length = 19
FEATURE                Location/Qualifiers
source                 1..19
                       mol_type = protein
                       organism = synthetic construct
SEQUENCE: 106
ARGDYSGYDR DVQVELMDV                                              19

SEQ ID NO: 107         moltype = AA  length = 6
FEATURE                Location/Qualifiers
source                 1..6
                       mol_type = protein
                       organism = synthetic construct
```

```
SEQUENCE: 107
QTISIF                                                                     6

SEQ ID NO: 108          moltype =   length =
SEQUENCE: 108
000

SEQ ID NO: 109          moltype = AA  length = 9
FEATURE                 Location/Qualifiers
source                  1..9
                        mol_type = protein
                        organism = synthetic construct
SEQUENCE: 109
QQSYSAPWT                                                                  9

SEQ ID NO: 110          moltype = AA  length = 8
FEATURE                 Location/Qualifiers
source                  1..8
                        mol_type = protein
                        organism = synthetic construct
SEQUENCE: 110
GYTFINHA                                                                   8

SEQ ID NO: 111          moltype = AA  length = 8
FEATURE                 Location/Qualifiers
source                  1..8
                        mol_type = protein
                        organism = synthetic construct
SEQUENCE: 111
IIPIFGLA                                                                   8

SEQ ID NO: 112          moltype = AA  length = 23
FEATURE                 Location/Qualifiers
source                  1..23
                        mol_type = protein
                        organism = synthetic construct
SEQUENCE: 112
ARDTVAVYED FDWSSPYFFY MDV                                                  23

SEQ ID NO: 113          moltype = AA  length = 7
FEATURE                 Location/Qualifiers
source                  1..7
                        mol_type = protein
                        organism = synthetic construct
SEQUENCE: 113
QSAGSKS                                                                    7

SEQ ID NO: 114          moltype =   length =
SEQUENCE: 114
000

SEQ ID NO: 115          moltype = AA  length = 9
FEATURE                 Location/Qualifiers
source                  1..9
                        mol_type = protein
                        organism = synthetic construct
SEQUENCE: 115
QRYGTSLVT                                                                  9

SEQ ID NO: 116          moltype = AA  length = 8
FEATURE                 Location/Qualifiers
source                  1..8
                        mol_type = protein
                        organism = synthetic construct
SEQUENCE: 116
GYTFTDYY                                                                   8

SEQ ID NO: 117          moltype = AA  length = 8
FEATURE                 Location/Qualifiers
source                  1..8
                        mol_type = protein
                        organism = synthetic construct
SEQUENCE: 117
IHPGSTNT                                                                   8

SEQ ID NO: 118          moltype = AA  length = 15
FEATURE                 Location/Qualifiers
source                  1..15
                        mol_type = protein
```

```
                        organism = synthetic construct
SEQUENCE: 118
AISLGDGYYV YAMVC                                                  15

SEQ ID NO: 119          moltype = AA  length = 6
FEATURE                 Location/Qualifiers
source                  1..6
                        mol_type = protein
                        organism = synthetic construct
SEQUENCE: 119
QNVVTN                                                            6

SEQ ID NO: 120          moltype =   length =
SEQUENCE: 120
000

SEQ ID NO: 121          moltype = AA  length = 9
FEATURE                 Location/Qualifiers
source                  1..9
                        mol_type = protein
                        organism = synthetic construct
SEQUENCE: 121
QQYHSYPFT                                                         9

SEQ ID NO: 122          moltype = AA  length = 9
FEATURE                 Location/Qualifiers
source                  1..9
                        mol_type = protein
                        organism = synthetic construct
SEQUENCE: 122
DSEVFPIVY                                                         9

SEQ ID NO: 123          moltype = AA  length = 8
FEATURE                 Location/Qualifiers
source                  1..8
                        mol_type = protein
                        organism = synthetic construct
SEQUENCE: 123
ILPSFGRT                                                          8

SEQ ID NO: 124          moltype = AA  length = 11
FEATURE                 Location/Qualifiers
source                  1..11
                        mol_type = protein
                        organism = synthetic construct
SEQUENCE: 124
ARGDHGNWLA Y                                                      11

SEQ ID NO: 125          moltype = AA  length = 6
FEATURE                 Location/Qualifiers
source                  1..6
                        mol_type = protein
                        organism = synthetic construct
SEQUENCE: 125
QDVSTN                                                            6

SEQ ID NO: 126          moltype =   length =
SEQUENCE: 126
000

SEQ ID NO: 127          moltype = AA  length = 9
FEATURE                 Location/Qualifiers
source                  1..9
                        mol_type = protein
                        organism = synthetic construct
SEQUENCE: 127
QQHYSAPWT                                                         9

SEQ ID NO: 128          moltype = AA  length = 8
FEATURE                 Location/Qualifiers
source                  1..8
                        mol_type = protein
                        organism = synthetic construct
SEQUENCE: 128
GLTFSGYA                                                          8

SEQ ID NO: 129          moltype = AA  length = 8
FEATURE                 Location/Qualifiers
source                  1..8
```

```
                        mol_type = protein
                        organism = synthetic construct
SEQUENCE: 129
IIASGGST                                                        8

SEQ ID NO: 130          moltype = AA  length = 14
FEATURE                 Location/Qualifiers
source                  1..14
                        mol_type = protein
                        organism = synthetic construct
SEQUENCE: 130
AQHTKSHYYS GMGV                                                 14

SEQ ID NO: 131          moltype = AA  length = 6
FEATURE                 Location/Qualifiers
source                  1..6
                        mol_type = protein
                        organism = synthetic construct
SEQUENCE: 131
QDISNY                                                          6

SEQ ID NO: 132          moltype =   length =
SEQUENCE: 132
000

SEQ ID NO: 133          moltype = AA  length = 9
FEATURE                 Location/Qualifiers
source                  1..9
                        mol_type = protein
                        organism = synthetic construct
SEQUENCE: 133
QQYDNLPLT                                                       9

SEQ ID NO: 134          moltype = AA  length = 8
FEATURE                 Location/Qualifiers
source                  1..8
                        mol_type = protein
                        organism = synthetic construct
SEQUENCE: 134
RYNIIELS                                                        8

SEQ ID NO: 135          moltype = AA  length = 8
FEATURE                 Location/Qualifiers
source                  1..8
                        mol_type = protein
                        organism = synthetic construct
SEQUENCE: 135
IDPDDSER                                                        8

SEQ ID NO: 136          moltype = AA  length = 17
FEATURE                 Location/Qualifiers
source                  1..17
                        mol_type = protein
                        organism = synthetic construct
SEQUENCE: 136
AAARRPIRGE YHYALDV                                              17

SEQ ID NO: 137          moltype = AA  length = 7
FEATURE                 Location/Qualifiers
source                  1..7
                        mol_type = protein
                        organism = synthetic construct
SEQUENCE: 137
QSVSSSY                                                         7

SEQ ID NO: 138          moltype =   length =
SEQUENCE: 138
000

SEQ ID NO: 139          moltype = AA  length = 6
FEATURE                 Location/Qualifiers
source                  1..6
                        mol_type = protein
                        organism = synthetic construct
SEQUENCE: 139
HHYAKV                                                          6

SEQ ID NO: 140          moltype = AA  length = 8
FEATURE                 Location/Qualifiers
```

```
source                  1..8
                        mol_type = protein
                        organism = synthetic construct
SEQUENCE: 140
GGSFGGYY                                                    8

SEQ ID NO: 141          moltype = AA  length = 7
FEATURE                 Location/Qualifiers
source                  1..7
                        mol_type = protein
                        organism = synthetic construct
SEQUENCE: 141
INHSGST                                                     7

SEQ ID NO: 142          moltype = AA  length = 18
FEATURE                 Location/Qualifiers
source                  1..18
                        mol_type = protein
                        organism = synthetic construct
SEQUENCE: 142
ARGRGGYATY YYYYYVDV                                         18

SEQ ID NO: 143          moltype = AA  length = 6
FEATURE                 Location/Qualifiers
source                  1..6
                        mol_type = protein
                        organism = synthetic construct
SEQUENCE: 143
QSVSSY                                                      6

SEQ ID NO: 144          moltype =   length =
SEQUENCE: 144
000

SEQ ID NO: 145          moltype = AA  length = 8
FEATURE                 Location/Qualifiers
source                  1..8
                        mol_type = protein
                        organism = synthetic construct
SEQUENCE: 145
QQRSNWLT                                                    8

SEQ ID NO: 146          moltype = AA  length = 9
FEATURE                 Location/Qualifiers
source                  1..9
                        mol_type = protein
                        organism = synthetic construct
SEQUENCE: 146
GFTFDDYGM                                                   9

SEQ ID NO: 147          moltype = AA  length = 9
FEATURE                 Location/Qualifiers
source                  1..9
                        mol_type = protein
                        organism = synthetic construct
SEQUENCE: 147
LNWNGDITA                                                   9

SEQ ID NO: 148          moltype = AA  length = 16
FEATURE                 Location/Qualifiers
source                  1..16
                        mol_type = protein
                        organism = synthetic construct
SEQUENCE: 148
TWGEYTTREE PINSWY                                           16

SEQ ID NO: 149          moltype = AA  length = 6
FEATURE                 Location/Qualifiers
source                  1..6
                        mol_type = protein
                        organism = synthetic construct
SEQUENCE: 149
DISSFL                                                      6

SEQ ID NO: 150          moltype =   length =
SEQUENCE: 150
000

SEQ ID NO: 151          moltype = AA  length = 9
```

```
FEATURE                 Location/Qualifiers
source                  1..9
                        mol_type = protein
                        organism = synthetic construct
SEQUENCE: 151
LNSYPLETF                                                                   9

SEQ ID NO: 152          moltype = AA  length = 9
FEATURE                 Location/Qualifiers
source                  1..9
                        mol_type = protein
                        organism = synthetic construct
SEQUENCE: 152
GFTFDDYGM                                                                   9

SEQ ID NO: 153          moltype = AA  length = 9
FEATURE                 Location/Qualifiers
source                  1..9
                        mol_type = protein
                        organism = synthetic construct
SEQUENCE: 153
LNWNGDITA                                                                   9

SEQ ID NO: 154          moltype = AA  length = 16
FEATURE                 Location/Qualifiers
source                  1..16
                        mol_type = protein
                        organism = synthetic construct
SEQUENCE: 154
TWGDYTTGEE IINSWY                                                           16

SEQ ID NO: 155          moltype = AA  length = 6
FEATURE                 Location/Qualifiers
source                  1..6
                        mol_type = protein
                        organism = synthetic construct
SEQUENCE: 155
DISSYL                                                                      6

SEQ ID NO: 156          moltype =   length =
SEQUENCE: 156
000

SEQ ID NO: 157          moltype = AA  length = 9
FEATURE                 Location/Qualifiers
source                  1..9
                        mol_type = protein
                        organism = synthetic construct
SEQUENCE: 157
LKSYPLETF                                                                   9

SEQ ID NO: 158          moltype = AA  length = 9
FEATURE                 Location/Qualifiers
source                  1..9
                        mol_type = protein
                        organism = synthetic construct
SEQUENCE: 158
GFKFDDYAM                                                                   9

SEQ ID NO: 159          moltype = AA  length = 9
FEATURE                 Location/Qualifiers
source                  1..9
                        mol_type = protein
                        organism = synthetic construct
SEQUENCE: 159
LNWNGDITA                                                                   9

SEQ ID NO: 160          moltype = AA  length = 16
FEATURE                 Location/Qualifiers
source                  1..16
                        mol_type = protein
                        organism = synthetic construct
SEQUENCE: 160
SWGDYTRGPE PKITWY                                                           16

SEQ ID NO: 161          moltype = AA  length = 6
FEATURE                 Location/Qualifiers
source                  1..6
                        mol_type = protein
```

```
                        organism = synthetic construct
SEQUENCE: 161
GIDGYL                                                                     6

SEQ ID NO: 162          moltype =   length =
SEQUENCE: 162
000

SEQ ID NO: 163          moltype = AA  length = 9
FEATURE                 Location/Qualifiers
source                  1..9
                        mol_type = protein
                        organism = synthetic construct
SEQUENCE: 163
LDSYPLETF                                                                  9

SEQ ID NO: 164          moltype = AA  length = 5
FEATURE                 Location/Qualifiers
source                  1..5
                        mol_type = protein
                        organism = synthetic construct
SEQUENCE: 164
NAWMS                                                                      5

SEQ ID NO: 165          moltype = AA  length = 19
FEATURE                 Location/Qualifiers
source                  1..19
                        mol_type = protein
                        organism = synthetic construct
SEQUENCE: 165
RIKTKTEGET VDYAAPVKG                                                       19

SEQ ID NO: 166          moltype = AA  length = 15
FEATURE                 Location/Qualifiers
source                  1..15
                        mol_type = protein
                        organism = synthetic construct
SEQUENCE: 166
TTGLTRSSLG GFVDY                                                           15

SEQ ID NO: 167          moltype = AA  length = 17
FEATURE                 Location/Qualifiers
source                  1..17
                        mol_type = protein
                        organism = synthetic construct
SEQUENCE: 167
RSSQTVLSSS NNENFLA                                                         17

SEQ ID NO: 168          moltype = AA  length = 7
FEATURE                 Location/Qualifiers
source                  1..7
                        mol_type = protein
                        organism = synthetic construct
SEQUENCE: 168
WASTRAS                                                                    7

SEQ ID NO: 169          moltype = AA  length = 9
FEATURE                 Location/Qualifiers
source                  1..9
                        mol_type = protein
                        organism = synthetic construct
SEQUENCE: 169
LQYLTTPRT                                                                  9

SEQ ID NO: 170          moltype = AA  length = 5
FEATURE                 Location/Qualifiers
source                  1..5
                        mol_type = protein
                        organism = synthetic construct
SEQUENCE: 170
DYYMS                                                                      5

SEQ ID NO: 171          moltype = AA  length = 17
FEATURE                 Location/Qualifiers
source                  1..17
                        mol_type = protein
                        organism = synthetic construct
SEQUENCE: 171
YISSSSTYTD YADSVKG                                                         17
```

```
SEQ ID NO: 172          moltype = AA  length = 20
FEATURE                 Location/Qualifiers
source                  1..20
                        mol_type = protein
                        organism = synthetic construct
SEQUENCE: 172
ATVADTAYSR GRPQITHFDN                                         20

SEQ ID NO: 173          moltype = AA  length = 11
FEATURE                 Location/Qualifiers
source                  1..11
                        mol_type = protein
                        organism = synthetic construct
SEQUENCE: 173
FGDKLGEKYA Y                                                  11

SEQ ID NO: 174          moltype = AA  length = 7
FEATURE                 Location/Qualifiers
source                  1..7
                        mol_type = protein
                        organism = synthetic construct
SEQUENCE: 174
QDTKRPS                                                       7

SEQ ID NO: 175          moltype = AA  length = 9
FEATURE                 Location/Qualifiers
source                  1..9
                        mol_type = protein
                        organism = synthetic construct
SEQUENCE: 175
QTWDSTLVF                                                     9

SEQ ID NO: 176          moltype = AA  length = 5
FEATURE                 Location/Qualifiers
source                  1..5
                        mol_type = protein
                        organism = synthetic construct
SEQUENCE: 176
DLVIH                                                         5

SEQ ID NO: 177          moltype = AA  length = 17
FEATURE                 Location/Qualifiers
source                  1..17
                        mol_type = protein
                        organism = synthetic construct
SEQUENCE: 177
VMGYDGGNKD YAESVKG                                            17

SEQ ID NO: 178          moltype = AA  length = 20
FEATURE                 Location/Qualifiers
source                  1..20
                        mol_type = protein
                        organism = synthetic construct
SEQUENCE: 178
ARASYFGELR DEYYSFAMDV                                         20

SEQ ID NO: 179          moltype = AA  length = 12
FEATURE                 Location/Qualifiers
source                  1..12
                        mol_type = protein
                        organism = synthetic construct
SEQUENCE: 179
RASQSVSRSY LA                                                 12

SEQ ID NO: 180          moltype = AA  length = 7
FEATURE                 Location/Qualifiers
source                  1..7
                        mol_type = protein
                        organism = synthetic construct
SEQUENCE: 180
GASSRAT                                                       7

SEQ ID NO: 181          moltype = AA  length = 10
FEATURE                 Location/Qualifiers
source                  1..10
                        mol_type = protein
                        organism = synthetic construct
SEQUENCE: 181
```

```
QLYGTSPPYT                                                  10

SEQ ID NO: 182          moltype = AA  length = 5
FEATURE                 Location/Qualifiers
source                  1..5
                        mol_type = protein
                        organism = synthetic construct
SEQUENCE: 182
NAWMS                                                       5

SEQ ID NO: 183          moltype = AA  length = 19
FEATURE                 Location/Qualifiers
source                  1..19
                        mol_type = protein
                        organism = synthetic construct
SEQUENCE: 183
RIKKESEGGT IDYGAPVKG                                        19

SEQ ID NO: 184          moltype = AA  length = 17
FEATURE                 Location/Qualifiers
source                  1..17
                        mol_type = protein
                        organism = synthetic construct
SEQUENCE: 184
TIPNPQIVVV TTTPHSH                                          17

SEQ ID NO: 185          moltype = AA  length = 11
FEATURE                 Location/Qualifiers
source                  1..11
                        mol_type = protein
                        organism = synthetic construct
SEQUENCE: 185
GGNNIGSKNV H                                                11

SEQ ID NO: 186          moltype = AA  length = 7
FEATURE                 Location/Qualifiers
source                  1..7
                        mol_type = protein
                        organism = synthetic construct
SEQUENCE: 186
YDSDRPS                                                     7

SEQ ID NO: 187          moltype = AA  length = 11
FEATURE                 Location/Qualifiers
source                  1..11
                        mol_type = protein
                        organism = synthetic construct
SEQUENCE: 187
QVWDSSSDHW V                                                11

SEQ ID NO: 188          moltype = AA  length = 125
FEATURE                 Location/Qualifiers
source                  1..125
                        mol_type = protein
                        organism = synthetic construct
SEQUENCE: 188
QVQLQESGPG LVRPSETLSL TCTVSGDSIG GSYWNWIRQP PGKGLQWIGY IYYTGITNYN  60
PSLKSRVTMS LDTSKNQISL KMDSVTAADT ALYFCARGDY SGYDRDVQVE LMDVWGKGTT  120
VTVSS                                                       125

SEQ ID NO: 189          moltype = AA  length = 107
FEATURE                 Location/Qualifiers
source                  1..107
                        mol_type = protein
                        organism = synthetic construct
SEQUENCE: 189
DIQMTQSPSS LSASVRDKVT FVCRASQTIS IFLNWYQHKP GEAPKLLIYA ASRLQSGVPS  60
RFSGSGSGTD FTLTISGLQP EDFATYYCQQ SYSAPWTFGQ GTKVEIK            107

SEQ ID NO: 190          moltype = AA  length = 130
FEATURE                 Location/Qualifiers
source                  1..130
                        mol_type = protein
                        organism = synthetic construct
SEQUENCE: 190
EVQLVQSGAE VKKPGSSVKV SCKASGYTFI NHALSWVRQA PGQGLEWVGG IIPIFGLAKY  60
GQKFQDRVTI TADESTKTAY MDLRSLRSDD TAVYYCARDT VAVYEDFDWS SPYFFYMDVW  120
GKGTTVTVSS                                                  130
```

```
SEQ ID NO: 191         moltype = AA  length = 108
FEATURE                Location/Qualifiers
source                 1..108
                       mol_type = protein
                       organism = synthetic construct
SEQUENCE: 191
EIVLTQSPAT LSLFPGERAT LSCRASQSAG SKSLAWYQHK VGQPPRLLIN GASSRATGIP  60
DRFSGSGSGP DFNLTISRLE PEDFAVYYCQ RYGTSLVTFG GGTKVEIK              108

SEQ ID NO: 192         moltype = AA  length = 122
FEATURE                Location/Qualifiers
source                 1..122
                       mol_type = protein
                       organism = synthetic construct
SEQUENCE: 192
QVHLQQSGPE VARPGASVKL SCKASGYTFT DYYLNWVKQR PRQGLEWIGQ IHPGSTNTYY  60
NEKFKGKATL TADKSSSTAY MQLSSLTFED SAVYFCAISL GDGYYVYAMV CWGQGTAVTV  120
SS                                                                 122

SEQ ID NO: 193         moltype = AA  length = 78
FEATURE                Location/Qualifiers
source                 1..78
                       mol_type = protein
                       organism = synthetic construct
SEQUENCE: 193
DIVMTQSQKF MSTSVGDRVS VTCKASQNVV TNVVWYQQKP GQSPKPLIYS ASYRYSGVPD  60
RFTGSGSGTD FTLTISNV                                                78

SEQ ID NO: 194         moltype = AA  length = 119
FEATURE                Location/Qualifiers
source                 1..119
                       mol_type = protein
                       organism = synthetic construct
SEQUENCE: 194
QVHLQQSGSE LRSPGSSVKL SCKDFDSEVF PIVYMRWIRQ KPGHGFEWIG DILPSFGRTI  60
YGEKFEDKAT LDADTVSNTA YLELNSLTSE DSAIYYCARG DHGNWLAYWG QGTLVTVSA   119

SEQ ID NO: 195         moltype = AA  length = 107
FEATURE                Location/Qualifiers
source                 1..107
                       mol_type = protein
                       organism = synthetic construct
SEQUENCE: 195
DIVMTQSHKF MSTSVGDRVT ITCKASQDVS TNVAWYQQKP GQSPKLLIYW ASTRHTGVPN  60
RFTGIISGTD YTLTISSVQA EDRALYYCQQ HYSAPWTFGG GTKLEIK               107

SEQ ID NO: 196         moltype = AA  length = 121
FEATURE                Location/Qualifiers
source                 1..121
                       mol_type = protein
                       organism = synthetic construct
SEQUENCE: 196
EVQLLQSGGG LVQPGGSLRL SCAASGLTFS GYAMSWVRQV PGKGPECVSG IIASGGSTYF  60
ADSVKGRFTI SRDNSKNTLD LEMNSLRAED TAVYYCAQHT KSHYYSGMGV WGQGTTVTVS  120
S                                                                  121

SEQ ID NO: 197         moltype = AA  length = 107
FEATURE                Location/Qualifiers
source                 1..107
                       mol_type = protein
                       organism = synthetic construct
SEQUENCE: 197
DIQMTQSPSS LSASVGDRVT ITCQASQDIS NYLNWYQQRP GKAPKLLIYD AANLETGVPS  60
RFSGSGSATQ FTFTISGLQP EDFATYYCQQ YDNLPLTFGG GTKVEIK               107

SEQ ID NO: 198         moltype = AA  length = 124
FEATURE                Location/Qualifiers
source                 1..124
                       mol_type = protein
                       organism = synthetic construct
SEQUENCE: 198
QVQLVQSGAE VRKPGASVKV SCKVSRYNII ELSMDWVRQA PGKGLEWMGG IDPDDSERIY  60
AQKLQGRVTM TEDTSTDTAY MELSGLRSED TAIYYCAAAR RPIRGEYHYA LDVWGQGTAV  120
TVSS                                                               124

SEQ ID NO: 199         moltype = AA  length = 105
FEATURE                Location/Qualifiers
source                 1..105
                       mol_type = protein
```

```
                          organism = synthetic construct
SEQUENCE: 199
EIVLTQSPGT LSLSPGERAT LSCRASQSVS SSYLGWYQQK PGQAPRLLIY RASSRATGIP  60
HRFSGSGSGT EFTLTITRLE PEDFAVYYCH HYAKVFGQGT KVEIK                 105

SEQ ID NO: 200            moltype = AA  length = 124
FEATURE                   Location/Qualifiers
source                    1..124
                          mol_type = protein
                          organism = synthetic construct
SEQUENCE: 200
QVQLQQWGAG LLKPSETLSL TCAVYGGSFG GYYWNWIRQP PGKGLEWIGE INHSGSTNYN  60
PSLKSRVTLS VDTSKNQVSL NVSSVTAADT AVYYCARGRG GYATYYYYYY VDVWGKGTTV  120
TVSS                                                              124

SEQ ID NO: 201            moltype = AA  length = 106
FEATURE                   Location/Qualifiers
source                    1..106
                          mol_type = protein
                          organism = synthetic construct
SEQUENCE: 201
EIVLTQSPAT LSLSPGERAT LSCRASQSVS SYLAWYQQKP GQAPRLLIYD ASKRATGIPA  60
RFSGSGSGTD FTLTISSLEP EDFAVYYCQQ RSNWLTFGGG TKVELE                106

SEQ ID NO: 202            moltype = AA  length = 130
FEATURE                   Location/Qualifiers
source                    1..130
                          mol_type = protein
                          organism = synthetic construct
SEQUENCE: 202
EVQLVESGGR VVRPGGSLRL SCAASGFTFD DYGMSWVRQP PGKGLEFVSG LNWNGDITAF  60
TDSVKGRETI SRDNVKSSLY LQMNSLRADD TAFYYCARVR TWGDYTTGEE IINSWYFDLW  120
GRGTLVTVSS                                                        130

SEQ ID NO: 203            moltype = AA  length = 107
FEATURE                   Location/Qualifiers
source                    1..107
                          mol_type = protein
                          organism = synthetic construct
SEQUENCE: 203
DIQLTQSPSF LSASVGDRVT ITCRASQDIS SYLAWYQQKP GNAPKVLIYA ASLLSGVPSR  60
FSAFGSGTEF TLTISSLQPE DFATYYCQHL KSYPLETFGP GTKVDIK               107

SEQ ID NO: 204            moltype = AA  length = 130
FEATURE                   Location/Qualifiers
source                    1..130
                          mol_type = protein
                          organism = synthetic construct
SEQUENCE: 204
EVQLVESGGR VVRPGGSLRL SCAASGFTFD DYGMSWVRQA PGKGLEFVSG LNWNGDITAF  60
TDSVKGRETI SRDNAKSSLY LQMNSLRADD TAFYYCARVR TWGEYTTREE PIHSWYFDLW  120
GRGTLVTVSS                                                        130

SEQ ID NO: 205            moltype = AA  length = 107
FEATURE                   Location/Qualifiers
source                    1..107
                          mol_type = protein
                          organism = synthetic construct
SEQUENCE: 205
DIQLTQSPSF LSASVGDRVT ITCRASQDIS SYLAWYQQKP GNAPKLLIYA ASLLSGVPSR  60
FSAFGSGTEF TLTISSLQPE DFATYYCQHL KSYPLETFGP GTKVDIK               107

SEQ ID NO: 206            moltype = AA  length = 130
FEATURE                   Location/Qualifiers
source                    1..130
                          mol_type = protein
                          organism = synthetic construct
SEQUENCE: 206
EVQLVESGGR ALRPGGSLRL SCAASGFKFD DYAMSWVRQV PGKGLEFVSG LNWNGDITAY  60
TDSVKGRETV SRDNAKNSLY LHINSPKPED TALYYCARTS SWGDYTRGPE PKITWYFDLW  120
GRGTLVTVSS                                                        130

SEQ ID NO: 207            moltype = AA  length = 107
FEATURE                   Location/Qualifiers
source                    1..107
                          mol_type = protein
                          organism = synthetic construct
SEQUENCE: 207
DIQLTQSPSF LSASVGDRIT ITCRASQGID GYLAWYQQRP GKAPNLLIYA ASLLSGVPSR  60
```

```
FSGSGYGTEF TLTISSLQPE DFATYYCQHL DSYPLETFGP GTKVDIK               107

SEQ ID NO: 208          moltype = AA  length = 124
FEATURE                 Location/Qualifiers
source                  1..124
                        mol_type = protein
                        organism = synthetic construct
SEQUENCE: 208
EVQLVESGGG LVKPGQSLRL SCAASGFTFT NAWMSWVRQA PGKGLEWVGR IKTKTEGETV  60
DYAAPVKGRI TISRDDSKNM VYLQLKSLKI EDAAVYYCTT GLTRSSLGGF VDYWGPGTLV  120
TVSS                                                              124

SEQ ID NO: 209          moltype = AA  length = 113
FEATURE                 Location/Qualifiers
source                  1..113
                        mol_type = protein
                        organism = synthetic construct
SEQUENCE: 209
DIVMTQSPDS LTVSLGERAT INCRSSQTVL SSSNNENFLA WYQQKSGQPP NLLIYWASTR  60
ASGVPDRFSG SGSGTDFTLT ISSLQTEDVA VYYCLQYLTT PRTFGQGTKV EIK         113

SEQ ID NO: 210          moltype = AA  length = 126
FEATURE                 Location/Qualifiers
source                  1..126
                        mol_type = protein
                        organism = synthetic construct
SEQUENCE: 210
VQLVESGGGL VKPGGSLRLS CAASGFTFSD YYMSWIRQAP GKGLEWISYI SSSSTYTDYA  60
DSVKGRFTVS RDNAKNSLYL QMNNLRAEDT AVYYCATVAD TAYSRGRPQI THFDNWGQGT  120
LVTVSS                                                            126

SEQ ID NO: 211          moltype = AA  length = 106
FEATURE                 Location/Qualifiers
source                  1..106
                        mol_type = protein
                        organism = synthetic construct
SEQUENCE: 211
SYELTQPPSM SVSPGQTATI TCFGDKLGEK YAYWYQQKPG QSPLLVIYQD TKRPSGIPER  60
FSGSNSGNTA TLTISGTQAM DEADYYCQTW DSTLVFFGGG TKLTVL                106

SEQ ID NO: 212          moltype = AA  length = 126
FEATURE                 Location/Qualifiers
source                  1..126
                        mol_type = protein
                        organism = synthetic construct
SEQUENCE: 212
VQLVESGGGV VQPGGSLRLS CAVSGLTIND LVIHWVRQPP DKGLEWVAVM GYDGGNKDYA  60
ESVKGRFSIS GDNPQNTLYL QINSLRVEDT AVYYCARASY FGELRDEYYS FAMDVWGQGT  120
TVTVSS                                                            126

SEQ ID NO: 213          moltype = AA  length = 109
FEATURE                 Location/Qualifiers
source                  1..109
                        mol_type = protein
                        organism = synthetic construct
SEQUENCE: 213
EIVLTQSPGT LSLSPGERGT LSCRASQSVS RSYLAWYQQK PGQAPRLLIY GASSRATGIP  60
DRFSGSGSGT DFTLTISRLE PEDFALYYCQ LYGTSPPYTF GQGTKVEIK             109

SEQ ID NO: 214          moltype = AA  length = 126
FEATURE                 Location/Qualifiers
source                  1..126
                        mol_type = protein
                        organism = synthetic construct
SEQUENCE: 214
EVQLVESGGG LVKPGGSLRL SCAASGFTVS NAWMSWVRQA PGKGLEWVGR IKKESEGGTI  60
DYGAPVKGRF TISRDESKNI LYLHMKSLIT DDTAVYYCTI PNPQIVVVTT TPHSHWGQGT  120
LVTVSS                                                            126

SEQ ID NO: 215          moltype = AA  length = 108
FEATURE                 Location/Qualifiers
source                  1..108
                        mol_type = protein
                        organism = synthetic construct
SEQUENCE: 215
SYELTQPPSV SVAPGKTARI TCGGNNIGSK NVHWYQQKPG QAPVLVIYYD SDRPSAIPER  60
FSGSNSGNTA TLTISRVEAG DEADYYCQVW DSSSDHWVFG GGTKLAVL              108

SEQ ID NO: 216          moltype = AA  length = 455
```

```
FEATURE                 Location/Qualifiers
source                  1..455
                        mol_type = protein
                        organism = synthetic construct
SEQUENCE: 216
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSSS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKH HHHHH                            455

SEQ ID NO: 217          moltype = AA  length = 217
FEATURE                 Location/Qualifiers
source                  1..217
                        mol_type = protein
                        organism = synthetic construct
SEQUENCE: 217
DIVMTQSPDS LAVSLGERAT INCKSSQSVT FNYKNYLAWY QQKPGQPPKL LIYWASTRES  60
GVPDRFSGSG SGTDFTLTIS SLQAEDVAVY YCQQHYRTPP TFGQGTKVEI KGQPKANPTV  120
TLFPPSSEEL QANKATLVCL ISDFYPGAVT VAWKADGSPV KAGVETTKPS KQSNNKYAAS  180
SYLSLTPEQW KSHRSYSCQV THEGSTVEKT VAPTECS                          217

SEQ ID NO: 218          moltype = AA  length = 461
FEATURE                 Location/Qualifiers
source                  1..461
                        mol_type = protein
                        organism = synthetic construct
SEQUENCE: 218
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSSS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKH HHHHHHHHHH H                     461

SEQ ID NO: 219          moltype = AA  length = 479
FEATURE                 Location/Qualifiers
source                  1..479
                        mol_type = protein
                        organism = synthetic construct
SEQUENCE: 219
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSSS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKH HHHHHHHHHH HHHHHHHHHH HHHHHHHHH   479

SEQ ID NO: 220          moltype = AA  length = 455
FEATURE                 Location/Qualifiers
source                  1..455
                        mol_type = protein
                        organism = synthetic construct
SEQUENCE: 220
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSSS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKK KKKKK                            455

SEQ ID NO: 221          moltype = AA  length = 466
FEATURE                 Location/Qualifiers
source                  1..466
                        mol_type = protein
                        organism = synthetic construct
SEQUENCE: 221
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSSS VFPLAPSSKS TSGGTAALGC LVKDYFPEPV TVSWNSGALT SGVHTFPAVL  180
```

```
QSSGLYSLSS VVTVPSSSLG TQTYICNVNH KPSNTKVDKR VEPKSCTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKG GGGSKKKKKK KKKKKK                466

SEQ ID NO: 222          moltype = AA  length = 479
FEATURE                 Location/Qualifiers
source                  1..479
                        mol_type = protein
                        organism = synthetic construct
SEQUENCE: 222
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSSS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKK KKKKKKKKK KKKKKKKKK KKKKKKKK    479

SEQ ID NO: 223          moltype = AA  length = 455
FEATURE                 Location/Qualifiers
source                  1..455
                        mol_type = protein
                        organism = synthetic construct
SEQUENCE: 223
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSSS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKR RRRRR                            455

SEQ ID NO: 224          moltype = AA  length = 461
FEATURE                 Location/Qualifiers
source                  1..461
                        mol_type = protein
                        organism = synthetic construct
SEQUENCE: 224
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSSS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKR RRRRRRRRR R                      461

SEQ ID NO: 225          moltype = AA  length = 479
FEATURE                 Location/Qualifiers
source                  1..479
                        mol_type = protein
                        organism = synthetic construct
SEQUENCE: 225
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSSS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKR RRRRRRRRR RRRRRRRRR RRRRRRRR    479

SEQ ID NO: 226          moltype = AA  length = 455
FEATURE                 Location/Qualifiers
source                  1..455
                        mol_type = protein
                        organism = synthetic construct
SEQUENCE: 226
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSSS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
```

```
QGNVFSCSVM HEALHNHYTQ KSLSLSPGKO OOOOO                           455

SEQ ID NO: 227          moltype = AA  length = 461
FEATURE                 Location/Qualifiers
source                  1..461
                        mol_type = protein
                        organism = synthetic construct
SEQUENCE: 227
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSSS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKO OOOOOOOOOO O                    461

SEQ ID NO: 228          moltype = AA  length = 479
FEATURE                 Location/Qualifiers
source                  1..479
                        mol_type = protein
                        organism = synthetic construct
SEQUENCE: 228
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSSS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKO OOOOOOOOOO OOOOOOOOOO OOOOOOOOO   479

SEQ ID NO: 229          moltype = AA  length = 455
FEATURE                 Location/Qualifiers
source                  1..455
                        mol_type = protein
                        organism = synthetic construct
SEQUENCE: 229
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSSS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKH HKKOO                           455

SEQ ID NO: 230          moltype = AA  length = 455
FEATURE                 Location/Qualifiers
source                  1..455
                        mol_type = protein
                        organism = synthetic construct
SEQUENCE: 230
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSSS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKH ORKHR                           455

SEQ ID NO: 231          moltype = AA  length = 455
FEATURE                 Location/Qualifiers
source                  1..455
                        mol_type = protein
                        organism = synthetic construct
SEQUENCE: 231
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSSS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKH KRSOH                           455

SEQ ID NO: 232          moltype = AA  length = 455
FEATURE                 Location/Qualifiers
```

```
source                  1..455
                        mol_type = protein
                        organism = synthetic construct
SEQUENCE: 232
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSSS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKR RHTHR                            455

SEQ ID NO: 233          moltype = AA  length = 461
FEATURE                 Location/Qualifiers
source                  1..461
                        mol_type = protein
                        organism = synthetic construct
SEQUENCE: 233
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSSS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKH HHKKKRRROO O                     461

SEQ ID NO: 234          moltype = AA  length = 479
FEATURE                 Location/Qualifiers
source                  1..479
                        mol_type = protein
                        organism = synthetic construct
SEQUENCE: 234
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSSS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKH KROHKROHKR OHKROHKROH KROHKROHK   479

SEQ ID NO: 235          moltype = AA  length = 13
FEATURE                 Location/Qualifiers
source                  1..13
                        mol_type = protein
                        organism = synthetic construct
SEQUENCE: 235
SGSRSNIGGN TVN                                                    13

SEQ ID NO: 236          moltype = AA  length = 461
FEATURE                 Location/Qualifiers
source                  1..461
                        mol_type = protein
                        organism = synthetic construct
SEQUENCE: 236
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSSS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKH HOAKKRCOOQ H                     461

SEQ ID NO: 237          moltype = AA  length = 479
FEATURE                 Location/Qualifiers
source                  1..479
                        mol_type = protein
                        organism = synthetic construct
SEQUENCE: 237
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSSS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
```

QGNVFSCSVM HEALHNHYTQ KSLSLSPGKK OHRSOKRHTO RHKAHORKCK ROKQRKHOS 479

SEQ ID NO: 238 moltype = AA length = 7
FEATURE Location/Qualifiers
source 1..7
mol_type = protein
organism = synthetic construct
SEQUENCE: 238
SSNQRSS 7

SEQ ID NO: 239 moltype = AA length = 461
FEATURE Location/Qualifiers
source 1..461
mol_type = protein
organism = synthetic construct
SEQUENCE: 239
QVQLVESGGG VVQPGRSLRL SCAASGFTFS TYAMHWVRQA PGKGLEWVAV ISYDANYKYY 60
ADSVKGRFTI SRDNSKNTLY LQMNSLRAED TAVYYCAKDS QLRSLLYFEW LSQGYFDYWG 120
QGTLVTVSSS VFPLAPSSKS TSGGTAALGC LVKDYFPEPV TVSWNSGALT SGVHTFPAVL 180
QSSGLYSLSS VVTVPSSSLG TQTYICNVNH KPSNTKVDKR VEPKSCTCPP CPAPELLGGP 240
SVFLFPPKPK DTLMISRTPE VTCVVVDVSH EDPEVKFNWY VDGVEVHNAK TKPREEQYNS 300
TYRVVSVLTV LHQDWLNGKE YKCKVSNKAL PAPIEKTISK AKGQPREPQV YTLPPSRDEL 360
TKNQVSLTCL VKGFYPSDIA VEWESNGQPE NNYKTTPPVL DSDGSFFLYS KLTVDKSRWQ 420
QGNVFSCSVM HEALHNHYTQ KSLSLSPGKH RKOORKHHRK K 461

SEQ ID NO: 240 moltype = AA length = 479
FEATURE Location/Qualifiers
source 1..479
mol_type = protein
organism = synthetic construct
SEQUENCE: 240
QVQLVESGGG VVQPGRSLRL SCAASGFTFS TYAMHWVRQA PGKGLEWVAV ISYDANYKYY 60
ADSVKGRFTI SRDNSKNTLY LQMNSLRAED TAVYYCAKDS QLRSLLYFEW LSQGYFDYWG 120
QGTLVTVSSS VFPLAPSSKS TSGGTAALGC LVKDYFPEPV TVSWNSGALT SGVHTFPAVL 180
QSSGLYSLSS VVTVPSSSLG TQTYICNVNH KPSNTKVDKR VEPKSCTCPP CPAPELLGGP 240
SVFLFPPKPK DTLMISRTPE VTCVVVDVSH EDPEVKFNWY VDGVEVHNAK TKPREEQYNS 300
TYRVVSVLTV LHQDWLNGKE YKCKVSNKAL PAPIEKTISK AKGQPREPQV YTLPPSRDEL 360
TKNQVSLTCL VKGFYPSDIA VEWESNGQPE NNYKTTPPVL DSDGSFFLYS KLTVDKSRWQ 420
QGNVFSCSVM HEALHNHYTQ KSLSLSPGKK KROSRRHOTO OHHAROKHCK HROQRHKKS 479

SEQ ID NO: 241 moltype = AA length = 461
FEATURE Location/Qualifiers
source 1..461
mol_type = protein
organism = synthetic construct
SEQUENCE: 241
QVQLVESGGG VVQPGRSLRL SCAASGFTFS TYAMHWVRQA PGKGLEWVAV ISYDANYKYY 60
ADSVKGRFTI SRDNSKNTLY LQMNSLRAED TAVYYCAKDS QLRSLLYFEW LSQGYFDYWG 120
QGTLVTVSSS VFPLAPSSKS TSGGTAALGC LVKDYFPEPV TVSWNSGALT SGVHTFPAVL 180
QSSGLYSLSS VVTVPSSSLG TQTYICNVNH KPSNTKVDKR VEPKSCTCPP CPAPELLGGP 240
SVFLFPPKPK DTLMISRTPE VTCVVVDVSH EDPEVKFNWY VDGVEVHNAK TKPREEQYNS 300
TYRVVSVLTV LHQDWLNGKE YKCKVSNKAL PAPIEKTISK AKGQPREPQV YTLPPSRDEL 360
TKNQVSLTCL VKGFYPSDIA VEWESNGQPE NNYKTTPPVL DSDGSFFLYS KLTVDKSRWQ 420
QGNVFSCSVM HEALHNHYTQ KSLSLSPGKK RAHOKCORKS H 461

SEQ ID NO: 242 moltype = AA length = 479
FEATURE Location/Qualifiers
source 1..479
mol_type = protein
organism = synthetic construct
SEQUENCE: 242
QVQLVESGGG VVQPGRSLRL SCAASGFTFS TYAMHWVRQA PGKGLEWVAV ISYDANYKYY 60
ADSVKGRFTI SRDNSKNTLY LQMNSLRAED TAVYYCAKDS QLRSLLYFEW LSQGYFDYWG 120
QGTLVTVSSS VFPLAPSSKS TSGGTAALGC LVKDYFPEPV TVSWNSGALT SGVHTFPAVL 180
QSSGLYSLSS VVTVPSSSLG TQTYICNVNH KPSNTKVDKR VEPKSCTCPP CPAPELLGGP 240
SVFLFPPKPK DTLMISRTPE VTCVVVDVSH EDPEVKFNWY VDGVEVHNAK TKPREEQYNS 300
TYRVVSVLTV LHQDWLNGKE YKCKVSNKAL PAPIEKTISK AKGQPREPQV YTLPPSRDEL 360
TKNQVSLTCL VKGFYPSDIA VEWESNGQPE NNYKTTPPVL DSDGSFFLYS KLTVDKSRWQ 420
QGNVFSCSVM HEALHNHYTQ KSLSLSPGKH RKQOHRSOOK TRRRAHROCH HHSRHOTHR 479

SEQ ID NO: 243 moltype = AA length = 457
FEATURE Location/Qualifiers
source 1..457
mol_type = protein
organism = synthetic construct
SEQUENCE: 243
EVQLVESGAE VKKPGSSVKV SCRASGTFYK YAINWVRQAP GQGLEWMGGI IPFFGTTNYA 60
QKFQGRLTIT ADGSTNTAYM QLDSLRSEDT AVYYCAGPSI TESHYCLDCA AKDYYYGLDV 120
WGQGTTVTVS SSVFPLAPSS KSTSGGTAAL GCLVKDYFPE PVTVSWNSGA LTSGVHTFPA 180

```
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KHHHHHH                          457

SEQ ID NO: 244          moltype = AA  length = 217
FEATURE                 Location/Qualifiers
source                  1..217
                        mol_type = protein
                        organism = synthetic construct
SEQUENCE: 244
QSVLTQPPSA SGTPGQSVTI SCSGSRSNIG GNTVNWYQHL PGMAPKLLIY SSNQRSSGVP  60
DRFSGSKSGT SASLAISGLQ SEDDADYYCA SWDDSLNGVV FGGGTKLTVL GGQPKAAPSV  120
TLFPPSSEEL QANKATLVCL ISDFYPGAVT VAWKADSSPV KAGVETTTPS KQSNNKYAAS  180
SYLSLTPEQW KSHRSYSCQV THEGSTVEKT VAPTECS                          217

SEQ ID NO: 245          moltype = AA  length = 463
FEATURE                 Location/Qualifiers
source                  1..463
                        mol_type = protein
                        organism = synthetic construct
SEQUENCE: 245
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS SSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KHHHHHHHHH HHH                   463

SEQ ID NO: 246          moltype = AA  length = 481
FEATURE                 Location/Qualifiers
source                  1..481
                        mol_type = protein
                        organism = synthetic construct
SEQUENCE: 246
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS SSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KHHHHHHHHH HHHHHHHHHH HHHHHHHHHH  480
H                                                                 481

SEQ ID NO: 247          moltype = AA  length = 457
FEATURE                 Location/Qualifiers
source                  1..457
                        mol_type = protein
                        organism = synthetic construct
SEQUENCE: 247
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS SSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KKKKKKK                          457

SEQ ID NO: 248          moltype = AA  length = 468
FEATURE                 Location/Qualifiers
source                  1..468
                        mol_type = protein
                        organism = synthetic construct
SEQUENCE: 248
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS SSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KGGGGSKKKK KKKKKKK                468

SEQ ID NO: 249          moltype = AA  length = 481
```

```
FEATURE                Location/Qualifiers
source                 1..481
                       mol_type = protein
                       organism = synthetic construct
SEQUENCE: 249
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS SSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KKKKKKKKKK KKKKKKKKKK KKKKKKKKKK  480
K                                                                  481

SEQ ID NO: 250         moltype = AA  length = 457
FEATURE                Location/Qualifiers
source                 1..457
                       mol_type = protein
                       organism = synthetic construct
SEQUENCE: 250
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS SSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KRRRRRR                           457

SEQ ID NO: 251         moltype = AA  length = 463
FEATURE                Location/Qualifiers
source                 1..463
                       mol_type = protein
                       organism = synthetic construct
SEQUENCE: 251
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS SSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KRRRRRRRRR RRR                    463

SEQ ID NO: 252         moltype = AA  length = 481
FEATURE                Location/Qualifiers
source                 1..481
                       mol_type = protein
                       organism = synthetic construct
SEQUENCE: 252
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS SSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KRRRRRRRRR RRRRRRRRRR RRRRRRRRRR  480
R                                                                  481

SEQ ID NO: 253         moltype = AA  length = 458
FEATURE                Location/Qualifiers
source                 1..458
                       mol_type = protein
                       organism = synthetic construct
SEQUENCE: 253
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS SSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KCOOOOOO                          458

SEQ ID NO: 254         moltype = AA  length = 464
FEATURE                Location/Qualifiers
source                 1..464
```

```
                         mol_type = protein
                         organism = synthetic construct
SEQUENCE: 254
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS SSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KCOOOOOOOO OOOO                   464

SEQ ID NO: 255           moltype = AA  length = 481
FEATURE                  Location/Qualifiers
source                   1..481
                         mol_type = protein
                         organism = synthetic construct
SEQUENCE: 255
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS SSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KOOOOOOOOO OOOOOOOOOO OOOOOOOOOO  480
O                                                                  481

SEQ ID NO: 256           moltype = AA  length = 457
FEATURE                  Location/Qualifiers
source                   1..457
                         mol_type = protein
                         organism = synthetic construct
SEQUENCE: 256
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS SSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KKKOORR                           457

SEQ ID NO: 257           moltype = AA  length = 463
FEATURE                  Location/Qualifiers
source                   1..463
                         mol_type = protein
                         organism = synthetic construct
SEQUENCE: 257
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS SSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KKKRROOHHH RRR                    463

SEQ ID NO: 258           moltype = AA  length = 481
FEATURE                  Location/Qualifiers
source                   1..481
                         mol_type = protein
                         organism = synthetic construct
SEQUENCE: 258
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS SSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KHKROHKROH KROHKROHKR OHKROHKROH  480
K                                                                  481

SEQ ID NO: 259           moltype = AA  length = 451
FEATURE                  Location/Qualifiers
source                   1..451
                         mol_type = protein
                         organism = synthetic construct
```

```
SEQUENCE: 259
QVQLQESGPG LVRPSETLSL TCTVSGDSIG GSYWNWIRQP PGKGLQWIGY IYYTGITNYN  60
PSLKSRVTMS LDTSKNQISL KMDSVTAADT ALYFCARGDY SGYDRDVQVE LMDVWGKGTT  120
VTVSSSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGKHHHHH H                                451

SEQ ID NO: 260          moltype = AA  length = 213
FEATURE                 Location/Qualifiers
source                  1..213
                        mol_type = protein
                        organism = synthetic construct
SEQUENCE: 260
DIQMTQSPSS LSASVRDKVT FVCRASQTIS IFLNWYQHKP GEAPKLLIYA ASRLQSGVPS  60
RFSGSGSGTD FTLTISGLQP EDFATYYCQQ SYSAPWTFGQ GTKVEIKGQP KANPTVTLFP  120
PSSEELQANK ATLVCLISDF YPGAVTVAWK ADGSPVKAGV ETTKPSKQSN NKYAASSYLS  180
LTPEQWKSHR SYSCQVTHEG STVEKTVAPT ECS                              213

SEQ ID NO: 261          moltype = AA  length = 457
FEATURE                 Location/Qualifiers
source                  1..457
                        mol_type = protein
                        organism = synthetic construct
SEQUENCE: 261
QVQLQESGPG LVRPSETLSL TCTVSGDSIG GSYWNWIRQP PGKGLQWIGY IYYTGITNYN  60
PSLKSRVTMS LDTSKNQISL KMDSVTAADT ALYFCARGDY SGYDRDVQVE LMDVWGKGTT  120
VTVSSSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGKHHHHH HHHHHHH                          457

SEQ ID NO: 262          moltype = AA  length = 262
FEATURE                 Location/Qualifiers
source                  1..262
                        mol_type = protein
                        organism = synthetic construct
SEQUENCE: 262
QVQLQESGPG LVRPSETLSL TCTVSGDSIG GSYWNWIRQP PGKGLQWIGY IYYTGITNYN  60
PSLKSRVTMS LDTSKNQISL KMDSVTAADT ALYFCARGDY SGYDRDVQVE LMDVWGKGTT  120
VTVSSSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCRSLVPRGS SGHHHHHHHH  240
HHHHHHHHHH HHHHHHHHHH HH                                          262

SEQ ID NO: 263          moltype = AA  length = 451
FEATURE                 Location/Qualifiers
source                  1..451
                        mol_type = protein
                        organism = synthetic construct
SEQUENCE: 263
QVQLQESGPG LVRPSETLSL TCTVSGDSIG GSYWNWIRQP PGKGLQWIGY IYYTGITNYN  60
PSLKSRVTMS LDTSKNQISL KMDSVTAADT ALYFCARGDY SGYDRDVQVE LMDVWGKGTT  120
VTVSSSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGKKKKKK K                                451

SEQ ID NO: 264          moltype = AA  length = 462
FEATURE                 Location/Qualifiers
source                  1..462
                        mol_type = protein
                        organism = synthetic construct
SEQUENCE: 264
QVQLQESGPG LVRPSETLSL TCTVSGDSIG GSYWNWIRQP PGKGLQWIGY IYYTGITNYN  60
PSLKSRVTMS LDTSKNQISL KMDSVTAADT ALYFCARGDY SGYDRDVQVE LMDVWGKGTT  120
VTVSSSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGKGGGGS KKKKKKKKKK KK                    462

SEQ ID NO: 265          moltype = AA  length = 475
```

```
FEATURE                Location/Qualifiers
source                 1..475
                       mol_type = protein
                       organism = synthetic construct
SEQUENCE: 265
QVQLQESGPG LVRPSETLSL TCTVSGDSIG GSYWNWIRQP PGKGLQWIGY IYYTGITNYN  60
PSLKSRVTMS LDTSKNQISL KMDSVTAADT ALYFCARGDY SGYDRDVQVE LMDVWGKGTT  120
VTVSSSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGKKKKKK KKKKKKKKKK KKKKKKKKKK KKKKK       475

SEQ ID NO: 266         moltype = AA  length = 451
FEATURE                Location/Qualifiers
source                 1..451
                       mol_type = protein
                       organism = synthetic construct
SEQUENCE: 266
QVQLQESGPG LVRPSETLSL TCTVSGDSIG GSYWNWIRQP PGKGLQWIGY IYYTGITNYN  60
PSLKSRVTMS LDTSKNQISL KMDSVTAADT ALYFCARGDY SGYDRDVQVE LMDVWGKGTT  120
VTVSSSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGKRRRRR R                                451

SEQ ID NO: 267         moltype = AA  length = 457
FEATURE                Location/Qualifiers
source                 1..457
                       mol_type = protein
                       organism = synthetic construct
SEQUENCE: 267
QVQLQESGPG LVRPSETLSL TCTVSGDSIG GSYWNWIRQP PGKGLQWIGY IYYTGITNYN  60
PSLKSRVTMS LDTSKNQISL KMDSVTAADT ALYFCARGDY SGYDRDVQVE LMDVWGKGTT  120
VTVSSSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGKRRRRR RRRRRRR                          457

SEQ ID NO: 268         moltype = AA  length = 475
FEATURE                Location/Qualifiers
source                 1..475
                       mol_type = protein
                       organism = synthetic construct
SEQUENCE: 268
QVQLQESGPG LVRPSETLSL TCTVSGDSIG GSYWNWIRQP PGKGLQWIGY IYYTGITNYN  60
PSLKSRVTMS LDTSKNQISL KMDSVTAADT ALYFCARGDY SGYDRDVQVE LMDVWGKGTT  120
VTVSSSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGKRRRRR RRRRRRRRRR RRRRRRRRRR RRRRR       475

SEQ ID NO: 269         moltype = AA  length = 451
FEATURE                Location/Qualifiers
source                 1..451
                       mol_type = protein
                       organism = synthetic construct
SEQUENCE: 269
QVQLQESGPG LVRPSETLSL TCTVSGDSIG GSYWNWIRQP PGKGLQWIGY IYYTGITNYN  60
PSLKSRVTMS LDTSKNQISL KMDSVTAADT ALYFCARGDY SGYDRDVQVE LMDVWGKGTT  120
VTVSSSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGKOOOOO O                                451

SEQ ID NO: 270         moltype = AA  length = 457
FEATURE                Location/Qualifiers
source                 1..457
                       mol_type = protein
                       organism = synthetic construct
```

```
SEQUENCE: 270
QVQLQESGPG LVRPSETLSL TCTVSGDSIG GSYWNWIRQP PGKGLQWIGY IYYTGITNYN  60
PSLKSRVTMS LDTSKNQISL KMDSVTAADT ALYFCARGDY SGYDRDVQVE LMDVWGKGTT  120
VTVSSSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGKOOOOO OOOOOOO                          457

SEQ ID NO: 271          moltype = AA  length = 475
FEATURE                 Location/Qualifiers
source                  1..475
                        mol_type = protein
                        organism = synthetic construct
SEQUENCE: 271
QVQLQESGPG LVRPSETLSL TCTVSGDSIG GSYWNWIRQP PGKGLQWIGY IYYTGITNYN  60
PSLKSRVTMS LDTSKNQISL KMDSVTAADT ALYFCARGDY SGYDRDVQVE LMDVWGKGTT  120
VTVSSSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGKOOOOO OOOOOOOOOO OOOOOOOOOO OOOOO      475

SEQ ID NO: 272          moltype = AA  length = 451
FEATURE                 Location/Qualifiers
source                  1..451
                        mol_type = protein
                        organism = synthetic construct
SEQUENCE: 272
QVQLQESGPG LVRPSETLSL TCTVSGDSIG GSYWNWIRQP PGKGLQWIGY IYYTGITNYN  60
PSLKSRVTMS LDTSKNQISL KMDSVTAADT ALYFCARGDY SGYDRDVQVE LMDVWGKGTT  120
VTVSSSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGKKKHHR R                                451

SEQ ID NO: 273          moltype = AA  length = 457
FEATURE                 Location/Qualifiers
source                  1..457
                        mol_type = protein
                        organism = synthetic construct
SEQUENCE: 273
QVQLQESGPG LVRPSETLSL TCTVSGDSIG GSYWNWIRQP PGKGLQWIGY IYYTGITNYN  60
PSLKSRVTMS LDTSKNQISL KMDSVTAADT ALYFCARGDY SGYDRDVQVE LMDVWGKGTT  120
VTVSSSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGKKKRRO OHHHRRR                          457

SEQ ID NO: 274          moltype = AA  length = 475
FEATURE                 Location/Qualifiers
source                  1..475
                        mol_type = protein
                        organism = synthetic construct
SEQUENCE: 274
QVQLQESGPG LVRPSETLSL TCTVSGDSIG GSYWNWIRQP PGKGLQWIGY IYYTGITNYN  60
PSLKSRVTMS LDTSKNQISL KMDSVTAADT ALYFCARGDY SGYDRDVQVE LMDVWGKGTT  120
VTVSSSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGKHKROH KROHKROHKR OHKROHKROH KROHK      475

SEQ ID NO: 275          moltype = AA  length = 456
FEATURE                 Location/Qualifiers
source                  1..456
                        mol_type = protein
                        organism = synthetic construct
SEQUENCE: 275
EVQLVQSGAE VKKPGSSVKV SCKASGYTFI NHALSWVRQA PGQGLEWVGG IIPIFGLAKY  60
GQKFQDRVTI TADESTKTAY MDLRSLRSDD TAVYYCARDT VAVYEDFDWS SPYFFYMDVW  120
GKGTTVTVSS SVFPLAPSSK STSGGTAALG CLVKDYFPEP VTVSWNSGAL TSGVHTFPAV  180
```

```
LQSSGLYSLS SVVTVPSSSL GTQTYICNVN HKPSNTKVDK RVEPKSCTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK HHHHHH                           456

SEQ ID NO: 276          moltype = AA  length = 214
FEATURE                 Location/Qualifiers
source                  1..214
                        mol_type = protein
                        organism = synthetic construct
SEQUENCE: 276
EIVLTQSPAT LSLFPGERAT LSCRASQSAG SKSLAWYQHK VGQPPRLLIN GASSRATGIP  60
DRFSGSGSGP DFNLTISRLE PEDFAVYYCQ RYGTSLVTFG GGTKVEIKGQ PKANPTVTLF  120
PPSSEELQAN KATLVCLISD FYPGAVTVAW KADGSPVKAG VETTKPSKQS NNKYAASSYL  180
SLTPEQWKSH RSYSCQVTHE GSTVEKTVAP TECS                             214

SEQ ID NO: 277          moltype = AA  length = 462
FEATURE                 Location/Qualifiers
source                  1..462
                        mol_type = protein
                        organism = synthetic construct
SEQUENCE: 277
EVQLVQSGAE VKKPGSSVKV SCKASGYTFI NHALSWVRQA PGQGLEWVGG IIPIFGLAKY  60
GQKFQDRVTI TADESTKTAY MDLRSLRSDD TAVYYCARDT VAVYEDFDWS SPYFFYMDVW  120
GKGTTVTVSS SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK RVEPKSCTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK HHHHHHHHHH HH                    462

SEQ ID NO: 278          moltype = AA  length = 480
FEATURE                 Location/Qualifiers
source                  1..480
                        mol_type = protein
                        organism = synthetic construct
SEQUENCE: 278
EVQLVQSGAE VKKPGSSVKV SCKASGYTFI NHALSWVRQA PGQGLEWVGG IIPIFGLAKY  60
GQKFQDRVTI TADESTKTAY MDLRSLRSDD TAVYYCARDT VAVYEDFDWS SPYFFYMDVW  120
GKGTTVTVSS SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK RVEPKSCTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK HHHHHHHHHH HHHHHHHHHH HHHHHHHHHH  480

SEQ ID NO: 279          moltype = AA  length = 456
FEATURE                 Location/Qualifiers
source                  1..456
                        mol_type = protein
                        organism = synthetic construct
SEQUENCE: 279
EVQLVQSGAE VKKPGSSVKV SCKASGYTFI NHALSWVRQA PGQGLEWVGG IIPIFGLAKY  60
GQKFQDRVTI TADESTKTAY MDLRSLRSDD TAVYYCARDT VAVYEDFDWS SPYFFYMDVW  120
GKGTTVTVSS SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK RVEPKSCTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK KKKKKK                           456

SEQ ID NO: 280          moltype = AA  length = 467
FEATURE                 Location/Qualifiers
source                  1..467
                        mol_type = protein
                        organism = synthetic construct
SEQUENCE: 280
EVQLVQSGAE VKKPGSSVKV SCKASGYTFI NHALSWVRQA PGQGLEWVGG IIPIFGLAKY  60
GQKFQDRVTI TADESTKTAY MDLRSLRSDD TAVYYCARDT VAVYEDFDWS SPYFFYMDVW  120
GKGTTVTVSS SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK RVEPKSCTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK GGGGSKKKKK KKKKKKK                467

SEQ ID NO: 281          moltype = AA  length = 480
FEATURE                 Location/Qualifiers
```

```
source                  1..480
                        mol_type = protein
                        organism = synthetic construct
SEQUENCE: 281
EVQLVQSGAE VKKPGSSVKV SCKASGYTFI NHALSWVRQA PGQGLEWVGG IIPIFGLAKY  60
GQKFQDRVTI TADESTKTAY MDLRSLRSDD TAVYYCARDT VAVYEDFDWS SPYFFYMDVW  120
GKGTTVTVSS SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK RVEPKSCTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK KKKKKKKKKK KKKKKKKKKK KKKKKKKKKK  480

SEQ ID NO: 282          moltype = AA  length = 457
FEATURE                 Location/Qualifiers
source                  1..457
                        mol_type = protein
                        organism = synthetic construct
SEQUENCE: 282
EVQLVQSGAE VKKPGSSVKV SCKASGYTFI NHALSWVRQA PGQGLEWVGG IIPIFGLAKY  60
GQKFQDRVTI TADESTKTAY MDLRSLRSDD TAVYYCARDT VAVYEDFDWS SPYFFYMDVW  120
GKGTTVTVSS ASVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KRRRRRR                         457

SEQ ID NO: 283          moltype = AA  length = 462
FEATURE                 Location/Qualifiers
source                  1..462
                        mol_type = protein
                        organism = synthetic construct
SEQUENCE: 283
EVQLVQSGAE VKKPGSSVKV SCKASGYTFI NHALSWVRQA PGQGLEWVGG IIPIFGLAKY  60
GQKFQDRVTI TADESTKTAY MDLRSLRSDD TAVYYCARDT VAVYEDFDWS SPYFFYMDVW  120
GKGTTVTVSS SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK RVEPKSCTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK RRRRRRRRRR RR                    462

SEQ ID NO: 284          moltype = AA  length = 480
FEATURE                 Location/Qualifiers
source                  1..480
                        mol_type = protein
                        organism = synthetic construct
SEQUENCE: 284
EVQLVQSGAE VKKPGSSVKV SCKASGYTFI NHALSWVRQA PGQGLEWVGG IIPIFGLAKY  60
GQKFQDRVTI TADESTKTAY MDLRSLRSDD TAVYYCARDT VAVYEDFDWS SPYFFYMDVW  120
GKGTTVTVSS SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK RVEPKSCTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK RRRRRRRRRR RRRRRRRRRR RRRRRRRRRR  480

SEQ ID NO: 285          moltype = AA  length = 456
FEATURE                 Location/Qualifiers
source                  1..456
                        mol_type = protein
                        organism = synthetic construct
SEQUENCE: 285
EVQLVQSGAE VKKPGSSVKV SCKASGYTFI NHALSWVRQA PGQGLEWVGG IIPIFGLAKY  60
GQKFQDRVTI TADESTKTAY MDLRSLRSDD TAVYYCARDT VAVYEDFDWS SPYFFYMDVW  120
GKGTTVTVSS SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK RVEPKSCTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK OOOOOO                        456

SEQ ID NO: 286          moltype = AA  length = 462
FEATURE                 Location/Qualifiers
source                  1..462
                        mol_type = protein
                        organism = synthetic construct
SEQUENCE: 286
```

```
EVQLVQSGAE VKKPGSSVKV SCKASGYTFI NHALSWVRQA PGQGLEWVGG IIPIFGLAKY  60
GQKFQDRVTI TADESTKTAY MDLRSLRSDD TAVYYCARDT VAVYEDFDWS SPYFFYMDVW  120
GKGTTVTVSS SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK RVEPKSCTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK OOOOOOOOOO OO                   462

SEQ ID NO: 287          moltype = AA  length = 480
FEATURE                 Location/Qualifiers
source                  1..480
                        mol_type = protein
                        organism = synthetic construct
SEQUENCE: 287
EVQLVQSGAE VKKPGSSVKV SCKASGYTFI NHALSWVRQA PGQGLEWVGG IIPIFGLAKY  60
GQKFQDRVTI TADESTKTAY MDLRSLRSDD TAVYYCARDT VAVYEDFDWS SPYFFYMDVW  120
GKGTTVTVSS SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK RVEPKSCTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK OOOOOOOOOO OOOOOOOOOO OOOOOOOOOO  480

SEQ ID NO: 288          moltype = AA  length = 455
FEATURE                 Location/Qualifiers
source                  1..455
                        mol_type = protein
                        organism = synthetic construct
SEQUENCE: 288
EVQLVQSGAE VKKPGSSVKV SCKASGYTFI NHALSWVRQA PGQGLEWVGG IIPIFGLAKY  60
GQKFQDRVTI TADESTKTAY MDLRSLRSDD TAVYYCARDT VAVYEDFDWS SPYFFYMDVW  120
GKGTTVTVSS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKO ORRHH                            455

SEQ ID NO: 289          moltype = AA  length = 462
FEATURE                 Location/Qualifiers
source                  1..462
                        mol_type = protein
                        organism = synthetic construct
SEQUENCE: 289
EVQLVQSGAE VKKPGSSVKV SCKASGYTFI NHALSWVRQA PGQGLEWVGG IIPIFGLAKY  60
GQKFQDRVTI TADESTKTAY MDLRSLRSDD TAVYYCARDT VAVYEDFDWS SPYFFYMDVW  120
GKGTTVTVSS SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK RVEPKSCTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK OOORRRKKKH HH                   462

SEQ ID NO: 290          moltype = AA  length = 481
FEATURE                 Location/Qualifiers
source                  1..481
                        mol_type = protein
                        organism = synthetic construct
SEQUENCE: 290
EVQLVQSGAE VKKPGSSVKV SCKASGYTFI NHALSWVRQA PGQGLEWVGG IIPIFGLAKY  60
GQKFQDRVTI TADESTKTAY MDLRSLRSDD TAVYYCARDT VAVYEDFDWS SPYFFYMDVW  120
GKGTTVTVSS ASVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KHKROHKROH KROHKROHKR OHKROHKROH  480
K                                                                 481

SEQ ID NO: 291          moltype = AA  length = 6
FEATURE                 Location/Qualifiers
source                  1..6
                        mol_type = protein
                        organism = synthetic construct
SEQUENCE: 291
HHHHHH                                                            6

SEQ ID NO: 292          moltype = AA  length = 12
```

```
FEATURE                Location/Qualifiers
source                 1..12
                       mol_type = protein
                       organism = synthetic construct
SEQUENCE: 292
HHHHHHHHHH HH                                                      12

SEQ ID NO: 293         moltype = AA  length = 30
FEATURE                Location/Qualifiers
source                 1..30
                       mol_type = protein
                       organism = synthetic construct
SEQUENCE: 293
HHHHHHHHHH HHHHHHHHHH HHHHHHHHHH                                   30

SEQ ID NO: 294         moltype = AA  length = 6
FEATURE                Location/Qualifiers
source                 1..6
                       mol_type = protein
                       organism = synthetic construct
SEQUENCE: 294
KKKKKK                                                             6

SEQ ID NO: 295         moltype = AA  length = 12
FEATURE                Location/Qualifiers
source                 1..12
                       mol_type = protein
                       organism = synthetic construct
SEQUENCE: 295
KKKKKKKKKK KK                                                      12

SEQ ID NO: 296         moltype = AA  length = 30
FEATURE                Location/Qualifiers
source                 1..30
                       mol_type = protein
                       organism = synthetic construct
SEQUENCE: 296
KKKKKKKKKK KKKKKKKKKK KKKKKKKKKK                                   30

SEQ ID NO: 297         moltype = AA  length = 6
FEATURE                Location/Qualifiers
source                 1..6
                       mol_type = protein
                       organism = synthetic construct
SEQUENCE: 297
RRRRRR                                                             6

SEQ ID NO: 298         moltype = AA  length = 12
FEATURE                Location/Qualifiers
source                 1..12
                       mol_type = protein
                       organism = synthetic construct
SEQUENCE: 298
RRRRRRRRRR RR                                                      12

SEQ ID NO: 299         moltype = AA  length = 30
FEATURE                Location/Qualifiers
source                 1..30
                       mol_type = protein
                       organism = synthetic construct
SEQUENCE: 299
RRRRRRRRRR RRRRRRRRRR RRRRRRRRRR                                   30

SEQ ID NO: 300         moltype = AA  length = 6
FEATURE                Location/Qualifiers
source                 1..6
                       mol_type = protein
                       organism = synthetic construct
SEQUENCE: 300
OOOOOO                                                             6

SEQ ID NO: 301         moltype = AA  length = 12
FEATURE                Location/Qualifiers
source                 1..12
                       mol_type = protein
                       organism = synthetic construct
SEQUENCE: 301
OOOOOOOOOO OO                                                      12
```

```
SEQ ID NO: 302          moltype = AA  length = 30
FEATURE                 Location/Qualifiers
source                  1..30
                        mol_type = protein
                        organism = synthetic construct
SEQUENCE: 302
OOOOOOOOOO OOOOOOOOOO OOOOOOOOOO                                     30

SEQ ID NO: 303          moltype = AA  length = 6
FEATURE                 Location/Qualifiers
source                  1..6
                        mol_type = protein
                        organism = synthetic construct
SEQUENCE: 303
HHKKOO                                                               6

SEQ ID NO: 304          moltype = AA  length = 6
FEATURE                 Location/Qualifiers
source                  1..6
                        mol_type = protein
                        organism = synthetic construct
SEQUENCE: 304
HORKHR                                                               6

SEQ ID NO: 305          moltype = AA  length = 6
FEATURE                 Location/Qualifiers
source                  1..6
                        mol_type = protein
                        organism = synthetic construct
SEQUENCE: 305
HKRSOH                                                               6

SEQ ID NO: 306          moltype = AA  length = 6
FEATURE                 Location/Qualifiers
source                  1..6
                        mol_type = protein
                        organism = synthetic construct
SEQUENCE: 306
RRHTHR                                                               6

SEQ ID NO: 307          moltype = AA  length = 6
FEATURE                 Location/Qualifiers
source                  1..6
                        mol_type = protein
                        organism = synthetic construct
SEQUENCE: 307
KKOORR                                                               6

SEQ ID NO: 308          moltype = AA  length = 6
FEATURE                 Location/Qualifiers
source                  1..6
                        mol_type = protein
                        organism = synthetic construct
SEQUENCE: 308
KKHHRR                                                               6

SEQ ID NO: 309          moltype = AA  length = 6
FEATURE                 Location/Qualifiers
source                  1..6
                        mol_type = protein
                        organism = synthetic construct
SEQUENCE: 309
OORRHH                                                               6

SEQ ID NO: 310          moltype = AA  length = 12
FEATURE                 Location/Qualifiers
source                  1..12
                        mol_type = protein
                        organism = synthetic construct
SEQUENCE: 310
HHHKKKRRRO OO                                                        12

SEQ ID NO: 311          moltype = AA  length = 12
FEATURE                 Location/Qualifiers
source                  1..12
                        mol_type = protein
                        organism = synthetic construct
SEQUENCE: 311
HHOAKKRCOO QH                                                        12
```

```
SEQ ID NO: 312          moltype = AA  length = 12
FEATURE                 Location/Qualifiers
source                  1..12
                        mol_type = protein
                        organism = synthetic construct
SEQUENCE: 312
HRKOORKHHR KK                                                     12

SEQ ID NO: 313          moltype = AA  length = 12
FEATURE                 Location/Qualifiers
source                  1..12
                        mol_type = protein
                        organism = synthetic construct
SEQUENCE: 313
KRAHOKCORK SH                                                     12

SEQ ID NO: 314          moltype = AA  length = 12
FEATURE                 Location/Qualifiers
source                  1..12
                        mol_type = protein
                        organism = synthetic construct
SEQUENCE: 314
KKRROOHHHR RR                                                     12

SEQ ID NO: 315          moltype = AA  length = 12
FEATURE                 Location/Qualifiers
source                  1..12
                        mol_type = protein
                        organism = synthetic construct
SEQUENCE: 315
OOORRRKKKH HH                                                     12

SEQ ID NO: 316          moltype = AA  length = 30
FEATURE                 Location/Qualifiers
source                  1..30
                        mol_type = protein
                        organism = synthetic construct
SEQUENCE: 316
HKROHKROHK ROHKROHKRO HKROHKROHK                                  30

SEQ ID NO: 317          moltype = AA  length = 30
FEATURE                 Location/Qualifiers
source                  1..30
                        mol_type = protein
                        organism = synthetic construct
SEQUENCE: 317
KOHRSOKRHT ORHKAHORKC KROKQRKHOS                                  30

SEQ ID NO: 318          moltype = AA  length = 30
FEATURE                 Location/Qualifiers
source                  1..30
                        mol_type = protein
                        organism = synthetic construct
SEQUENCE: 318
KKROSRRHOT OOHHAROKHC KHROTRHKKS                                  30

SEQ ID NO: 319          moltype = AA  length = 30
FEATURE                 Location/Qualifiers
source                  1..30
                        mol_type = protein
                        organism = synthetic construct
SEQUENCE: 319
HRKQOHRSOO KTRRRAHROC HHHSRHOTHR                                  30

SEQ ID NO: 320          moltype = AA  length = 35
FEATURE                 Location/Qualifiers
source                  1..35
                        mol_type = protein
                        organism = synthetic construct
SEQUENCE: 320
GRHKAKNHIR RPKSRWKKWH KYRKVHRHKV HKGRR                            35

SEQ ID NO: 321          moltype = AA  length = 40
FEATURE                 Location/Qualifiers
source                  1..40
                        mol_type = protein
                        organism = synthetic construct
SEQUENCE: 321
```

```
WRKVHHYKKQ HKNRAHGKLK LRAKIHQRSR MHGKQKHYHR                   40

SEQ ID NO: 322          moltype = AA  length = 42
FEATURE                 Location/Qualifiers
source                  1..42
                        mol_type = protein
                        organism = synthetic construct
SEQUENCE: 322
AHHKCRRGHK QKILHRRPHK FHRWKRVHKG RHGKKHRRHK HR                 42

SEQ ID NO: 323          moltype = AA  length = 45
FEATURE                 Location/Qualifiers
source                  1..45
                        mol_type = protein
                        organism = synthetic construct
SEQUENCE: 323
QHRGKAKYHR THHVKKQRHG RKNHKVHRHA RKFHKIRRLK CHKKH              45

SEQ ID NO: 324          moltype = AA  length = 50
FEATURE                 Location/Qualifiers
source                  1..50
                        mol_type = protein
                        organism = synthetic construct
SEQUENCE: 324
HNKRFKKGRH VRHSRHKSHR RTHKYHHWRH YRKVHRCKKA HKSHHRVHHK         50

SEQ ID NO: 325          moltype = AA  length = 50
FEATURE                 Location/Qualifiers
source                  1..50
                        mol_type = protein
                        organism = synthetic construct
SEQUENCE: 325
AHGRPHOFKR OCKAHOVKHI LKRTOSHOYK OVHQRNKOAO KMRKIRGGHK         50

SEQ ID NO: 326          moltype = AA  length = 566
FEATURE                 Location/Qualifiers
source                  1..566
                        mol_type = protein
                        organism = Influenza A virus
SEQUENCE: 326
MKTIIALSCI LCLVFAQKIP GNDNSTATLC LGHHAVPNGT IVKTITDDRI EVTNATELVQ  60
NSSIGEICDS PHQILDGENC TLIDALLGDP QCDGFQNKKW DLFVERNKAY SNCYPYDVPD  120
YASLRSLVAS SGTLEFNNES FNWAGVTQNG TSSSCIRGSK SSFFSRLNWL THLNSKYPAL  180
NVTMPNNEQF DKLYIWGVHH PGTDKDQISL YAQSSGRITV STKRSQQAVI PNIGSRPRIR  240
DIPSRISIYW TIVKPGDILL INSTGNLIAP RGYFKIRSGK SSIMRSDAPI GKCKSECITP  300
NGSIPNDKPF QNVNRITYGA CPRYVKQSTL KLATGMRNVP ERQTRGIFGA IAGFIENGWE  360
GLVDGWYGFR HQNSEGRGQA ADLKSTQAAI DQINGKLNRL IGKTNEKFHQ IEKEFSEVEG  420
RIQDLEKYVE DTKIDLWSYN AELLVALENQ HTIDLTDSEM NKLFEKTKKQ LRENAEDMGN  480
GCFKIYHKCD NACMGSIRNG TYDHNVYRDE ALNNRFQIKG VELKSGYKDW ILWISFAISC  540
FLLCVVLLGF IMWACQKGNI RCNICI                                   566

SEQ ID NO: 327          moltype = AA  length = 469
FEATURE                 Location/Qualifiers
source                  1..469
                        mol_type = protein
                        organism = Influenza A virus
SEQUENCE: 327
MNPNQKIITI GSICMTIGMA NLILQIGNII SIWVSHSIQI GNQSQIETCN KSVITYENNT  60
WVNQTYVNIS NTNSAARQSV ASVKLAGNSS LCPVSGWAIY SKDNSVRIGS KGDVFVIREP  120
FISCSPLECR TFFLTQGALL NDKHSNGTIK DRSPYRTLMS CPIGEVPSPY NSRFESVAWS  180
ASACHDGTNW LTIGVSGPDS GAVAVLKYNG IITDTIKSWR NNILRTQESE CACVNGSCFT  240
IMTDGPSDGQ ASYKIFRIEK GKIIKSVEMK APNYHYEECS CYPDSSEITC VCRDNWHGSN  300
RPWVSFNQNL EYQMGYICSG VFGDNPRPND KTGSCGPVSS NGANGVKGFA FKYGNGVWIG  360
RTKSISSRKG FEMIWDPNGW TGTDNKFSKK QDIVGINEWS GYSGSFVQHP ELTGLNCIRP  420
CFWVELIRGR PEENTIWTSG SSISFCGVDS DIVGWSWPDG AELPFTIDK          469

SEQ ID NO: 328          moltype = AA  length = 546
FEATURE                 Location/Qualifiers
source                  1..546
                        mol_type = protein
                        organism = Influenza A virus
SEQUENCE: 328
VFAQKIPGND NSTATLCLGH HAVPNGTIVK TITNDRIEVT NATELVQNSS IGEICDSPHL  60
ILDGKNCTLI DALLGDPQCD GFQNKKWDLF VERSKAYSNC YPYDVPDYAS LRSLVASSGT  120
LEFNNESFNW TGVKQNGTSS ACIRKSSSSF FSRLNWLTHL NYTYPALNVT MPNNEQFDKL  180
YIWGVHHPGT DKDQIFLYAQ SSGRITVSTK RSQQTVIPNI GSRPRIRDIP SRISIYWTIV  240
KPGDILLINS TGNLIAPRGY FKIQSGKSSI MRSDAPIGKC KSECITPNGS IPNDKPFQNV  300
NRITYGTCPR YVKHSTLKLA TGMRNVPEKQ TRGIFGAIAG FIENGWEGMV DGWYGFRHQN  360
SEGRGQAADL KSTQAAIDQI NGKLNRLIGK TNEKFHQIEK EFSEVEGRIQ DLEKYVEDTK  420
```

```
IDLWSYNAEL LVALENQHTI DLTDSEMNKL FEKTKKQLRE NAEDMGNGCF KIYHKCDNAC  480
IGSIRNGTYD HNVYRDEALN NRFQIKGVEL KSGYKDWILW ISFAISCFLL CVALLGFIMW  540
ACQKGN                                                            546

SEQ ID NO: 329         moltype = AA  length = 442
FEATURE                Location/Qualifiers
source                 1..442
                       mol_type = protein
                       organism = Influenza A virus
SEQUENCE: 329
SLTISTICFF MQIAILITTV TLHFKQYEFN SPPNNQVMLC EPTIIERNIT EIVYLTNTTI  60
EKEICLKPAE YRNWSKPQCG ITGFAPFSKD NSIRLSAGGD IWVTREPYVS CDPDKCYQFA  120
LGQGTTLNNV HSNNTVRDRT PYRTLLMNEL GVPFHLGTKQ VCMAWSSSSC HDGKAWLHVC  180
ITGDDKNATA SFIYNGRLVD SVVSWSKDIL RTQESECVCI NGTCTVVMTD GNATGKADTK  240
ILFIEEGKIV HTSKLSGSAQ HVEECSCYPR YPGVRCVCRD NWKGSNRPIV DINIKDHSIV  300
SSYVCSGLVG DTPRKSDSSS SSHCLNPNNE EGGHGVKGWA FDDGNDVWMG RTINETSRLG  360
YETFKVVEGW SNSKSKLQIN RQVIVDRGDR SGYSGIFSVE GKSCINRCFY VELIRGRKEE  420
TEVLWTSNSI VVFCGTSGTY GT                                          442

SEQ ID NO: 330         moltype = AA  length = 566
FEATURE                Location/Qualifiers
source                 1..566
                       mol_type = protein
                       organism = Influenza A virus
SEQUENCE: 330
MKTIIALSCI LCLVFAQKIP GNDNSTATLC LGHHAVPNGT IVKTITNDRI EVTNATELVQ  60
NSSIGEICDS PHQILDGENC TLIDALLGDP QCDGFQNKKW DLFVERNKAY SNCYPYDVPD  120
YASLRSLVAS SGTLEFNNES FNWAGVTQNG TSSSCIRGSK SSFFSRLNWL THLNSKYPAL  180
NVTMPNNEQF DKLYIWGVHH PGTDKDQTSL YAQSSGRITV STKRSQQAVI PNIGSRPRIR  240
DIPSRISIYW TIVKPGDILL INSTGNLIAP RGYFKIRSGK SSIMKSDAPI GKCKSECITP  300
NGSIPNDKPF QNVNRITYGA CPRYVKQSTL KLATGMRNVP EKQTRGIFGA IAGFIENGWE  360
GLVDGWYGFR HQNSEGRGQA ADLKSTQAAI DQINGKLNRL IGKTNEKFHQ IEKEFSEVEG  420
RIQDLEKYVE DTKIDLWSYN AELLVALENQ HTIDLTDSEM NKLFEKTKKQ LRENAEDMGN  480
GCFKIYHKCD NACMGSIRNG TYDHNVYRDE ALNNRFQIKG VELKSGYKDW ILWISFAISC  540
FLLCVVLLGF IMWACQKGNI RCNICI                                      566

SEQ ID NO: 331         moltype = AA  length = 469
FEATURE                Location/Qualifiers
source                 1..469
                       mol_type = protein
                       organism = Influenza A virus
SEQUENCE: 331
MNPNQKIITI SSVSLTISTI CFFMQIAILI TTVTLHFKQY EFNPPPNNQV MLCEPTIIER  60
NITEIVYLTN TTIEREICPK PAEYRNWSKP QCGITGFAPF SKDNSIRLSA GGDIWVTREP  120
YVSCDPDKCY QFALGQGTTI NNVHSNNTAR DRTPHRTLLM SELGVPFHLG TKQVCIAWSS  180
SSCHDGKAWL HVCITGDDKN ATASFIYNGR LVDSVVSWSK DILRTQESEC VCINGTCTVV  240
MTDGNATGKA DTKILFIEEG KIVHTSKLSG SAQHVEECSC YPRYPGVRCV CRDNWKGSNR  300
PIVDINIKDH SIVSSYVCSG LVGDTPRKTD SSSSSHCLNP NNEKGGHGVK GWAFDDGNDV  360
WMGRTINETS RLGYETFKVV EGWSNSKSKL QINRQVIVDR GDRSGYSGIF SVEGKSCINR  420
CFYVELIRGR KEETEVLWTS NSIVVFCGTS GTYGTGSWPD GADLNLMHI              469

SEQ ID NO: 332         moltype = AA  length = 469
FEATURE                Location/Qualifiers
source                 1..469
                       mol_type = protein
                       organism = Influenza A virus
SEQUENCE: 332
MNPNQKIITI GSICMTIGTA NLILQIGNII SIWVSHSIQI GNQSQIETCN KSVITYENNT  60
WVNQTFVNIS NTNSAARQSV ASVKLAGNSS LCPVSGWAIY SKDNSVRIGS KGDVFVIREP  120
FISCSPLECR TFFLTQGALL NDKHSNGTIK DRSPYRTLMS CPIGEVPSPY NSRFESVAWS  180
ASACHDGTNW LTIGISGPDS GAVAVLKYNG IITDTIKSWR NKILRTQESE CACVNGSCFT  240
IMTDGPSDGQ ASYKIFRIEK GKIIKSVEMK APNYHYEECS CYPDSSEITC VCRDNWHGSN  300
RPWVSFNQNL EYQMGYICSG VFGDNPRPND KTGSCGPVSS NGANGVKGFS FKYGNGVWIG  360
RTKSISSRKG FEMIWDPNGW TGTDNKFSKK QDIVGINEWS GYSGSFVQHP ELTGLNCIRP  420
CFWVELIRGR PEENTIWTSG SSISFCGVDS DIVGWSWPDG AELPFTIDK              469

SEQ ID NO: 333         moltype = AA  length = 469
FEATURE                Location/Qualifiers
source                 1..469
                       mol_type = protein
                       organism = Influenza A virus
SEQUENCE: 333
MNPNQKIITI GSICMTIGMA NLILQIGNII SIWVSHSIQT GNQSQIETCN KNVITYENNT  60
WVNQTYVNIS NTNSAARQSV ASVKLAGNSS LCPVSGWAIY SKDNSVRIGS KGDVFVIREP  120
FISCSPLECR TFFLTQGALL NDKHSNGTIK DRSPYRTLMS CPIGEVPSPY NSRFESVAWS  180
ASACHDGTNW LTIGISGPDS GAVAVLKYNG IITDTIKSWR NNILRTQESE CACVNGSCFT  240
MMTDGPSDGQ ASYKIFRIEK GKIIKSVEMK APNYHYEECS CYPDSSEITC VCRDNWHGSN  300
RPWVSFNQNL EYQMGYICSG VFGDNPRPND KTGSCGPVSS NGANGVKGFS FKYGNGVWIG  360
RTKSISSRKG FEMIWDPNGW TGTDNKFSKK QDIVGINEWS GYSGSFVQHP ELTGLNCIRP  420
```

```
CFWVELIRGR PEENTIWTSG SSISFCGVDS DIVGWSWPDG AELPFTIDK              469

SEQ ID NO: 334          moltype = AA  length = 583
FEATURE                 Location/Qualifiers
source                  1..583
                        mol_type = protein
                        organism = Influenza B virus
SEQUENCE: 334
MKAIIVLLMV VTSNADRICT GITSSNSPHV VKTATQGEVN VTGVIPLTTT PTKSHFANLK  60
GTETRGKLCP KCLNCTDLDV ALGRPKCTGK IPSARVSILH EVRPVTSGCF PIMHDRTKIR  120
QLPNLLRGYE HVRLSTHNVI NAEGAPGGPY KIGTSGSCPN ITNGNGFFAT MAWAVPDKNK  180
TATNPLTIEV PYVCTEGEDQ ITVWGFHSDN ETQMAKLYGD SKPQKFTSSA NGVTTHYVSQ  240
IGGFPNQTED GGLPQSGRIV VDYMVQKSGK TGTITYQRGI LLPQKVWCAX GRSKVIKGSL  300
PLIGEADCLH EKYGGLNKSK PYYTGEHAKA IGNCPIWVKT PLKLANGTKY RPPAKLLKER  360
GFFGAIAGFL EGGWEGMIAG WHGYTSHGAH GVAVAADLKS TQEAINKITK NLNSLSELEV  420
KNLQRLSGAM DELHNEILEL DEKVDDLRAD TISSQIELAV LLSNEGIINS EDEHLLALER  480
KLKKMLGPSA VEIGNGCFET KHKCNQTCLD KIAAGTFDAG EFSLPTFDSL NITAASLNDD  540
GLDNHTILLY YSTAASSLAV TLMIAIFVVY MVSRDNVSCS ICL                    583

SEQ ID NO: 335          moltype = AA  length = 466
FEATURE                 Location/Qualifiers
source                  1..466
                        mol_type = protein
                        organism = Influenza B virus
SEQUENCE: 335
MLPSTIQTLT LFLTSGGVLL SLYVSASLSY LLYSDILLKF SPTEITAPTM PLDCANASNV  60
QAVNRSATKG VILLLPEPEW TYPRLSCPGS TFQKALLISP HRFGETKGNS APLIIREPFV  120
ACGPNECKHF ALTHYAAQPG GYYNGTRGDR NKLRHLISVK LGKIPTVENS IFHMAAWSGS  180
ACHDGKEWTY IGVDGPDNNA LLKIKYGEAY TDTYHSYANN ILRTQESACN CIGGNCYLMI  240
TDGSXSGVSE CRFLKIREGR IIKEIFPTGR VKHTEECTCG FASNKTIECA CRDNRYTAKR  300
PFVKLNVETD TAEIRLMCTD TYLDTPRPND GSITGPCESD GDKGSGGIKG GFVHQRMKSK  360
IGRWYSRTMS QTERMGMGLY VKYGGDPWAD SDALAFSGVM VSMKEPGWYS FGFEIKDKKC  420
DVPCIGIEMV HDGGKETWHS AATAIYCLMG SGQLLWDTVT GVDMAL                 466

SEQ ID NO: 336          moltype = AA  length = 585
FEATURE                 Location/Qualifiers
source                  1..585
                        mol_type = protein
                        organism = Influenza B virus
SEQUENCE: 336
MKAIIVLLMV VTSNADRICT GITSSNSPHV VKTATQGEVN VTGVIPLTTT PTKSHFANLK  60
GTETRGKLCP KCLNCTDLDV ALGRPKCTGK IPSARVSILH EVRPVTSGCF PIMHDRTKIR  120
QLPNLLRGYE HVRLSTHNVI NAEDAPGGPY KIGTSGSCPN ITNGNGFFAT MAWAVPKNDK  180
NKTATNPLTI EVPYICTEGE DQITVWGFHS DNETQMAKLY GDSKPQKFTS SANGVTTHYV  240
SQIGGFPNQT EDGGLPQSGR IVVDYMVQKS GKTGTITYQR GILLPQKVWC ASGRSKVIKG  300
SLPLIGEADC LHEKYGGLNK SKPYYTGEHA KAIGNCPIWV KTPLKLANGT KYRPPAKLLK  360
ERGFFGAIAG FLEGGWEGMI AGWHGYTSHG AHGIAVAADL KSTQEAINKI TKNLNSLSEL  420
EVKNLQRLSG AMDELHNEIL ELDEKVDDLR ADTISSQIEL AVLLSNEGII NSEDEHLLAL  480
ERKLKKMLGP SAVEIGNGCF ETKHKCNQTC LDRIAAGTFD AGEFSLPTFD SLNITAASLN  540
DDGLDNHTIL LYYSTAASSL AVTLMIAIFV VYMVSRDNVS CSICL                  585

SEQ ID NO: 337          moltype = AA  length = 466
FEATURE                 Location/Qualifiers
source                  1..466
                        mol_type = protein
                        organism = Influenza B virus
SEQUENCE: 337
MLPSTIQTLT LFLTSGGVLL SLYVSASLSY LLYSDILLKF SPTEITAPTM PLDCANASNV  60
QAVNRSATKG ATLLLPEPEW TYPRLSCPGS TFQKALLISP HRFGETKGNS APLIIREPFV  120
ACGPNECKHF ALTHYAAQPG GYYNGTRGDR NKLRHLISVK LGKIPTVENS IFHMAAWSGS  180
ACHDGKEWTY IGVDGPDNNA LLKVKYGEAY TDTYHSYANN ILRTQESACN CIGGNCYLMI  240
TDGSASGVSE CRFLKIREGR IIKEIFPTGR VKHTEECTCG FASNKTIECA CRDNRYTAKR  300
PFVKLNVETD TAEIRLMCTD TYLDTPRPND GSITGPCESD GDEGSGGIKG GFVHQRMKSK  360
IGRWYSRTMS KTERMGMGLY VKYGGDPWAD SDALVFSGVM ISMKEPGWYS FGFEIKDKKC  420
DVPCIGIEMV HDGGKETWHS AATAIYCLMG SGQLLWDTVT GVDMAL                 466

SEQ ID NO: 338          moltype = AA  length = 582
FEATURE                 Location/Qualifiers
source                  1..582
                        mol_type = protein
                        organism = Influenza B virus
SEQUENCE: 338
MKAIIVLLMV VTSNADRICT GITSSNSPHV VKTATQGEVN VTGVIPLTTT PTKSHFANLK  60
GTETRGKLCP KCLNCTDLDV ALGRPKCTGK IPSARVSILH EVRPVTSGCF PIMHDRTKIR  120
QLPNILRGYE HVRLSTHNVI NAEDAPGRPY EIGTSGSCPN ITNGNGFFAT MAWAVPKNKT  180
ATNPLTIEVP YICTEGEDQI TVWGFHSDNE TQMAKLYGDS KPQKFTSSAN GVTTHYVSQI  240
GGFPNQTEDG GLPQSGRIVV DYMVQKSGKT GTITYQRGIL LPQKVWCASG RSKVIKGSLP  300
LIGEADCLHE KYGGLNKSKP YYTGEHAKAI GNCPIWVKTP LKLANGTKYR PPAKLLKERG  360
FFGAIAGFLE GGWEGMIAGW HGYTSHGAHG VAVAADLKST QEAINKITKN LNSLSELEVK  420
```

```
NLQRLSGAMD ELHNEILELD EKVDDLRADT ISSQIELAVL LSNEGIINSE DEHLLALERK  480
LKKMLGPSAV EIGNGCFETK HKCNQTCLDR IAAGTFDAGE FSLPTFDSLN ITAASLNDDG  540
LDNHTILLYY STAASSLAVT LMIAIFVVYM VSRDNVSCSI CL                     582

SEQ ID NO: 339          moltype = AA  length = 466
FEATURE                 Location/Qualifiers
source                  1..466
                        mol_type = protein
                        organism = Influenza B virus
SEQUENCE: 339
MLPSTIQTLT LFLTSGGVLL SLYVSASLSY LLYSDILLKF SPTEITAPTM PLDCANASNV  60
QAVNRSATKG VTLLLPEPEW TYPRLSCPGS TFQKALLISP HRFGETKGNS APLIIREPFV  120
ACGPNECKHF ALTHYAAQPG GYYNGTRGDR NKLRHLISVK LGKIPTVENS IFHMAAWSGS  180
ACHDGKEWTY IGVDGPDNNA LLKVKYGEAY TDTYHSYANN ILRTQESACN CIGGNCYLMI  240
TDGSASGVSE CRFLKIREGR IIKEIFPTGR VKHTEECTCG FASNKTIECA CRDNKYTAKR  300
PFVKLNVETD TAEIRLMCTD TYLDTPRPND GSITGPCESD GDKGSGGIKG GFVHQRMKSK  360
IGRWYSRTMS KTERMGMGLY VKYGGDPWAD SDALTFSGVM VSMKEPGWYS FGFEIKDKKC  420
DVPCIGIEMV HDGGKETWHS AATAIYCLMG SGQLLWDTVT GVDMAL                 466

SEQ ID NO: 340          moltype = AA  length = 583
FEATURE                 Location/Qualifiers
source                  1..583
                        mol_type = protein
                        organism = Influenza B virus
SEQUENCE: 340
MKAIIVLLMV VTSNADRICT GITSSNSPHV VKTATQGEVN VTGVIPLTTT PTKSHFANLK  60
GTETRGKLCP KCLNCTDLDV ALGRPKCTGK IPSARVSILH EVKPVTSGCF PIMHDRTKIR  120
QLPNLLRGYE HVRLSTHNVI NAEGAPGGPY KIGTSGSCPN ITNGNGFFAT MAWAVPDKNK  180
TATNPLTIEV PYICTEGEDQ ITVWGFHSDN ETQMAKLYGD SKPQKFTSSA NGVTTHYVSQ  240
IGGFPNQTED GGLPQSGRIV VDYMVQKSGK TGTITYQRGI LLPQKVWCAS GRSKVIKGSL  300
PLIGEADCLH EKYGGLNKSK PYYTGEHAKA IGNCPIWVKT PLKLANGTKY RPPAKLLKER  360
GFFGAIAGFL EGGWEGMIAG WHGYTSHGAH GVAVAADLKS TQEAINKITK NLNSLSELEV  420
KNLQRLSGAM DELHNEILEL DEKVDDLRAD TISSQIELAV LLSNEGIINS EDEHLLALER  480
KLKKMLGPSA VEIGNGCFET KHKCNQTCLD KIAAGTFDAG EFSLPTFDSL NITAASLNDD  540
GLDNHTILLY YSTAASSLAV TLMIAIFVVY MVSRDNVSCS ICL                    583

SEQ ID NO: 341          moltype = AA  length = 466
FEATURE                 Location/Qualifiers
source                  1..466
                        mol_type = protein
                        organism = Influenza B virus
SEQUENCE: 341
MLPSTIQTLT LFLTSGGVLL SLYVSASLSY LLYSDILLKF SPTEITAPTM PLDCANASNV  60
QAVNRSATKG VTLLLPEPEW TYPRLSCPGS TFQKALLISP HRFGETKGNS APLIIREPFV  120
ACGPNECKHF ALTHYAAQPG GYYNGTRGDR NKLRHLISVK LGKIPTVENS IFHMAAWSGS  180
ACHDGKEWTY IGVDGPDNNA LLKVKYGEAY TDTYHSYANN ILRTQESACN CIGGNCYLMI  240
TDGSASGVSE CRFLKIREGR IIKEIFPTGR VKHTEECTCG FASNKTIECA CRDNRYTAKR  300
PFVKLNVETD TAEIRLMCTD TYLDTPRPND GSITGPCESD GDKGSGGIKG GFVHQRMKSK  360
IGRWYSRTMS KTERMGMGLY VKYGGDPWAD SNALAFSGVM ISMKEPGWYS FGFEIKDKKC  420
DVPCIGIEMV HDGGKETWHS AATAIYCLMG SGQLLWDTVT GVDMAL                 466

SEQ ID NO: 342          moltype = AA  length = 14
FEATURE                 Location/Qualifiers
source                  1..14
                        mol_type = protein
                        organism = synthetic construct
SEQUENCE: 342
DYKDDDDKHH HHHH                                                    14

SEQ ID NO: 343          moltype = AA  length = 21
FEATURE                 Location/Qualifiers
source                  1..21
                        mol_type = protein
                        organism = synthetic construct
SEQUENCE: 343
SRGGGGSGGG GSGGGGSLEM A                                            21

SEQ ID NO: 344          moltype = AA  length = 5
FEATURE                 Location/Qualifiers
source                  1..5
                        mol_type = protein
                        organism = synthetic construct
SEQUENCE: 344
GGGGS                                                              5

SEQ ID NO: 345          moltype = AA  length = 4
FEATURE                 Location/Qualifiers
source                  1..4
                        mol_type = protein
```

```
                         organism = synthetic construct
VARIANT                  3..4
                         note = can be absent or present in repeats of any integer
SEQUENCE: 345
GSGS                                                                4

SEQ ID NO: 346           moltype = AA  length = 5
FEATURE                  Location/Qualifiers
source                   1..5
                         mol_type = protein
                         organism = synthetic construct
VARIANT                  1..5
                         note = can be present in repeats of any integer
SEQUENCE: 346
GSGGS                                                               5

SEQ ID NO: 347           moltype = AA  length = 5
FEATURE                  Location/Qualifiers
source                   1..5
                         mol_type = protein
                         organism = synthetic construct
VARIANT                  1..5
                         note = can be present in repeats of any integer
SEQUENCE: 347
GGGGS                                                               5

SEQ ID NO: 348           moltype = AA  length = 4
FEATURE                  Location/Qualifiers
source                   1..4
                         mol_type = protein
                         organism = synthetic construct
VARIANT                  1..4
                         note = can be present in repeats of any integer
SEQUENCE: 348
GGGS                                                                4

SEQ ID NO: 349           moltype = AA  length = 566
FEATURE                  Location/Qualifiers
source                   1..566
                         mol_type = protein
                         organism = synthetic construct
SEQUENCE: 349
MKTIIVLSYL FCLALSQDYS ENNNSTATLC LGHHAVPNGT VVKTITDDQI EVTNATELVQ  60
SSSTGKICNN PHRILDGRDC TLIDALLGDP HCDVFQDETW DLYVERSSAF SNCYPYDVPD  120
YASLRSLVAS SGTLEFITEG FTWTGVTQNG GSSACKRGPA SGFFSRLNWL TKSGSAYPVL  180
NVTMPNNDNF DKLYVWGVHH PSTNQEQTNL YVQASGRVTV STRKSQQTII PNIGSRPWVR  240
GQSGRISIYW TIVKPGDVLV INSNGNLIAP RGYFKMRTGK SSIMRSDAPI DTCISECITP  300
NGSIPNDKPF QNVNKITYGA CPKYVKQSTL KLATGMRNVP EKQTRGLFGA IAGFIENGWE  360
GMIDGWYGFR HQNSEGTGQA ADLKSTQAAI DQINGKLNRV IEKTNEKFHQ IEKEFSEVEG  420
RIQDLEKYVE DTKIDLWSYN AELLVALENQ HTIDLTDSEM NKLFEKTRRQ LRENAEDMGN  480
GCFKIYHKCD NACIESIRNG TYDHDIYRDE ALNNRFQIKG VELKSGYKDW ILWISFAISC  540
FLLCVVLLGF IMWACQRGNI RCNICI                                        566

SEQ ID NO: 350           moltype = AA  length = 469
FEATURE                  Location/Qualifiers
source                   1..469
                         mol_type = protein
                         organism = synthetic construct
SEQUENCE: 350
MNPNQKIITI GSICMAIGIM SLVLQIGNII SIWVSHSIQT ESKSHPETCN QSVITYENNT  60
WVNQTYLNIS NTNLIVEQIV APVTLAGNSS LCPISGWAIY SKDNGIRIGS KGDVFVIREP  120
FISCSHLECR TFFLTQGALL NDKHSNGTVK DRSPYRTLMS CPVGEAPSPY NSRFESVAWS  180
ASACHDGISW LTIGISGPDN GAVAVLKYNG IITDTVKSWR NNILRTQESE CACINGSCFT  240
IMTDGPSNGQ ASYKIFKIEK GKVVKSVELN APNYHYEECS CYPDASEVMC VCRDNWHGSN  300
RPWVSFNQDL EYQIGYICSG VFGDNPRPND GTGSCGPVSS NGAYGVKGFS FRYGNGVWIG  360
RTKSTSSRSG FEMIWDPNGW TETDNSFSVK QDIVAITDWS GYSGSFVQHP ELTGLDCVRP  420
CFWVELIRGR PKENTIWTSG SSISFCGVNS DTVGWSWPDG AELPFTIDK              469

SEQ ID NO: 351           moltype = AA  length = 566
FEATURE                  Location/Qualifiers
source                   1..566
                         mol_type = protein
                         organism = synthetic construct
SEQUENCE: 351
MRTVIALSYI FCLAFGQNLK GNENNAATLC LGHHAVPNGT MVKTITSDQI EVTNATEQVQ  60
NSSTGKICNN PHKILDGRDC TLIDALLGDP HCDVFQNETW DLFVERSNAF SNCYPYDVQD  120
YASLRSIVAS SGTLEFITEG FTWAGVTQNG GSGACKRGPA NGFFSRLNWL TKSGNTYQVL  180
NVTMPNNNNF DKLYIWGVHH PSTNQEQTSL YIQASGRVTV STRRSKQTII LNIESRPLVR  240
CQSGRISVYW TIVKPGVILV INSNGNLIAP RGYFKMHIGK STIMRSDAPV DTCISECITP  300
```

```
NGSIPNEKPF QNVNKITYGA CPKYVKQNTL KLSTGMRNVP ERQTRGLFGA IAGFIENGWE  360
GMVDGWYGFR HQNSEGTGQA ADLKSTQAAI DQINGKLNRV IEKTNEKFHQ IEKEFSEVEG  420
RIQDLERYVE DTKVDLWSYN AELLVALENQ NTIDLTDSEM NKLFEKTRRQ LRENAEDMGN  480
GCFKIYHKCD NACIESIRNG TYDHNIYRDE AVNNRFQIKG VELKSGYKDL ILWISFAISC  540
FLLCVVLLGF IMWACQRGNI RCNICI                                       566

SEQ ID NO: 352         moltype = AA  length = 469
FEATURE                Location/Qualifiers
source                 1..469
                       mol_type = protein
                       organism = synthetic construct
SEQUENCE: 352
MNPNQKIIAI GSVSLIIATV CFLLQIAILA TNVTLYFKQN ECNIPSNSQV VPCKPIIIER  60
NITEVVYLNN TTIEKEIYSV VLEYRNWSKP QCQITGFAPF SKDNSIRLSA GGDIWVTREP  120
YVSCDPSKCY QFALGQGTTL NNKHSNGTIH DRISHRTLLM NELGVPFHLG TKQVCIAWSS  180
SSCHDGKAWL HVCVTGDDKN ATASFVYNGM LVDSIGSWSR NILRTQESEC VCINGTCTVV  240
MTDGSASGRA DTRILFIREG KIVHISPLSG SAQHIEECSC YPRYPNVRCV CRDNWKGSNR  300
PVIDINMADY SIDSSYVCSG LVGDTPRNDD SFSSSNCRDP NNERGNPGVK GWAFDNENDV  360
WMGRTISKDL RSGYETFKVI GCRTTANSKS QVNRQVIVDN NNWSGYSGIF SVEGKSCVNR  420
CFYVELIRGG PQETRVWWTS NSIVVFCGTS GTYGAGSWPD GANINFMPI              469

SEQ ID NO: 353         moltype = AA  length = 566
FEATURE                Location/Qualifiers
source                 1..566
                       mol_type = protein
                       organism = synthetic construct
SEQUENCE: 353
MKTVIALSYI FCLAFGQNLL GNENNAATLC LGHHAVPNGT MVKTITDDQI EVTNATELVQ  60
NSSTGKICNN PHKILDGRDC TLIDALLGDP HCDVFQNETW DLFVERSNAF SNCYPYDVPD  120
YASLRSIVAS SGTLEFITEG FTWAGVTQNG GSGACKRGPA NSFFSRLNWL TKSGNTYPVL  180
NVTMPNNNNF DKLYIWGVHH PSTDQEQTSL YIQASGRVTV STRKSQQTII PNIGSRPLVR  240
GQSGRISVYW TIVEPGDILV INSNGNLIAP RGYFKMHIGK SSIMRSDAPI DTCISECITP  300
NGSIPTEKPF QNVNKITYGA CPKYVKQNTL KLATGMRNVP ERQTRGLFGA XAGFIENGWE  360
GMVDGWYGFR HQNSEGTGQA ADLKSTQAAI DQINGKLNRV IEKTNEKFHQ IEKEFSEVEG  420
RIQDLERYVE DTKIDLWSYN AELLVALENQ NTIDLTDSEM NKLFEKTRRQ LRENAEDMGN  480
GCFKIYHKCD NACIESIRNG TYDHNIYRDE AVNNRFQIKG VELKSGYKDW ILWISFAISC  540
FLLCVVLLGF IMWACQRGNI RCNICI                                       566

SEQ ID NO: 354         moltype = AA  length = 469
FEATURE                Location/Qualifiers
source                 1..469
                       mol_type = protein
                       organism = synthetic construct
SEQUENCE: 354
MNPNQKIIAI GSVSLAIATV CFLLQIATLA TTVTLYFKQN ECNIPSNSQI VPCKPIIIER  60
NITEVVHLNN TTIEKEIYSV VLEYRNWSKP QCQITGFAPF SKDNSIRLSA GGDIWVTREP  120
YVSCDPSKCY QFALGQGTTL NNKHSNSTIH DRTSYRTLLM NELGVPXHLG TKQVCIAWSS  180
SSCHDGKAWL HVCVTGDDRN ATASFVYNGM LVDSIGSWSR NILRTQESEC VCINGTCTVV  240
MTDGSASGKA DTRILFIKEG KIIHISPLSG SAQHIEECSC YPQYPNVRCV CRDNWKGSNR  300
PVIDINMADY NINSSYVCSG LVGDTPRNDD SSSSSNCKDP NNERGNPGVK GWAFDNDNDV  360
WMGRTISKDL RSGYETFKVI GGWTTANSKS QVNRQVIVDN NNWSGYSGIF SVEGKSCVNR  420
CFYVELIRGG PQETRVWWTS NSIVVFCGTS GTYGTGSWPD GANINFMPI              469

SEQ ID NO: 355         moltype = AA  length = 470
FEATURE                Location/Qualifiers
source                 1..470
                       mol_type = protein
                       organism = synthetic construct
SEQUENCE: 355
MNPNQKIITI GTASLGILII NVILHVVSII VTVLVLNNNE TGLNCKGTII REYNETVRVE  60
KITQWHNTSA IKYIERPPNE YYMNNTEPLC EAQGFAPFSK DNGIRIGSRG HVFVIREPFV  120
SCSPSECRTF FLTQGSLLND KHSNGTVKDR SPYRTLMSVK IGQSPNVYQA RFESVAWSAT  180
ACHDGKKWMT IGVTGPDNQA IAVVNYGGIP VDIINSWEGD ILRTQESSCT CIKGNCYWVM  240
TDGPANRQAK YRIFKAKDGR VIGQTDISFN GGHIEECSCY PNEGKVECIC RDNWTGTNRP  300
ILVISSDLSY TVGYLCAGIP TDTPRGEDSQ FTGSCTSPLG NKGYGVKGFG FRQGTDVWAG  360
RTISRTSRSR FEIIKIRNGW TQNSKDQIRR QVIIDDPNWS GYSGSFTLPV ELTKKGCLVP  420
CFWVEMIRGK PEETTIWTSS SSIVMCGVDH KIASWSWHDG AILPFDIDKM             470

SEQ ID NO: 356         moltype = AA  length = 567
FEATURE                Location/Qualifiers
source                 1..567
                       mol_type = protein
                       organism = synthetic construct
SEQUENCE: 356
MKTTTIFIFI LLTHWAYSQN PISNNNTATL CLGHHAVANG TLVKTISDDQ IEVTNATELV  60
QSISMGKICN NSYRILDGRN CTLIDAMLGD PHCDVFQYEN WDLFIERSSA FSNCYPYDIP  120
DYASLRSIVA SSGTLEFTAE GFTWTGVTQN GRSGACKRGS TDSFFSRLNW LTKSGNSYPT  180
LNVTMPNNKN FDKLYIWGIH HPSSNQEQTK LYIQGSGRVT VSTKRSQQTI IPNIGSRPWV  240
RGQSGRISIY WTIVKPGDIL MINSNGNLVA PRGYFKLKTG KSSVMRSDVP IDICVSECIT  300
```

```
PNGSISNDKP FQNVNKVTYG KCPKYIRQNT LKLATGMRNV PEKQIRGIFG AIAGFIENGW  360
EGMVDGWYGF RYQNSEGTGQ AADLKSTQTA IDQINEKLNR VIERTNEKFH QIEKEFSEVE  420
GRIQDLEKYV EDTKIDLWSY NAELLVALEN QHTIDLTDAE MNKLFEKTRR QLRENAEDMG  480
GGCFKIYHKC DNACIGSIRN GTYDHYIYRD EALNNRFQIK GVELKSGYKD WILWISFAIS  540
CFLICVVLLG FIMWACQKGN IRCNICI                                      567

SEQ ID NO: 357         moltype = AA  length = 566
FEATURE                Location/Qualifiers
source                 1..566
                       mol_type = protein
                       organism = synthetic construct
SEQUENCE: 357
MKAILLVLLY TFVPTNADTL CIGYHANNST DTVDTILERN VTVTHSVNLL EDKHNGRLCK  60
LGGIAPLHLG KCNIAGWLLG NPECESLFTV SSWSYIVETS NSYNGTCYPG DFINYEELRE  120
QLSSVSSFER FEIFPKASSW PNHETNKGVT AACSHAGTKS FYRNLIWLVK KGNSYPNISK  180
SYFNNKGNEV LVLWGIHHPS TNNDQQTLYQ NADTYVFVGT SKYNKKFKPE IAIRPKVRDQ  240
EGRMNYYWTL VEPGDKITFE ATGNLVVPRY AFAMERNAGS GIIISDTPVH DCNTTCQTPK  300
GAINTSLPFQ NIHPTTIGKC PKYVKSTKLR LATGLRNVPS IQSRGLFGAI AGFIEGGWTG  360
MVDGWYGYHH QNEQGSGYAA DQKSTQNAID GITNKVNSVI EKMNTQFTAV GKEFNHLEKR  420
IENLNKKVDD GFLDVWTYNA ELLILLENER TLDFHDSNVK NLYEKARRQL KNNAKEIGNG  480
CFEFYHKCDN ACMESVKNGT YDYPKYSEES RLNREEISGV KLDSTRIYQI LAIYSTVASS  540
SVLLVSLGAI SFWMCSNGSL QCRICI                                       566

SEQ ID NO: 358         moltype = AA  length = 469
FEATURE                Location/Qualifiers
source                 1..469
                       mol_type = protein
                       organism = synthetic construct
SEQUENCE: 358
MNTNQRIITI GTVCLTVGII SLLLQIGNIV SLWISHSIQT GGKNHTEMCN KNVITYVNNT  60
WVNRTYVNIS NTKIVNVQDV VSVILTGNSS LCPISGWAIY SKDNSIRIGS KGDIFVIREP  120
FISCSHLECR TFFLTQGALL NDKHSNGTVK DRSPYRTLMS CPIGEAPSPY NSRFESVAWS  180
ASACHDGMGW LTIGISGPDN GAVAVLKYNG IITDTIKSWR NKILRTQESE CVCMNGSCFT  240
VLTDGPSNGQ ASYKIFKMEK GKIIKSIELD APNYHYEECS CYPDAGKVMC VCRDNWHASN  300
RPWVSFDQNL DYQIGYICSG VFGDNPRSND GKGNCGPVHS NGANGVKGFS YRYGNGVWIG  360
RTKSINSRSG FEMIWDPNGW TGTDSSFSMK QDIIALTDWS GYSGSFVQHP ELTGMNCIRP  420
CFWVELIRGQ PKENTIWASG SSISFCGVNG ETASWSWPDG ADLPFTIDK              469

SEQ ID NO: 359         moltype = AA  length = 9
FEATURE                Location/Qualifiers
source                 1..9
                       mol_type = protein
                       organism = synthetic construct
SEQUENCE: 359
SGFSFSSSY                                                          9

SEQ ID NO: 360         moltype = AA  length = 17
FEATURE                Location/Qualifiers
source                 1..17
                       mol_type = protein
                       organism = synthetic construct
SEQUENCE: 360
LEWIACIYAG SSGSAYF                                                 17

SEQ ID NO: 361         moltype = AA  length = 20
FEATURE                Location/Qualifiers
source                 1..20
                       mol_type = protein
                       organism = synthetic construct
SEQUENCE: 361
APSYTYGYAG YAYAYSYYFN                                              20

SEQ ID NO: 362         moltype = AA  length = 5
FEATURE                Location/Qualifiers
source                 1..5
                       mol_type = protein
                       organism = synthetic construct
SEQUENCE: 362
QSINN                                                              5

SEQ ID NO: 363         moltype = AA  length = 11
FEATURE                Location/Qualifiers
source                 1..11
                       mol_type = protein
                       organism = synthetic construct
SEQUENCE: 363
PKLLYDASDL A                                                       11

SEQ ID NO: 364         moltype = AA  length = 6
```

```
FEATURE                Location/Qualifiers
source                 1..6
                       mol_type = protein
                       organism = synthetic construct
SEQUENCE: 364
DYSTNN                                                                     6

SEQ ID NO: 365         moltype = AA  length = 7
FEATURE                Location/Qualifiers
source                 1..7
                       mol_type = protein
                       organism = synthetic construct
SEQUENCE: 365
SNNAVWN                                                                    7

SEQ ID NO: 366         moltype = AA  length = 18
FEATURE                Location/Qualifiers
source                 1..18
                       mol_type = protein
                       organism = synthetic construct
SEQUENCE: 366
RTYYRSKWYN DYAESVKS                                                        18

SEQ ID NO: 367         moltype = AA  length = 16
FEATURE                Location/Qualifiers
source                 1..16
                       mol_type = protein
                       organism = synthetic construct
SEQUENCE: 367
SGHITVFGVN VDAFDM                                                          16

SEQ ID NO: 368         moltype = AA  length = 11
FEATURE                Location/Qualifiers
source                 1..11
                       mol_type = protein
                       organism = synthetic construct
SEQUENCE: 368
TRSQSLSSYL H                                                               11

SEQ ID NO: 369         moltype = AA  length = 7
FEATURE                Location/Qualifiers
source                 1..7
                       mol_type = protein
                       organism = synthetic construct
SEQUENCE: 369
AASSLQS                                                                    7

SEQ ID NO: 370         moltype = AA  length = 5
FEATURE                Location/Qualifiers
source                 1..5
                       mol_type = protein
                       organism = synthetic construct
SEQUENCE: 370
QQSRT                                                                      5

SEQ ID NO: 371         moltype = AA  length = 16
FEATURE                Location/Qualifiers
source                 1..16
                       mol_type = protein
                       organism = synthetic construct
SEQUENCE: 371
LIYTGGTTYY ADSVKG                                                          16

SEQ ID NO: 372         moltype = AA  length = 16
FEATURE                Location/Qualifiers
source                 1..16
                       mol_type = protein
                       organism = synthetic construct
SEQUENCE: 372
VSALRFLQWP NYAMDV                                                          16

SEQ ID NO: 373         moltype = AA  length = 14
FEATURE                Location/Qualifiers
source                 1..14
                       mol_type = protein
                       organism = synthetic construct
SEQUENCE: 373
SGTRSDVGGH NYVS                                                            14
```

```
SEQ ID NO: 374          moltype = AA  length = 7
FEATURE                 Location/Qualifiers
source                  1..7
                        mol_type = protein
                        organism = synthetic construct
SEQUENCE: 374
EVSHRPS                                                            7

SEQ ID NO: 375          moltype = AA  length = 11
FEATURE                 Location/Qualifiers
source                  1..11
                        mol_type = protein
                        organism = synthetic construct
SEQUENCE: 375
SSYTGEGPLG V                                                       11

SEQ ID NO: 376          moltype = AA  length = 5
FEATURE                 Location/Qualifiers
source                  1..5
                        mol_type = protein
                        organism = synthetic construct
SEQUENCE: 376
SYWMS                                                              5

SEQ ID NO: 377          moltype = AA  length = 5
FEATURE                 Location/Qualifiers
source                  1..5
                        mol_type = protein
                        organism = synthetic construct
SEQUENCE: 377
RHGIS                                                              5

SEQ ID NO: 378          moltype = AA  length = 17
FEATURE                 Location/Qualifiers
source                  1..17
                        mol_type = protein
                        organism = synthetic construct
SEQUENCE: 378
WISAYTGDTD YAQKFQG                                                 17

SEQ ID NO: 379          moltype = AA  length = 11
FEATURE                 Location/Qualifiers
source                  1..11
                        mol_type = protein
                        organism = synthetic construct
SEQUENCE: 379
GWGAVTSPFD F                                                       11

SEQ ID NO: 380          moltype = AA  length = 11
FEATURE                 Location/Qualifiers
source                  1..11
                        mol_type = protein
                        organism = synthetic construct
SEQUENCE: 380
GWGAVTSPFD F                                                       11

SEQ ID NO: 381          moltype = AA  length = 7
FEATURE                 Location/Qualifiers
source                  1..7
                        mol_type = protein
                        organism = synthetic construct
SEQUENCE: 381
DASNRAT                                                            7

SEQ ID NO: 382          moltype = AA  length = 8
FEATURE                 Location/Qualifiers
source                  1..8
                        mol_type = protein
                        organism = synthetic construct
SEQUENCE: 382
QQRSNWLK                                                           8

SEQ ID NO: 383          moltype = AA  length = 130
FEATURE                 Location/Qualifiers
source                  1..130
                        mol_type = protein
                        organism = synthetic construct
SEQUENCE: 383
QSLEESGGDL VKPGASLTLT CTASGFSFSS SYWICWVRQA PGKGLEWIAC IYAGSSGSAY  60
```

```
FASWAKGRFT ISETSSTTVT LQMTSLTAAD TATYFCARAP SYTYGYAGYA YAYSYYFNLW  120
GPGTLVTVSS                                                         130

SEQ ID NO: 384          moltype = AA  length = 108
FEATURE                 Location/Qualifiers
source                  1..108
                        mol_type = protein
                        organism = synthetic construct
SEQUENCE: 384
VMTQTPASVE VTMGGTVTIN CQASQSINNE LCWYQQKPGQ RPKLLIYDAS DLASGVPSRF  60
KGSGSGTEFT LTISDLECAD AATYYCQQDY STNNVDNLFG GGTEVVVK               108

SEQ ID NO: 385          moltype = AA  length = 128
FEATURE                 Location/Qualifiers
source                  1..128
                        mol_type = protein
                        organism = synthetic construct
SEQUENCE: 385
QVQLQQSGPG LVKPSQTLSL TCAISGDSVS SNNAVWNWIR QSPSRGLEWL GRTYYRSKWY  60
NDYAESVKSR ITINPDTSKN QFSLQLNSVT PEDTAVYYCA RSGHITVFGV NVDAFDMWGQ  120
GTMVTVSS                                                           128

SEQ ID NO: 386          moltype = AA  length = 103
FEATURE                 Location/Qualifiers
source                  1..103
                        mol_type = protein
                        organism = synthetic construct
SEQUENCE: 386
DIQMTQSPSS LSASVGDRVT ITCRTSQSLS SYTHWYQQKP GKAPKLLIYA ASSRGSGVPS  60
RFSGSGSGTD FTLTISSLQP EDFATYYCQQ SRTFGQGTKV EIK                    103

SEQ ID NO: 387          moltype = AA  length = 113
FEATURE                 Location/Qualifiers
source                  1..113
                        mol_type = protein
                        organism = synthetic construct
SEQUENCE: 387
EVQLVESGGG LIQPGGSLRL SCAASGFTVS SNYVSWVRQA PGKGLEWLSL IYTGGTTYYA  60
DSVKGRFTIS RDNSKNTVFL QMNSLRAEDA AMYYCARVSA LRFLQWPNYA MDV          113

SEQ ID NO: 388          moltype = AA  length = 101
FEATURE                 Location/Qualifiers
source                  1..101
                        mol_type = protein
                        organism = synthetic construct
SEQUENCE: 388
QSALTQPASV SGSPGRSITI SCSGTRSDVG GHNYVSWYQQ HPGKAPKLMI YEVSHRPSGV  60
SNRFSGSKSG STASLTISGL QSEDEADYYC SSYTGEGPLG V                      101

SEQ ID NO: 389          moltype = AA  length = 128
FEATURE                 Location/Qualifiers
source                  1..128
                        mol_type = protein
                        organism = synthetic construct
SEQUENCE: 389
QVQLVQSGAE VRKPGASVKV SCKASGYTFT RHGISWVRQA PGQGLEWMGW ISAYTGDTDY  60
AQKFQGRVTM TTDTSTNTAY MELRSLRSDD AAVYYCARLR LQGEVVVPPS QSNWFDPWGQ  120
GTLVTVSS                                                           128

SEQ ID NO: 390          moltype = AA  length = 114
FEATURE                 Location/Qualifiers
source                  1..114
                        mol_type = protein
                        organism = synthetic construct
SEQUENCE: 390
EIVLTQSPAT LSLYPGERAT LSCRASQSVS RYLAWYQQKP GQAPRLLIYD ASNRATGIPA  60
RFSGSGSGTD FTLTISSLEP EDFAVYYCCD RQQRSNWLKI TFGQGTRLEI KGTV        114

SEQ ID NO: 391          moltype = AA  length = 223
FEATURE                 Location/Qualifiers
source                  1..223
                        mol_type = protein
                        organism = synthetic construct
SEQUENCE: 391
TCPPCPAPEL LGGPSVFLFP PKPKDTLMIS RTPEVTCVVV DVSHEDPEVK FNWYVDGVEV  60
HNAKTKPREE QYNSTYRVVS VLTVLHQDWL NGKEYKCKVS NKALPAPIEK TISKAKGQPR  120
EPQVYTLPPS RDELTKNQVS LTCLVKGFYP SDIAVEWESN GQPENNYKTT PPVLDSDGSF  180
FLYSKLTVDK SRWQQGNVFS CSVMHEALHN HYTQKSLSLS PGK                    223
```

```
SEQ ID NO: 392         moltype = AA  length = 106
FEATURE                Location/Qualifiers
source                 1..106
                       mol_type = protein
                       organism = synthetic construct
SEQUENCE: 392
GQPKANPTVT LFPPSSEELQ ANKATLVCLI SDFYPGAVTV AWKADGSPVK AGVETTKPSK  60
QSNNKYAASS YLSLTPEQWK SHRSYSCQVT HEGSTVEKTV APTECS                 106

SEQ ID NO: 393         moltype = AA  length = 103
FEATURE                Location/Qualifiers
source                 1..103
                       mol_type = protein
                       organism = synthetic construct
SEQUENCE: 393
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSC                    103

SEQ ID NO: 394         moltype = AA  length = 121
FEATURE                Location/Qualifiers
source                 1..121
                       mol_type = protein
                       organism = synthetic construct
SEQUENCE: 394
TCPPCPAPEL LGGPSVFLFP PKPKDTLMIS RTPEVTCVVV DVSHEDPEVK FNWYVDGVEV  60
HNAKTKPREE QYNSTYRVVS VLTVLHQDWL NGKEYKCKVS NKALPAPIEK TISKAKGQPR  120
E                                                                  121

SEQ ID NO: 395         moltype = AA  length = 102
FEATURE                Location/Qualifiers
source                 1..102
                       mol_type = protein
                       organism = synthetic construct
SEQUENCE: 395
PQVYTLPPSR DELTKNQVSL TCLVKGFYPS DIAVEWESNG QPENNYKTTP PVLDSDGSFF  60
LYSKLTVDKS RWQQGNVFSC SVMHEALHNH YTQKSLSLSP GK                     102

SEQ ID NO: 396         moltype = AA  length = 107
FEATURE                Location/Qualifiers
source                 1..107
                       mol_type = protein
                       organism = synthetic construct
SEQUENCE: 396
PDVYLLPPAR EQLNLRESAT ITCLVTGFSP ADVFVQWMQR GQPLSPEKYV TSAPMPEPQA  60
PGRYFAHSIL TVSEEEWNTG ETYTCVVAHE ALPNRVTERT VDKSTGK                107

SEQ ID NO: 397         moltype = AA  length = 525
FEATURE                Location/Qualifiers
source                 1..525
                       mol_type = protein
                       organism = synthetic construct
SEQUENCE: 397
MWWRLWWLLL LLLLLWGSSA SAAIIPVEEE NPDFWNREAA EALGAAKKLQ PAQTAAKNLI  60
IFLGDGMGVS TVTAARILKG QKKDKLGPEI PLAMDRFPYV ALSKTYNVDK HVPDSGATAT  120
AYLCGVKGNF QTIGLSAAAR FNQCNTTRGN EVISVMNRAK KAGKSVGVVT TTRVQHASPA  180
GTYAHTVNRN WYSDADVPAS ARQEGCQDIA TQLISNMDID VILGGGRKYM FRMGTPDPEY  240
PDDYSQGGTR LDGKNLVQEW LAKRQGARYV WNRTELMQAS LDPSVTHLMG LFEPGDMKYE  300
IHRDSTLDPS LMEMTEAALR LLSRNPRGFF LFVEGGRIDH GHHESRAYRA LTETIMFDDA  360
IERAGQLTSE EDTLSLVTAD HSHVFSFGGY PLRGSSIFGL APGKARDRKA YTVLLYGNGP  420
GYVLKDGARP DVTESESGSP EYRQQSAVPL DEETHAGEDV AVFARGPQAH LVHGVQEQTF  480
IAHVMAFAAC LEPYTACDLA PPAGTTDAAH PGYSRVGAAG RFEQT                  525

SEQ ID NO: 398         moltype = AA  length = 202
FEATURE                Location/Qualifiers
source                 1..202
                       mol_type = protein
                       organism = synthetic construct
SEQUENCE: 398
MKLVGSYTSP FVRKLSILLL EKGITFEFIN ELPYNADNGV AQFNPLGKVP VLVTEEGECW  60
FDSPIIAEYI ELMNVAPAML PRDPLESLRV RKIEALADGI MDAGLVSVRE QARPAAQQSE  120
DELLRQREKI NRSLDVLEGY LVDGTLKTDT VNLATIAIAC AVGYLNFRRV APGWCVDRPH  180
LVKLVENLFS RESFARTEPP KA                                           202

SEQ ID NO: 399         moltype = AA  length = 22
FEATURE                Location/Qualifiers
source                 1..22
                       mol_type = protein
                       organism = synthetic construct
SEQUENCE: 399
```

```
LENHSRRLEM TNKQLWLRIQ EL                                          22

SEQ ID NO: 400          moltype = AA  length = 27
FEATURE                 Location/Qualifiers
source                  1..27
                        mol_type = protein
                        organism = synthetic construct
SEQUENCE: 400
LSIIAICLGS LGLILIILLS VVVWKLL                                     27

SEQ ID NO: 401          moltype = AA  length = 6
FEATURE                 Location/Qualifiers
source                  1..6
                        mol_type = protein
                        organism = synthetic construct
VARIANT                 4..6
                        note = can be absent or present in repeats of any integer
SEQUENCE: 401
GPPGPP                                                            6

SEQ ID NO: 402          moltype = AA  length = 31
FEATURE                 Location/Qualifiers
source                  1..31
                        mol_type = protein
                        organism = synthetic construct
SEQUENCE: 402
EYFTLQIRGR ERFEMFRELN EALELKDAQA G                                31

SEQ ID NO: 403          moltype = AA  length = 128
FEATURE                 Location/Qualifiers
source                  1..128
                        mol_type = protein
                        organism = synthetic construct
SEQUENCE: 403
MAEAGITGTW YNQLGSTFIV TAGADGALTG TYESAVGNAE GDYVLTGRYD SAPATDGSGT  60
ALGWTVAWKN NYRNAHSATT WSGQYVGGAE ARINTQWLLT SGTTEANAWK STLVGHDTFT  120
KVKPSAAS                                                          128

SEQ ID NO: 404          moltype = AA  length = 27
FEATURE                 Location/Qualifiers
source                  1..27
                        mol_type = protein
                        organism = synthetic construct
SEQUENCE: 404
GYIPEAPRDG QAYVRKDGEW VLLSTFL                                     27

SEQ ID NO: 405          moltype = AA  length = 42
FEATURE                 Location/Qualifiers
source                  1..42
                        mol_type = protein
                        organism = synthetic construct
SEQUENCE: 405
GPQMLRELGE TNAALQDVRE LLRQQVREIT FLKNTVMECD AC                    42

SEQ ID NO: 406          moltype = AA  length = 344
FEATURE                 Location/Qualifiers
source                  1..344
                        mol_type = protein
                        organism = synthetic construct
SEQUENCE: 406
PPKVSVFVPP RDGFFGNPRK SKLICQATGF SPRQIQVSWL REGKQVGSGV TTDQVQAEAK  60
ESGPTTYKVT STLTIKESDW LSQSMFTCRV DHRGLTFQQN ASSMCVPDQD TAIRVFAIPP  120
SFASIFLTKS TKLTCLVTDL TTYDSVTISW TRQNGEAVKT HTNISESHPN ATFSAVGEAS  180
ICEDDWNSGE RFTCTVTHTD LPSPLKQTIS RPKGVALHRP DVYLLPPARE QLNLRESATI  240
TCLVTGFSPA DVFVQWMQRG QPLSPEKYVT SAPMPEPQAP GRYFAHSILT VSEEEWNTGE  300
TYTCVVAHEA LPNRVTERTV DKSTGKPTLY NVSLVMSDTA GTCY                  344

SEQ ID NO: 407          moltype = AA  length = 5
FEATURE                 Location/Qualifiers
source                  1..5
                        mol_type = protein
                        organism = synthetic construct
SEQUENCE: 407
HHHHH                                                             5

SEQ ID NO: 408          moltype = AA  length = 7
FEATURE                 Location/Qualifiers
source                  1..7
                        mol_type = protein
```

```
                        organism = synthetic construct
SEQUENCE: 408
KKKGKKK                                                           7

SEQ ID NO: 409          moltype = AA  length = 12
FEATURE                 Location/Qualifiers
source                  1..12
                        mol_type = protein
                        organism = synthetic construct
SEQUENCE: 409
KKAHHGKKAH HV                                                     12

SEQ ID NO: 410          moltype = AA  length = 12
FEATURE                 Location/Qualifiers
source                  1..12
                        mol_type = protein
                        organism = synthetic construct
SEQUENCE: 410
KKARRGKKAR RV                                                     12

SEQ ID NO: 411          moltype = AA  length = 12
FEATURE                 Location/Qualifiers
source                  1..12
                        mol_type = protein
                        organism = synthetic construct
SEQUENCE: 411
KLIHKKARVR GK                                                     12

SEQ ID NO: 412          moltype = AA  length = 15
FEATURE                 Location/Qualifiers
source                  1..15
                        mol_type = protein
                        organism = synthetic construct
SEQUENCE: 412
ILRRKAHHGK IKKVR                                                  15

SEQ ID NO: 413          moltype = AA  length = 14
FEATURE                 Location/Qualifiers
source                  1..14
                        mol_type = protein
                        organism = synthetic construct
SEQUENCE: 413
GHRVKKAVRH IKRL                                                   14

SEQ ID NO: 414          moltype = AA  length = 352
FEATURE                 Location/Qualifiers
source                  1..352
                        mol_type = protein
                        organism = synthetic construct
SEQUENCE: 414
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSST CPPCPAPELL GGPSVFLFPP KPKDTLMISR TPEVTCVVVD VSHEDPEVKF  180
NWYVDGVEVH NAKTKPREEQ YNSTYRVVSV LTVLHQDWLN GKEYKCKVSN KALPAPIEKT  240
ISKAKGQPRE PQVYTLPPSR DELTKNQVSL TCLVKGFYPS DIAVEWESNG QPENNYKTTP  300
PVLDSDGSFF LYSKLTVDKS RWQQGNVFSC SVMHEALHNH YTQKSLSLSP GK          352

SEQ ID NO: 415          moltype = AA  length = 9
FEATURE                 Location/Qualifiers
source                  1..9
                        mol_type = protein
                        organism = synthetic construct
SEQUENCE: 415
ASWDDSLNG                                                         9

SEQ ID NO: 416          moltype = AA  length = 357
FEATURE                 Location/Qualifiers
source                  1..357
                        mol_type = protein
                        organism = synthetic construct
SEQUENCE: 416
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSST CPPCPAPELL GGPSVFLFPP KPKDTLMISR TPEVTCVVVD VSHEDPEVKF  180
NWYVDGVEVH NAKTKPREEQ YNSTYRVVSV LTVLHQDWLN GKEYKCKVSN KALPAPIEKT  240
ISKAKGQPRE PQVYTLPPSR DELTKNQVSL TCLVKGFYPS DIAVEWESNG QPENNYKTTP  300
PVLDSDGSFF LYSKLTVDKS RWQQGNVFSC SVMHEALHNH YTQKSLSLSP GKHHHHH     357

SEQ ID NO: 417          moltype = AA  length = 359
```

```
FEATURE                 Location/Qualifiers
source                  1..359
                        mol_type = protein
                        organism = synthetic construct
SEQUENCE: 417
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSST CPPCPAPELL GGPSVFLFPP KPKDTLMISR TPEVTCVVVD VSHEDPEVKF  180
NWYVDGVEVH NAKTKPREEQ YNSTYRVVSV LTVLHQDWLN GKEYKCKVSN KALPAPIEKT  240
ISKAKGQPRE PQVYTLPPSR DELTKNQVSL TCLVKGFYPS DIAVEWESNG QPENNYKTTP  300
PVLDSDGSFF LYSKLTVDKS RWQQGNVFSC SVMHEALHNH YTQKSLSLSP GKKKKGKKK   359

SEQ ID NO: 418          moltype = AA  length = 364
FEATURE                 Location/Qualifiers
source                  1..364
                        mol_type = protein
                        organism = synthetic construct
SEQUENCE: 418
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSST CPPCPAPELL GGPSVFLFPP KPKDTLMISR TPEVTCVVVD VSHEDPEVKF  180
NWYVDGVEVH NAKTKPREEQ YNSTYRVVSV LTVLHQDWLN GKEYKCKVSN KALPAPIEKT  240
ISKAKGQPRE PQVYTLPPSR DELTKNQVSL TCLVKGFYPS DIAVEWESNG QPENNYKTTP  300
PVLDSDGSFF LYSKLTVDKS RWQQGNVFSC SVMHEALHNH YTQKSLSLSP GKKKAHHGKK  360
AHHV                                                              364

SEQ ID NO: 419          moltype = AA  length = 364
FEATURE                 Location/Qualifiers
source                  1..364
                        mol_type = protein
                        organism = synthetic construct
SEQUENCE: 419
QVQLVESGGG VVQPGRSLRL SCAASGFTFS TYAMHWVRQA PGKGLEWVAV ISYDANYKYY  60
ADSVKGRFTI SRDNSKNTLY LQMNSLRAED TAVYYCAKDS QLRSLLYFEW LSQGYFDYWG  120
QGTLVTVSST CPPCPAPELL GGPSVFLFPP KPKDTLMISR TPEVTCVVVD VSHEDPEVKF  180
NWYVDGVEVH NAKTKPREEQ YNSTYRVVSV LTVLHQDWLN GKEYKCKVSN KALPAPIEKT  240
ISKAKGQPRE PQVYTLPPSR DELTKNQVSL TCLVKGFYPS DIAVEWESNG QPENNYKTTP  300
PVLDSDGSFF LYSKLTVDKS RWQQGNVFSC SVMHEALHNH YTQKSLSLSP GKKKARRGKK  360
ARRV                                                              364

SEQ ID NO: 420          moltype = AA  length = 451
FEATURE                 Location/Qualifiers
source                  1..451
                        mol_type = protein
                        organism = synthetic construct
SEQUENCE: 420
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS SSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 421          moltype = AA  length = 254
FEATURE                 Location/Qualifiers
source                  1..254
                        mol_type = protein
                        organism = Influenza A virus
SEQUENCE: 421
AGSGIIISDT PVHDCNTTCQ TPKGAINTSL PFQNIHPITI GKCPKYVKST KLRLATGLRN  60
VPSIQSRGLF GAIAGFIEGG WTGMVDGWYG YHHQNEQGSG YAADLKSTQN AIDKITNKVN  120
SVIEKMNTQF TAVGKEFNHL EKRIENLNKK VDDGFLDIWT YNAELLVLLE NERTLDYHDS  180
NVKNLYEKVR NQLKNNAKEI GNGCFEFYHK CDNTCMESVK NGTYDYPKYS EEAKLNREEI  240
DGVKLESTRI YQIL                                                   254

SEQ ID NO: 422          moltype = AA  length = 456
FEATURE                 Location/Qualifiers
source                  1..456
                        mol_type = protein
                        organism = synthetic construct
SEQUENCE: 422
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS SSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
```

```
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KHHHHH                           456

SEQ ID NO: 423          moltype = AA  length = 458
FEATURE                 Location/Qualifiers
source                  1..458
                        mol_type = protein
                        organism = synthetic construct
SEQUENCE: 423
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS SSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KKKKGKKK                         458

SEQ ID NO: 424          moltype = AA  length = 463
FEATURE                 Location/Qualifiers
source                  1..463
                        mol_type = protein
                        organism = synthetic construct
SEQUENCE: 424
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS SSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KKKAHHGKKA HHV                    463

SEQ ID NO: 425          moltype = AA  length = 463
FEATURE                 Location/Qualifiers
source                  1..463
                        mol_type = protein
                        organism = synthetic construct
SEQUENCE: 425
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS SSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KKKARRGKKA RRV                    463

SEQ ID NO: 426          moltype = AA  length = 445
FEATURE                 Location/Qualifiers
source                  1..445
                        mol_type = protein
                        organism = synthetic construct
SEQUENCE: 426
QVQLQESGPG LVRPSETLSL TCTVSGDSIG GSYWNWIRQP PGKGLQWIGY IYYTGITNYN  60
PSLKSRVTMS LDTSKNQISL KMDSVTAADT ALYFCARGDY SGYDRDVQVE LMDVWGKGTT  120
VTVSSSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGK                                        445

SEQ ID NO: 427          moltype = AA  length = 255
FEATURE                 Location/Qualifiers
source                  1..255
                        mol_type = protein
                        organism = Influenza A virus
SEQUENCE: 427
RTGKSSIMRS DAPIGTCSSE CITPNGSIPN DKPFQNVNKI TYGACPKYVK QNTLKLATGM  60
RNVPEKQTRG IFGAIAGFIE NGWEGMIDGW YGFRHQNSEG TGQAADLKST QAAIDQINGK  120
LNRVIEKTNE KFHQIEKEFS EVEGRIQDLE KYVEDTKIDL WSYNAELLVA LENQHTIDLT  180
DSEMNKLFEK TRRQLRENAE DMGNGCFKIY HKCDNACIGS IRNGTYDHDV YRDEALNNRF  240
QIKGVELKSG YKDWI                                                   255

SEQ ID NO: 428          moltype = AA  length = 450
FEATURE                 Location/Qualifiers
source                  1..450
                        mol_type = protein
```

```
                         organism = synthetic construct
SEQUENCE: 428
QVQLQESGPG LVRPSETLSL TCTVSGDSIG GSYWNWIRQP PGKGLQWIGY IYYTGITNYN  60
PSLKSRVTMS LDTSKNQISL KMDSVTAADT ALYFCARGDY SGYDRDVQVE LMDVWGKGTT  120
VTVSSSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGKHHHHH                                  450

SEQ ID NO: 429           moltype = AA  length = 452
FEATURE                  Location/Qualifiers
source                   1..452
                         mol_type = protein
                         organism = synthetic construct
SEQUENCE: 429
QVQLQESGPG LVRPSETLSL TCTVSGDSIG GSYWNWIRQP PGKGLQWIGY IYYTGITNYN  60
PSLKSRVTMS LDTSKNQISL KMDSVTAADT ALYFCARGDY SGYDRDVQVE LMDVWGKGTT  120
VTVSSSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGKKKKGK KK                                452

SEQ ID NO: 430           moltype = AA  length = 457
FEATURE                  Location/Qualifiers
source                   1..457
                         mol_type = protein
                         organism = synthetic construct
SEQUENCE: 430
QVQLQESGPG LVRPSETLSL TCTVSGDSIG GSYWNWIRQP PGKGLQWIGY IYYTGITNYN  60
PSLKSRVTMS LDTSKNQISL KMDSVTAADT ALYFCARGDY SGYDRDVQVE LMDVWGKGTT  120
VTVSSSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGKKKAHH GKKAHHV                           457

SEQ ID NO: 431           moltype = AA  length = 457
FEATURE                  Location/Qualifiers
source                   1..457
                         mol_type = protein
                         organism = synthetic construct
SEQUENCE: 431
QVQLQESGPG LVRPSETLSL TCTVSGDSIG GSYWNWIRQP PGKGLQWIGY IYYTGITNYN  60
PSLKSRVTMS LDTSKNQISL KMDSVTAADT ALYFCARGDY SGYDRDVQVE LMDVWGKGTT  120
VTVSSSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGKKKARR GKKARRV                           457

SEQ ID NO: 432           moltype = AA  length = 450
FEATURE                  Location/Qualifiers
source                   1..450
                         mol_type = protein
                         organism = synthetic construct
SEQUENCE: 432
EVQLVQSGAE VKKPGSSVKV SCKASGYTFI NHALSWVRQA PGQGLEWVGG IIPIFGLAKY  60
GQKFQDRVTI TADESTKTAY MDLRSLRSDD TAVYYCARDT VAVYEDFDWS SPYFFYMDVW  120
GKGTTVTVSS SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK RVEPKSCTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 433           moltype = AA  length = 255
FEATURE                  Location/Qualifiers
source                   1..255
                         mol_type = protein
                         organism = Influenza A virus
SEQUENCE: 433
RTGKSSIMRS DAPIGTCSSE CITPNGSIPN DKPFQNVNKI TYGACPKYVK QNTLKLATGM  60
RNVPEKQTRG IFGAIAGFIE NGWEGMIDGW YGFRHQNSEG TGQAADLKST QAAIDQINGK  120
```

```
LNRVIEKTNE KFHQIEKEFS EVEGRIQDLE KYVEDTKIDL WSYNAELLVA LENQHTIDLT  180
DSEMNKLFEK TRRQLRENAE DMGNGCFKIY HKCDNACIGS IRNGTYDHDV YRDEALNNRF  240
QIKGVELKSG YKDWI                                                  255

SEQ ID NO: 434          moltype = AA  length = 456
FEATURE                 Location/Qualifiers
source                  1..456
                        mol_type = protein
                        organism = synthetic construct
SEQUENCE: 434
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS SSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KHHHHH                            456

SEQ ID NO: 435          moltype = AA  length = 458
FEATURE                 Location/Qualifiers
source                  1..458
                        mol_type = protein
                        organism = synthetic construct
SEQUENCE: 435
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS SSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KKKKGKKK                          458

SEQ ID NO: 436          moltype = AA  length = 463
FEATURE                 Location/Qualifiers
source                  1..463
                        mol_type = protein
                        organism = synthetic construct
SEQUENCE: 436
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS SSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KKKAHHGKKA HHV                    463

SEQ ID NO: 437          moltype = AA  length = 463
FEATURE                 Location/Qualifiers
source                  1..463
                        mol_type = protein
                        organism = synthetic construct
SEQUENCE: 437
EVQLVESGAE VKKPGSSVKV SCRASGTFYK YAINWVRQAP GQGLEWMGGI IPFFGTTNYA  60
QKFQGRLTIT ADGSTNTAYM QLDSLRSEDT AVYYCAGPSI TESHYCLDCA AKDYYYGLDV  120
WGQGTTVTVS SSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KRVEPKSCTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG KKKARRGKKA RRV                    463

SEQ ID NO: 438          moltype = AA  length = 121
FEATURE                 Location/Qualifiers
source                  1..121
                        mol_type = protein
                        organism = synthetic construct
SEQUENCE: 438
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
S                                                                 121

SEQ ID NO: 439          moltype = AA  length = 8
FEATURE                 Location/Qualifiers
source                  1..8
                        mol_type = protein
                        organism = synthetic construct
```

```
SEQUENCE: 439
GGTSNNYA                                                          8

SEQ ID NO: 440          moltype = AA  length = 8
FEATURE                 Location/Qualifiers
source                  1..8
                        mol_type = protein
                        organism = synthetic construct
SEQUENCE: 440
ISPIFGST                                                          8

SEQ ID NO: 441          moltype = AA  length = 14
FEATURE                 Location/Qualifiers
source                  1..14
                        mol_type = protein
                        organism = synthetic construct
SEQUENCE: 441
ARHGNYYYYS GMDV                                                   14

SEQ ID NO: 442          moltype = AA  length = 110
FEATURE                 Location/Qualifiers
source                  1..110
                        mol_type = protein
                        organism = synthetic construct
SEQUENCE: 442
QSALTQPPAV SGTPGQRVTI SCSGSDSNIG RRSVNWYQQF PGTAPKLLIY SNDQRPSVVP  60
DRFSGSKSGT SASLAISGLQ SEDEAEYYCA AWDDSLKGAV FGGGTQLTVL             110

SEQ ID NO: 443          moltype = AA  length = 8
FEATURE                 Location/Qualifiers
source                  1..8
                        mol_type = protein
                        organism = synthetic construct
SEQUENCE: 443
DSNIGRRS                                                          8

SEQ ID NO: 444          moltype = AA  length = 256
FEATURE                 Location/Qualifiers
source                  1..256
                        mol_type = protein
                        organism = Influenza A virus
SEQUENCE: 444
STIMKSELEY GNCNTKCQTP MGAINSSMPF HNIHPLTIGE CPKYVKSNRL VLATGLRNTP  60
QRERRRKKRG LFGAIAGFIE GGWQGMVDGW YGYHHSNEQG SGYAADKEST QKAIDGVTNK  120
VNSIINKMNT QFEAVGREFN NLERRIENLN KKMEDGFLDV WTYNAELLVL MENERTLDFH  180
DSNVKNLYDK VRLQLRDNAK ELGNGCFEFY HKCDNECMES VKNGTYDYPQ YSEEARLNRE  240
EISGVKLESM GTYQIL                                                 256

SEQ ID NO: 445          moltype = AA  length = 11
FEATURE                 Location/Qualifiers
source                  1..11
                        mol_type = protein
                        organism = synthetic construct
SEQUENCE: 445
AAWDDSLKGA V                                                      11

SEQ ID NO: 446          moltype = AA  length = 441
FEATURE                 Location/Qualifiers
source                  1..441
                        mol_type = protein
                        organism = synthetic construct
SEQUENCE: 446
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG K                                           441

SEQ ID NO: 447          moltype = AA  length = 216
FEATURE                 Location/Qualifiers
source                  1..216
                        mol_type = protein
                        organism = synthetic construct
SEQUENCE: 447
QSALTQPPAV SGTPGQRVTI SCSGSDSNIG RRSVNWYQQF PGTAPKLLIY SNDQRPSVVP  60
DRFSGSKSGT SASLAISGLQ SEDEAEYYCA AWDDSLKGAV FGGGTQLTVL GQPKANPTVT  120
```

```
LFPPSSEELQ ANKATLVCLI SDFYPGAVTV AWKADGSPVK AGVETTKPSK QSNNKYAASS  180
YLSLTPEQWK SHRSYSCQVT HEGSTVEKTV APTECS                            216

SEQ ID NO: 448          moltype = AA  length = 446
FEATURE                 Location/Qualifiers
source                  1..446
                        mol_type = protein
                        organism = synthetic construct
SEQUENCE: 448
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KHHHHH                                       446

SEQ ID NO: 449          moltype = AA  length = 447
FEATURE                 Location/Qualifiers
source                  1..447
                        mol_type = protein
                        organism = synthetic construct
SEQUENCE: 449
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KHHHHHH                                      447

SEQ ID NO: 450          moltype = AA  length = 453
FEATURE                 Location/Qualifiers
source                  1..453
                        mol_type = protein
                        organism = synthetic construct
SEQUENCE: 450
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KHHHHHHHHH HHH                               453

SEQ ID NO: 451          moltype = AA  length = 471
FEATURE                 Location/Qualifiers
source                  1..471
                        mol_type = protein
                        organism = synthetic construct
SEQUENCE: 451
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KHHHHHHHHH HHHHHHHHHH HHHHHHHHHH H           471

SEQ ID NO: 452          moltype = AA  length = 447
FEATURE                 Location/Qualifiers
source                  1..447
                        mol_type = protein
                        organism = synthetic construct
SEQUENCE: 452
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KKKKKKK                                      447

SEQ ID NO: 453          moltype = AA  length = 457
```

```
FEATURE                 Location/Qualifiers
source                  1..457
                        mol_type = protein
                        organism = synthetic construct
SEQUENCE: 453
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG GGGSKKKKKK KKKKKKK                          457

SEQ ID NO: 454          moltype = AA  length = 471
FEATURE                 Location/Qualifiers
source                  1..471
                        mol_type = protein
                        organism = synthetic construct
SEQUENCE: 454
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KKKKKKKKKK KKKKKKKKKK KKKKKKKKKK K          471

SEQ ID NO: 455          moltype = AA  length = 447
FEATURE                 Location/Qualifiers
source                  1..447
                        mol_type = protein
                        organism = synthetic construct
SEQUENCE: 455
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KRRRRRR                                     447

SEQ ID NO: 456          moltype = AA  length = 453
FEATURE                 Location/Qualifiers
source                  1..453
                        mol_type = protein
                        organism = synthetic construct
SEQUENCE: 456
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KRRRRRRRRR RRR                              453

SEQ ID NO: 457          moltype = AA  length = 471
FEATURE                 Location/Qualifiers
source                  1..471
                        mol_type = protein
                        organism = synthetic construct
SEQUENCE: 457
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KRRRRRRRRR RRRRRRRRRR RRRRRRRRRR R          471

SEQ ID NO: 458          moltype = AA  length = 447
FEATURE                 Location/Qualifiers
source                  1..447
                        mol_type = protein
                        organism = synthetic construct
```

```
SEQUENCE: 458
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KOOOOOO                                     447

SEQ ID NO: 459          moltype = AA  length = 453
FEATURE                 Location/Qualifiers
source                  1..453
                        mol_type = protein
                        organism = synthetic construct
SEQUENCE: 459
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KOOOOOOOOO OOO                              453

SEQ ID NO: 460          moltype = AA  length = 471
FEATURE                 Location/Qualifiers
source                  1..471
                        mol_type = protein
                        organism = synthetic construct
SEQUENCE: 460
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KOOOOOOOOO OOOOOOOOOO OOOOOOOOOO O          471

SEQ ID NO: 461          moltype = AA  length = 447
FEATURE                 Location/Qualifiers
source                  1..447
                        mol_type = protein
                        organism = synthetic construct
SEQUENCE: 461
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KHHKKOO                                     447

SEQ ID NO: 462          moltype = AA  length = 447
FEATURE                 Location/Qualifiers
source                  1..447
                        mol_type = protein
                        organism = synthetic construct
SEQUENCE: 462
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KHORKHR                                     447

SEQ ID NO: 463          moltype = AA  length = 447
FEATURE                 Location/Qualifiers
source                  1..447
                        mol_type = protein
                        organism = synthetic construct
SEQUENCE: 463
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
```

```
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KHKRSOH                                      447

SEQ ID NO: 464          moltype = AA  length = 447
FEATURE                 Location/Qualifiers
source                  1..447
                        mol_type = protein
                        organism = synthetic construct
SEQUENCE: 464
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KRRHTHR                                      447

SEQ ID NO: 465          moltype = AA  length = 447
FEATURE                 Location/Qualifiers
source                  1..447
                        mol_type = protein
                        organism = synthetic construct
SEQUENCE: 465
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KKKHHRR                                      447

SEQ ID NO: 466          moltype = AA  length = 447
FEATURE                 Location/Qualifiers
source                  1..447
                        mol_type = protein
                        organism = synthetic construct
SEQUENCE: 466
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KOORRHH                                      447

SEQ ID NO: 467          moltype = AA  length = 447
FEATURE                 Location/Qualifiers
source                  1..447
                        mol_type = protein
                        organism = synthetic construct
SEQUENCE: 467
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KKKOORR                                      447

SEQ ID NO: 468          moltype = AA  length = 448
FEATURE                 Location/Qualifiers
source                  1..448
                        mol_type = protein
                        organism = synthetic construct
SEQUENCE: 468
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
```

```
VMHEALHNHY TQKSLSLSPG KKKKGKKK                                448

SEQ ID NO: 469          moltype = AA  length = 453
FEATURE                 Location/Qualifiers
source                  1..453
                        mol_type = protein
                        organism = synthetic construct
SEQUENCE: 469
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KHHHKKKRRR OOO                          453

SEQ ID NO: 470          moltype = AA  length = 453
FEATURE                 Location/Qualifiers
source                  1..453
                        mol_type = protein
                        organism = synthetic construct
SEQUENCE: 470
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KHHOAKKRCO OQH                          453

SEQ ID NO: 471          moltype = AA  length = 453
FEATURE                 Location/Qualifiers
source                  1..453
                        mol_type = protein
                        organism = synthetic construct
SEQUENCE: 471
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KHRKOORKHH RKK                          453

SEQ ID NO: 472          moltype = AA  length = 453
FEATURE                 Location/Qualifiers
source                  1..453
                        mol_type = protein
                        organism = synthetic construct
SEQUENCE: 472
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KKRAHOKCOR KSH                          453

SEQ ID NO: 473          moltype = AA  length = 453
FEATURE                 Location/Qualifiers
source                  1..453
                        mol_type = protein
                        organism = synthetic construct
SEQUENCE: 473
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KKKRROOHHH RRR                          453

SEQ ID NO: 474          moltype = AA  length = 453
FEATURE                 Location/Qualifiers
```

```
source                1..453
                      mol_type = protein
                      organism = synthetic construct
SEQUENCE: 474
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KOOORRRKKK HHH                              453

SEQ ID NO: 475        moltype = AA  length = 453
FEATURE               Location/Qualifiers
source                1..453
                      mol_type = protein
                      organism = synthetic construct
SEQUENCE: 475
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KKKAHHGKKA HHV                              453

SEQ ID NO: 476        moltype = AA  length = 453
FEATURE               Location/Qualifiers
source                1..453
                      mol_type = protein
                      organism = synthetic construct
SEQUENCE: 476
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KKKARRGKKA RRV                              453

SEQ ID NO: 477        moltype = AA  length = 473
FEATURE               Location/Qualifiers
source                1..473
                      mol_type = protein
                      organism = synthetic construct
SEQUENCE: 477
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SASVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCT CPPCPAPELL GGPSVFLFPP  240
KPKDTLMISR TPEVTCVVVD VSHEDPEVKF NWYVDGVEVH NAKTKPREEQ YNSTYRVVSV  300
LTVLHQDWLN GKEYKCKVSN KALPAPIEKT ISKAKGQPRE PQVYTLPPSR DELTKNQVSL  360
TCLVKGFYPS DIAVEWESNG QPENNYKTTP PVLDSDGSFF LYSKLTVDKS RWQQGNVFSC  420
SVMHEALHNH YTQKSLSLSP GKKHKROHKR OHKROHKROH KROHKROHKR OHK        473

SEQ ID NO: 478        moltype = AA  length = 471
FEATURE               Location/Qualifiers
source                1..471
                      mol_type = protein
                      organism = synthetic construct
SEQUENCE: 478
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KKOHRSOKRH TORHKAHORK CKROKQRKHO S           471

SEQ ID NO: 479        moltype = AA  length = 471
FEATURE               Location/Qualifiers
source                1..471
                      mol_type = protein
                      organism = synthetic construct
SEQUENCE: 479
```

```
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KKKROSRRHO TOOHHAROKH CKHROTRHKK S           471

SEQ ID NO: 480          moltype = AA  length = 470
FEATURE                 Location/Qualifiers
source                  1..470
                        mol_type = protein
                        organism = synthetic construct
SEQUENCE: 480
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK RVEPKSCTCP PCPAPELLGG PSVFLFPPKP  240
KDTLMISRTP EVTCVVVDVS HEDPEVKFNW YVDGVEVHNA KTKPREEQYN STYRVVSVLT  300
VLHQDWLNGK EYKCKVSNKA LPAPIEKTIS KAKGQPREPQ VYTLPPSRDE LTKNQVSLTC  360
LVKGFYPSDI AVEWESNGQP ENNYKTTPPV LDSDGSFFLY SKLTVDKSRW QQGNVFSCSV  420
MHEALHNHYT QKSLSLSPGK HRKQOHRSOO KTRRRAHROC HHHSRHOTHR             470

SEQ ID NO: 481          moltype = AA  length = 476
FEATURE                 Location/Qualifiers
source                  1..476
                        mol_type = protein
                        organism = synthetic construct
SEQUENCE: 481
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KGRHKAKNHI RRPKSRWKKW HKYRKVHRHK VHKGRR      476

SEQ ID NO: 482          moltype = AA  length = 481
FEATURE                 Location/Qualifiers
source                  1..481
                        mol_type = protein
                        organism = synthetic construct
SEQUENCE: 482
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KWRKVHHYKK QHKNRAHGKL KLRAKIHQRS RMHGKQKHYH  480
R                                                                 481

SEQ ID NO: 483          moltype = AA  length = 483
FEATURE                 Location/Qualifiers
source                  1..483
                        mol_type = protein
                        organism = synthetic construct
SEQUENCE: 483
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KAHHKCRRGH KQKILHRRPH KFHRWKRVHK GRHGKKHRRH  480
KHR                                                               483

SEQ ID NO: 484          moltype = AA  length = 486
FEATURE                 Location/Qualifiers
source                  1..486
                        mol_type = protein
                        organism = synthetic construct
SEQUENCE: 484
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
```

```
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KQHRGKAKYH RTHHVKKQRH GRKNHKVHRH ARKFHKIRRL  480
KCHKKH                                                             486

SEQ ID NO: 485         moltype = AA  length = 491
FEATURE                Location/Qualifiers
source                 1..491
                       mol_type = protein
                       organism = synthetic construct
SEQUENCE: 485
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KHNKRFKKGR HVRHSRHKSH RRTHKYHHWR HYRKVHRCKK  480
AHKSHHRVHH K                                                       491

SEQ ID NO: 486         moltype = AA  length = 491
FEATURE                Location/Qualifiers
source                 1..491
                       mol_type = protein
                       organism = synthetic construct
SEQUENCE: 486
QVQLVQSGAE VKKPGSSVKV SCKSSGGTSN NYAISWVRQA PGQGLDWMGG ISPIFGSTAY  60
AQKFQGRVTI SADIFSNTAY MELNSLTSED TAVYFCARHG NYYYYSGMDV WGQGTTVTVS  120
SSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCTC PPCPAPELLG GPSVFLFPPK  240
PKDTLMISRT PEVTCVVVDV SHEDPEVKFN WYVDGVEVHN AKTKPREEQY NSTYRVVSVL  300
TVLHQDWLNG KEYKCKVSNK ALPAPIEKTI SKAKGQPREP QVYTLPPSRD ELTKNQVSLT  360
CLVKGFYPSD IAVEWESNGQ PENNYKTTPP VLDSDGSFFL YSKLTVDKSR WQQGNVFSCS  420
VMHEALHNHY TQKSLSLSPG KAHGRPHOFK ROCKAHOVKH ILKRTOSHOY KOVHQRNKOA  480
OKMRKIRGGH K                                                       491

SEQ ID NO: 487         moltype = AA  length = 129
FEATURE                Location/Qualifiers
source                 1..129
                       mol_type = protein
                       organism = synthetic construct
SEQUENCE: 487
QVQLLETGGG LVKPGQSLKL SCAASGFTFT SYAMHWVRQP PGKGLEWVAV VSYDGNYKYY  60
ADSVQGRFTI SRDNSKNTLY LQMNSLRAED TAVYYCAKDS RLRSLLYFEW LSQGYFNPWG  120
QGTTLTVSS                                                          129

SEQ ID NO: 488         moltype = AA  length = 5
FEATURE                Location/Qualifiers
source                 1..5
                       mol_type = protein
                       organism = synthetic construct
SEQUENCE: 488
SYAMH                                                              5

SEQ ID NO: 489         moltype = AA  length = 17
FEATURE                Location/Qualifiers
source                 1..17
                       mol_type = protein
                       organism = synthetic construct
SEQUENCE: 489
VVSYDGNYKY YADSVQG                                                 17

SEQ ID NO: 490         moltype = AA  length = 20
FEATURE                Location/Qualifiers
source                 1..20
                       mol_type = protein
                       organism = synthetic construct
SEQUENCE: 490
DSRLRSLLYF EWLSQGYFNP                                              20

SEQ ID NO: 491         moltype = AA  length = 111
FEATURE                Location/Qualifiers
source                 1..111
                       mol_type = protein
                       organism = synthetic construct
```

-continued

```
SEQUENCE: 491
DIQMTQSPSS LSASVGDRVT ITCRSSQSIT FDYKNYLAWY QQKPGKAPKL LIYWGSYLES  60
GVPSRFSGSG SGTDFTLTIS SLQPEDFATY YCQQHYRTPP SFGQGTKVEI K           111

SEQ ID NO: 492          moltype = AA  length = 7
FEATURE                 Location/Qualifiers
source                  1..7
                        mol_type = protein
                        organism = synthetic construct
SEQUENCE: 492
WGSYLES                                                            7

SEQ ID NO: 493          moltype = AA  length = 9
FEATURE                 Location/Qualifiers
source                  1..9
                        mol_type = protein
                        organism = synthetic construct
SEQUENCE: 493
QQHYRTPPS                                                          9

SEQ ID NO: 494          moltype = AA  length = 12
FEATURE                 Location/Qualifiers
source                  1..12
                        mol_type = protein
                        organism = synthetic construct
SEQUENCE: 494
QSITFDYKNY LA                                                      12

SEQ ID NO: 495          moltype = AA  length = 258
FEATURE                 Location/Qualifiers
source                  1..258
                        mol_type = protein
                        organism = Influenza A virus
SEQUENCE: 495
LSGESHGRIL KTDLNSGNCV VQCQTEKGGL NSTLPFHNIS KYAFGDCPKY IGVKSLKLAI  60
GLRNVPARSS RGLFGAIAGF IEGGWPGLVA GWYGFQHSND QGVGMAADRD STQKAVDKIT  120
SKVNNIVDKM NKQYEIIDHE FSEVETRLNM INNKIDDQIQ DVWAYNAELL VLLENQKTLD  180
EHDANVNNLY NKVKRALGSN AMEDGKGCFE LYHKCDDQCM ETIRNGTYNR RKYMEESRLG  240
RQKIEGVKLE SEGTYKIL                                                258

SEQ ID NO: 496          moltype = AA  length = 722
FEATURE                 Location/Qualifiers
source                  1..722
                        mol_type = protein
                        organism = Homo sapiens
SEQUENCE: 496
STIEEQAKTF LDKFNHEAED LFYQSSLASW NYNTNITEEN VQNMNNAGDK WSAFLKEQST  60
LAQMYPLQEI QNLTVKLQLQ ALQQNGSSVL SEDKSKRLNT ILNTMSTIYS TGKVCNPDNP  120
QECLLLEPGL NEIMANSLDY NERLWAWESW RSEVGKQLRP LYEEYVVLKN EMARANHYED  180
YGDYWRGDYE VNGVDGYDYS RGQLIEDVEH TFEEIKPLYE HLHAYVRAKL MNAYPSYISP  240
IGCLPAHLLG DMWGRFWTNL YSLTVPFGQK PNIDVTDAMV DQAWDAQRIF KEAEKFFVSV  300
GLPNMTQGFW ENSMLTDPGN VQKAVCHPTA WDLGKGDFRI LMCTKVTMDD FLTAHHEMGH  360
IQYDMAYAAQ PFLLRNGANE GFHEAVGEIM SLSAATPKHL KSIGLLSPDF QEDNETEINF  420
LLKQALTIVG TLPFTYMLEK WRWMVFKGEI PKDQWMKKWW EMKREIVGVV EPVPHDETYC  480
DPASLFHVSN DYSFIRYYTR TLYQFQFQEA LCQAAKHEGP LHKCDISNST EAGQKLFNML  540
RLGKSEPWTL ALENVVGAKN MNVRPLLNYF EPLFTWLKDQ NKNSFVGWST DWSPYADQSI  600
KVRISLKSAL GDKAYEWNDN EMYLFRSSVA YAMRQYFLKV KNQMILFGEE DVRVANLKPR  660
ISFNFFVTAP KNVSDIIPRT EVEKAIRMSR SRINDAFRLN DNSLEFLGIQ PTLGPPNQPP  720
VS                                                                 722
```

What is claimed is:

1. A chimeric protein comprising:

(a) an antibody moiety that specifically binds to a component of an influenza virus or an influenza virus variant; and (b) a mucoadhesive peptide fragment comprising at least 5 positively charged amino acid residues, wherein the mucoadhesive peptide fragment facilitates attachment of the chimeric protein to a mucosa.

2. The chimeric protein of claim 1, wherein the chimeric protein comprises:

(i) a single polypeptide chain; or (ii) two or more polypeptide chains, and wherein the chimeric protein comprises two or more mucoadhesive peptide fragments.

3. The chimeric protein of claim 1, wherein the mucoadhesive peptide fragment comprises at least 6 positively charged amino acid residues.

4. The chimeric protein of claim 1, wherein the positively charged amino acid residues are selected from the group consisting of lysine, arginine, histidine, ornithine, and combinations thereof.

5. The chimeric protein of claim 1, wherein the mucoadhesive peptide fragment comprises at least 5 contiguous positively charged amino acid residues.

6. The chimeric protein of claim 1, wherein the positively charged amino acid residues are interspersed with one or more non-positively charged amino acid residues.

7. The chimeric protein of claim 1, wherein the mucoadhesive peptide fragment is no more than 15 kD.

8. The chimeric protein of claim 1, wherein the mucoadhesive peptide fragment has an isoelectric point (pI) higher than the pH of the mucosa.

9. The chimeric protein of claim 1, wherein the mucoadhesive peptide fragment comprises an amino acid sequence of any one of SEQ ID NOs: 291-325 and 407-413, or variants thereof comprising up to 3 amino acid substitutions.

10. The chimeric protein of claim 9, wherein the mucoadhesive peptide fragment comprises the amino acid sequence of SEQ ID NO: 294.

11. The chimeric protein of claim 1, wherein the antibody moiety is a full-length antibody, and wherein:
- (i) the mucoadhesive peptide fragment is fused to the C-terminus of a heavy chain (HC) of the full-length antibody via an optional peptide linker; or
- (ii) the mucoadhesive peptide fragment is fused to the C-terminus of a light chain (LC) of the full-length antibody via an optional peptide linker.

12. The chimeric protein of claim 11, wherein the chimeric protein comprises two mucoadhesive peptide fragments, and wherein the chimeric protein comprises:
- (i) a first and a second polypeptide chain each comprising from the N-terminus to the C-terminus: an HC of the full-length antibody, an optional peptide linker, and one of the two mucoadhesive peptide fragments; and
- (ii) a third and a fourth polypeptide chain each comprising an LC of the full-length antibody.

13. The chimeric protein of claim 12, wherein the component of the influenza virus or influenza virus variant is HA, and wherein the chimeric protein comprises:
- (i) a first and a second polypeptide chain each comprising the amino acid sequence of any one of SEQ ID NOs: 216, 218-234, 236, 237, 239-242, and 416-419, or a variant thereof having at least 90% sequence identity to the amino acid sequence of any one of SEQ ID NOs: 216, 218-234, 236, 237, 239-242, and 416-419, and a third and a fourth polypeptide chain each comprising the amino acid sequence of SEQ ID NO: 217, or a variant thereof having at least 90% sequence identity to the amino acid sequence of SEQ ID NO: 217;
- (ii) a first and a second polypeptide chain each comprising the amino acid sequence of any one of SEQ ID NOs: 243, 245-258, and 422-425, or a variant thereof having at least 90% sequence identity to the amino acid sequence of any one of SEQ ID NOs: 243, 245-258, and 422-425, and a third and a fourth polypeptide chain each comprising the amino acid sequence of SEQ ID NO: 244, or a variant thereof having at least 90% sequence identity to the amino acid sequence of SEQ ID NO: 244; or
- (iii) a first and a second polypeptide chain each comprising the amino acid sequence of any one of SEQ ID NOs: 448-486, or a variant thereof having at least 90% sequence identity to the amino acid sequence of any one of SEQ ID NOs: 448-486, and a third and a fourth polypeptide chain each comprising the amino acid sequence of SEQ ID NO: 447, or a variant thereof having at least 90% sequence identity to the amino acid sequence of SEQ ID NO: 447.

14. The chimeric protein of claim 12, wherein the component of the influenza virus or influenza virus variant is NA, and wherein the chimeric protein comprises:
- (i) a first and a second polypeptide chain each comprising the amino acid sequence of any one of SEQ ID NOs: 259, 261-274, and 428-431, or a variant thereof having at least 90% sequence identity to the amino acid sequence of any one of SEQ ID NOs: 259, 261-274, and 428-431, and a third and a fourth polypeptide chains each comprising the amino acid sequence of SEQ ID NO: 260, or a variant thereof having at least 90% sequence identity to the amino acid sequence of SEQ ID NO: 260; or
- (ii) a first and a second polypeptide chain each comprising the amino acid sequence of any one of SEQ ID NOs: 275, 277-290, and 434-437, or a variant thereof having at least 90% sequence identity to the amino acid sequence of any one of SEQ ID NOs: 275, 277-290, and 434-437, and a third and a fourth polypeptide chains each comprising the amino acid sequence of SEQ ID NO: 276, or a variant thereof having at least 90% sequence identity to the amino acid sequence of SEQ ID NO: 276.

15. The chimeric protein of claim 1, wherein the influenza virus is a Type A influenza virus (IAV), a Type B influenza virus (IBV), a Type C influenza virus (ICV), a Type D influenza virus (IDV), or a variant, subtype, or reassortant thereof.

16. The chimeric protein of claim 1, wherein the component of the influenza virus or influenza virus variant is a viral surface protein or fragment thereof.

17. The chimeric protein of claim 16, wherein the viral surface protein is a hemagglutinin (HA) antigen, and wherein the antibody moiety comprises:
- (i) a heavy chain complementarity determining region (HC-CDR) 1 comprising the amino acid sequence of SEQ ID NO: 1, an HC-CDR2 comprising the amino acid sequence of SEQ ID NO: 2, an HC-CDR3 comprising the amino acid sequence of SEQ ID NO: 3, a light chain complementarity determining region (LC-CDR) 1 comprising the amino acid sequence of SEQ ID NO: 4, an LC-CDR2 comprising the amino acid sequence of WAS, and an LC-CDR3 comprising the amino acid sequence of SEQ ID NO: 6;
- (ii) an HC-CDR1 comprising the amino acid sequence of SEQ ID NO: 7, an HC-CDR2 comprising the amino acid sequence of SEQ ID NO: 8, an HC-CDR3 comprising the amino acid sequence of SEQ ID NO: 9, an LC-CDR1 comprising the amino acid sequence of SEQ ID NO: 235, an LC-CDR2 comprising the amino acid sequence of SEQ ID NO: 238, and an LC-CDR3 comprising the amino acid sequence of SEQ ID NO: 415; or
- (iii) an HC-CDR1 comprising the amino acid sequence of SEQ ID NO: 439, an HC-CDR2 comprising the amino acid sequence of SEQ ID NO: 440, an HC-CDR3 comprising the amino acid sequence of SEQ ID NO: 441, an LC-CDR1 comprising the amino acid sequence of SEQ ID NO: 443, an LC-CDR2 comprising the amino acid sequence of SND, and an LC-CDR3 comprising the amino acid sequence of SEQ ID NO: 445.

18. The chimeric protein of claim 17, wherein the antibody moiety comprises:
- (i) a heavy chain variable domain ($V_H$) comprising the amino acid sequence of SEQ ID NO: 76, or a variant thereof having at least 90% sequence identity to the amino acid sequence of SEQ ID NO: 76, and a light chain variable domain ($V_L$) comprising the amino acid sequence of SEQ ID NO: 77, or a variant thereof having at least 90% sequence identity to the amino acid sequence of SEQ ID NO: 77;
- (ii) a $V_H$ comprising the amino acid sequence of SEQ ID NO: 78, or a variant thereof having at least 90% sequence identity to the amino acid sequence of SEQ ID NO: 78, and a $V_L$ comprising the amino acid sequence of SEQ ID NO: 79, or a variant thereof having at least 90% sequence identity to the amino acid sequence of SEQ ID NO: 79; or (iii) a $V_H$ comprising the amino acid sequence of SEQ ID NO: 438, or a variant thereof having at least 90% sequence identity to the amino acid sequence of SEQ ID NO: 438, and a $V_L$ comprising the amino acid sequence of SEQ ID NO: 442, or a variant thereof having at least 90% sequence identity to the amino acid sequence of SEQ ID NO: 442.

19. The chimeric protein of claim 18, wherein the antibody moiety is a full-length antibody comprising:

(i) an HC comprising the amino acid sequence of SEQ ID NO: 414, or a variant thereof having at least 90% sequence identity to the amino acid sequence of SEQ ID NO: 414, and a LC comprising the amino acid sequence of SEQ ID NO: 217, or a variant thereof having at least 90% sequence identity to the amino acid sequence of SEQ ID NO: 217;

(ii) an HC comprising the amino acid sequence of SEQ ID NO: 420, or a variant thereof having at least 90% sequence identity to the amino acid sequence of SEQ ID NO: 420, and an LC comprising the amino acid sequence of SEQ ID NO: 244, or a variant thereof having at least 90% sequence identity to the amino acid sequence of SEQ ID NO: 244; or (iii) an HC comprising the amino acid sequence of SEQ ID NO: 446, or a variant thereof having at least 90% sequence identity to the amino acid sequence of SEQ ID NO: 446, and an LC comprising the amino acid sequence of SEQ ID NO: 447, or a variant thereof having at least 90% sequence identity to the amino acid sequence of SEQ ID NO: 447.

20. The chimeric protein of claim 16, wherein the viral surface protein is a neuraminidase (NA) antigen, and wherein the antibody moiety comprises:

(i) an HC-CDR1 comprising the amino acid sequence of SEQ ID NO: 104, an HC-CDR2 comprising the amino acid sequence of SEQ ID NO: 105, an HC-CDR3 comprising the amino acid sequence of SEQ ID NO: 106, an LC-CDR1 comprising the amino acid sequence of SEQ ID NO: 107, an LC-CDR2 comprising the amino acid sequence of AAS, and an LC-CDR3 comprising the amino acid sequence of SEQ ID NO: 109; or (ii) an HC-CDR1 comprising the amino acid sequence of SEQ ID NO: 110, an HC-CDR2 comprising the amino acid sequence of SEQ ID NO: 111, an HC-CDR3 comprising the amino acid sequence of SEQ ID NO: 112, an LC-CDR1 comprising the amino acid sequence of SEQ ID NO: 113, an LC-CDR2 comprising the amino acid sequence of GAS, and an LC-CDR3 comprising the amino acid sequence of SEQ ID NO: 115.

21. The chimeric protein of claim 20, wherein the antibody moiety comprises:

(i) a $V_H$ comprising the amino acid sequence of SEQ ID NO: 188, or a variant thereof having at least 90% sequence identity to the amino acid sequence of SEQ ID NO: 188, and a $V_L$ comprising the amino acid sequence of SEQ ID NO: 189, or a variant thereof having at least 90% sequence identity to the amino acid sequence of SEQ ID NO: 189; or (ii) a $V_H$ comprising the amino acid sequence of SEQ ID NO: 190, or a variant thereof having at least 90% sequence identity to the amino acid sequence of SEQ ID NO: 190, and a $V_L$ comprising the amino acid sequence of SEQ ID NO: 191, or a variant thereof having at least 90% sequence identity to the amino acid sequence of SEQ ID NO: 191.

22. The chimeric protein of claim 21, wherein the antibody moiety is a full-length antibody comprising:

(i) an HC comprising the amino acid sequence of SEQ ID NO: 426, or a variant thereof having at least 90% sequence identity to the amino acid sequence of SEQ ID NO: 426, and an LC comprising the amino acid sequence of SEQ ID NO: 260, or a variant thereof having at least 90% sequence identity to the amino acid sequence of SEQ ID NO: 260; or (ii) an HC comprising the amino acid sequence of SEQ ID NO: 432, or a variant thereof having at least 90% sequence identity to the amino acid sequence of SEQ ID NO: 432, and an LC comprising the amino acid sequence of SEQ ID NO: 276, or a variant thereof having at least 90% sequence identity to the amino acid sequence of SEQ ID NO: 276.

23. A pharmaceutical composition comprising the chimeric protein of claim 1, and a pharmaceutically acceptable carrier.

24. A method of preventing or treating an infection caused by an influenza virus or an influenza virus variant in an individual, comprising administering to the individual an effective amount of the pharmaceutical composition of claim 23, wherein the chimeric protein specifically binds to a component of the influenza virus or influenza virus variant.

25. A method of killing or neutralizing an influenza virus or an influenza virus variant in an individual, comprising administering to the individual an effective amount of the pharmaceutical composition of claim 23, wherein the chimeric protein specifically binds to a component of the influenza virus or influenza virus variant.

26. A method of activating the complement pathway in an individual, comprising administering to the individual an effective amount of the pharmaceutical composition of claim 23.

* * * * *